US011938158B2

United States Patent
Schott et al.

(10) Patent No.: US 11,938,158 B2
(45) Date of Patent: Mar. 26, 2024

(54) METHODS AND COMPOSITIONS FOR TREATING MUSCULOSKELETAL DISEASES, TREATING INFLAMMATION, AND MANAGING SYMPTOMS OF MENOPAUSE

(71) Applicant: Solarea Bio, Inc., Cambridge, MA (US)

(72) Inventors: Eric Michael Schott, West Roxbury, MA (US); Maria Juliana Soto-Giron, Cambridge, MA (US); Gerardo V. Toledo, Hopkinton, MA (US)

(73) Assignee: Solarea Bio, Inc., Cambridge, MA (US)

( * ) Notice: Subject to any disclaimer, the term of this patent is extended or adjusted under 35 U.S.C. 154(b) by 0 days.

(21) Appl. No.: 18/181,495

(22) Filed: Mar. 9, 2023

(65) Prior Publication Data

US 2023/0346859 A1 Nov. 2, 2023

Related U.S. Application Data

(63) Continuation of application No. PCT/US2022/080362, filed on Nov. 22, 2022.

(Continued)

(51) Int. Cl.

*A61K 35/741* (2015.01)
*A61K 9/00* (2006.01)

(Continued)

(52) U.S. Cl.

CPC .......... *A61K 35/747* (2013.01); *A61K 9/0056* (2013.01); *A61K 31/122* (2013.01);

(Continued)

(58) Field of Classification Search

CPC .................................................... A61K 35/741

See application file for complete search history.

(56) References Cited

U.S. PATENT DOCUMENTS 3,048,526 A 8/1962 Bloswell
3,108,046 A 10/1963 Harbit (Continued)

FOREIGN PATENT DOCUMENTS

AU 2008231930 A1 10/2008
BR PI0905590 A2 8/2011

(Continued)

OTHER PUBLICATIONS

Gouda et al.., Endophytes: A Treasure House of Bioactive Compounds of Medicinal Importance, Frontiers in Microbiology, Mini Review, Sep. 29, 2016, vol. 7, article 1538, total pp. 1-8. (Front. Microbiol. 7:1538. doi: 10. 3389/fmich.2016.01538). (Year: 2016).

(Continued)

*Primary Examiner* — Rosanne Kosson

(74) *Attorney, Agent, or Firm* — Goodwin Procter LLP

(57) ABSTRACT

Described herein are methods and compositions for using microbial agents (probiotics) and agents that promote growth of certain microbes (prebiotics) for management (including prevention and treatment) of musculoskeletal disorders, including osteoporosis, osteopenia, Paget's disease, stunting, osteoarthritis, osteomyelitis, and delayed or non-union fractures. Also described herein are methods and compositions for using probiotics and prebiotics for management of inflammation, and symptoms of menopause.

18 Claims, 13 Drawing Sheets

Specification includes a Sequence Listing.

Related U.S. Application Data

(60) Provisional application No. 63/382,666, filed on Nov. 7, 2022, provisional application No. 63/282,155, filed on Nov. 22, 2021.

(51) Int. Cl.

| | |
|---|---|
| ***A61K 31/122*** | (2006.01) |
| ***A61K 31/355*** | (2006.01) |
| ***A61K 31/375*** | (2006.01) |
| ***A61K 31/593*** | (2006.01) |
| ***A61K 35/744*** | (2015.01) |
| ***A61K 35/747*** | (2015.01) |
| ***A61K 36/064*** | (2006.01) |
| ***A61K 47/26*** | (2006.01) |
| ***A61K 47/46*** | (2006.01) |
| ***A61P 15/12*** | (2006.01) |

(52) U.S. Cl.
CPC .......... *A61K 31/355* (2013.01); *A61K 31/375* (2013.01); *A61K 31/593* (2013.01); *A61K 35/744* (2013.01); *A61K 36/064* (2013.01); *A61K 47/26* (2013.01); *A61K 47/46* (2013.01); *A61P 15/12* (2018.01)

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,478,822 | A | 10/1984 | Haslam et al. |
| 4,532,126 | A | 7/1985 | Ebert et al. |
| 4,625,494 | A | 12/1986 | Iwatschenko |
| 4,671,953 | A | 6/1987 | Stanley et al. |
| 4,786,505 | A | 11/1988 | Lovgren et al. |
| 4,800,083 | A | 1/1989 | Hom et al. |
| 4,904,479 | A | 2/1990 | Illum |
| 4,919,939 | A | 4/1990 | Baker |
| 4,935,243 | A | 6/1990 | Borkan et al. |
| 4,950,484 | A | 8/1990 | Olthoff et al. |
| 5,013,726 | A | 5/1991 | Ivy et al. |
| 5,059,595 | A | 10/1991 | Grazie |
| 5,073,543 | A | 12/1991 | Marshall et al. |
| 5,120,548 | A | 6/1992 | McClelland et al. |
| 5,225,202 | A | 7/1993 | Hodges et al. |
| 5,354,556 | A | 10/1994 | Sparks et al. |
| 5,591,767 | A | 1/1997 | Mohr et al. |
| 5,610,184 | A | 3/1997 | Shahinian, Jr. |
| 5,639,476 | A | 6/1997 | Oshlack et al. |
| 5,674,533 | A | 10/1997 | Santus et al. |
| 5,733,556 | A | 3/1998 | Schrier et al. |
| 5,733,575 | A | 3/1998 | Mehra et al. |
| 5,837,284 | A | 11/1998 | Mehta |
| 5,871,776 | A | 2/1999 | Mehta |
| 5,902,632 | A | 5/1999 | Mehta |
| 6,139,875 | A | 10/2000 | Adams et al. |
| 6,258,380 | B1 | 7/2001 | Overholt |
| 6,420,473 | B1 | 7/2002 | Chittamuru et al. |
| 6,455,052 | B1 | 9/2002 | Marcussen et al. |
| 6,482,435 | B1 | 11/2002 | Stratton et al. |
| 6,544,510 | B2 | 4/2003 | Olshenitsk et al. |
| 6,569,457 | B2 | 5/2003 | Ullah et al. |
| 6,572,871 | B1 | 6/2003 | Church et al. |
| 6,750,331 | B1 | 6/2004 | Takaichi et al. |
| 7,214,370 | B2 | 5/2007 | Naidu et al. |
| 8,318,151 | B2 | 11/2012 | Darimont-Nicolau et al. |
| 8,460,726 | B2 | 6/2013 | Harel et al. |
| 8,802,158 | B2 | 8/2014 | Boileau et al. |
| 8,871,266 | B2 | 10/2014 | Sanguansri et al. |
| 8,877,178 | B2 | 11/2014 | Boileau et al. |
| 9,040,101 | B2 | 5/2015 | Heiman et al. |
| 9,095,604 | B2 | 8/2015 | Ikegami et al. |
| 9,173,910 | B2 | 11/2015 | Kaplan et al. |
| 9,301,983 | B2 | 4/2016 | Huang et al. |
| 9,371,510 | B2 | 6/2016 | Moore |
| 9,386,793 | B2 | 7/2016 | Blaser et al. |
| 9,487,764 | B2 | 11/2016 | Falb et al. |
| 9,549,955 | B2 | 1/2017 | Rittmann et al. |
| 9,636,367 | B2 | 5/2017 | Garcia-Rodenas et al. |
| 9,937,211 | B2 | 4/2018 | Kelly et al. |
| 10,064,895 | B2 | 9/2018 | Vincent |
| 2004/0213828 | A1 | 10/2004 | Smith |
| 2005/0147710 | A1 | 7/2005 | Teckoe et al. |
| 2010/0172874 | A1 | 7/2010 | Turnbaugh et al. |
| 2011/0111094 | A1 | 5/2011 | Lavermicocca et al. |
| 2011/0177567 | A1 | 7/2011 | Bakker et al. |
| 2011/0177976 | A1 | 7/2011 | Gordon et al. |
| 2012/0015075 | A1 | 1/2012 | Davis et al. |
| 2012/0040387 | A1 | 2/2012 | Matsuoka |
| 2014/0044858 | A1 | 2/2014 | Quevedo |
| 2014/0065209 | A1 | 3/2014 | Putaala et al. |
| 2014/0147425 | A1 | 5/2014 | Henn et al. |
| 2014/0179726 | A1 | 6/2014 | Bajaj et al. |
| 2014/0314719 | A1 | 10/2014 | Smith et al. |
| 2015/0126463 | A1 | 5/2015 | Hsiao et al. |
| 2015/0259728 | A1 | 9/2015 | Cutcliffe et al. |
| 2015/0366941 | A1 | 12/2015 | Menear et al. |
| 2016/0067289 | A1 | 3/2016 | Berggren et al. |
| 2016/0081309 | A1 | 3/2016 | Newton et al. |
| 2016/0143961 | A1 | 5/2016 | Berry et al. |
| 2016/0199424 | A1 | 7/2016 | Berry et al. |
| 2016/0206666 | A1 | 7/2016 | Falb et al. |
| 2016/0235792 | A1 | 8/2016 | Berry et al. |
| 2016/0263166 | A1 | 9/2016 | Elinav et al. |
| 2016/0271189 | A1 | 9/2016 | Cutcliffe et al. |
| 2016/0302464 | A1 | 10/2016 | Egli et al. |
| 2016/0354417 | A1 | 12/2016 | Smittle et al. |
| 2017/0326190 | A1 | 11/2017 | Ansell et al. |
| 2020/0164002 | A1 | 5/2020 | Toledo et al. |
| 2022/0354907 | A1 | 11/2022 | Toledo et al. |

FOREIGN PATENT DOCUMENTS

| | | | |
|---|---|---|---|
| CA | 2334877 | A1 | 10/2000 |
| EP | 1495109 | A1 | 1/2005 |
| EP | 1794283 | A1 | 6/2007 |
| WO | WO-2004/080200 | A1 | 9/2004 |
| WO | WO-2010/099617 | A1 | 9/2010 |
| WO | WO-2012/098254 | A1 | 7/2012 |
| WO | WO-2012/170047 | A2 | 12/2012 |
| WO | WO-2013/067146 | A1 | 5/2013 |
| WO | WO-2013/176774 | A1 | 11/2013 |
| WO | WO-2014/068338 | A1 | 5/2014 |
| WO | WO-2014/145958 | A2 | 9/2014 |
| WO | WO-2015/172191 | A1 | 11/2015 |
| WO | WO-2015/177246 | A2 | 11/2015 |
| WO | WO-2015/200842 | A1 | 12/2015 |
| WO | WO-2016/065075 | A1 | 4/2016 |
| WO | WO-2016/086205 | A2 | 6/2016 |
| WO | WO-2016/086210 | A1 | 6/2016 |
| WO | WO-2016/124940 | A1 | 8/2016 |
| WO | WO-2017/160711 | A1 | 9/2017 |
| WO | WO-2020/051379 | A1 | 3/2020 |
| WO | WO-2020/257722 | A2 | 12/2020 |

OTHER PUBLICATIONS

Boden, G (2011) Obesity, Insulin Resistance and Free Fatty Acids. Curr Opin Endocrinol Diabetes Obes 18(2): 139-143.

Das, S (2013) Prevention of Diabetes—A Historical Note. IJHS 48.4: 625-642.

Gonzalez-Garcia, RA et al (2017) Microbial Propionic Acid Production. Fermentation 3(21): 1-20.

Ley et al (2005) Obesity alters gut microbial ecology. PNAS 102(31): 11070-11075.

Lin, H et al (2016) Correlations of Fecal Metabonomic and Microbiomic Changes Induced by High-fat Diet in the Pre-Obesity State. Sci Rep 6(21618):1-14.

(56) References Cited

OTHER PUBLICATIONS

Magnusdottir, S et al., (2017) Generation of genome-scale metabolic reconstructions for 773 members of the human gut microbiota. Nature biotechnol 35(1):81-89.
Olson, O et al (2017) Obesity and the tumor microenvironment, Science 358(6367): 1130-1131.
Pryor, Rand Cabriero, F (2015) Repurposing metformin: an old drug with new tricks in its binding pockets. Biochem J 471: 307-322.
Stull, AJ (2016) Blueberries' Impact on Insulin Resistance and Glucose Intolerance. Antioxidants 5(44): 1-11.
Truong, DT et al (2015) MetaPhlAn2 for enhanced metagenomic taxonomic profiling. Nature Methods 12(10): 902-904.
Vijay-Kumar et al (2010) Metabolic syndrome and altered gut microbiota in mice lacking toll-like receptor 5. Science 328(5975): 228-231.
White, J (2014) A Brief History of the Development of Diabetes Medications. Diabetes Spectr 27(2): 82-86.
U.S. Appl. No. 16/826,078—Office Action, dated Oct. 5, 2022, 54 pages.
Abdulla OA, Neamah W, Sultan M, Alghetaa HK, Singh N, Busbee PB, Nagarkatti M and Nagarkatti P (2021) The Abilfority of AhR Ligands to Attenuate Delayed Type Hypersensitivity Reaction Is Associated With Alterations in the Gut Microbiota. Front. Immunol. 12:684727. doi: 10.3389/fimmu.2021.684727.
Agus et al. "Gut Microbiota Regulation of Tryptophan Metabolism in Health and Disease," Cell Host & Microbe, vol. 23, Issue 6, 2018, pp. 716-724, ISSN 1931-3128, https://doi.org/10.1016/j.chom.2018.05.003.
Aletaha et al. "2010 Rheumatoid arthritis classification criteria: An American College of Rheumatology/European League Against Rheumatism collaborative initiative." Arthritis & Rheumatism, 62: 2569-2581. https://doi.org/10.1002/art.27584.
Alipour, B. et.al. Effects of Lactobacillus casei supplementation on disease activity and inflammatory cytokines in rheumatoid arthritis patients: a randomized double-blind clinical trial. (2014) Int J Rheum Dis, 17: 519-527. https://doi.org/10.1111/1756-185X.12333.
Allen. P. et al. "Immunomodulatory Roles of Polysaccharide Capsules in the Intestine Frontiers in Immunology" vol. 11 (2020) https://www.frontiersin.org/articles/10.3389/fimmu.2020.00690, DOI=10.3389/fimmu.2020.00690.
Bürkle, et al., "Mechanisms of Ageing and Development", Mechanisms of Ageing and Development 151 (2015), pp. 2-12.
Caffaratti, et al., "What We Know So Far about the Metabolite-Mediated Microbiota-Intestinal Immunity Dialogue and How to Hear the Sound of This Crosstalk", Metabolites 2021, 11, 406. https://doi.org/10.3390/metabo11060406 https://www.mdpi.com/journal/metabolites: pp. 1-37.
Cario, "Barrier-protective function of intestinal epithelial Toll-like receptor 2", nature publishing group, vol. 1 Supplement 1 | Nov. 2008 | www.nature.com/mi, doi:10.1038/mi.2008.47: pp. S62-S66.
Catrina, et al., "RA: from risk factors and pathogenesis to prevention, Gene, environment, microbiome and mucosal immune tolerance in rheumatoid arthritis", Rheumatology Advance Access published Dec. 23, 2014, doi:10.1093/rheumatology/keu469, Downloaded from http://rheumatology.oxfordjournals.org/ at University of California, San Francisco on Mar. 11, 2015: pp. 1-12.
Chassaing, et al., "Intestinal Epithelial cell Toll-like Receptor 5 Regulates the Intestinal Microbiota to Prevent Low-grade Inflammation and Metabolic Syndrome in Mice", Published in final edited form as: Gastroenterology. Dec. 2014 ; 147(6): 1363-1377.e17. doi:10.1053/j.gastro.2014.08.033,; pp. 1-19.
Choi, et al., "Diet mimicking fasting promotes regeneration and reduces autoimmunity and multiple sclerosis symptoms", Published in final edited form as: Cell Rep. Jun. 7, 2016; 15(10): 2136-2146. doi:10.1016/j.celrep.2016.05.009: pp. 1-18.
Chriswell, et al., "Microbiota mediated mucosal inflammation in arthritis", Published in final edited form as: Best Pract Res Clin Rheumatol. Dec. 2019 ; 33(6): 101492. doi:10.1016/j.berh.2020.101492; pp. 1-17.
Costa, et al., "Microbial Extracellular Polymeric Substances: Ecological Function and Impact on Soil Aggregation", Frontiers in Microbiology | www.frontiersin.org | Jul. 23, 2018 | vol. 9 | Article 1636 | doi: 10.3389/fmicb.2018.01636: pp. 1-14.
Crimmins, et al., "Quest for a summary measure of biological age: the health and retirement study", GeroScience (2021) 43:395-408, https://doi.org/10.1007/s11357-021-00325-1: pp. 395-408.
Cunha, et al., "Nisin Influence on the Antimicrobial Resistance Ability of Canine Oral Enterococci", Antibiotics 2020, 9, 890; doi:10.3390/antibiotics9120890 www.mdpi.com/journal/antibiotics: pp. 1-14.
Cuollo, et al., "The Senescence-Associated Secretory Phenotype (SASP) in the Challenging Future of Cancer Therapy and Age-Related Diseases", Biology 2020, 9, 485; doi:10.3390/biology9120485 www.mdpi.com/journal/biology: pp. 1-16.
Deshpande, et al., "Para-probiotics for Preterm Neonates—The Next Frontier", Nutrients 2018, 10, 871; doi:10.3390/nu10070871 www.mdpi.com/journal/nutrients: pp. 1-9.
Diebel, et al., "Determination of Biological Age: Geriatric Assessment vs Biological Biomarkers", Current Oncology Reports (2021) 23: 104 | https://doi.org/10.1007/s11912-021-01097-9: pp. 1-8.
Fan, et al., "Protective effects of Bifidobacterium adolescentis on collagen-induced arthritis in rats depend on timing of administration", Food Funct., 2020, 11, 4499-4511 | DOI: 10.1039/d0fo00077a | Published on Apr. 29, 2020. Downloaded by Harvard University on Dec. 7, 2021 9:17:48 PM: pp. 4499-4511.
Feres, et al., "The subgingival periodontal microbiota of the aging mouth", Periodontology 2000, vol. 72, 2016, 30-53 | Printed in Singapore. All rights reserved | © 2016 John Wiley & Sons A/S. Published by John Wiley & Sons Ltd.: pp. 30-53.
Ferro, et al., "Probiotic Supplementation for Rheumatoid Arthritis: A Promising Adjuvant Therapy in the Gut Microbiome Era", Frontiers in Pharmacology | www.frontiersin.org | Jul. 23, 2021 | vol. 12 | Article 711788 | doi: 10.3389/fphar.2021.711788: pp. 1-17.
Fiorucci, et al., "Bile Acids Activated Receptors Regulate innate immunity", Frontiers in Immunology | www.frontiersin.org | Aug. 13, 2018 | vol. 9 | Article 1853 | doi: 10.3389/fimmu.2018.01853: pp. 1-17.
Flanagan, et al., "Annual Review of Nutrition Calorie Restriction and Aging in Humans", Annu. Rev. Nutr. 2020.40:105-133. Downloaded from www.annualreviews.org | Access provided by CASA Institution Identity on Feb. 20, 2023 | https://doi.org/10.1146/annurev-nutr-122319-034601: pp. 105-135.
Yoneno, Kazuaki et al, "TGR5 signalling inhibits the production of pro-inflammatory cytokines by in vitro differentiated inflammatory and intestinal macrophages in Crohn's disease", Immunology, 2013, 139, pp. 19-29.
Forster, et al., "Identification of gut microbial species linked with disease variability in a widely used mouse model of colitis", https://doi.org/10.1038/s41564-022-01094-z | Nat ure Microbiology | vol. 7 | Apr. 2022 | www.nature.com/naturemicrobiology: pp. 590-599.
You, Xin-yu, et al., "Intestinal Mucosal Barrier Is Regulated by Intestinal Tract Neuro-Immune Interplay", Frontiers in Pharmacology, May 2021, vol. 12, Article 659716.
Yu, Haitao, et al., "Protective Ability of Biogenic Antimicrobial Peptide Microcin J25 Against Enterotoxigenic *Escherichia coli*-Induced Intestinal Epithelial Dysfunction and Inflammatory Reponses IPEC-J2 Cells", Frontiers in Cellular and Infection Microbiology, Jul. 2018, vol. 8, Article 242.
Almutairi et al., "The global prevalence of rheumatoid arthritis: a meta-analysis based on a systematic review", Rheumatology International, 2020, https://doi.org/10.1007/s00296-020-04731-0: pp. 1-15.
Yusufu, Ibrahim, et al., "A Tryptophan-Deficient Diet Induces Gut Microbiota Dysbiosis and Increases Systemic Inflammation in Aged Mice", Int. J. Mol. Sci., 2021, 22, 5005, <https://doi.org/10.3390/ijms22095005>.
Zaiss, Mario M., et al., "The gut-joint axis in rheumatoid arthritis", Nature Reviews Rheumatology, vol. 17, Apr. 2021, pp. 224-237.
Zamani, Batol, et al., "Synbiotic supplementation and the effects on clinical and metabolic responses in patients with rheumatoid arthritis: a randomised, double-blind, placebo-controlled trial", British Journal of Nutrition, 2017, 117, pp. 1095-1102.

(56) References Cited

OTHER PUBLICATIONS

Alpert, et al., "A clinically meaningful metric of immune age derived from high-dimensional longitudinal monitoring", Nature Medcine, Mar. 2019, vol. 25, pp. 487-495.
Zampieri, Raffaella Margherita, et al., "Anti-Inflammatory Activity of Exopolysaccharides from *Phormidium* sp. ETS05, the Most Abundant Cyanobacterium of the Therapeutic Euganean Thermal Muds, Using the Zebrafish Model", Biomolecules, Apr. 10, 2020, 10, 582.
Zhang, Yiqiang, et al., "Rapamycin Extends Life and Health in C57BL/6 Mice", J Gerontol A Biol Sci Med Sci, Feb. 2014, 69(2), pp. 119-130.
Zhang, Yuanyuan, et al., "Anti-inflammatory Activity and Mechanism of Surfactin in Lipopolysaccharide-Activated Macrophages", Inflammation, vol. 38, No. 2, Apr. 2015, pp. 756-764.
Zhou, Bin and Zhang, Defeng, "Antibacterial effects of bacteriocins isolated from Lactobacillus rhamnosus (ATCC 53103) in a rabbit model of knee implant infection", Experimental and Therapeutic Medicine, 15, 2018, pp. 2985-2989.
Amdekar, et al., "Lactobacillus casei reduces the Inflammatory Joint Damage Associated with Collagen-Induced Arthritis (CIA) by Reducing the Pro-Inflammatory Cytokines", J Clin Immunol (2011) 31:147-154.
Zhao, Ruixiang, et al., "Purification and characterization of bacteriocin produced by Lactobacillus rhamnosus zrx01", Food Bioscience, 38, 2020, 100754.
Zhang, Xuan, et al., "The oral and gut microbiomes are perturbed in rheumatoid arthritis and partly normalized after treatment", Nature Medicine, vol. 21, No. 8, Aug. 2015, pp. 895-907.
Apweiler, et al., "Protein sequence databases", Current Opinion in Chemical Biology (2004) 8:76-80.
Woo, Jae-Yeon, et al., "*Lactobacillus pentosus* var. plantarum C29 ameliorates memory impairment and inflammaging in a D-galactose-induced accelerated aging mouse model", Anaerobe, 27, 2014, pp. 22-26.
Xu, Huihui, et al., "Interactions between Gut Microbiota and Immunomodulatory Cells in Rheumatoid Arthritis", Hindawi, Mediators of Inflammation, vol. 2020, Article ID 1430605, 14 Pages, https://doi.org/10.1155/2020/1430605.
Yamashita, Maya, et al., "Preventive Effect of Lactobacillus helveticus SBT2171 on Collagen-Induced Arthritis in Mice", Frontiers in Microbiology, Jun. 2017, vol. 8, Article 1159.
Yamashita, Maya, et al., "Lactobacillus helveticus SBT2171 Attenuates Experimental Autoimmune Encephalomyelitis in Mice", Frontiers in Microbiology, Jan. 2018, vol. 8, Article 2596.
Yamazaki, Munchiro, et al., "Dopamine inhibition of superoxide anion production by polymorphonuclear leukocytes", J. Allergy Clin. Immunol., May 1989, pp. 967-972.
Yan, Yiqing, et al., "Dopamine Controls Systemic Inflammation through Inhibition of NLRP3 Inflammasome", Cell, 160, Jan. 15, 2015, pp. 62-73.
Artacho, et al., "The Pretreatment Gut Microbiome Is Associated With Lack of Response to Methotrexate in New-Onset Rheumatoid Arthritis", American College of Rheumatology, vol. 73, No. 6, Jun. 2021, pp. 931-942.
Wells, et al., "Associations between gut microbiota and genetic risk for rheumatoid arthritis in the absence of disease: a cross-sectional study", Lancet Rheumatology, Jul. 2020, vol. 2, No. 7: pp. e418-e427.
Wilson, et al., "Microbial Influences of Mucosal Immunity in Rheumatoid Arthritis", Current Rheumatology Reports, Oct. 2020, vol. 22, No. 11: pp. 1-8.
Atkinson, et al., "Establishment and characterization of a sustained delayed-type hypersensitivity model with arthritic manifestations in C57BL/6J mice", Arthritis Research & Therapy (2012) 14:R134, pp. 1-16.
Atkinson, et al., "Pharmacological Value of Murine Delayed-type Hypersensitivity Arthritis: A Robust Mouse Model of Rheumatoid Arthritis in C57BL/6 Mice", Basic & Clinical Pharmacology & Toxicology, 2017, 120, 108-114.
Weyand, et al., "The immunology of rheumatoid arthritis", Nature Immunology, Jan. 2021, vol. 22, No. 1: pp. 10-18.
Watanabe, et al., "Impact of senescence-associated secretory phenotype and its potential as a therapeutic target for senescence-associated diseases", Cancer Science, Apr. 2017, vol. 108, No. 4: pp. 563-569.
Bae, et al., "Akkermansia muciniphila phospholipid induces homeostatic immune responses", Nature, Jul. 27, 2022, pp. 1-21.
Bagga, et al., "Differential effects of prostaglandin derived from w-6 and w-3 polyunsaturated fatty acids on COX-2 expression and IL-6 secretion", PNAS, Feb. 18, 2003, vol. 100, pp. 1751-1756.
United Nations, et al., "World Population Prospects 2019: Highlights", Department of Economic and Social Affairs, Statistical Papers—United Nations (Ser. A), Population and Vital Statistics Report, Jun. 2019: pp. 1-2.
Bodkhe, et al., "The role of microbiome in rheumatoid arthritis treatment", Therapeutic Advances in Musculoskeletal Disease, Feb. 2019, vol. 11: pp. 1-16.
Gao, et al., "Impact of the Gut Microbiota on Intestinal Immunity Mediated by Tryptophan Metabolism", Frontiers in Cellular and Infection Microbiology, Feb. 2018, vol. 8, Article 13: pp. 1-22.
Bander, et al., "The Gut Microbiota and Inflammation: An Overview", Int. J. Environ. Res. Public Health 2020, 17, 7618; doi:10.3390/ijerph17207618.
Fransen, et al., "Aged Gut Microbiota Contributes to Systemical Inflammaging after Transfer to Germ-Free Mice", Frontiers in Immunology, Nov. 2017, vol. 8, Article 1385: pp. 1-12.
Franceschi, et al., "Inflammaging: a new immune-metabolic viewpoint for age-related diseases", Nat Rev Endocrinol., Oct. 2018, vol. 14, No. 10: pp. 576-590.
Bansal, et al., "The bacterial signal indole increases epithelial-cell tight-junction resistance and attenuates indicators of inflammation", PNAS, Jan. 5, 2010, vol. 107, pp. 1-6.
Gatej, et al., "Probiotic Lactobacillus rhamnosus GG prevents alveolar bone loss in a mouse model of experimental periodontitis", J Clin Periodontol., Nov. 2017, vol. 45, No. 2: pp. 1-21. doi: 10.1111/jcpe.12838.
Griffiths, et al., "Psoriasis and Atopic Dermatitis", Dermatol Ther (Heidelb), Epub: Feb. 2017, vol. 7 (Suppl 1): pp. S31-S41.
Belsky, et al., "Change in the Rate of Biological Aging in Response to Caloric Restriction: Calerie Biobank Analysis", J Gerontol A Biol Sci Med Sci, 2018, vol. 73, No. 1, 4-10 doi:10.1093/gerona/glx096.
Guttman-Yassky, et al., "Contrasting pathogenesis of atopic dermatitis and psoriasis—Part I: Clinical and pathologic concepts", J Allergy Clin Immunol., Epub Mar. 2011, vol. 127, No. 5: pp. 1110-1118.
Bharath, et al., "Metformin Enhances Autophagy and Normalizes Mitochondrial Function to Alleviate Aging-Associated Inflammation", Cell Metabolism, 2020, 32, 44-55. https://doi.org/10.1016/j.cmet.2020.04.015.
Grootaert, et al., "Adherence and viability of intestinal bacteria to differentiated Caco-2 cells quantified by flow cytometry", Journal of Microbiological Methods, Epub: Apr. 2011, vol. 86, No. 1: pp. 33-41.
Brand, et al., "Collagen-induced arthritis", Nature Protocols, 2007, vol. 2 No. 5., 1269-1275. doi:10.1038/nprot.2007.173.
Gusmao-Silva, et al., "Hsp65-Producing Lactococcocus lactis Prevents Antigen-Induced Arthritis in Mice", Frontiers in Immunology, Sep. 2020, vol. 11, Article: 562905: pp. 1-15.
Braun, et al., "Ankylosing spondylitis", Lancet 2007; 369: 1379-90.
Guo, et al., "*Clostridium* species as probiotics: potentials and challenges", Journal of Animal Science and Biotechnology, Feb. 2020, vol. 11, No. 24: pp. 1-10.
Amalraj, et al., "A Novel Highly Bioavailable Curcumin Formulation Improves Symptoms and Diagnostic Indicators in Rheumatoid Arthritis Patients: A Randomized, Double-Blind, Placebo-Controlled, Two-Dose, Three-Arm, and Parallel-Group Study", J Med Food 20 (10) 2017, 1022-1030. DOI: 10.1089/jmf.2017.3930.
Ge, et al., "Helicobacter pylori-infected C57BL/6 mice with different gastrointestinal microbiota have contrasting gastric pathology, microbial and host immune responses", Science Reports, May 2018, vol. 8, No. 1, Article: 8014: pp. 1-15.

(56) References Cited

OTHER PUBLICATIONS

Ghosh, et al., "The gut microbiome as a modulator of healthy ageing", Nature Reviews Gastroenterology & Hepatology, Epub: Apr. 2022, vol. 19, No. 9: pp. 565-584.
Giri, et al., "Role of Bacillus licheniformis VS16-Derived Biosurfactant in Mediating Immune Responses in Carp Rohu and its Application to the Food Industry", Frontiers in Microbiology, Mar. 2017, vol. 8, Article 514: pp. 1-13.
Glowacki, et al., "Prevention of inflammation-mediated bone loss in murine and canine periodontal disease via recruitment of regulatory lymphyocytes", Nov. 2013, Nov. 2013, vol. 110, No. 46: pp. 18525-18530 (7 pages). Epub Oct. 2013.
Han, et al., "Probiotic Gastrointestinal Transit and Colonization After Oral Administration: A Long Journey", Frontiers in Cellular and Infection Microbiology, Mar. 2021, vol. 11, Article 609722: pp. 1-12.
Higgins, et al., "Toll-Like Receptor 4-Mediated Innate IL-10 Activates Antigen-Specific Regulatory T Cells and Confers Resistance to Bordetella pertussis by Inhibiting Inflammatory Pathology", The Journal of Immunology, Sep. 2003, vol. 171, No. 6: pp. 3119-3127.
Hofer, et al., "Caloric Restriction Mimetics in Nutrition and Clinical Trials", Frontiers in Nutrition, Sep. 2021, vol. 8, Article 717343: pp. 1-20.
Hang, et al., "Bile acid metabolites control Th17 and Treg cell differentiation", Nature, Dec. 2019, vol. 576 (7785): pp. 143-148 (34 pages). Epub Nov. 2019. Author Manuscript.
Heinken, et al., "Systematic assessment of secondary bile acid metabolism in gut microbes reveals distinct metabolic capabilities in inflammatory bowel disease", Microbiome, May 2019, vol. 7, No. 1: pp. 1-18.
An, et al., "GABA-producing Lactobacillus plantarum inhibits metastatic properties and induces apoptosis of 5-FU-resistant colorectal cancer cells via GABAB receptor signaling§", Journal of Microbiology (2021) vol. 59, No. 2, pp. 202-216.
Aghaloo, et al. "Periodontal Diseas and Bisphosphonates Induce Osteonecrosis of the Jaws in the Rat", Journal of Bone and Mineral Research, vol. 26, No. 8, Aug. 2011, pp. 1871-1882 DOI: 10.1002/jbmr.379.
Holmdahl, et al., "The molecular pathogenesis of collagen-induced arthritis in mice—a model for rheumatoid arthritis", Ageing Research Reviews, Feb. 2002, vol. 1, No. 1: pp. 135-147.
Huang, et al., "Bacteriocins: Potential for Human Health", Oxidative Medicine and Cellular Longevity, Apr. 2021, vol. 2021, Article 5518825: pp. 1-17.
Hug, et al., "Toll-Like Receptors: Regulators of the Immune Response in the Human Gut", Nutrients, Feb. 2018, vol. 10(2):203: pp. 1-16.
Holers, et al., "Rheumatoid arthritis and the mucosal origins hypothesis: protection turns to destruction", Nature Reviews Rheumatology, Sep. 2018, vol. 14, No. 9: pp. 542-557 (16 pages).
Holden, et al., "Enteropathic arthritis", Rheumatic Disease Clinics of North America, Aug. 2003, vol. 29, No. 3: pp. 513-530.
Hunter, et al., "Prevalence of rheumatoid arthritis in the United States adult population in healthcare claims databases, 2004-2014", Rheumatology International, Sep. 2017, vol. 37, No. 9: pp. 1551-1557. Epub Apr. 2017.
Jhun, et al., "Lactobacillus sakei suppresses collagen-induced arthritis and modulates the differentiation of T helper 17 cells and regulatory B cells", Journal of Translational Medicine, Month 2020, vol. 18(1):317: pp. 1-11.
Jenab, et al., "Bacterial Natural Compounds with Anti-Inflammatory and Immunomodulatory Properties (Mini Review)", Drug Design, Development and Therapy, Sep. 2020, vol. 14: pp. 3787-3801.
Jang, et al., "IL-6 and IL-10 Induction from Dendritic Cells in Response to *Mycobacterium tuberculosis* Is Predominantly Dependent on TLR2-Mediated Recognition", The Journal of Immunology, Sep. 2004, vol. 173, No. 5: pp. 3392-3397.
Jin, et al., "Isolation and characterization of high exopolysaccharide-producing Weissella confuse VP30 from young children's feces", Microbial Cell Factories, Jun. 2019, vol. 18(1):110: pp. 1-13.
Jubair, et al., "Modulation of inflammatory arthritis by gut microbiota through mucosal inflammation and autoantibody generation", Arthritis Rheumatol, Aug. 2018, vol. 70, No. 8: pp. 1220-1233 (21 pages). Author manuscript. Epub Jul. 2018.
Klemera, et al., "A new approach to the concept and computation of biological age", Mechanisms of Ageing and Development, Mar. 2006, vol. 127, No. 3: pp. 240-248. Epub Nov. 2005.
Jia, et al., "Common methods of biological age estimation", Clinical Interventions in Aging, May 2017, vol. 12: pp. 759-772 (15 pages).
Justice, et al., "Frameworks for Proof-of-Concept Clinical Trials of Interventions That Target Fundamental Aging Processes", J Gerontol A Biol Sci Med Sci, Nov. 2016, vol. 71, No. 11: pp. 1415-1423. Epub Aug. 2016.
Kindt, et al., "The G Protein-Coupled Bile Acid Receptor TGR5 (Gpbar1) Modulates Endothelin-1 Signaling in Liver", Cells, Nov. 2019, vol. 8(11):1467: pp. 1-21.
Justice, et al., "A framework for selection of blood-based biomarkers for geroscience-guided clinical trials: report from the TAME Biomarkers Workgroup", GeroScience, Dec. 2018, vol. 40, No. 5-6: pp. 419-436 (18 pages). Epub Aug. 2018.
Jin, et al., "Localization and Function of GABA Transporters GAT-1 and GAT-3 in the Basal Ganglia", Frontiers in Systems Neuroscience, Jul. 2011, vol. 5, Article 63: pp. 1-10.
Kang, et al., "Modulation of Inflammatory Cytokines by Omega-3 Fatty Acids", Subcell Biochem., 2008, vol. 49: pp. 133-143.
Kinane, et al., "Periodontal diseases", Nature Reviews Disease Primers, Jun. 2017, vol. 3, Article 17038: pp. 1-14.
Komura, et al., "Mechanism underlying prolongevity induced by bifidobacteria in Caenorhabditis elegans", Biogerontology, Feb. 2013, vol. 14, No. 1: pp. 73-87. Epub Jan. 2013.
Ku, et al., "Anti-inflammatory effects of 27 selected terpenoid compounds tested through modulating Th1/Th2 cytokine secretion profiles using murine primary splenocytes", Food Chemistry, Nov. 2013, vol. 141, No. 2: pp. 1104-1113. Epub Apr. 2013.
Kolmogorov, et al., "Assembly of long, error-prone reads using repeat graphs", Nature Biotechnology, May 2019, vol. 37, No. 5: pp. 540-546. Epub Apr. 2019.
Komura, et al., "Caenorhabditis elegans as an alternative model host for legionella pneumophila, and protective effects of Bifidobacterium infantis", Applied and Environmental Microbiology, Jun. 2010, vol. 76, No. 12: pp. 4105-4108. Epub Apr. 2010.
Kushkevych, et al., "Sulfate-Reducing Bacteria of the Oral Cavity and Their Relation with Periodontitis-Recent Advances", Journal of Clinical Medicine, Jul. 2020, vol. 9, No. 8, Article 2347: pp. 1-20.
Kobayashi, et al., "Oral administration of Lactobacillus gasseri SBT2055 is effective in preventing Porphyromonas gingivalis-accelerated periodontal disease", Scientific Reports, Apr. 2017, vol. 7, No. 1, Article 545: pp. 1-10.
Kumar, et al., " A Potential Probiotic Lactobacillus plantarum JBC5 Improves Longevity and Healthy Aging by Modulating Antioxidative, Innate Immunity and Serotonin-Signaling Pathways in Caenorhabditis elegans", Antioxidants (Basel), Jan. 2022, vol. 11, No. 2, Article 268: pp. 1-25.
Kumari, et al., "Mechanisms of Cellular Senescence: Cell Cycle Arrest and Senescence Associated Secretory Phenotype", Frontiers in Cell and Developmental Biology, Mar. 2021, vol. 9, Article 645593: pp. 1-24.
Kulkarni, et al., "Benefits of Metformin in Attenuating the Hallmarks of Aging", Cell Metabolism, Jul. 2020, vol. 32, No. 1: pp. 15-30. Epub Apr. 2020.
Liu et al., "Role of the Gut Microbiome in Modulating Arthritis Progression in Mice," Scientific Reports (2016) 6:30594 11 pgs.
Wang, et al., "FXR: a metabolic regulator and cell protector", Cell Research, Nov. 2008, vol. 18, No. 11: pp. 1087-1095.
Vlyhlidalova, et al., "Gut Microbial Catabolites of Tryptophan are Ligands and Agonists of the Aryl Hydrocarbon Receptor: A Detailed Characterization", International Journal of Molecular Sciences, Apr. 2020, vol. 21, No. 7, Article 2614: pp. 1-17.
Wan, et al., "Serotonin: A Potent Immune Cell Modulator in Autoimmune Diseases", Frontiers in Immunology, Feb. 2020, vol. 11, Article 186: pp. 1-12.

(56) References Cited

OTHER PUBLICATIONS

Walter, et al., "Screening Concepts for the Isolation of Biosurfactant Producing Microorganisms", Part of the Advances in Experimental Medicine and Biology (AEMB) book series, 2010, vol. 672: pp. 1-13 (20 pages).
Walsham, et al., "Lactobacillus reuteri Inhibition of Enteropathogenic *Escherichia coli* Adherence to Human Intestinal Epithelium", Frontiers in Microbiology, Mar. 2016, vol. 7, Article 244: pp. 1-10.
Vavassori, et al., "The bile acid receptor FXR is a modulator of intestinal innate immunity", The Journal of Immunology, Nov. 2009, vol. 183, No. 10: pp. 6251-6261 (12 pages). Epub Oct. 2009.
Villageliu, et al., "Dopamine production in Enterococcus faecium: A microbial endocrinology-based mechanism for the selection of probiotics based on neurochemical-producing potential", PLoS One, Nov. 2018, vol. 13, No. 11: e0207038 (10 pages).
Vijayakumar, et al., "A Microplate Growth Inhibition Assay for Screening Bacteriocins against Listeria monocytogenes to Differentiate Their Mode-of-Action", Biomolecules, Jun. 2015, vol. 5, No. 2: pp. 1178-1194.
Vivekananda, et al., "Effect of the probiotic Lactobacilli reuteri (Prodentis) in the management of periodontal disease: a preliminary randomized clinical trial", Journal of Oral Microbiology, Nov. 2010, vol. 2, Article 5344: pp. 1-10.
Verginer, et al., "Production of Volatile Metabolites by Grape-Associated Microorganisms", Journal Agricultural and Food Chemistry, Jul. 2010, vol. 58, No. 14: pp. 8344-8350.
Langan, et al., "Microbiota-Derived Metabolites, Indole-3 aldehyde and Indole-3-acetic Acid, Differentially Modulate Innate Cytokines and Stromal Remodeling Processes Associated with Autoimmune Arthritis," Int. J. of Molecular Sciences 2021, 22:1-17.
Lavasani, et all., "A Novel Probiotic Mixture Exerts a Therapeutic Effect on Experimental Autoimmune Encephalomyelitis Mediated by IL-10 Producing Regulatory T Cells," PLoS ONE, 2010 5(2):1-11.
The Tabula Muris Consortium, et al., "A single-cell transcriptomic atlas characterizes ageing tissues in the mouse", Nature, Jul. 2020, vol. 583, No. 7817: pp. 590-595. Epub Jul. 2020.
Théatre, et al., "The Surfactin-Like Lipopeptides From *Bacillus* spp.: Natural Biodiversity and Synthetic Biology for a Broader Application Range", Frontiers in Bioengineering and Biotechnology, Mar. 2021, vol. 9, Article 623701: pp. 1-20.
Ternes, et al., "The gut microbial metabolite formate exacerbates colorectal cancer progression", Nature Metabolism, Apr. 2022, vol. 4, No. 4: pp. 458-475. Epub Apr. 2022.
Le, et al., "Host Hepatic Metabolism is Modulated by Gut Microbiota-Derived Sphingolipids," Cell Host & Microbe, 2022 30:798-808.
Sutphin, et al., "Caenorhabditis elegans orthologs of human genes differentially expressed with age are enriched for determinants of longevity", Aging Cell, Aug. 2017, vol. 16, No. 4: pp. 672-682. Epub Apr. 2017.
Nair, et al., "A simple practice guide for dose conversion between animals and human", Journal of Basic and Clinical Pharmacy, Mar.-May 2016, vol. 7, Issue. 2: pp. 27-31.
Thevaranjan, et al., "Age-Associated Microbial Dysbiosis Promotes Intestinal Permeability, Systemic Inflammation, and Macrophage Dysfunction", Cell Host & Microbe, Apr. 2017, vol. 21, No. 4: pp. 455-466 (19 pages).
Lebeer, et al., "Functional Analysis of Lactobacillus rhamnosus GG Pili in Relation to Adhesition and Immunomodulatory Interactions with Intestinal Epithelial Cells," Applied and Environmental Microbiology, 2011, pp. 185-193.
Nakagawa, et al., "Effects and mechanisms of prolongevity induced by Lactobacillus gasseri SBT2055 in Caenorhabditis elegans", Aging Cell (2016) 15, pp. 227-236.
Nayak, et al., "Methotrexate impacts conserved pathways in diverse human gut bacteria leading to decreased host immune activation", Cell Host & Microbe, Mar. 10, 2021, pp. 362-377.
Lee, et al., "Heliobacter pylori Eradication Prevents Progression of Gastric Cancer in Hypergastrinemic INS-GAS Mice," Cancer Research 2008, 68:(9):3540-3548.
Mulligan, et al., "Selection of Microbes Producing Biosurfactants in Media without Hydrocarbons", J. Ferment. Technol., vol. 62, No. 4, pp. 311-314, 1984.
Lee, et al., "Elucidating the Mechanism of Weissella-dependent Lifespan Extension in Caenorhabditis elegans," Scientific Reports, 2015, 5:17128, pp. 1-13.
Liao, et al., "Mouse Models and Aging:Longevity and Progeria," Current Topics in Developmental Biology (2014), 109:249-285.
Vanzanten, et al., "Gastric transitional zones, areas where Helicobacter treatment fails: results of a treatment trial using the Sydney strain mouse model", Antimicrobial Agents and Chemotherapy, Jul. 2003, vol. 47, No. 7: pp. 2249-2255.
Veghef-Mehrabany, et al., "Effects of Probiotic Supplementation on Oxidative Stress Indices in Women with Rheumatoid Arthritis: A Randomized Double-Blind Clinical Trial", Journal of the American College of Nutrition, May-Jun. 2016, vol. 35, No. 4: pp. 291-299 (10 pages). Epub Apr. 2015.
Tsai, et al., "Gerobiotics: probiotics targeting fundamental aging processes", Bioscience of Microbiota, Food and Health, 2021, vol. 40, No. 1: pp. 1-11. Epub Oct. 2020.
Neff, et al., "Rapamycin extends murine lifespan but has limited effects on aging", The Journal of Clinical Investigation, Aug. 2013, vol. 123, No. 8, pp. 3272-3291.
Veghef-Mehrabany, et al., "Probiotic supplementation improves inflammatory status in patients with rheumatoid arthritis", Nutrition, Apr. 2014, vol. 30, No. 4: pp. 430-435. Epub Dec. 2013.
Liu, et al., "Deep Sequencing of the Oral Microbiome Reveals Signatures of Periodontal Disease," PLoS One 2012, 6:e7919, pp. 1-16.
Liu, et al.., "Lactobacillus salivarius Isolated from Patients with Rheumatoid Arthritis Suppresses Collagen-Induced Arthritis and Increases Treg Frequency in Mice," J. of Interferon & Cytokine Research, 2016 36(12):1-7.
Negatu, et al., "Indole Propionic Acid, an Unusual Antibiotic Produced by the Gut Microbiota, With Anti-inflammatory and Antioxidant Properties", Frontiers in Microbiology, Oct. 2020, vol. 11, Article 575586, pp. 1-8.
Visser, et al., "Optimal dosage and route of administration of methotrexate in rheumatoid arthritis: a systematic review of the literature", Ann Rheum Dis., Jul. 2009, vol. 68, No. 7: pp. 1094-1099. Epub Nov. 2009.
Newman, et al., "Strategies and Challenges in Clinical Trials Targeting Human Aging", Gerontol A Biol Sci Med Sci, 2016, vol. 71, No. 11, pp. 1424-1434.
Nguyen, et al., "TLR2 and endosomal TLR-mediated secretion of IL-10 and immune suppression in response to phagosome-confined Listeria monocytogenes", PLOS Pathogens, Jul. 7, 2020, pp. 1-20.
Liu, et al., "The Anti-Periodontitis Effects of Ethanol Extract Prepared Using *Lactobacillus paracasei* subsp. paracasei NTU 101," Nutrients 2018, 10:472 pp. 1-13.
Ni, et al., "TGR5-HNF4a axis contributes to bile acid-induced gastric intestinal metaplasia markers expression", Cell Death Discovery, pp. 1-20 (2020).
Liu, et al., "Targeted Small Molecule-Mediated Immunomodulation of GP130 Receptor Attenuates Rheumatoid Arthritis in Rats," Osteoarthritis and Cartilage, 2019 27:S381-S382.
Lopez-Otin, et al., "Hallmarks of Health," Cell 2021, 184:33-63.
MacFarlane, et al,, "Session: Short-chain Fatty Acids: Regulation of Short-chain Fatty Acid Production," Proceedings of the Nutrition Society 2003, 62:67-72.
MacFarlane et al., "Synbiotic Consumption Changes the Metabolism and Composition of the Gut Microbiota in Older People and Modifies Inflammatory Processes: a Randomized, Double-blind, Placebo-Controlled Crossover Study," Aliment Pharmacol. Ther. 2013, 38:804-816.
Maeda, et al., "Dysbiosis Contributes to Arthritis Development via Activation of Autoreactive TCells in the Intestine," Arthritis & Rheumatology 2016, 10.1002: 1-35.
Maeda et al., "Host-microbiota Interactions in Rheumatoid Arthritis," Experimental & Molecular Medicine 51:150 pp. 1-6.

(56) References Cited

OTHER PUBLICATIONS

Mandel, et al., "Bacillus Coagulans: a Viable Adjunct Therapy for Relieving Symptoms of Rheumatoid Arthritis According to a Randomized, Controlled Trial," BMC Complementary and Alternative Medicine 2010, 10:1-7.
Marietta, et al., "Human Gut-derived Prevotella histicola Suppresses Inflammatory Arthritis in Humanized Mice," Arthritis Rheumatol 2016, 68(12):2878-2888.
Marinelli, et al., "Identification of the Novel Role of Butyrate as AhR Ligand in Human Intestinal Epithelial Cells," Scientific Reports 2019, 10.1038 pp. 1-14.
McIntyre, et al., "Inhibition of the Neuromuscular Acetylcholine Receptor with Atracurium Activates FOXO/DAF-16-induced longevity," Aging Cell 2021 13381 pp. 1-16.
Millar, et al., "A Proinflammatory Diet is Associated with Increased Odds of Frailty after 12-year Follow-up in a Cohort of Adults," Am. J. Clin. Nutr. 2022, 115:334-343.
Mohammed, et al., "The Therapeutic Effect of Probiotics on Rheumatoid Arthritis: a Systemic Review and Meta-analysis of Randomized Control Trials," Clin. Rheumatol. 36:2697-2707 (2017).
Monteagudo-Mera, et al., "Adhesion Mechanisms Mediated by Probiotics and Prebiotics and their Potential Impact on Human Health," Applied Microbiology and Biotechnology 2019, 10.1007 pp. 1-10.
Morikawa, et al., "A Study on the Structure-function Relationship of Lipopeptide Biosurfactants," Biochimica et Biophysica Acta 2000, pp. 211-218.
Smollen, et al., "Rheumatoid arthritis", Nature Reviews Disease Primers, Feb. 2018, vol. 4, Article 18001: pp. 1-23.
Sonowal, et al., "Indoles from commensal bacteria extend healthspan", Proc Natl Acad Sci USA, Sep. 2017, vol. 114, No. 36: pp. E7506-E7515. Epub Aug. 2017.
Soto-Giron, et al., "The Edible Plant Microbiome represents a diverse genetic reservoir with functional potential in the human host", Scientific Reports, Dec. 2021, vol. 11, No. 1, Article 24017: pp. 1-14.
Sun, et al., "Assessments of Probiotic Potentials of Lactiplantibacillus plantarum Strains Isolated From Chinese Traditional Fermented Food: Phenotypic and Genomic Analysis", Frontiers in Microbiology, May 2022, vol. 13, Article 895132: pp. 1-10.
Smolen, et al., "Clinical trials of new drugs for the treatment of rheumatoid arthritis: focus on early disease", Ann Rheum Dis., Jul. 2016, vol. 75, No. 7: pp. 1268-1271. Epub Apr. 2016.
Pineda, et al., "A randomized, double-blinded, placebo-controlled pilot study of probiotics in active rheumatoid arthritis", Med Sci Monit, 2011; 17(6): CR347-354, Published: Jun. 1, 2011, http://www.medscimonit.com/fulltxt.php?ICID=881808: pp. 348-354.
Pinoli, et al., "Dopaminergic Regulation of Innate Immunity: a Review", J Neuroimmune Pharmacol, DOI 10.1007/s11481-017-9749-2, Published online: Jun. 3, 2017: pp. 1-22.
Poupet, et al., "Caenorhabditis elegans, a Host to Investigate the Probiotic Properties of Beneficial Microorganisms", Frontiers in Nutrition | www.frontiersin.org, Aug. 2020 | vol. 7 | Article 135, published: Aug. 21, 2020, doi: 10.3389/fnut.2020.00135: pp. 1-22.
Quinn, et al., "Global chemical effects of the microbiome include new bile-acid conjugations", https://doi.org/10.1038/s41586-020-2047-9, Published online: Feb. 26, 2020, Nature | vol. 579 | Mar. 5, 2020: pp. 123-129—Total pp. 22.
Raftis, et al., "An immunomodulatory member of the gut microbiota reduces clinical signs and inflammatory joint damage in an animal model of rheumatoid arthritis": 4D Pharma PLC, pp. 1.
Rahman, et al., "NemaLife chip: a micropillar-based microfluid culture device optimized for aging studies in crawling C. elegans", www.nature.com/scientificreports, (2020) 10:16190 | https://doi.org/10.1038/s41598-020-73002-6: pp. 1-19.
Rao, et al., "Human Peripheral Blood Mononuclear Cells Exhibit Heterogeneous CD52 Expression Levels and Show Differential Sensitivity to Alemtuzumab Mediated Cytolysis", PLoS ONE | Heterogeneous CD52 Expression on Human PBMCs, www.plosone.org, Jun. 2012 | vol. 7 | Issue 6 | e39416: pp. 1-12.
Reinhoud, et al., "Analysis of Glutamate, GABA, Noradrenaline, Dopamine, Serotonin, and Metabolites Using Microbore UHPLC with Electrochemical Detection", ACS Chemical Neuroscience, pubs.acs.org/chemneuro, 2013 American Chemical Society, dx.doi.org/10.1021/cn400044s | ACS Chem. Neurosci. 2013, 4: pp. 888?894.
Riskedal, et al., "Development and Performance of a Diagnostic Precision Biomarker for Seronegative Rheumatoid Arthritis Based on DNA Methylation in Blood", Meeting: ACR Convergence 2022, Date: Saturday, Nov. 12, 2022: pp. 1-4.
Robida-Stubbs, et al., "TOR Signaling and Rapamycin Influence Longevity by Regulating SKN-1/Nrf and DAF-16/FoxO", Cell Metabolism 15, 713-724, May 2, 2012 ©2012 Elsevier Inc.: pp. 713-724.
Rogier, et al., "Alteration of the intestinal microbiome characterizes preclinical inflammatory arthritis in mice and its modulation attenuates established arthritis", Published online: Nov. 15, 2017, www.nature.com/scientificreports | Scientific Reports 7:15613 DOI:10.1038/s41598-017-15802-x: pp. 1-12.
Romanin, et al., "Probiotic yeast *Kluyveromyces marxianus* CIDCA 8154 shows anti-inflammatory and anti-oxidative stress properties in in vivo models", Beneficial Microbes, 2016; 7(1): 83-93, ISSN 1876-2833 print, ISSN 1876-2891 online, DOI 10.3920/BM2015.0066, http://www.wageningenacademic.com/doi/pdf/10.3920/BM2015.0066—Friday, Sep. 22, 2017 8:40:22 AM—Göteborgs Universitet IP Address:130.241.16.16: pp. 83-93.
Santano, et al., "Comparative Evaluation of the Antimicrobial and Mucus Induction Properties of Selected Bacillus Strains against Enterotoxigenic *Escherichia coli*", Antibiotics 2020, 9, 849; doi:10.3390/antibiotics9120849 www.mdpi.com/journal/antibiotics: pp. 1-10.
Roon, et al., "Methotrexate bioavailability", Clinical and Experimental Rheumatology 2010, Clin Exp Rheumatol 2010; 28 (suppl. 61): pp. s27-s32.
Roshchina, "Chapter 2 Evolutionary Considerations of Neurotransmitters in Microbial, Plant, and Animal Cells", M. Lyte and P.P.E. Freestone (eds.), Microbial Endocrinology, Interkingdom Signaling in Infectious Disease and Health, DOI 10.1007/978-1-4419-5576-0_2: pp. 17-52.
Roselli, et al., "Caenorhabditis Elegans and Probiotics Interactions from a Prolongevity Perspective", International Journal of Molecular Sciences, Int. J. Mol. Sci. 2019, 20, 5020; doi:10.3390/ijms20205020, www.mdpi.com/journal/ijms: pp. 1-14.
Rühmann, et al., "Methods to identify the unexplored diversity of microbial exopolysaccharides", Frontiers in Microbiology | www.frontiersin.org, Jun. 2015 | vol. 6 | Article 565, published: Jun. 9, 2015, doi: 10.3389/fmich.2015.00565: pp. 1-8.
Rutledge, et a;., "Measuring biological age using omics data", Nature Reviews | Genetics vol. 23 | Dec. 2022: pp. 715-727.
Saccon, et al., "Senolytic Combination of Dasatinib and Quercetin Alleviates Intestinal Senescence and Inflammation and Modulates the Gut Microbiome in Aged Mice", Journals of Gerontology: Biological Sciences, cite as: J Gerontol A Biol Sci Med Sci, 2021, vol. 76, No. 11, 1895-1905, doi:10.1093/gerona/glab002, Advance Access publication Jan. 6, 2021: pp. 1895-1905.
Salminen, et al., "Activation of innate immunity system during aging: NF-kB signaling is the molecular culprit of inflamm-aging", Ageing Research Reviews 7 (2008), doi:10.1016/j.arr.2007.09.002: pp. 83-105.
Sanchez, et al., "Efficacy of Probiotics in Rheumatoid Arthritis and Spondyloarthritis: A Systematic Review and Meta-Analysis of Randomized Controlled Trials", Published: Jan. 14, 2022, Nutrients 2022, 14, 354. https://doi.org/10.3390/nu14020354, https://www.mdpi.com/journal/nutrients: pp. 1-19.
Sandrini, et al., "Microbial endocrinology: host-bacteria communication within the gut microbiome", Journal of Endocrinology, (2015) 225, R21-R34, http://joe.endocrinology-journals.org, DOI: 10.1530/JOE-14-0615: pp. R21-R34.
Saraiva, et al., "The regulation of IL-10 production by immune cells", doi:10.1038/nri2711, Published online Feb. 15, 2010, Mar. 2010 | vol. 10, www.nature.com/reviews/immunol: pp. 170-181.

(56) References Cited

OTHER PUBLICATIONS

Saul, et al., "A new gene set identifies senescent cells and predicts senescence-associated pathways across tissues", Published online: Aug. 16, 2022, Nature Communications (2022)13:4827, https://doi.org/10.1038/s41467-022-32552-1: pp. 1-15.
Sayed, et a;., "An inflammatory aging clock (iAge) based on deep learning tracks multimorbidity, immunosenescence, frailty and cardiovascular aging", https://doi.org/10.1038/s43587-021-00082-y, Nature Aging | vol. 1 | Jul. 2021 | 598-615 | www.nature.com/nataging: pp. 598-615, Total pp. 31.
Oliviero, et al., "Benefits of Probiotics in Rheumatic Diseases", Frontiers in Nutrition, Sep. 2020, vol. 7, Article 157, pp. 1-6.
Ozogul, et al., "The Function of Lactic Acid Bacteria on Biogenic Amines Production by Food-Borne Pathogens in Arginine Decarboxylase Broth", Food Sci. Technol. Res., 18 (6), 795-804, 2012.
Pahor, et al., "Effect of Losartan and Fish Oil on Plasma IL-6 and Mobility in Older Persons. The Enrgise Pilot Randomized Clinical Trial.", J Gerontol A Biol Sci Med Sci, 2019, vol. 74, No. 10, 1612-1619.
Paine, et al., "Dysregulation of bile acids, lipids, and nucleotides in psoriatic arthritis revealed by unbiased profiling of serum metabolites", American College of Rheumatology , Jul. 11, 2022. https:// doi: 10.1002/art.42288.
Pan, et al., "Key proteins and pathways that regulate lifespan", J. Biol. Chem. (2017) 292(16) 6452-6460.
Pan, et al., "Predominant gut Lactobacillus murinus strain mediates anti-inflammaging effects in calorie-restricted mice", Microbiome, vol. 6, Iss 1, pp. 1-17 (2018).
Park, et al., "Short communication: Development of a direct in vivo screening model to identify potential probiotic bacteria using Caenorhabditis elegans", Journal of Dairy Science, 2014, vol. 97, No. 11, pp. 6828-6834.
Park, et al., "Probiotic Lactobacillus fermentum strain JDFM216 stimulates the longevity and immune response of Caenorhabditis elegans through a nuclear hormone receptor", Scientific Reports, 2018, pp. 1-10.
Paul, et al., "Probiotics and Amelioration of Rheumatoid Arthritis: Significant Roles of Lactobacillus casei and Lactobacillus acidophilus", Microorganisms, 2021, pp. 1-17.
Paynich, et al., "Exopolysaccharide from Bacillus subtilis Induces Anti-Inflammatory M2 Macrophages That Prevent T Cell -Mediated Disease", The Journal of Immunology, 2017, pp. 1-10.
Peng, et al., "IDBA-UD: a de novo assembler for single-cell and metagenomic sequencing data with highly uneven depth", Bioinformatics, 2012, vol. 28, No. 11, 1420-1428.
Pérez-Chaparro, "Newly Identified Pathogens Associated with Periodontitis: A Systematic Review", Journal of Dental Research, Jul. 29, 2014, pp. 846-858.
Peters, et al., "The transcriptional landscape of age in human peripheral blood", Nature Communications, 2015, pp. 1-14.
Piatek, et al., "In-Vitro Growth Inhibition of Bacterial Pathogens by Probiotics and a Synbiotic: Product Composition Matters", Int. J. Environ. Res. Public Health, 2020, pp. 1-10.
Parks, et al., "CheckM: assessing the quality of microbial genomes recovered from isolates, single cells, and metagenomes", Genome Research, 2015, pp. 1043-1055.
Schiavi, et al., "The Surface-Associated Exopolysaccharide of Bifidobacterium longum 35624 Plays an Essential Role in Dampening Host Proinflammatory Responses and Repressing Local TH17 Responses", Appl Environ Microbiol, Nov. 2016, vol. 82, No. 24: pp. 7185-7196.
Scher, et al., "Expansion of intestinal Prevotella copri correlates with enhanced susceptibility to arthritis", Elife, Nov. 2013, vol. 2:e01202 (20 pages).
Schott, et al., "Targeting the gut microbiome to treat the osteoarthritis of obesity", JCI Insight, Apr. 2018, vol. 3, No. 8: e95997 (18 pages).
Scortichini, et al., "Development and validation of a GC-FID method for the analysis of short chain fatty acids in rat and human faeces and in fermentation fluids", J Chromatogr B Analyt Technol Biomed Life Sci., Apr. 2020, vol. 1143, Article 121972: pp. 1-9. Epub Jan. 13, 2020.
Schorpion, et al., "Can Probiotic Supplements Improve Outcomes in Rheumatoid Arthritis?", Curr Rheumatol Rep, Nov. 2017, vol. 19, No. 11, Article 73: pp. 7.
Segata, et al., "Metagenomic microbial community profiling using unique clade-specific marker genes", Nature Methods, Jun. 2012, vol. 9, No. 8: pp. 811-814.
Sethi, et al., "Design, synthesis and computational studies involving Indole-Coumarin hybrids as galectin-1 inhibitors", Chemical Paper, Month 2021, vol. 75: pp. 2791-2805. Epub Feb. 2, 2021.
Shahbizi, et al., "Anti-Inflammatory and Immunomodulatory Properties of Fermented Plant Foods", Nutrients, Apr. 2021, vol. 13, No. 5, Article 1516: pp. 1-20.
Skelly, et al., "Mining the microbiota for microbial and metabolite-based immunotherapies", Nat Rev Immunol, May 2019, vol. 19, No. 5: pp. 305-323 (19 pages).
Skirbekk, et al., "How to Measure Population Aging? The Answer Is Less than Obvious: A Review", Gerontology, 2019, vol. 65, No. 2: pp. 136-144. Epub Dec. 13, 2018.
Fan, et al., "Lactobacillus casei CCFM1074 Alleviates Collagen-Induced Arthritis in Rats via Balancing Treg/Th 17 and Modulating the Metabolites and Gut Microbiota", Frontiers in Immunology | www.frontiersin.org | May 17, 2021 | vol. 12 | Article 680073 | doi: 10.3389/fimmu.2021.680073: pp. 1-15.
U.S. Appl. No. 16/694,876, filed Nov. 25, 2019, Pending.
U.S. Appl. No. 17/816,371, filed Jul. 29, 2022, Pending.
U.S. Appl. No. 18/053,262, filed Nov. 7, 2022, Pending.
U.S. Appl. No. 16/235,858, filed Dec. 28, 2018, U.S. Pat. No. 10,596,209, Mar. 24, 2020, Issued.
U.S. Appl. No. 16/826,078, filed Mar. 20, 2020, Pending.
U.S. Appl. No. 17/555,261, filed Dec. 17, 2021, Pending.
U.S. Appl. No. 17/816,932, filed Aug. 2, 2022, Pending.
U.S. Appl. No. 18/304,264, filed Apr. 20, 2023, Pending.
"Bone Density Study in Post-Menopausal Women", RDC Clinical, New Study Announcement, Dec. 3, 2021 [online], [Retrieved Jun. 9, 2022]. Retrieved from the internet: https://www.rdcclinical.com.au/trials/bone-density-study/. 8 Pages.
"Solarea Bio Announces Licensing Agreement with ADM", Solarea Bio Press Release, Oct. 19, 2021, 10:17 ET: pp. 1-3.
"Solarea Bio Investigators Receive National Academy of Medicine Healthy Longevity 2022 Quickfire Challenge Award", Solarea Bio Press Release, Sep. 29, 2022, 09:17 ET: pp. 1-3.
"Solarea Bio Teams up with Hebrew SeniorLife Investigators on a Newly Awarded U.S. National Academy of Medicine Catalyst Grant", Solarea Bio Press Release, Nov. 4, 2021, 10:17 ET: pp. 1-4.
"Solarea peer-review publication reveals green olives and other fruits and vegetables have vast microbial diversity with the potential to deliver probiotic functionality", Solarea Bio Press Release, Solarea Bio Press Release, Dec. 15, 2021, 10:17 ET: pp. 1-3.
Abuajah, et al., "Functional components and medicinal properties of food: a review", J Food Sci Technol, 2015, vol. 52, No. 5: pp. 2522-2529.
Abubucker, et al., "Metabolic Reconstruction for Metagenomic Data and Its Application to the Human Microbiome", PLOS Computational Biology, Jun. 2012, vol. 8, No. 6: pp. 1-17.
Ahlborg, et al., "Bone Loss and Bone Size after Menopause", The New England Journal of Medicine, Jul. 24, 2003, vol. 349, No. 4: pp. 327-334.
Akamatsu, et al., "Conversion of antigen-specific effector/memory T cells Into Foxp3-expressing Treg cells by inhibition of CDK8/19", Science Immunology, Oct. 25, 2019, vol. 4: pp. 1-16.
Alcock, et al., "Is eating behavior manipulated by the gastrointestinal microbiota? Evolutionary pressures and potential mechanisms", Bioessays 2014, vol. 36: pp. 940-949.
Allgeier, et al., "A colorimetric method for the determination of butyric acid", J Bacteriol, 1929, vol. 17, No. 2: pp. 79-87.
Altman, et al., "Development of Criteria for the Classification and Reporting of Osteoarthritis," Arthritis and Rheumatism, Aug. 1986, vol. 29, No. 8: pp. 1039-1049.

(56) References Cited

OTHER PUBLICATIONS

Altschul, et al., "Basic Local Alignment Search Tool", J Mol Biol., Oct. 5, 1990, vol. 215, No. 3: pp. 403-410.
Ananthakrishnan, et al., "Gut Microbiome Function Predicts Response to Anti-integrin Biologic Therapy in Inflammatory Bowel Diseases", Cell Host & Microbe, May 10, 2017, vol. 21: pp. 603-610.
Anastasilakis, et al., "Head-to-head comparison of risedronate vs. teriparatideon bone turnover markers in women with postmenopausal osteoporosis: a randomised trial", Int J Clin Pract, Jun. 2008, vol. 62, No. 6: pp. 919-924.
Arjmandi, et al., "Bone-Protective Effects of Dried Plum in Postmenopausal Women: Efficacy and Possible Mechanisms", Nutrients, 2019, vol. 9, No. 496: pp. 1-19.
Aron-Wisnewsky, et al., "The importance of the gut microbiota after bariatric surgery", Nature, 2012, vol. 9, No. 10: pp. 590-598.
Arumugam, et al., "Enterotypes of the human gut microbiome", Nature, 2011, vol. 473, No. 7346: pp. 174-180.
Asgari, et al., "Nucleotide-pair encoding of 16S rRNA sequences for host phenotype and biomarker detection", bioRxiv, Jul. 19, 2018, pp. 1-25. https://doi.org/10.1101/334722.
Atarashi, et al., "Induction of Colonic Regulatory T Cells by Indigenous *Clostridium* Species", Science, Jan. 21, 2011, vol. 331: pp. 337-341.
Atarashi, et al., "Treg induction by a rationally selected mixture of Clostridia strains from the human microbiota", Nature, Aug. 8, 2013, vol. 500: pp. 232-236.
Backhed, et al., "Mechanisms underlying the resistance to diet-induced obesity in germ-free mice", PNAS, 2007, vol. 104, No. 3: pp. 979-984.
Backhed, et al., "The gut microbiota as an environmental factor that regulates fat storage", PNAS, 2004, vol. 101, No. 44: pp. 15718-15723.
Bahr, et al., "Risperidone-induced weight gain is mediated through shifts in the gut microbiome and suppression of energy expenditure", EBioMedicine, 2015, vol. 2: pp. 1725-1734.
Bai, et al., "Response of gut microbiota and inflammatory status to bitter melon (*Momordica charantia* L.) in high fat diet induced obese rats", J Ethnopharmacol, 2016, vol. 194: pp. 717-726.
Baker, et al., "Estrogen-gut microbiome axis: Physiological and clinical implications", Maturitas, 2017, vol. 103: pp. 45-53.
Bakker-Zierikzee, et al., "Effects of infant formula containing a mixture of galacto- and fructo-oligosaccharides or viable Bifidobacterium animalis on the intestinal microflora during the first 4 months of life", Br J Nutr, 2005, vol. 94: pp. 783-790.
Basu, et al., "Blueberries decrease cardiovascular risk factors in obese men and women with metabolic syndrome", J Nutr, 2010, vol. 140, No. 9: pp. 1582-1587.
Bellamy, et al., "Validation study of WOMAC: a health status instrument for measuring clinically important patient relevant outcomes to antirheumatic drug therapy in patients with osteoarthritis of the hip or knee", J Rheumatol, Dec. 1988, vol. 15, No. 12: pp. 1833-1840.
Berg, et al., "The Edible plant microbiome: importance and health issues", In: Lugtenberg B. (eds) Principles of plant-microbe interactions. Springer, Cham, 2015.
Bernini, et al., "Beneficial effects of Bifidobacterium lactis on lipid profile and cytokines in patients with metabolic syndrome", Nutrition, 2016, vol. 32: pp. 716-719.
Biaggini, et al., "The pathogenic potential of Pseudomonas fluorescens MFN1032 on enterocytes can be modulated by serotonin, substance P and epinephrine." *Archives of microbiology* 197, No. 8 (2015): 983-990.
Bischoff, et al., "Role of serotonin in intestinal inflammation: knockout of serotonin reuptake transporter exacerbates 2,4,6-trinitrobenzene sulfonic acid colitis in mice", Am J Physiol Gastrointest Liver Physiol, Mar. 2009, vol. 296, No. 3: pp. G685-G695.
Black, et al., "Postmenopausal Osteoporosis", The New England Journal of Medicine, Jan. 21, 2016, vol. 374, No. 3: pp. 254-262.
Bleau, et al., "Crosstalk between intestinal microbiota, adipose tissue and skeletal muscle as an early event in systemic low-grade inflammation and the development of obesity and diabetes". Diabetes Metab Res Rev, 2015, vol. 31, No. 6: pp. 545-561.
Boden, et al., "Obesity, Insulin Resistance and Free Fatty Acids", Curr Opin Endocrinol Diabetes Obes, 2011, vol. 18, No. 2: pp. 139-143.
Body, et al., "A Randomized Double-Blind Trial to Compare the Efficacy of Teriparatide [Recombinant Human Parathyroid Hormone (1-34)] with Alendronate in Postmenopausal Women with Osteoporosis", The Journal of Clinical Endocrinology & Metabolism, Oct. 2002, vol. 87, No. 10: pp. 4528-4535.
Bouxsein, et al., "Considerations for Development of Surrogate Endpoints for Antifracture Efficacy of New Treatments in Osteoporosis: A Perspective", Journal of Bone and Mineral Research, Mar. 3, 2008, vol. 23, No. 8: pp. 1155-1167.
Bouxsein, et al., "Ovariectomy-Induced Bone Loss Varies Among Inbred Strains of Mice", Journal of Bone and Mineral Research, Mar. 7, 2005, vol. 20, No. 7: pp. 1085-1092.
Brahe, et al., "Is butyrate the link between diet, intestinal microbiota and obesity-related metabolic diseases?", Obes Rev, 2013, vol. 14: pp. 950-959.
Britton, et al., "Probiotic *L. reuteri* Treatment Prevents Bone Loss in a Menopausal Ovariectomized Mouse Model", Journal of Cellular Physiology, 2014, vol. 229: pp. 1822-1830.
Bron, et al., "Emerging molecular insights into the interaction between probiotics and the host intestinal mucosa", Nat Rev Microbiol, 2012, vol. 10: pp. 66-78.
Brown, et al., "Comparison of the Effect of Denosumab and Alendronate on BMD and Biochemical Markers of Bone Turnover in Postmenopausal Women With Low Bone Mass: A Randomized, Blinded, Phase 3 Trial*", Journal of Bone and Mineral Research, 2009, vol. 24: pp. 153-161.
Brown, et al., "Gut Microbiota Regulation of T Cells During Inflammation and Autoimmunity", Annual Review of Immunology, 2019, vol. 37: pp. 599-624.
Brunkwall, et al., "The gut microbiome as a target for prevention and treatment of hyperglycemia in type 2 diabetes: from current human evidence to future possibilities", Diabetalogia, 2017, vol. 60: pp. 943-951.
Calise, et el., "Immune Response-Dependent Assembly of IMP Dehydrogenase Filaments", Frontiers in Immunology, Nov. 29, 2018, vol. 9, Article 2789: pp. 1-15.
Camacho, et al., "Metformin in breast cancer—an evolving mystery", Breast Cancer Res, 2015, vol. 17, No. 88: pp. 1-4.
Campbell, et al., "The China Study: The most comprehensive study of nutrition ever conducted and startling implications for diet, weight loss, and long term health," Benbella, 2006, 425 pages.
Cani, et al., "Changes in gut microbiota control metabolic endotoxemia-induced inflammation in high-fat diet-induced obesity and diabetes in mice", Diabetes, 2008, vol. 57: pp. 1470-1481.
Cani, et al., "Improvement of glucose tolerance and hepatic insulin sensitivity by oligofructose requires a functional glucagon-like peptide 1 receptor", Diabetes, 2006, vol. 55: pp. 1484-1490.
Cani, et al., "Metabolic endotoxemia initiates obesity and insulin resistance", Diabetes, 2007, vol. 56: pp. 1761-1772.
Cani, et al., "Selective increases of bifidobacteria in gut microflora improve high-fat-diet-induced diabetes in mice through a mechanism associated with endotoxaemia", Diabetologica, 2007, vol. 50: pp. 2374-2383.
Carbonero, et al., "Microbial pathways in colonic sulfur metabolism and links with health and disease", Frontiers in Immunology, Nov. 28, 2012, vol. 3, Article 448: pp. 1-11.
Chambers, et al., "Effects of targeted delivery of propionate to the human colon on appetite regulation, body weight maintenance and adiposity in overweight adults", Gut, 2015, vol. 64: pp. 1744-1754.
Chanclud, et al., "Plant hormones: key players in gut microbiota and human diseases?", Trends Plant Sci, 2017, vol. 22, No. 9: 754-758.
Charbonneau, et al., "Sialylated Milk Oligosaccharides Promote Microbiota-Dependent Growth in Models of Infant Undernutrition", Cell, Feb. 25, 2016, vol. 164, pp. 859-871.

(56) References Cited

OTHER PUBLICATIONS

Chaudhury, et al., "Clinical Review of Antidiabetic Drugs: Implications for Type 2 Diabetes Mellitus Management", Front Endocrinol, 2017, vol. 8, No. 6: pp. 1-12.
Chelliah, et al., "Evaluation of antimicrobial activity and probiotic properties of wild-strain *Pichia kudriavzevii* isolated from frozen *idli* batter", Yeast, 2016, vol. 33, pp. 385-401.
Chen, et al., "Estrogen and Microbiota Crosstalk: Should We Pay Attention?", Trends in Endocrinology & Metabolism, Nov. 2016, vol. 27, No. 11, pp. 752-755.
Chen, et al., "Metabolism of Fructooligosaccharides in Lactobacillus plantarum ST-III via Differential Gene Transcription and Alteration of Cell Membrane Fluidity", Appl Environ Microbiol, 2015, vol. 81, No. 22: pp. 7697-7707.
Chiang, et al., "Antiosteoporotic Effects of Lactobacillus-Fermented Soy Skim Milk on Bone Mineral Density and the Microstructure of Femoral Bone in Ovariectomized Mice", Journal of Agricultural and Food Chemistry, 2011, vol. 59: pp. 7734-7742.
Choi, et al., "Difference in the Gut Microbiome between Ovariectomy-Induced Obesity and Diet-Induced Obesity", J. Microbiol. Biotechnol, Dec. 28, 2017, vol. 27, No. 12: pp. 2228-2236.
Cockburn, et al., "Polysaccharide Degradation by the Intestinal Microbiota and Its Influence on Human Health and Disease", J Mol Biol, 2016, vol. 428, pp. 3230-3252.
Codella, et al., "Exercise has the guts: how physical activity may positively modulate gut microbiota in chronic and immune-based diseases", Digest Liv Dis, 2018, vol. 50: pp. 331-341.
Collins, et al., "Beneficial effects of Lactobacillus reuteri 6475 on bone density in male mice is dependent on lymphocytes", Scientific Reports, 2019, vol. 9: pp. 1-17.
Correa, et al., "Regulation of immune cell function by short-chain fatty acids", Clinical & Translational Immunology, 2016, vol. 5, pp. 1-8.
Cosman, et al., "Clinician's Guide to Prevention and Treatment of Osteoporosis", 2014, vol. 25, pp. 2359-2381.
Cowardin, et al., "Mechanisms by which sialylated milk oligosaccharides impact bone biology in a gnotobiotic mouse model of infant undernutrition", PNAS, Jun. 11, 2019, vol. 116, No. 24: pp. 11988-11996.
Cowardin, et al., "Supplementary Information for: Mechanisms by which sialylated milk oligosaccharides impact bone biology in a gnotobiotic mouse model of infant undernutrition", PNAS, www.pnas.org/cgi/doi/10.1073/pnas.1821770116.
Cox, et al., "SolexaQA: At-a-glance quality assessment of Illumina second-generation sequencing data", BMC Bioinformatics, 2010, vol. 11, No. 485: pp. 1-6.
Coyle, et al., "Metformin as an adjuvant treatment for cancer: a systematic review and meta analysis", Ann Onc, 2016, vol. 27, pp. 2184-2195.
Cristofori, et al., "Anti-Inflammatory and Immunomodulatory Effects of Probiotics in Gut Inflammation: A Door to the Body", Frontiers of Immunology, Feb. 26, 2021, vol. 12, Article 578386: pp. 1-21.
Dalby, et al., "Dietary Uncoupling of Gut Microbiota and Energy Harvesting from Obesity and Glucose Tolerance in Mice", Cell Reports, 2017, vol. 21 pp. 1521-1533.
Damani, et al., "The Role of Prunes in Modulating Inflammatory Pathways to Improve Bone Health in Postmenopausal Women", Adv Nutr, Oct. 2, 2022, vol. 13, No. 5: pp. 1476-1492.
Dane, et al., "Effect of risedronate on biochemical marker of bone resorption in postmenopausal women with osteoporosis or osteopenia", Gynecological Endocrinology, 2008, vol. 24, No. 4: pp. 207-213.
Dar, et al., "*Bacillus clausii* inhibits bone loss by skewing Treg-Th17 cell equilibrium in postmenopausal osteoporotic mice model", Nutrition, 2018, vol. 54, pp. 118-128.
Das, et al., "Prevention of Diabetes—A Historical Note", IJHS, 2013, vol. 48, No. 4, pp. 625-642.
David, et al., "Diet rapidly and reproducibly alters the human gut microbiome", Nature, 2014, vol. 505, pp. 559-563.
Davies, et al., "Effect of Oral Semaglutide Compared With Placebo and Subcutaneous Semaglutide on Glycemic Control in Patients With Type 2 Diabetes", JAMA, 2017, vol. 318, No. 15: pp. 1460-1470.
De Jesus Raposo, et al., "Emergent Sources of prebiotics: seaweed and microalgae", Mar. Drugs, 2016, vol. 14, No. 2: doi: 10.3390/md14020027.
De La Cuesta-Zuluaga, et al., "Metformin Is Associated With Higher Relative Abundance of Mucin-Degrading Akkermansia muciniphila and Several Short-Chain Fatty Acid-Producig Microbiota in the Gut", Diabetes Care, 2017, vol. 40: pp. 54-62.
De Vadder, et al., "Microbiota-Produced Succinate Improves Glucose Homeostasis via Intestinal Gluconeogenesis", Cell Metab, 2016, vol. 24: pp. 151-157.
Deehan, et al., "Precision Microbiome Modulation with Discrete Dietary Fiber Structures Directs Short-Chain Fatty Acid Production", Cell Host & Microbe, Mar. 11, 2020, vol. 27: pp. 1-16.
Delzenne, et al., "Gut microorganisms as promising targets for the management of type 2 diabetes", Diabetalogia, 2015, vol. 58: pp. 2206-2217.
Derrien, et al., "Fate, activity, and impact of ingested bacteria within the human gut microbiota", Trends in Microbiol, 2015, vol. 23, No. 6: pp. 354-366.
Devaraj, et al., "The Human Gut Microbiome and Body Metabolism: Implications for Obesity and Diabetes", Clin Chem, 2013, vol. 59, No. 4: pp. 617-628.
Di Francesco, et al., "A time to fast", Science, 2018, vol. 362: pp. 770-775.
Ding, et al., "The regulation of immune cells by Lactobacilli: a potential therapeutic target for anti-atherosclerosis therapy", Oncotarget, 2017, vol. 8, No. 35: pp. 59915-59928.
Drew, et al., "Reseeding the gut", Nature, 2016, 540:s109-s112.
Duncan, et al., "Contribution of acetate to butyrate formation by human faecal bacteria", Br J Nutr, 2004, vol. 91: pp. 915-923.
Duong-Ly, et al., "T cell activation triggers reversible inosine-5'-monophosphate dehydrogenase assembly", Journal of Cell Science, 2018, vol. 131: pp. 1-8.
Easson, et al., "Food safety assessment and toxicity study of the synbiotic consortium SBD111", Food and Chemical Toxicology, Oct. 2022, vol. 168, Article 113329: pp. 1-14.
Eastell, et al., "Use of bone turnover markers in postmenopausal osteoporosis", Lancet Diabetes Endocrinol 2017, vol. 5: pp. 908-923.
Edgar, "Updating the 97% identity threshold for 16S ribosomal RNA OTUs." *Bioinformatics* 34, No. 14 (2018): 2371-2375.
Elzinga, et al., "The Use of Defined Microbial Communities to Model Host-Microbe Interactions in the Human Gut", Microbiology and Molecular Biology Reviews, Jun. 2019, vol. 83, No. 2: pp. 1-40.
Engelke, et al., "Clinical Use of Quantitative Computed Tomography (QCT) of the Hip in the Management of Osteoporosis in Adults: the 2015 ISCD Official Positions—Part I", Journal of Clinical Densitometry: Assessment & Management of Musculoskeletal Health, 2015, vol. 18, No. 3: pp. 338-358.
Engelke, et al., "Clinical Use of Quantitative Computed Tomography and Peripheral Quantitative Computed Tomography in the Management of Osteoporosis in Adults: The 2007 ISCD Official Positions", Journal of Clinical Densitometry, 2008, vol. 11, No. 1: pp. 123-162.
Engelke, et al., "Regional distribution of spine and hip QCT BMD responses after one year of once-monthly ibandronate in postmenopausal osteoporosis", Bone, 2010, vol. 46: pp. 1626-1632.
Ericsson, et al., "Variable Colonization after Reciprocal Fecal Microbiota Transfer between Mice with Low and High Richness Microbiota", Front Microbiol, 2017, vol. 8, No. 196: pp. 1-13.
Everard, et al., "Cross-talk between Akkermansia muciniphila and intestinal epithelium controls diet-induced obesity", PNAS, 2013, vol. 11, No. 22: pp. 9066-9071.
Everard, et al., "Diabetes, obesity and gut microbiota", Best Pract Res Clin Gastroenterol, 2013, vol. 27: pp. 73-83.
Everard, et al., "Microbiome of prebiotic-treated mice reveals novel targets involved in host response during obesity", ISME, 2014, vol. 8: pp. 2116-2130.

(56) References Cited

OTHER PUBLICATIONS

Fairbanks, et al., "Importance of Ribonucleotide Availability to ProliferatingT-lymphocytes from Healthy Humans", The Journal of Biological Chemistry, 1995, vol. 270, No. 50; pp. 29682-29689.
Famouri, et al., "Effects of Probiotics on Nonalcoholic Fatty Liver Disease in Obese Children and Adolescents", JPGN, 2017, vol. 64, No. 3: pp. 413-417.
Fang, et al., "Intestinal FXR agonism promotes adipose tissue browning and reduces obesity and insulin resistance", Nature, 2015, vol. 21, No. 2: pp. 159-167.
Fletcher, et al., "Shifts in the Gut Metabolome and *Clostridium difficile* Transcriptome throughout Colonization and Infection in a Mouse Model", mSphere, Mar. 2018, vol. 3, No. 2: pp. 1-18.
Flores, et al., "Fecal microbial determinants of fecal and systemic estrogens and estrogen metabolites: a cross-sectional study", Journal of Translational Medicine, Dec. 21, 2012, vol. 10, No. 253: pp. 1-11.
Forslund, et al (2015) Disentangling type 2 diabetes and metformin treatment signatures in the human gut microbiota. Nature 528(7581): 262-266.
Forslund, et al., "Corrigendum: Disentangling type 2 diabetes and metformin treatment signatures in the human gut microbiota", Nature, 2015, vol. 528, No. 7581: pp. 262-266.
Franzosa, et al., "Species-level functional profiling of metagenomes and metatranscriptomes", Nature Methods, Nov. 2018, vol. 15, pp. 962-968.
Frost, et al., "The short-chain fatty acid acetate reduces appetite via a central homeostatic mechanism", Nat Commun, 2014, vol. 5, No. 3611: pp. 1-11.
Gad, et al., "Anti-aging effects of L-arginine", Journal of Advanced Research, 2010, vol. 1: pp. 169-177.
Gagnon, et al., "Bone Health After Bariatric Surgery", JBMR Plus, 2017, vol. 2: pp. 1-13.
Garidou, et al., "The Gut Microbiota Regulates Intestinal CD4 T Cells Expressing RORγt and Controls Metabolic Disease", Cell Metab, 2015, vol. 22: pp. 100-112.
Gehrig, et al., "Effects of microbiota-directed foods in gnotobiotic animals and undernourished children", Science, Jul. 12, 2019, vol. 365, No. 139: pp. 1-12.
Gehrig, et al., "Supplementary Material for: Effects of microbiota-directed foods in gnotobiotic animals and undernourished children", Science, Jul. 12, 2019, vol. 365, No. 139: pp. 1-42.
GenBank KC111446.1. Hanseniaspora opuntiae strain JEY269 18S ribosomal RNA gene, partial sequence; internal transcribed spacer 1, 5.8S ribosomal RNA gene, and internal transcribed spacer 2, complete sequence; and 28S ribosomal RNA gene, partial sequence. Jul. 24, 2013 [online]. [Retrieved Dec. 10, 2019]. Retrieved from the internet: <URL: https:/twww.ncbi.nlm.nih.gov/nuccore/KC111446.1/>. Especially p. 1.
Gentile, et al., "The gut microbiota at the intersection of diet and human health", Science, 2018, vol. 362: pp. 776-780.
Geva-Zatorsky, et al., "Mining the Human Gut for Immunomodulatory Organisms", Cell, Feb. 23, 2017, vol. 168: pp. 928-943.
Gibson, et al., "Dietary modulation of the human colonic microbiota: introducing the concept of prebiotics", J Nutr, 1995, vol. 125, No. 6: pp. 1401-1412.
Gilbert, et al., "Current understanding of the human microbiome", Nature Medicine, Apr. 2018, vol. 24, No. 4: pp. 392-400.
Gold, et al., "Longitudinal Analysis of the Association Between Vasomotor Symptoms and Race/Ethnicity Across the Menopausal Transition: Study of Women's Health Across the Nation", American Journal of Public Health, Jul. 2006, vol. 96, No. 7: pp. 1226-1235.
Gonzalez-Garcia, et al., "Microbial propionic acid production", Fermentation, 2017, vol. 3, No. 21: pp. 1-20.
Gosalbes, et al., "Metabolic adaptation in the human gut microbiota during pregnancy and the first year of life", EBioMedicine, 2019, vol. 39: pp. 497-509.
Graessler, et al., "Metagenomic sequencing of the human gut microbiome before and after bariatric surgery in obese patients with type 2 diabetes: correlation with inflammatory and metabolic parameters", Pharmacogenetics J, 2013, vol. 13: pp. 514-522.
Greenblatt, et al., "Bone Turnover Markers in the Diagnosis and Monitoring of Metabolic Bone Disease", Clinical Chemistry, 2017, vol. 63, No. 2: pp. 464-474.
Greenspan, et al., "Early Changes in Biochemical Markers of Bone Turnover Predict the Long-Term Response to Alendronate Therapy in Representative Elderly Women: A Randomized Clinical Trial", Journal of Bone and Mineral Research, 1998, vol. 13, No. 9: pp. 1431-1438.
Grey, et al., "Duration of Antiresorptive Effects of Low-Dose Zoledronate in Osteopenic Postmenopausal Women: A Randomized, Placebo-Controlled Trial", Journal of Bone and Mineral Research, Jan. 2014, vol. 29, No. 1: pp. 166-172.
Gu, et al., "Analyses of gut microbiota and plasma bile acids enable stratification of patients for antidiabetic treatment", Nature Commun, 2017, vol. 8: p. 1785.
Gunnarsson, et al., "Potential of Jerusalem artichoke (*Helianthus tuberosus* L.) as a biorefinery crop." *Industrial Crops and Products* 56 (2014): 231-240.
Guo, et al., "Secretions of Bifidobacterium infantis and Lactobacillus acidophilus Protect Intestinal Epithelial Barrier Function", JPGN, 2017, vol. 64, No. 3: pp. 404-412.
Hacquard, et al., "Microbiota and Host Nutrition across Plant and Animal Kingdoms", Cell Host & Microbe, 2015, vol. 17: pp. 603-616.
Harley, et al., "Obesity and the gut microbiome: Striving for causality", Mol Metab, 2012, vol. 1: pp. 21-31.
Heaney, et al., "Dairy and Bone Health", Journal of the American College of Nutrition, 2009, vol. 28, No. 1: pp. 82S-90S.
Hehemann, et al., "Transfer of carbohydrate-active enzymes from marine bacteria to Japanese gut microbiota", Nature, 2010, vol. 464: pp. 908-914.
Heineken, et al., "Systems-level characterization of a host-microbe metabolic symbiosis in the mammalian gut", Gut microbes, 2013, vol. 4, No. 1: pp. 28-40.
Heinemann, et al., "The Menopause Rating Scale (MRS) scale: A methodological review", Health and Quality of Life Outcomes, Sep. 2004, vol. 2, No. 45: pp. 1-8.
Henao-Mejia, et al., "Inflammasome-mediated dysbiosis regulates progression of NAFLD and obesity", Nature, 2012, vol. 482, No. 7384: p. 179-185.
Herr, et al., "The Effects of Serotonin in Immune Cells", Frontiers in Cardiovascular Medicine, Jul. 2017, vol. 4, Article 48: pp. 1-11.
Hess, et al., "Dairy Foods: Current Evidence of their Effects on Bone, Cardiometabolic, Cognitive, and Digestive Health", Comprehensive Reviews in Food Science and Food Safety, 2016, vol. 15: pp. 251-268.
Hildebrandt, et al., "High Fat Diet Determines the Composition of the Murine Gut Microbiome Independently of Obesity", Gastroenterology, 2009, vol. 137, No. 5: p. 1716.
Holmes, et al., "Diet-Microbiome Interactions in Health are Controlled by Intestinal Nitrogen Source Constraints", Cell Metab, 2017, vol. 25: pp. 140-151.
Hooper, et al., "Interactions Between the Microbiota and the Immune System", Science, 2012, vol. 336, No. 6086: pp. 1268-1273.
Hugenholtz, et al., "Mouse models for human intestinal microbiota research: a critical evaluation", Cellular and Molecular Life Sciences, 2018, vol. 75: pp. 149-160.
Ibanez, et al., "Gut microbiome and bone", Joint Bone Spine, 2019, vol. 86: pp. 43-47.
Ilhan, et al., (2017) "Distinctive microbiomes and metabolites linked with weight loss after gastric bypass, but not gastric banding", ISME J 11(9): 2047-2058.
Imaoka, et al., "Anti-inflammatory activity of probiotic Bifidobacterium: enhancement of IL-10 production in peripheral blood mononuclear cells from ulcerative colitis patients and inhibition of IL-8 secretion in HT-29 cells", World J Gastroenterol, 2008, vol. 14, No. 16: pp. 2511-2516.

(56) References Cited

OTHER PUBLICATIONS

Imlay, et al., “Diagnosing oxidative stress in bacteria: not as easy as you might think”, Current Opinion in Microbiology, 2015, vol. 24: pp. 124-131.
Iwami, et al., “Effects of Short Chain Fatty Acid, Sodium Butyrate, on Osteoblastic Cells and Osteoclastic Cells”, Int. J. Biochem., 1993, vol. 25, No. 11: pp. 1631-1635.
Jackson, et al., “Culture dependent and independent analysis of bacterial communities associated with commercial salad leaf vegetables”, BMC Microbiol, 2013, vol. 13, No. 274: pp. 1-12.
Jackson, et al., “Emerging Perspectives on the Natural Microbiome of Fresh Produce Vegetables”, Agriculture, 2015, vol. 5: pp. 170-187.
Jafarnejad, et al., “Effects of a Multispecies Probiotic Supplement on Bone Health in Osteopenic Postmenopausal Women: A Randomized, Double-blind, Controlled Trial”, Journal of the American College of Nutrition, 2017, vol. 36, No. 7: pp. 497-506.
Jahangir, et al., “Type 2 Diabetes Current and Future Medications: A Short Review”, Int J Pharm Pharmacol, 2017, vol. 1, No. 1: p. 101.
Jain, et al., “High throughput ANI analysis of 90K prokaryotic genomes reveals clear species boundaries”, Nature Communications, 2018, vol. 9, No. 5114: pp. 1-8.
Jain, et al., “Nanopore sequencing and assembly of a human genome with ultra-long reads”, Nature Biotechnology, 2018, vol. 36, No. 4: p. 338.
Jansson, et al., “Probiotic treatment using a mix of three *Lactobacillus* strains for lumbar spine bone loss in postmenopausal women: a randomised, double-blind, placebo-controlled, multicentre trial”, Lancet Rheumatol, Nov. 2019, vol. 1: e154-62.
Jarvis, et al., “Microbiomes Associated With Foods From Plant and Animal Sources”, Front Microbiol, 2018, vol. 9: p. 2540.
Jennings, et al., “Amino Acid Intakes are Associated With Bone Mineral Density and Prevalence of Low Bone Mass in Women: Evidence From Discordant Monozygotic Twins”, Journal of Bone and Mineral Research, Feb. 2016, vol. 31, No. 2: pp. 326-335.
Jia, et al., “Card 2017: expansion and model-centric curation of the comprehensive antibiotic resistance database”, Nucleic Acids Res, 2017, No. 45: p. D566-D573.
Kaluzna-Czaplinska, et al., “Is there a relationship between intestinal microbiota, dietary compounds, and obesity?” Trends Food Sci Technol, 2017, vol. 70: p. 105-113.
Kapitza, et al., “Effects of semaglutide on beta cell function and glycaemic control in participants with type 2 diabetes: a randomized, double-blind, placebo-controlled trial”, Diabetalogia, 2017, vol. 60: pp. 1390-1399.
Kaplan, et al., “Fermentation of Fructooligosaccharides by Lactic Acid Bacteria and Bifidobacterial”, Appl Environ Microbiol, 2000, vol. 66, No. 6: pp. 2682-2684.
Kasubuchi, et al., “Dietary Gut Microbial Metabolites, Short-chain Fatty Acids, and Host Metabolic Regulation”, Nutrients, 2015, vol. 7: pp. 2839-2849.
Kau, et al., “Human nutrition, the gut microbiome and the immune system”, Nature, 2011, vol. 474: pp. 327-336.
Kellgren, et al., “Radiological Assessment of Osteo-Arthrosis”, Ann. Rheum. Dis., Dec. 1957, vol. 16, No. 4: pp. 494-502.
Kim, et al., “Immune regulation by microbiome metabolites”, Immunology, 2018, vol. 154, pp. 220-229.
Kim, et al., “Impact of L-Arginine Metabolism on Immune Response and Anticancer Immunotherapy”, Frontiers in Oncology, Mar. 2018, vol. 8, No. 67: pp. 1-5.
Kimura, et al., “The gut microbiota suppresses insulin-mediated fat accumulation via the short-chain fatty acid receptor GPR43”, Nat Commun, 2013, vol. 4, No. 1829: pp. 1-12.
King, et al., “Regulation of de novo purine synthesis inhuman bone marrow mononuclear cells by hypoxanthine.”, The Journal of Clinical Investigation, 1983;72(3):965-970.
Kishida, et al., “Effect of miglitol on the suppression of nonalcoholic steatohepatitis development and improvement of thegut environment in a rodent model”, J Gastroenterol, 2017, vol. 52, No. 11: pp. 1180-1191.
Koh, et al., “From Dietary Fiber to Host Physiology: Short Chain Fatty Acids as Key Bacterial Metabolites”, Cell, 2016, vol. 165: pp. 1332-1345.
Kreznar, et al., “Host Genotype and Gut Microbiome Modulate Insulin Secretion and Diet-Induced Metabolic Phenotypes”, Cell Rep, 2017, vol. 18: pp. 1739-1750.
Kuo, et al., “Bone biomarker for the clinical assessment of osteoporosis: recent developments and future perspectives”, Biomarker Research, 2017, vol. 5, No. 18: pp. 1-9.
König, et al., “Specific Collagen Peptides Improve Bone Mineral Density and Bone Markers in Postmenopausal Women—A Randomized Controlled Study”, Nutrients, 2018, vol. 10. No, 97: pp. 1-11.
Lambert, et al., “Combined bioavailable isoflavones and probiotics improve bone status and estrogen metabolism in postmenopausal osteopenic women: a randomized controlled trial”, Am J Clin Nutr, 2017, vol. 106: pp. 909-920.
Lambert, et al., “Combined Red Clover isoflavones and probiotics potently reduce menopausal vasomotor symptoms”, PLOS ONE, Jun. 7, 2017, vol. 12, No. 6: pp. 1-16.
Lang, et al., “The microbes we eat: abundance and taxonomy of microbes consumed in a day’s worth of meals for three diet types”, PeerJ, 2014, 2:e659; doi 10.7717/peerj.659.
Langmead, at al., “Fast gapped-read alignment with Bowtie 2”, Nat Methods, 2012, vol. 9, No. 4: pp. 357-359.
Lawenius, et al., “A probiotic mix partially protects against castration-induced bone loss in male mice”, Journal of Endocrinology, Jun. 2022, vol. 254, No. 2: pp. 91-101.
Lawenius, et al., “Development of a synbiotic that protects against ovariectomy-induced trabecular bone loss”, Am J Physiol Endocrinol Metab., Apr. 1, 2022, vol. 322, No. 4: pp. E344-E354.
Lee, et al., “Blueberry Supplementation Influences the Gut Microbiota, Inflammation, and Insulin Resistance in High-Fat-Diet-Fed Rats”, J Nutr, 2018, vol. 148, No. 2: pp. 209-219.
Lee, et al., “Effect of Enterotoxigenic *Escherichia coli* on Microbial Communities during Kimchi Fermentation”, J. Microbiol. Biotechnol., Nov. 2021, vol. 31, No. 11: pp. 1552-1558.
Lee, et al., “Effect of Metformin on Metabolic Improvement and Gut Microbiota”, Appl Environ Microbiol, 2014, vol. 80, No. 19: p. 59355943.
Lee, et al., “Gut microbiota-generated metabolites in animal health and disease”, Nat Chem Biol, 2014, vol. 10: pp. 416-424.
Lewiecki, et al., “Once-Monthly Oral Ibandronate Improves Biomechanical Determinants of Bone Strength in Women with Postmenopausal Osteoporosis”, J Clin Endocrinol Metab, Jan. 2009, vol. 94, No. 1: pp. 171-180.
Ley, et al., “Obesity alters gut microbial ecology”, PNAS, 2005, vol. 102, No. 31: pp. 11070-11075.
Li, et al., “Butyrate reduces appetite and activates brown adipose tissue via the gut-brain neural circuit”, Gut, 2017: pp. 1-11.
Li, et al., “Intermittent Fasting Promotes White Adipose Browning and Decreases Obesity by Shaping the Gut Microbiota”, Cell Metab, 2017, vol. 26: pp. 672-685.
Li, et al., “Metabolic Surgery Profoundly Influences Gut Microbial-Host Metabolic Crosstalk”, Gut, 2011, vol. 60, No. 9: pp. 1214-1223.
Li, et al., “Microbial osteoporosis: The interplay between the gut microbiota and bones via host metabolism and immunity”, MicrobiologyOpen, 2019: pp. 1-15.
Li, et al., “Pro-and anti-inflammatory effects of short chain fatty acids on immune and endothelial cells.” *European journal of pharmacology* 831 (2018): 52-59.
Li, et al., “Sex steroid deficiency-associated bone loss is microbiota dependent and prevented by probiotics”, The Journal of Clinical Investigation, Jun. 2016, vol. 126, No. 6: pp. 2049-2063.
Lim, et al., “The Effect of Lactobacillus acidophilus YT1(Menolacto) on Improving Menopausal Symptoms: A Randomized, Double-Blinded, Placebo-Controlled Clinical Trial”, Journal of Clinical Medicine, Jul. 9, 2020, vol. 9, No. 7, Article 2173: pp. 1-16.

(56) References Cited

OTHER PUBLICATIONS

Lin, et al., "Butyrate and propionate protect against diet-induced obesity and regulate gut hormones via free fatty acid receptor 3-independent mechanisms", PLoS ONE, 2012, vol. 7, No. 4: pp. 1-9.
Liu, et al., "The relationship between menopausal syndrome and gut microbes", BMC Women's Health, Nov. 2022, vol. 22, Article 437: pp. 1-11.
Liu, et al., "VFDB 2019: a comparative pathogenomic platform with an interactive web interface", Nucleic Acids Res, 2019, vol. 47: D687-D692.
Louis, et al., "Formation of propionate and butyrate by the human colonic microbiota", Environ Microbiol, 2017, vol. 19, No. 1: pp. 29-41.
Lu, et al., "Short Chain Fatty Acids Prevent High-fat-diet-induced Obesity in Mice by Regulating G Protein-coupled Receptors and Gut Microbiota", Sci Rep, 2016, vol. 6, No. 37589: pp. 1-13.
Lucas, et al., "Short-chain fatty acids regulate systemic bone mass and protect from pathological bone loss", Nature Communications, 2018, vol. 9, No. 55: pp. 1-10.
Lyu, et al., "Balancing Herbal Medicine and Functional Food for Prevention and Treatment of Cardiometabolic Diseases through Modulating Gut Microbiota", Front Microbiol, 2017, vol. 8, No. 2146: pp. 1-21.
Madiraju, et al., "Metformin suppresses gluconeogenesis by inhibiting mitochondrial glycerophosphate dehydrogenase", Nature, 2014, vol. 510: pp. 542-546.
Magnusdottir, et al., "Generation of genome-scale metabolic reconstructions for 773 members of the human gut microbiota", Nature Biotechnology, Jan. 2017, vol. 35, No. 1: pp. 81-89.
Maier, et al., Extensive impact of non-antibiotic drugs on human gut bacteria, Nature, 2018: pp. 1-6.
Martinez-Lopez, et al., "System-wide Benefits of Intermeal Fasting by Autophagy", Cell Metab, 2017, vol. 26: pp. 856-871.
McCabe, et al., "Exercise prevents high fat diet induced bone loss, marrow adiposity and dysbiosis in male mice", Bone, 2018: https://doi.org/10.1016/j.bone.2018.03.024.
McCabe, et al., "Prebiotic and Probiotic Regulation of Bone Health: Role of the Intestine and its Microbiome", Curr Osteoporosis Rep., Dec. 2015, vol. 13, No. 6: pp. 636-371.
Meng, et al., "Anti-inflammatory effects of *Bifidobacterium longum* subsp infantis secretions on fetal human enterocytes are mediated by TLR-4 receptors", Am J Physiol Gastrointest Liver Physiol, 2016, vol. 311:G744-G753.
Milajerdi, et al., "The effect of probiotics on inflammatory biomarkers: a meta-analysis of randomized clinical trials", European Journal of Nutrition, Mar. 11, 2020, vol. 59, No. 2: pp. 633-649.
Milani, et al., "Bifidobacteria exhibit social behavior through carbohydrate resource sharing in the gut", Sci Rep, 2015, vol. 5, No. 15782: pp. 1-14.
Montandon, et al., "Effects of Antidiabetic Drugs on Gut Microbiota Composition", Genes, 2017, vol. 8, No. 250: pp. 1-12.
Morishita, et al., "Production of menaquinones by lactic acid bacteria." Journal of dairy science 82, No. 9 (1999): 1897-1903.
Moriwake, et al., "Delphinidin, One of the Major Anthocyanidins, Prevents Bone Loss through the Inhibition of Excessive Osteoclastogenesis in Osteoporosis Model Mice", PLoS ONE, May 2014, vol. 9, No. 5: pp. 1-11.
Morrison, et al., "Formation of short chain fatty acids by the gut microbiota and their impact on human metabolism", Gut Microbes, 2016, vol. 7, No. 3: pp. 189-200.
Moslehi-Jenabian, et al., "Beneficial Effects of Probiotic and Food Borne Yeasts on Human Health", Nutrients, 2010, vol. 2: pp. 449-473.
Muller, et al., "The Plant Microbiota: Systems-Level Insights and Perspectives", The Annual Review of Genetics, 2016, vol. 50: pp. 211-234.
Munder, et al., "Arginase: an emerging key player in the mammalian immune system", British Journal of Pharmacology, 2009, vol. 158: pp. 638-651.
Myneni, et al., "Regulation of bone remodeling by vitamin K2", Oral Diseases, 2017, vol. 23 pp. 1021-1028.
Napolitano, et al., "Novel Gut-Based Pharmacology of Metformin in Patients with Type 2 Diabetes Mellitus", PLoS ONE, 2014, vol. 9, No. 7: e100778.
Naylor, et al., "Response of bone turnover markers to three oral bisphosphonatetherapies in postmenopausal osteoporosis: the TRIO study", Osteoporos Int, 2016, vol. 27: pp. 21-31.
Needleman, et al., "A General Method Applicable to the Search for Similarities in the Amino Acid Sequence of Two Proteins", J. Mol. Biol., Mar. 1970, vol. 48: pp. 443-453.
Nguyen, et al., "A perspective on 16S rRNA operational taxonomic unit clustering using sequence similarity." *NPJ biofilms and microbiomes* 2, No. 1 (2016): 1-8.
Ni, et al., "A Molecular-Level Landscape of Diet-Gut Microbiome Interactions: Toward Dietary Interventions Targeting Bacterial Genes", mBio, 2015, vol. 6, No. 6: e01263-15.
Nilsson, et al., "*Lactobacillus reuteri* reduces bone loss in older women with low bone mineral density: a randomized, placebo-controlled, double-blind, clinical trial", The Journal of Internal Medicine, 2018, vol. 284: pp. 307-317.
Ohlsson, et al., "Mild stimulatory effect of a probiotic mix on bone mass when treatment is initiated 1.5 weeks after ovariectomy in mice", Am J Physiol Endocrinol Metab., Feb. 1, 2021, vol. 320: pp. 591-E597.
Ohlsson, et al., "Probiotics Protect Mice from Ovariectomy-Induced Cortical Bone Loss", PLOS ONE, Mar. 2014, vol. 9, No. 3: pp. 1-8.
Okeke, et al., "The Role of the Gut Microbiome in the Pathogenesis and Treatment of Obesity", GAHMJ, 2014, vol. 3, No. 3: pp. 44-57.
Olar, et al., "Prospects for new antimicrobials based on N,N-dimethylbiguanide complexes as effective agents on both planktonic and adhered strains", Eur J Med Chem, 2010, vol. 45: pp. 2868-2875.
Olson, et al., "Obesity and the tumor microenvironment", Science, 2017, vol. 358, No. 6367: pp. 1130-1131.
Ozaki, et al., "The L-type amino acid transporter LAT1 inhibits osteoclastogenesis and maintains bone homeostasis through the mTORC1 pathway", Science Signaling, Jul. 9, 2019, vol. 12: pp. 1-14.
Ozcan, et al., "A Human Gut Commensal Ferments Cranberry Carbohydrates to Produce Formate", Appl Environ Microbiol, 2017, vol. 83, No. 17, pp. 1-16.
Pacifici, et al., "Bone Remodeling and the Microbiome", Cold Spring Harb Perspect Med, 2018, vol. 8, pp. 1-20.
Pacifici, et al., "T cells: Critical bone regulators in health and disease", Bone, 2010, vol. 47, pp. 461-471.
Palacios, et al., "The effect of a novel probiotic on metabolic biomarkers in adults with prediabetes and recently diagnosed type 2 diabetes mellitus: study protocol for a randomized controlled trial", Trials, 2017, vol. 18, No. 7: pp. 1-8.
Pan, et al., "A single bacterium restores the microbiome dysbiosis to protect bones from destruction in a rat model of rheumatoid arthritis", Microbiome, 2019, vol. 7, No. 107: pp. 1-11.
Pandiyan, et al., "Microbiome Dependent Regulation of Treg and Th17 Cells in Mucosa", Frontiers in Immunology, Mar. 8, 2019, vol. 10, Article 426: pp. 1-17.
Parekh, et al., "The role and influence of gut microbiota in pathogenesis and management of obesity and metabolic syndrome", Front Endocrinol, 2014, vol. 5, No. 47: pp. 1-7.
Patnode, et al., "Interspecies Competition Impacts Targeted Manipulation of Human Gut Bacteria by Fiber-Derived Glycans", Cell, Sep. 19, 2019, vol. 159: pp. 59-73.
PCT/US2019/049823—International Search Report and Written Opinion, daetd Feb. 20, 2020, 12 pages.
PCT/US2019/049823—Invitation to Pay Additional Fees, dated Dec. 10, 2019, 2 pages.
PCT/US2020/038830—International Search Report and Written Opinion, dated Dec. 16, 2020, 23 pages.
PCT/US2020/038830—Invitation to Pay Additional Fees, dated Oct. 29, 2020, 24 pages.
Pearson, et al., "Improved tools for biological sequence comparison", Proc. Natl. Acad. Sci. USA, Apr. 1988, vol. 85: pp. 2444-2448.

(56) References Cited

OTHER PUBLICATIONS

Perry, et al., "Acetate mediates a microbiome-brain-β-cell axis to promote metabolic syndrome", Nature, 2016, vol. 534: pp. 213-217.
Plovier, et al., "A purified membrane protein from *Akkermansia muciniphila* or the pasteurized bacterium improves metabolism in obese and diabetic mice", Nat. Med., 2017, vol. 23, No. 1: pp. 107-113.
Postler, et al., "Understanding the Holobiont: How Microbial Metabolites Affect Human Health and Shape the Immune System", Cell, 2017, vol. 26: pp. 110-130.
Psichas, et al., "The short chain fatty acid propionate stimulates GLP-1 and PYY secretion via free fatty acid receptor 2 in rodents", Int J Obes, 2015, vol. 39: pp. 424-429.
Puertollano, et al., "Biological significance of short-chain fatty acid metabolism by the intestinal microbiome", Curr Opin Clin Nutr Metab Care, 2014, vol. 17, No. 2: pp. 139-144.
Pyra, et al., "Prebiotic Fiber Increases Hepatic Acetyl CoA Carboxylase Phosphorylation and Suppresses Glucose-Dependent Insulinotropic Polypeptide Secretion More Effectively When Used with Metformin in Obese Rats", J Nutr, 2012, vol. 142, No. 2: pp. 213-220.
Qin, et al., "A human gut microbial gene catalogue established by metagenomic sequencing", Nature, 2010, vol. 464; pp. 59-65.
Quach, et al., "Characterizing how probiotic *Lactobacillus reuteri* 6475 and lactobacillic acid mediate suppression of osteoclast differentiation", Bone Reports, 2019, vol. 11, pp. 1-14.
Raisz, et al., "Short-Term Risedronate Treatment in Postmenopausal Women: Effects on Biochemical Markers of Bone Turnover", Osteoporosis International, 2000, vol. 11: pp. 615-620.
Ramirez-Puebla, et al., "Gut and Root Microbiota Commonalities", App Environ Microbiol, 2013, vol. 79, No. 1: pp. 2-9.
Rastall, et al., "Recent developments in prebiotics to selectively impact beneficial microbes and promote intestinal health", Curr Opin Biotechnol, 2015, vol. 32, pp. 42-46.
Rastogi, et al., "Leaf microbiota in an agroecosystem: spatiotemporal variation in bacterial community composition on field-grown lettuce", ISME J, 2012, vol. 6: pp. 1812-1822.
Ravussin, et al., "Responses of Gut Microbiota to Diet Composition and Weight Loss in Lean and Obese Mice", Obesity, 2012, vol. 20, No. 4: pp. 738-747.
Reichardt, et al., "Phylogenetic distribution of three pathways for propionate production within the human gut microbiota", ISME J, 2014, vol. 8: pp. 1323-1335.
Reichold, et al., "*Bifidobacterium adolescentis* protects from the development of nonalcoholic steatohepatitis in a mouse model", J Nutr Biochem, 2014, vol. 25: pp. 118-125.
Rendina, et al., "Dried Plum's Unique Capacity to Reverse Bone Loss and Alter Bone Metabolism in Postmenopausal Osteoporosis Model", PLoS ONE, Mar. 2013, vol. 8, No. 3: pp. 1-10.
Rios-Covain, et al., "Enhanced butyrate formation by cross-feeding between *Faecalibacterium prausnitzii* and *Bifidobacterium adolescentis*", FEMS Microbiol Lett, 2015, vol. 362, No. 21: pp. 1-7.
Rodriguez-R, et al., "The enveomics collection: a toolbox for specialized analyses of microbial genomes and metagenomes", PeerJ Preprints, 2016, vol. 4: e1900v1.
Rosales-Bravo, et al., "Novel consortium of *Klebsiella variicola* and *Lactobacillus* species enhances the functional potential of fermented dairy products by increasing the availability of branched-chain amino acids and the amount of distinctive volatiles." Journal of applied microbiology 123, No. 5 (2017): 1237-1250.
Rosario, et al., "Understanding the Representative Gut Microbiota Dysbiosis in Metformin-Treated Type 2 Diabetes Patients Using Genome-Scale Metabolic Modeling", Front Physiol, 2018, vol. 9: p. 775.
Rosen, et al., "Treatment With Once-Weekly Alendronate 70 mg Compared With Once-Weekly Risedronate 35 mg in Women With Postmenopausal Osteoporosis: A Randomized Double-Blind Study", Journal of Bone and Mineral Research, 2005, vol. 20, No. 1: pp. 141-151.
Rosenbaum, et al., "The gut microbiota in human energy homeostasis and obesity", Trends Endocrinol Metab, 2015, vol. 26, No. 9: pp. 493-501.
Rosenberg, et al., "Interaction between the Microbiome and Diet: The Hologenome Concept", J Nutr Food Sci, 2016, vol. 6, No. 5: p. 1000545.
Rosenblatt, et al., "Is It Ethical to Conduct Placebo-Controlled Clinical Trials in the Development of New Agents for Osteoporosis? An Industry Perspective", Journal of Bone and Mineral Research, 2003, vol. 18, No. 6: pp. 1142-1145.
Rothschild, et al., "Environment dominates over host genetics in shaping human gut microbiota", Nature, 2018: pp. 1-6.
Round, et al., "The gut microbiota shapes intestinal immune responses during health and disease", Nat Rev Immunol, 2009, vol. 9: pp. 313-324.
Saltiel, et al., "Inflammatory mechanisms linking obesity and metabolic disease", J Clin Invest, 2017, vol. 127, No. 1: pp. 1-4.
Saltiel, et al., "New therapeutic approaches for the treatment of obesity", Sci Transl Med, 2016, vol. 8, No. 323: p. 1-12.
Sam, et al., "The Fungal Mycobiome and Its Interaction with Gut Bacteria in the Host", Int J Mol Sci, 2017, vol. 18, No. 330: pp. 1-11.
Samah, et al., "Probiotics for the management of type 2 diabetes mellitus: A systematic review and meta- analysis", Diabetes Res Clin Pract, 2016, vol. 118: pp. 172-182.
Samuel, et al., "A humanized gnotobiotic mouse model of host-archaeal-bacteria mutualism", PNAS, 2006, vol. 103, No. 26: pp. 10011-10016.
Samuel, et al., "Effects of the gut microbiota on host adiposity are modulated by the short-chain fatty-acid binding G protein-coupled receptor, Gpr41", PNAS, 2008, vol. 105, No. 43: pp. 16767-16772.
Santos-Marcos, et al., "Influence of gender and menopausal status on gut microbiota", Maturitas, Oct. 2018, vol. 116: pp. 43-53.
Sarioglu, et al., "Comparison of the effects of alendronate and risedronate on bone mineral density and bone turnover markers in postmenopausal osteoporosis", Rheumatol Int, 2006, vol. 26: pp. 195-200.
Sawin, et al., "Glycomacropeptide is a prebiotic that reduces *Desulfovibrio* bacteria, increases cecal short-chain fatty acids, and is anti-inflammatory in mice", Am J Physiol Gastrointest Liver Physiol, 2015, vol. 309: G590-G601.
Schirmer, et al., "Linking the Human Gut Microbiome to Inflammatory Cytokine Production Capacity", Cell, 2016, vol. 167, No. 4: pp. 1125-1136.
Schoch, C.L. et al., "Nuclear ribosomal internal transcribed spacer (ITS) region as a universal DNA barcode marker for *Fungi*," Proceedings of the National Academy of Sciences, 2012, vol. 109, No. 16, pp. 6241-6246.
Schroeder, et al., "Bifidobacteria or Fiber Protects against Diet-Induced Microbiota-Mediated Colonic Mucus Deterioration", Cell Host & Microbe, 2018, vol. 23: pp. 27-40.
Schroeder, et al., "Signals from the gut microbiota to distant organs in physiology and disease", Nat Med, 2016, vol. 22, No. 10: pp. 1079-1089.
Schwarzer, et al., "*Lactobacillus plantarum* strain maintains growth of infant mice during chronic undernutrition", Science, Feb. 19, 2016, vol. 351, No. 6275: pp. 854-857.
Scott, et al., "Manipulating the gut microbiota to maintain health and treat disease", Micro Ecol Health Dis, 2015, vol. 26, No. 25877: pp. 1-10.
Seeman, et al., "Age- and Menopause-Related Bone Loss Compromise Cortical and Trabecular Microstructure", J Gerontol A Biol Sci Med Sci, Oct. 2013, vol. 10: pp. 1218-1225.
Serino, et al., "Metabolic adaptation to a high-fat diet is associated with a change in the gut microbiota", Gut, 2012, vol. 61: pp. 543-553.
Shajib, et al., "Diverse Effects of Gut-Derived Serotonin in Intestinal Inflammation", ACS Chemical Neuroscience, May 2017, vol. 8: pp. 920-931.
Sheikhi, et al., "Probiotic Yogurt Culture *Bifidobacterium animalis* Subsp Lactis BB-12 and Lactobacillus Acidophilus LA-5 Modulate the Cytokine Secretion by Peripheral Blood Mononuclear Cells from Patients with Ulcerative Colitis", Drug Res, 2016, vol. 66: pp. 300-305.

(56) References Cited

OTHER PUBLICATIONS

Sheth, et al., "Spatial metagenomic characterization of microbial biogeography in the gut", Nature Biotechnology, Aug. 2019, vol. 37, pp. 877-883.
Shin, et al., "An increase in the *Akkermansia* spp population induced by metformin treatment improves glucose homeostasis in diet-induced obese mice", Gut, 2014, vol. 63: pp. 727-735.
Shoaie, et al., "Quantifying Diet-Induced Metabolic Changes of the Human Gut Microbiome", Cell Metab, 2015, vol. 22: pp. 320-331.
Simpson, et al., "Review article: dietary fibre-microbiota interactions", Aliment Pharmacol Ther, 2015, vol. 42: pp. 158-179.
Singer, et al., "The initiation of metabolic inflammation in childhood obesity", J Clin Invest, 2017, vol. 127, No. 1: pp. 65-73.
Singh, et al., "Dysregulated Microbial Fermentation of Soluble Fiber Induces Cholestatic Liver Cancer", Cell, 2018, vol. 175: pp. 679-694.
Sjogren, et al., "The Gut Microbiota Regulates Bone Mass in Mice", Journal of Bone and Mineral Research, Jun. 2012, vol. 27, No. 6: pp. 1357-1367.
Slavin, et al., "Fiber and Prebiotics: Mechanisms and Health Benefits", Nutrients, 2013, vol. 5: pp. 1417-1435.
Smith, et al., "Comparison of Biosequences", Advances in Applied Mathematics 2, 1981: pp. 482-489.
Smith, et al., "Yeast Modulation of Human Dendritic Cell Cytokine Secretion: An In Vitro Study", PLoS ONE, 2014, vol. 9, No. 5: pp. 1-14.
Solarea Bio, "Managing inflammatory diseases and aging with edible plant microbes", www.nature.com/biopharmdeal, Dec. 2022: pp. B2-B3.
Solarea Bio, Inc., "Food Trial Evaluating the Efficacy of SBD111 Versus Placebo for the Clinical Dietary Management of the Metabolic Processes of Osteopenia", NIH U.S. National Library of Medicine, Last updated Jan. 28, 2022: pp. 1-6. <https://beta.clinicaltrials.gov/study/NCT05009875>.
Sonnenburg, et al., "Diet-microbiota interactions as moderators of human metabolism", Nature, 2016, vol. 535: pp. 56-64.
Strorelli, et al., "Metformin, Microbes, and Aging", Cell Metab, 2013, vol. 17: pp. 809-811.
Stuible, et al., "Mechanism and Function of Monoclonal Antibodies Targeting Siglec-15 for Therapeutic Inhibition of Osteoclastic Bone Resorption*", The Journal of Biological Chemistry, vol. 289, No. 10: pp. 6498-6512.
Stull, et al., "Bioactives in Blueberries Improve Insulin Sensitivity in Obese, Insulin-Resistant Men and Women", J Nutr, 2010, vol. 140, No. 10: pp. 1764-1768.
Stull, et al., "Blueberries' Impact on Insulin Resistance and Glucose Intolerance", Antioxidants, 2016, vol. 5, No. 44: pp. 1-11.
Suez, et al., "Post-Antibiotic Gut Mucosal Microbiome Reconstitution Is Impaired by Probiotics and Improved by Autologous FMT", Cell, 2018, vol. 174: pp. 1406-1423.
Sun, et al., "Gut mirobiota and intestinal FXR mediate the clinical benefits of metformin", Nat Med, 2018, vol. 24: pp. 1919-1929.
Suzek, et al., "UniRef clusters: a comprehensive and scalable alternative for improving sequence similarity searches", Bioinformatics, 2015, vol. 31, No. 6: pp. 926-932.
Sweeney, et al., "Metabolic surgery: action via hormonal milieu changes, changes in bile acids or gut microbiota? A summary of the literature", Best Pract Res Clin Gastroenterol, 2014, vol. 28: pp. 727-740.
Takimoto, et al., "Effect of *Bacillus subtilis* C-3102 on bone mineral density in healthy postmenopausal Japanese women: a randomized, placebo-controlled, double-blind clinical trial", Bioscience of Microbiota, Food and Health, 2018, vol. 37, No. 4: pp. 87-96.
Tan, et al., "The Role of Short-Chain Fatty Acids in Health and Disease", Advances in Immunology, 2014, vol. 121: pp. 91-119.
Terrapon, et al., "How do gut microbes break down dietary fiber?", Trends Biochem Sci, 2014, vol. 39, No. 4: pp. 156-158.
Tilg, et al., "The intestinal microbiota fuelling metabolic inflammation", Nature Reviews, Aug. 6, 2019: pp. 1-15.
Tohidi, et al., "Omentin-1, visfatin and adiponectin levels in relation to bone mineral density in Iranian postmenopausal women", Bone, 2012, vol. 51: pp. 876-881.
Tolhurst, et al., "Short-Chain Fatty Acids Stimulate Glucagon-Like Peptide-1 Secretion via the G-Protein-Coupled Receptor FFAR2", Diabetes, 2012, vol. 61: pp. 364-371.
Truong, et al., "MetaPhlAn2 for enhanced metagenomic taxonomic profiling", Nature Methods, Oct. 2015, vol. 12, No. 10: pp. 902-904.
Tuohy, et al., "Up-regulating the Human Intestinal Microbiome Using Whole Plant Foods, Polyphenols, and/or Fiber", J Agric Food Chem, 2012, vol. 60: pp. 8776-8782.
Turnbaugh, et al., "A core gut microbiome in obese and lean twins", Nature, 2009, vol. 457, No. 7228: pp. 480-484.
Turnbaugh, et al., "An obesity-associated gut microbiome with increased capacity for energy harvest", Nature, 2006, vol. 444: pp. 1027-1031.
Turnbaugh, et al., "Diet-Induced Obesity is Linked to Marked but Reversible Alterations in the Mouse Distal Gut Microbiome", Cell Host Microbe, 2008, vol. 3: pp. 213-223.
Turnbaugh, et al., "Supplementary Materials for : The Effect of Diet on the Human Gut Microbiome: A Metagenomic Analysis in Humanized Gnotobiotic Mice", Sci Transi Med, 2009: pp. 1-23.
Turnbaugh, et al., "The Effect of Diet on the Human Gut Microbiome: A Metagenomic Analysis in Humanized Gnotobiotic Mice", Sci Transl Med, 2009: pp. 1-23.
Tyagi, et al., "The Microbial Metabolite Butyrate Stimulates Bone Formation via T Regulatory Cell-Mediated Regulation of WNT10B Expression", Immunity, 2018, vol. 49: pp. 1116-1131.
U.S. Appl. No. 16/235,858—Notice of Allowance, dated Jan. 23, 2020.
U.S. Appl. No. 16/235,858—Office Action, dated Aug. 6, 2019.
U.S. Appl. No. 16/694,876—Office Action, dated Dec. 8, 2021, 41 pages.
U.S. Appl. No. 16/694,876—Office Action, dated Nov. 5, 2020, 34 pages.
U.S. Appl. No. 16/694,876—Office Action,m dated Jul. 20, 2022, 26 pages.
Van Der Beek, et al., "Streptococcal dTDP-L-rhamnose biosynthesis enzymes: functional characterization and lead compound identification", Molecular Microbiology, Jan. 1, 2019, vol. 111, No. 4: pp. 1-32.
Van Hul, et al., "Reduced obesity, diabetes and steatosis upon cinnamon and grape pomace are associated with changes in gut microbiota and markers of gut barrier", Am J Physiol Endocrinol Metab, 2017, vol. 314, No. 4: E3340E352.G.
Van Wyk, et al., "Current perspectives on the families of glycoside hydrolases of *Mycobacterium tuberculosis*: their importance and prospects for assigning function to unknowns", Glycobiology, 2017, vol. 27, No. 2: pp. 112-122.
Vatanen, et al., "Variation in Microbiome LPS Immunogenicity Contributes to Autoimmunity in Humans", Cell, 2016, vol. 165: pp. 842-853.
Verma, et al. "Cell surface polysaccharides of *Bifidobacterium bifidum* induce the generation of Foxp3+ regulatory T cells", Sci Immunol. 3, Oct. 19, 2018: pp. 1-14.
Vital, et al., "A gene-targeted approach to investigate the intestinal butyrate-producing bacterial community", Microbiome, 2013, vol. 1, No. 8: pp. 1-14.
Vogt, et al., "L-Rhamnose increases serum propionate in humans1-3", Am J Clin Nutr, 2004, vol. 80: pp. 89-94.
Voreades, et al., "Diet and the development of the human intestinal microbiome", Front Microbiol, 2014, vol. 5, No. 494: 1-9.
Vorholt, et al., "Microbial life in the phyllosphere", Institute of Microbiology, Dec. 2012, vol. 10: pp. 828-840.
Wagner, et al., "Pyruvate fermentation by Oenococcus oeni and Leuconostoc mesenteroides and role of pyruvate dehydrogenase in anaerobic fermentation." Applied and environmental microbiology 71, No. 9 (2005): 4966-4971.
Wagner, et al., "The Pentose Phosphate Pathway in Regenerating Skeletal Muscle", Biochem. 1978, vol. 170: pp. 17-22.
Wahlstrom, et al., "Intestinal Crosstalk between Bile Acids and Microbiota and Its Impact on Host Metabolism", Cell Metab, 2016, vol. 24: pp. 41-50.

(56) References Cited

OTHER PUBLICATIONS

Wallace, et al., "Use and Abuse of HOMA Modeling", Diabetes Care, 2004, vol. 27, No. 6: pp. 1487-1495.
Wang, et al., "Modulation of gut microbiota during probiotic-mediated attenuation of metabolic syndrome in high fat diet-fed mice", ISME J, 2015, vol. 9: pp. 1-15.
Wasserman, et al., "An Apple a Day: Which Bacteria Do We Eat With Organic and Conventional Apples", Frontiers in Microbiology, Jul. 24, 2019, vol. 10, Article 1629: pp. 1-13.
Wassermann, et al., "Harnessing the microbiomes of *Brassica* vegetables for health issues", Sci Rep, 2017, vol. 7: p. 17649.
Weitkunat, et al., "Short-chain fatty acids and inulin, but not guar gum, prevent diet-induced obesity and insulin resistance through differential mechanisms in mice", Sci Rep, 2017, vol. 7, No. 6109: pp. 1-13.
Weitzmann, et al., "Estrogen deficiency and bone loss: an inflammatory tale", The Journal of Clinical Investigation, May 2006, vol. 116, No. 5: pp. 1186-1194.
Welch, et al., "The Effects of Flavonoids on Bone", Curr Osteoporos Rep., 2014, vol. 12: pp. 205-210.
Whisner, et al., "Prebiotics, Bone and Mineral Metabolism", Calcif Tissue Int, 2018, vol. 102: pp. 443-479.
White, et al., "A Brief History of the Development of Diabetes Medications", Diabetes Spectr, 2015, vol. 27, No. 2: pp. 82-86.
Wikipedia, https://en.wikipedia.org/wiki/Pyruvate_dehydrogenase_complex, accessed Dec. 3, 2021.
Williams, et al., "Ethanol and volatile fatty acid production from lignocellulose by Clostridium cellulolyticum." *International Scholarly Research Notices* 2013, pp. 1-7.
Winer, et al., "The Intestinal Immune System in Obesity and Insulin Resistance", Cell Metab, 2016, vol. 23: pp. 413-426.
Winer, et al., "Immunologic impact of the intestine in metabolic disease", J Clin Invest, 2017, vol. 127, No. 1: pp. 33-42.
Wolfert, et al., "Adaptive immune activation: glycosylation does matter", Nat Chem Biol, Dec. 2013, vol. 9, No. 12: pp. 776-784.
Woo, et al., "Metformin Ameliorates Hepatic Steatosis and Inflammation without Altering Adipose Phenotype in Diet-Induced Obesity", PLoS ONE, 2014, vol. 9, No. 3: e91111.
Wu, et al., "Arginine metabolism and nutrition in growth, health and disease", Amino Acids, May 2009, vol. 31, No. 1: pp. 153-168.
Wu, et al., "Metformin alters the gut microbiome of individuals with treatment-naïve type 2 diabetes, contributing to the therapeutic effects of the drug", Nat Med, 2017, vol. 23, No. 7: pp. 850-858.
Wu, et al., "Supplement: Metformin alters the gut microbiome of individuals with treatment-naïve type 2 diabetes, contributing to the therapeutic effects of the drug", Nat Med, 2017, vol. 23, No. 7.
Xu, et al., "Intestinal microbiota: a potential target for the treatment of postmenopausal osteoporosis", Bone Research, 2017, vol. 5: pp. 1-18.
Xu, et al., "Paenibacillus panacisoli enhances growth of *Lactobacillus* spp. by producing xylooligosaccharides in corn stover ensilages." Carbohydrate polymers 184 (2018): 435-444.
Yan, et al., "Gut microbiota induce IGF-1 and promote bone formation and growth", PNAS, Nov. 7, 2016: pp. 1-10.
Yang et al., "The prospects of Jerusalem artichoke in functional food ingredients and bioenergy production," Biotechnology Reports 5: 77-88 (2015).
Yang, et al., "Potent Anti-Inflammatory and Antiadipogenic Properties of Bamboo (*Sasa coreana* Nakai) Leaves Extract and Its Major Constituent Flavonoids", J Agric Food Chem, 2017, vol. 65: pp. 6665-6673.
Yassour, et al., "Natural history of the infant gut microbiome and impact of antibiotic treatment on bacterial strain diversity and stability", Sci Transl Med, 2016, vol. 8, No. 343: pp. 1-12.
Yousef, et al., "Metformin: A Unique Herbal Origin Medication", GJMR-B: Pharma, Drug Discovery, Toxicology, and Medicine, 2017, vol. 17, No. 3: pp. 31-37.
Zaiss, et al., "Increased Bone Density and Resistance to Ovariectomy-Induced Bone Loss in FoxP3-Transgenic Mice Based on Impaired Osteoclast Differentiation", Arthritis & Rheumatism, Aug. 2010, vol. 62, No. 8: pp. 2328-2338.
Zaiss, et al., "Treg Cells Suppress Osteoclast Formation", Arthritis & Rheumatism, Dec. 2017, vol. 56, No. 12: pp. 4104-4112.
Zhang, et al., "Effect of probiotics on glucose metabolism in patients with type 2 diabetes mellitus: a meta-analysis of randomized controlled trials", Medicina, 2016, vol. 52: pp. 28-34.
Zhang, et al., "Effects of Acarbose on the Gut Microbiota of Prediabetic Patients: A Randomized, Double-blind, Controlled Crossover Trial", 2017, vol. 8: pp. 293-307.
Zhang, et al., "Human gut microbiota in obesity and after gastric bypass", PNAS, 2009, vol. 106, No. 7: pp. 2365-2370.
Zhang, et al., "Modulation of gut microbiota by berberine and metformin during the treatment of high-fat diet- induced obesity in rats", Sci Rep, 2015, vol. 5, No. 14405: pp. 1-10.
Zhang, et al., "Structural Changes of Gut Microbiota during Berberine-Mediated Prevention of Obesity and Insulin Resistance in High-Fat Diet-Fed Rats", PLoS ONE, 2012, vol. 7, No. 8: e42529.
Zhao, et al., "Gut bacteria selectively promoted by dietary fibers alleviate type 2 diabetes", Science, 2018, vol. 359: pp. 1151-1156.
Zheng, et al., "Prebiotic mannan-oligosaccharides augment the hypoglycemic effects of metformin in correlation with modulating gut microbiota", J Agric Food Chem, 2018, vol. 66, No. 23: pp. 5821-5831.
Zhou, et al., "Age-dependent variations of cancellous bone in response to ovariectomy in C57BL/6J mice", Experimental and Therapeutic Medicine, 2018, vol. 15: pp. 3623-3632.
Zmora, et al., "Personalized Gut Mucosal Colonization Resistance to Empiric Probiotics Is Associated with Unique Host and Microbiome Features", Cell, 2018, vol. 174: pp. 1388-1405.

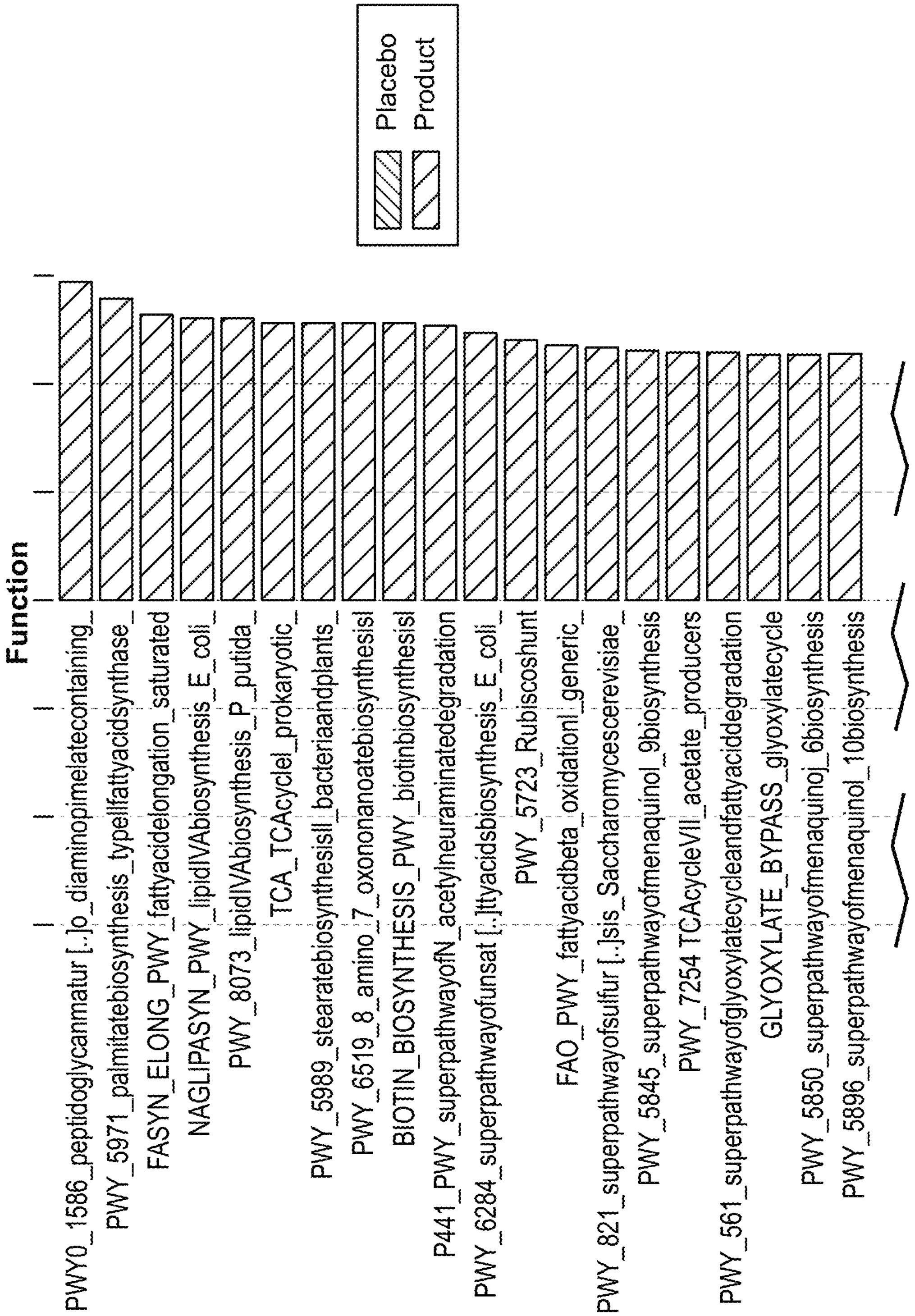
FIG. 7B (Cont. 1)

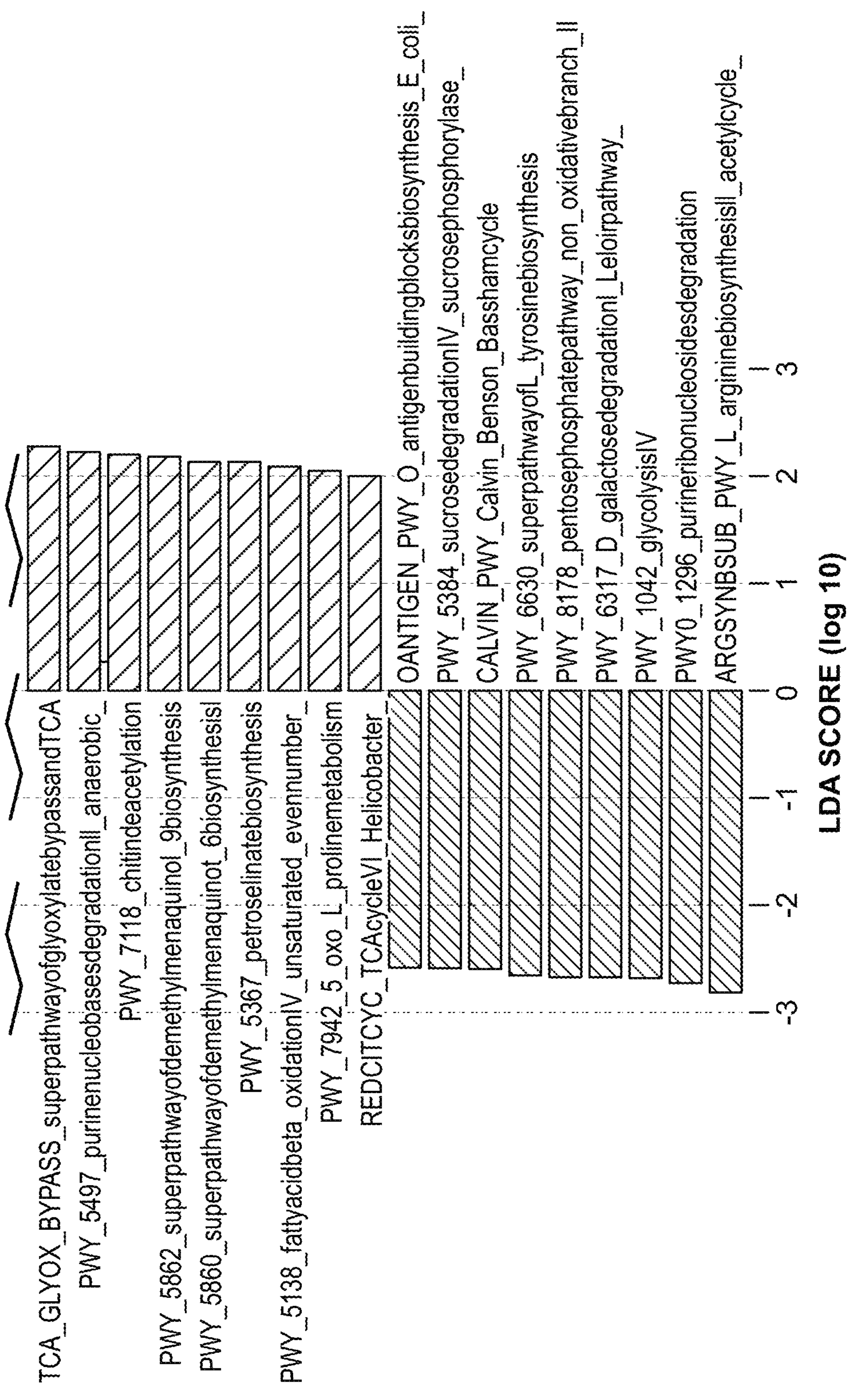
FIG. 7B (Cont. 2)

SEQUENCE LISTING

```
Sequence total quantity: 102
SEQ ID NO: 1            moltype = DNA  length = 1490
FEATURE                 Location/Qualifiers
source                  1..1490
                        mol_type = genomic DNA
                        organism = Pseudomonas fluorescens
SEQUENCE: 1
agtcagacat gcaagtcgag cggtagagag aagcttgctt ctcttgagag cggcggacgg  60
gtgagtaaag cctaggaatc tgcctggtag tgggggataa cgttcggaaa cggacgctaa  120
taccgcatac gtcctacggg agaaagcagg ggaccttcgg gccttgcgct atcagatgag  180
cctaggtcgg attagctagt tggtgaggta atggctcacc aaggcgacga tccgtaactg  240
gtctgagagg atgatcagtc acactggaac tgagacacgg tccagactcc tacgggaggc  300
agcagtgggg aatattggac aatgggcgaa agcctgatcc agccatgccg cgtgtgtgaa  360
gaaggtcttc ggattgtaaa gcactttaag ttgggaggaa gggcattaac ctaatacgtt  420
agtgttttga cgttaccgac agaataagca ccggctaact ctgtgccagc agccgcggta  480
atacagaggg tgcaagcgtt aatcggaatt actgggcgta aagcgcgcgt aggtggtttg  540
ttaagttgga tgtgaaatcc ccgggctcaa cctgggaact gcattcaaaa ctgactgact  600
agagtatggt agagggtggt ggaatttcct gtgtagcggt gaaatgcgta gatataggaa  660
ggaacaccag tggcgaaggc gaccacctgg actaatactg acactgaggt gcgaaagcgt  720
ggggagcaaa caggattaga taccctggta gtccacgccg taaacgatgt caactagccg  780
ttgggagcct tgagctctta gtggcgcagc taacgcatta agttgaccgc ctggggagta  840
cggccgcaag gttaaaactc aaatgaattg acgggggccc gcacaagcgg tggagcatgt  900
ggtttaattc gaagcaacgc gaagaacctt accaggcctt gacatccaat gaactttcta  960
gagatagatt ggtgccttcg ggaacattga gacaggtgct gcatggctgt cgtcagctcg  1020
tgtcgtgaga tgttgggtta agtcccgtaa cgagcgcaac ccttgtcctt agttaccagc  1080
acgtaatggt gggcactcta aggagactgc cggtgacaaa ccggaggaag gtggggatga  1140
cgtcaagtca tcatggccct tacggcctgg gctacacacg tgctacaatg gtcggtacag  1200
agggttgcca agccgcgagg tggagctaat cccataaaac cgatcgtagt ccggatcgca  1260
gtctgcaact cgactgcgtg aagtcggaat cgctagtaat cgcgaatcag aatgtcgcgg  1320
tgaatacgtt cccgggcctt gtacacaccg cccgtcacac catgggagtg ggttgcacca  1380
gaagtagcta gtctaacctt cgggaggacg gttaccacgg tgtgattcat gactggggtg  1440
aagtcgtaac aaggtagccg taggggaacc tgcggctgga tcacctcctt             1490

SEQ ID NO: 2            moltype = DNA  length = 1017
FEATURE                 Location/Qualifiers
source                  1..1017
                        mol_type = genomic DNA
                        organism = Hanseniaspora occidentalis
SEQUENCE: 2
ttgttgctcg agttcttgtt tagatctttt acaataatgt gtatctttaa tgaagatgng  60
ngcttaattg cgctgcttta ttagagtgtc gcagtagaag tagtcttgct tgaatctcag  120
tcaacgttta cacacattgg agttttttta ctttaattta attctttctg ctttgaatcg  180
aaaggttcaa ggcaaaaaac aaacacaaac aattttattt tattataatt ttttaaacta  240
aaccaaaatt cctaacggaa attttaaaat aatttaaaac tttcaacaac ggatctcttg  300
gttctcgcat cgatgaaaaa cgtaccgaat tgcgataagt aatgtgaatt gcaaatactc  360
```

```
gtgaatcatt gaatttttga acgcacattg cgcccttgag cattctcaag ggcatgcctg  420
tttgagcgtc atttccttct caaaaaataa ttttttattt tttggttgtg ggcgatactc  480
agggttagct tgaaattgga gactgtttca gtctttttta attcaacact tancttcttt  540
ggagacgctg ttctcgctgt gatgtattta tggatttatt cgttttactt tacaagggaa  600
atggtaatgt accttaggca aagggttgct tttaatattc atcaagtttg acctcaaatc  660
aggtaggatt acccgctgaa cttaagcata tcaataagcg gaggaaaaga aaccaactgg  720
gattacctta gtaacggcga gtgaagcggt aaaagctcaa atttgaaatc tggtactttc  780
agtgcccgag ttgtaatttg tagaatttgt ctttgattag gtccttgtct atgttccttg  840
gaacaggacg tcatagaggg tgagantccc gtttgnngag gataccttt ctctgtanna  900
ctttttcnaa gagtcgagtt gnttgggaat gcagctcaaa nngggtngna aattccatct  960
aaagctaaat attngncnag agaccganag cgacantaca gngatggaaa gangaaa     1017

SEQ ID NO: 3           moltype = DNA  length = 1548
FEATURE                Location/Qualifiers
source                 1..1548
                       mol_type = genomic DNA
                       organism = Leuconostoc mesenteroides
SEQUENCE: 3
attgagagtt tgatcctggc tcaggatgaa cgctggcggc gtgcctaata catgcaagtc  60
gaacgcacag cgaaaggtgc ttgcaccttt caagtgagtg gcgaacgggt gagtaacacg  120
tggacaacct gcctcaaggc tggggataac atttggaaac agatgctaat accgaataaa  180
actcagtgtc gcatgacaca aagttaaaag gcgctttggc gtcacctaga gatggatccg  240
cggtgcatta gttagttggt ggggtaaagg cctaccaaga caatgatgca tagccgagtt  300
gagagactga tcggccacat tggactgag acacggccca aactcctacg ggaggctgca  360
gtagggaatc ttccacaatg ggcgaaagcc tgatggagca acgccgcgtg tgtgatgaag  420
gctttcgggt cgtaaagcac tgttgtacgg gaagaacagc tagaataggg aatgatttta  480
gtttgacggt accataccag aaagggacgg ctaaatacgt gccagcagcc gcggtaatac  540
gtatgtcccg agcgttatcc ggatttattg ggcgtaaagc gagcgcagac ggttgattaa  600
gtctgatgtg aaagcccgga gctcaactcc ggaatggcat tggaaactgg ttaacttgag  660
tgcagtagag gtaagtggaa ctccatgtgt agcggtggaa tgcgtagata tatggaagaa  720
caccagtggc gaaggcggct tactggactg taactgacgt tgaggctcga aagtgtgggt  780
agcaaacagg attagatacc ctggtagtcc acaccgtaaa cgatgaacac taggtgttag  840
gaggtttccg cctcttagtg ccgaagctaa cgcattaagt gttccgcctg gggagtacga  900
ccgcaaggtt gaaactcaaa ggaattgacg gggacccgca caagcggtgg agcatgtggt  960
ttaattcgaa gcaacgcgaa gaaccttacc aggtcttgac atcctttgaa gcttttagag  1020
atagaagtgt tctcttcgga gacaaagtga caggtggtgc atggtcgtcg tcagctcgtg  1080
tcgtgagatg ttgggttaag tcccgcaacg agcgcaaccc ttattgttag ttgccagcat  1140
tcagatgggc actctagcga gactgccggt gacaaaccgg aggaaggcgg ggacgacgtc  1200
agatcatcat gccccttatg acctgggcta cacacgtgct acaatggcgt atacaacgag  1260
ttgccaaccc gcgagggtga gctaatctct taaagtacgt ctcagttcgg attgtagtct  1320
gcaactcgac tacatgaagt cggaatcgct agtaatcgcg gatcagcacg ccgcggtgaa  1380
tacgttcccg ggtcttgtac acaccgcccg tcacaccatg ggagtttgta atgcccaaag  1440
ccggtggcct aacctttag gaaggagccg tctaaggcag gacagatgac tggggtgaag  1500
tcgtaacaag gtagccgtag gagaacctgc ggctggatca cctccttt         1548

SEQ ID NO: 4           moltype = DNA  length = 916
FEATURE                Location/Qualifiers
source                 1..916
                       mol_type = genomic DNA
                       organism = Aureobasidium pullulans
SEQUENCE: 4
ctttgttgtt aaaactacct tgttgctttg gcgggaccgc tcggtctcga gccgctgggg  60
attcgtccca ggcgagcgcc cgccagagtt aaaccaaact cttgttattt aaccggtcgt  120
ctgagttaaa attttgaata aatcaaaact ttcaacaacg gatctcttgg ttctcgcatc  180
gatgaagaac gcagcgaaat gcgataagta atgtgaattg cagaattcag tgaatcatcg  240
aatctttgaa cgcacattgc gccccttggt attccgaggg gcatgcctgt tcgagcgtca  300
ttacaccact caagctatgc ttggtattgg gcgtcgtcct tagttgggcg cgccttaaag  360
acctcggcga ggccactccg gctttaggcg tagtagaatt tattcgaacg tctgtcaaag  420
gagaggaact ctgccgactg aaacctttat ttttctaggt tgacctcgga tcaggtaggg  480
atacccgctg aacttaagca tatcaataag cggaggaaaa gaaaccaaca gggattgccc  540
tagtaacggc gagtgaagcg gcaacagctc aaatttgaaa gctagccttc gggttcgcat  600
tgtaatttgt agaggatgat ttggggaagc cgcctgtcta agttccttgg aacaggacgt  660
catagagggt gagaatcccg tatgtgacag gaaatggcac cctatgtaaa tctccttcga  720
cgagtcgagt tgtttgggaa tgcagctcta aatgggaggt aaatttcttc taaagctaaa  780
tattggcgag agaccgatag cgcacaagta gagtgatcga aagatgaaaa gcactttgga  840
aagagagtta aaaagcacgt gaaattgttg aaagggaagc gcttgcaatc agacttgttt  900
aaactgttcg gccggt                                           916

SEQ ID NO: 5           moltype = DNA  length = 1042
FEATURE                Location/Qualifiers
source                 1..1042
                       mol_type = genomic DNA
                       organism = Debaromyces hansenii
SEQUENCE: 5
gcgcttattg cgcggcgaaa aaaccttaca cacagtgttt tttgttatta cannaacttt  60
tgctttggtc tggactagaa atagtttggg ccagaggtta ctaaactaaa cttcaatatt  120
tatattgaat tgttatttat ttaattgtca atttgttgat taaattcaaa aaatcttcaa  180
aactttcaac aacggatctc ttggttctcg catcgatgaa gaacgcagcg aaatgcgata  240
agtaatatga attgcagatt ttcgtgaatc atcgaatctt tgaacgcaca ttgcgccctc  300
```

```
tggtattcca gagggcatgc ctgtttgagc gtcatttctc tctcaaacct tcgggtttgg  360
tattgagtga tactcttagt cgaactaggc gtttgcttga aatgtattgg catgagtggt  420
actggatagt gctatatgac tttcaatgta ttaggtttat ccaactcgtt gaatagttta  480
atggtatatt tctcggtatt ctaggctcgg ccttacaata taacaaacaa gtttgacctc  540
aaatcaggta ggattacccg ctgaacttaa gcatatcaat aagcggagga aaagaaacca  600
acagggattg ccttagtaac ggcgagtgaa gcggcaaaag ctcaaatttg aaatctggca  660
ccttcggtgt ccgagttgta atttgaagaa ggtaactttg gagttggctc ttgtctatgt  720
tccttggaac aggacgtcac agagggtgag aatcccgtgc gatgagatgc ccaattctat  780
gtaaagtgct ttcgaagagt cgagttgttt gggaatgcag ctctaagtgg gtggtaaatt  840
ccatctaaag ctaaatattg gcgagagacc gatagcgaac aagtacagtg atggaaagat  900
gaaaagaact ttgaaaagag agtgaaaaag tacgtgaaat tgttgaaagg gaaagggctt  960
gagatcagac ttggtatttt gcgatccttt ccttcttggt tgggttcctc gcagcttact  1020
gggncagcat cggtttggat gg                                          1042

SEQ ID NO: 6            moltype = DNA  length = 1165
FEATURE                 Location/Qualifiers
source                  1..1165
                        mol_type = genomic DNA
                        organism = Bacillus wiedmannii
SEQUENCE: 6
gaaaggcggc ttcggctgtc acttatggat ggacccgcgt cgcattagct agttggtgag  60
gtaacggctc accaaggcaa cgatgcgtag ccgacctgag agggtgatcg gccacactgg  120
gactgagaca cggcccagac tcctacggga ggcagcagta gggaatcttc cgcaatggac  180
gaaagtctga cggagcaacg ccgcgtgagt gatgaaggct ttcgggtcgt aaaactctgt  240
tgttagggaa gaacaagtgc tagttgaata agctgcacct tgacggtacc taaccagaaa  300
gccacggcta actacgtgcc agcagccgcg gtaatacgta ggtggcaagc gttatccgga  360
attattgggc gtaaagcgcg cgcaggtggt ttcttaagtc tgatgtgaaa gcccacggct  420
caaccgtgga gggtcattgg aaactgggag acttgagtgc agaagaggaa agtggaattc  480
catgtgtagc ggtgaaatgc gtagagatat ggaggaacac cagtggcgaa ggcgactttc  540
tggtctgtaa ctgacactga ggcgcgaaag cgtggggagc aaacaggatt agataccctg  600
gtagtccacg ccgtaaacga tgagtgctaa gtgttagagg gtttccgccc tttagtgctg  660
aagttaacgc attaagcact ccgcctgggg agtacggccg caaggctgaa actcaaagga  720
attgacgggg gcccgcacaa gcggtggagc atgtggttta attcgaagca acgcgaagaa  780
ccttaccagg tcttgacatc ctctgaaaac cctagagata gggcttctcc ttcgggagca  840
gagtgacagg tggtgcatgg ttgtcgtcag ctcgtgtcgt gagatgttgg gttaagtccc  900
gcaacgagcg caacccttga tcttagttgc catcattaag ttgggcactc taaggtgact  960
gccggtgaca aaccggagga aggtggggat gacgtcaaat catcatgccc cttatgacct  1020
gggctacaca cgtgctacaa tggacggtac aaagagctgc aagaccgcga ggtggagcta  1080
atctcataaa accgttctca gttcggattg taggctgcaa ctcgcctaca tgaagctgga  1140
atcgctagta atcgcggatc agcat                                       1165

SEQ ID NO: 7            moltype = DNA  length = 871
FEATURE                 Location/Qualifiers
source                  1..871
                        mol_type = genomic DNA
                        organism = Pichia fermentans
SEQUENCE: 7
ccacnctgcg tgggcgacac gaaacaccga aaccgaacgc acgccgtcaa gcaagaaatc  60
cacaaaactt tcaacaacgg atctcttggt tctcgcatcg atgaagagcg cagcgaaatg  120
cgatacctag tgtgaattgc agccatcgtg aatcatcgag ttcttgaacg cacattgcgc  180
ccgctggtat tccggcgggc atgcctgtct gagcgtcgtt tccttcttgg agcggagctt  240
cagacctggc gggctgtctt tcgggacggc gcgcccaaag cgaggggcct tctgcgcgaa  300
ctagactgtg cgcgcggggc ggccggcgaa cttataccaa gctcgacctc agatcaggca  360
ggagtacccg ctgaacttaa gcatatcaat aagcggagga aaagaaacca acagggattg  420
ccccagtagc ggcgagtgaa gcggcaaaag ctcagatttg gaatcgcttc ggcgagttgt  480
gaattgcagg ttggcgcctc tgcggcggcg gcggtccaag tcccttggaa cagggcgcca  540
ttgagggtga gagccccgtg ggaccgtttg cctatgctct gaggcccttc tgacgagtcg  600
agttgtttgg gaatgcagct ctaagcgggt ggtaaattcc atctaaggct aaatactggc  660
gagagaccga tagcgaacaa gtactgtgaa ggaaagatga aaagcacttt gaaaagagag  720
tgaaacagca cgtgaaattg ttgaaaggga agggtattgc gcccgacatg gagcgtgcgc  780
accgctgccc ctcgtgggcg gcgctctggg cgtgctctgg gccagcatcg gtttttgccg  840
cgggagaagg gcggcgggca tgtagctctt c                                871

SEQ ID NO: 8            moltype = DNA  length = 942
FEATURE                 Location/Qualifiers
source                  1..942
                        mol_type = genomic DNA
                        organism = Hanseniaspora opuntiae
SEQUENCE: 8
gttgctcgag ttcttgttta gatcttttac nataatgtgt atctttaatg aagatgtgcg  60
cttaattgcg ctgctttatt agagtgtcgc agtagaagta gtcttgcttg aatctcagtc  120
aacgtttaca cacattggag ttttttttact ttaatttaat tctttctgct ttgaatcgaa  180
aggttcaagg caaaaaacaa acacaaacaa ttttatttta ttataatttt ttaaactaaa  240
ccaaaattcc taacggaaat tttaaaataa tttaaaactt tcaacaacgg atctcttggt  300
tctcgcatcg atgaaaaacg tagcgaattg cgataagtaa tgtgaattgc aaatactcgt  360
gaatcattga atttttgaac gcacattgcg cccttgagca ttctcaaggg catgcctgtt  420
tgagcgtcat ttccttctca aaagataatt ttttattttt tggttgtggg cgatactcag  480
ggttagcttg aaattggaga ctgtttcagt ctttttaat tcaacactta ncttctttgg  540
agacgctgtt ctcgctgtga tgtatttatg gatttattcg ttttacttta caagggaaat  600
```

```
ggtaatgtac cttaggcaaa gggttgcttt taatattcat caagtttgac ctcaaatcag  660
gtaggattac ccgctgaact taagcatatc aataagcgga ggaaaagaaa ccaactggga  720
ttaccttagt aacggcgagt gaagcggtaa aagctcaaat ttgaaatctg gtactttcan  780
ngcccgagtt gtaatttgta gaatttgtct ttgattaggt ccttgtctat gttccttgga  840
ncaggacgtc atanagggtg antcccnttt ggcgangana ccttttctct gtanactttt  900
tcnanagtcg agttgtttng gatgcagctc naagtggggn gg                     942

SEQ ID NO: 9            moltype = DNA  length = 1572
FEATURE                 Location/Qualifiers
source                  1..1572
                        mol_type = genomic DNA
                        organism = Pediococcus pentosaceus
SEQUENCE: 9
atgagagttt gatcttggct caggatgaac gctggcggcg tgcctaatac atgcaagtcg  60
aacgaacttc cgttaattga ttatgacgta cttgtactga ttgagatttt aacacgaagt  120
gagtggcgaa cgggtgagta acacgtgggt aacctgccca gaagtagggg ataacacctg  180
gaaacagatg ctaataccgt ataacagaga aaaccgcatg gttttctttt aaaagatggc  240
tctgctatca cttctggatg gacccgcggc gtattagcta gttggtgagg caaaggctca  300
ccaaggcagt gatacgtagc cgacctgaga gggtaatcgg ccacattggg actgagacac  360
ggcccagact cctacgggag gcagcagtag ggaatcttcc acaatggacg caagtctgat  420
ggagcaacgc cgcgtgagtg aagaagggtt tcggctcgta aagctctgtt gttaaagaag  480
aacgtgggta agagtaactg tttacccagt gacggtattt aaccagaaag ccacggctaa  540
ctacgtgcca gcagccgcgg taatacgtag gtggcaagcg ttatccggat ttattgggcg  600
taaagcgagc gcaggcggtc ttttaagtct aatgtgaaag ccttcggctc aaccgaagaa  660
gtgcattgga aactgggaga cttgagtgca gaagaggaca gtggaactcc atgtgtagcg  720
gtgaaatgcg tagatatatg gaagaacacc agtggcgaag gcggctgtct ggtctgcaac  780
tgacgctgag gctcgaaagc atgggtagcg aacaggatta gataccctgg tagtccatgc  840
cgtaaacgat gattactaag tgttggaggg tttccgccct tcagtgctgc agctaacgca  900
ttaagtaatc cgcctgggga gtacgaccgc aaggttgaaa ctcaaaagaa ttgacggggg  960
cccgcacaag cggtggagca tgtggtttaa ttcgaagcta cgcgaagaac cttaccaggt  1020
cttgacatct tctgacagtc taagagatta gaggttccct tcggggacag aatgacaggt  1080
ggtgcatggt tgtcgtcagc tcgtgtcgtg agatgttggg ttaagtcccg caacgagcgc  1140
aacccttatt actagttgcc agcattaagt tgggcactct agtgagactg ccggtgacaa  1200
accggaggaa ggtggggacg acgtcaaatc atcatgcccc ttatgacctg ggctacacac  1260
gtgctacaat ggatggtaca acgagtcgcg agaccgcgag gttaagctaa tctcttaaaa  1320
ccattctcag ttcggactgt aggctgcaac tcgcctacac gaagtcggaa tcgctagtaa  1380
tcgcggatca gcatgccgcg gtgaatacgt tcccgggcct tgtacacacc gcccgtcaca  1440
ccatgagagt ttgtaacacc caaagccggt ggggtaacct tttaggagct agccgtctaa  1500
ggtgggacag atgattaggg tgaagtcgta acaaggtagc cgtaggagaa cctgcggctg  1560
gatcacctcc tt                                                     1572

SEQ ID NO: 10           moltype = DNA  length = 1300
FEATURE                 Location/Qualifiers
source                  1..1300
                        mol_type = genomic DNA
                        organism = Bacillus velezensis
SEQUENCE: 10
cagatagttg gtgaggtaac ggctcaccaa ggcaacgatg cgtagccgac ctgagagggt  60
gatcggccac actgggactg agacacggcc cagactccta cgggaggcag cagtagggaa  120
tcttccgcaa tggacgaaag tctgacggag caacgccgcg tgagtgatga aggttttcgg  180
atcgtaaagc tctgttgtta gggaagaaca agtgccgttc aaatagggcg gcaccttgac  240
ggtacctaac cagaaagcca cggctaacta cgtgccagca gccgcggtaa tacgtaggtg  300
gcaagcgttg tccggaatta ttgggcgtaa agggctcgca ggcggtttct taagtctgat  360
gtgaaagccc ccggctcaac cggggagggt cattggaaac tggggaactt gagtgcagaa  420
gaggagagtg gaattccacg tgtagcggtg aaatgcgtag agatgtggag gaacaccagt  480
ggcgaaggcg actctctggt ctgtaactga cgctgaggag cgaaagcgtg gggagcgaac  540
aggattagat accctggtag tccacgccgt aaacgatgag tgctaagtgt tagggggttt  600
ccgcccctta gtgctgcagc taacgcatta agcactccgc ctggggagta cggtcgcaag  660
actgaaactc aaaggaattg acgggggccc gcacaagcgg tggagcatgt ggtttaattc  720
gaagcaacgc gaagaacctt accaggtctt gacatcctct gacaatccta gagataggac  780
gtccccttcg ggggcagagt gacaggtggt gcatggttgt cgtcagctcg tgtcgtgaga  840
tgttgggtta agtcccgcaa cgagcgcaac ccttgatctt agttgccagc attcagttgg  900
gcactctaag gtgactgccg gtgacaaacc ggaggaaggt ggggatgacg tcaaatcatc  960
atgcccctta tgacctgggc tacacacgtg ctacaatgga cagaacaaag ggcagcgaaa  1020
ccgcgaggtt aagccaatcc cacaaatctg ttctcagttc ggatcgcagt ctgcaactcg  1080
actgcgtgaa gctggaatcg ctagtaatcg cggatcagca tgccgcggtg aatacgttcc  1140
cgggccttgt acacaccgcc cgtcacacca cgagagtttg taacacccga agtcggtgag  1200
gtaacctttt aggagccagc cgccgaaggt gggacagatg attggggtga agtcgtaaca  1260
aggtagccgt atcggaaggt gcggctggat cacctccttt                       1300

SEQ ID NO: 11           moltype = DNA  length = 1419
FEATURE                 Location/Qualifiers
source                  1..1419
                        mol_type = genomic DNA
                        organism = Pseudomonas putida
SEQUENCE: 11
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
```

-continued

```
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt cgttaagttg gatgtgaaag  600
ccccgggctc aacctgggaa ctgcattcaa aactgacgag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttggaatc cttgagattt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga tgggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac atcccacacg aattgcttg                         1419

SEQ ID NO: 12          moltype = DNA  length = 1520
FEATURE                Location/Qualifiers
source                 1..1520
                       mol_type = genomic DNA
                       organism = Microbacterium sp.
SEQUENCE: 12
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagcc  180
ttcatcgcat ggtgggggtt ggaaagattt tttggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catacaccag aacgggccag aaatggtcaa ctctttggac actggtgaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaagtcgg taacacctga agccggtggc ccaacccttg tggagggagc  1440
cgtcgaaggt gggatcggta attaggacta agtcgtaaca aggtagccgt accggaaggt  1500
gcggctggat cacctccttt                                             1520

SEQ ID NO: 13          moltype = DNA  length = 1457
FEATURE                Location/Qualifiers
source                 1..1457
                       mol_type = genomic DNA
                       organism = Bacillus mycoides
SEQUENCE: 13
agttagcggc ggacgggtga gtaacacgtg ggtaacctgc ctataagact gggataactc  60
cgggaaaccg gggctaatac cggataacat tttgcaccgc atggtgcgaa attgaaaggc  120
ggcttcggct gtcacttata gatggacctg cggcgcatta gctagttggt gaggtaacgg  180
ctcaccaagg cgacgatgcg tagccgacct gagagggtga tcggccacac tgggactgag  240
acacggccca gactcctacg ggaggcagca gtagggaatc ttccgcaatg gacgaaagtc  300
tgacggagca acgccgcgtg aacgatgaag gctttcgggt cgtaaagttc tgttgttagg  360
gaagaacaag tgctagttga ataagctggc accttgacgg tacctaacca gaaagccacg  420
gctaactacg tgccagcagc cgcggtaata cgtaggtggc aagcgttatc cggaattatt  480
gggcgtaaag cgcgcgcagg tggtttctta agtctgatgt gaaagcccac ggctcaaccg  540
tggagggtca ttggaaactg ggagacttga gtgcagaaga ggaaagtgga attccatgtg  600
tagcggtgaa atgcgtagag atatggagga acaccagtgg cgaaggcgac tttctggtct  660
gcaactgaca ctgaggcgcg aaagcgtggg gagcaaacag gattagatac cctggtagtc  720
cacgccgtaa acgatgagtg ctaagtgtta gagggtttcc gccctttagt gctgaagtta  780
acgcattaag cactccgcct ggggagtacg gccgcaaggc tgaaactcaa aggaattgac  840
gggggcccgc acaagcggtg gagcatgtgg tttaattcga agcaacgcga agaaccttac  900
caggtcttga catcctctga aaccctaga gatagggctt ccccttcggg ggcagagtga  960
caggtggtgc atggttgtcg tcagctcgtg tcgtgagatg ttgggttaag tcccgcaacg  1020
agcgcaaccc ttgatcttag ttgccatcat taagttgggc actctaaggt gactgccggt  1080
```

-continued

```
gacaaaccgg aggaaggtgg ggatgacgtc aaatcatcat gccccttatg acctgggcta  1140
cacacgtgct acaatggacg gtacaaagag tcgcaagacc gcgaggtgga gctaatctca  1200
taaaaccgtt ctcagttcgg attgtaggct gcaactcgcc tacatgaagc tggaatcgct  1260
agtaatcgcg gatcagcatg ccgcggtgaa tacgttcccg ggccttgtac acaccgcccg  1320
tcacaccacg agagtttgta acacccgaag tcggtggggt aacctttttgg agccagccgc  1380
ctaaggtggg acagatgatt ggggtgaagt cgtaacaagg tagccgtatc ggaaggtgcg  1440
gctggatcac ctccttt                                                 1457

SEQ ID NO: 14          moltype = DNA  length = 1526
FEATURE                Location/Qualifiers
source                 1..1526
                       mol_type = genomic DNA
                       organism = Arthrobacter luteolus
SEQUENCE: 14
tacggagagt ttgatcctgg ctcaggatga acgctggcgg cgtgcttaac acatgcaagt  60
cgaacgatga cttctgtgct tgcacagaat gattagtggc gaacgggtga gtaacacgtg  120
agtaacctgc ccttaacttc gggataagcc tgggaaaccg ggtctaatac cggatacgac  180
ctcctggcgc atgccatggt ggtggaaagc tttagcggtt ttggatggac tcgcggccta  240
tcagcttgtt ggtggggta atggcccacc aaggcgacga cgggtagccg gcctgagagg  300
gtgaccggcc acactgggac tgagacacgg cccagactcc tacgggaggc agcagtgggg  360
aatattgcac aatgggcgaa agcctgatgc agcgacgccg cgtgagggat gacggccttc  420
gggttgtaaa cctctttcag cagggaagaa gcgaaagtga cggtacctgc agaagaagcg  480
ccggctaact acgtgccagc agccgcggta atacgtaggg cgcaagcgtt atccggaatt  540
attgggcgta aagagctcgt aggcggtttg tcgcgtctgc tgtgaaagcc cggggctcaa  600
ccccgggtct gcagtgggta cgggcagact agagtgcagt aggggagact ggaattcctg  660
gtgtagcggt gaaatgcgca gatatcagga ggaacaccga tggcgaaggc aggtctctgg  720
gctgtaactg acgctgagga gcgaaagcat ggggagcgaa caggattaga taccctggta  780
gtccatgccg taaacgttgg gcactaggtg tgggggacat tccacgtttt ccgcgccgta  840
gctaacgcat taagtgcccc gcctggggag tacggccgca aggctaaaac tcaaaggaat  900
tgacgggggc ccgcacaagc ggcggagcat gcggattaat tcgatgcaac gcgaagaacc  960
ttaccaaggc ttgacatgaa ccggtaagac ctggaaacag gtcccccact tgtggccggt  1020
ttacaggtgg tgcatggttg tcgtcagctc gtgtcgtgag atgttgggtt aagtcccgca  1080
acgagcgcaa ccctcgttct atgttgccag cgggttatgc cggggactca taggagactg  1140
ccggggtcaa ctcggaggaa ggtggggacg acgtcaaatc atcatgcccc ttatgtcttg  1200
ggcttcacgc atgctacaat ggccggtaca aagggttgcg atactgtgag gtggagctaa  1260
tcccaaaaag ccggtctcag ttcggattga ggtctgcaac tcgacctcat gaagttggag  1320
tcgctagtaa tcgcagatca gcaacgctgc ggtgaatacg ttcccgggcc ttgtacacac  1380
cgcccgtcaa gtcacgaaag ttggtaacac ccgaagccgg tggcctaacc ccttgtggga  1440
gggagccgtc gaaggtggga ccggcgattg ggactaagtc gtaacaaggt agccgtaccg  1500
gaaggtgcgg ctggatcacc tccttt                                      1526

SEQ ID NO: 15          moltype = DNA  length = 1520
FEATURE                Location/Qualifiers
source                 1..1520
                       mol_type = genomic DNA
                       organism = Curtobacterium sp.
SEQUENCE: 15
tacggagagt ttgatcctgg ctcaggacga acgctggcgg cgtgcttaac acatgcaagt  60
cgaacgatga tcaggagctt gctcctgtga ttagtggcga acgggtgagt aacacgtgag  120
taacctgccc ctgactctgg gataagcgtt ggaaacgacg tctaatactg gatatgatca  180
ctggccgcat ggtctggtgg tggaaagatt ttttggttgg ggatggactc gcggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggccttcggg  420
ttgtaaacct cttttagtag ggaagaagcg aaagtgacgg tacctgcaga aaaagcaccg  480
gctaactacg tgccagcagc cgcggtaata cgtagggtgc aagcgttgtc cggaattatt  540
gggcgtaaag agctcgtagg cggtttgtcg cgtctgctgt gaaatcccga ggctcaacct  600
cgggcttgca gtgggtacgg gcagactaga gtgcggtagg ggagattgga attcctggtg  660
tagcggtgga atgcgcagat atcaggagga acaccgatgg cgaaggcaga tctctgggcc  720
gtaactgacg ctgaggagcg aaagcgtggg gagcgaacag gattagatac cctggtagtc  780
cacgccgtaa acgttgggcg ctagatgtag ggacctttcc acggtttctg tgtcgtagct  840
aacgcattaa gcgccccgcc tggggagtac ggccgcaagg ctaaaactca aaggaattga  900
cgggggcccg cacaagcggc ggagcatgcg gattaattcg atgcaacgcg aagaacctta  960
ccaaggcttg acatacaccg gaaacggcca gagatggtcg ccccccttgtg gtcggtgtac  1020
aggtggtgca tggttgtcgt cagctcgtgt cgtgagatgt tgggttaagt cccgcaacga  1080
gcgcaaccct cgttctatgt tgccagcgcg ttatggcggg gactcatagg agactgccgg  1140
ggtcaactcg gaggaaggtg gggatgacgt caaatcatca tgccccttat gtcttgggct  1200
tcacgcatgc tacaatggcc ggtacaaagg gctgcgatac cgtaaggtgg agcgaatccc  1260
aaaaagccgg tctcagttcg gattgaggtc tgcaactcga cctcatgaag tcggagtcgc  1320
tagtaatcgc agatcagcaa cgctgcggtg aatacgttcc cgggccttgt acacaccgcc  1380
cgtcaagtca tgaaagtcgg taacacccga agccggtggc ctaacccttg tggaaggagc  1440
cgtcgaaggt gggatcggtg attaggacta agtcgtaaca aggtagccgt accggaaggt  1500
gcggctggat cacctccttt                                             1520

SEQ ID NO: 16          moltype =   length =
SEQUENCE: 16
000
```

-continued

```
SEQ ID NO: 17          moltype = DNA  length = 898
FEATURE                Location/Qualifiers
source                 1..898
                       mol_type = genomic DNA
                       organism = Rahnella aquatilis
SEQUENCE: 17
gtgattgacg ttactcgcag aagaagcacc ggctaactcc gtgccagcag ccgcggtaat  60
acggagggtg caagcgttaa tcggaattac tgggcgtaaa gcgcacgcag gcggtttgtt  120
aagtcagatg tgaaatcccc gcgcttaacg tgggaactgc atttgaaact ggcaagctag  180
agtcttgtag aggggggtag aattccaggt gtagcggtga aatgcgtaga gatctggagg  240
aataccggtg gcgaaggcgg ccccctggac aaagactgac gctcaggtgc gaaagcgtgg  300
ggagcaaaca ggattagata ccctggtagt ccacgctgta aacgatgtcg acttggaggt  360
tgtgcccttg aggcgtggct tccggagcta acgcgttaag tcgaccgcct ggggagtacg  420
gccgcaaggt taaaactcaa atgaattgac gggggcccgc acaagcggtg gagcatgtgg  480
tttaattcga tgcaacgcga agaaccttac ctactcttga catccacgga attcgccaga  540
gatggcttag tgccttcggg aaccgtgaga caggtgctgc atggctgtcg tcagctcgtg  600
ttgtgaaatg ttgggttaag tcccgcaacg agcgcaaccc ttatcctttg ttgccagcac  660
gtaatggtgg gaactcaaag gagactgccg gtgataaacc ggaggaaggt ggggatgacg  720
tcaagtcatc atggccctta cgagtagggc tacacacgtg ctacaatggc atatacaaag  780
agaagcgaac tcgcgagagc aagcggacct cataaagtat gtcgtagtcc ggattggagt  840
ctgcaactcg actccatgaa gtcggaatcg ctagtaatcg tagatcagaa tgctacgg    898

SEQ ID NO: 18          moltype = DNA  length = 1532
FEATURE                Location/Qualifiers
source                 1..1532
                       mol_type = genomic DNA
                       organism = Pseudomonas sp.
SEQUENCE: 18
tgaagagttt gatcatggct cagattgaac gctggcggca ggcctaacac atgcaagtcg  60
agcggatgaa aggagcttgc tcctggattc agcggcggac gggtgagtaa tgcctaggaa  120
tctgcctggt agtgggggac aacgtttcga aaggaacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagta aattaatact ttgctgtttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttgggagc cttgagctct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                                1532

SEQ ID NO: 19          moltype = DNA  length = 1526
FEATURE                Location/Qualifiers
source                 1..1526
                       mol_type = genomic DNA
                       organism = Curtobacterium pusillum
SEQUENCE: 19
tacggagagt ttgatcctgg ctcaggacga acgctggcgg cgtgcttaac acatgcaagt  60
cgaacgatga tgcccagctt gctgggtgga ttagtggcga acgggtgagt aacacgtgag  120
taacctgccc ctgactctgg gataagcgtt ggaaacgacg tctaatactg gatatgactg  180
ccggccgcat ggtctggtgg tggaaagatt ttttggttgg ggatggactc gcggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggccttcggg  420
ttgtaaacct cttttagtag ggaagaaggg agcttgctct tgacggtacc tgcagaaaaa  480
gcaccggcta actacgtgcc agcagccgcg gtaatacgta gggtgcaagc gttgtccgga  540
attattgggc gtaaagagct cgtaggcggt ttgtcgcgtc tgctgtgaaa tcccgaggct  600
caacctcggg cttgcagtgg gtacgggcag actagagtgc ggtaggggag attggaattc  660
ctggtgtagc ggtggaatgc gcagatatca ggaggaacac cgatggcgaa ggcagatctc  720
tgggccgtaa ctgacgctga ggagcgaaag catggggagc gaacaggatt agataccctg  780
gtagtccatg ccgtaaacgt tgggcgctag atgtagggac ctttccacgg tttctgtgtc  840
gtagctaacg cattaagcgc cccgcctggg gagtacggcc gcaaggctaa aactcaaagg  900
aattgacggg ggcccgcaca agcggcggag catgcggatt aattcgatgc aacgcgaaga  960
accttaccaa ggcttgacat acaccggaaa cggccagaga tggtcgcccc cttgtggtcg  1020
gtgtacaggt ggtgcatggt tgtcgtcagc tcgtgtcgtg agatgttggg ttaagtcccg  1080
```

-continued

```
caacgagcgc aaccctcgtt ctatgttgcc agcgcgttat ggcggggact cataggagac  1140
tgccggggtc aactcggagg aaggtgggga tgacgtcaaa tcatcatgcc ccttatgtct  1200
tgggcttcac gcatgctaca atggccggta caaagggctg cgataccgta aggtggagcg  1260
aatcccaaaa agccggtctc agttcggatt gaggtctgca actcgacctc atgaagtcgg  1320
agtcgctagt aatcgcagat cagcaacgct gcggtgaata cgttcccggg ccttgtacac  1380
accgcccgtc aagtcatgaa agtcggtaac acccgaagcc ggtggcctaa cccttgtgga  1440
aggagccgtc gaaggtggga tcggtgatta ggactaagtc gtaacaaggt agccgtaccg  1500
gaaggtgcgg ctggatcacc tccttt                                     1526

SEQ ID NO: 20          moltype = DNA  length = 1543
FEATURE                Location/Qualifiers
source                 1..1543
                       mol_type = genomic DNA
                       organism = Stenotrophomonas rhizophila
SEQUENCE: 20
tgaagagttt gatcctggct cagagtgaac gctggcggta ggcctaacac atgcaagtcg  60
aacggcagca cagtaagagc ttgctcttat gggtggcgag tggcggacgg gtgaggaata  120
catcggaatc taccttttcg tgggggataa cgtagggaaa cttacgctaa taccgcatac  180
gaccttcggg tgaaagcagg ggaccttcgg gccttgcgcg gatagatgag ccgatgtcgg  240
attagctagt tggcggggta aaggcccacc aaggcgacga tccgtagctg gtctgagagg  300
atgatcagcc acactggaac tgagacacgg tccagactcc tacgggaggc agcagtgggg  360
aatattggac aatgggcgca agcctgatcc agccataccg cgtgggtgaa gaaggccttc  420
gggttgtaaa gcccttttgt tgggaaagaa aagcagtcgg ctaatacccg gttgttctga  480
cggtacccaa agaataagca ccggctaact tcgtgccagc agccgcggta atacgaaggg  540
tgcaagcgtt actcggaatt actgggcgta aagcgtgcgt aggtggttgt ttaagtctgt  600
tgtgaaagcc ctgggctcaa cctgggaatt gcagtggata ctgggcgact agagtgtggt  660
agagggtagt ggaattcccg gtgtagcagt gaaatgcgta gagatcggga ggaacatcca  720
tggcgaaggc agctacctgg accaacactg acactgaggc acgaaagcgt ggggagcaaa  780
caggattaga taccctggta gtccacgccc taaacgatgc gaactggatg ttgggtgcaa  840
tttggcacgc agtatcgaag ctaacgcgtt aagttcgccg cctggggagt acggtcgcaa  900
gactgaaact caaaggaatt gacgggggcc cgcacaagcg gtggagtatg tggtttaatt  960
cgatgcaacg cgaagaacct tacctggtct tgacatgtcg agaactttcc agagatggat  1020
tggtgccttc gggaactcga acacaggtgc tgcatggctg tcgtcagctc gtgtcgtgag  1080
atgttgggtt aagtcccgca acgagcgcaa cccttgtcct tagttgccag cacgtaatgg  1140
tgggaactct aaggagaccg ccggtgacaa accggaggaa ggtggggatg acgtcaagtc  1200
atcatggccc ttacgaccag ggctacacac gtactacaat ggtagggaca gagggctgca  1260
aacccgcgag ggcaagccaa tcccagaaac cctatctcag tccggattgg agtctgcaac  1320
tcgactccat gaagtcggaa tcgctagtaa tcgcagatca gcattgctgc ggtgaatacg  1380
ttcccgggcc ttgtacacac cgcccgtcac accatgggag tttgttgcac cagaagcagg  1440
tagcttaacc ttcgggaggg cgcttgccac ggtgtggccg atgactgggg tgaagtcgta  1500
acaaggtagc cgtatcggaa ggtgcggctg gatcacctcc ttt                  1543

SEQ ID NO: 21          moltype = DNA  length = 927
FEATURE                Location/Qualifiers
source                 1..927
                       mol_type = genomic DNA
                       organism = Candida santamariae
SEQUENCE: 21
gggggcatca gtattcagtt gtcagaggtg aaattcttgg atttactgaa gactaactac  60
tgcgaaagca tttgccaagg acgttttcat taatcaagaa cgaaagttag gggatcgaag  120
atgatcagat accgtcgtag tcttaaccat aaactatgcc gactagggat cgggtgttgt  180
tcttttttttg acgcactcgg caccttacga gaaatcaaag tctttgggtt ctgggggggag  240
tatggtcgca aggctgaaac ttaaaggaat tgacggaagg gcaccaccag gagtggagcc  300
tgcggcttaa tttgactcaa cacggggaaa ctcaccaggt ccagacacaa taaggattga  360
cagattgaga gctctttctt gattttgtgg gtggtggtgc atggccgttc ttagttggtg  420
gagtgatttg tctgcttaat tgcgataacg aacgagacct taacctacta aatagtgctg  480
ctagcttttg ctggtatagt cacttcttag agggactatc gatttcaagt cgatggaagt  540
ttgaggcaat aacaggtctg tgatgccctt agacgttctg ggccgcacgc gcgctacact  600
gacggagcca gcgagttcta accttggccg agaggtctgg gtaatcttgt gaaactccgt  660
cgtgctgggg atagagcatt gtaattattg ctcttcaacg aggaattcct agtaagcgca  720
agtcatcagc ttgcgttgat tacgtccctg ccctttgtac acaccgcccg tcgctactac  780
cgattgaatg gcttagtgag gcttccggat tggtttaaag aagggggcaa ctccatcttg  840
gaaccgaaaa gctagtcaaa cttggtcatt tagaggaagt aaaagtcgta acaaggtttc  900
cgtaggtgaa cctgcggaag gatcatt                                    927

SEQ ID NO: 22          moltype = DNA  length = 1539
FEATURE                Location/Qualifiers
source                 1..1539
                       mol_type = genomic DNA
                       organism = Rahnella sp.
SEQUENCE: 22
ttgaagagtt tgatcatggc tcagattgaa cgctggcggc aggcctaaca catgcaagtc  60
gagcggtagc acaggagagc ttgctctccg ggtgacgagc ggcggacggg tgagtaatgt  120
ctgggaaact gcctgatgga gggggataac tactggaaac ggtagctaat accgcatgac  180
gtcgcaagac caaagtgggg gaccttcggg cctcacgcca tcggatgtgc ccagatggga  240
ttagctagta ggtgaggtaa tggctcacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtgtgaag aaggccttag  420
ggttgtaaag cactttcagc gaggaggaag gcgttgcagt taatagctgc agcgattgac  480
```

-continued

```
gttactcgca gaagaagcac cggctaactc cgtgccagca gccgcggtaa tacggagggt  540
gcaagcgtta atcggaatta ctgggcgtaa agcgcacgca ggcggtttgt taagtcagat  600
gtgaaatccc cgagcttaac ttgggaactg catttgaaac tggcaagcta gagtcttgta  660
gaggggggta gaattccagg tgtagcggtg aaatgcgtag agatctggag gaataccggt  720
ggcgaaggcg gccccctgga caaagactga cgctcaggtg cgaaagcgtg gggagcaaac  780
aggattagat accctggtag tccacgctgt aaacgatgtc gacttggagg ttgtgccctt  840
gaggcgtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctactcttg acatccagag aattcgctag agatagctta  1020
gtgccttcgg gaactctgag acaggtgctg catggctgtc gtcagctcgt gttgtgaaat  1080
gttgggttaa gtcccgcaac gagcgcaacc cttatccttt gttgccagca cgtaatggtg  1140
ggaactcaaa ggagactgcc ggtgataaac cggaggaagg tggggatgac gtcaagtcat  1200
catggccctt acgagtaggg ctacacacgt gctacaatgg catatacaaa gagaagcgaa  1260
ctcgcgagag caagcggacc tcataaagta tgtcgtagtc cggattggag tctgcaactc  1320
gactccatga agtcggaatc gctagtaatc gtagatcaga atgctacggt gaatacgttc  1380
ccgggccttg tacacaccgc ccgtcacacc atgggagtgg gttgcaaaag aagtaggtag  1440
cttaaccttc gggagggcgc ttaccacttt gtgattcatg actggggtga agtcgtaaca  1500
aggtaaccgt aggggaacct gcggttggat cacctcctt                        1539

SEQ ID NO: 23          moltype = DNA  length = 1536
FEATURE                Location/Qualifiers
source                 1..1536
                       mol_type = genomic DNA
                       organism = Erwinia billingiae
SEQUENCE: 23
ttgaagagtt tgatcatggc tcagattgaa cgctggcggc aggcctaaca catgcaagtc  60
gaacggtagc acagagagct tgctctcttgg tgacgagtgg cggacgggtg agtaatgtct  120
gggaaactgc ccgatggagg gggataacta ctggaaacgg tagctaatac cgcataacgt  180
cttcggacca aagtggggga ccttcgggcc tcacaccatc ggatgtgccc agatgggatt  240
agctagtagg tggggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gatacggtta ataaccgtgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtca agtcagatgt  600
gaaatccccg ggcttaacct gggaactgca tttgaaactg gcaggcttga gtctcgtaga  660
ggggggtaga attccaggtg tagcggtgaa atgcgtagag atctggagga ataccggtgg  720
cgaaggcggc cccctggacg aagactgacg ctcaggtgcg aaagcgtggg gagcaaacag  780
gattagatac cctggtagtc cacgctgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg gggcccgca caagcggtgg agcatgtggt ttaattcgat  960
gcaacgcgaa gaaccttacc tggccttgac atccacagaa ttcggcagag atgccttagt  1020
gccttcggga actgtgagac aggtgctgca tggctgtcgt cagctcgtgt tgtgaaatgt  1080
tgggttaagt cccgcaacga gcgcaaccct tatcctttgt tgccagcgat tcggtcggga  1140
actcaaagga gactgccggt gataaaccgg aggaaggtgg ggatgacgtc aagtcatcat  1200
ggcccttacg gccagggcta cacacgtgct acaatggcgc atacaaagag aagcgacctc  1260
gcgagagcaa gcggacctca taaagtgcgt cgtagtccgg atcggagtct gcaactcgac  1320
tccgtgaagt cggaatcgct agtaatcgta gatcagaatg ctacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536

SEQ ID NO: 24          moltype = DNA  length = 1441
FEATURE                Location/Qualifiers
source                 1..1441
                       mol_type = genomic DNA
                       organism = Filobasidium globisporum
SEQUENCE: 24
cggggaatta gggttcgatt ccggagaggg agcctgagaa acggctacca catccaagga  60
aggcagcagg cgcgcaaatt acccaatccc gacacgggga ggtagtgaca ataaataaca  120
atacagggcc ctttgggtct tgtaattgga atgagtacaa tttaaatccc ttaacgagga  180
acaattggag ggcaagtctg gtgccagcag ccgcggtaat tccagctcca atagcgtata  240
ttaaagttgt tgcagttaaa aagctcgtag ttgaacttca ggcttggcgg ggtggtctgc  300
ctcacggtat gtactatccg gctgagcctt acctcctggt gagcctgcat gtcgtttatt  360
cggtgtgtag gggaaccagg aattttactt tgaaaaaatt agagtgttca aagcaggcat  420
atgcccgaat acattagcat ggaataatag aataggacgt gcggttctat tttgttggtt  480
tctaggatcg ccgtaatgat taatagggac ggttgggggc attagtattc agttgctaga  540
ggtgaaattc ttagatttac tgaagactaa ctactgcgaa agcatttgcc aaggacgttt  600
tcattaatca agaacgaagg ttaggggatc aaaaacgatt agataccgtt gtagtcttaa  660
cagtaaacta tgccgactag ggatcgggcc acgttcatct tttgactggc tcggcacctt  720
acgagaaatc aaagtctttg ggttctgggg ggagtatggt cgcaaggctg aaacttaaag  780
gaattgacgg aagggcacca ccaggcgtgg agcctgcggc ttaatttgac tcaacacggg  840
gaaactcacc aggtccagac atagtaagga ttgacagatt gatagctctt tcttgattct  900
atgggtggtg gtgcatggcc gttcttagtt ggtggagtga tttgtctggt taattccgat  960
aacgaacgag accttaacct gctaaatagt ccggccggct tcggctggtc gctgacttct  1020
tagagggact aacagcgttt agctgttgga agtttgaggc aataacaggt ctgtgatgcc  1080
cttagatgtt ctgggccgca cgcgcgctac actgactgag ccagcgagtt tataaccttg  1140
gccgaaaggt ctgggtaatc ttgtgaaact cagtcgtgct ggggatagag cattgcaatt  1200
attgctcttc aacgaggaat gcctagtaag cgtgagtcat cagctcacgt tgattacgtc  1260
```

```
cctgcccttt gtacacaccg cccgtcgcta ctaccgattg aatggcttag tgagatctcc  1320
ggattggctt tgggaagctg gcaacggcta cctattgctg aaaagctgat caaacttggt  1380
catttagagg aagtaaaagt cgtaacaagg tttccgtagg tgaacctgcg gaaggatcat  1440
t                                                                  1441

SEQ ID NO: 25          moltype =   length =
SEQUENCE: 25
000

SEQ ID NO: 26          moltype = DNA  length = 1482
FEATURE                Location/Qualifiers
source                 1..1482
                       mol_type = genomic DNA
                       organism = Methylobacterium sp.
SEQUENCE: 26
cttgagagtt tgatcctggc tcagagcgaa cgctggcggc aggcttaaca catgcaagtc  60
gagcgggcat cttcggatgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
atgacggtac cggaagaata agccccggct aacttcgtgc cagcagccgc ggtaatacga  480
aggggggctag cgttgctcgg aatcactggg cgtaaagggc gcgtaggcgg ccattcaagt  540
cgggggtgaa agcctgtggc tcaaccacag aattgccttc gatactgttt ggcttgagta  600
tggtagaggt tggtggaact gcgagtgtag aggtgaaatt cgtagatatt cgcaagaaca  660
ccggtggcga aggcggccaa ctggaccatt actgacgctg aggcgcgaaa gcgtggggag  720
caaacaggat tagataccct ggtagtccac gccgtaaacg atgaatgcca gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgg catgttaccc ggagagattc  960
ggggtccact tcggtggcgt gcacacaggt gctgcatggc tgtcgtcagc tcgtgtcgtg  1020
agatgttggg ttaagtcccg caacgagcgc aacccacgtc cttagttgcc atcattcagt  1080
tgggcactct agggagactg ccggtgataa gccgcgagga aggtgtggat gacgtcaagt  1140
cctcatggcc cttacgggat gggctacaca cgtgctacaa tggcggtgac agtgggacgc  1200
gaaggagcga tctggagcaa atccccaaaa accgtctcag ttcagattgc actctgcaac  1260
tcgagtgcat gaaggcggaa tcgctagtaa tcgtggatca gcatgccacg gtgaatacgt  1320
tcccgggcct tgtacacacc gcccgtcaca ccatgggagt tggtcttacc cgacggcgct  1380
gcgccaaccg caaggaggca ggcgaccacg gtagggtcag cgactggggt gaagtcgtaa  1440
caaggtagcc gtaggggaac ctgcggctgg atcacctcct tt                    1482

SEQ ID NO: 27          moltype = DNA  length = 935
FEATURE                Location/Qualifiers
source                 1..935
                       mol_type = genomic DNA
                       organism = Sphingomonas sp.
SEQUENCE: 27
cttgagagtt tgatcctggc tcagaacgaa cgctggcggc atgcctaaca catgcaagtc  60
gaacgatgct ttcgggcata gtggcgcacg ggtgcgtaac gcgtgggaat ctgccctcag  120
gttcggaata acagctggaa acggctgcta ataccggatg atatcgcaag atcaaagatt  180
tatcgcctga ggatgagccc gcgttggatt aggtagttgg tggggtaaag gcctaccaag  240
ccgacgatcc atagctggtc tgagaggatg atcagccaca ctgggactga gacacggccc  300
agactcctac gggaggcagc agtggggaat attggacaat gggcgcaagc ctgatccagc  360
aatgccgcgt gagtgatgaa ggccctaggg ttgtaaagct cttttacccg ggaagataat  420
gactgtaccg ggagaataag ccccggctaa ctccgtgcca gcagccgcgg taatacggag  480
ggggctagcg ttgttcggaa ttactgggcg taaagcgcac gtaggcggct ttgtaagtca  540
gaggtgaaag cctggagctc aactccagaa ctgcctttga gactgcatcg cttgaatcca  600
ggagaggtca gtggaattcc gagtgtagag gtgaaattcg tagatattcg gaagaacacc  660
agtggcgaag gcggctgact ggactggtat tgacgctgag gtgcgaaagc gtggggagca  720
aacaggatta gataccctgg tagtccacgc cgtaaacgat gataactagc tgtccgggca  780
cttggtgctt gggtggcgca gctaacgcat taagttatcc gcctggggag tacggccgca  840
aggttaaaac tcaaaggaat tgacgggggc ctgcacaagc ggtggagcat gtggtttaat  900
tcgaagcaac gcgcagaacc ttaccagcgt ttgac                             935

SEQ ID NO: 28          moltype = DNA  length = 931
FEATURE                Location/Qualifiers
source                 1..931
                       mol_type = genomic DNA
                       organism = Aureobasidium pullulans
SEQUENCE: 28
atagtcgggg gcatcagtat tcaattgtca gaggtgaaat tcttggattt attgaagact  60
aactactgcg aaagcatttg ccaaggatgt tttcattaat cagtgaacga aagttagggg  120
atcgaagacg atcagatacc gtcgtagtct taaccataaa ctatgccgac tagggatcgg  180
gcgatgttat cattttgact cgctcggcac cttacgagaa atcaaagtct ttgggttctg  240
gggggagtat ggtcgcaagg ctgaaactta aagaaattga cggaagggca ccaccaggcg  300
tggagcctgc ggcttaattt gactcaacac ggggaaactc accaggtcca gacacaataa  360
ggattgacag attgagagct ctttcttgat tttgtgggtg gtggtgcatg gccgttctta  420
gttggtggag tgatttgtct gcttaattgc gataacgaac gagaccttaa cctgctaaat  480
agcccggccc gctttggcgg gtcgccggct tcttagaggg actatcggct caagccgatg  540
```

```
gaagtttgag gcaataacag gtctgtgatg cccttagatg ttctgggccg cacgcgcgct  600
acactgacag agccaacgag ttcatttcct tgcccggaag ggttgggtaa tcttgttaaa  660
ctctgtcgtg ctggggatag agcattgcaa ttattgctct tcaacgagga atgcctagta  720
agcgtacgtc atcagcgtgc gttgattacg tccctgccct ttgtacacac cgcccgtcgc  780
tactaccgat tgaatggctg agtgaggcct tcggactggc ccagggaggt cggcaacgac  840
cacccagggc cggaaagttg gtcaaactcc gtcatttaga ggaagtaaaa gtcgtaacaa  900
ggtttccgta ggtgaacctg cggaaggatc a                                 931

SEQ ID NO: 29          moltype = DNA  length = 1002
FEATURE                Location/Qualifiers
source                 1..1002
                       mol_type = genomic DNA
                       organism = Pseudoclavibacter helvolus
SEQUENCE: 29
tacggagagt ttgatcctgg ctcaggacga acgctggcgg cgtgcttaac acatgcaagt  60
cgaacgatga agcccagctt gctgggttga ttagtggcga acgggtgagt aacacgtgag  120
caacgtgccc ataactctgg gataacctcc ggaaacggtg gctaatactg gatatctaac  180
acgatcgcat ggtctgtgtt tggaaagatt ttttggttat ggatcggctc acggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggcattcggg  420
ttgtaaacct cttttagtag ggaagaagcg aaagtgacgg tacctgcaga aaaagcaccg  480
gctaactacg tgccagcagc cgctgtaata cgtagggtgc aagcgttgtc cggaattatt  540
gggcgtaaag agctcgtagg cggtttgtcg cgtctgctgt gaaatcccga ggctcaacct  600
cgggtctgca gtgggtacgg gcagactaga gtgtggtagg ggagattgga attcctggtg  660
tagcggtgga atgcgcagat atcaggagga acaccgatgg cgaaggcaga tctctgggcc  720
attactgacg ctgaggagcg aaagcatggg gagcgaacag gattagatac cctggtagtc  780
catgccgtaa acgttgggcg ctagatgtgg ggaccattcc acggtttccg tgtcgtagct  840
aacgcattaa gcgccccgcc tggggagtac ggccgcaagg ctaaaactca aaggaattga  900
cgggggcccg cacaagcggc ggagcatgcg gattaattcg atgcaacgcg aagaacctta  960
ccaaggcttg acatataccg gaaacgttca gaaatgttcg cc                     1002

SEQ ID NO: 30          moltype = DNA  length = 1520
FEATURE                Location/Qualifiers
source                 1..1520
                       mol_type = genomic DNA
                       organism = Microbacterium testaceum
SEQUENCE: 30
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagac  180
gtgatcgcat ggtcgtgttt ggaaagattt ttcggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catatacgag aacgggccag aaatggtcaa ctctttggac actcgtaaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaagtcgg taacacctga agccggtggc ccaacccttg tggagggagc  1440
cgtcgaaggt gggatcggta attaggacta agtcgtaaca aggtagccgt accggaaggt  1500
gcggctggat cacctccttt                                              1520

SEQ ID NO: 31          moltype = DNA  length = 941
FEATURE                Location/Qualifiers
source                 1..941
                       mol_type = genomic DNA
                       organism = Sporisorium reilianum
SEQUENCE: 31
cagccggggg cattagtatt tgcacgctag aggtgaaatt cttggattgt gcaaagactt  60
cctactgcga aagcatttgc caagaatgtt ttcattaatc aagaacgaag gttagggtat  120
cgaaaacgat tagataccgt tgtagtctta acagtaaact atgccgactc cgaatcggtc  180
gatgctcatt tcactggctc gatcggcgcg gtacgagaaa tcaaagtttt tgggttctgg  240
ggggagtatg gtcgcaaggc tgaaacttaa agaaattgac ggaagggcac caccaggagt  300
ggagcctgcg gcttaatttg actcaacacg ggaaaactca ccgggtccgg acatagtaag  360
gattgacaga ttgatggcgc tttcatgatt ctatgggtgg tggtgcatgg ccgttcttag  420
ttggtggagt gatttgtctg gttaattccg ataacgaacg agaccttgac ctgctaaata  480
```

```
gacgggttga cattttgttg gccccttatg tcttcttaga gggacaatcg accgtctagg  540
tgatggaggc aaaaggcaat aacaggtctg tgatgccctt agatgttccg ggctgcacgc  600
gcgctacact gacagagaca acgagtgggg ccccttgtcc gaaatgactg ggtaaacttg  660
tgaaactttg tcgtgctggg gatggagctt tgtaattttt gctcttcaac gaggaattcc  720
tagtaagcgc aagtcatcag cttgcgttga ctacgtccct gccctttgta cacaccgccc  780
gtcgctacta ccgattgaat ggcttagtga ggacttggga gagtacatcg ggagccagc  840
aatggcaccc tgacggctca aactcttaca aacttggtca tttagaggaa gtaaaagtcg  900
taacaaggta tctgtaggtg aacctgcaga tggatcattt c                       941

SEQ ID NO: 32          moltype = DNA  length = 1072
FEATURE                Location/Qualifiers
source                 1..1072
                       mol_type = genomic DNA
                       organism = Hafnia paralvei
SEQUENCE: 32
actgagcatt gacgttactc gcagaagaag caccggctaa ctccgtgcca gcagccgcgg  60
taatacggag ggtgcaagcg ttaatcggaa ttactgggcg taaagcgcac gcaggcggtt  120
tgttaagtca gatgtgaaat ccccgagctt aacttgggaa ctgcatttga aactggcaag  180
ctagagtctt gtagaggggg gtagaattcc aggtgtagcg gtgaaatgcg tagagatctg  240
gaggaatacc ggtggcgaag gcggccccct ggacaaagac tgacgctcag gtgcgaaagc  300
gtggggagca aacaggatta gataccctgg tagtccacgc tgtaaacgat gtcgacttgg  360
aggttgtgcc cttgaggcgt ggcttccgga gctaacgcgt taagtcgacc gcctggggag  420
tacggccgca aggttaaaac tcaaatgaat tgacgggggc ccgcacaagc ggtggagcat  480
gtggtttaat tcgatgcaac gcgaagaacc ttacctactc ttgacatcca gagaattcgc  540
tagagatagc ttagtgcctt cgggaactct gagacaggtg ctgcatggct gtcgtcagct  600
cgtgttgtga aatgttgggt taagtcccgc aacgagcgca acccttatcc tttgttgcca  660
gcgagtaatg tcgggaactc aaaggagact gccggtgata aaccggagga aggtggggat  720
gacgtcaagt catcatggcc cttacgagta gggctacaca cgtgctacaa tggcatatac  780
aaagagaagc gaactcgcga gagcaagcgg acctcataaa gtatgtcgta gtccggattg  840
gagtctgcaa ctcgactcca tgaagtcgga atcgctagta atcgtagatc agaatgctac  900
ggtgaatacg ttcccgggcc ttgtacacac cgcccgtcac accatgggag tgggttgcaa  960
aagaagtagg tagcttaacc ttcgggaggg cgcttaccac tttgtgattc atgactgggg  1020
tgaagtcgta acaaggtaac cgtaggggaa cctgcggttg gatcacctcc tt           1072

SEQ ID NO: 33          moltype = DNA  length = 853
FEATURE                Location/Qualifiers
source                 1..853
                       mol_type = genomic DNA
                       organism = Erwinia persicinus
SEQUENCE: 33
ggaggaaggc gtagagatct ggaggaatac cggtggcgaa ggcggccccc tggacaaaga  60
ctgacgctca ggtgcgaaag cgtggggagc aaacaggatt agataccctg gtagtccacg  120
ccgtaaacga tgtcgacttg gaggttgtgc ccttgaggcg tggcttccgg agctaacgcg  180
ttaagtcgac cgcctgggga gtacggccgc aaggttaaaa ctcaaatgaa ttgacggggg  240
cccgcacaag cggtggagca tgtggtttaa ttcgatgcaa cgcgaagaac cttacctggc  300
cttgacatcc acggaattcg gcagagatgc cttagtgcct tcgggaaccg tgagacaggt  360
gctgcatggc tgtcgtcagc tcgtgttgtg aaatgttggg ttaagtcccg caacgagcgc  420
aacccttatc ctttgttgcc agcacgtaat ggtgggaact caaaggagac tgccggtgat  480
aaaccggagg aaggtgggga tgacgtcaag tcatcatggc ccttacggcc agggctacac  540
acgtgctaca atggcgcata caaagagaag cgacctcgcg agagcaagcg gacctcataa  600
agtgcgtcgt agtccggatc ggagtctgca actcgactcc gtgaagtcgg aatcgctagt  660
aatcgtagat cagaatgcta cggtgaatac gttcccgggc cttgtacaca ccgcccgtca  720
caccatggga gtgggttgca aaagaagtag gtagcttaac cttcgggagg gcgcttacca  780
ctttgtgatt catgactggg gtgaagtcgt aacaaggtaa ccgtagggga acctgcggtt  840
ggatcacctc ctt                                                      853

SEQ ID NO: 34          moltype = DNA  length = 1519
FEATURE                Location/Qualifiers
source                 1..1519
                       mol_type = genomic DNA
                       organism = Plantibacter flavus
SEQUENCE: 34
tacggagagt ttgatcctgg ctcaggacga acgctggcgg cgtgcttaac acatgcaagt  60
cgaacgatga agcccagctt gctgggtgga ttagtggcga acgggtgagt aacacgtgag  120
taacctgccc ttgactctgg gataagcgtt ggaaacgacg tctaataccg gatacgagct  180
tccaccgcat ggtgagttgc tggaaagaat tttggtcaag gatggactcg cggcctatca  240
gcttgttggt gaggtaatgg ctcaccaagg cgacgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggacgacg gccttcgggt  420
tgtaaacctc ttttagcagg gaagaagcga aagtgacggt acctgcagaa aaagcaccgg  480
ctaactacgt gccagcagcc gcggtaatac gtagggtgca agcgttgtcc ggaattattg  540
ggcgtaaaga gctcgtaggc ggtttgtcgc gtctgctgtg aaatcccgag gctcaacctc  600
gggtctgcag tgggtacggg cagactagag tgcggtaggg gagattggaa ttcctggtgt  660
agcggtggaa tgcgcagata tcaggaggaa caccgatggc gaaggcagat ctctgggccg  720
ctactgacgc tgaggagcga aagggtgggg agcaaacagg cttagatacc ctggtagtcc  780
accccgtaaa cgttgggcgc tagatgtggg gaccattcca cggtttccgt gtcgtagcta  840
acgcattaag cgccccgcct ggggagtacg gccgcaaggc taaaactcaa aggaattgac  900
gggggcccgc acaagcggcg gagcatgcgg attaattcga tgcaacgcga agaaccttac  960
caaggcttga catatacgag aacgggccag aaatggtcaa ctctttggac actcgtaaac  1020
```

-continued

```
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggacgacgt caaatcatca tgccccttat gtcttgggct  1200
tcacgcatgc tacaatggcc agtacaaagg gctgcaatac cgtaaggtgg agcgaatccc  1260
aaaaagctgg tcccagttcg gattgaggtc tgcaactcga cctcatgaag tcggagtcgc  1320
tagtaatcgc agatcagcaa cgctgcggtg aatacgttcc cgggccttgt acacaccgcc  1380
cgtcaagtca tgaaagtcgg taacacccga agccagtggc ctaaccgcaa ggatggagct  1440
gtctaaggtg ggatcggtaa ttaggactaa gtcgtaacaa ggtagccgta ccggaaggtg  1500
cggctggatc acctcctttt                                              1519

SEQ ID NO: 35          moltype = DNA  length = 1536
FEATURE                Location/Qualifiers
source                 1..1536
                       mol_type = genomic DNA
                       organism = Pantoea ananatis
SEQUENCE: 35
ttgaagagtt tgatcatggc tcagattgaa cgctggcggc aggcctaaca catgcaagtc  60
ggacggtagc acagagagct tgctcttggg tgacgagtgg cggacgggtg agtaatgtct  120
ggggatctgc ccgatagagg gggataacca ctggaaacgg tggctaatac cgcataacgt  180
cgcaagacca aagaggggga ccttcgggcc tctcactatc ggatgaaccc agatgggatt  240
agctagtagg cggggtaatg gcccacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gatgaggtta ataaccgcgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtta agtcagatgt  600
gaaatccccg ggcttaacct gggaactgca tttgaaactg gcaggcttga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gttcccttga  840
ggagtggctt ccggagctaa cgcgttaagt cgaccgcctg gggagtacgg ccgcaaggtt  900
aaaactcaaa tgaattgacg gggcccgca caagcggtgg agcatgtggt ttaattcgat  960
gcaacgcgaa gaaccttacc tactcttgac atccagcgaa cttagcagag atgctttggt  1020
gccttcggga acgctgagac aggtgctgca tggctgtcgt cagctcgtgt tgtgaaatgt  1080
tgggttaagt cccgcaacga gcgcaaccct tatcctttgt tgccagcgat tcggtcggga  1140
actcaaagga gactgccggt gataaaccgg aggaaggtgg ggatgacgtc aagtcatcat  1200
ggcccttacg agtagggcta cacacgtgct acaatggcgc atacaaagag aagcgacctc  1260
gcgagagcaa gcggacctca caaagtgcgt cgtagtccgg atcggagtct gcaactcgac  1320
tccgtgaagt cggaatcgct agtaatcgtg gatcagaatg ccacggtgaa tacgttcccg  1380
ggccttgtac acaccgcccg tcacaccatg ggagtgggtt gcaaaagaag taggtagctt  1440
aaccttcggg agggcgctta ccactttgtg attcattact ggggtgaagt cgtaacaagg  1500
taaccgtagg ggaacctgcg gttggatcac ctcctt                            1536

SEQ ID NO: 36          moltype = DNA  length = 993
FEATURE                Location/Qualifiers
source                 1..993
                       mol_type = genomic DNA
                       organism = Pantoea vagans
SEQUENCE: 36
ttgaagagtt tgatcatggc tcagattgaa cgctggcggc aggcctaaca catgcaagtc  60
ggacggtagc acagagagct tgctcttggg tgacgagtgg cggacgggtg agtaatgtct  120
ggggatctgc ccgatagagg gggataacca ctggaaacgg tggctaatac cgcataacgt  180
cgcaagacca aagaggggga ccttcgggcc tctcactatc ggatgaaccc agatgggatt  240
agctagtagg cggggtaatg gcccacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gatgcggtta ataaccgcgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtta agtcagatgt  600
gaaatccccg ggcttaacct gggaactgca tttgaaactg gcaggcttga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gttcccttga  840
ggagtggctt ccggagctaa cgcgttaagt cgaccgcctg gggagtacgg ccgcaaggtt  900
aaaactcaaa tgaattgacg gggcccgca caagcggtgg agcatgtggt ttaattcgat  960
gcaacgcgaa gaaccttacc tactcttgac atc                               993

SEQ ID NO: 37          moltype = DNA  length = 1532
FEATURE                Location/Qualifiers
source                 1..1532
                       mol_type = genomic DNA
                       organism = Pseudomonas rhodesiae
SEQUENCE: 37
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacgaacgct aataccgcat acgtcctacg  180
ggagaaagca ggggaccttc gggccttgcg ctatcagatg agcctaggtc ggattagcta  240
gttggtgggg taatggctca ccaaggcgac gatccgtaac tggtctgaga ggatgatcag  300
tcacactgga actgagacac ggtccagact cctacgggag gcagcagtgg ggaatattgg  360
```

-continued

```
acaatgggcg aaagcctgat ccagccatgc cgcgtgtgtg aagaaggtct tcggattgta  420
aagcacttta agttgggagg aagggccatt acctaatacg tgatggtttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg gatgtgaaat  600
ccccgggctc aacctgggaa ctgcattcaa aactgactga ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttgggagc cttgagctct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac agagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggggga cggttaccac ggtgtgattc atgactgggg tgaagtcgta acaaggtagc  1500
cgtaggggaa cctgcggctg gatcacctcc tt                                1532

SEQ ID NO: 38           moltype = DNA  length = 1517
FEATURE                 Location/Qualifiers
source                  1..1517
                        mol_type = genomic DNA
                        organism = Rhodococcus sp.
SEQUENCE: 38
tacggagagt ttgatcctgg ctcaggacga acgctggcgg cgtgcttaac acatgcaagt  60
cgagcggtaa ggcctttcgg ggtacacgag cggcgaacgg gtgagtaaca cgtgggtgat  120
ctgccctgca ctctgggata agcttgggaa actgggtcta ataccggata tgaccacagc  180
atgcatgtgt tgtggtggaa agatttatcg gtgcaggatg ggcccgcggc ctatcagctt  240
gttggtgggg taatggccta ccaaggcgac gacgggtagc cgacctgaga gggtgaccgg  300
ccacactggg actgagacac ggcccagact cctacgggag gcagcagtgg ggaatattgc  360
acaatgggcg gaagcctgat gcagcgacgc cgcgtgaggg atgaaggcct tcgggttgta  420
aacctctttc agcagggacg aagcgtgagt gacggtacct gcagaagaag caccggctaa  480
ctacgtgcca gcagccgcgg taatacgtag ggtgcgagcg ttgtccggaa ttactgggcg  540
taaagagttc gtaggcggtt tgtcgcgtcg tttgtgaaaa cccggggctc aacttcgggc  600
ttgcaggcga tacgggcaga cttgagtgtt tcaggggaga ctggaattcc tggtgtagcg  660
gtgaaatgcg cagatatcag gaggaacacc ggtggcgaag gcgggtctct gggaaacaac  720
tgacgctgag gaacgaaagc gtgggtagca aacaggatta gataccctgg tagtccacgc  780
cgtaaacggt gggcgctagg tgtgggttcc ttccacggga tctgtgccgt agctaacgca  840
ttaagcgccc cgcctgggga gtacggccgc aaggctaaaa ctcaaaggaa ttgacggggg  900
cccgcacaag cggcggagca tgtggattaa ttcgatgcaa cgcgaagaac cttacctggg  960
tttgacatac accggaaaac cgtagagata cggtccccct tgtggtcggt gtacaggtgg  1020
tgcatggctg tcgtcagctc gtgtcgtgag atgttgggtt aagtcccgca acgagcgcaa  1080
cccttgtctt atgttgccag cacgtaatgg tggggactcg taagagactg ccggggtcaa  1140
ctcggaggaa ggtggggacg acgtcaagtc atcatgcccc ttatgtccag ggcttcacac  1200
atgctacaat ggccagtaca gagggctgcg agaccgtgag gtggagcgaa tcccttaaag  1260
ctggtctcag ttcggatcgg ggtctgcaac tcgaccccgt gaagtcggag tcgctagtaa  1320
tcgcagatca gcaacgctgc ggtgaatacg ttcccgggcc ttgtacacac cgcccgtcac  1380
gtcatgaaag tcggtaacac ccgaagccgg tggcctaacc ccttacgggg agggagccgt  1440
cgaaggtggg atcggcgatt gggacgaagt cgtaacaagg tagccgtacc ggaaggtgcg  1500
gctggatcac ctccttt                                                 1517

SEQ ID NO: 39           moltype = DNA  length = 1482
FEATURE                 Location/Qualifiers
source                  1..1482
                        mol_type = genomic DNA
                        organism = Agrobacterium tumefaciens
SEQUENCE: 39
cttgagagtt tgatcctggc tcagaacgaa cgctggcggc aggcttaaca catgcaagtc  60
gaacgccccg caaggggagt ggcagacggg tgagtaacgc gtgggaatct accgtgccct  120
gcggaatagc tccgggaaac tggaattaat accgcatacg ccctacgggg gaaagattta  180
tcggggtatg atgagcccgc gttggattag ctagttggtg gggtaaaggc ctaccaaggc  240
gacgatccat agctggtctg agaggatgat cagccacatt gggactgaga cacggcccaa  300
actcctacgg gaggcagcag tggggaatat tggacaatgg gcgcaagcct gatccagcca  360
tgccgcgtga gtgatgaagg ccttagggtt gtaaagctct ttcaccggag aagataatga  420
cggtatccgg agaagaagcc ccggctaact tcgtgccagc agccgcggta atacgaaggg  480
ggctagcgtt gttcggaatt actgggcgta aagcgcacgt aggcggatat ttaagtcagg  540
ggtgaaatcc cagagctcaa ctctggaact gcctttgata ctgggtatct tgagtatgga  600
agaggtaagt ggaattccga gtgtagaggt gaaattcgta gatattcgga ggaacaccag  660
tggcgaaggc ggcttactgg tccattactg acgctgaggt gcgaaagcgt ggggagcaaa  720
caggattaga taccctggta gtccacgccg taaacgatga atgttagccg tcgggcagta  780
tactgttcgg tggcgcagct aacgcattaa acattccgcc tggggagtac ggtcgcaaga  840
ttaaaactca aaggaattga cgggggcccg cacaagcggt ggagcatgtg gtttaattcg  900
aagcaacgcg cagaacctta ccagctcttg acattcgggg tttgggcagt ggagacattg  960
tccttcagtt aggctggccc cagaacaggt gctgcatggc tgtcgtcagc tcgtgtcgtg  1020
agatgttggg ttaagtcccg caacgagcgc aaccctcgcc cttagttgcc agcatttagt  1080
tgggcactct aaggggactg ccggtgataa gccgagagga aggtggggat gacgtcaagt  1140
```

cctcatggcc cttacgggct gggctacaca cgtgctacaa tggtggtgac agtgggcagc 1200
gagacagcga tgtcgagcta atctccaaaa gccatctcag ttcggattgc actctgcaac 1260
tcgagtgcat gaagttggaa tcgctagtaa tcgcagatca gcatgctgcg gtgaatacgt 1320
tcccgggcct tgtacacacc gcccgtcaca ccatgggagt tggttttacc cgaaggtagt 1380
gcgctaaccg caaggaggca gctaaccacg gtagggtcag cgactggggt gaagtcgtaa 1440
caaggtagcc gtaggggaac ctgcggctgg atcacctcct tt 1482

SEQ ID NO: 40 moltype = DNA length = 903
FEATURE Location/Qualifiers
source 1..903
mol_type = genomic DNA
organism = Pantoea sp.
SEQUENCE: 40
ttgacgttac ccgcagaaga agcaccggct aactccgtgc cagcagccgc ggtaatacgg 60
agggtgcaag cgttaatcgg aattactggg cgtaaagcgc acgcaggcgg tctgttaagt 120
cagatgtgaa atccccgggc ttaacctggg aactgcattt gaaactggca ggcttgagtc 180
ttgtagaggg gggtagaatt ccaggtgtag cggtgaaatg cgtagagatc tggaggaata 240
ccggtggcga aggcggcccc ctggacaaag actgacgctc aggtgcgaaa gcgtggggag 300
caaacaggat tagataccct ggtagtccac gccgtaaacg atgtcgactt ggaggttgtt 360
cccttgagga gtggcttccg gagctaacgc gttaagtcga ccgcctgggg agtacggccg 420
caaggttaaa actcaaatga attgacgggg gcccgcacaa gcggtggagc atgtggttta 480
attcgatgca acgcgaagaa ccttacctac tcttgacatc cagagaactt tccagagatg 540
gattggtgcc ttcgggaact ctgagacagg tgctgcatgg ctgtcgtcag ctcgtgttgt 600
gaaatgttgg gttaagtccc gcaacgagcg caacccttat cctttgttgc cagcgcgtga 660
tggcgggaac tcaaaggaga ctgccggtga taaaccggag gaaggtgggg atgacgtcaa 720
gtcatcatgg cccttacgag tagggctaca cacgtgctac aatggcgcat acaaagagaa 780
gcgacctcgc gagagcaagc ggacctcaca aagtgcgtcg tagtccggat cggagtctgc 840
aactcgactc cgtgaagtcg gaatcgctag taatcgtgga tcagaatgcc acggtgaata 900
cgt 903

SEQ ID NO: 41 moltype = DNA length = 1457
FEATURE Location/Qualifiers
source 1..1457
mol_type = genomic DNA
organism = Corynebacterium mucifaciens
SEQUENCE: 41
gtggagagtt tgatcctggc tcaggatgaa cgctggcggc gtgcttaaca catgcaagtc 60
gaacggaaag gcccaagctt gcttgggtac tcgagtggcg aacgggtgag taacacgtgg 120
gtgatctgcc ctgcacttcg ggataagcct gggaaactgg gtctaatacc ggataggacg 180
atggtttgga tgccattgtg gaaagttttt tcggtgtggg atgagctcgc ggcctatcag 240
cttgttggtg gggtaatggc ctaccaaggc gtcgacgggt agccggcctg agagggtgta 300
cggccacatt gggactgaga tacggcccag actcctacgg gaggcagcag tggggaatat 360
tgcacaatgg gcgcaagcct gatgcagcga cgccgcgtgg gggatgacgg ccttcgggtt 420
gtaaactcct ttcgctaggg acgaagcgtt ttgtgacggt acctggagaa gaagcaccgg 480
ctaactacgt gccagcagcc gcggtaatac gtagggtgcg agcgttgtcc ggaattactg 540
ggcgtaaaga gctcgtaggt ggtttgtcgc gtcgtttgtg taagcccgca gcttaactgc 600
gggactgcag gcgatacggg cataacttga gtgctgtagg ggagactgga attcctggtg 660
tagcggtgga atgcgcagat atcaggagga acaccgatgg cgaaggcagg tctctgggca 720
gtaactgacg ctgaggagcg aaagcatggg tagcgaacag gattagatac cctggtagtc 780
catgccgtaa acggtgggcg ctaggtgtga gtcccttcca cggggttcgt gccgtagcta 840
acgcattaag cgccccgcct ggggagtacg gccgcaaggc taaaactcaa aggaattgac 900
gggggcccgc acaagcggcg gagcatgtgg attaattcga tgcaacgcga agaaccttac 960
ctgggcttga catacaccag atcgccgtag agatacggtt tccctttgtg gttggtgtac 1020
aggtggtgca tggttgtcgt cagctcgtgt cgtgagatgt tgggttaagt cccgcaacga 1080
gcgcaaccct tgtcttatgt tgccagcacg tgatggtggg gactcgtgag agactgccgg 1140
ggttaactcg gaggaaggtg gggatgacgt caaatcatca tgccccttat gtccagggct 1200
tcacacatgc tacaatggtc ggtacaacgc gcatgcgagc ctgtgagggt gagcgaatcg 1260
ctgtgaaagc cggtcgtagt tcggattggg gtctgcaact cgaccccatg aagtcggagt 1320
cgctagtaat cgcagatcag caacgctgcg gtgaatacgt tcccgggcct tgtacacacc 1380
gcccgtcaca ccatgggagt gggttgcaaa agaagtaggt agcttaacct tcgggagggc 1440
gcttaccact ttgtgat 1457

SEQ ID NO: 42 moltype = DNA length = 1532
FEATURE Location/Qualifiers
source 1..1532
mol_type = genomic DNA
organism = Pseudomonas lundensis
SEQUENCE: 42
tgaagagttt gatcatggct cagattgaac gctggcggca ggcctaacac atgcaagtcg 60
agcggtagag aggtgcttgc acctcttgag agcggcggac gggtgagtaa tacctaggaa 120
tctgcctgat agtgggggat aacgttcgga aacggacgct aataccgcat acgtcctacg 180
ggagaaagca ggggaccttc gggccttgcg ctatcagatg agcctaggtc ggattagcta 240
gttggtgagg taatggctca ccaaggctac gatccgtaac tggtctgaga ggatgatcag 300
tcacactgga actgagacac ggtccagact cctacgggag gcagcagtgg ggaatattgg 360
acaatgggcg aaagcctgat ccagccatgc cgcgtgtgtg aagaaggtct tcggattgta 420
aagcacttta agttgggagg aagggcatta acctaatacg ttagtgtctt gacgttaccg 480
acagaataag caccggctaa ctctgtgcca gcagccgcgg taatacagag ggtgcaagcg 540
ttaatcggaa ttactgggcg taaagcgcgc gtaggtggtt tgttaagttg aatgtgaaat 600
ccccgggctc aacctgggaa ctgcatccaa aactggcaag ctagagtatg gtagagggta 660
gtggaatttc ctgtgtagcg gtgaaatgcg tagatatagg aaggaacacc agtggcgaag 720

-continued

```
gcgactacct ggactgatac tgacactgag gtgcgaaagc gtggggagca aacaggatta  780
gataccctgg tagtccacgc cgtaaacgat gtcaactagc cgttgggaac cttgagttct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatgggag tgggttgcac cagaagtagc tagtctaacc  1440
ctcgggagga cggttaccac ggtgtgattc atgactgggg tgaagtcgta acaaggtagc  1500
cgtaggggaa cctgcggctg gatcacctcc tt                               1532

SEQ ID NO: 43          moltype = DNA  length = 1525
FEATURE                Location/Qualifiers
source                 1..1525
                       mol_type = genomic DNA
                       organism = Janthinobacterium sp.
SEQUENCE: 43
ctgagtttga tcctggctca gattgaacgc tggcggcatg ccttacacat gcaagtcgaa  60
cggcagcacg gagcttgctc tggtggcgag tggcgaacgg gtgagtaata tatcggaacg  120
taccctggag tgggggataa cgtagcgaaa gttacgctaa taccgcatac gatctaagga  180
tgaaagtggg ggatcgcaag acctcatgct cgtggagcgg ccgatatctg attagctagt  240
tggtagggta aaagcctacc aaggcatcga tcagtagctg gtctgagagg acgaccagcc  300
acactggaac tgagacacgg tccagactcc tacgggaggc agcagtgggg aattttggac  360
aatgggcgaa agcctgatcc agcaatgccg cgtgagtgaa gaaggccttc gggttgtaaa  420
gctcttttgt cagggaagaa acggtgagag ctaatatctc ttgctaatga cggtacctga  480
agaataagca ccggctaact acgtgccagc agccgcggta atacgtaggg tgcaagcgtt  540
aatcggaatt actgggcgta aagcgtgcgc aggcggtttt gtaagtctga tgtgaaatcc  600
ccgggctcaa cctgggaatt gcattggaga ctgcaaggct agaatctggc agagggggt  660
agaattccac gtgtagcagt gaaatgcgta gatatgtgga ggaacaccga tggcgaaggc  720
agccccctgg gtcaagattg acgctcatgc acgaaagcgt ggggagcaaa caggattaga  780
taccctggta gtccacgccc taaacgatgt ctactagttg tcgggtctta attgacttgg  840
taacgcagct aacgcgtgaa gtagaccgcc tggggagtac ggtcgcaaga ttaaaactca  900
aaggaattga cggggacccg cacaagcggt ggatgatgtg gattaattcg atgcaacgcg  960
aaaaacctta cctacccttg acatggctgg aatccttgag agatcaggga gtgctcgaaa  1020
gagaaccagt acacaggtgc tgcatggctg tcgtcagctc gtgtcgtgag atgttgggtt  1080
aagtcccgca acgagcgcaa cccttgtcat tagttgctac gaaagggcac tctaatgaga  1140
ctgccggtga caaaccggag gaaggtgggg atgacgtcaa gtcctcatgg cccttatggg  1200
tagggcttca cacgtcatac aatggtacat acagagcgcc gccaacccgc gagggggagc  1260
taatcgcaga aagtgtatcg tagtccggat tgtagtctgc aactcgactg catgaagttg  1320
gaatcgctag taatcgcgga tcagcatgtc gcggtgaata cgttcccggg tcttgtacac  1380
accgcccgtc acaccatggg agcgggtttt accagaagta ggtagcttaa ccgtaaggag  1440
ggcgcttacc acggtaggat tcgtgactgg ggtgaagtcg taacaaggta gccgtatcgg  1500
aaggtgcggc tggatcacct ccttt                                        1525

SEQ ID NO: 44          moltype = DNA  length = 1497
FEATURE                Location/Qualifiers
source                 1..1497
                       mol_type = genomic DNA
                       organism = Herbaspirillum sp.
SEQUENCE: 44
tggcggcatg ccttacacat gcaagtcgaa cggcagcata ggagcttgct cctgatggcg  60
agtggcgaac gggtgagtaa tatatcggaa cgtgccctag agtgggggat aactagtcga  120
aagactagct aataccgcat acgatctacg gatgaaagtg ggggatcgca agacctcatg  180
ctcctggagc ggccgatatc tgattagcta gttggtgggg taaaagctca ccaaggcgac  240
gatcagtagc tggtctgaga ggacgaccag ccacactggg actgagacac ggcccagact  300
cctacgggag gcagcagtgg ggaattttgg acaatggggg caaccctgat ccagcaatgc  360
cgcgtgagtg aagaaggcct tcgggttgta aagctctttt gtcagggaag aaacggttct  420
ggataatacc taggactaat gacggtacct gaagaataag caccggctaa ctacgtgcca  480
gcagccgcgg taatacgtag ggtgcaagcg ttaatcggaa ttactgggcg taaagcgtgc  540
gcaggcggtt gtgtaagtca gatgtgaaat ccccgggctc aacctgggaa ttgcatttga  600
gactgcacgg ctagagtgtg tcagaggggg gtagaattcc acgtgtagca gtgaaatgcg  660
tagatatgtg gaggaatacc gatggcgaag gcagccccct gggataacac tgacgctcat  720
gcacgaaagc gtggggagca aacaggatta gataccctgg tagtccacgc cctaaacgat  780
gtctactagt tgtcgggtct taattgactt ggtaacgcag ctaacgcgtg aagtagaccg  840
cctggggagt acggtcgcaa gattaaaact caaaggaatt gacggggacc cgcacaagcg  900
gtggatgatg tggattaatt cgatgcaacg cgaaaaacct tacctaccct tgacatggat  960
ggaatcccga agagatttgg gagtgctcga aagagaacca tcacacaggt gctgcatggc  1020
tgtcgtcagc tcgtgtcgtg agatgttggg ttaagtcccg caacgagcgc aacccttgtc  1080
attagttgct acgaaagggc actctaatga gactgccggt gacaaaccgg aggaaggtgg  1140
ggatgacgtc aagtcctcat ggcccttatg ggtagggctt cacacgtcat acaatggtac  1200
atacagaggg ccgccaaccc gcgaggggga gctaatccca gaaagtgtat cgtagtccgg  1260
attggagtct gcaactcgac tccatgaagt tggaatcgct agtaatcgcg gatcagcatg  1320
tcgcggtgaa tacgttcccg ggtcttgtac acaccgcccg tcacaccatg ggagcgggtt  1380
ttaccagaag tgggtagcct aaccgcaagg agggcgctca ccacggtagg attcgtgact  1440
ggggtgaagt cgtaacaagg tagccgtatc ggaaggtgcg gctggatcac ctccttt     1497
```

```
SEQ ID NO: 45          moltype = DNA  length = 1522
FEATURE                Location/Qualifiers
source                 1..1522
                       mol_type = genomic DNA
                       organism = Sanguibacter keddieii
SEQUENCE: 45
tacggagagt ttgatcctgg ctcaggacga acgctggcgg cgtgcttaac acatgcaagt  60
cgaacggtga cgctagagct tgctctggtt gatcagtggc gaacgggtga gtaacacgtg  120
agtaacctgc ccttgactct gggataactc cgggaaaccg gggctaatac cggatacgag  180
acgcgaccgc atggtcggcg tctggaaagt tttcggtca aggatggact cgcggcctat  240
cagcttgttg gtgaggtaat ggctcaccaa ggcgtcgacg ggtagccggc ctgagagggc  300
gaccggccac actgggactg agacacggcc cagactccta cgggaggcag cagtggggaa  360
tattgcacaa tgggcgaaag cctgatgcag cgacgccgcg tgagggatga aggccttcgg  420
gttgtaaacc tctttcagta gggaagaagc gaaagtgacg gtacctgcag aagaagcgcc  480
ggctaactac gtgccagcag ccgcggtaat acgtagggcg caagcgttgt ccggaattat  540
tgggcgtaaa gagctcgtag gcggtttgtc gcgtctggtg tgaaaactca aggctcaacc  600
ttgagcttgc atcgggtacg ggcagactag agtgtggtag gggtgactgg aattcctggt  660
gtagcggtgg aatgcgcaga tatcaggagg aacaccgatg gcgaaggcag gtcactgggc  720
cactactgac gctgaggagc gaaagcatgg ggagcgaaca ggattagata ccctggtagt  780
ccatgccgta aacgttgggc actaggtgtg gggctcattc cacgagttcc gcgccgcagc  840
taacgcatta agtgccccgc ctggggagta cggccgcaag gctaaaactc aaaggaattg  900
acgggggccc gcacaagcgg cggagcatgc ggattaattc gatgcaacgc gaagaacctt  960
accaaggctt gacatacacc ggaatcatgc agagatgtgt gcgtcttcgg actggtgtac  1020
aggtggtgca tggttgtcgt cagctcgtgt cgtgagatgt tgggttaagt cccgcaacga  1080
gcgcaaccct cgtcctatgt tgccagcacg ttatggtggg gactcatagg agactgccgg  1140
ggtcaactcg gaggaaggtg gggatgacgt caaatcatca tgccccttat gtcttgggct  1200
tcacgcatgc tacaatggcc ggtacaaagg gctgcgatac cgcgaggtgg agcgaatccc  1260
aaaaagccgg tctcagttcg gattggggtc tgcaactcga ccccatgaag tcggagtcgc  1320
tagtaatcgc agatcagcaa cgctgcggtg aatacgttcc cgggccttgt acacaccgcc  1380
cgtcaagtca cgaaagtcgg taacacccga agccggtggc ctaacccctt gtgggatgga  1440
gccgtcgaag gtgggattgg cgattgggac taagtcgtaa caaggtagcc gtaccggaag  1500
gtgcggctgg atcacctcct tt                                          1522

SEQ ID NO: 46          moltype = DNA  length = 831
FEATURE                Location/Qualifiers
source                 1..831
                       mol_type = genomic DNA
                       organism = Pantoea agglomerans
SEQUENCE: 46
ttgaagagtt tgatcatggc tcagattgaa cgctggcggc aggcctaaca catgcaagtc  60
ggacggtagc acagaggagc ttgctccttg ggtgacgagt ggcggacggg tgagtaatgt  120
ctggggatct gcccgataga gggggataac cactggaaac ggtggctaat accgcataac  180
gtcgcaagac caaagagggg gaccttcggg cctctcacta tcggatgaac ccagatggga  240
ttagctagta ggcggggtaa tggcccacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtatgaag aaggccttcg  420
ggttgtaaag tactttcagc ggggaggaag gcgacagggt taataaccct gtcgattgac  480
gttacccgca gaagaagcac cggctaactc cgtgccagca gccgcggtaa tacggagggt  540
gcaagcgtta atcggaatta ctgggcgtaa agcgcacgca ggcggtctgt taagtcagat  600
gtgaaatccc cgggcttaac ctgggaactg catttgaaac tggcaggctt tagtcttgta  660
gagtggggta gaattccagg tgtagcggtg aaatgcgtag agatgtggag gaacaccagt  720
ggcgaaggcg gctttttggt ctgtaactga cgctgaggcg cgaaagcgtg gggagcaaac  780
aggattagat accctggtag tccacgccgt aaacgatgag tgctaagtgt t          831

SEQ ID NO: 47          moltype = DNA  length = 960
FEATURE                Location/Qualifiers
source                 1..960
                       mol_type = genomic DNA
                       organism = Cronobacter dublinensis
SEQUENCE: 47
agggtgcaag cgttaatcgg aattactggg cgtaaagcgc gcgtaggtgg tttgttaagt  60
tgaatgtgaa atccccgggc tcaacctggg aactgcattt gaaactggca agctagagtc  120
tcgtagaggg gggtagaatt ccaggtgtag cggtgaaatg cgtagagatc tggaggaata  180
ccggtggcga aggcggcccc ctggacgaag actgacgctc aggtgcgaaa gcgtggggag  240
caaacaggat tagataccct ggtagtccac gccgtaaacg atgtcaacta gccgttggaa  300
gccttgagct tttagtggcg cagctaacgc attaagttga ccgcctgggg agtacggccg  360
caaggttaaa actcaaatga attgacgggg gcccgcacaa gcggtggagc atgtggttta  420
attcgaagca acgcgaagaa ccttaccagg ccttgacatc caatgaactt tctagagata  480
gattggtgcc ttcgggaaca ttgagacagg tgctgcatgg ctgtcgtcag ctcgtgtcgt  540
gagatgttgg gttaagtccc gcaacgagcg caacccttgt cctgtgttgc cagcgcgtaa  600
tggcggggac tcgcaggaga ctgccggggt caactcggag gaaggtgggg atgacgtcaa  660
atcatcatgc cccttatgtc ttgggcttca cgcatgctac aatggccggt acaaagggct  720
gcaataccgt gaggtggagc gaatcccaaa aagccggtcc cagttcggat tgaggtctgc  780
aactcgacct catgaagtcg gagtcgctag taatcgcaga tcagcaacgc tgcggtgaat  840
acgttcccgg gtcttgtaca caccgcccgt caagtcatga aagtcggtaa cacctgaagc  900
cggtggccca acccttgtgg agggagccgt cgaaggtggg atcggtaatt aggactaagt  960
```

```
SEQ ID NO: 48          moltype = DNA  length = 1548
FEATURE                Location/Qualifiers
source                 1..1548
                       mol_type = genomic DNA
                       organism = Bacillus paralicheniformis
SEQUENCE: 48
catggagagt ttgatcctgg ctcaggacga acgctggcgg cgtgcctaat acatgcaagt  60
cgagcggaca gatgggagct tgctccctga tgttagcggc ggacgggtga gtaacacgtg  120
ggtaacctgc ctgtaagact gggataactc cgggaaaccg gggctaatac cggatgcttg  180
attgaaccgc atggttcaat tataaaaggt ggcttttagc taccacttac agatggaccc  240
gcggcgcatt agctagttgg tgaggtaacg gctcaccaag gcaacgatgc gtagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggttttcgga tcgtaaaact ctgttgttag ggaagaacaa gtaccgttcg aatagggcgg  480
taccttgacg gtacctaacc agaaagccac ggctaactac gtgccagcag ccgcggtaat  540
acgtaggtgg caagcgttgt ccggaattat tgggcgtaaa gcgcgcgcag gcggtttctt  600
aagtctgatg tgaaagcccc cggctcaacc ggggagggtc attggaaact ggggaacttg  660
agtgcagaag aggagagtgg aattccacgt gtagcggtga aatgcgtaga gatgtggagg  720
aacaccagtg gcgaaggcga ctctctggtc tgtaactgac gctgaggcgc gaaagcgtgg  780
ggagcgaaca ggattagata ccctggtagt ccacgccgta aacgatgagt gctaagtgtt  840
agagggtttc cgccctttag tgctgcagca aacgcattaa gcactccgcc tggggagtac  900
ggtcgcaaga ctgaaactca aaggaattga cgggggcccg cacaagcggt ggagcatgtg  960
gtttaattcg aagcaacgcg aagaacctta ccaggtcttg acatcctctg acaaccctag  1020
agatagggct tccccttcgg gggcagagtg acaggtggtg catggttgtc gtcagctcgt  1080
gtcgtgagat gttgggttaa gtcccgcaac gagcgcaacc cttgatctta gttgccagca  1140
ttcagttggg cactctaagg tgactgccgg tgacaaaccg gaggaaggtg gggatgacgt  1200
caaatcatca tgccccttat gacctgggct acacacgtgc tacaatgggc agaacaaagg  1260
gcagcgaagc cgcgaggcta agccaatccc acaaatctgt tctcagttcg gatcgcagtc  1320
tgcaactcga ctgcgtgaag ctggaatcgc tagtaatcgc ggatcagcat gccgcggtga  1380
atacgttccc gggccttgta cacaccgccc gtcacaccac gagagtttgt aacacccgaa  1440
gtcggtgagg taacctttg gagccagccg ccgaaggtgg gacagatgat tggggtgaag  1500
tcgtaacaag gtagccgtat cggaaggtgc ggctggatca cctccttt              1548

SEQ ID NO: 49          moltype = DNA  length = 1551
FEATURE                Location/Qualifiers
source                 1..1551
                       mol_type = genomic DNA
                       organism = Bacillus gibsonii
SEQUENCE: 49
tatggagagt ttgatcctgg ctcaggacga acgctggcgg cgtgcctaat acatgcaagt  60
cgagcggacg tttttgaagc ttgcttcaaa aacgttagcg gcggacgggt gagtaacacg  120
tgggcaacct gccttatcga ctgggataac tccgggaaac cggggctaat accggataat  180
atctagcacc tcctggtgca agattaaaag agggccttcg ggctctcacg gtgagatggg  240
cccgcggcgc attagctagt tggagaggta atggctcccc aaggcgacga tgcgtagccg  300
acctgagagg gtgatcggcc acactgggac tgagacacgg cccagactcc tacgggaggc  360
agcagtaggg aatcttccgc aatggacgaa agtctgacgg agcaacgccg cgtgagtgat  420
gaagggtttc ggctcgtaaa gctctgttat gagggaagaa cacgtaccgt tcgaataggg  480
cggtaccttg acggtacctc atcagaaagc cacggctaac tacgtgccag cagccgcggt  540
aatacgtagg tggcaagcgt tgtccggaat tattgggcgt aaagcgcgcg caggcggcct  600
tttaagtctg atgtgaaatc ttgcggctca accgcaagcg gtcattggaa actgggaggc  660
ttgagtacag aagaggagag tggaattcca cgtgtagcgg tgaaatgcgt agatatgtgg  720
aggaacacca gtggcgaagg cgactctctg gtctgtaact gacgctgagg cgcgaaagcg  780
tggggagcaa acaggattag ataccctggt agtccacgcc gtaaacgatg agtgctaggt  840
gttaggggtt tcgatgcccg tagtgccgaa gttaacacat taagcactcc gcctggggag  900
tacggccgca aggctgaaac tcaaaggaat tgacgggggc ccgcacaagc agtggagcat  960
gtggtttaat tcgaagcaac gcgaagaacc ttaccaggtc ttgacatcct ttgaccactc  1020
tggagacaga gcttcccctt cgggggcaaa gtgacaggtg gtgcatggtt gtcgtcagct  1080
cgtgtcgtga gatgttgggt taagtcccgc aacgagcgca acccttgacc ttagttgcca  1140
gcatttagtt gggcactcta aggtgactgc cggtgacaaa ccggaggaag gtggggatga  1200
cgtcaaatca tcatgcccct tatgacctgg gctacacacg tgctacaatg gatggtacaa  1260
agggttgcga agccgcgagg tgaagccaat cccataaagc cattctcagt tcggattgta  1320
ggctgcaact cgcctgcatg aagctggaat tgctagtaat cgcggatcag catgccgcgg  1380
tgaatacgtt cccgggcctt gtacacaccg cccgtcacac cacgagagtt tgtaacaccc  1440
gaagtcggtg aggtaacctt ttggagccag ccgccgaagg tgggacagat gattggggtg  1500
aagtcgtaac aaggtagccg tatcggaagg tgcggctgga tcacctcctt t          1551

SEQ ID NO: 50          moltype = DNA  length = 1536
FEATURE                Location/Qualifiers
source                 1..1536
                       mol_type = genomic DNA
                       organism = Enterobacter sp.
SEQUENCE: 50
ttgaagagtt tgatcatggc tcagattgaa cgctggcggc aggcctaaca catgcaagtc  60
gaacggtagc acagagagct tgctcttggg tgacgagtgg cggacgggtg agtaatgtct  120
gggaaactgc ccgatggagg gggataacta ctggaaacgg tagctaatac cgcataacgt  180
cgcaagacca aagtggggga ccttcgggcc tcacaccatc ggatgtgccc agatgggatt  240
agctagtagg tggggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
```

```
ttgtaaagta ctttcagcga ggaggaaggc attgtggtta ataaccgcag tgattgacgt  480
tactcgcaga agaagcaccg gctaactccg tgccagcagc cgcggtaata cggagggtgc  540
aagcgttaat cggaattact gggcgtaaag cgcacgcagg cggtctgtca agtcggatgt  600
gaaatccccg ggctcaacct gggaactgca ttcgaaactg gcaggctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccacggaa tttagcagag atgctttagt  1020
gccttcggga accgtgagac aggtgctgca tggctgtcgt cagctcgtgt tgtgaaatgt  1080
tgggttaagt cccgcaacga gcgcaaccct tatcctttgt tgccagcggt tcggccggga  1140
actcaaagga gactgccagt gataaactgg aggaaggtgg ggatgacgtc aagtcatcat  1200
ggcccttacg agtagggcta cacacgtgct acaatggcat atacaaagag aagcgacctc  1260
gcgagagcaa gcggacctca taaagtatgt cgtagtccgg atcggagtct gcaactcgac  1320
tccgtgaagt cggaatcgct agtaatcgta gatcagaatg ctacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536

SEQ ID NO: 51          moltype = DNA  length = 1537
FEATURE                Location/Qualifiers
source                 1..1537
                       mol_type = genomic DNA
                       organism = Klebsiella aerogenes
SEQUENCE: 51
ttgaagagtt tgatcatggc tcagattgaa cgctggcggc aggcctaaca catgcaagtc  60
gagcggtagc acagggagct tgctcctggg tgacgagcgg cggacgggtg agtaatgtct  120
gggaaactgc ctgatggagg gggataacta ctggaaacgg tagctaatac cgcataacgt  180
cgcaagacca aagaggggga ccttcgggcc tcttgccatc agatgtgccc agatgggatt  240
agctagtagg tgaggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcga ggaggaaggc attaaggtta ataaccttgg tgattgacgt  480
tactcgcaga agaagcaccg gctaactccg tgccagcagc cgcggtaata cggggggtgc  540
aagcgttaat cggaattact gggcgtaaag cgcacgcagg cggtttgtca agtcggatgt  600
gaaatccccg ggctcaacct gggaactgca ttcgaaacgg gcaagctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccagagaa ctttccagag atggattggt  1020
gccttcggga actctgagac aggtgctgca tggctgtcgt cagctcgtgt tgtgaaatgt  1080
tgggttaagt cccgcaacga gcgcaaccct tatcctttgt tgccagcgag taatgtcggg  1140
aactcaaagg agactgccag tgacaaactg gaggaaggtg gggatgacgt caagtcatca  1200
tggcccttac gagtagggct acacacgtgc tacaatggca tatacaaaga gaagcgacct  1260
cgcgagagca agcggacctc acaaagtatg tcgtagtccg gatcggagtc tgcaactcga  1320
ctccgtgaag tcggaatcgc tagtaatcgt agatcagaat gctacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                           1537

SEQ ID NO: 52          moltype = DNA  length = 1517
FEATURE                Location/Qualifiers
source                 1..1517
                       mol_type = genomic DNA
                       organism = Arthrobacter sp.
SEQUENCE: 52
acggagagtt tgatcctggc tcaggatgaa cgctggcggc gtgcttaaca catgcaagtc  60
gaacgatgat cccagcttgc tgggggatta gtggcgaacg ggtgagtaac acgtgagtaa  120
cctgcccttg actctgggat aagcctggga aactgggtct aataccggat atgactgtct  180
gacgcatgtc aggtggtgga aagcttttgt ggttttggat ggactcgcgg cctatcagct  240
tgttggtggg gtaatggcct accaaggcga cgacgggtag ccggcctgag agggtgaccg  300
gccacactgg gactgagaca cggcccagac tcctacggga ggcagcagtg gggaatattg  360
cacaatgggc gcaagcctga tgcagcgacg ccgcgtgagg gatgacggcc ttcgggttgt  420
aaacctcttt cagtagggaa gaagcgaaag tgacggtacc tgcagaagaa gcgccggcta  480
actacgtgcc agcagccgcg gtaatacgta gggcgcaagc gttatccgga attattgggc  540
gtaaagagct cgtaggcggt ttgtcgcgtc tgctgtgaaa gaccggggct caactccggt  600
tctgcagtgg gtacgggcag actagagtgc agtaggggag actggaattc ctggtgtagc  660
ggtgaaatgc gcagatatca ggaggaacac cgatggcgaa ggcaggtctc tgggctgtaa  720
ctgacgctga ggagcgaaag catggggagc gaacaggatt agataccctg gtagtccatg  780
ccgtaaacgt tgggcactag gtgtggggga cattccacgt tttccgcgcc gtagctaacg  840
cattaagtgc cccgcctggg gagtacggcc gcaaggctaa aactcaaagg aattgacggg  900
ggcccgcaca agcggcggag catgcggatt aattcgatgc aacgcgaaga accttaccaa  960
ggcttgacat gaaccggtaa tacctggaaa caggtgcccc gcttgcggtc ggtttacagg  1020
tggtgcatgg ttgtcgtcag ctcgtgtcgt gagatgttgg gttaagtccc gcaacgagcg  1080
caaccctcgt tctatgttgc cagcgcgtta tggcggggac tcataggaga ctgccggggt  1140
caactcggag gaaggtgggg acgacgtcaa atcatcatgc cccttatgtc ttgggcttca  1200
```

```
cgcatgctac aatggccggt acaaagggtt gcgatactgt gaggtggagc taatcccaaa  1260
aagccggtct cagttcggat tggggtctgc aactcgaccc catgaagtcg gagtcgctag  1320
taatcgcaga tcagcaacgc tgcggtgaat acgttcccgg gccttgtaca caccgcccgt  1380
caagtcacga aagttggtaa cacccgaagc cggtggccta acccttgtgg ggggagccgt  1440
cgaaggtggg accggcgatt gggactaagt cgtaacaagg tagccgtacc ggaaggtgcg  1500
gctggatcac ctccttt                                                 1517

SEQ ID NO: 53          moltype = DNA  length = 1406
FEATURE                Location/Qualifiers
source                 1..1406
                       mol_type = genomic DNA
                       organism = Pseudomonas fragi
SEQUENCE: 53
tgaagagttt gatcatggct cagattgaac gctggcggca ggcctaacac atgcaagtcg  60
agcggtagag agaagcttgc ttctcttgag agcggcggac gggtgagtaa tacctaggaa  120
tctgcctgat agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggctac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagtt acctaatacg tgattgtctt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggta  660
gtggaatttc ctgtgtagcg gtgaaatgcg tagatatagg aaggaacacc agtggcgaag  720
gcgactacct ggactgatac tgacactgag gtgcgaaagc gtggggagca aacaggatta  780
gataccctgg tagtccacgc cgtaaacgat gtcaactagc cgttgggagt cttgaactct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatg                                       1406

SEQ ID NO: 54          moltype = DNA  length = 1136
FEATURE                Location/Qualifiers
source                 1..1136
                       mol_type = genomic DNA
                       organism = Methylobacterium adhaesivum
SEQUENCE: 54
cttgagagtt tgatcctggc tcagagcgaa cgctggcggc aggcttaaca catgcaagtc  60
gagcgggcac cttcgggtgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
atgacggtac cggaagaata agccccggct aacttcgtgc cagcagccgc ggtaatacga  480
agggggctag cgttgctcgg aatcactggg cgtaaagggc gcgtaggcgg ccattcaagt  540
cggggtgaa agcctgtggc tcaaccacag aattgccttc gatactgttt ggcttgagtt  600
tggtagaggt tggtggaact gcgagtgtag aggtgaaatt cgtagatatt cgcaagaaca  660
ccagtggcga aggcggccaa ctggaccaat actgacgctg aggcgcgaaa gcgtggggag  720
caaacaggat tagataccct ggtagtccac gccgtaaacg atgaatgcta gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgt cgtgccatcc ggagagatcc  960
ggggttccct tcggggacgc gaacacaggt gctgcatggc tgtcgtcagc tcgtgtcgtg  1020
agatgttggg ttaagtcccg caacgagcgc aacccacgtc cttagttgcc atcatttagt  1080
tgggcactct agggagactg ccggtgataa gccgcgagga aggtgtggat gacgtc      1136

SEQ ID NO: 55          moltype = DNA  length = 1374
FEATURE                Location/Qualifiers
source                 1..1374
                       mol_type = genomic DNA
                       organism = Bacillus megaterium
SEQUENCE: 55
tcggagagtt tgatcctggc tcaggatgaa cgctggcggc gtgcctaata catgcaagtc  60
gagcgaactg attagaagct tgcttctatg acgttagcgg cggacgggtg agtaacacgt  120
gggcaacctg cctgtaagac tgggataact tcgggaaacc gaagctaata ccggatagga  180
tcttctcctt catgggagat gattgaaaga tggtttcggc tatcacttac agatgggccc  240
gcggtgcatt agctagttgg tgaggtaacg gctcaccaag gcaacgatgc atagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggctttcggg tcgtaaaact ctgttgttag ggaagaacaa gtacaagagt aactgcttgt  480
accttgacgg tacctaacca gaaagccacg gctaactacg tgccagcagc cgcggtaata  540
```

-continued

```
cgtaggtggc aagcgttatc cggaattatt gggcgtaaag cgcgcgcagg cggtttctta  600
agtctgatgt gaaagcccac ggctcaaccg tggagggtca ttggaaactg ggaacttga   660
gtgcagaaga gaaaagcgga attccacgtg tagcggtgaa atgcgtagag atgtggagga  720
acaccagtgg cgaaggcggc tttttggtct gtaactgacg ctgaggcgcg aaagcgtggg  780
gagcaaacag gattagatac cctggtagtc cacgccgtaa acgatgagtg ctaagtgtta  840
gagggtttcc gccctttagt gctgcagcta acgcattaag cactccgcct ggggagtacg  900
gtcgcaagac tgaaactcaa aggaattgac gggggcccgc acaagcggtg gagcatgtgg  960
tttaattcga agcaacgcga agaaccttac caggtcttga catcctctga caactctaga  1020
gatagagcgt tccccttcgg gggacagagt gacaggtggt gcatggttgt cgtcagctcg  1080
tgtcgtgaga tgttgggtta agtcccgcaa cgagcgcaac ccttgatctt agttgccagc  1140
atttagttgg gcactctaag gtgactgccg gtgacaaacc ggaggaaggt ggggatgacg  1200
tcaaatcatc atgcccctta tgacctgggc tacacacgtg ctacaatgga tggtacaaag  1260
ggctgcaaga ccgcgaggtc aagccaatcc cataaaacca ttctcagttc ggattgtagg  1320
ctgcaactcg cctacatgaa gctggaatcg ctagtaatcg cggatcagca tgct        1374

SEQ ID NO: 56          moltype = DNA  length = 1554
FEATURE                Location/Qualifiers
source                 1..1554
                       mol_type = genomic DNA
                       organism = Paenibacillus lautus
SEQUENCE: 56
attggagagt ttgatcctgg ctcaggacga acgctggcgg cgtgcctaat acatgcaagt  60
cgagcggacc tgatggagtg cttgcactcc tgatggttag cggcggacgg gtgagtaaca  120
cgtaggcaac ctgccctcaa gactgggata actaccggaa acggtagcta ataccggata  180
atttatttca cagcattgtg gaataatgaa agacggagca atctgtcact tggggatggg  240
cctgcggcgc attagctagt tggtggggta acggctcacc aaggcgacga tgcgtagccg  300
acctgagagg gtgaacggcc acactgggac tgagacacgg cccagactcc tacgggaggc  360
agcagtaggg aatcttccgc aatgggcgaa agcctgacgg agcaacgccg cgtgagtgat  420
gaaggttttc ggatcgtaaa gctctgttgc caaggaagaa cgtcttctag agtaactgct  480
aggagagtga cggtacttga gaagaaagcc ccggctaact acgtgccagc agccgcggta  540
atacgtaggg ggcaagcgtt gtccggaatt attgggcgta aagcgcgcgc aggcggttct  600
ttaagtctgg tgtttaaacc cgaggctcaa cttcgggtcg cactggaaac tggggaactt  660
gagtgcagaa gaggagagtg gaattccacg tgtagcggtg aaatgcgtag atatgtggag  720
gaacaccagt ggcgaaggcg actctctggg ctgtaactga cgctgaggcg cgaaagcgtg  780
gggagcaaac aggattagat accctggtag tccacgccgt aaacgatgaa tgctaggtgt  840
taggggtttc gatacccttg gtgccgaagt taacacatta agcattccgc ctggggagta  900
cggtcgcaag actgaaactc aaaggaattg acggggaccc gcacaagcag tggagtatgt  960
ggtttaattc gaagcaacgc gaagaacctt accaagtctt gacatccctc tgaatcctct  1020
agagatagag gcggccttcg ggacagaggt gacaggtggt gcatggttgt cgtcagctcg  1080
tgtcgtgaga tgttgggtta agtcccgcaa cgagcgcaac ccttgatttt agttgccagc  1140
acatcatggt gggcactcta gaatgactgc cggtgacaaa ccggaggaag gcggggatga  1200
cgtcaaatca tcatgcccct tatgacttgg gctacacacg tactacaatg gctggtacaa  1260
cgggaagcga agccgcgagg tggagccaat cctataaaag ccagtctcag ttcggattgc  1320
aggctgcaac tcgcctgcat gaagtcggaa ttgctagtaa tcgcggatca gcatgccgcg  1380
gtgaatacgt tcccgggtct tgtacacacc gcccgtcaca ccacgagagt ttacaacacc  1440
cgaagtcggt ggggtaaccc gcaagggagc cagccgccga aggtggggta gatgattggg  1500
gtgaagtcgt aacaaggtag ccgtatcgga aggtgcggct ggatcacctc cttt        1554

SEQ ID NO: 57          moltype = DNA  length = 1550
FEATURE                Location/Qualifiers
source                 1..1550
                       mol_type = genomic DNA
                       organism = Bacillus mycoides
SEQUENCE: 57
attggagagt ttgatcctgg ctcaggatga acgctggcgg cgtgcctaat acatgcaagt  60
cgagcgaatg gattaagagc ttgctcttat gaagttagcg gcggacgggt gagtaacacg  120
tgggtaacct gcccataaga ctgggataac tccgggaaac cggggctaat accggataac  180
attttgcacc gcatggtgcg aaattcaaag gcggcttcgg ctgtcactta tggatggacc  240
cgcgtcgcat tagctagttg gtgaggtaac ggctcaccaa ggcaacgatg cgtagccgac  300
ctgagagggt gatcggccac actgggactg agacacggcc cagactccta cgggaggcag  360
cagtagggaa tcttccgcaa tggacgaaag tctgacggag caacgccgcg tgagtgatga  420
aggctttcgg gtcgtaaaac tctgttgtta gggaagaaca agtgctagtt gaataagctg  480
gcaccttgac ggtacctaac cagaaagcca cggctaacta cgtgccagca gccgcggtaa  540
tacgtaggtg gcaagcgtta tccggaatta ttgggcgtaa agcgcgcgca ggtggtttct  600
taagtctgat gtgaaagccc acggctcaac cgtggagggt cattggaaac tgggagactt  660
gagtgcagaa gaggaaagtg gaattccatg tgtagcggtg aaatgcgtag agatatggag  720
gaacaccagt ggcgaaggcg actttctggt ctgtaactga cactgaggcg cgaaagcgtg  780
gggagcaaac aggattagat accctggtag tccacgccgt aaacgatgag tgctaagtgt  840
tagagggttt ccgcccttta gtgctgaagt taacgcatta agcactccgc ctggggagta  900
cggccgcaag gctgaaactc aaaggaattg acgggggccc gcacaagcgg tggagcatgt  960
ggtttaattc gaagcaacgc gaagaacctt accaggtctt gacatcctct gacaacccta  1020
gagatagggc ttccccttcg gggcagagt gacaggtggt gcatggttgt cgtcagctcg   1080
tgtcgtgaga tgttgggtta agtcccgcaa cgagcgcaac ccttgatctt agttgccatc  1140
attaagttgg gcactctaag gtgactgccg gtgacaaacc ggaggaaggt ggggatgacg  1200
tcaaatcatc atgcccctta tgacctgggc tacacacgtg ctacaatgga cggtacaaag  1260
agctgcaaga ccgcgaggtg gagctaatct cataaaaccg ttctcagttc ggattgtagg  1320
ctgcaactcg cctacatgaa gctggaatcg ctagtaatcg cggatcagca tgccgcggtg  1380
aatacgttcc cgggccttgt acacaccgcc cgtcacacca cgagagtttg taacacccga  1440
agtcggtggg gtaacctttt tggagccagc cgcctaaggt gggacagatg attggggtga  1500
```

```
agtcgtaaca aggtagccgt atcggaaggt gcggctggat cacctccttt            1550

SEQ ID NO: 58          moltype = DNA  length = 1060
FEATURE                Location/Qualifiers
source                 1..1060
                       mol_type = genomic DNA
                       organism = Janthinobacterium svalbardensis
SEQUENCE: 58
aatgacggta cctgaagaat aagcaccggc taactacgtg ccagcagccg cggtaatacg  60
tagggtgcaa gcgttaatcg gaattactgg gcgtaaagcg tgcgcaggcg gttttgtaag  120
tctgatgtga aatccccggg ctcaacctgg gaattgcatt ggagactgca aggctagaat  180
ctggcagagg ggggtagaat tccacgtgta gcagtgaaat gcgtagatat gtggaggaac  240
accgatggcg aaggcagccc cctgggtcaa gattgacgct catgcacgaa agcgtgggga  300
gcaaacagga ttagataccc tggtagtcca cgccctaaac gatgtctact agttgtcggg  360
tcttaattga cttggtaacg cagctaacgc gtgaagtaga ccgcctgggg agtacggtcg  420
caagattaaa actcaaagga attgacgggg acccgcacaa gcggtggatg atgtggatta  480
attcgatgca acgcgaaaaa ccttacctac ccttgacatg gctggaatcc tcgagagatt  540
ggggagtgct cgaaagagaa ccagtacaca ggtgctgcat ggctgtcgtc agctcgtgtc  600
gtgagatgtt gggttaagtc ccgcaacgag cgcaaccctt gtcattagtt gctacgaaag  660
ggcactctaa tgagactgcc ggtgacaaac cggaggaagg tggggatgac gtcaagtcct  720
catggccctt atgggtaggg cttcacacgt catacaatgg tacatacaga gcgccgccaa  780
cccgcgaggg ggagctaatc gcagaaagtg tatcgtagtc cggattgtag tctgcaactc  840
gactgcatga agttggaatc gctagtaatc gcggatcagc atgtcgcggt gaatacgttc  900
ccgggtcttg tacacaccgc ccgtcacacc atgggagcgg gttttaccag aagtaggtag  960
cttaaccgta aggagggcgc ttaccacggt aggattcgtg actggggtga agtcgtaaca  1020
aggtagccgt atcggaaggt gcggctggat cacctccttt                        1060

SEQ ID NO: 59          moltype = DNA  length = 1538
FEATURE                Location/Qualifiers
source                 1..1538
                       mol_type = genomic DNA
                       organism = Kosakonia cowanii
SEQUENCE: 59
ttgaagagtt tgatcatggc tcagattgaa cgctggcggc aggcctaaca catgcaagtc  60
gaacggtaac aggaagcagc ttgctgcttt gctgacgagt ggcggacggg tgagtaatgt  120
ctgggaaact gcctgatgga gggggataac tactggaaac ggtagctaat accgcataac  180
gtcgcaagac caaagagggg gaccttcggg cctcttgcca tcagatgtgc ccagatggga  240
ttagctagta ggtggggtaa cggctcacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtatgaag aaggccttcg  420
ggttgtaaag tactttcagc ggggaggaag gcgatgcggt taataaccgc gtcgattgac  480
gttacccgca gaagaagcac cggctaactc cgtgccagca gccgcggtaa tacggagggt  540
gcaagcgtta atcggaatta ctgggcgtaa agcgcacgca ggcggtctgt caagtcggat  600
gtgaaatccc cgggctcaac ctgggaactg catccgaaac tggcaggctt gagtctcgta  660
gaggggggta gaattccagg tgtagcggtg aaatgcgtag agatctggag gaataccggt  720
ggcgaaggcg gccccctgga cgaagactga cgctcaggtg cgaaagcgtg gggagcaaac  780
aggattagat accctggtag tccacgccgt aaacgatgtc gacttggagg ttgtgccctt  840
gaggcgtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctggtcttg acatccacag aacttggcag agatgccttg  1020
gtgccttcgg gaactgtgag acaggtgctg catggctgtc gtcagctcgt gttgtgaaat  1080
gttgggttaa gtcccgcaac gagcgcaacc cttatccttt gttgccagcg gttaggccgg  1140
gaactcaaag gagactgcca gtgataaact ggaggaaggt ggggatgacg tcaagtcatc  1200
atggccctta cgaccagggc tacacacgtg ctacaatggc gcatacaaag agaagcgatc  1260
tcgcgagagc cagcggacct cataaagtgc gtcgtagtcc ggattggagt ctgcaactcg  1320
actccatgaa gtcggaatcg ctagtaatcg tgaatcagaa tgtcacggtg aatacgttcc  1380
cgggccttgt acacaccgcc cgtcacacca tgggagtggg ttgcaaaaga agtaggtagc  1440
ttaaccttcg ggagggcgct taccactttg tgattcatga ctggggtgaa gtcgtaacaa  1500
ggtaaccgta ggggaacctg cggttggatc acctcctt                          1538

SEQ ID NO: 60          moltype = DNA  length = 1547
FEATURE                Location/Qualifiers
source                 1..1547
                       mol_type = genomic DNA
                       organism = Bacillus simplex
SEQUENCE: 60
tcggagagtt tgatcctggc tcaggacgaa cgctggcggc gtgcctaata catgcaagtc  60
gagcgaatcg atgggagctt gctccctgag attagcggcg gacgggtgag taacacgtgg  120
gcaacctgcc tataagactg ggataacttc gggaaaccgg agctaatacc ggatacgttc  180
ttttctcgca tgagagaaga tggaaagacg gttttgctgt cacttataga tgggcccgcg  240
gcgcattagc tagttggtga ggtaatggct caccaaggcg acgatgcgta gccgacctga  300
gagggtgatc ggccacactg ggactgagac acggcccaga ctcctacggg aggcagcagt  360
agggaatctt ccgcaatgga cgaaagtctg acggagcaac gccgcgtgaa cgaagaaggc  420
cttcgggtcg taaagttctg ttgttaggga agaacaagta ccagagtaac tgctggtacc  480
ttgacggtac ctaaccagaa agccacggct aactacgtgc cagcagccgc ggtaatacgt  540
aggtggcaag cgttgtccgg aattattggg cgtaaagcgc gcgcaggtgg ttccttaagt  600
ctgatgtgaa agcccacggc tcaaccgtgg agggtcattg gaaactgggg aacttgagtg  660
cagaagagga aagtggaatt ccaagtgtag cggtgaaatg cgtagagatt tggaggaaca  720
ccagtggcga aggcgacttt ctggtctgta actgacactg aggcgcgaaa gcgtggggag  780
```

```
caaacaggat tagataccct ggtagtccac gccgtaaacg atgagtgcta agtgttagag  840
ggtttccgcc ctttagtgct gcagctaacg cattaagcac tccgcctggg gagtacggcc  900
gcaaggctga aactcaaagg aattgacggg ggcccgcaca agcggtggag catgtggttt  960
aattcgaagc aacgcgaaga accttaccag gtcttgacat cctctgacaa ccctagagat  1020
agggcgttcc ccttcggggg acagagtgac aggtggtgca tggttgtcgt cagctcgtgt  1080
cgtgagatgt tgggttaagt cccgcaacga gcgcaaccct tgatcttagt tgccagcatt  1140
cagttgggca ctctaaggtg actgccggtg acaaaccgga ggaaggtggg gatgacgtca  1200
aatcatcatg ccccttatga cctgggctac acacgtgcta caatggatgg tacaaagggc  1260
tgcaaacctg cgaaggtaag cgaatcccat aaagccattc tcagttcgga ttgtaggctg  1320
caactcgcct acatgaagcc ggaatcgcta gtaatcgcgg atcagcatgc cgcggtgaat  1380
acgttcccgg gccttgtaca caccgcccgt cacaccacga gagtttgtaa cacccgaagt  1440
cggtgaggta acctttatgg agccagccgc ctaaggtggg acagatgatt ggggtgaagt  1500
cgtaacaagg tagccgtatc ggaaggtgcg gctggatcac ctcctt                1547

SEQ ID NO: 61          moltype = DNA  length = 962
FEATURE                Location/Qualifiers
source                 1..962
                       mol_type = genomic DNA
                       organism = Lelliottia sp.
SEQUENCE: 61
ggaaggcggt ctgtcaagtc ggatgtgaaa tccccgggct caacctggga actgcattcg  60
aaactggcag gctagagtct tgtagagggg ggtagaattc caggtgtagc ggtgaaatgc  120
gtagagatct ggaggaatac cggtggcgaa ggcggccccc tggacaaaga ctgacgctca  180
ggtgcgaaag cgtggggagc aaacaggatt agataccctg gtagtccacg ccgtaaacga  240
tgtcgacttg gaggttgttc ccttgaggag tggcttccgg agctaacgcg ttaagtcgac  300
cgcctgggga gtacggccgc aaggttaaaa ctcaaatgaa ttgacggggg cccgcacaag  360
cggtggagca tgtggtttaa ttcgatgcaa cgcgaagaac cttacctact cttgacatcc  420
acggaattta gcagagatgc tttagtgcct tcgggaaccg tgagacaggt gctgcatggc  480
tgtcgtcagc tcgtgttgtg aaatgttggg ttaagtcccg caacgagcgc aacccttatc  540
ctttgttgcc agcggtccgg ccgggaactc aaaggagact gccagtgata aactggagga  600
aggtggggat gacgtcaagt catcatggcc cttacgagta gggctacaca cgtgctacaa  660
tggcgcatac aaagagaagc gacctcgcga gagcaagcgg acctcataaa gtgcgtcgta  720
gtccggatcg gagtctgcaa ctcgactccg tgaagtcgga atcgctagta atcgtagatc  780
agaatgctac ggtgaatacg ttcccgggcc ttgtacacac cgcccgtcac accatgggag  840
tgggttgcaa aagaagtagg tagcttaacc ttcgggaggg cgcttaccac tttgtgattc  900
atgactgggg tgaagtcgta acaaggtaac cgtaggggaa cctgcggttg gatcacctcc  960
tt                                                                962

SEQ ID NO: 62          moltype = DNA  length = 876
FEATURE                Location/Qualifiers
source                 1..876
                       mol_type = genomic DNA
                       organism = Erwinia sp.
SEQUENCE: 62
tggctcagat tgaacgctgg cggcaggcct aacacatgca agtcgaacgg tagcacagag  60
gagcttgctc cttgggtgac gagtggcgga cgggtgagta atgtctggga aactgcccga  120
tggaggggga taactactgg aaacggtagc taataccgca taacgtcttc ggaccaaagt  180
gggggacctt cgggcctcac accatcggat gtgcccagat gggattagct agtaggtggg  240
gtaatggctc acctaggcga cgatccctag ctggtctgag aggatgacca gccacactgg  300
aactgagaca cggtccagac tcctacggga ggcagcagtg gggaatattg cacaatgggc  360
gcaagcctga tgcagccatg ccgcgtgtat gaagaaggcc ttcgggttgt aaagtacttt  420
cagtggggag gaaggcgtta aggttaataa ccttggcgat tgacgttacc cgcagaagaa  480
gcaccggcta actccgtgcc agcagccgcg gtaatacgga gggtgcaagc gttaatcgga  540
attactgggc gtaaagcgca cgcaggcggt ctgtcaagtc ggatgtgaaa tccccgggct  600
caacctggga actgcattcg aaactggcag gctagagtct tgtagagggg ggtagaattc  660
caggtgtagc ggtgaaatgc gtagagatct ggaggaatac cggtggcgaa ggcggccccc  720
tggacaaaga ctgacgctca ggtgcgaaag cgtggggagc aaacaggatt agataccctg  780
gtagtccacg ccgtaaacga tgtcgacttg gaggttgttc ccttgaggag tggcttccgg  840
agctaacgcg ttaagtcgac cgcctgggga gtacgg                            876

SEQ ID NO: 63          moltype = DNA  length = 1532
FEATURE                Location/Qualifiers
source                 1..1532
                       mol_type = genomic DNA
                       organism = Pseudomonas azotoformans
SEQUENCE: 63
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg gatgtgaaat  600
ccccgggctc aacctgggaa ctgcattcaa aactgactga ctagagtatg gtagagggtg  660
gtggaatttc ctgtgtagcg gtgaaatgcg tagatatagg aaggaacacc agtggcgaag  720
gcgaccacct ggactaatac tgacactgag gtgcgaaagc gtggggagca aacaggatta  780
```

```
gataccctgg tagtccacgc cgtaaacgat gtcaactagc cgttggaagc cttgagcttt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgttc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac agagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                                1532

SEQ ID NO: 64           moltype = DNA  length = 1024
FEATURE                 Location/Qualifiers
source                  1..1024
                        mol_type = genomic DNA
                        organism = Hanseniaspora uvarum
SEQUENCE: 64
gctcgagttc ttgtttagat cttttacaat aatgtgtatc tttactgaag atgtgcgctt  60
aattgcgctg cttctttaga gtgtcgcagt gaaagtagtc ttgcttgaat ctcagtcaac  120
gctacacaca ttggagtttt tttactttaa tttaattctt tctgctttga atcgaaaggt  180
tcaaggcaaa aaacaaacac aaacaatttt attttattat aattttttaa actaaaccaa  240
aattcctaac ggaaatttta aaataattta aaactttcaa caacggatct cttggttctc  300
gcatcgatga agaacgtagc gaattgcgat aagtaatgtg aattgcagat actcgtgaat  360
cattgaattt ttgaacgcac attgcgccct tgagcattct caggggcatg cctgtttgag  420
cgtcatttcc ttctcaaaag ataatttatt attttttggt tgtgggcgat actcagggtt  480
agcttgaaat tggagactgt ttcagtcttt tttaattcaa cacttagctt ctttggagac  540
gctgttctcg ctgtgatgta tttatggatt tattcgtttt actttacaag ggaaatggta  600
acgtacctta ggcaaagggt tgcttttaat attcatcaag tttgacctca aatcaggtag  660
gattacccgc tgaacttaag catatcaata agcggaggaa aagaaaccaa ctgggattac  720
cttagtaacg gcgagtgaag cggtaaaagc tcaaatttga aatctggtac tttcagtgcc  780
cgagttgtaa tttgtagaat ttgtctttga ttaggtcctt gtctatgttc cttggnanca  840
ggacgtcata gagggtgaga atcccgtttg gcgaggatac cttttctctg taagactttt  900
tcgaanantc gagttgtttg ggaatgcagc tcaaagtggg tggtaaantt ccatctaaag  960
ctaaatnttg gcgagagacc gatagcgaac nagtacagtg atggaaagat gaaaaagaan  1020
tttn                                                               1024

SEQ ID NO: 65           moltype = DNA  length = 1550
FEATURE                 Location/Qualifiers
source                  1..1550
                        mol_type = genomic DNA
                        organism = Bacillus sp.
SEQUENCE: 65
attggagagt ttgatcctgg ctcaggatga acgctggcgg cgtgcctaat acatgcaagt  60
cgagcgaatg gattaagagc ttgctcttat gaagttagcg gcggacgggt gagtaacacg  120
tgggtaacct gcccataaga ctgggataac tccgggaaac cggggctaat accggataac  180
attttgaact gcatggttcg aaattgaaag gcggcttcgg ctgtcactta tggatggacc  240
cgcgtcgcat tagctagttg gtgaggtaac ggctcaccaa ggcaacgatg cgtagccgac  300
ctgagagggt gatcggccac actgggactg agacacggcc cagactccta cgggaggcag  360
cagtagggaa tcttccgcaa tggacgaaag tctgacggag caacgccgcg tgagtgatga  420
aggctttcgg gtcgtaaaac tctgttgtta gggaagaaca agtgctagtt gaataagctg  480
gcaccttgac ggtacctaac cagaaagcca cggctaacta cgtgccagca gccgcggtaa  540
tacgtaggtg gcaagcgtta tccggaatta ttgggcgtaa agcgcgcgca ggtggtttct  600
taagtctgat gtgaaagccc acggctcaac cgtggagggt cattggaaac tgggagactt  660
gagtgcagaa gaggaaagtg gaattccatg tgtagcggtg aaatgcgtag agatatggag  720
gaacaccagt ggcgaaggcg actttctggt ctgtaactga cactgaggcg cgaaagcgtg  780
gggagcaaac aggattagat accctggtag tccacgccgt aaacgatgag tgctaagtgt  840
tagagggttt ccgcccttta gtgctgaagt taacgcatta agcactccgc ctggggagta  900
cggccgcaag gctgaaactc aaaggaattg acgggggccc gcacaagcgg tggagcatgt  960
ggtttaattc gaagcaacgc gaagaacctt accaggtctt gacatcctct gaaaacccta  1020
gagatagggc ttctccttcg ggagcagagt gacaggtggt gcatggttgt cgtcagctcg  1080
tgtcgtgaga tgttgggtta agtcccgcaa cgagcgcaac ccttgatctt agttgccatc  1140
attaagttgg gcactctaag gtgactgccg gtgacaaacc ggaggaaggt ggggatgacg  1200
tcaaatcatc atgcccctta tgacctgggc tacacacgtg ctacaatgga cggtacaaag  1260
agctgcaaga ccgcgaggtg gagctaatct cataaaaccg ttctcagttc ggattgtagg  1320
ctgcaactcg cctacatgaa gctggaatcg ctagtaatcg cggatcagca tgccgcggtg  1380
aatacgttcc cgggccttgt acacaccgcc cgtcacacca cgagagtttg taacacccga  1440
agtcggtggg gtaacctttt tggagccagc cgcctaaggt gggacagatg attggggtga  1500
agtcgtaaca aggtagccgt atcggaaggt gcggctggat cacctccttt            1550
```

-continued

```
SEQ ID NO: 66          moltype = DNA  length = 1034
FEATURE                Location/Qualifiers
source                 1..1034
                       mol_type = genomic DNA
                       organism = Hanseniaspora occidentalis
SEQUENCE: 66
gatttttgg ggttgcttcg aacttgcaga cagagtgtcg agacttgtga gcctgcgctt  60
aattgcgcgg cctagagtcg agtgcttgtt attggctgcg agggacgagt gccttttgaa  120
aaaatccatt acacactgtg aagatttttt ttcatacatt ttacttcttt ggggctttcg  180
agctccaaag gctataaaca caaaccaaac ttttttttt attatttgtt aatcaagaaa  240
ttttcttatt gaaattaaat attttaaaac tttcaacaac ggatctcttg gttctcgcat  300
cgatgaagaa cgtagcgaat tgcgataagt aatgtgaatt gcagattctc gtgaatcatt  360
gaatttttga acgcacattg cgccctctgg tattccaggg ggcatgcctg tttgagcgtc  420
atttccttct caaaatctcg attttggttg tgagtgatac tctgttacag ggttaacttg  480
aaagtgctat tgccctagct actctttttt ttacttgcta agaaaaagat ttttggataa  540
tttcaatgta tttaggtatt tataccgact ttcattggat gctgagagtc ttgtctaagc  600
gcttttgtga gattgagcag aagggattaa cagtattcat aaagtttgac ctcaaatcag  660
gtaggattac ccgctgaact taagcatatc aataagcgga ggaaaagaaa ccaaccggga  720
ttgcctcagt aacggcgagt gaagcggcaa aagctcaaat ttgaaatctg gcactttcag  780
tgtccgagtt gtaatttgta gaagtagttt tgggactggt ccttatctat gtttcttgga  840
acaggacgtc atagagggtg aganccccgta tgatgaggcc cccagtcctt tgtaaaacgc  900
tncgaagagt cgagttgttt gggaatgcag ctctaagtgg gtngnaattn ntctaaagct  960
aaatnnnnnn nanacnntng cganagtacn gtgatgnnga tgannacttt gaaananant  1020
gaaaagtacg tgaa                                                1034

SEQ ID NO: 67          moltype = DNA  length = 980
FEATURE                Location/Qualifiers
source                 1..980
                       mol_type = genomic DNA
                       organism = Bacillus sp.
SEQUENCE: 67
tcgagcggac agatgggagc ttgctccctg atgttagcgg cggacgggtg agtaacacgt  60
gggtaacctg cctgtaagac tgggataact ccgggaaacc ggggctaata ccggatgctt  120
gtttgaaccg catggttcaa acataaaagg tggcttcggc taccacttac agatggaccc  180
gcggcgcatt agctagttgg tgaggtaatg gctcaccaag gcaacgatgc gtagccgacc  240
tgagagggtg atcggccaca ctgggactga gacacggccc agactcctac gggaggcagc  300
agtagggaat cttccgcaat ggacgaaagt ctgacggagc aacgccgcgt gagtgatgaa  360
ggttttcgga tcgtaaagct ctgttgttag ggaagaacaa gtgccgttca aatagggcgg  420
caccttgacg gtacctaacc agaaagccac ggctaactac gtgccagcag ccgcggtaat  480
acgtaggtgg caagcgttgt ccggaattat tgggcgtaaa gggctcgcag gcggtttctt  540
aagtctgatg tgaaagcccc cggctcaacc ggggagggtc attggaaact ggggaacttg  600
agtgcagaag aggagagtgg aattccacgt gtagcggtga aatgcgtaga gatgtggagg  660
aacaccagtg gcgaaggcga ctctctggtc tgtaactgac gctgaggagc gaaagcgtgg  720
ggagcgaaca ggattagata ccctggtagt ccacgccgta aacgatgagt gctaagtgtt  780
agggggtttc cgccccttag tgctgcagct aacgcattaa gcactccgcc tggggagtac  840
ggtcgcaaga ctgaaactca aaggaattga cgggggcccg cacaagcggt ggagcatgtg  900
gtttaattcg aagcaacgcg aagaacctta ccaggtcttg acatcctctg acaccctaga  960
gatagggctt cccttcgggg                                          980

SEQ ID NO: 68          moltype = DNA  length = 680
FEATURE                Location/Qualifiers
source                 1..680
                       mol_type = genomic DNA
                       organism = Bacillus atrophaeus
SEQUENCE: 68
tgcagtcgag cggacagatg ggagcttgct ccctgatgtt agcggcggac gggtgagtaa  60
cacgtgggta acctgcctgt aagactggga taactccggg aaaccggggc taataccgga  120
tgcttgtttg aaccgcatgg ttcaaacata aaaggtggct tcggctacca cttacagatg  180
gacccgcggc gcattagcta gttggtgagg taatggctca ccaaggcaac gatgcgtagc  240
cgacctgaga gggtgatcgg ccacactggg actgagacac ggcccagact cctacgggag  300
gcagcagtag ggaatcttcc gcaatggacg aaagtctgac ggagcaacgc cgcgtgagtg  360
atgaaggttt tcggatcgta aagctctgtt gttagggaag aacaagtgcc gttcaaatag  420
ggcggcacct tgacggtacc taaccagaaa gccacggcta actacgtgcc agcagccgcg  480
gtaatacgta ggtggcaagc gttgtccgga attattgggc gtaaagggct cgcaggcggt  540
ttcttaagtc tgatgtgaaa gcccccggct caaccgggga gggtcattgg aaactgggga  600
acttgagtgc agaagaggag agtggaattc cacgtgtagc ggtgaaatgc gtagagatgt  660
ggaggaacac cagtggcgaa                                          680

SEQ ID NO: 69          moltype = DNA  length = 644
FEATURE                Location/Qualifiers
source                 1..644
                       mol_type = genomic DNA
                       organism = Bacillus sp.
SEQUENCE: 69
tgcagtcgag cggacagatg ggagcttgct ccctgatgtt agcggcggac gggtgagtaa  60
cacgtgggta acctgcctgt aagactggga taactccggg aaaccggggc taataccgga  120
tgcttgtttg aaccgcatgg ttcaaacata aaaggtggct tcggctacca cttacagatg  180
gacccgcggc gcattagcta gttggtgagg taatggctca ccaaggcaac gatgcgtagc  240
cgacctgaga gggtgatcgg ccacactggg actgagacac ggcccagact cctacgggag  300
```

```
gcagcagtag ggaatcttcc gcaatggacg aaagtctgac ggagcaacgc cgcgtgagtg  360
atgaaggttt tcggatcgta aagctctgtt gttagggaag aacaagtgcc gttcaaatag  420
ggcggcacct tgacggtacc taaccagaaa gccacggcta actacgtgcc agcagccgcg  480
gtaatacgta ggtggcaagc gttgtccgga attattgggc gtaaagggct cgcaggcggt  540
ttcttaagtc tgatgtgaaa gcccccggct caaccgggga gggtcattgg aaactgggga  600
acttgagtgc agaagaggag agtggaattc cacgtgtagc ggtg                  644

SEQ ID NO: 70          moltype = DNA  length = 787
FEATURE                Location/Qualifiers
source                 1..787
                       mol_type = genomic DNA
                       organism = Bacillus subtilis
SEQUENCE: 70
tgcaagtcga gcggacagat gggagcttgc tccctgatgt tagcggcgga cgggtgagta  60
acacgtgggt aacctgcctg taagactggg ataactccgg gaaaccgggg ctaataccgg  120
atggttgttt gaaccgcatg gttcaaacat aaaaggtggc ttcggctacc acttacagat  180
ggacccgcgg cgcattagct agttggtgag gtaacggctc accaaggcaa cgatgcgtag  240
ccgacctgag agggtgatcg gccacactgg gactgagaca cggcccagac tcctacggga  300
ggcagcagta gggaatcttc cgcaatggac gaaagtctga cggagcaacg ccgcgtgagt  360
gatgaaggtt ttcggatcgt aaagctctgt tgttagggaa gaacaagtac cgttcgaata  420
gggcggtacc ttgacggtac ctaaccagaa agccacggct aactacgtgc cagcagccgc  480
ggtaatacgt aggtggcaag cgttgtccgg aattattggg cgtaaagggc tcgcaggcgg  540
tttcttaagt ctgatgtgaa agcccccggc tcaaccgggg agggtcattg gaaactgggg  600
aacttgagtg cagaagagga gagtggaatt ccacgtgtag cggtgaaatg cgtagagatg  660
tggaggaaca ccagtggcga aggcgactct ctggtctgta actgacgctg angagcgaaa  720
gcgtggggag cgaacaggat tagataccct ggtagtccac gccgtaaacg atgagtgcta  780
agtgtta                                                           787

SEQ ID NO: 71          moltype = DNA  length = 914
FEATURE                Location/Qualifiers
source                 1..914
                       mol_type = genomic DNA
                       organism = Rhodotorula sp.
SEQUENCE: 71
ttacttggag tccgaactct cactttttaa ccctgtgcat ctgttaattg gaatagtagc  60
tcttcggagt gaaccaccat tcacttataa aacacaaagt ctatgaatgt atacaaattt  120
ataacaaaac aaaactttca acaacggatc tcttggctct cgcatcgatg aagaacgcag  180
cgaaatgcga tacgtaatgt gaattgcaga attcagtgaa tcatcgaatc tttgaacgca  240
ccttgcgctc cttggtattc cgaggagcat gcctgtttga gtgtcatgaa atcttcaacc  300
cacctctttc ttagtgaatc tggtggtgct tggtttctga gcgctgctct gcttcggctt  360
agctcgttcg taatgcatta gcatccgcaa ccgaacttcg gattgacttg gcgtaataga  420
ctattcgctg aggattctag tttactagag ccgagttggg ttaaaggaag ctcctaatcc  480
taaagtctat tttttgatta gatctcaaat caggtaggac tacccgctga acttaagcat  540
atcaataagc ggaggaaaag aaactaacaa ggattcccct agtagcggcg agcgaagcgg  600
gaagagctca aatttataat ctggcacctt cggtgtccga gttgtaatct ctagaagtgt  660
tttccgcgtt ggaccgcaca caagtctgtt ggaatacagc ggcatagtgg tgaaaccccc  720
gtatatggtg cggacgccca gcgctttgtg atacactttc aatgagtcga gttgtttggg  780
aatgcagctc aaattgggtg gtaaattcca tctaaagcta aatattggcg agagaccgat  840
agcgaacaag taccgtgagg gaaagatgaa aagcactttg gaaagagagt taacagtacg  900
tgaaattgtt ggaa                                                   914

SEQ ID NO: 72          moltype = DNA  length = 1547
FEATURE                Location/Qualifiers
source                 1..1547
                       mol_type = genomic DNA
                       organism = Bacillus zhangzhouensis
SEQUENCE: 72
ttcggagagt ttgatcctgg ctcaggacga acgctggcgg cgtgcctaat acatgcaagt  60
cgagcggaca gaagggagct tgctcccgga tgttagcggc ggacgggtga gtaacacgtg  120
ggtaacctgc ctgtaagact gggataactc cgggaaaccg gagctaatac cggatagttc  180
cttgaaccgc atggttcaag gatgaaagac ggtttcggct gtcacttaca gatggacccg  240
cggcgcatta gctagttggt ggggtaatgg ctcaccaagg cgacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgatgaag  420
gttttcggat cgtaaagctc tgttgttagg gaagaacaag tgcgagagta actgctcgca  480
ccttgacggt acctaaccag aaagccacgg ctaactacgt gccagcagcc gcggtaatac  540
gtaggtggca agcgttgtcc ggaattattg ggcgtaaagg gctcgcaggc ggtttcttaa  600
gtctgatgtg aaagcccccg gctcaaccgg ggagggtcat tggaaactgg gaaacttgag  660
tgcagaagag gagagtggaa ttccacgtgt agcggtgaaa tgcgtagaga tgtggaggaa  720
caccagtggc gaaggcgact ctctggtctg taactgacgc tgaggagcga aagcgtgggg  780
agcgaacagg attagatacc ctggtagtcc acgccgtaaa cgatgagtgc taagtgttag  840
ggggtttccg ccccttagtg ctgcagctaa cgcattaagc actccgcctg gggagtacgg  900
tcgcaagact gaaactcaaa ggaattgacg ggggcccgca caagcggtgg agcatgtggt  960
ttaattcgaa gcaacgcgaa gaaccttacc aggtcttgac atcctctgac aaccctagag  1020
atagggcttt cccttcgggg acagagtgac aggtggtgca tggttgtcgt cagctcgtgt  1080
cgtgagatgt tgggttaagt cccgcaacga gcgcaaccct tgatcttagt tgccagcatt  1140
tagttgggca ctctaaggtg actgccggtg acaaaccgga ggaaggtggg gatgacgtca  1200
aatcatcatg ccccttatga cctgggctac acacgtgcta caatggacag aacaaagggc  1260
tgcgagaccg caaggtttag ccaatcccat aaatctgttc tcagttcgga tcgcagtctg  1320
```

```
caactcgact gcgtgaagct ggaatcgcta gtaatcgcgg atcagcatgc cgcggtgaat  1380
acgttcccgg gccttgtaca caccgcccgt cacaccacga gagtttgcaa cacccgaagt  1440
cggtgaggta acctttatgg agccagccgc cgaaggtggg gcagatgatt ggggtgaagt  1500
cgtaacaagg tagccgtatc ggaaggtgcg gctggatcac ctcctttt               1547

SEQ ID NO: 73          moltype = DNA  length = 841
FEATURE                Location/Qualifiers
source                 1..841
                       mol_type = genomic DNA
                       organism = Bacillus clausii
SEQUENCE: 73
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc cccttagact gggataactc cgggaaaccg gagctaatac cggataatcc  180
ctttctccac ctggagagag ggtgaaagat ggcttcggct atcactaagg gatgggcccg  240
cggcgcatta gctagttggt aaggtaacgg cttaccaagg cgacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgaggaag  420
gccttcgggt cgtaaagctc tgttgtgagg gaagaagcgg tgccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
g                                                                  841

SEQ ID NO: 74          moltype = DNA  length = 1105
FEATURE                Location/Qualifiers
source                 1..1105
                       mol_type = genomic DNA
                       organism = Bacillus coagulans
SEQUENCE: 74
gcctaataca tgcaagtcgt gcggaccttt taaaagcttg cttttaaaag gttagcggcg  60
aacgggtgag taacacgtgg gcaacctgcc tgtaagatcg ggataatgcc gggaaaccgg  120
ggctaatacc ggatagtttt ttcctccgca tggaggaaaa aggaaagacg gcttcggctg  180
tcacttacag atgggcccgc ggcgcattag cttgttggtg gggtaacggc tcaccaaggc  240
aacgatgcgt agccgacctg agagggtgat cggccacatt gggactgaga cacggcccaa  300
actcctacgg gaggcagcag tagggaatct tccgcaatgg acgaaagtct gacggagcaa  360
cgccgcgtga gtgaagaagg ccttcgggtc gtaaaactct gttgccgggg aagaacaagt  420
gccgttcgaa cagggcggcg ccttgacggt acccggccag aaagccacgg ctaactacgt  480
gccagcagcc gcggtaatac gtaggtggca agcgttgtcc ggaattattg ggcgtaaagc  540
gcgcgcaggc ggcttcttaa gtctgatgtg aaatcttgcg gctcaaccgc aagcggtcat  600
tggaaactgg gaggcttgag tgcagaagag gagagtggaa ttccacgtgt agcggtgaaa  660
tgcgtagaga tgtggaggaa caccagtggc gaaggcggct ctctggtctg taactgacgc  720
tgaggcgcga aagcgtgggg agcaaacagg attagatacc ctggtagtcc acgccgtaaa  780
cgatgagtgc taagtgttag agggtttccg ccctttagtg ctgcagctaa cgcattaagc  840
actccgcctg gggagtacgg ccgcaaggct gaaactcaaa ggaattgacg gggcccgca   900
caagcggtgg agcatgtggt ttaattcgaa gcaacgcgaa gaaccttacc aggtcttgac  960
atcctctgac ctccctggag acagggcctt ccccttcggg ggacagagtg acaggtggtg  1020
catggttgtc gtcagctcgt gtcgtgagat gttgggttaa gtcccgcaac gagcgcaacc  1080
cttgacctta gttgccagca ttcag                                        1105

SEQ ID NO: 75          moltype = DNA  length = 1515
FEATURE                Location/Qualifiers
source                 1..1515
                       mol_type = genomic DNA
                       organism = Pseudomonas gessardii
SEQUENCE: 75
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt cgttaagttg gatgtgaaag  600
ccccgggctc aacctgggaa ctgcattcaa aactgacgag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttggaatc cttgagattt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga tgggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
```

```
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaacggga ggacggttac  1440
cacggtgtga ttcatgactg gggtgaagtc gtaacaaggt agccgtaggg gaacctgcgg  1500
ctggatcacc tcctt                                                   1515

SEQ ID NO: 76          moltype = DNA  length = 1479
FEATURE                Location/Qualifiers
source                 1..1479
                       mol_type = genomic DNA
                       organism = Ochrobactrum sp.
SEQUENCE: 76
cttgagagtt tgatcctggc tcagaacgaa cgctggcggc aggcttaaca catgcaagtc  60
gagcgccccg caaggggagc ggcagacggg tgagtaacgc gtgggaatct accttttgct  120
acggaacaac agttggaaac gactgctaat accgtatgtg cccttcgggg gaaagattta  180
tcggcaaagg atgagcccgc gttggattag ctagttggtg aggtaaaggc tcaccaaggc  240
gacgatccat agctggtctg agaggatgat cagccacact gggactgaga cacggcccag  300
actcctacgg gaggcagcag tggggaatat tggacaatgg gcgcaagcct gatccagcca  360
tgccgcgtga gtgatgaagg ccctagggtt gtaaagctct ttcaccggtg aagataatga  420
cggtaaccgg agaagaagcc ccggctaact tcgtgccagc agccgcggta atacgaaggg  480
ggctagcgtt gttcggattt actgggcgta aagcgcacgt aggcggattt ttaagtcagg  540
ggtgaaatcc cggggctcaa ccccggaact gcctttgata ctggaagtct tgagtatggt  600
agaggtgagt ggaattccga gtgtagaggt gaaattcgta gatattcgga ggaacaccag  660
tggcgaaggc ggctcactgg accattactg acgctgaggt gcgaaagcgt ggggagcaaa  720
caggattaga taccctggta gtccacgccg taaacgatga atgttagccg tcggggggtt  780
tacctttcgg tggcgcagct aacgcattaa acattccgcc tggggagtac ggtcgcaaga  840
ttaaaactca aaggaattga cgggggcccg cacaagcggt ggagcatgtg gtttaattcg  900
aagcaacgcg cagaacctta ccagcccttg acataccggt cgcggacaca gagatgtgtc  960
tttcagttcg gctggaccgg atacaggtgc tgcatggctg tcgtcagctc gtgtcgtgag  1020
atgttgggtt aagtcccgca acgagcgcaa ccctcgcctt tagttgccag catttagttg  1080
ggcactctaa agggactgcc agtgataagc tggaggaagg tggggatgac gtcaagtcct  1140
catggccctt acgggctggg ctacacacgt gctacaatgg tggtgacagt gggcagcaag  1200
cacgcgagtg tgagctaatc tccaaaagcc atctcagttc ggattgcact ctgcaactcg  1260
agtgcatgaa gttggaatcg ctagtaatcg cggatcagca tgccgcggtg aatacgttcc  1320
cgggccttgt acacaccgcc cgtcacacca tgggagttgg ttttacccga aggcactgtg  1380
ctaaccgcaa ggaggcaggt gaccacggta gggtcagcga ctggggtgaa gtcgtaacaa  1440
ggtagccgta ggggaacctg cggctggatc acctcctt                          1479

SEQ ID NO: 77          moltype = DNA  length = 1549
FEATURE                Location/Qualifiers
source                 1..1549
                       mol_type = genomic DNA
                       organism = Bacillus aryabhattai
SEQUENCE: 77
tcggagagtt tgatcctggc tcaggatgaa cgctggcggc gtgcctaata catgcaagtc  60
gagcgaactg attagaagct tgcttctatg acgttagcgg cggacgggtg agtaacacgt  120
gggcaacctg cctgtaagac tgggataact tcgggaaacc gaagctaata ccggatagga  180
tcttctcctt catgggagat gattgaaaga tggtttcggc tatcacttac agatgggccc  240
gcggtgcatt agctagttgg tgaggtaacg gctcaccaag gcaacgatgc atagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggctttcggg tcgtaaaact ctgttgttag ggaagaacaa gtacaagagt aactgcttgt  480
accttgacgg tacctaacca gaaagccacg gctaactacg tgccagcagc cgcggtaata  540
cgtaggtggc aagcgttatc cggaattatt gggcgtaaag cgcgcgcagg cggtttctta  600
agtctgatgt gaaagcccac ggctcaaccg tggagggtca ttggaaactg gggaacttga  660
gtgcagaaga gaaaagcgga attccacgtg tagcggtgaa atgcgtagag atgtggagga  720
acaccagtgg cgaaggcggc tttttggtct gtaactgacg ctgaggcgcg aaagcgtggg  780
gagcaaacag gattagatac cctggtagtc cacgccgtaa acgatgagtg ctaagtgtta  840
gagggtttcc gccctttagt gctgcagcta acgcattaag cactccgcct ggggagtacg  900
gtcgcaagac tgaaactcaa aggaattgac gggggcccgc acaagcggtg gagcatgtgg  960
tttaattcga agcaacgcga agaaccttac caggtcttga catcctctga caactctaga  1020
gatagagcgt tccccttcgg gggacagagt gacaggtggt gcatggttgt cgtcagctcg  1080
tgtcgtgaga tgttgggtta agtcccgcaa cgagcgcaac ccttgatctt agttgccagc  1140
attcagttgg gcactctaag gtgactgccg gtgacaaacc ggaggaaggt ggggatgacg  1200
tcaaatcatc atgcccctta tgacctgggc tacacacgtg ctacaatgga tggtacaaag  1260
ggctgcaaga ccgcgaggtc aagccaatcc cataaaacca ttctcagttc ggattgtagg  1320
ctgcaactcg cctacatgaa gctggaatcg ctagtaatcg cggatcagca tgccgcggtg  1380
aatacgttcc cgggccttgt acacaccgcc cgtcacacca cgagagtttg taacacccga  1440
agtcggtgga gtaaccgtaa ggagctagcc gcctaaggtg ggacagatga ttggggtgaa  1500
gtcgtaacaa ggtagccgta tcggaaggtg cggctggatc acctcctt                1549
```

```
SEQ ID NO: 78          moltype = DNA  length = 1537
FEATURE                Location/Qualifiers
source                 1..1537
                       mol_type = genomic DNA
                       organism = Erwinia rhapontici
SEQUENCE: 78
ttgaagagtt tgatcatggc tcagattgaa cgctggcggc aggcctaaca catgcaagtc  60
gaacggtagc acagagagct tgctcttggg tgacgagtgg cggacgggtg agtaatgtct  120
gggaaactgc ccgatggagg gggataacta ctggaaacgg tagctaatac cgcataacgt  180
cttcggacca aagtggggga ccttcgggcc tcacaccatc ggatgtgccc agatgggatt  240
agctagtagg tggggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagtgg ggaggaaggc gatgaagtta atagcttcgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtca agtcggatgt  600
gaaatccccg ggctcaacct gggaactgca ttcgaaactg gcaggctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tggccttgac atccacggaa ttcggcagag atgccttagt  1020
gccttcggga accgtgagac aggtgctgca tggctgtcgt cagctcgtgt tgtgaaatgt  1080
tgggttaagt cccgcaacga gcgcaaccct tatcctttgt tgccagcgag taatgtcggg  1140
aactcaaagg agactgccgg tgataaaccg gaggaaggtg gggatgacgt caagtcatca  1200
tggcccttac ggccagggct acacacgtgc tacaatggcg catacaaaga gaagcgacct  1260
cgcgagagca agcggacctc ataaagtgcg tcgtagtccg gatcggagtc tgcaactcga  1320
ctccgtgaag tcggaatcgc tagtaatcgt agatcagaat gctacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                          1537

SEQ ID NO: 79          moltype = DNA  length = 1532
FEATURE                Location/Qualifiers
source                 1..1532
                       mol_type = genomic DNA
                       organism = Pseudomonas fragi
SEQUENCE: 79
tgaagagttt gatcatggct cagattgaac gctggcggca ggcctaacac atgcaagtcg  60
agcggtagag agaagcttgc ttctcttgag agcggcggac gggtgagtaa tacctaggaa  120
tctgcctgat agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggctac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagtt acctaatacg tgactgtctt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggta  660
gtggaatttc ctgtgtagcg gtgaaatgcg tagatatagg aaggaacacc agtggcgaag  720
gcgactacct ggactgatac tgacactgag gtgcgaaagc gtggggagca aacaggatta  780
gataccctgg tagtccacgc cgtaaacgat gtcaactagc cgttgggagt cttgaactct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                               1532

SEQ ID NO: 80          moltype = DNA  length = 1136
FEATURE                Location/Qualifiers
source                 1..1136
                       mol_type = genomic DNA
                       organism = Methylobacterium adhaesivum
SEQUENCE: 80
cttgagagtt tgatcctggc tcagagcgaa cgctggcggc aggcttaaca catgcaagtc  60
gagcgggcac cttcgggtgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
```

-continued

```
atgacggtac cggaagaata agccccggct aacttcgtgc cagcagccgc ggtaatacga  480
agggggctag cgttgctcgg aatcactggg cgtaaagggc gcgtaggcgg ccattcaagt  540
cgggggtgaa agcctgtggc tcaaccacag aattgccttc gatactgttt ggcttgagtt  600
tggtagaggt tggtggaact gcgagtgtag aggtgaaatt cgtagatatt cgcaagaaca  660
ccagtggcga aggcggccaa ctggaccaat actgacgctg aggcgcgaaa gcgtggggag  720
caaacaggat tagataccct ggtagtccac gccgtaaacg atgaatgcta gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgt cgtgccatcc ggagagatcc  960
ggggttccct tcggggacgc gaacacaggt gctgcatggc tgtcgtcagc tcgtgtcgtg  1020
agatgttggg ttaagtcccg caacgagcgc aacccacgtc cttagttgcc atcatttagt  1080
tgggcactct agggagactg ccggtgataa gccgcgagga aggtgtggat gacgtc      1136

SEQ ID NO: 81          moltype = DNA  length = 1547
FEATURE                Location/Qualifiers
source                 1..1547
                       mol_type = genomic DNA
                       organism = Bacillus clausii
SEQUENCE: 81
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc cccttagact gggataactc cgggaaaccg gagctaatac cggataatcc  180
ctttctccac ctggagagag ggtgaaagat ggcttcggct atcactaggg gatgggcccg  240
cggcgcatta gctagttggt aaggtaacgg cttaccaagg cgacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgaggaag  420
gctttcgggt cgtaaagctc tgttgtgagg gaagaagcgg taccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
ggggtttcga tgcccgtagt gccgaagtta acacattaag cactccgcct ggggagtacg  900
gccgcaaggc tgaaactcaa aggaattgac ggggacccgc acaagcagtg gagcatgtgg  960
tttaattcga agcaacgcga agaaccttac caggtcttga catcctttga ccacccaaga  1020
gattgggctt ccccttcggg ggcaaagtga caggtggtgc atggttgtcg tcagctcgtg  1080
tcgtgagatg ttgggttaag tcccgcaacg agcgcaaccc ttgatcttag ttgccagcat  1140
tgagttgggc actctaaggt gactgccggt gacaaaccgg aggaaggtgg ggatgacgtc  1200
aaatcatcat gccccttatg acctgggcta cacacgtgct acaatggatg gtacaaaggg  1260
cagcgaaacc gcgaggtgaa gccaatccca taaagccatt ctcagttcgg attgcaggct  1320
gcaactcgcc tgcatgaagc cggaattgct agtaatcgcg gatcagcatg ccgcggtgaa  1380
tacgttcccg ggtcttgtac acaccgcccg tcacaccacg agagtttgta acacccgaag  1440
tcggtgaggc aacctttttgg agccagccgc ctaaggtggg acaaatgatt ggggtgaagt  1500
cgtaacaagg tagccgtatc ggaaggtgcg gctggatcac ctccttt            1547

SEQ ID NO: 82          moltype = DNA  length = 1547
FEATURE                Location/Qualifiers
source                 1..1547
                       mol_type = genomic DNA
                       organism = Bacillus clausii
SEQUENCE: 82
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc cccttagact gggataactc cgggaaaccg gagctaatac cggataatcc  180
ctttctccac ctggagagag ggtgaaagat ggcttcggct atcactaagg gatgggcccg  240
cggcgcatta gctagttggt aaggtaacgg cttaccaagg caacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgaggaag  420
gccttcgggt cgtaaagctc tgttgtgagg gaagaagcgg taccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
ggggtttcga tgcccgtagt gccgaagtta acacattaag cactccgcct ggggagtacg  900
gccgcaaggc tgaaactcaa aggaattgac ggggacccgc acaagcagtg gagcatgtgg  960
tttaattcga agcaacgcga agaaccttac caggtcttga catcctttga ccacccaaga  1020
gattgggctt ccccttcggg ggcaaagtga caggtggtgc atggttgtcg tcagctcgtg  1080
tcgtgagatg ttgggttaag tcccgcaacg agcgcaaccc ttgatcttag ttgccagcat  1140
tcagttgggc actctaaggt gactgccggt gacaaaccgg aggaaggtgg ggatgacgtc  1200
aaatcatcat gccccttatg acctgggcta cacacgtgct acaatggatg gtacaaaggg  1260
cagcgaaacc gcgaggtgaa gccaatccca taaagccatt ctcagttcgg attgcaggct  1320
gcaactcgcc tgcatgaagc cggaattgct agtaatcgcg gatcagcatg ccgcggtgaa  1380
tacgttcccg ggtcttgtac acaccgcccg tcacaccacg agagtttgta acacccgaag  1440
tcggtgaggc aacctttttgg agccagccgc ctaaggtggg acaaatgatt ggggtgaagt  1500
cgtaacaagg tagccgtatc ggaaggtgcg gctggatcac ctccttt            1547
```

```
SEQ ID NO: 83          moltype = DNA  length = 1548
FEATURE                Location/Qualifiers
source                 1..1548
                       mol_type = genomic DNA
                       organism = Bacillus clausii
SEQUENCE: 83
acggagagtt tgatcctggc tcaggacgaa cgctggcggc gtgcctaata catgcaagtc  60
gagcggagtt tcaagaagct tgctttttga aacttagcgg cggacgggtg agtaacacgt  120
gggcaacctg cccccttagac tgggataact ccgggaaacc ggagctaata ccggataatc  180
cctttctcca cctggagaga gggtgaaaga tggcttcggc tatcactaag ggatgggccc  240
gcggcgcatt agctagttgg taaggtaacg gcttaccaag gcaacgatgc gtagccgacc  300
tgagagggtg atcggccaca ctgggactga gacacggccc agactcctac gggaggcagc  360
agtagggaat cttccgcaat ggacgaaagt ctgacggagc aacgccgcgt gagtgaggaa  420
ggccttcggg tcgtaaagct ctgttgtgag ggaagaagcg gtaccgttcg aatagggcgg  480
taccttgacg gtacctcacc agaaagccac ggctaactac gtgccagcag ccgcggtaat  540
acgtaggtgg caagcgttgt ccggaattat tgggcgtaaa gcgcgcgcag gcggcttctt  600
aagtctgatg tgaaatctcg gggctcaacc ccgagcggcc attggaaact ggggagcttg  660
agtgcagaag aggagagtgg aattccacgt gtagcggtga aatgcgtaga gatgtggagg  720
aacaccagtg gcgaaggcga ctctctggtc tgtaactgac gctgaggcgc gaaagcgtgg  780
ggagcaaaca ggattagata ccctggtagt ccacgccgta aacgatgagt gctaggtgtt  840
aggggtttcg atgcccgtag tgccgaagtt aacacattaa gcactccgcc tggggagtac  900
ggccgcaagg ctgaaactca aaggaattga cggggacccg cacaagcagt ggagcatgtg  960
gtttaattcg aagcaacgcg aagaacctta ccaggtcttg acatcctttg accacccaag  1020
agattgggct tccccttcgg gggcaaagtg acaggtggtg catggttgtc gtcagctcgt  1080
gtcgtgagat gttgggttaa gtcccgcaac gagcgcaacc cttgatctta gttgccagca  1140
ttcagttggg cactctaagg tgactgccgg tgacaaaccg gaggaaggtg gggatgacgt  1200
caaatcatca tgccccttat gacctgggct acacacgtgc tacaatggat ggtacaaagg  1260
gcagcgaagc cgcgaggtga agccaatccc ataaagccat tctcagttcg gattgcaggc  1320
tgcaactcgc ctgcatgaag ccggaattgc tagtaatcgc ggatcagcat gccgcggtga  1380
atacgttccc gggtcttgta cacaccgccc gtcacaccac gagagtttgt aacacccgaa  1440
gtcggtgagg caacctttg gagccagccg cctaaggtgg gacaaatgat tggggtgaag  1500
tcgtaacaag gtagccgtat cggaaggtgc ggctggatca cctccttt              1548

SEQ ID NO: 84          moltype = DNA  length = 1480
FEATURE                Location/Qualifiers
source                 1..1480
                       mol_type = genomic DNA
                       organism = Microbacterium sp.
SEQUENCE: 84
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagct  180
ctcatcgcat ggtgggggtt ggaaagattt tttggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catacaccag aacgggccag aaatggtcaa ctctttggac actggtgaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaaggagc cgtcgaaggt gggatcggta attaggacta agtcgtaaca  1440
aggtagccgt accggaaggt gcggctggat cacctccttt                        1480

SEQ ID NO: 85          moltype = DNA  length = 992
FEATURE                Location/Qualifiers
source                 1..992
                       mol_type = genomic DNA
                       organism = Methanolacinia petrolearia
SEQUENCE: 85
tgcagtcgta cgcttctttt tccnccggag cttgctccac cggaaaaaga ggagtggcga  60
acgggtgagt aacacgtggg taacctgccc atcagaaggg gataacactt ggaaacaggt  120
gctaataccg tataacaatc gaaaccgcat ggttttgatt tgaaaggcgc tttcgggtgt  180
cgctgatgga tggacccgcg gtgcattagc tagttggtga ggtaacggct caccaaggcc  240
acgatgcata gccgacctga gagggtgatc ggccacattg ggactgagac acggcccaaa  300
ctcctacggg aggcagcagt agggaatctt cggcaatgga cgaaagtctg accgagcaac  360
gccgcgtgag tgaagaaggt tttcggatcg taaaactctg ttgttagaga agaacaagga  420
tgagagtaac tgttcatccc ttgacggtat ctaaccagaa agccacggct aactacgtgc  480
```

```
cagcagccgc ggtaatacgt aggtggcaag cgttgtccgg atttattggg cgtaaagcga  540
gcgcaggcgg tttcttaagt ctgatgtgaa agcccccggc tcaaccgggg agggtcattg  600
gaaactggga gacttgagtg cagaagagga gagtggaatt ccatgtgtag cggtgaaatg  660
cgtagatata tggaggaaca ccagtggcga aggcggctct ctggtctgta actgacgctg  720
nnctcgaaag cgtggggagc aaacaggatt agataccctg gtagtccacg ccgtaaacga  780
tgagtgctaa gtgttggagg gtttccgccc ttcagtgctg cagctaacgc attaagcact  840
ccgcctgggg agtacgaccg caaggttgaa actcaaggaa ttgacggggg cccgcacagc  900
ggtggagcat gnngnttann gancacgcga nanntacnnn ctnacatcnt tgacnctcta  960
nagatagagc ttcccttcgg ggcaagtgac ng                                992

SEQ ID NO: 86          moltype = DNA  length = 881
FEATURE                Location/Qualifiers
source                 1..881
                       mol_type = genomic DNA
                       organism = Bacillus velezensis
SEQUENCE: 86
cgatgcgtag ccgacctgag agggtgatcg gccacactgg gactgagaca cggcccagac  60
tcctacggga ggcagcagta gggaatcttc cgcaatggac gaaagtctga cggagcaacg  120
ccgcgtgagt gatgaaggtt ttcggatcgt aaagctctgt tgttagggaa gaacaagtgc  180
cgttcaaata gggcggcacc ttgacggtac ctaaccagaa agccacggct aactacgtgc  240
cagcagccgc ggtaatacgt aggtggcaag cgttgtccgg aattattggg cgtaaagggc  300
tcgcaggcgg tttcttaagt ctgatgtgaa agcccccggc tcaaccgggg agggtcattg  360
gaaactgggg aacttgagtg cagaagagga gagtggaatt ccacgtgtag cggtgaaatg  420
cgtagagatg tggaggaaca ccagtggcga aggcgactct ctggtctgta actgacgctg  480
aggagcgaaa gcgtggggag cgaacaggat tagataccct ggtagtccac gccgtaaacg  540
atgagtgcta agtgttaggg ggtttccgcc ccttagtgct gcagctaacg cattaagcac  600
tccgcctggg gagtacggtc gcaagactga aactcaaagg aattgacggg ggcccgcaca  660
agcggtggag catgtggttt aattcgaagc aacgcgaaga accttaccag gtcttgacat  720
cctctgacaa tcctagagat aggacgtccc cttcgggggc agagtgacag gtggtgcatg  780
gttgtcgtca gctcgtgtcg tgagatgttg ggttaagtcc cgcaacgagc gcaacccttg  840
atcttagttg ccagcattca gttgggtgtt ctttgaaaac t                      881

SEQ ID NO: 87          moltype = DNA  length = 1563
FEATURE                Location/Qualifiers
source                 1..1563
                       mol_type = genomic DNA
                       organism = Lactobacillus plantarum
SEQUENCE: 87
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcgggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tggatggtac aacgagttgc gaactcgcga gagtaagcta atctcttaaa gccattctca  1320
gttcggattg taggctgcaa ctcgcctaca tgaagtcgga atcgctagta atcgcggatc  1380
agcatgccgc ggtgaatacg ttcccgggcc ttgtacacac cgcccgtcac accatgagag  1440
tttgtaacac ccaaagtcgg tggggtaacc ttttaggaac cagccgccta aggtgggaca  1500
gatgattagg gtgaagtcgt aacaaggtag ccgtaggaga acctgcggct ggatcacctc  1560
ctt                                                                1563

SEQ ID NO: 88          moltype = DNA  length = 1546
FEATURE                Location/Qualifiers
source                 1..1546
                       mol_type = genomic DNA
                       organism = Bacillus velezensis
SEQUENCE: 88
tagtgggttt gatcctggct caggacgaac gctggcggcg tgcctaatac atgcaagtcg  60
agcggacaga tgggagcttg ctccctgatg ttagcggcgg acgggtgagt aacacgtggg  120
taacctgcct gtaagactgg gataactccg ggaaaccggg gctaataccg gatggttgtc  180
tgaaccgcat ggttcagaca taaaaggtgg cttcggctac cacttacaga tggacccgcg  240
gcgcattagc tagttggtga ggtaacggct caccaaggcg acgatgcgta gccgacctga  300
gagggtgatc ggccacactg ggactgagac acggcccaga ctcctacggg aggcagcagt  360
agggaatctt ccgcaatgga cgaaagtctg acggagcaac gccgcgtgag tgatgaaggt  420
```

```
tttcggatcg taaagctctg ttgttaggga agaacaagtg ccgttcaaat agggcggcac  480
cttgacggta cctaaccaga aagccacggc taactacgtg ccagcagccg cggtaatacg  540
taggtggcaa gcgttgtccg gaattattgg gcgtaaaggg ctcgcaggcg gtttcttaag  600
tctgatgtga aagcccccgg ctcaaccggg gagggtcatt ggaaactggg gaacttgagt  660
gcagaagagg agagtggaat tccacgtgta gcggtgaaat gcgtagagat gtggaggaac  720
accagtggcg aaggcgactc tctggtctgt aactgacgct gaggagcgaa agcgtgggga  780
gcgaacagga ttagataccc tggtagtcca cgccgtaaac gatgagtgct aagtgttagg  840
gggtttccgc cccttagtgc tgcagctaac gcattaagca ctccgcctgg ggagtacggt  900
cgcaagactg aaactcaaag gaattgacgg gggcccgcac aagcggtgga gcatgtggtt  960
taattcgaag caacgcgaag aaccttacca ggtcttgaca tcctctgaca atcctagaga  1020
taggacgtcc ccttcggggg cagagtgaca ggtggtgcat ggttgtcgtc agctcgtgtc  1080
gtgagatgtt gggttaagtc ccgcaacgag cgcaaccctt gatcttagtt gccagcattc  1140
agttgggcac tctaaggtga ctgccggtga caaaccggag gaaggtgggg atgacgtcaa  1200
atcatcatgc cccttatgac ctgggctaca cacgtgctac aatggacaga acaaagggca  1260
gcgaaaccgc gaggttaagc caatcccaca aatctgttct cagttcggat cgcagtctgc  1320
aactcgactg cgtgaagctg gaatcgctag taatcgcgga tcagcatgcc gcggtgaata  1380
cgttcccggg ccttgtacac accgcccgtc acaccacgag agtttgtaac acccgaagtc  1440
ggtgaggtaa cctttatgga gccagccgcc gaaggtggga cagatgattg gggtgaagtc  1500
gtaacaaggt agccgtatcg gaaggtgcgg ctggatcacc tccttt                1546

SEQ ID NO: 89          moltype = DNA  length = 1285
FEATURE                Location/Qualifiers
source                 1..1285
                       mol_type = genomic DNA
                       organism = Bacillus subtilis
SEQUENCE: 89
gtaacggctc accaaggcaa cgatgcgtag ccgacctgag agggtgatcg gccacactgg  60
gactgagaca cggcccagac tcctacggga ggcagcagta gggaatcttc cgcaatggac  120
gaaagtctga cggagcaacg ccgcgtgagt gatgaaggtt ttcggatcgt aaagctctgt  180
tgttagggaa gaacaagtac cgttcgaata gggcggtacc ttgacggtac ctaaccagaa  240
agccacggct aactacgtgc cagcagccgc ggtaatacgt aggtggcaag cgttgtccgg  300
aattattggg cgtaaagggc tcgcaggcgg tttcttaagt ctgatgtgaa agcccccggc  360
tcaaccgggg agggtcattg gaaactgggg aacttgagtg cagaagagga gagtggaatt  420
ccacgtgtag cggtgaaatg cgtagagatg tggaggaaca ccagtggcga aggcgactct  480
ctggtctgta actgacgctg aggagcgaaa gcgtggggag cgaacaggat tagataccct  540
ggtagtccac gccgtaaacg atgagtgcta agtgttaggg ggtttccgcc ccttagtgct  600
gcagctaacg cattaagcac tccgcctggg gagtacggtc gcaagactga aactcaaagg  660
aattgacggg ggcccgcaca agcggtggag catgtggttt aattcgaagc aacgcgaaga  720
accttaccag gtcttgacat cctctgacaa tcctagagat aggacgtccc cttcgggggc  780
agagtgacag gtggtgcatg gttgtcgtca gctcgtgtcg tgagatgttg ggttaagtcc  840
cgcaacgagc gcaacccttg atcttagttg ccagcattca gttgggcact ctaaggtgac  900
tgccggtgac aaaccggagg aaggtgggga tgacgtcaaa tcatcatgcc ccttatgacc  960
tgggctacac acgtgctaca atggacagaa caaagggcag cgaaaccgcg aggttaagcc  1020
aatcccacaa atctgttctc agttcggatc gcagtctgca actcgactgc gtgaagctgg  1080
aatcgctagt aatcgcggat cagcatgccg cggtgaatac gttcccgggc cttgtacaca  1140
ccgcccgtca caccacgaga gtttgtaaca cccgaagtcg gtgaggtaac cttttaggag  1200
ccagccgccg aaggtgggac agatgattgg ggtgaagtcg taacaaggta gccgtatcgg  1260
aaggtgcggc tggatcacct ccttt                                       1285

SEQ ID NO: 90          moltype = DNA  length = 1563
FEATURE                Location/Qualifiers
source                 1..1563
                       mol_type = genomic DNA
                       organism = Lactobacillus plantarum
SEQUENCE: 90
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tggatggtac aacgagttgc gaactcgcga gagtaagcta atctcttaaa gccattctca  1320
gttcggattg taggctgcaa ctcgcctaca tgaagtcgga atcgctagta atcgcggatc  1380
agcatgccgc ggtgaatacg ttcccgggcc ttgtacacac cgcccgtcac accatgagag  1440
```

```
tttgtaacac ccaaagtcgg tggggtaacc ttttaggaac cagccgccta aggtgggaca  1500
gatgattagg gtgaagtcgt aacaaggtag ccgtaggaga acctgcggct ggatcacctc  1560
ctt                                                                1563

SEQ ID NO: 91          moltype =   length =
SEQUENCE: 91
000

SEQ ID NO: 92          moltype = DNA  length = 1265
FEATURE                Location/Qualifiers
source                 1..1265
                       mol_type = genomic DNA
                       organism = Bacillus subtilis
SEQUENCE: 92
cgatgcgtag ccgacctgag agggtgatcg gccacactgg gactgagaca cggcccagac  60
tcctacggga ggcagcagta gggaatcttc cgcaatggac gaaagtctga cggagcaacg  120
ccgcgtgagt gatgaaggtt ttcggatcgt aaagctctgt tgttagggaa gaacaagtac  180
cgttcgaata gggcggtacc ttgacggtac ctaaccagaa agccacggct aactacgtgc  240
cagcagccgc ggtaatacgt aggtggcaag cgttgtccgg aattattggg cgtaaagggc  300
tcgcaggcgg tttcttaagt ctgatgtgaa agcccccggc tcaaccgggg agggtcattg  360
gaaactgggg aacttgagtg cagaagagga gagtggaatt ccacgtgtag cggtgaaatg  420
cgtagagatg tggaggaaca ccagtggcga aggcgactct ctggtctgta actgacgctg  480
aggagcgaaa gcgtggggag cgaacaggat tagataccct ggtagtccac gccgtaaacg  540
atgagtgcta agtgttaggg ggtttccgcc ccttagtgct gcagctaacg cattaagcac  600
tccgcctggg gagtacggtc gcaagactga aactcaaagg aattgacggg ggcccgcaca  660
agcggtggag catgtggttt aattcgaagc aacgcgaaga accttaccag gtcttgacat  720
cctctgacaa tcctagagat aggacgtccc cttcgggggc agagtgacag gtggtgcatg  780
gttgtcgtca gctcgtgtcg tgagatgttg ggttaagtcc cgcaacgagc gcaacccttg  840
atcttagttg ccagcattca gttgggcact ctaaggtgac tgccggtgac aaaccggagg  900
aaggtgggga tgacgtcaaa tcatcatgcc ccttatgacc tgggctacac acgtgctaca  960
atggacagaa caaagggcag cgaaaccgcg aggttaagcc aatcccacaa atctgttctc  1020
agttcggatc gcagtctgca actcgactgc gtgaagctgg aatcgctagt aatcgcggat  1080
cagcatgccg cggtgaatac gttcccgggc cttgtacaca ccgcccgtca caccacgaga  1140
gtttgtaaca cccgaagtcg gtgaggtaac cttttaggag ccagccgccg aaggtgggac  1200
agatgattgg ggtgaagtcg taacaaggta gccgtatcgg aaggtgcggc tggatcacct  1260
ccttt                                                              1265

SEQ ID NO: 93          moltype = DNA  length = 1548
FEATURE                Location/Qualifiers
source                 1..1548
                       mol_type = genomic DNA
                       organism = Leuconostoc mesenteroides
SEQUENCE: 93
attgagagtt tgatcctggc tcaggatgaa cgctggcggc gtgcctaata catgcaagtc  60
gaacgcacag cgaaaggtgc ttgcaccttt caagtgagtg gcgaacgggt gagtaacacg  120
tggacaacct gcctcaaggc tggggataac atttggaaac agatgctaat accgaataaa  180
acttagtgtc gcatgacaaa aagttaaaag gcgcttcggc gtcacctaga gatggatccg  240
cggtgcatta gttagttggt ggggtaaagg cctaccaaga caatgatgca tagccgagtt  300
gagagactga tcggccacat tggactgag acacggccca aactcctacg ggaggctgca  360
gtagggaatc ttccacaatg ggcgaaagcc tgatggagca acgccgcgtg tgtgatgaag  420
gctttcgggt cgtaaagcac tgttgtatgg gaagaacagc tagaatagga aatgatttta  480
gtttgacggt accataccag aaagggacgg ctaaatacgt gccagcagcc gcggtaatac  540
gtatgtcccg agcgttatcc ggatttattg ggcgtaaagc gagcgcagac ggtttattaa  600
gtctgatgtg aaagcccgga gctcaactcc ggaatggcat tggaaactgg ttaacttgag  660
tgcagtagag gtaagtggaa ctccatgtgt agcggtggaa tgcgtagata tatggaagaa  720
caccagtggc gaaggcggct tactggactg caactgacgt tgaggctcga aagtgtgggt  780
agcaaacagg attagatacc ctggtagtcc acaccgtaaa cgatgaacac taggtgttag  840
gaggtttccg cctcttagtg ccgaagctaa cgcattaagt gttccgcctg gggagtacga  900
ccgcaaggtt gaaactcaaa ggaattgacg gggacccgca caagcggtgg agcatgtggt  960
ttaattcgaa gcaacgcgaa gaaccttacc aggtcttgac atcctttgaa gcttttagag  1020
atagaagtgt tctcttcgga gacaaagtga caggtggtgc atggtcgtcg tcagctcgtg  1080
tcgtgagatg ttgggttaag tcccgcaacg agcgcaaccc ttattgttag ttgccagcat  1140
tcagatgggc actctagcga gactgccggt gacaaaccgg aggaaggcgg ggacgacgtc  1200
agatcatcat gccccttatg acctgggcta cacacgtgct acaatggcgt atacaacgag  1260
ttgccaaccc gcgagggtga gctaatctct taaagtacgt ctcagttcgg attgtagtct  1320
gcaactcgac tacatgaagt cggaatcgct agtaatcgcg gatcagcacg ccgcggtgaa  1380
tacgttcccg ggtcttgtac acaccgcccg tcacaccatg ggagtttgta atgcccaaag  1440
ccggtggcct aacctttttag gaaggagccg tctaaggcag gacagatgac tggggtgaag  1500
tcgtaacaag gtagccgtag gagaacctgc ggctggatca cctccttt              1548
```

```
SEQ ID NO: 94          moltype = DNA  length = 1421
FEATURE                Location/Qualifiers
source                 1..1421
                       mol_type = genomic DNA
                       organism = Lactobacillus brevis
SEQUENCE: 94
atctgcccag aagcagggga taacacttgg aaacaggtgc taataccgta taacaacaaa  60
atccgcatgg attttgtttg aaaggtggct tcggctatca cttctggatg atcccgcggc  120
gtattagtta gttggtgagg taaaggccca ccaagacgat gatacgtagc cgacctgaga  180
gggtaatcgg ccacattggg actgagacac ggcccaaact cctacgggag gcagcagtag  240
ggaatcttcc acaatggacg aaagtctgat ggagcaatgc cgcgtgagtg aagaagggtt  300
tcggctcgta aaactctgtt gttaaagaag aacacctttg agagtaactg ttcaagggtt  360
gacggtattt aaccagaaag ccacggctaa ctacgtgcca gcagccgcgg taatacgtag  420
gtggcaagcg ttgtccggat ttattgggcg taaagcgagc gcaggcggtt ttttaagtct  480
gatgtgaaag ccttcggctt aaccggagaa gtgcatcgga aactgggaga cttgagtgca  540
gaagaggaca gtggaactcc atgtgtagcg gtggaatgcg tagatatatg gaagaacacc  600
agtggcgaag gcggctgtct agtctgtaac tgacgctgag gctcgaaagc atgggtagcg  660
aacaggatta gataccctgg tagtccatgc cgtaaacgat gagtgctaag tgttggaggg  720
tttccgccct tcagtgctgc agctaacgca ttaagcactc cgcctgggga gtacgaccgc  780
aaggttgaaa ctcaaaggaa ttgacggggg cccgcacaag cggtggagca tgtggtttaa  840
ttcgaagcta cgcgaagaac cttaccaggt cttgacatct tctgccaatc ttagagataa  900
gacgttccct tcggggacag aatgacaggt ggtgcatggt tgtcgtcagc tcgtgtcgtg  960
agatgttggg ttaagtcccg caacgagcgc aacccttatt atcagttgcc agcattcagt  1020
tgggcactct ggtgagactg ccggtgacaa accggaggaa ggtggggatg acgtcaaatc  1080
atcatgcccc ttatgacctg ggctacacac gtgctacaat ggacggtaca acgagttgcg  1140
aagtcgtgag gctaagctaa tctcttaaag ccgttctcag ttcggattgt aggctgcaac  1200
tcgcctacat gaagttggaa tcgctagtaa tcgcggatca gcatgccgcg gtgaatacgt  1260
tcccgggcct tgtacacacc gcccgtcaca ccatgagagt ttgtaacacc caaagccggt  1320
gagataacct tcgggagtca gccgtctaag gtgggacaga tgattagggt gaagtcgtaa  1380
caaggtagcc gtaggagaac ctgcggctgg atcacctcct t                    1421

SEQ ID NO: 95          moltype = DNA  length = 1388
FEATURE                Location/Qualifiers
source                 1..1388
                       mol_type = genomic DNA
                       organism = Lactobacillus paracasei
SEQUENCE: 95
tgctaatacc gcatagatcc aagaaccgca tggttcttgg ctgaaagatg gcgtaagcta  60
tcgcttttgg atggacccgc ggcgtattag ctagttggtg aggtaatggc tcaccaaggc  120
gatgatacgt agccgaactg agaggttgat cggccacatt gggactgaga cacggcccaa  180
actcctacgg gaggcagcag tagggaatct tccacaatgg acgcaagtct gatggagcaa  240
cgccgcgtga gtgaagaagg ctttcgggtc gtaaaactct gttgttggag aagaatggtc  300
ggcagagtaa ctgttgtcgg cgtgacggta tccaaccaga aagccacggc taactacgtg  360
ccagcagccg cggtaatacg taggtggcaa gcgttatccg gatttattgg gcgtaaagcg  420
agcgcaggcg gtttttttaag tctgatgtga aagccctcgg cttaaccgag gaagcgcatc  480
ggaaactggg aaacttgagt gcagaagagg acagtggaac tccatgtgta gcggtgaaat  540
gcgtagatat atggaagaac accagtggcg aaggcggctg tctggtctgt aactgacgct  600
gaggctcgaa agcatgggta gcgaacagga ttagataccc tggtagtcca tgccgtaaac  660
gatgaatgct aggtgttgga gggtttccgc ccttcagtgc cgcagctaac gcattaagca  720
ttccgcctgg ggagtacgac cgcaaggttg aaactcaaag gaattgacgg gggcccgcac  780
aagcggtgga gcatgtggtt taattcgaag caacgcgaag aaccttacca ggtcttgaca  840
tcttttgatc acctgagaga tcaggtttcc ccttcggggg caaaatgaca ggtggtgcat  900
ggttgtcgtc agctcgtgtc gtgagatgtt gggttaagtc ccgcaacgag cgcaaccctt  960
atgactagtt gccagcattt agttgggcac tctagtaaga ctgccggtga caaaccggag  1020
gaaggtgggg atgacgtcaa atcatcatgc cccttatgac ctgggctaca cacgtgctac  1080
aatggatggt acaacgagtt gcgagaccgc gaggtcaagc taatctctta aagccattct  1140
cagttcggac tgtaggctgc aactcgccta cacgaagtcg gaatcgctag taatcgcgga  1200
tcagcacgcc gcggtgaata cgttcccggg ccttgtacac accgcccgtc acaccatgag  1260
agtttgtaac acccgaagcc ggtggcgtaa cccttttagg gagcgagccg tctaaggtgg  1320
gacaaatgat tagggtgaag tcgtaacaag gtagccgtag gagaacctgc ggctggatca  1380
cctccttt                                                         1388

SEQ ID NO: 96          moltype = DNA  length = 1219
FEATURE                Location/Qualifiers
source                 1..1219
                       mol_type = genomic DNA
                       organism = Lactobacillus casei
SEQUENCE: 96
acacggccca aactcctacg ggaggcagca gtagggaatc ttccacaatg gacgcaagtc  60
tgatggagca acgccgcgtg agtgaagaag gctttcgggt cgtaaaactc tgttgttgga  120
gaagaatggt cggcagagta actgttgtcg gcgtgacggt atccaaccag aaagccacgg  180
ctaactacgt gccagcagcc gcggtaatac gtaggtggca agcgttatcc ggatttattg  240
ggcgtaaagc gagcgcaggc ggtttttttaa gtctgatgtg aaagccctcg gcttaaccga  300
ggaagcgcat cggaaactgg gaaacttgag tgcagaagag gacagtggaa ctccatgtgt  360
agcggtgaaa tgcgtagata tatggaagaa caccagtggc gaaggcggct gtctggtctg  420
taactgacgc tgaggctcga aagcatgggt agcgaacagg attagatacc ctggtagtcc  480
atgccgtaaa cgatgaatgc taggtgttgg agggtttccg cccttcagtg ccgcagctaa  540
cgcattaagc attccgcctg gggagtacga ccgcaaggtt gaaactcaaa ggaattgacg  600
ggggcccgca caagcggtgg agcatgtggt ttaattcgaa gcaacgcgaa gaaccttacc  660
```

```
aggtcttgac atcttttgat cacctgagag atcaggtttc cccttcgggg gcaaaatgac  720
aggtggtgca tggttgtcgt cagctcgtgt cgtgagatgt tgggttaagt cccgcaacga  780
gcgcaaccct tatgactagt tgccagcatt tagttgggca ctctagtaag actgccggtg  840
acaaaccgga ggaaggtggg gatgacgtca aatcatcatg ccccttatga cctgggctac  900
acacgtgcta caatggatgg tacaacgagt tgcgagaccg cgaggtcaag ctaatctctt  960
aaagccattc tcagttcgga ctgtaggctg caactcgcct acacgaagtc ggaatcgcta  1020
gtaatcgcgg atcagcacgc cgcggtgaat acgttcccgg gccttgtaca caccgcccgt  1080
cacaccatga gagtttgtaa cacccgaagc cggtggcgta acccttttag ggagcgagcc  1140
gtctaaggtg ggacaaatga ttagggtgaa gtcgtaacaa ggtagccgta ggagaacctg  1200
cggctggatc acctcctt                                                1219

SEQ ID NO: 97          moltype = DNA  length = 1546
FEATURE                Location/Qualifiers
source                 1..1546
                       mol_type = genomic DNA
                       organism = Lactococcus garvieae
SEQUENCE: 97
aatgagagtt tgatcctggc tcaggacgaa cgctggcggc gtgcctaata catgcaagtc  60
gagcgatgat taaagatagc ttgctatttt tatgaagagc ggcgaacggg tgagtaacgc  120
gtgggaaatc tgccgagtag cgggggacaa cgtttggaaa cgaacgctaa taccgcataa  180
caatgagaat cgcatgattc ttatttaaaa gaagcaattg cttcactact tgatgatccc  240
gcgttgtatt agctagttgg tagtgtaaag gactaccaag gcgatgatac atagccgacc  300
tgagagggtg atcggccaca ctgggactga gacacggccc agactcctac gggaggcagc  360
agtagggaat cttcggcaat gggggcaacc ctgaccgagc aacgccgcgt gagtgaagaa  420
ggttttcgga tcgtaaaact ctgttgttag agaagaacgt taagtagagt ggaaaattac  480
ttaagtgacg gtatctaacc agaaagggac ggctaactac gtgccagcag ccgcggtaat  540
acgtaggtcc caagcgttgt ccggatttat tgggcgtaaa gcgagcgcag gtggtttctt  600
aagtctgatg taaaaggcag tggctcaacc attgtgtgca ttggaaactg ggagacttga  660
gtgcaggaga ggagagtgga attccatgtg tagcggtgaa atgcgtagat atatggagga  720
acaccggagg cgaaagcggc tctctggcct gtaactgaca ctgaggctcg aaagcgtggg  780
gagcaaacag gattagatac cctggtagtc cacgccgtaa acgatgagtg ctagctgtag  840
ggagctataa gttctctgta gcgcagctaa cgcattaagc actccgcctg gggagtacga  900
ccgcaaggtt gaaactcaaa ggaattgacg gggcccgca caagcggtgg agcatgtggt  960
ttaattcgaa gcaacgcgaa gaaccttacc aggtcttgac atactcgtga tatccttaga  1020
gataaggagt tccttcggga cacgggatac aggtggtgca tggttgtcgt cagctcgtgt  1080
cgtgagatgt tgggttaagt cccgcaacga gcgcaaccct tattactagt tgccatcatt  1140
aagttgggca ctctagtgag actgccggtg ataaaccgga ggaaggtggg gatgacgtca  1200
aatcatcatg ccccttatga cctgggctac acacgtgcta caatggatgg tacaacgagt  1260
cgccaacccg cgagggtgcg ctaatctctt aaaaccattc tcagttcgga ttgcaggctg  1320
caactcgcct gcatgaagtc ggaatcgcta gtaatcgcgg atcagcacgc cgcggtgaat  1380
acgttcccgg gccttgtaca caccgcccgt cacaccacgg aagttgggag tacccaaagt  1440
aggttgccta accgcaagga gggcgcttcc taaggtaaga ccgatgactg gggtgaagtc  1500
gtaacaaggt agccgtatcg gaaggtgcgg ctggatcacc tccttt                 1546

SEQ ID NO: 98          moltype = DNA  length = 1546
FEATURE                Location/Qualifiers
source                 1..1546
                       mol_type = genomic DNA
                       organism = Lactococcus garvieae
SEQUENCE: 98
aatgagagtt tgatcctggc tcaggacgaa cgctggcggc gtgcctaata catgcaagtc  60
gagcgatgat taaagatagc ttgctatttt tatgaagagc ggcgaacggg tgagtaacgc  120
gtgggaaatc tgccgagtag cgggggacaa cgtttggaaa cgaacgctaa taccgcataa  180
caatgagaat cgcatgattc ttatttaaaa gaagcaattg cttcactact tgatgatccc  240
gcgttgtatt agctagttgg tagtgtaaag gactaccaag gcgatgatac atagccgacc  300
tgagagggtg atcggccaca ctgggactga gacacggccc agactcctac gggaggcagc  360
agtagggaat cttcggcaat gggggcaacc ctgaccgagc aacgccgcgt gagtgaagaa  420
ggttttcgga tcgtaaaact ctgttgttag agaagaacgt taagtagagt ggaaaattac  480
ttaagtgacg gtatctaacc agaaagggac ggctaactac gtgccagcag ccgcggtaat  540
acgtaggtcc caagcgttgt ccggatttat tgggcgtaaa gcgagcgcag gtggtttctt  600
aagtctgatg taaaaggcag tggctcaacc attgtgtgca ttggaaactg ggagacttga  660
gtgcaggaga ggagagtgga attccatgtg tagcggtgaa atgcgtagat atatggagga  720
acaccggagg cgaaagcggc tctctggcct gtaactgaca ctgaggctcg aaagcgtggg  780
gagcaaacag gattagatac cctggtagtc cacgccgtaa acgatgagtg ctagctgtag  840
ggagctataa gttctctgta gcgcagctaa cgcattaagc actccgcctg gggagtacga  900
ccgcaaggtt gaaactcaaa ggaattgacg gggcccgca caagcggtgg agcatgtggt  960
ttaattcgaa gcaacgcgaa gaaccttacc aggtcttgac atactcgtga tatccttaga  1020
gataaggagt tccttcggga cacgggatac aggtggtgca tggttgtcgt cagctcgtgt  1080
cgtgagatgt tgggttaagt cccgcaacga gcgcaaccct tattactagt tgccatcatt  1140
aagttgggca ctctagtgag actgccggtg ataaaccgga ggaaggtggg gatgacgtca  1200
aatcatcatg ccccttatga cctgggctac acacgtgcta caatggatgg tacaacgagt  1260
cgccaacccg cgagggtgcg ctaatctctt aaaaccattc tcagttcgga ttgcaggctg  1320
caactcgcct gcatgaagtc ggaatcgcta gtaatcgcgg atcagcacgc cgcggtgaat  1380
acgttcccgg gccttgtaca caccgcccgt cacaccacgg aagttgggag tacccaaagt  1440
aggttgccta accgcaagga gggcgcttcc taaggtaaga ccgatgactg gggtgaagtc  1500
gtaacaaggt agccgtatcg gaaggtgcgg ctggatcacc tccttt                 1546
```

-continued

```
SEQ ID NO: 99          moltype = DNA  length = 619
FEATURE                Location/Qualifiers
source                 1..619
                       mol_type = genomic DNA
                       organism = Weissella cibaria
SEQUENCE: 99
gatttgaaga gcttgctcag atatgacgat ggacattgca aagagtggcg aacgggtgag  60
taacacgtgg gaaacctacc tcttagcagg ggataacatt tggaaacaga tgctaatacc  120
gtataacaat agcaaccgca tggttgctac ttaaaagatg gttctgctat cactaagaga  180
tggtcccgcg gtgcattagt tagttggtga ggtaatggct caccaagacg atgatgcata  240
gccgagttga gagactgatc ggccacaatg ggactgagac acggcccata ctcctacggg  300
aggcagcagt agggaatctt ccacaatggg cgaaagcctg atggagcaac gccgcgtgtg  360
tgatgaaggg tttcggctcg taaaacactg ttgtaagaga agaatgacat tgagagtaac  420
tgttcaatgt gtgacggtat cttaccagaa aggaacggct aaatacgtgc cagcagccgc  480
ggtaatacgt atgttccaag cgttatccgg atttattggg cgtaaagcga gcgcagacgg  540
ttatttaagt ctgaagtgaa agccctcagc tcaactgagg aattgctttg gaaactggat  600
gacttgagtg cagtagagg                                               619

SEQ ID NO: 100         moltype = DNA  length = 1263
FEATURE                Location/Qualifiers
source                 1..1263
                       mol_type = genomic DNA
                       organism = Lactobacillus plantarum
SEQUENCE: 100
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tgg                                                                1263

SEQ ID NO: 101         moltype = DNA  length = 1457
FEATURE                Location/Qualifiers
source                 1..1457
                       mol_type = genomic DNA
                       organism = Pediococcus pentosaceus
SEQUENCE: 101
atgagagttt gatcttggct caggatgaac gctggcggcg tgcctaatac atgcaagtcg  60
aacgaacttc cgttaattga ttatgacgta cttgtactga ttgagatttt aacacgaagt  120
gagtggcgaa cgggtgagta acacgtgggt aacctgccca gaagtagggg ataacacctg  180
gaaacagatg ctaataccgt ataacagaga aaaccgcatg gttttctttt aaaagatggc  240
tctgctatca cttctggatg gacccgcggc gtattagcta gttggtgagg caaaggctca  300
ccaaggcagt gatacgtagc cgacctgaga gggtaatcgg ccacattggg actgagacac  360
ggcccagact cctacgggag gcagcagtag ggaatcttcc acaatggacg caagtctgat  420
ggagcaacgc cgcgtgagtg aagaagggtt tcggctcgta aagctctgtt gttaaagaag  480
aacgtgggta agagtaactg tttacccagt gacggtattt aaccagaaag ccacggctaa  540
ctacgtgcca gcagccgcgg taatacgtag gtggcaagcg ttatccggat ttattgggcg  600
taaagcgagc gcaggcggtc ttttaagtct aatgtgaaag ccttcggctc aaccgaagaa  660
gtgcattgga aactgggaga cttgagtgca gaagaggaca gtggaactcc atgtgtagcg  720
gtgaaatgcg tagatatatg gaagaacacc agtggcgaag gcggctgtct ggtctgcaac  780
tgacgctgag gctcgaaagc atgggtagcg aacaggatta gataccctgg tagtccatgc  840
cgtaaacgat gattactaag tgttggaggg tttccgccct tcagtgctgc agctaacgca  900
ttaagtaatc cgcctgggga gtacgaccgc aaggttgaaa ctcaaaagaa ttgacggggg  960
cccgcacaag cggtggagca tgtggtttaa ttcgaagcta cgcgaagaac cttaccaggt  1020
cttgacatct tctgacagtc taagagatta gaggttccct tcggggacag aatgacaggt  1080
ggtgcatggt tgtcgtcagc tcgtgtcgtg agatgttggg ttaagtcccg caacgagcgc  1140
aacccttatt actagttgcc agcattaagt tgggcactct agtgagactg ccggtgacaa  1200
accggaggaa ggtggggacg acgtcaaatc atcatgcccc ttatgacctg ggctacacac  1260
gtgctacaat ggatggtaca acgagtcgcg agaccgcgag gttaagctaa tctcttaaaa  1320
ccattctcag ttcggactgt aggctgcaac tcgcctacac gaagtcggaa tcgctagtaa  1380
tcgcggatca gcatgccgcg gtgaatacgt tcccgggcct tgtacacacc gcccgtcaca  1440
ccatgagagt ttgtaac                                                 1457
```

-continued

```
SEQ ID NO: 102          moltype = DNA  length = 1415
FEATURE                 Location/Qualifiers
source                  1..1415
                        mol_type = genomic DNA
                        organism = Pichia kudriazevii
SEQUENCE: 102
tccgtaggtg aacctgcgga aggatcatta ctgtgattta gtactacact gcgtgagcgg  60
aacgaaaaca acaacaccta aaatgtggaa tatagcatat agtcgacaag agaaatctac  120
gaaaaacaaa caaaactttc aacaacggat ctcttggttc tcgcatcgat gaagagcgca  180
gcgaaatgcg atacctagtg tgaattgcag ccatcgtgaa tcatcgagtt cttgaacgca  240
cattgcgccc ctcggcattc cgggggggcat gcctgtttga gcgtcgtttc catcttgcgc  300
gtgcgcagag ttgggggagc ggagcggacg acgtgtaaag agcgtcggag ctgcgactcg  360
cctgaaaggg agcgaagctg gccgagcgaa ctagactttt tttcagggac gcttggcggc  420
cgagagcgag tgttgcgaga caacaaaaag ctcgacctca aatcaggtag gaatacccgc  480
tgaacttaag catatcaata agcggaggaa aagaaaccaa cagggattgc ctcagtagcg  540
gcgagtgaag cggcaagagc tcagatttga aatcgtgctt tgcggcacga gttgtagatt  600
gcaggttgga gtctgtgtgg aaggcggtgt ccaagtccct tggaacaggg cgcccaggag  660
ggtgagagcc ccgtgggatg ccggcggaag cagtgaggcc cttctgacga gtcgagttgt  720
ttgggaatgc agctccaagc gggtggtaaa ttccatctaa ggctaaatac tggcgagaga  780
ccgatagcga acaagtactg tgaaggaaag atgaaaagca ctttgaaaag agagtgaaac  840
agcacgtgaa attgttgaaa gggaagggta ttgcgcccga catggggatt gcgcaccgct  900
gcctctcgtg ggcggcgctc tgggctttcc ctgggccagc atcggttctt gctgcaggag  960
aaggggttct ggaacgtggc tcttcggagt gttatagcca gggccagatg ctgcgtgcgg  1020
ggaccgagga ctgcggccgt gtaggtcacg gatgctggca gaacggcgca acaccgcccg  1080
tcttgaaaca tggaccaagg agtctaacgt ctatgcgagt gtttgggtgt gaaacccgta  1140
cgcgtaatga aagtgaacgt aggtcggacc ccctgccctc ggggagggga gcacgatcga  1200
ccgatcccga tgtttatcgg aaggatttga gtaggagcat agctgttggg acccgaaaga  1260
tggtgaacta tgcctgaata gggtgaagcc agaggaaact ctggtggagg ctcgtagcgg  1320
ttctgacgtg caaatcgatc gtcgaatttg ggtatagggg cgaaagacta atcgaaccat  1380
ctagtagctg gttcctgccg aagtttccct cagga                              1415
```

METHODS AND COMPOSITIONS FOR TREATING MUSCULOSKELETAL DISEASES, TREATING INFLAMMATION, AND MANAGING SYMPTOMS OF MENOPAUSE

CROSS-REFERENCE TO RELATED APPLICATIONS

This application is a continuation application of International Application No. PCT/US2022/080362, filed on Nov. 22, 2022, which claims the benefit of and priority to U.S. Provisional Patent Application No. 63/282,155, filed Nov. 22, 2021, and U.S. Provisional Patent Application No. 63/382,666, filed Nov. 7, 2022, the entire disclosures of each of which are incorporated herein by reference in their entirety for all purposes.

REFERENCE TO A SEQUENCE LISTING

This application contains a Sequence Listing in computer readable form. The computer readable form is incorporated herein by reference. Said XML copy, created on Mar. 9, 2023, is named SBI-013WOC1_SL.xml and is 215,925 bytes in size.

FIELD OF THE INVENTION

The invention relates generally to methods and compositions for the treatment of musculoskeletal diseases, the treatment of inflammation, and the management of symptoms of perimenopause, menopause, and postmenopause.

BACKGROUND

Menopause symptoms severely reduce the quality of life of women worldwide. Up to 80% of women may experience menopause symptoms and it is estimated that, in 2030, the at risk groups of peri- and post-menopausal women will reach 1.2 billion globally (Gold et al. (2006) Am J Pub Health 96:1226-1235). The core symptoms are hot flushes (HF) and night sweats (NS), collectively referred to as vasomotor symptoms (VMS); sleep disturbance and other secondary symptoms such as vaginal dryness, urinary urgency, insomnia, irritability, depression, dry skin, dry mouth, dry eyes, headaches, joint and muscle aches, weight gain, racing heart, and changes in libido are also often present (Lim et al. (2020) J Clin Med 9:2173). These symptoms are largely a consequence of natural endogenous estrogen decline and dysregulation during peri- and post-menopause (Lambert et al. (2017) PLoS One 12(6): e0176590). Hormone therapy (HT) is the current gold standard treatment for VMS. However, substantial evidence supports that therapy increases cancer risk in estrogen receptor (ER) $\alpha$ rich tissues (Lambert et al. (2017) PLoS One 12(6):e0176590). Thus, there is a significant need for new approaches to alleviating VMS in peri- and post-menopausal women.

Intriguingly, menopause has been demonstrated to shift the composition of the gut microbiome (Choi et al. (2017) J Microbiol Biotechnol 27:2228-2236; Santos-Marcos et al. (2018) Maturitas 116:43-53) and increase gastrointestinal permeability in both animal and clinical studies (Li et al. (2016) J Clin Investig 126:2049-2063). Furthermore, the microbiome has been shown to effect circulating levels of estrogen, and thus may be a therapeutic target to improve menopausal symptoms (Flores et al. (2012) J Transl Med 10:253).

Probiotics have emerged as an intriguing new approach to treating VMS. *Lactobacillus gasseri* was shown to reduce postmenopausal symptoms in ovariectomized rats (Lee et al. (2021) J Microbiol Biotechnol 31(9):1-10). Further, recent clinical trials with probiotics have shown promise, leading to a reduction in the VMS associated with menopause (Lambert et al. (2017) PLoS One 12(6):e0176590, Lim et al. (2020) J Clin Med 9:2173). Despite the efficacy observed in these studies, the mechanism of how probiotics impact VMS is not completely understood. One potential mechanism is via alteration of dietary isoflavone metabolite availability by probiotics, increasing the uptake of these estrogen receptor agonists (Lambert et al. (2017) PLoS One 12(6):e0176590). Therefore, there is a need for novel treatments for alleviating menopausal symptoms that utilize the beneficial properties of probiotics.

SUMMARY OF THE INVENTION

The disclosure relates generally to methods and compositions for the treatment of musculoskeletal diseases, the treatment of inflammation, and the management of symptoms of perimenopause, menopause, and postmenopause.

For example, in one aspect, provided herein is a dietary supplement comprising a combination of four heterologous microbes consisting of *Lactobacillus brevis, Lactobacillus plantarum, Leuconostoc mesenteroides*, and *Pichia kudriavzevii* formulated in an amount effective for lessening a decrease in, maintaining, or improving bone health in a subject, wherein the dietary supplement is formulated for oral delivery. In certain embodiments, lessening a decrease in, maintaining, or improving bone health in the subject comprises lessening a decrease in, maintaining, or improving bone mineral density (BMD) in the subject. In certain embodiments, lessening a decrease in, maintaining, or improving bone health in the subject comprises lessening a decrease in, maintaining, or improving trabecular bone score (TBS) in the subject.

In certain embodiments, the heterologous microbes are co-formulated as a synthetic microbial consortium in a unit dose.

In certain embodiments, the dietary supplement is formulated as a medical food or a pharmaceutical composition.

In certain embodiments, the unit dosage amount is a dosage amount of about $1.0\times10^8$ to $1.0\times10^{12}$ CFU of each of the heterologous microbes. In certain embodiments, the unit dosage amount is a dosage amount of about $2.5\times10^9$ to $3.0\times10^{10}$ CFU of each of the heterologous microbes.

In certain embodiments, following administration of the dietary supplement to the subject over a period of time: (i) BMD in the subject is maintained or improved as compared to a suitable control, and/or (ii) a decrease in BMD in the subject is less severe as compared to a suitable control. In certain embodiments, the suitable control comprises (i) a control group that has not been administered the dietary supplement, (ii) the subject's BMD prior to the first administration of the dietary supplement to the subject and/or (iii) the rate of decline of the subject's BMD prior to the first administration of the dietary supplement to the subject.

In certain embodiments, BMD is measured as areal BMD (aBMD) or volumetric BMD (vBMD).

In certain embodiments, following administration of the dietary supplement to the subject over a period of time: (i) the subject's TBS is maintained or improved as compared to a suitable control, and/or (ii) a decrease in TBS in the subject is less severe as compared to a suitable control. In certain embodiments, the suitable control comprises (i) a control group that has not been administered the dietary supplement, (ii) the subject's TBS prior to the first administration of the dietary supplement to the subject and/or (iii) the rate of decline of the subject's TBS prior to the first administration of the dietary supplement to the subject.

In certain embodiments, the taxonomic or functional composition of the microbiome of the subject is altered after administration of the dietary supplement to the subject, as compared to a suitable control. In certain embodiments, the suitable control comprises (i) a control group that has not been administered the dietary supplement, and/or (ii) the taxonomic or functional composition of the microbiome of the subject prior to the first administration of the dietary supplement.

In certain embodiments, the microbiome is altered by an increase in the abundance of the microbial species present in the dietary supplement. In certain embodiments, the microbiome is altered by increased gene abundance of vitamin K2 biosynthesis pathways.

In certain embodiments, administration of the dietary supplement to the subject results in (i) altering the amount of at least one biochemical marker of bone turnover in the subject and/or (ii) altering the amount of at least one circulatory inflammatory cytokine or marker of inflammation in the subject, wherein the amount of the at least one biochemical marker of bone turnover and/or at least one circulatory inflammatory cytokine or marker of inflammation is altered as compared to a suitable control. In certain embodiments, the suitable control comprises (a) a control group that has not been administered the dietary supplement, and/or (b) the amount of the at least one biochemical marker of bone turnover and/or the at least one circulatory inflammatory cytokine or marker of inflammation in the subject prior to the first administration of the dietary supplement.

In certain embodiments, the at least one biochemical marker of bone turnover comprises CTX and/or P1NP. In certain embodiments, the amount of CTX decreases, the amount of P1NP increases, and/or the ratio of P1NP to CTX increases.

In certain embodiments, the at least one circulatory inflammatory cytokine or marker of inflammation is selected from the group consisting of CRP, IL-17, TNF, IL-1B, IL-4, RANKL, and IFNγ. In certain embodiments, the amount of the at least one circulatory inflammatory cytokine or marker of inflammation decreases.

In another aspect, provided herein is a a dietary supplement comprising a combination of four heterologous microbes consisting of *Lactobacillus brevis, Lactobacillus plantarum, Leuconostoc mesenteroides*, and *Pichia kudriavzevii* for improving one or more symptoms of menopause in a subject, wherein the dietary supplement is formulated for oral delivery.

In certain embodiments, following administration of the dietary supplement to the subject over a period of time, the one or more symptoms of menopause are improved as compared to a suitable control. In certain embodiments, the suitable control is (i) a control group that has not been administered the dietary supplement and/or (ii) the presence or severity of the subject's one or more symptoms prior to the first administration of the dietary supplement.

In certain embodiments, the one or more symptoms of menopause are selected from the group consisting of: hot flushes, sweating, episodes of sweating, night sweats, heart discomfort, unusual awareness of heart beat, heart skipping, heart racing, heart tightness, depressive mood, feeling down, feeling sad, feeling on verge of tears, lack of drive, mood swings, irritability, feeling nervous, inner tension, feeling aggressive, anxiety, inner restlessness, feeling panicky, physical exhaustion, mental exhaustion, general decrease in performance, impaired memory, decrease in concentration, forgetfulness, sexual problems, change in sexual desire, change in sexual activity, change in sexual satisfaction, bladder problems, difficulty in urinating, increased need to urinate, bladder incontinence, dryness of the vagina, sensation of dryness or burning in the vagina, difficulty with sexual intercourse, joint and muscular discomfort, pain in the joints, and rheumatoid arthritis. In certain embodiments, the one or more symptoms of menopause comprise a vasomotor symptom, wherein the vasomotor symptom is selected from hot flushes, sweating, night sweats, and combinations thereof.

In certain embodiments, severity of the one or more symptoms of menopause is measured by the Menopause Rating Scale (MRS), optionally wherein the improvement of the symptom is measured in the same subject about 2 months, 4 months, 6 months, 8 months, 10 months, and/or 12 months after the first administration of the dietary supplement.

In certain embodiments, the dietary supplement further comprises a prebiotic. In certain embodiments, the prebiotic is oligofructose and/or a dried fruit or vegetable powder. In certain embodiments, the dried fruit or vegetable powder is a dried berry powder. In certain embodiments, the prebiotic is dried blueberry powder.

In certain embodiments, the dietary supplement further comprises a bulking agent. In certain embodiments, the bulking agent is magnesium stearate.

In certain embodiments of any of the foregoing dietary supplements, at least one of the heterologous microbes comprises a 16S rRNA or fungal ITS sequence, having at least 97%, at least 98%, at least 98.5%, at least 99%, or at least 100% similarity to any one of SEQ ID NOs: 93, 94, 100 and 102 at the 16S rRNA or fungal ITS sequence.

In certain embodiments, the dietary supplement further comprises at least one additional microbe from Table 1 or Table 2.

In certain embodiments of a dietary supplement disclosed herein, the unit dose further comprises a cryoprotectant present in an effective amount to extend survival of the heterologous microbes after thawing the unit dose from a cryogenic temperature.

In another aspect, provided herein is a method of producing a dietary supplement comprising a combination of four heterologous microbes consisting of *Lactobacillus brevis, Lactobacillus plantarum, Leuconostoc mesenteroides*, and *Pichia kudriavzevii* for lessening a decrease in, maintaining, or improving bone health in a subject, the method comprising co-formulating the heterologous microbes as a synthetic microbial consortia in a unit dose formulated for oral administration to the subject.

In another aspect, provided herein is a method of (i) lessening a decrease in, maintaining, or improving bone health in a subject and/or (ii) improving one or more symptoms of menopause in a subject, the method comprising administering to the subject a therapeutically effective amount of each of four heterologous microbes consisting of *Lactobacillus brevis, Lactobacillus plantarum, Leuconostoc mesenteroides*, and *Pichia kudriavzevii*. In certain embodiments, lessening a decrease in, maintaining, or improving bone health in the subject comprises (i) lessening a decrease in, maintaining, or improving bone mineral density (BMD)

in the subject and/or (ii) lessening a decrease in, maintaining, or improving trabecular bone score (TBS) in the subject.

In certain embodiments, the subject has, is diagnosed with, or is at risk for one or more of the group consisting of: osteoporosis, osteopenia, osteoarthritis, suboptimal fracture healing, osteomyelitis, Paget's disease, stunting, and delayed or non-union fractures.

BRIEF DESCRIPTION OF FIGURES

These and other features, aspects, and advantages of the present invention will become better understood with regard to the following description, and accompanying drawings, where:

FIG. 5A summarizes the results for total-body BMD, as measured by Faxitron DXA scan. FIG. 5B summarizes the results for total-body BMD, as measured by Pixi DXA scan. FIG. 5C summarizes the results for spine BMD, as measured by Pixi DXA scan. FIG. 5D summarizes the results for femur BMD, as measured by Pixi DXA scan.

DETAILED DESCRIPTION

Advantages and Utility

Figure 1:
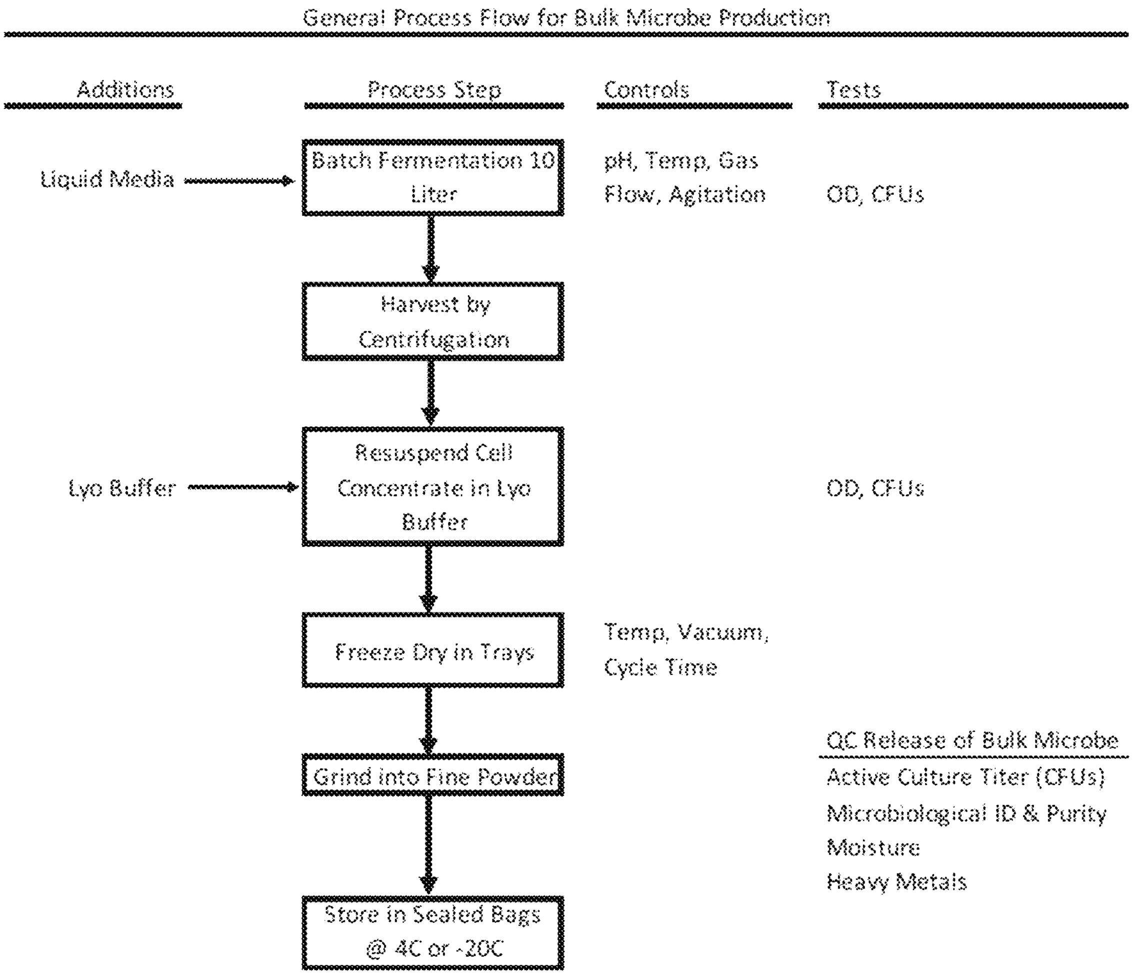
FIG. 1 summarizes the Defined Microbial Assemblage manufacturing process described in Example 1.

Briefly, and as described in more detail below, described herein are methods and compositions for using microbial agents (probiotics) and agents that promote growth of certain microbes (prebiotics) for management (including prevention and treatment) of musculoskeletal disorders, including osteoporosis and osteopenia, for the management of inflammation, and for the management of symptoms of menopause, perimenopause and postmenopause.

Several features of the current approach should be noted. It is based on development of synergistic combinations of microbes as on those found in fruits and vegetables consumed as part of a plant-based diet. The combinations are based, in part, on analyses of biochemical pathways catalyzed by genes in these microbes and selection of microbial combinations that promote beneficial metabolic changes in a subject through the biochemical reactions they catalyze such as, but not limited to, the production of short chain fatty acids (SCFA).

Advantages of this approach are numerous. They include reduction of the morbidity associated with musculoskeletal disorders, such as osteoporosis or osteopenia, without the use of traditional drugs and the side effects they can sometimes cause. This approach may also be used to reduce inflammation and alleviate symptoms or effects of menopause, perimenopause or postmenopause.

In certain aspects, this disclosure is useful for providing health benefits associated with consumption of a plant-based diet, as the diet microbes and fibers are delivered in concentrated form. This can reduce the burden on a subject to ingest potentially unreasonable or inconvenient amounts of particular plants and/or plant-based products, such as fermented foods.

Definitions

Terms used in the claims and specification are defined as set forth below unless otherwise specified.

The term "ameliorating" refers to any therapeutically beneficial result in the treatment of a disease state, e.g., a musculoskeletal disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

As used herein, the term "derived from" includes microbes immediately taken from an environmental sample and also microbes isolated from an environmental source and subsequently grown in pure culture. The term "derived from" also includes material isolated from the recited source, and materials obtained using the isolated materials (e.g., cultures of microorganisms made from microorganisms isolated from the recited source).

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

In some cases, alignment of an entire sequence is not necessary for identification or comparison purposes regarding a microbial entity. In such a case, a so-called diagnostic subsequence can be used. The term "diagnostic subsequence" refers to a portion of a known sequence which would be identified and used by one of skill in the art to identify or compare two or more microbial entities. One, non-limiting example is utilization of subsequences of 16S rRNA sequences found in Asgari et al (2018, bioRxiv).

The term "effective amount" is an amount that is effective to ameliorate or manage a symptom of a disease, disorder, state, or condition. An effective amount can also be an amount effective for prophylaxis of a particular disease, disorder, state, or condition (e.g., symptoms of menopause). More generally, an effective amount is an amount sufficient to produce a desired effect, e.g., an amount effective for alteration of the microbial content of a subject's microbiota. As used herein, nonlimiting examples of a disease, disorder, state, or condition include, e.g., osteoporosis, osteopenia, chronic inflammation, menopause, perimenopause, and postmenopause.

The term "dietary supplement", as used herein refers to a substance that is not a conventional food and that is manufactured to be administered to a subject over a period of time, wherein the substance is an addition to the subject's diet and is effective to produce a desired effect when administered to the subject over a period of time. In certain embodiments, the desired effect is treating, ameliorating, preventing, or managing one or more symptoms of a disease, disorder, state, or condition in the subject.

The term "medical food", as used herein refers to a dietary supplement which is formulated to be consumed or administered enterally with or without the supervision of a physician and which is intended for the dietary management of a disease, state, disorder, or condition or one or more symptoms thereof.

The term "menopause", as used herein in relation to a subject, refers to the time at which 12 months have elapsed since the last menstruation of the subject. The term "perimenopause", as used herein in relation to a subject, refers to the period of time about 6 months to about 10 years prior to menopause in the subject, and ending at menopause. In some embodiments, perimenopause is characterized by a decrease in estrogen levels/production, irregular menstrual cycles, and/or an alteration of menstrual cycle patterns in the subject. The term "postmenopause", as used herein in relation to a subject, refers to the period of time beginning 12 months after the last menstruation of the subject and concluding at the end of the subject's life.

The term "symptoms of menopause", as used herein includes symptoms of menopause, perimenopause, and postmenopause, and includes, but is not limited to, hot flushes, sweating and night sweats, collectively referred to as vasomotor symptoms; sleep disturbance and other secondary symptoms such as vaginal dryness, urinary urgency, insomnia, irritability, depression, dry skin, dry mouth, dry eyes, headaches, joint and muscle aches, weight gain, racing heart, changes in libido, and increased risk or occurrence of cancer.

The term "defined microbial assemblage" or "DMA" refers to a combination of two or more microbial strains (e.g., bacterial or fungal) wherein the two or more microbial strains are chosen because they are predicted to achieve a particular synergistic result when applied in concert. DMA compositions may further comprise prebiotics or other fiber sources predicted to increase the desired effect of the microbial strains applied. A DMA is rationally designed to achieve a particular benefit, such as, but not limited to, increased SCFA production in the gut lumen.

As used herein, the term "treating" includes abrogating, substantially inhibiting, slowing or reversing the progression of a disease, disorder, state, or condition, or clinical or aesthetical symptoms of a disease, disorder, state, or condition.

As used herein, the term "preventing" includes completely or substantially reducing the likelihood or occurrence or the severity of initial clinical or aesthetical symptoms of a disease, disorder, state, or condition.

As used herein, the term "about" includes variation of up to approximately +/−10% and that allows for functional equivalence in the product, composition, or method unless otherwise indicated or inferred. Where the use of the term "about" appears before a quantitative value, the present invention also includes the specific quantitative value itself, unless specifically stated otherwise.

As used herein, the term "colony-forming unit" or "cfu" is an individual cell that is able to clone itself into an entire colony of identical cells.

As used herein all percentages are weight percent unless otherwise indicated.

As used herein, "viable organisms" are organisms that are capable of growth and proliferation. In some embodiments, viability can be assessed by numbers of colony-forming units that can be cultured. In some embodiments viability can be assessed by other means, such as, but not limited to, quantitative polymerase chain reaction.

"Microbiota" refers to the community of microorganisms that occur (sustainably or transiently) in and on a plant or an animal subject, typically a mammal such as a human, including eukaryotes, archaea, bacteria, and viruses (including bacterial viruses i.e., phage).

"Microbiome" refers to the genetic content of the communities of microbes that live inside and on the human body, or inside or outside a plant, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

As used herein, the term "prebiotic" refers to a substance or composition (either alone or in combination with one or more other substances) that enhances or supports the growth of microbes. In some embodiments, a prebiotic enhances or supports the growth of a probiotic in a subject. In some embodiments, a prebiotic enhances or supports the growth of a DMA in a subject.

The term "subject" refers to any organism to be treated by the methods and compositions described herein. Such organisms preferably include, but are not limited to, mammals (e.g. murines, simians, equines, bovines, porcines, canines, felines, and the like), and more preferably include humans. In some embodiments, the subject may be suffering from a dysbiosis, including, but not limited to, an infection due to a gastrointestinal pathogen or may be at risk of developing or transmitting to others an infection due to a gastrointestinal pathogen. In some embodiments, the subject may have or be at risk for a musculoskeletal disease such as osteoporosis or osteopenia. In some embodiments, the subject may be in menopause, perimenopause, postmenopause, or may be undergoing or may have undergone a menopause transition. In some embodiments, the subject may have chronic inflammation.

The "colonization" of a host organism includes the non-transitory residence of a bacterium or other microscopic organism. In some embodiments, a "colonizing" microbial strain may remain in in a host subject's gastrointestinal tract for a period of time following administration of a composition comprising said microbial strain to the subject. For example, in some embodiments, a "colonizing" microbe or strain may remain in the host subject's gastrointestinal tract for at least 1 hour, at least 6 hours, at least 12 hours, at least 1 day, at least 7 days, at least one month, at least one year, etc., following administration of a composition comprising said microbial strain to the subject.

As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

As used herein "heterologous" designates organisms to be administered that are not naturally present in the same proportions as in the therapeutic composition as in subjects to be treated with the therapeutic composition. These can be organisms that are not normally present in individuals in need of the composition described herein, or organisms that are not present in sufficient proportion in said individuals. These organisms can comprise a synthetic composition of organisms derived from separate plant sources or can comprise a composition of organisms derived from the same plant source, or a combination thereof.

As used herein, the terms "administer", "administering", or "administration" refer to the placement or delivery of a composition or substance (e.g., a DMA composition described herein) onto or into a subject, e.g. orally, rectally, parenterally, or intranasally. In some embodiments, one or more persons who are not the subject (e.g., an investigator or medical worker) may administer a composition or substance to the subject. In some embodiments, the subject may administer a composition or substance to themselves.

In some embodiments, compositions and methods disclosed herein can be used to treat osteoporosis or osteopenia. Osteoporosis is a systemic skeletal disease characterized by decreasing bone mass and microarchitectural deterioration of bone tissue that leads to an increased risk for bone fragility and fracture. In patients without fragility fracture, osteoporosis is often diagnosed by low bone mineral density (BMD). The international reference standard for the description of osteoporosis in postmenopausal women and in men is a femoral neck or lumbar spine BMD of 2.5 standard deviations (SD) or more below the young female adult mean. Osteopenia is a less severe form of low BMD, defined by the international standard as between 1 and 2.5 SD below the young female average. In certain embodiments, "osteoporosis or osteopenia" indicates a condition where the subject's bone mass per unit volume is reduced (e.g., as compared to an appropriate population average). Osteoporosis indicates bone mass reduction to a level below that required for the adequate mechanical support function of the bone. Osteopenia is a milder disease where bone mass per unit is reduced but not to the extent seen in osteoporosis. Patients with osteopenia may subsequently suffer from osteoporosis. Trabecular bone score (TBS) can also be used as a risk marker and/or diagnostic marker for osteoporosis or osteopenia.

As used herein, the term "bone health" refers to an assessment of bone quality, bone integrity, bone density, and/or bone turnover. Bone health may be assessed using any appropriate standard, metric, or method known in the art, including, e.g., by bone mineral density (BMD) or trabecular bone score (TBS).

As used herein, "bone density" indicates "bone mineral density" (BMD). In some embodiments, compositions and methods disclosed herein can be used to improve or increase BMD.

In some embodiments, compositions and methods disclosed herein can be used to treat osteoarthritis. As used herein, the term "osteoarthritis" (abbreviated as "OA"), refers to the disease also known as osteoarthrosis and degenerative joint disease, characterized by inflammation and damage to, or loss of cartilage in any joint or joints, and joint pain. Clinical standards for diagnosing osteoarthritis in subjects including mammalian subjects such as canines and humans are well known and include, for example, swelling or enlargement of joints, joint tenderness or pain, decreased range of motion in joints, visible joint deformities such as bony growths, and crepitus. Symptoms can be identified by clinical observation and history, or imaging including MRI and X-ray. Criteria for diagnosing the presence or absence of OA and severity or degree of OA include but are not limited to the ACR Criteria for knee OA (R. Altman et al., Development of criteria for the classification and reporting of osteoarthritis: Classification of osteoarthritis of the knee: Diagnostic and Therapeutic Criteria Committee of the American Rheumatism Association. Arthritis Rheum. August 29(8):1039-1049(1986)), functional status criteria according to WOMAC (N. Bellamy et al., 1988, Validation study of WOMAC: a health status instrument for measuring clinically important patient relevant outcomes to antirheumatic drug therapy in patients with osteoarthritis of the hip or knee. J Rheumatol 15:1833-1840), and radiological standards for evaluating OA disease severity according to the Kellgren and Lawrence method for knee OA (Kellgren, J. H. and J. S. Lawrence, Radiological assessment of osteoarthrosis. Ann Rheum Dis 16:494-502).

In some embodiments, compositions and methods disclosed herein can be used to improve fracture healing. The term "fracture", as used herein, refers to a disruption in the integrity of a living bone involving injury to bone marrow, periosteum, and adjacent soft tissues. Many types of fractures exist such as, for example, pathological, stress, non-union, delayed-union, and greenstick fractures. A fracture includes open and closed fractures.

The term "fracture line" refers to the line across where disruption of the integrity of the living bone has occurred.

The term "non-union" fracture refers to the fractures which are not completely healed nine months after the initial fracture. These are commonly found in clavicle fractures that are not healed usually within three months, and are usually painful and require surgical fixation.

The term "delayed-union" refers to a fracture that has not healed at least about six months post injury.

In some embodiments, compositions and methods disclosed herein can be used to prevent or treat osteomyelitis. As used herein, "osteomyelitis" is defined as inflammation of the bone or bone marrow. In some embodiments, osteomyelitis is caused by an infection.

In some embodiments, compositions and methods disclosed herein can be used to improve trabecular bone score (TBS).

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

In the application, where an element or component is said to be comprised in and/or selected from a list of recited elements or components, it should be understood that the element or component can be any one of the recited elements or components, or the element or component can be selected from a group consisting of two or more of the recited elements or components.

Throughout this application, various embodiments of this disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range.

It is appreciated that certain features of the disclosure, which are, for clarity, described in the context of separate embodiments, can also be provided in combination in a single embodiment. Conversely, various features of the disclosure, which are, for brevity, described in the context of a single embodiment, can also be provided separately or in any suitable subcombination or as suitable in any other described embodiment of the disclosure. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

Compositions

In certain embodiments, compositions of the disclosure comprise probiotic compositions formulated for administration and/or consumption, with a prebiotic and any necessary or useful excipient. In other embodiments, compositions of the disclosure comprise probiotic compositions formulated for consumption without a prebiotic. Probiotic compositions are preferably isolated from foods normally consumed raw and isolated for cultivation. In some embodiments, microbes are isolated from different foods normally consumed raw, but multiple microbes from the same food source may be used.

It is known to those of skill in the art how to identify microbial strains. Bacterial strains are commonly identified by 16S rRNA gene sequence. Fungal species can be identified by sequence of the internal transcribed space (ITS) regions of rDNA.

One of skill in the art will recognize that the 16S rRNA gene and the ITS region comprise a small portion of the overall genome, and so sequence of the entire genome (whole genome sequence) may also be obtained and compared to known species.

Additionally, multi-locus sequence typing (MLST) is known to those of skill in the art. This method uses the sequences of 7 known bacterial genes, typically 7 housekeeping genes, to identify bacterial species based upon sequence identity of known species as recorded in the publicly available PubMLST database. Housekeeping genes are genes involved in basic cellular functions.

In certain embodiments, bacterial entities are identified by comparison of the 16S rRNA sequence to those of known bacterial species, as is well understood by those of skill in the art. In certain embodiments, fungal species are identified based upon comparison of the ITS sequence to those of known species (Schoch et al PNAS 2012). In certain embodiments, microbial strains are identified by whole genome sequencing and subsequent comparison of the whole genome sequence to a database of known microbial genome sequences. While microbes identified by whole genome sequence comparison, in some embodiments, are described and discussed in terms of their closest defined genetic match, in certain embodiments as indicated by 16S rRNA gene sequence, it should be understood that these microbes are not identical to their closest genetic match and are novel microbial entities. This can be shown by examining the Average Nucleotide Identity (ANI) of microbial entities of interest as compared to the reference strain that most closely matches the genome of the microbial entity of interest (see, e.g., WO2020051379A1).

In other embodiments, microbial entities described herein are functionally equivalent to previously described strains with homology at the 16S rRNA or ITS region. In certain embodiments, functionally equivalent bacterial strains have at least 95% identity at the 16S rRNA region and functionally equivalent fungal strains have at least 95% identity at the ITS region. In certain embodiments, functionally equivalent bacterial strains have at least 96% identity at the 16S rRNA region and functionally equivalent fungal strains have at least 96% identity at the ITS region. In certain embodiments, functionally equivalent bacterial strains have at least 97% identity at the 16S rRNA region and functionally equivalent fungal strains have at least 97% identity at the ITS region. In certain embodiments, functionally equivalent bacterial strains have at least 98% identity at the 16S rRNA region and functionally equivalent fungal strains have at least 98% identity at the ITS region. In certain embodiments, functionally equivalent bacterial strains have at least 99% identity at the 16S rRNA region and functionally equivalent fungal strains have at least 99% identity at the ITS region. In certain embodiments, functionally equivalent bacterial strains have at least 99.5% identity at the 16S rRNA region and functionally equivalent fungal strains have at least 99.5% identity at the ITS region. In certain embodiments, functionally equivalent bacterial strains have 100% identity at the 16S rRNA region and functionally equivalent fungal strains have 100% identity at the ITS region.

16S rRNA sequences for strains tolerant of relevant stressors are found in SEQ ID NOs 1-102 (Table 2). 16S rRNA is one way to classify bacteria into operational taxonomic units (OTUs). Bacterial strains with 97% sequence identity at the 16S rRNA locus are considered to belong to the same OTU. A similar calculation can be done with fungi using the ITS locus in place of the bacterial 16S rRNA sequence.

In some embodiments, the invention provides a probiotic composition for the treatment of, e.g., osteoporosis, osteopenia, Paget's disease, stunting, inflammation, menopause symptoms, perimenopause symptoms, or postmenopause symptoms. In some embodiments, the composition comprises a mixture of lactic acid bacteria, such as *Pediococcus* spp, *Leuconostoc* spp, *Leuconostoc mesenteroides, Lactobacillus* spp, *Lactobacillus crispatus, Lactobacillus plantarum, Lactobacillus brevis*, and/or *Lactobacillus reuteri*, optionally combined with non-lactic acid bacteria such as one or more of the non-lactic acid bacteria described in Table 1 or Table 2. In some embodiments, the invention provides a fermented probiotic composition for the treatment of bone diseases, inflammation, or symptoms of menopause, perimenopause, or postmenopause, comprising a mixture of *Lactobacillus plantarum, Lactobacillus brevis*, and/or *Leuconostoc mesenteroides* and at least one non-lactic acid bacterium, preferably a bacterium classified as a gamma proteobacterium or a filamentous fungus or yeast (e.g. *Pichia kudrivzevii*). Some embodiments comprise the probiotic being in a capsule or microcapsule adapted for enteric delivery.

In some embodiments, the invention provides a probiotic composition comprising a fungal microbe. In some embodiments, the fungal microbe is a yeast, such as *Pichia kudriavzevii, Candida krusei, Issatchenkia orientalis*, and/or *Candida glycerinogenes*. In some embodiments, the fungal microbe is selected from a fungal microbe listed in Table 1 or Table 2.

In some embodiments, the invention provides a probiotic composition comprising a mixture of lactic acid bacteria (such as *Pediococcus* spp, *Leuconostoc* spp, *Leuconostoc mesenteroides, Lactobacillus* spp, *Lactobacillus crispatus, Lactobacillus plantarum, Lactobacillus brevis, Lactobacillus reuteri*) and fungal microbes (such as yeast, e.g. *Pichia kudriavzevii, Candida krusei, Issatchenkia orientalis*, and/or *Candida glycerinogenes*). In some embodiments, the composition comprises at least one, at least two, at least three, at least four, at least five, etc., heterologous lactic acid bacteria and at least one, at least two, at least three, at least four, at least five, etc. heterologous fungal microbes. In some embodiments, the composition comprises three species of lactic acid bacteria. In some embodiments, the composition comprises *Lactobacillus brevis, Lactobacillus plantarum*, and *Leuconostoc mesenteroides*. In some embodiments, the composition comprises one species of fungal microbe. In some embodiments, the composition comprises *Pichia kudriavzevii*. In some embodiments, the composition comprises *Lactobacillus brevis, Lactobacillus plantarum, Leuconostoc mesenteroides*, and *Pichia kudriavzevii.*

In some embodiments, the compositions disclosed herein are derived from edible plants and can comprise a mixture of microorganisms, comprising bacteria, fungi, archaea, and/or other indigenous or exogenous microorganisms, all of which work together to form a microbial ecosystem with a role for one or more of its members. In some embodiments, the compositions disclosed herein comprise a microorganism listed in Table 1, which were isolated from edible plant samples. The isolation and identification of the strains in Table 1 is described in WO2020051379A1, which is hereby incorporated by reference in its entirety.

TABLE 1

Bacteria identified in a 15-sample survey of edible plants and identified by hole genome matching to reference genomes.

| Strain identified by k-mer based on entire genome | Strain number | Collection |
|---|---|---|
| *Acinetobacter baumannii* | — | |
| *Acinetobacter soli* | — | |
| *Acinetobacter* 41764 Branch | — | |
| *Acinetobacter* 41930 Branch | — | |
| *Acinetobacter* 41981 Branch | — | |
| *Acinetobacter* 41982 Branch | — | |
| *Acinetobacter baumannii* 348935 | — | |
| *Acinetobacter baumannii* 40298 Branch | — | |
| *Acinetobacter beijerinckii* 41969 Branch | — | |
| *Acinetobacter beijerinckii* CIP 110307 | CIP 110307 | WFCC |
| *Acinetobacter bohemicus* ANC 3994 | — | |
| *Acinetobacter guillouiae* 41985 Branch | — | |
| *Acinetobacter guillouiae* 41986 Branch | — | |
| *Acinetobacter gyllenbergii* 41690 Branch | — | |
| *Acinetobacter haemolyticus* TG19602 | — | |
| *Acinetobacter harbinensis* strain HITLi 7 | — | |
| *Acinetobacter johnsonii* 41886 Branch | — | |
| *Acinetobacter johnsonii* ANC 3681 | — | |
| *Acinetobacter junii* 41994 Branch | — | |
| *Acinetobacter lwoffii* WJ10621 | — | |
| *Acinetobacter* sp 41945 Branch | — | |
| *Acinetobacter* sp 41674 Branch | — | |
| *Acinetobacter* sp 41698 Branch | — | |
| *Acinetobacter* sp ETR1 | — | |
| *Acinetobacter* sp NIPH 298 | — | |
| *Acinetobacter tandoii* 41859 Branch | — | |
| *Acinetobacter tjernbergiae* 41962 Branch | — | |
| *Acinetobacter towneri* 41848 Branch | — | |
| *Acinetobacter venetianus* VE C3 | — | |
| *Actinobacterium* LLX17 | — | |
| *Aeromonas bestiarum* strain CECT 4227 | CECT 4227 | CECT |
| *Aeromonas caviae* strain CECT 4221 | CECT 4221 | CECT |
| *Aeromonas hydrophila* 4AK4 | — | |
| *Aeromonas media* 37528 Branch | — | |
| *Aeromonas media* strain ARB 37524 Branch | — | |
| *Aeromonas salmonicida* subsp 37538 Branch | — | |
| *Aeromonas* sp ZOR0002 | — | |
| *Agrobacterium* 22298 Branch | — | |
| *Agrobacterium* 22301 Branch | — | |
| *Agrobacterium* 22313 Branch | — | |
| *Agrobacterium* 22314 Branch | — | |
| *Agrobacterium* sp ATCC 31749 | ATCC 31749 | ATCC |
| *Agrobacterium tumefaciens* 22306 Branch | | |
| *Agrobacterium tumefaciens* strain MEJ076 | — | |
| *Agrobacterium tumefaciens* strain S2 | — | |
| *Alkanindiges illinoisensis* DSM 15370 | DSM 15370 | WFCC |
| alpha proteobacterium L41A | — | |
| *Arthrobacter* 20515 Branch | — | |
| *Arthrobacter arilaitensis* Re117 | — | |
| *Arthrobacter chlorophenolicus* A6 | — | |
| *Arthrobacter nicotinovorans* 20547 Branch | — | |
| *Arthrobacter phenanthrenivorans* Sphe3 | — | |
| *Arthrobacter* sp 20511 Branch | — | |
| *Arthrobacter* sp PAO19 | — | |
| *Arthrobacter* sp W1 | — | |
| *Aureimonas* sp. Leaf427 | — | |
| *Aureobasidium pullulans* | — | |
| Bacillaceae Family 24 4101 12691 Branch | — | |
| *Bacillus* sp. LL01 | — | |
| *Bacillus* 12637 Branch | — | |
| *Bacillus aerophilus* strain C772 | — | |
| *Bacillus thuringiensis* serovar 12940 Branch | — | |
| *Brevundimonas nasdae* strain TPW30 | — | |
| *Brevundimonas* sp 23867 Branch | — | |
| *Brevundimonas* sp EAKA | — | |
| *Buchnera aphidicola* str 28655 Branch | — | |
| Burkholderiales Order 15 6136 Node 25777 | — | |
| *Buttiauxella agrestis* 35837 Branch | — | |
| *Candidatus Burkholderia verschuerenii* | — | |
| *Carnobacterium* 5833 Branch | — | |
| *Carnobacterium maltaromaticum* ATCC 35586 | ATCC 35586 | ATCC |
| *Chryseobacterium* 285 Branch | — | |

TABLE 1-continued

Bacteria identified in a 15-sample survey of edible plants and identified by hole genome matching to reference genomes.

| Strain identified by k-mer based on entire genome | Strain number | Collection |
|---|---|---|
| *Chryseobacterium daeguense* DSM 19388 | DSM 19388 | WFCC |
| *Chryseobacterium formosense* | — | |
| *Chryseobacterium* sp YR005 | — | |
| *Clavibacter* 20772 Branch | — | |
| *Clostridium diolis* DSM 15410 | DSM 15410 | WFCC |
| *Comamonas* sp B 9 | — | |
| *Curtobacterium flaccumfaciens* 20762 Branch | — | |
| *Curtobacterium flaccumfaciens* UCD AKU | — | |
| *Curtobacterium* sp UNCCL17 | — | |
| *Deinococcus aquatilis* DSM 23025 | DSM 23025 | WFCC |
| *Debaromyces hansenii* | ATCC 36239 | ATCC |
| *Duganella zoogloeoides* | ATCC 25935 | |
| *Dyadobacter* 575 Branch | — | |
| *Elizabethkingia anophelis* | — | |
| *Empedobacter falsenii* strain 282 | — | |
| *Enterobacter* sp 638 | — | |
| Enterobacteriaceae Family 9 3608 Node 35891 | — | |
| Enterobacteriaceae Family 9 593 Node 36513 | — | |
| *Epilithonimonas lactis* | — | |
| *Epilithonimonas tenax* DSM 16811 | DSM 16811 | WFCC |
| *Erwinia* 35491 Branch | — | |
| *Erwinia amylovora* 35816 Branch | — | |
| *Erwinia pyrifoliae* 35813 Branch | — | |
| *Erwinia tasmaniensis* Et1 99 | DSM 17950 | WFCC |
| *Escherichia coli* ISC11 | — | |
| *Exiguobacterium* 13246 Branch | — | |
| *Exiguobacterium* 13260 Branch | — | |
| *Exiguobacterium sibiricum* 255 15 | DSM 17290 | WFCC |
| *Exiguobacterium* sp 13263 Branch | — | |
| *Exiguobacterium undae* 13250 Branch | — | |
| *Exiguobacterium undae* DSM 14481 | DSM 14481 | WFCC |
| *Flavobacterium* 237 Branch | — | |
| *Flavobacterium aquatile* LMG 4008 | LMG 4008 | WFCC |
| *Flavobacterium chungangense* LMG 26729 | LMG 26729 | WFCC |
| *Flavobacterium daejeonense* DSM 17708 | DSM 17708 | WFCC |
| *Flavobacterium hibernum* strain DSM 12611 | DSM 12611 | WFCC |
| *Flavobacterium hydatis* | — | |
| *Flavobacterium johnsoniae* UW101 | ATCC 17061D-5 | ATCC |
| *Flavobacterium reichenbachii* | — | |
| *Flavobacterium soli* DSM 19725 | DSM 19725 | WFCC |
| *Flavobacterium* sp 238 Branch | — | |
| *Flavobacterium* sp EM1321 | — | |
| *Flavobacterium* sp MEB061 | — | |
| *Hanseniaspora uvarum* | ATCC 18859 | |
| *Hanseniaspora occidentalis* | ATCC 32053 | |
| *Herminiimonas arsenicoxydans* | — | |
| *Hymenobacter swuensis* DY53 | — | |
| *Janthinobacterium* 25694 Branch | — | |
| *Janthinobacterium agaricidamnosum* NBRC 102515 | DSM 9628 | WFCC |
| *Janthinobacterium lividum* strain RIT308 | — | |
| *Janthinobacterium* sp RA13 | — | |
| *Kocuria* 20614 Branch | — | |
| *Kocuria rhizophila* 20623 Branch | — | |
| *Lactobacillus acetotolerans* | — | |
| *Lactobacillus brevis* | — | |
| *Lactobacillus buchneri* | — | |
| *Lactobacillus futsaii* | — | |
| *Lactobacillus kefiranofaciens* | — | |
| *Lactobacillus panis* | — | |
| *Lactobacillus parafarraginis* | — | |
| *Lactobacillus plantarum* | — | |
| *Lactobacillus rapi* | — | |
| *Lactobacillus crispatus* 5565 Branch | — | |
| *Lactobacillus plantarum* WJL | — | |
| *Lactobacillus reuteri* 5515 Branch | — | |
| *Leuconostoc mesenteroides* | ATCC 8293 | |
| *Luteibacter* sp 9135 | — | |
| *Massilia timonae* CCUG 45783 | — | |
| *Methylobacterium extorquens* 23001 Branch | — | |
| *Methylobacterium* sp 22185 Branch | — | |
| *Methylobacterium* sp 285MFTsu5 1 | — | |
| *Methylobacterium* sp 88A | — | |
| *Methylotenera versatilis* 7 | — | |
| *Microbacterium laevaniformans* OR221 | — | |
| *Microbacterium oleivorans* | — | |

TABLE 1-continued

| Bacteria identified in a 15-sample survey of edible plants and identified by hole genome matching to reference genomes. | | |
|---|---|---|
| Strain identified by k-mer based on entire genome | Strain number | Collection |
| *Microbacterium* sp MEJ108Y | — | |
| *Microbacterium* sp UCD TDU | — | |
| *Microbacterium testaceum* StLB037 | — | |
| *Micrococcus luteus* strain RIT304 | NCTC 2665 | NCTC |
| *Mycobacterium abscessus* 19573 Branch | — | |
| *Neosartorya fischeri* | — | |
| *Oxalobacteraceae bacterium* AB 14 | — | |
| *Paenibacillus* sp FSL 28088 Branch | — | |
| *Paenibacillus* sp FSL H7 689 | — | |
| *Pantoea* sp. SL1 M5 | — | |
| *Pantoea* 36041 Branch | — | |
| *Pantoea agglomerans* strain 4 | — | |
| *Pantoea agglomerans* strain 4 | — | |
| *Pantoea agglomerans* strain LMAE 2 | — | |
| *Pantoea agglomerans* Tx10 | — | |
| *Pantoea* sp 36061 Branch | — | |
| *Pantoea* sp MBLJ3 | — | |
| *Pantoea* sp SL1 M5 | — | |
| *Paracoccus* sp PAMC 22219 | — | |
| *Patulibacter minatonensis* DSM 18081 | DSM 18081 | WFCC |
| *Pectobacterium carotovorum* subsp *carotovorum* strain 28625 Branch | — | |
| *Pediococcus ethanolidurans* | — | |
| *Pediococcus pentosaceus* | ATCC 33314 | |
| *Pedobacter* 611 Branch | — | |
| *Pedobacter agri* PB92 | — | |
| *Pedobacter borealis* DSM 19626 | DSM 19626 | WFCC |
| *Pedobacter kyungheensis* strain KACC 16221 | — | |
| *Pedobacter* sp R20 19 | — | |
| *Periglandula ipomoeae* | — | |
| *Planomicrobium glaciei* CHR43 | — | |
| *Propionibacterium acnes* | — | |
| *Propionibacterium* 20955 Branch | — | |
| *Propionibacterium acnes* 21065 Branch | — | |
| *Pseudomonas fluorescens* | — | |
| *Pseudomonas* sp. DSM 29167 | — | |
| *Pseudomonas* sp. Leaf15 | — | |
| *Pseudomonas syringae* | — | |
| *Pseudomonas* 39524 Branch | — | |
| *Pseudomonas* 39642 Branch | — | |
| *Pseudomonas* 39733 Branch | — | |
| *Pseudomonas* 39744 Branch | — | |
| *Pseudomonas* 39791 Branch | — | |
| *Pseudomonas* 39821 Branch | — | |
| *Pseudomonas* 39834 Branch | — | |
| *Pseudomonas* 39875 Branch | — | |
| *Pseudomonas* 39880 Branch | — | |
| *Pseudomonas* 39889 Branch | — | |
| *Pseudomonas* 39894 Branch | — | |
| *Pseudomonas* 39913 Branch | — | |
| *Pseudomonas* 39931 Branch | — | |
| *Pseudomonas* 39942 Branch | — | |
| *Pseudomonas* 39979 Branch | — | |
| *Pseudomonas* 39996 Branch | — | |
| *Pseudomonas* 40058 Branch | — | |
| *Pseudomonas* 40185 Branch | — | |
| *Pseudomonas abietaniphila* strain KF717 | — | |
| *Pseudomonas chlororaphis* strain EA105 | — | |
| *Pseudomonas cremoricolorata* DSM 17059 | DSM 17059 | WFCC |
| *Pseudomonas entomophila* L48 | — | |
| *Pseudomonas extremaustralis* 14 3 substr 14 3b | — | |
| *Pseudomonas fluorescens* BBC6R8 | — | |
| *Pseudomonas fluorescens* BS2 | ATCC 12633 | ATCC |
| *Pseudomonas fluorescens* EGD AQ6 | — | |
| *Pseudomonas fluorescens* strain AU 39831 Branch | — | |
| *Pseudomonas fluorescens* strain AU10973 | — | |
| *Pseudomonas fluorescens* strain AU14440 | — | |
| *Pseudomonas fragi* B25 | NCTC 10689 | NCTC |
| *Pseudomonas frederiksbergensis* strain SI8 | — | |
| *Pseudomonas fulva* strain MEJ086 | — | |
| *Pseudomonas fuscovaginae* 39768 Branch | — | |
| *Pseudomonas gingeri* NCPPB 3146 | NCPPB 3146 | NCPPB |
| *Pseudomonas lutea* | — | |
| *Pseudomonas luteola* XLDN4 9 | — | |
| *Pseudomonas mandelii* JR 1 | — | |
| *Pseudomonas moraviensis* R28 S | — | |

TABLE 1-continued

Bacteria identified in a 15-sample survey of edible plants and identified by hole genome matching to reference genomes.

| Strain identified by k-mer based on entire genome | Strain number | Collection |
|---|---|---|
| *Pseudomonas mosselii* SJ10 | — | |
| *Pseudomonas plecoglossicida* NB 39639 Branch | — | |
| *Pseudomonas poae* RE*1 1 14 | — | |
| *Pseudomonas pseudoalcaligenes* AD6 | — | |
| *Pseudomonas psychrophila* HA 4 | — | |
| *Pseudomonas putida* DOT TIE | — | |
| *Pseudomonas putida* strain KF703 | — | |
| *Pseudomonas putida* strain MC4 5222 | — | |
| *Pseudomonas rhizosphaerae* | — | |
| *Pseudomonas rhodesiae* strain FF9 | — | |
| *Pseudomonas* sp 39813 Branch | — | |
| *Pseudomonas simiae* strain 2 36 | — | |
| *Pseudomonas simiae* strain MEB105 | — | |
| *Pseudomonas* sp 11 12A | — | |
| *Pseudomonas* sp 2 922010 | — | |
| *Pseudomonas* sp CF149 | — | |
| *Pseudomonas* sp Eur1 9 41 | — | |
| *Pseudomonas* sp LAMO17WK12 I2 | — | |
| *Pseudomonas* sp PAMC 25886 | — | |
| *Pseudomonas* sp PTA1 | — | |
| *Pseudomonas* sp R62 | — | |
| *Pseudomonas* sp WCS374 | — | |
| *Pseudomonas synxantha* BG33R | — | |
| *Pseudomonas synxantha* BG33R | — | |
| *Pseudomonas syringae* 39550 Branch | — | |
| *Pseudomonas syringae* 39596 Branch | — | |
| *Pseudomonas syringae* 40123 Branch | — | |
| *Pseudomonas syringae* CC 39499 Branch | — | |
| *Pseudomonas syringae* pv panici str LMG 2367 | — | |
| *Pseudomonas syringae* strain mixed | — | |
| *Pseudomonas tolaasii* 39796 Branch | — | |
| *Pseudomonas tolaasii* PMS117 | — | |
| *Pseudomonas veronii* 1YdBTEX2 | — | |
| *Pseudomonas viridiflava* CC1582 | — | |
| *Pseudomonas viridiflava* strain LMCA8 | — | |
| *Pseudomonas viridiflava* TA043 | — | |
| *Pseudomonas viridiflava* UASWS0038 | — | |
| *Rahnella* 35969 Branch | — | |
| *Rahnella* 35970 Branch | — | |
| *Rahnella* 35971 Branch | — | |
| *Rahnella aquatilis* HX2 | — | |
| *Rahnella* sp WP5 | — | |
| *Raoultella ornithinolytica* | — | |
| Rhizobiales Order 22324 Branch | — | |
| *Rhizobium* sp YR528 | — | |
| *Rhodococcus fascians* A76 | — | |
| *Rhodococcus* sp BS 15 | — | |
| *Saccharomyces cerevisiae* | — | |
| *Sanguibacter keddieii* | DSM 10542 | WFCC |
| *Serratia fonticola* AU 35657 Branch | — | |
| *Serratia fonticola* AU AP2C | — | |
| *Serratia liquefaciens* ATCC 27592 | ATCC 27592 | ATCC |
| *Serratia* sp H 35589 Branch | — | |
| *Shewanella* 37294 Branch | — | |
| *Shewanella baltica* 37301 Branch | — | |
| *Shewanella baltica* 37315 Branch | — | |
| *Shewanella baltica* OS 37308 Branch | — | |
| *Shewanella baltica* OS 37312 Branch | — | |
| *Shewanella baltica* OS185 | — | |
| *Shewanella baltica* OS223 | — | |
| *Shewanella baltica* OS678 | — | |
| *Shewanella oneidensis* MR 1 | — | |
| *Shewanella putrefaciens* HRCR 6 | — | |
| *Shewanella* sp W3 18 1 | — | |
| *Sphingobacterium* sp ML3W | — | |
| *Sphingobium japonicum* BiD32 | — | |
| *Sphingobium xenophagum* 24443 Branch | — | |
| *Sphingomonas echinoides* ATCC 14820 | ATCC 14820 | ATCC |
| *Sphingomonas parapaucimobilis* NBRC 15100 | ATCC 51231 | ATCC |
| *Sphingomonas paucimobilis* NBRC 13935 | ATCC 29837 | ATCC |
| *Sphingomonas phyllosphaerae* 5 2 | — | |
| *Sphingomonas* sp 23777 Branch | — | |
| *Sphingomonas* sp STIS6 2 | — | |
| *Staphylococcus* 6317 Branch | — | |
| *Staphylococcus equorum* UMC CNS 924 | — | |

TABLE 1-continued

| Bacteria identified in a 15-sample survey of edible plants and identified by hole genome matching to reference genomes. | | |
|---|---|---|
| Strain identified by k-mer based on entire genome | Strain number | Collection |
| *Staphylococcus* sp 6275 Branch | — | |
| *Staphylococcus* sp 6240 Branch | — | |
| *Staphylococcus* sp OJ82 | — | |
| *Staphylococcus xylosus* strain LSR 02N | — | |
| *Stenotrophomonas* 14028 Branch | — | |
| *Stenotrophomonas* 42816 Branch | — | |
| *Stenotrophomonas maltophilia* 42817 Branch | — | |
| *Stenotrophomonas maltophilia* PML168 | — | |
| *Stenotrophomonas maltophilia* strain ZBG7B | — | |
| *Stenotrophomonas rhizophila* | — | |
| *Stenotrophomonas* sp RIT309 | — | |
| *Streptococcus gallolyticus* subsp *gallolyticus* TX20005 | — | |
| *Streptococcus infantarius* subsp *infantarius* 2242 Branch | — | |
| *Streptococcus infantarius* subsp *infantarius* ATCC BAA 102 | ATCC BAA 102 | ATCC |
| *Streptococcus macedonicus* ACA DC 198 | ATCC BAA-249 | ATCC |
| *Streptomyces olindensis* | — | |
| *Variovorax paradoxus* 110B | — | |
| *Variovorax paradoxus* ZNC0006 | — | |
| *Variovorax* sp CF313 | — | |
| *Vibrio fluvialis* 44473 Branch | — | |
| *Xanthomonas campestris* 37936 Branch | — | |
| *Xanthomonas campestris* pv *raphani* 756C | — | |

In some embodiments, the compositions disclosed herein comprise a microorganism listed in Table 2. These microbes are characterized in WO2020051379A1, which is incorporated by reference in its entirety.

TABLE 2

| Strains | | |
|---|---|---|
| Strain Number | Genus | Species |
| DP1 | *Pseudomonas* | *fluorescens* |
| DP2 | *Hanseniaspora* | *occidentalis* |
| DP3 | *Leuconostoc* | *mesenteroides* |
| DP4 | *Aureobasidium* | *pullulans* |
| DP5 | *Debaromyces* | *hansenii* |
| DP6 | *Bacillus* | *wiedmannii* |
| DP7 | *Pichia* | *fermentans* |
| DP8 | *Hanseniaspora* | *opuntiae* |
| DP9 | *Pediococcus* | *pentosaceus* |
| DP10 | *Bacillus* | *velezensis* |
| DP11 | *Pseudomonas* | *putida* |
| DP12 | *Microbacterium* | sp. |
| DP13 | *Bacillus* | *mycoides* |
| DP14 | *Arthrobacter* | *luteolus* |
| DP15 | *Curtobacterium* | sp. |
| DP16 | *Lacihabitans* | *lacunae* |
| DP17 | *Rahnella* | *aquatilis* |
| DP18 | *Pseudomonas* | sp. |
| DP19 | *Curtobacterium* | *pusillum* |
| DP20 | *Stenotrophomonas* | *rhizophila* |
| DP21 | *Candida* | *santamariae* |
| DP22 | *Rahnella* | sp. |
| DP23 | *Erwinia* | *billingiae* |
| DP24 | *Filobasidium* | *globisporum* |
| DP25 | *Penicillium* | *solitum* |
| DP26 | *Methylobacterium* | sp. |
| DP27 | *Sphingomonas* | sp. |
| DP28 | *Aureobasidium* | *pullulans* |
| DP29 | *Pseudoclavibacter* | *helvolus* |
| DP30 | *Microbacterium* | *testaceum* |
| DP31 | *Sporisorium* | *reilianum* |
| DP32 | *Hafnia* | *paralvei* |
| DP33 | *Erwinia* | *persicinus* |
| DP34 | *Plantibacter* | *flavus* |
| DP35 | *Pantoea* | *ananatis* |
| DP36 | *Pantoea* | *vagans* |

TABLE 2-continued

| Strains | | |
|---|---|---|
| Strain Number | Genus | Species |
| DP37 | *Pseudomonas* | *rhodesiae* |
| DP38 | *Rhodococcus* | sp. |
| DP39 | *Agrobacterium* | *tumefaciens* |
| DP40 | *Pantoea* | sp. |
| DP41 | *Corynebacterium* | *mucifaciens* |
| DP42 | *Pseudomonas* | *lundensis* |
| DP43 | *Janthinobacterium* | sp. |
| DP44 | *Herbaspirillum* | sp. |
| DP45 | *Sanguibacter* | *keddieii* |
| DP46 | *Pantoea* | *agglomerans* |
| DP47 | *Cronobacter* | *dublinensis* |
| DP48 | *Bacillus* | *paralicheniformis* |
| DP49 | *Bacillus* | *gibsonii* |
| DP50 | *Enterobacter* | sp. |
| DP51 | *Klebsiella* | *aerogenes* |
| DP52 | *Arthrobacter* | sp. |
| DP53 | *Pseudomonas* | *fragi* |
| DP54 | *Methylobacterium* | *adhaesivum* |
| DP55 | *Bacillus* | *megaterium* |
| DP56 | *Paenibacillus* | *lautus* |
| DP57 | *Bacillus* | *mycoides* |
| DP58 | *Janthinobacterium* | *svalbardensis* |
| DP59 | *Kosakonia* | *cowanii* |
| DP60 | *Bacillus* | *simplex* |
| DP61 | *Lelliottia* | sp. |
| DP62 | *Erwinia* | sp. |
| DP63 | *Pseudomonas* | *azotoformans* |
| DP64 | *Hanseniaspora* | *uvarum* |
| DP65 | *Bacillus* | *sp.* |
| DP66 | *Hanseniaspora* | occidentalis |
| DP67 | *Bacillus* | sp. |
| DP68 | *Bacillus* | *atrophaeus* |
| DP69 | *Bacillus* | sp. |
| DP70 | *Bacillus* | *subtilis* |
| DP71 | *Rhodotorula* | sp. |
| DP72 | *Bacillus* | *zhangzhouensis* |
| DP73 | *Bacillus* | *clausii* |
| DP74 | *Bacillus* | *coagulans* |
| DP75 | *Pseudomonas* | *gessardii* |
| DP76 | *Ochrobactrum* | sp. |
| DP77 | *Bacillus* | *aryabhattai* |
| DP78 | *Erwinia* | *rhapontici* |

TABLE 2-continued

| Strains | | |
|---|---|---|
| Strain Number | Genus | Species |
| DP79 | *Pseudomonas* | *fragi* |
| DP80 | *Methylobacterium* | *adhaesivum* |
| DP81 | *Bacillus* | *clausii* |
| DP82 | *Bacillus* | *clausii* |
| DP83 | *Bacillus* | *clausii* |
| DP84 | *Microbacterium* | sp. |
| DP85 | *Methanolacinia* | *petrolearia* |
| DP86 | *Bacillus* | *velezensis* |
| DP87 | *Lactobacillus* | *plantarum* |
| DP88 | *Bacillus* | *velezensis* |
| DP89 | *Bacillus* | *subtilis* |
| DP90 | *Lactobacillus* | *plantarum* |
| DP92 | *Bacillus* | *subtilis* |
| DP93 | *Leuconostoc* | *mesenteroides* |
| DP94 | *Lactobacillus* | *brevis* |
| DP95 | *Lactobacillus* | *paracasei* |
| DP96 | *Lactobacillus* | *casei* |
| DP97 | *Lactococcus* | *garvieae* |
| DP98 | *Lactococcus* | *garvieae* |
| DP99 | *Weissella* | *cibaria* |
| DP100 | *Lactobacillus* | *plantarum* |
| DP101 | *Pediococcus* | *pentosaceus* |
| DP102 | *Pichia* | *kudriavzevii* |

In some embodiments, species of interest are isolated from plant-based food sources normally consumed raw. These isolated compositions of microorganisms from individual plant sources can be combined to create a new mixture of organisms. Particular species from individual plant sources can be selected and mixed with other species cultured from other plant sources, which have been similarly isolated and grown. In some embodiments, species of interest are grown in pure cultures before being prepared for consumption or administration. In some embodiments, the species of interest are grown by bulk fermentation. In certain embodiments, the species of interest are grown in fermenters under controlled conditions of temperature, pH, aeration/gas flow and/or agitation. In some embodiments, the organisms grown in pure culture are combined to form a synthetic combination of organisms.

In some embodiments, the microbial composition comprises proteobacteria or gamma proteobacteria. In some embodiments, at least one species from each of four groups is present, the four groups being: lactic acid bacteria, Bacilli, proteobacteria, and yeast. In some embodiments, at least one additional microbe from a group other than the four stated above is also present. In some embodiments, the microbial composition comprises several species of *Pseudomonas*. In some embodiments, species from another genus are also present. In some embodiments, a species from the genus *Duganella* is also present. In some embodiments of said microbial composition, the population comprises at least three unique isolates selected from the group consisting of *Pseudomonas, Acinetobacter, Aeromonas, Curtobacterium, Escherichia, Lactobacillus, Serratia, Streptococcus*, and *Stenotrophomonas*. In some embodiments, the bacteria are selected based upon their ability to degrade fibers, including plant fibers, and/or to modulate production of one or more branch chain fatty acids, short chain fatty acids, and/or flavones in a mammalian gut.

In some embodiments, microbial compositions comprise isolates that are capable of modulating production or activity of the enzymes involved in fatty acid metabolism, such as acetolactate synthase I, N-acetylglutamate synthase, acetate kinase, Acetyl-CoA synthetase, acetyl-CoA hydrolase, Glucan 1,4-alpha-glucosidase, or Bile acid symporter Acr3.

In some embodiments, microbial compositions of the disclosure comprise microbial strains that are capable of producing one or more neurotransmitters, e.g., neurotransmitters selected from the group consisting of serotonin, gamma-aminobutyric acid (GABA), dopamine, acetylcholine and combinations thereof. In some embodiments, the microbial compositions of the disclosure are capable of producing one or more neurotransmitters, e.g., neurotransmitters selected from the group consisting of serotonin, GABA, dopamine, acetylcholine and combinations thereof. In some embodiments, compositions of the disclosure comprise a metabolite (e.g., a neurotransmitter) produced by one or more microbial strains of the microbial composition.

In some embodiments, the administered microbial compositions colonize the treated mammal's digestive tract. In some embodiments, these colonizing microbes comprise bacterial assemblages present in whole food plant-based diets. In some embodiments, these colonizing microbes comprise *Pseudomonas* with a diverse species denomination that is present and abundant in whole food plant-based diets. In some embodiments, these colonizing microbes reduce free fatty acids absorbed into the body of a host by absorbing the free fatty acids in the gastrointestinal tract of mammals. In some embodiments, these colonizing microbes comprise genes encoding metabolic functions related to desirable health outcomes such as increased bone mineral density, prevention of loss of bone mineral density, improved bone turnover markers, improved inflammatory metabolic indicators, improvement of symptoms of menopause, perimenopause, or postmenopause, increased vitamin K production, etc.

Some embodiments comprise bacteria that are not completely viable but act by releasing metabolites that act in the gastro-intestinal tract of a patient promoting bone health or other desirable outcome. Some embodiments comprise a prebiotic composition derived from metabolites present in whole food plant-based materials, identified and enriched as part of the formula for oral delivery.

In some embodiments, biological materials (such as microbial strains including bacteria and fungi) are refrigerated at temperatures of about −20° C. or at about −80° C., e.g., with use of laboratory freezers. In some embodiments, biological materials are refrigerated at temperatures of about 4° C. In some embodiments, biological materials are stored using the vapor phase of liquid nitrogen that brings the temperature to −170° C. In some embodiments, biological materials are lyophilized.

In some embodiments, the constituent microbial strains of an assemblage are grown or produced separately and stored below room temperature (e.g. at about 4° C., about −20° C., about −80° C., or about −170° C.) prior to mixing. In some embodiments, the constituent microbial strains are stored in this manner for about 1 day to about 5 years, for example, for about 1 day to 1 week, about 1 week to 2 weeks, about 1 week to 1 month, about 1 month to 3 months, about 3 months to 6 months, about 6 months to 1 year, or about 1 year to 5 years. In some embodiments, the constituent microbial strains of an assemblage are combined into a composition or formulation, optionally in combination with other components (e.g. prebiotic components), and the composition or formulation is stored below room temperature (e.g. at about 4° C., about −20° C., about −80° C., or about −170° C.) prior to administration. In some embodiments, the composition or formulation is stored in this manner for about 1 day to about 5 years, for example, for about 1 day to 1 week, about 1 week to 2 weeks, about 1 week to 1 month, about 1 month to 3 months, about 3 months to 6 months, about 6 months to 1 year, or about 1 year to 5 years. In some embodiments, the foregoing storage conditions prevent or reduce a loss of viability or potency of the microbial strains.

In embodiments, compositions of the disclosure comprise dietary supplements, medical food compositions, and/or pharmaceutical compositions.

Prebiotics

Prebiotics, in accordance with the teachings of this disclosure, comprise compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect a subject's naturally-occurring gastrointestinal microflora and thereby impart health benefits apart from just nutrition. Prebiotic foods enter the colon and serve as substrate for the endogenous microbes, thereby indirectly providing the host with energy, metabolic substrates, and essential micronutrients. The body's digestion and absorption of prebiotic foods is dependent upon microbial metabolic activity, which salvages energy for the host from nutrients that escaped digestion and absorption in the small intestine.

Prebiotics help probiotics flourish in the gastrointestinal tract, and accordingly, their health benefits largely are indirect. Metabolites generated by colonic fermentation by intestinal microflora, such as short-chain fatty acids, can play important functional roles in the health of the host. Prebiotics can be useful agents for enhancing the ability of intestinal microflora to provide benefits to their host.

Prebiotics, in accordance with the embodiments of this disclosure, include, without limitation, mucopolysaccharides, oligosaccharides, polysaccharides, amino acids, vitamins, nutrient precursors, proteins, and combinations thereof.

According to particular embodiments, compositions comprise a prebiotic comprising a dietary fiber, including, without limitation, polysaccharides and oligosaccharides. These compounds have the ability to increase the number of probiotics, and augment their associated benefits. For example, an increase of beneficial *Bifidobacteria* likely changes the intestinal pH to support the increase of *Bifidobacteria*, thereby decreasing pathogenic organisms.

Non-limiting examples of oligosaccharides that are categorized as prebiotics in accordance with particular embodiments include fructooligosaccharides (i.e. oligofructose), inulins, isomalto-oligosaccharides, lactilol, lactosucrose, lactulose, pyrodextrins, soy oligosaccharides, transgalacto-oligosaccharides, cellulose, and xylo-oligosaccharides.

According to particular embodiments, compositions comprise a prebiotic comprising one or more amino acids.

Prebiotics are found naturally in a variety of foods including, without limitation, cabbage, bananas, berries (e.g., blueberries), asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans). Accordingly, in some embodiments, the composition comprises a prebiotic comprising a substance derived from one or more of the foregoing foods. In some embodiments, the substance is derived from berries, e.g., blueberries. In some embodiments, the prebiotic is a liquid, juice, or extract derived from a fruit or vegetable. In some embodiments, preparing and/or processing the prebiotic comprises a filtration step. In some embodiments, the prebiotic comprises a dried substance derived from a fruit or vegetable. In some embodiments, the prebiotic comprises a dried (and optionally, ground) fruit and/or vegetable powder. In some embodiments, the prebiotic comprises a dried (and optionally, ground) berry powder. In certain embodiments, the prebiotic comprises a dried (and optionally, ground) blueberry powder. In some embodiments, the prebiotic is processed or prepared via dehydration. In some embodiments, the prebiotic is processed or prepared via freeze-drying or lyophilization.

In some embodiments, the prebiotic may comprise a substrate that enables the production of a metabolite. For example, in certain embodiments, the prebiotic comprises a substance that enables the production of a short chain fatty acid (e.g. acetate, propionate, or butyrate). For example, in some embodiments, the prebiotic comprises a substance that enables the production of acetate. In some embodiments, prebiotics comprise one or more beneficial compounds such as flavonoids, anti-cyanines, phytoestrogens, and resberetrol.

According to particular embodiments, compositions comprise a prebiotic present in a sweetener composition or functional sweetened composition in an amount sufficient to promote health and wellness.

In particular embodiments, prebiotics also can be added to high-potency sweeteners or sweetened compositions. Non-limiting examples of prebiotics that can be used in this manner include fructooligosaccharides (i.e. oligofructose), xylooligosaccharides, galactooligosaccharides, and combinations thereof.

Many prebiotics have been discovered from dietary intake including, but not limited to: antimicrobial peptides, polyphenols, Okara (soybean pulp by product from the manufacturing of tofu), polydextrose, lactosucrose, malto-oligosaccharides, gluco-oligosaccharides (GOS), fructo-oligosaccharides (FOS), xantho-oligosaccharides, and soluble dietary fiber in general. Types of soluble dietary fiber include, but are not limited to, psyllium, pectin, or inulin. Phytoestrogens (plant-derived isoflavone compounds that have estrogenic effects) have been found to have beneficial growth effects of intestinal microbiota through increasing microbial activity and microbial metabolism by increasing the blood testosterone levels, in humans and farm animals. Phytoestrogen compounds include but are not limited to: Oestradiol, Daidzein, Formononetin, Biochainin A, Genistein, and Equol. Accordingly, in some embodiments, prebiotics comprising soluble dietary fiber and/or phytoestrogens (e.g. dried (optionally, ground) berry powder, e.g. blueberry powder) are beneficial when used in a composition of the disclosure.

Dosage for the compositions described herein are deemed to be "effective doses," indicating that the probiotic or prebiotic composition is administered in a sufficient quantity to alter the physiology of a subject in a desired manner. In some embodiments, the desired alterations include reducing, preventing, treating, or managing osteoporosis or osteopenia and sequelae associated with these conditions. In some embodiments, the desired alterations include reducing, preventing, treating, or managing inflammation. In some embodiments, the desired alterations occur in a menopausal, perimenopausal or postmenopausal subject. In some embodiments, the desired alterations include reducing or managing the severity of one or more symptoms of menopause, perimenopause or postmenopause.

Vitamin K is found in many fruits and vegetables including broccoli, grapes, lettuce, and olives and plays a role in a wide range of biological activities including calcium metabolism, cell proliferation, oxidative stress, and inflammation. Vitamin K2 (menaquinone) plays a vital role in bone synthesis and is produced by bacteria residing in the gastrointestinal tract. Vitamin K2 affects the proliferation and differentiation of osteoblasts, leading to increased osteoblast activity and bone matrix production. Specifically, Vitamin K2 stimulates the expression of osteoprotegerin (OPG) and inhibits the expression of receptor activator of nuclear factor kappa-B ligand (RANKL) on osteoblasts, leading to increased proliferation and activation. Vitamin K2 has also been shown to inhibit osteoclastic bone resorption, preventing the breakdown of bone.

In some embodiments, the compositions of the disclosure improve Vitamin K2 absorption. In some embodiments, the compositions of the disclosure produce Vitamin K2 in the gut of a subject. In some embodiments, the microbes of the disclosure are selected based upon their having genes involved in biosynthetic pathways for producing Vitamin K2.

In some embodiments, administering the compositions of the disclosure to a subject alters the microbiome of the subject, as compared to a suitable control. In some embodiments, the alteration is an increase in abundance of a microbial strain which is administered as part of the composition. In some embodiments, administering the compositions of the disclosure to a subject increases the abundance of genes involved in metabolic pathways for producing Vitamin K in the microbiome of the subject, as compared to a suitable control. In some embodiments, the suitable control is the microbiome of an appropriate control subject or control group that is not administered the composition. In some embodiments, the suitable control is a historical control, e.g., the microbiome of the subject prior to the first administration of the composition. In some embodiments, genes involved in the biosynthesis of menaquinol-6, menaquinol-9, menaquinol-10, demethylmenaquinol-6, and demethylmenaquinol-9 are increased in abundance following administration of a composition of the disclosure. Analysis of a subject's microbiome and any alterations thereto may be accomplished by any suitable technique known in the art, e.g., via metagenomic sequencing of an appropriate sample, e.g., a stool sample.

In some embodiments, the composition comprises a cryoprotectant. In general, a cryoprotectant functions through work by dissolving in water, lowering the melting point or a composition containing cells, and preventing or limiting intracellular and extracellular crystals from forming in cells during a freezing process. A cryoprotectant can allow for preservation of strain viability for prolonged periods of time, including extending viability for years. In some embodiments, the cryoprotectant is a prebiotic. In some embodiments, the cryoprotectant includes glycerol, trehalose, or Dimethyl sulfoxide (DMSO). In some embodiments, the cryoprotectant is derived from a plant source. In some embodiments, viability, measured at room temperature, is increased for at least one microbe by addition of cryoprotectant to a composition comprising said microbe wherein the composition is stored frozen. In some embodiments, viability is increased by at least 10, 15, 25, 35, 45, 50, 55, 65, 75, 85, 95, or 100 percent. Typically, a cryoprotectant (e.g., glycerol, trehalose, or DMSO) concentration of about 5% to 15% (e.g., about 5% to 12.5%, about 5% to 10%, about 5% to 7.5%, about 7.5% to 15%, about 7.5% to 12.5%, about 7.5% to 10%, about 10% to 15%, about 10% to 12.5%, or about 12.5% to 15%) is used and permits survival of a substantial fraction of isolated cells after freezing and thawing from cryogenic temperatures. One skilled in the art will recognize a cryoprotectant formulation can adjusted dependent on the cellular species to be preserved. For example, certain species (e.g., gamma proteobacteria) are sensitive to cryopreservation and lose considerable viability after few days in cryo-storage.

Methods of Use

Included within the scope of this disclosure are methods for treatment and/or management of musculoskeletal disorders including osteoporosis, osteopenia, Paget's disease, stunting, osteoarthritis, osteomyelitis, and delayed or non-union fractures. Also included within the scope of this disclosure are methods for preventing or prophylactically treating one of the aforementioned musculoskeletal disorders, e.g. by administering a composition of the disclosure to a subject at risk for having or developing one of said disorders. Also included within the scope of the disclosure are methods for managing, preventing, or reducing inflammation. Also included within the scope of the disclosure are methods for managing, treating, or preventing a symptom of menopause, perimenopause or postmenopause, e.g. a vasomotor symptom.

These methods include treatment with a prebiotic composition (e.g., a composition comprising or consisting of dried fruit or vegetable powder, FOS, GOS, and/or other appropriate polysaccharide), optionally in conjunction with a probiotic composition as described herein, one or more digestible saccharides (e.g., lactose, glucose, or galactose), a buffer, or a combination thereof. These methods optionally are used in combination with other treatments to treat, manage or prevent the disease, disorder, or condition. Any suitable treatment can be used. In some embodiments the additional treatment is administered before, during, or after treatment with a prebiotic composition, or any combination thereof. In an embodiment, when the disease or disorder (e.g., a musculoskeletal disorder) is not completely or substantially completely eliminated by treatment with a prebiotic composition, the additional treatment is administered after prebiotic treatment is terminated. The additional treatment is used on an as-needed basis.

In certain embodiments, the methods include additional treatment with vitamin D. In certain embodiments, a composition of the disclosure (e.g., a DMA composition as described herein) and vitamin D are administered to a subject simultaneously. In certain embodiments, a composition of the disclosure (e.g., a DMA composition as described herein) and vitamin D are administered to a subject separately. In certain embodiments, a composition of the disclosure (e.g., a DMA composition as described herein) and vitamin D are administered to a subject sequentially. In certain embodiments, vitamin D is administered to a subject prior to administration of a composition of the disclosure (e.g., a DMA composition as described herein). In certain embodiments, vitamin D is administered to a subject following administration of a composition of the disclosure (e.g., a DMA composition as described herein).

In some embodiments, a subject to be treated or prophylactically treated for a musculoskeletal disorder (e.g. osteoporosis or osteopenia), inflammation, and/or one or more symptoms of perimenopause, menopause, or postmenopause is a human. In an embodiment, the human subject is a preterm newborn, a full term newborn, an infant up to one year of age, a young child (e.g., 1 yr to 12 yrs), a teenager (e.g., 13-19 yrs), an adult (e.g., 20-64 yrs), a pregnant women, an adult in perimenopause, an adult in menopause, an adult in postmenopause, an adult that has undergone a menopause transition, or an elderly adult (65 yrs and older). In some embodiments, about 1 year to about 6 years have passed since the subject's last menstruation. In some embodiments, about 1, about 2, about 3, about 4, about 5, or about 6 years have passed since the subject's last menstruation. In some embodiments, more than about 6 years, more than about 7 years, more than about 8 years, more than about 9 years, or more than about 10 years have elapsed since the subject's last menstruation. In some embodiments, the subject has a bone density T-score equal to or less than about −2.5. In some embodiments, the subject has a bone density T-score equal to or greater than about −2.49. In some embodiments, the subject has been diagnosed with a musculoskeletal disorder, e.g. osteoporosis or osteopenia. In some embodiments, the subject is at risk for a musculoskeletal disorder, e.g. osteoporosis or osteopenia.

In some embodiments, the condition to be treated is osteoporosis or osteopenia. In some embodiments, the condition to be treated is osteoporosis or osteopenia, and treating osteoporosis further involves administration of any one or combination of known anti-osteoporosis medications or treatments. These include, but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide).

In some embodiments, the compositions and methods of the disclosure may be used to lessen a decrease in, maintain, or improve bone health in a subject, e.g., as compared to a suitable control. In certain embodiments, the suitable control is a control group or a control subject that is not administered the composition. In certain embodiments, the suitable control is a historical control, e.g., the bone health in the subject prior to the first administration of the composition, or the rate of change (e.g., decline) in bone health in the subject prior to the first administration of the composition. Bone health may be assessed using any appropriate technique known in the art, including, e.g., by bone mineral density (BMD) or by trabecular bone score (TBS).

In some embodiments, the compositions and methods of the disclosure may be used to lessen a decrease in, maintain, or improve bone mineral density (BMD) in a subject as compared to a suitable control. In certain embodiments, the suitable control is a control group or a control subject that is not administered the composition. In certain embodiments, the suitable control is a historical control, e.g., the BMD in the subject prior to the first administration of the composition, or the rate of change (e.g., decline) in BMD in the subject prior to the first administration of the composition. In some embodiments, total-body BMD, lumbar spine BMD, femur BMD, femoral neck BMD, hip BMD, or any combination thereof are maintained or improved as compared to a suitable control. BMD may be measured by any appropriate technique known in the art, e.g. by dual energy X-ray absorptiometry.

In some embodiments, BMD is measured prior to the first administration of a composition of the invention to establish a "baseline", and BMD is measured again in the same subject following one or more repeated administrations of said composition. In some embodiments, BMD is measured after about, e.g., 2, 4, 6, 8, 10, 12, 14, 16, 18, 20, 22 or 24 months of regular administration (e.g., daily, twice daily, thrice daily or four-times daily administration) of a composition of the disclosure to the subject. In a particular embodiment, BMD is measured about 6 months and/or about 12 months after the first administration. In some embodiments, following repeated administration of a composition of the disclosure, BMD is improved relative to a control group which is not administered the composition. In some embodiments, following regular administration of a composition of the disclosure, BMD is maintained at about the pre-administration baseline or is improved relative to the pre-administration baseline. In some embodiments, BMD in a subject decreases following administration of a composition of the disclosure, and the rate of decrease is slower than the rate of decrease in the subject prior to the first administration of the composition. In some embodiments, BMD in a subject decreases following administration of a composition of the disclosure, and the decrease is less severe than would have occurred without administration of the composition. In some embodiments, BMD is improved relative to the pre-administration baseline or relative to a control group by at least about 0.5%, 1%, 2%, 3%, 4%, 5%, 6%, 8%, 10%, 15%, 20%, 25%, 30%, 40%, 50%, 60%, 70%, 80%, 90%, or at least about 100%. For example, in some embodiments, BMD of the subject decreases following administration of a composition of the disclosure, and the decrease is less severe than that of a control group which is not administered the composition, thereby representing an improvement over the control group.

In some embodiments, the compositions and methods of the disclosure may be used to lessen a decrease in, maintain, or improve areal bone mineral density (aBMD) in a subject as compared to a suitable control. In certain embodiments, the suitable control is a control group or a control subject that is not administered the composition. In certain embodiments, the suitable control is a historical control, e.g., the aBMD in the subject prior to the first administration of the composition, or the rate of change (e.g., decline) in aBMD in the subject prior to the first administration of the composition. In some embodiments, total body aBMD, lumbar spine aBMD, femur aBMD, femoral neck aBMD, hip aBMD, or any combination thereof are maintained or improved as compared to a suitable control. aBMD can be measured by any appropriate technique known in the art, e.g. by dual energy X-ray (DXA) absorptiometry.

In some embodiments, aBMD is measured prior to the first administration of a composition of the invention to establish a "baseline", and aBMD is measured again in the same subject following one or more repeated administrations of said composition. In some embodiments, aBMD is measured after about, e.g., 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, aBMD is measured about 6 months and/or about 12 months after the first administration. In some embodiments, following repeated administration of a composition of the disclosure, aBMD is improved relative to a control group which is not administered a composition of the disclosure. In some embodiments, following regular administration of a composition of the disclosure, aBMD is maintained at about the pre-administration baseline or is improved relative to the pre-administration baseline. In some embodiments, aBMD is improved relative to the pre-administration baseline or relative to a control group by at least about 0.5%, 1%, 2%, 3%, 4%, 5%, 6%, 8%, 10%, 15%, 20%, 25%, 30%, 40%, 50%, 60%, 70%, 80%, 90%, or at least about 100%. For example, in some embodiments, aBMD in the subject decreases following administration of a composition of the disclosure, and the decrease is less severe than that of a control group which is not administered the composition, thereby representing an improvement over the control group. In some embodiments, aBMD in a subject decreases following administration of a composition of the disclosure, and the decrease is less severe than would have occurred without administration of the composition. In some embodiments, aBMD in a subject decreases following administration of a composition of the disclosure, and the rate of decrease is slower than the rate of decrease in the subject prior to the first administration of the composition.

In some embodiments, the compositions and methods of the disclosure may be used to lessen a decrease in, maintain, or improve volumetric bone mineral density (vBMD) (e.g., lumbar spine vBMD) in a subject as compared to a suitable control. In certain embodiments, the suitable control is a control group or a control subject that is not administered the composition. In certain embodiments, the suitable control is a historical control, e.g., the vBMD in the subject prior to the first administration of the composition, or the rate of change (e.g., decline) in vBMD in the subject prior to the first administration of the composition. vBMD differs from areal BMD (aBMD): aBMD is measured by a DXA scan which allows for the measurement of bone density on a two-dimensional axis, whereas vBMD is measured by a CT scan, which allows for the measurement of the actual volume of bone in a subject's scan. vBMD can be measured by any appropriate technique known in the art, e.g. by quantitative computed tomography.

In some embodiments, vBMD is measured prior to the first administration of a composition of the invention to establish a "baseline", and vBMD is measured again in the same subject following one or more repeated administrations of said composition. In some embodiments, vBMD is measured after about, e.g., 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, vBMD is measured about 6 months and/or about 12 months after the first administration. In some embodiments, vBMD is improved relative to a control group which is not administered a composition of the disclosure. In some embodiments, following repeated administration of a composition of the disclosure, vBMD is maintained at about the pre-administration baseline or is improved relative to the pre-administration baseline. In some embodiments, vBMD is improved relative to the pre-administration baseline or relative to the control group by at least about 0.5%, 1%, 2%, 3%, 4%, 5%, 6%, 8%, 10%, 15%, 20%, 25%, 30%, 40%, 50%, 60%, 70%, 80%, 90%, or at least about 100%. For example, in some embodiments, vBMD in the subject decreases following administration of a composition of the disclosure, and the decrease is less severe than that of a control group which is not administered the composition, thereby representing an improvement over the control group. In some embodiments, vBMD in a subject decreases following administration of a composition of the disclosure, and the decrease is less severe than would have occurred without administration of the composition. In some embodiments, vBMD in a subject decreases following administration of a composition of the disclosure, and the rate of decrease is slower than the rate of decrease in the subject prior to the first administration of the composition.

In some embodiments, compositions and methods of the disclosure may be used to improve BMD, vBMD, and/or aBMD in a subject by about 0.5% to 100% relative to a suitable control, e.g., relative to a pre-administration baseline or relative to a control group. For example, in some embodiments, BMD, vBMD, and/or BMD are improved by about 0.5% to 100%, about 0.5% to 90%, about 0.5% to 80%, about 0.5% to 70%, about 0.5% to 60%, about 0.5% to 50%, about 0.5% to 40%, about 0.5% to 30%, about 0.5% to 25%, about 0.5% to 20%, about 0.5% to 15%, about 0.5% to 10%, about 0.5% to 8%, about 0.5% to 6%, about 0.5% to 5%, about 0.5% to 4%, about 0.5% to 3%, about 0.5% to 2%, about 0.5% to 1%, about 1% to 100%, about 1% to 90%, about 1% to 80%, about 1% to 70%, about 1% to 60%, about 1% to 50%, about 1% to 40%, about 1% to 30%, about 1% to 25%, about 1% to 20%, about 1% to 15%, about 1% to 10%, about 1% to 8%, about 1% to 6%, about 1% to 5%, about 1% to 4%, about 1% to 3%, about 1% to 2%, about 2% to 100%, about 2% to 90%, about 2% to 80%, about 2% to 70%, about 2% to 60%, about 2% to 50%, about 2% to 40%, about 2% to 30%, about 2% to 25%, about 2% to 20%, about 2% to 15%, about 2% to 10%, about 2% to 8%, about 2% to 6%, about 2% to 5%, about 2% to 4%, about 2% to 3%, about 3% to 100%, about 3% to 90%, about 3% to 80%, about 3% to 70%, about 3% to 60%, about 3% to 50%, about 3% to 40%, about 3% to 30%, about 3% to 25%, about 3% to 20%, about 3% to 15%, about 3% to 10%, about 3% to 8%, about 3% to 6%, about 3% to 5%, about 3% to 4%, about 4% to 100%, about 4% to 90%, about 4% to 80%, about 4% to 70%, about 4% to 60%, about 4% to 50%, about 4% to 40%, about 4% to 30%, about 4% to 25%, about 4% to 20%, about 4% to 15%, about 4% to 10%, about 4% to 8%, about 4% to 6%, about 4% to 5%, about 5% to 100%, about 5% to 90%, about 5% to 80%, about 5% to 70%, about 5% to 60%, about 5% to 50%, about 5% to 40%, about 5% to 30%, about 5% to 25%, about 5% to 20%, about 5% to 15%, about 5% to 10%, about 5% to 8%, about 5% to 6%, about 6% to 100%, about 6% to 90%, about 6% to 80%, about 6% to 70%, about 6% to 60%, about 6% to 50%, about 6% to 40%, about 6% to 30%, about 6% to 25%, about 6% to 20%, about 6% to 15%, about 6% to 10%, about 6% to 8%, about 8% to 100%, about 8% to 90%, about 8% to 80%, about 8% to 70%, about 8% to 60%, about 8% to 50%, about 8% to 40%, about 8% to 30%, about 8% to 25%, about 8% to 20%, about 8% to 15%, about 8% to 10%, about 10% to 100%, about 10% to 90%, about 10% to 80%, about 10% to 70%, about 10% to 60%, about 10% to 50%, about 10% to 40%, about 10% to 30%, about 10% to 25%, about 10% to 20%, about 10% to 15%, about 15% to 100%, about 15% to 90%, about 15% to 80%, about 15% to 70%, about 15% to 60%, about 15% to 50%, about 15% to 40%, about 15% to 30%, about 15% to 25%, about 15% to 20%, about 20% to 100%, about 20% to 90%, about 20% to 80%, about 20% to 70%, about 20% to 60%, about 20% to 50%, about 20% to 40%, about 20% to 30%, about 20% to 25%, about 25% to 100%, about 25% to 90%, about 25% to 80%, about 25% to 70%, about 25% to 60%, about 25% to 50%, about 25% to 40%, about 25% to 30%, about 30% to 100%, about 30% to 90%, about 30% to 80%, about 30% to 70%, about 30% to 60%, about 30% to 50%, about 30% to 40%, about 40% to 100%, about 40% to 90%, about 40% to 80%, about 40% to 70%, about 40% to 60%, about 40% to 50%, about 50% to 100%, about 50% to 90%, about 50% to 80%, about 50% to 70%, about 50% to 60%, about 60% to 100%, about 60% to 90%, about 60% to 80%, about 60% to 70%, about 70% to 100%, about 70% to 90%, about 70% to 80%, about 80% to 100%, about 80% to 90%, or about 90% to 100%, relative to a suitable control.

In some embodiments, the compositions and methods of the disclosure may be used to lessen a decrease in, maintain, alter, or improve (TBS). TBS is an analytical tool, based on the use of standard dual-energy X-ray absorptiometry images, which may be used to evaluate bone texture and which provides information about bone microarchitecture (see Harvey et al. (2015) Bone 78:216-224). TBS can provide information about bone health that is not captured by BMD. For example, TBS may be able to differentiate between two three-dimensional bone microarchitectures with the same BMD if they have different trabecular characteristics (e.g. trabecular number/separation and/or connectivity density). Without wishing to be bound by theory, an elevated TBS may correlate with stronger, better-connected, more fracture-resistant microarchitectures. By contrast, a lower TBS may correlate with weaker and more fracture-prone microarchitectures.

In some embodiments, administration of the compositions of the disclosure can be used to lessen a decrease in, maintain, alter, or increase TBS in a subject (e.g. lumbar TBS) as compared to a suitable control. In certain embodiments, the suitable control is a control group or a control subject that is not administered the composition, e.g., a control group that is administered a placebo. In certain embodiments, the suitable control is a historical control, e.g., the TBS in the subject prior to the first administration of the composition, or the rate of change (e.g., decline) in TBS in the subject prior to the first administration of the composition.

In certain embodiments, TBS is evaluated prior to the first administration of a composition of the invention to establish a "baseline", and TBS is measured again in the same subject following one or more repeated administrations of said composition. In some embodiments, TBS is measured again after about, e.g., 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, TBS is measured about 6 months and/or about 12 months after the first administration. In some embodiments, TBS is altered or improved relative to a control group which is not administered a composition of the disclosure. In some embodiments, following regular administration of a composition of the disclosure, TBS does not substantially decrease relative to the pre-administration baseline. In some embodiments, TBS is improved relative to the pre-administration baseline or relative to the control group by at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 8%, 10%, 15%, 20%, 25%, 30%, 40% or at least about 50%. For example, in some embodiments, TBS in the subject decreases following administration of a composition of the disclosure, and the decrease is less severe than that of a control group which is not administered the composition, thereby representing an improvement over the control group. In some embodiments, TBS in a subject decreases following administration of a composition of the disclosure, and the decrease is less severe than would have occurred without administration of the composition. In some embodiments, TBS in a subject decreases following administration of a composition of the disclosure, and the rate of decrease is slower than the rate of decrease in the subject prior to the first administration of the composition.

In some embodiments, compositions and methods of the disclosure may be used to improve TBS in a subject by about 0.01% to 50% relative to a suitable control, e.g., relative to a pre-administration baseline or relative to a control group. For example, in some embodiments, TBS is improved by about 0.01% to 50%, about 0.01% to 40%, about 0.01% to 30%, about 0.01% to 25%, about 0.01% to 20%, about 0.01% to 15%, about 0.01% to 10%, about 0.01% to 5%, about 0.01% to 1%, about 0.01% to 0.5%, about 0.01% to 0.1%, about 0.01% to 0.05%, about 0.05% to 50%, about 0.05% to 40%, about 0.05% to 30%, about 0.05% to 25%, about 0.05% to 20%, about 0.05% to 15%, about 0.05% to 10%, about 0.05% to 5%, about 0.05% to 1%, about 0.05% to 0.5%, about 0.05% to 0.1%, about 0.1% to 50%, about 0.1% to 40%, about 0.1% to 30%, about 0.1% to 25%, about 0.1% to 20%, about 0.1% to 15%, about 0.1% to 10%, about 0.1% to 5%, about 0.1% to 1%, about 0.1% to 0.5%, about 0.5% to 50%, about 0.5% to 40%, about 0.5% to 30%, about 0.5% to 25%, about 0.5% to 20%, about 0.5% to 15%, about 0.5% to 10%, about 0.5% to 5%, about 0.5% to 1%, about 1% to 50%, about 1% to 40%, about 1% to 30%, about 1% to 25%, about 1% to 20%, about 1% to 15%, about 1% to 10%, about 1% to 5%, about 5% to 50%, about 5% to 40%, about 5% to 30%, about 5% to 25%, about 5% to 20%, about 5% to 15%, about 5% to 10%, about 10% to 50%, about 10% to 40%, about 10% to 30%, about 10% to 25%, about 10% to 20%, about 10% to 15%, about 15% to 50%, about 15% to 40%, about 15% to 30%, about 15% to 25%, about 15% to 20%, about 20% to 50%, about 20% to 40%, about 20% to 30%, about 20% to 25%, about 25% to 50%, about 25% to 40%, about 25% to 30%, about 30% to 50%, about 30% to 40%, or about 40% to 50%, relative to a suitable control.

In some embodiments, the compositions and methods of the disclosure may be used to alter levels of one or more biochemical markers of bone turnover (i.e. bone turnover markers (BTM)) in a subject as compared to a suitable control. In some embodiments, the BTM is a marker of bone formation, e.g. procollagen type 1 N-terminal propeptide (P1NP). In other embodiments, the BTM is a marker of bone resorption, e.g. C-terminal telopeptide of type I collagen (CTX). In some embodiments, both a marker of bone formation and a marker of bone resorption are measured, either simultaneously or at different times. In some embodiments, levels of one or more BTMs are measured in the subject's blood, serum, plasma, or urine. BTMs can be measured using any appropriate technique known in the art (see, e.g., Szulc et al., Osteoporos Int. (2017)), for example by ELISA, ECLIA, or CLIA.

In some embodiments, administration of the compositions of the disclosure can alter or increase levels of a bone formation marker in the subject as compared to a suitable control. In some embodiments, the suitable control is a control group or a control subject that is not administered the composition, e.g., a control group that is administered a placebo. In certain embodiments, the suitable control is a historical control, e.g., the level(s) of one or more BTM in the subject prior to the first administration of the composition.

In some embodiments, the levels of one or more BTMs in a subject are evaluated prior to the first administration of a composition of the disclosure to establish a "baseline", and are measured again in the same subject following one or more repeated administrations of said composition. In some embodiments, the levels of the one or more BTMs are re-measured after about, e.g., 0.5, 1, 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, the levels of the one or more BTM levels are re-measured about 6 months and/or about 12 months after the first administration. In some embodiments, the level of a bone formation marker (e.g. P1NP) changes relative to the pre-administration baseline by at least about 5%, 10%, 15%, 20%, 25%, 30%, 35%, 40%, 45%, 50%, 60%, 70%, 80%, 90%, 100%, 125%, 150%, 175%, 100%, 200%, 300%, 400% or 500%. In certain embodiments, the change in the level of the bone formation marker is an increase relative to the pre-administration baseline. In some embodiments, the level of a bone resorption marker (e.g. CTX) changes relative to the pre-administration baseline by at least about 5%, 10%, 15%, 20%, 25%, 30%, 35%, 40%, 45%, 50%, 60%, 70%, 80%, 90%, 100%, 125%, 150%, 175%, 100%, 200%, 300%, 400%, or 500%. In certain embodiments, the change in the level of the bone resorption marker is a decrease relative to the pre-administration baseline. In some embodiments, the change in the level of the bone formation and/or bone resorption marker is relative to a control group which is not administered a composition of the disclosure.

In some embodiments, compositions and methods of the disclosure may be used to alter levels of one or more BTM in a subject by about 5% to 500% relative to a suitable control, e.g., relative to a pre-administration baseline or relative to a control group. For example, in some embodiments, the levels of one or more BTM are independently increased or decreased by about 5% to 500%, about 5% to 400%, about 5% to 300%, about 5% to 200%, about 5% to 150%, about 5% to 100%, about 5% to 75%, about 5% to 50%, about 5% to 40%, about 5% to 30%, about 5% to 25%, about 5% to 20%, about 5% to 15%, about 5% to 10%, about 10% to 500%, about 10% to 400%, about 10% to 300%, about 10% to 200%, about 10% to 150%, about 10% to 100%, about 10% to 75%, about 10% to 50%, about 10% to 40%, about 10% to 30%, about 10% to 25%, about 10% to 20%, about 10% to 15%, about 15% to 500%, about 15% to 400%, about 15% to 300%, about 15% to 200%, about 15% to 150%, about 15% to 100%, about 15% to 75%, about 15% to 50%, about 15% to 40%, about 15% to 30%, about 15% to 25%, about 15% to 20%, about 20% to 500%, about 20% to 400%, about 20% to 300%, about 20% to 200%, about 20% to 150%, about 20% to 100%, about 20% to 75%, about 20% to 50%, about 20% to 40%, about 20% to 30%, about 20% to 25%, about 25% to 500%, about 25% to 400%, about 25% to 300%, about 25% to 200%, about 25% to 150%, about 25% to 100%, about 25% to 75%, about 25% to 50%, about 25% to 40%, about 25% to 30%, about 30% to 500%, about 30% to 400%, about 30% to 300%, about 30% to 200%, about 30% to 150%, about 30% to 100%, about 30% to 75%, about 30% to 50%, about 30% to 40%, about 40% to 500%, about 40% to 400%, about 40% to 300%, about 40% to 200%, about 40% to 150%, about 40% to 100%, about 40% to 75%, about 40% to 50%, about 50% to 500%, about 50% to 400%, about 50% to 300%, about 50% to 200%, about 50% to 150%, about 50% to 100%, about 50% to 75%, about 75% to 500%, about 75% to 400%, about 75% to 300%, about 75% to 200%, about 75% to 150%, about 75% to 100%, about 100% to 500%, about 100% to 400%, about 100% to 300%, about 100% to 200%, about 100% to 150%, about 150% to 500%, about 150% to 400%, about 150% to 300%, about 150% to 200%, about 200% to 500%, about 200% to 400%, about 200% to 300%, about 300% to 500%, about 300% to 400%, or about 400% to 500%, relative to a suitable control.

Changes in levels of hormones during perimenopause, menopause, and postmenopause, and namely a reduction in estrogen levels, can lead to inflammation. Markers of osteoporosis or osteopenia can include elevated levels of inflammatory cytokines in the blood including, but not limited to: Tumor necrosis factor alpha (TNFα), Interleukin-17 (IL-17), Interleukin-4 (IL-4), Interferon gamma (IFNγ), and Receptor activator of nuclear factor kappa-B ligand (RANKL). In some embodiments, the compositions disclosed herein are rationally designed for the production of SCFAs, which have been identified as anti-inflammatory mediators. Accordingly, in some embodiments, the compositions and methods of the disclosure may be used to decrease inflammation.

In certain embodiments, the compositions and methods may be used to alter or decrease circulating levels of one or more inflammatory cytokines and/or markers of inflammation, including, e.g., C-reactive protein (CRP), IL-17, TNF, IL-1B, RANKL, IFNγ, or any combination thereof, as compared to a suitable control. In some embodiments, the suitable control is a control group or a control subject that is not administered the composition, e.g., a control group that is administered a placebo. In certain embodiments, the suitable control is a historical control, e.g., the level(s) of one or more inflammatory cytokines and/or markers of inflammation in the subject prior to the first administration of the composition. In some embodiments, levels of one or more inflammatory cytokines and/or markers of inflammation are measured in the subject's blood, serum, or plasma.

In certain embodiments, the levels of one or more inflammatory cytokines and/or markers of inflammation in a subject are evaluated prior to the first administration of a composition of the disclosure to establish a "baseline", and then said inflammatory cytokines/markers are measured again in the same subject following one or more repeated administrations of the composition. In some embodiments, the levels of the one or more inflammatory cytokines and/or markers of inflammation are re-measured after about, e.g., 0.5, 1, 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, the levels of the one or more inflammatory cytokines and/or markers of inflammation are re-measured about 6 months and/or about 12 months after the first administration. In some embodiments, the level of an inflammatory cytokine and/or marker of inflammation (e.g. CRP) decreases relative to the pre-administration baseline by at least about 5%, 10%, 15%, 20%, 25%, 30%, 35%, 40%, 45%, 50%, 60%, 70%, 80%, 90%, 100%, 125%, 150%, 175%, 100%, 200%, 300%, 400%, 500%, 1000%, 2500%, 5000%, or at least about 10000%. In some embodiments, the changes in levels of one or more inflammatory cytokines and/or markers of inflammation are relative to a control group which is not administered a composition of the disclosure. Inflammatory cytokines and/or markers of inflammation may be measured using any appropriate technique known in the art, e.g. by ELISA or by multiplex array.

In some embodiments, compositions and methods of the disclosure may be used to decrease the level of one or more inflammatory cytokine(s) and/or marker(s) of inflammation in a subject by about 5% to 10000% relative to a suitable control, e.g., relative to a pre-administration baseline or relative to a control group. For example, in some embodiments, the level of an inflammatory cytokine and/or marker of inflammation (e.g., CRP, IL-17, TNF, IL-1B, RANKL, or IFNγ) is decreased by about 5% to 10000%, about 5% to 5000%, about 5% to 2500%, about 5% to 1000%, about 5% to 500%, about 5% to 400%, about 5% to 300%, about 5% to 200%, about 5% to 100%, about 5% to 75%, about 5% to 50%, about 5% to 40%, about 5% to 30%, about 5% to 25%, about 5% to 20%, about 5% to 15%, about 5% to 10%, about 10% to 10000%, about 10% to 5000%, about 10% to 2500%, about 10% to 1000%, about 10% to 500%, about 10% to 400%, about 10% to 300%, about 10% to 200%, about 10% to 100%, about 10% to 75%, about 10% to 50%, about 10% to 40%, about 10% to 30%, about 10% to 25%, about 10% to 20%, about 10% to 15%, about 15% to 10000%, about 15% to 5000%, about 15% to 2500%, about 15% to 1000%, about 15% to 500%, about 15% to 400%, about 15% to 300%, about 15% to 200%, about 15% to 100%, about 15% to 75%, about 15% to 50%, about 15% to 40%, about 15% to 30%, about 15% to 25%, about 15% to 20%, about 20% to 10000%, about 20% to 5000%, about 20% to 2500%, about 20% to 1000%, about 20% to 500%, about 20% to 400%, about 20% to 300%, about 20% to 200%, about 20% to 100%, about 20% to 75%, about 20% to 50%, about 20% to 40%, about 20% to 30%, about 20% to 25%, about 25% to 10000%, about 25% to 5000%, about 25% to 2500%, about 25% to 1000%, about 25% to 500%, about 25% to 400%, about 25% to 300%, about 25% to 200%, about 25% to 100%, about 25% to 75%, about 25% to 50%, about 25% to 40%, about 25% to 30%, about 30% to 10000%, about 30% to 5000%, about 30% to 2500%, about 30% to 1000%, about 30% to 500%, about 30% to 400%, about 30% to 300%, about 30% to 200%, about 30% to 100%, about 30% to 75%, about 30% to 50%, about 30% to 40%, about 40% to 10000%, about 40% to 5000%, about 40% to 2500%, about 40% to 1000%, about 40% to 500%, about 40% to 400%, about 40% to 300%, about 40% to 200%, about 40% to 100%, about 40% to 75%, about 40% to 50%, about 50% to 10000%, about 50% to 5000%, about 50% to 2500%, about 50% to 1000%, about 50% to 500%, about 50% to 400%, about 50% to 300%, about 50% to 200%, about 50% to 100%, about 50% to 75%, about 75% to 10000%, about 75% to 5000%, about 75% to 2500%, about 75% to 1000%, about 75% to 500%, about 75% to 400%, about 75% to 300%, about 75% to 200%, about 75% to 100%, about 100% to 10000%, about 100% to 5000%, about 100% to 2500%, about 100% to 1000%, about 100% to 500%, about 100% to 400%, about 100% to 300%, about 100% to 200%, about 200% to 10000%, about 200% to 5000%, about 200% to 2500%, about 200% to 1000%, about 200% to 500%, about 200% to 400%, about 200% to 300%, about 300% to 10000%, about 300% to 5000%, about 300% to 2500%, about 300% to 1000%, about 300% to 500%, about 300% to 400%, about 400% to 10000%, about 400% to 5000%, about 400% to 2500%, about 400% to 1000%, about 400% to 500%, about 500% to 10000%, about 500% to 5000%, about 500% to 2500%, about 500% to 1000%, about 1000% to 10000%, about 1000% to 5000%, about 1000% to 2500%, about 2500% to 10000%, about 2500% to 5000%, or about 5000% to 10000%, relative to a suitable control.

In some embodiments, the condition to be treated is osteoarthritis. In some embodiments, the condition to be treated is osteoarthritis, and treating the condition further involves administration of any one or combination of known anti-osteoarthritis medications or treatments. In some embodiments, a composition of the disclosure (e.g., a DMA composition as described herein) is administered to a subject simultaneously with a treatment or medication for osteoarthritis. In some embodiments, a composition of the disclosure (e.g., a DMA composition as described herein) and a treatment or medication for osteoarthritis are administered to a subject separately. In some embodiments, a composition of the disclosure (e.g., a DMA composition as described herein) and a treatment or medication for osteoarthritis are administered to a subject sequentially. In some embodiments, a treatment or medication for osteoarthritis is administered to a subject prior to administration of a composition of the disclosure (e.g., a DMA composition as described herein). In certain embodiments, a treatment or medication for osteoarthritis is administered to a subject following administration of a composition of the disclosure (e.g., a DMA composition as described herein).

Treatments and medications for osteoarthritis include, but are not limited to, surgery, analgesics, non-steroidal anti-inflammatory drugs (aspirin, celecoxib, diclofenac, diflunisal, etodolac, ibuprofen, indomethacin, ketoprofen, ketorolac, nabumetone, naproxen, oxaprozin, piroxicam), menthol, weight loss regimens, physical exercise, acupuncture, narcotics (Codeine, Fentanyl, Hydrocodone, hydroporphone, meperidine, methadone, oxycodone), and physical therapy.

In some embodiments, the condition to be treated is a delayed or non-union fracture. In an embodiment, the condition to be treated is a delayed or non-union fracture, and treating the condition further involves administration of any one or combination of known treatments to improve delayed or non-union fractures. These include, but are not limited to surgical bone grafts or fixations and bone stimulation.

In some embodiments, the condition to be treated is osteomyelitis. The methods disclosed herein, optionally, are used in combination with other treatments to treat or prevent osteomyelitis. In some embodiments, a composition of the disclosure (e.g., a DMA composition as described herein) is administered to a subject simultaneously with a treatment for osteomyelitis. In some embodiments, a composition of the disclosure (e.g., a DMA composition as described herein) and a treatment for osteomyelitis are administered to a subject separately. In some embodiments, a composition of the disclosure (e.g., a DMA composition as described herein) and a treatment for osteomyelitis are administered to a subject sequentially. In some embodiments, a treatment for osteomyelitis is administered to a subject prior to administration of a composition of the disclosure (e.g., a DMA composition as described herein). In certain embodiments, a treatment for osteomyelitis is administered to a subject following administration of a composition of the disclosure (e.g., a DMA composition as described herein). Typical treatments for osteomyelitis include, but are not limited to, intravenous or oral antibiotics (clindamycin, cefotetan, ticarcillin/clavulanate, ceftriaxone, metronidazole, piperacillin/tazobactam, fluoroquinolone, cefepime, ciprofloxacin, imipenem/cilastin, vancomycin, trimethoprim/sulfamethoxazole, minocycline, nafcillin, oxacillin, cefazolin, penicillin) and surgery. Any suitable treatment for osteomyelitis can be used. These include, but are not limited to, removal of diseased tissue and antibiotics, administered either orally or intravenously.

In some embodiments, the condition to be treated or prevented is a symptom of menopause, perimenopause or postmenopause. In some embodiments, the symptom of menopause, perimenopause or postmenopause is hot flushes, sweating, episodes of sweating, night sweats, heart discomfort, unusual awareness of heart beat, heart skipping, heart racing, heart tightness, depressive mood, feeling down, feeling sad, feeling on verge of tears, lack of drive, mood swings, irritability, feeling nervous, inner tension, feeling aggressive, anxiety, inner restlessness, feeling panicky, physical exhaustion, mental exhaustion, general decrease in performance, impaired memory, decrease in concentration, forgetfulness, sexual problems, change in sexual desire, change in sexual activity, change in sexual satisfaction, bladder problems, difficulty in urinating, increased need to urinate, bladder incontinence, dryness of the vagina, sensation of dryness or burning in the vagina, difficulty with sexual intercourse, joint and muscular discomfort, pain in the joints or rheumatoid arthritis. In some embodiments, the symptom is a vasomotor symptom, e.g. hot flushes or sweating. In some embodiments, the presence and/or severity of a symptom of menopause in the subject is improved, as compared to a suitable control. In some embodiments, the suitable control is a control group or a control subject that is not administered the composition, e.g., a control group that is administered a placebo. In certain embodiments, the suitable control is a historical control, e.g., the presence or severity of the symptom of menopause in the subject prior to the first administration of the composition.

In some embodiments, the presence and severity of menopause symptoms are evaluated prior to the first administration of a composition of the disclosure to establish a "baseline", and then said symptoms are evaluated again following one or more repeated administrations of the composition. In some embodiments, the severity of the menopause, perimenopause, or postmenopause symptoms are re-measured after about, e.g., 0.5, 1, 2, 4, 6, 8, 10, 12, 14, 16, 18, 20, 22 or 24 months of regular administration (e.g., daily, twice daily, thrice daily or four times daily administration) of a composition of the disclosure to the subject. In a particular embodiment, the presence and severity of the one or more menopause, perimenopause, or postmenopause symptoms are re-evaluated about 1 month, about 2 months, about 4 months, about 6 months, about 8 months, about 10 months, and/or about 12 months after the first administration. In some embodiments, the presence and severity of the one or more menopause, perimenopause, or postmenopause symptoms are measured by the Menopause Rating Scale (MRS; see Heinemann et al. (2004) Health Qual Life Outcomes 2:45). In some embodiments, the severity of the symptom of menopause as measured by the MRS decreases by 1 to 4 points, 1 to 3 points, 1 to 2 points, 2 to 4 points, 2 to 3 points, or 3 to 4 points, as compared to a suitable control. In some embodiments, the severity of the menopause symptom as measured by the MRS decreases by 1, 2, 3 or 4 points, as compared to a suitable control. In a particular embodiment, the severity of hot flushes and/or sweating will decrease by 1, 2, 3 or 4 points as measured by the MRS, as compared to a suitable control.

Timing and Dose of Probiotics and Prebiotics

In certain embodiments, probiotic microbes (such as one or more *Lactobacillus* species, one or more *Leuconostoc* species, one or more *Pichia* species, or any combination of the foregoing) are given prior to beginning treatment with a prebiotic. In certain embodiments, probiotic microbes (such as one or more *Lactobacillus* species, one or more *Leuconostoc* species, one or more *Pichia* species, or any combination of the foregoing) are given in conjunction with treatment with a prebiotic (e.g., comprising or consisting essentially of dried fruit or vegetable powder, FOS, GOS, and/or other appropriate polysaccharide), for part or all of the treatment with the prebiotic. Thus, in certain embodiments, some or all doses of a prebiotic (e.g., comprising or consisting essentially of dried fruit or vegetable powder, FOS, GOS, and/or other appropriate polysaccharide) are accompanied by a dose of microbes, e.g., live cultured microbes, e.g., one or more *Lactobacillus* species, one or more *Leuconostoc* species, one or more *Pichia* species, or any combination of the foregoing. In an embodiment, microbes (e.g., one or more *Lactobacillus* species, one or more *Leuconostoc* species, one or more *Pichia* species, or any combination of the foregoing) are given initially with a prebiotic (e.g., comprising or consisting essentially of dried fruit or vegetable powder, FOS, GOS, and/or other appropriate polysaccharide), but then use of the microbes is discontinued. For example, the initial one, two, three, four, five, six, seven, eight, nine, ten or more than ten days of treatment with a prebiotic (e.g., comprising or consisting essentially of dried fruit or vegetable powder, FOS, GOS, and/or other appropriate polysaccharide) further comprises doses of microbes, with the use of microbes discontinued after that time. In an embodiment, microbes, (e.g., bacteria in yogurt), or microbes by themselves, can be given for the first two days of treatment; then the administration of microbes is discontinued. In another embodiment, probiotic microbes, either alone or in combination with other substances or treatments are used after the treatment with a prebiotic (comprising or consisting essentially of dried fruit or vegetable powder, FOS, GOS, and/or other appropriate polysaccharide) is terminated. The microbes can be taken for any suitable period after the termination of treatment with prebiotic and can be taken daily or at regular or irregular intervals. Doses can be as described below. Any suitable amount of probiotic per serving can be used that allows an effective microbiota in the GI as demonstrated by an increase in bone mineral density, improved bone architecture, protection from loss of bone mineral density, improved bone turnover markers, or improvement in other markers of osteoporosis or osteopenia. Markers of osteoporosis or osteopenia can include elevated levels of Inflammatory cytokines in the blood including, but not limited to: Tumor necrosis factor alpha (TNFα), Interleukin-17 (IL-17), Interleukin-4 (IL-4), Interferon gamma (IFNγ), Receptor activator of nuclear factor kappa-B ligand (RANKL). They can also include increased one resorption blood markers (breakdown) crosslinked C-telopeptide of type 1 collagen (CTX), or decreased Bone formation blood markers: osteocalcin, alkaline phosphatase, N-terminal propeptide of type 1 collagen.

Any suitable amount of probiotic per serving can be used that allows an effective microbiota in the GI as demonstrated by an improvement in the disorder, disease, state, or condition to be treated. This may be, e.g., a decrease in inflammation or a reduction in severity of menopause/perimenopause/postmenopause symptoms. This may also be healthy bone healing, in which the improvement may be a decreased incidence of delayed or non-union fractures or increased normal fracture callus formation. Markers of fracture healing defects include delayed healing, non-union fracture healing, or changes in fracture callus architecture (including increased size or adiposity of the fracture callus).

Any suitable amount of probiotic per serving can be used that allows an effective microbiota in the GI as demonstrated by a decrease in inflammation. Inflammatory cytokines or markers of inflammation may include, for example, CRP, IL-17, TNF, IL-1B, IL-4, RANKL, and IFNγ.

Any suitable amount of probiotic per serving can be used that allows an effective microbiota in the GI as demonstrated by a decrease in severity in a symptom of perimenopause, menopause, or postmenopause. By way of a nonlimiting example, the symptom may be a vasomotor symptom, e.g. hot flushes or sweating.

Typically, probiotics are given as live cultured microbes. The dose can be, e.g., 0.001 mg to 1 mg, or 0.5 mg to 5 mg, or 1 mg to 1000 mg, or 2 mg to 200 mg, or 2 mg to 100 mg, or 2 mg to 50 mg, or 2 mg to 25 mg, or 2 mg to 20 mg, or 4 mg to 50 mg, or 4 mg to 25 mg, or 5 mg to 50 mg, or 5 mg to 40 mg, or 5 mg to 30 mg or 5 mg to 25 mg, or 5 mg to 20 mg, or 10 mg to 100 mg, or 10 mg to 75 mg, or 10 mg to 50 mg, or 10 mg to 25 mg, or 10 mg to 15 mg, or 20 mg to 100 mg, or 20 mg to 75 mg, or 20 mg to 50 mg, or 20 mg to 40 mg, or 20 mg to 30 mg, or 20 mg to 25 mg, or 50 mg to 200 mg, or 50 mg to 150 mg, or 50 mg to 100 mg, or 50 mg to 75 mg, or 100 mg to 1000 mg, or 100 mg to 800 mg, or 100 mg to 600 mg, or 100 mg to 500 mg, or 100 mg to 400 mg, or 100 mg to 300 mg, or 100 mg to 200 mg, or 100 mg to 150 mg, or 200 mg to 1000 mg, or about 10 mg, about 11 mg, about 12 mg, about 12.5 mg, about 13 mg, about 14 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 125 mg, about 150 mg, about 175 mg, or about 200 mg per serving or per day. In certain embodiments, *Lactobacillus brevis* is used in a dose of about 25 mg to about 50 mg per serving or per day. In certain embodiments, *Lactobacillus plantarum* is used in a dose of about 25 mg to about 50 mg per serving or per day. In certain embodiments, *Leuconostoc mesenteroides* is used in a dose of about 25 mg to about 50 mg per serving or per day. In certain embodiments, *Pichia kudriavzevii* is used in a dose of about 100 mg to about 200 mg per serving or per day. In certain embodiments, *L. acidophilus* is used in a dose of about 12.5 mg per serving or per day. The probiotic microbes can also be 0.5% w/w to 20% w/w of the final composition. The dose of probiotics can be given in combination with one or more prebiotics.

Another common way of specifying the amount of probiotics is as a colony forming unit (cfu). In an embodiment, one or more strains of probiotic microbes are ingested in an amount of between 1×10^5 and 1×10^13 cfu's per serving or per day. In some embodiments, one or more strains of probiotic microbes (e.g., *Lactobacillus plantarum, Lactobacillus brevis, Leuconostoc mesenteroides*, and/or *Pichia kudriavzevii*) are ingested in a serving or in a total daily dose of about 1×10^5 cfu's to about 1×10^13 cfu's, or about 1×10^5 to about 1×10^12 cfu's, or about 1×10^5 cfu's to about 1×10^11 cfu's, or about 1×10^5 cfu's to about 3×10^10 cfu's, or about 1×10^5 cfu's to about 1.5×10^10 cfu's, or about 1×10^5 cfu's to about 1×10^10 cfu's, or about 1×10^5 cfu's to about 7.5×10^9 cfu's, or about 1×10^5 cfu's to about 5×10^9 cfu's, or about 1×10^5 cfu's to about 2.5×10^9 cfu's, or about 1×10^5 cfu's to about 1.25×10^9 cfu's, or about 1×10^5 cfu's to about 1×10^9 cfu's, or about 1×10^5 cfu's to about 1×10^8 cfu's, or about 1×10^5 cfu's to about 1×10^7 cfu's, or about 1×10^5 cfu's to about 1×10^6 cfu's, or about 1×10^6 to about 1×10^13 cfu's, or about 1×10^6 cfu's to about 1×10^12 cfu's, or about 1×10^6 cfu's to about 1×10^11 cfu's, or about 1×10^6 cfu's to about 3×10^10 cfu's, or about 1×10^6 cfu's to about 1.5×10^10 cfu's, or about 1×10^6 cfu's to about 1×10^10 cfu's, or about 1×10^6 cfu's to about 7.5×10^9 cfu's, or about 1×10^6 cfu's to about 5×10^9 cfu's, or about 1×10^6 cfu's to about 2.5×10^9 cfu's, or about 1×10^6 cfu's to about 1.25×10^9 cfu's, or about 1×10^6 cfu's to about 1×10^9 cfu's, or about 1×10^6 cfu's to about 1×10^8 cfu's, or about 1×10^6 cfu's to about 1×10^7 cfu's, or about 1×10^7 cfu's to about 1×10^13 cfu's, or about 1×10^7 cfu's to about 1×10^12 cfu's, or about 1×10^7 cfu's to about 1×10^11 cfu's, or about 1×10^7 cfu's to about 3×10^10 cfu's, or about 1×10^7 cfu's to about 1.5×10^10 cfu's, or about 1×10^7 cfu's to about 1×10^10 cfu's, or about 1×10^7 cfu's to about 7.5×10^9 cfu's, or about 1×10^7 cfu's to about 5×10^9 cfu's, or about 1×10^7 cfu's to about 2.5×10^9 cfu's, or about 1×10^7 cfu's to about 1.25×10^9 cfu's, or about 1×10^7 cfu's to about 1×10^9 cfu's, or about 1×10^7 cfu's to about 1×10^8 cfu's, or about 1×10^8 cfu's to about 1×10^13 cfu's, or about 1×10^8 cfu's to about 1×10^12 cfu's, or about 1×10^8 cfu's to about 1×10^11 cfu's, or about 1×10^8 cfu's to about 3×10^10 cfu's, or about 1×10^8 cfu's to about 1.5×10^10 cfu's, or about 1×10^8 cfu's to about 1×10^10 cfu's, or about 1×10^8 cfu's to about 7.5×10^9 cfu's, or about 1×10^8 cfu's to about 5×10^9 cfu's, or about 1×10^8 cfu's to about 2.5×10^9 cfu's, or about 1×10^8 cfu's to about 1.25×10^9 cfu's, or about 1×10^8 cfu's to about 1×10^9 cfu's, or about 1×10^9 cfu's to about 1×10^13 cfu's, or about 1×10^9 cfu's to about 1×10^12 cfu's, or about 1×10^9 cfu's to about 1×10^11 cfu's, or about 1×10^9 cfu's to about 3×10^10 cfu's, or about 1×10^9 cfu's to about 1.5×10^10 cfu's, or about 1×10^9 cfu's to about 1×10^10 cfu's, or about 1×10^9 cfu's to about 7.5×10^9 cfu's, or about 1×10^9 cfu's to about 5×10^9 cfu's, or about 1×10^9 cfu's to about 2.5×10^9 cfu's, or about 1×10^9 cfu's to about 1.25×10^9 cfu's, or about 1.25×10^9 cfu's to about 1×10^13 cfu's, or about 1.25×10^9 cfu's to about 1×10^12 cfu's, or about 1.25×10^9 cfu's to about 1×10^11 cfu's, or about 1.25×10^9 cfu's to about 3×10^10 cfu's, or about 1.25×10^9 cfu's to about 1.5×10^10 cfu's, or about 1.25×10^9 cfu's to about 1×10^10 cfu's, or about 1.25×10^9 cfu's to about 7.5×10^9 cfu's, or about 1.25×10^9 cfu's to about 5×10^9 cfu's, or about 1.25×10^9 cfu's to about 2.5×10^9 cfu's, or about 2.5×10^9 cfu's to about 1×10^13 cfu's, or about 2.5×10^9 cfu's to about 1×10^12 cfu's, or about 2.5×10^9 cfu's to about 1×10^11 cfu's, or about 2.5×10^9 cfu's to about 3×10^10 cfu's, or about 2.5×10^9 cfu's to about 1.5×10^10 cfu's, or about 2.5×10^9 cfu's to about 1×10^10 cfu's, or about 2.5×10^9 cfu's to about 7.5×10^9 cfu's, or about 2.5×10^9 cfu's to about 5×10^9 cfu's, or about 5×10^9 cfu's to about 1×10^13 cfu's, or about 5×10^9 cfu's to about 1×10^12 cfu's, or about 5×10^9 cfu's to about 1×10^11 cfu's, or about 5×10^9 cfu's to about 3×10^10 cfu's, or about 5×10^9 cfu's to about 1.5×10^10 cfu's, or about 5×10^9 cfu's to about 1×10^10 cfu's, or about 5×10^9 cfu's to about 7.5×10^9 cfu's, or about 7.5×10^9 cfu's to about 1×10^13 cfu's, or about 7.5×10^9 cfu's to about 1×10^12 cfu's, or about 7.5×10^9 cfu's to about 1×10^11 cfu's, or about 7.5×10^9 cfu's to about 3×10^10 cfu's, or about 7.5×10^9 cfu's to about 1.5×10^10 cfu's, or about 7.5×10^9 cfu's to about 1×10^10 cfu's, or about 1×10^10 cfu's to about 1×10^13 cfu's, or about 1×10^10 cfu's to about 1×10^12 cfu's, or about 1×10^10 cfu's to about 1×10^11 cfu's, or about 1×10^10 cfu's to about 3×10^10 cfu's, or about 1×10^10 cfu's to about 1.5×10^10 cfu's, or about 1.5×10^10 cfu's to about 1×10^13 cfu's, or about 1.5×10^10 cfu's to about 1×10^12 cfu's, or about 1.5×10^10 cfu's to about 1×10^11 cfu's, or about 1.5×10^10 cfu's to about 3×10^10 cfu's, or about 3×10^10 cfu's to about 1×10^13 cfu's, or about 13×10^10 cfu's to about 1×10^12 cfu's, or about 3×10^10 cfu's to about 1×10^11 cfu's, or about 1×10^11 cfu's to about 1×10^13 cfu's, or about 1×10^11 cfu's to about 1×10^12 cfu's, or about 1×10^12 cfu's to about 1×10^13 cfu's. In some embodiments, one or more strains of probiotic microbes (e.g. *Lactobacillus brevis, Lactobacillus plantarum, Leuconostoc mesenteroides*, and/or *Pichia kudriavzevii*) are ingested in an amount of about 1.5×10^10 cfu's per serving, or about 3×10^10 cfu's per serving, or about 1.25×10^9 cfu's per serving, or about 2.5×10^9 cfu's per serving, or about 5×10^9 cfu's per serving, or about 7.5×10^9 cfu's per serving. In some embodiments, one or more strains of probiotic microbes (e.g. *Lactobacillus brevis, Lactobacillus plantarum, Leuconostoc mesenteroides*, and/or *Pichia kudriavzevii*) are ingested in an amount of about 1.5×10^10 cfu's per day, or about 3×10^10 cfu's per day, or about 1.25×10^9 cfu's per day, or about 2.5×10^9 cfu's per day, or about 5×10^9 cfu's per day, or about 7.5×10^9 cfu's per day.

In another embodiment, one or more strains of probiotic microbes are administered as part of a dairy product. In an embodiment, a typical serving size for a dairy product such as fluid milk is 240 g. In other embodiments, a serving size is 245 g, or 240 g to 245 g, or 227 to 300 g. In an embodiment the dairy product is yogurt. Yogurt can have a serving size of 4 oz, or 6 oz, or 8 oz, or 4 oz to 10 oz, or half cup, or 1 cup, or 113 g, or 170 g, or 227 g, or 245 g or 277 g, or 100 g to 350 g.

In an embodiment, probiotic microbes are given as live cultured microbes, e.g., in combination with a prebiotic (e.g., comprising or consisting essentially of dried fruit or vegetable powder, FOS, GOS, and/or other appropriate polysaccharide) and, optionally, other substances. The dose can be 0.001 mg to 1 mg, or 0.5 mg to 5 mg, or 1 mg to 1000 mg, or 2 mg to 200 mg, or 2 mg to 100 mg, or 2 mg to 50 mg, or 2 mg to 25 mg, or 2 mg to 20 mg, or 4 mg to 50 mg, or 4 mg to 25 mg, or 5 mg to 50 mg, or 5 mg to 40 mg, or 5 mg to 30 mg or 5 mg to 25 mg, or 5 mg to 20 mg, or 10 mg to 100 mg, or 10 mg to 75 mg, or 10 mg to 50 mg, or 10 mg to 25 mg, or 10 mg to 15 mg, or 20 mg to 100 mg, or 20 mg to 75 mg, or 20 mg to 50 mg, or 20 mg to 40 mg, or 20 mg to 30 mg, or 20 mg to 25 mg, or 50 mg to 200 mg, or 50 mg to 150 mg, or 50 mg to 100 mg, or 50 mg to 75 mg, or 100 mg to 1000 mg, or 100 mg to 800 mg, or 100 mg to 600 mg, or 100 mg to 500 mg, or 100 mg to 400 mg, or 100 mg to 300 mg, or 100 mg to 200 mg, or 100 mg to 150 mg, or 200 mg to 1000 mg, or about 10, about 11, about 12, about 12.5, about 13, about 14, about 15, about 20, about 25, about 30, about 35, about 40, about 45, about 50, about 60, about 70, about 80, about 90, about 100, about 125, about 150, about 175, or about 200 mg of probiotic microbial cell culture dry weight per serving or per daily dose. In certain embodiments, *Lactobacillus brevis* is used in a dose of about 25 mg to about 50 mg per serving or per day. In certain embodiments, *Lactobacillus plantarum* is used in a dose of about 25 mg to about 50 mg per serving or per day. In certain embodiments, *Leuconostoc mesenteroides* is used in a dose of about 25 mg to about 50 mg per serving or per day. In certain embodiments, *Pichia kudriavzevii* is used in a dose of about 100 mg to about 200 mg per serving or per day. In certain embodiments, *L. acidophilus* is used in a dose of 12.5 mg per serving or per day. In some embodiments, as the administration of a prebiotic (e.g., comprising or consisting essentially of dried fruit or vegetable powder, FOS, GOS, and/or other appropriate polysaccharide) dose to a subject increases, the dose of microbes increases as well. For example, an initial dose of a prebiotic (e.g., comprising or consisting essentially of dried fruit or vegetable powder, FOS, GOS, and/or other appropriate polysaccharides) can be 0.3 g to 0.4 g, e.g., 0.35 g, given in combination with 25-50 mg, e.g., 37.5 mg, of a lactic acid bacterium. The dose of a prebiotic (e.g., comprising or consisting essentially of dried fruit or vegetable powder, FOS, GOS, and/or other appropriate polysaccharide) can be increased incrementally by 0.3 g to 0.4 g, e.g., 0.35 g, and the accompanying dose of the lactic acid bacterium can be increased by 25-50 mg, e.g., 37.5 mg, of the bacterium. Similarly, proportional incremental decreases of prebiotic and probiotic doses are also contemplated.

In certain embodiments, probiotic microbes and a prebiotic (e.g., comprising or consisting essentially of dried fruit or vegetable powder, FOS, GOS, and/or other appropriate polysaccharide) are administered in the same composition. In certain embodiments, the probiotic microbes constitute 1% to 99% of the weight of the composition. For example, in certain embodiments, the probiotic microbes constitute 1% to 99%, 1% to 95%, 1% to 90%, 1% to 80%, 1% to 70%, 1% to 60%, 1% to 50%, 1% to 40%, 1% to 30%, 1% to 25%, 1% to 20%, 1% to 15%, 1% to 10%, 1% to 5%, 5% to 99%, 5% to 95%, 5% to 90%, 5% to 80%, 5% to 70%, 5% to 60%, 5% to 50%, 5% to 40%, 5% to 30%, 5% to 25%, 5% to 20%, 5% to 15%, 5% to 10%, 10% to 99%, 10% to 95%, 10% to 90%, 10% to 80%, 10% to 70%, 10% to 60%, 10% to 50%, 10% to 40%, 10% to 30%, 10% to 25%, 10% to 20%, 10% to 15%, 15% to 99%, 15% to 95%, 15% to 90%, 15% to 80%, 15% to 70%, 15% to 60%, 15% to 50%, 15% to 40%, 15% to 30%, 15% to 25%, 15% to 20%, 20% to 99%, 20% to 95%, 20% to 90%, 20% to 80%, 20% to 70%, 20% to 60%, 20% to 50%, 20% to 40%, 20% to 30%, 20% to 25%, 25% to 99%, 25% to 95%, 25% to 90%, 25% to 80%, 25% to 70%, 25% to 60%, 25% to 50%, 25% to 40%, 25% to 30%, 30% to 99%, 30% to 95%, 30% to 90%, 30% to 80%, 30% to 70%, 30% to 60%, 30% to 50%, 30% to 40%, 40% to 99%, 40% to 95%, 40% to 90%, 40% to 80%, 40% to 70%, 40% to 60%, 40% to 50%, 50% to 99%, 50% to 95%, 50% to 90%, 50% to 80%, 50% to 70%, 50% to 60%, 60% to 99%, 60% to 95%, 60% to 90%, 60% to 80%, 60% to 70%, 70% to 99%, 70% to 95%, 70% to 90%, 70% to 80%, 80% to 99%, 80% to 95%, 80% to 90%, 90% to 99%, 90% to 95%, or 95% to 99% of the weight of the composition. In certain embodiments, the prebiotic constitutes 1% to 99% of the weight of the composition. For example, in certain embodiments, the prebiotic constitutes 1% to 99%, 1% to 95%, 1% to 90%, 1% to 80%, 1% to 70%, 1% to 60%, 1% to 50%, 1% to 40%, 1% to 30%, 1% to 25%, 1% to 20%, 1% to 15%, 1% to 10%, 1% to 5%, 5% to 99%, 5% to 95%, 5% to 90%, 5% to 80%, 5% to 70%, 5% to 60%, 5% to 50%, 5% to 40%, 5% to 30%, 5% to 25%, 5% to 20%, 5% to 15%, 5% to 10%, 10% to 99%, 10% to 95%, 10% to 90%, 10% to 80%, 10% to 70%, 10% to 60%, 10% to 50%, 10% to 40%, 10% to 30%, 10% to 25%, 10% to 20%, 10% to 15%, 15% to 99%, 15% to 95%, 15% to 90%, 15% to 80%, 15% to 70%, 15% to 60%, 15% to 50%, 15% to 40%, 15% to 30%, 15% to 25%, 15% to 20%, 20% to 99%, 20% to 95%, 20% to 90%, 20% to 80%, 20% to 70%, 20% to 60%, 20% to 50%, 20% to 40%, 20% to 30%, 20% to 25%, 25% to 99%, 25% to 95%, 25% to 90%, 25% to 80%, 25% to 70%, 25% to 60%, 25% to 50%, 25% to 40%, 25% to 30%, 30% to 99%, 30% to 95%, 30% to 90%, 30% to 80%, 30% to 70%, 30% to 60%, 30% to 50%, 30% to 40%, 40% to 99%, 40% to 95%, 40% to 90%, 40% to 80%, 40% to 70%, 40% to 60%, 40% to 50%, 50% to 99%, 50% to 95%, 50% to 90%, 50% to 80%, 50% to 70%, 50% to 60%, 60% to 99%, 60% to 95%, 60% to 90%, 60% to 80%, 60% to 70%, 70% to 99%, 70% to 95%, 70% to 90%, 70% to 80%, 80% to 99%, 80% to 95%, 80% to 90%, 90% to 99%, 90% to 95%, or 95% to 99% of the weight of the composition.

FOS, GOS, or Other Appropriate Polysaccharide Formulations

A. Formulations Introduction

In an aspect, a prebiotic composition for the treatment of one or more musculoskeletal disorder is provided. In an aspect, a prebiotic composition for the treatment of inflammation is provided. In an aspect, a prebiotic composition for the management of one or more symptoms of perimenopause, menopause, or postmenopause is provided. In an embodiment, a prebiotic composition comprises inulin, FOS, lactulose, GOS, raffinose, stachyose, or a combination thereof. In addition, other plant-derived polysaccharides such as xylan, pectin, isomalto-oligosaccharides, gentio-oligosaccharides, 4-O-methyl glucuronoxylan (GX), neutral arabinoxylan (AX), heteroxylan (HX) can be combined with the probiotics to enhance bacterial metabolic function. Some of these can be derived from plant material found in the plant host from which the probiotics were isolated from. Therefore, the probiotics are adapted to assimilate and digest the rich complexity and variety of polysaccharides present in the plant that play a role during digestion by the consumption of an animal.

In some embodiments, a prebiotic composition comprises or consists of FOS, GOS, or other appropriate polysaccharide. In an, embodiment a prebiotic composition comprises FOS, GOS, other, and one or more digestible saccharides. Digestible saccharides are saccharides that are digestible by humans and include, but are not limited to lactose, glucose, and galactose. In an embodiment, a prebiotic composition comprises FOS, GOS, or other appropriate polysaccharide, and less than 20% weight/weight of one or more digestible saccharides (e.g. lactose, glucose, or galactose). In an embodiment, a prebiotic composition comprises FOS, GOS, or other appropriate polysaccharide, and less than 10% of one or more digestible saccharides. In an embodiment, a prebiotic composition comprises FOS, GOS, or other appropriate polysaccharide, and less than 5% of one or more digestible saccharides. In an embodiment, a prebiotic composition contains less than 5% lactose. In an embodiment, a prebiotic composition contains less than 4% lactose. In an embodiment, a prebiotic composition contains less than 3% lactose. In an embodiment, a prebiotic composition contains less than 2% lactose. In an embodiment, a prebiotic composition contains less than 1% lactose. In an embodiment, a prebiotic composition contains less than 0.5% lactose. In an embodiment, a prebiotic composition contains less than 0.4% lactose. In an embodiment, a prebiotic composition contains less than 0.3% lactose. In an embodiment, a prebiotic composition contains less than 0.2% lactose. In an embodiment, a prebiotic composition contains less than 0.1% lactose. In an embodiment, a prebiotic composition contains less than 0.05% lactose. In an embodiment, a prebiotic composition contains less than 0.01% lactose. In an embodiment, a prebiotic composition contains less than 0.005% lactose. In an embodiment, a prebiotic composition comprises FOS, GOS, or other appropriate polysaccharide, and essentially no lactose. In an embodiment, a prebiotic composition does not contain any lactose. In an embodiment, a prebiotic composition contains FOS, GOS, or other appropriate polysaccharide, and at least one probiotic bacteria strain. In an embodiment, a prebiotic composition comprises FOS, GOS, or other appropriate polysaccharide, and optionally one or more of lactose, at least one probiotic bacteria strain, and a buffer. Additional ingredients include ingredients to improve handling, preservatives, antioxidants, flavorings and the like.

In certain embodiments, a prebiotic composition comprises FOS, GOS, or other appropriate polysaccharide, or a probiotic. In some embodiments, a prebiotic composition is in the form of a powder, tablet, capsule, or liquid. In some embodiments, a prebiotic composition can be administered with a dairy product and is in the form of milk or other common dairy product such as a yogurt, shake, smoothie, cheese, and the like.

In embodiments where a prebiotic composition comprises less than 100% by weight of FOS, GOS, or other appropriate polysaccharide, the remaining ingredients can be any suitable ingredients intended for the consumption of the subject in need thereof, e.g., human, including, but not limited to, other prebiotics (e.g., FOS), a buffer, one or more digestible saccharides (e.g. lactose, glucose, or galactose), ingredients intended to inhibit clumping and increase pourability, such as silicone dioxide, magnesium stearate, microcrystalline cellulose, or similar ingredients as are well-known in the art. Remaining ingredients can also include ingredients to improve handling, preservatives, antioxidants, flavorings, and the like.

B. Buffer Components

One or more buffers, optionally with a calcium counter ion, can also be administered in methods and compositions described herein. Any buffer suitable for consumption by the subject being treated, e.g., human, are useful for the compositions herein. The buffer neutralizes stomach acidity, which can, e.g., allow live microbes to reach the gut. Buffers include citrates, phosphates, and the like. One embodiment utilizes a buffer with a calcium counter ion, such as Calcium Phosphate Tribasic. The calcium can serve to restore the calcium that many lactose intolerant subjects are missing in their diet. Calcium phosphate can protect *Lactobacillus acidophilus* from bile. Calcium phosphate can help neutralize stomach acidity.

In an embodiment, a buffer such as calcium phosphate is given prior to beginning treatment with a prebiotic composition (such as a composition comprising or consisting essentially of dried fruit or vegetable powder, FOS, GOS, and/or other appropriate polysaccharide), optionally in conjunction with administration of microbes. As used herein FOS indications one or more fructo-oligosaccharides and GOS indicates one or more galacto-oligosaccharides. In an embodiment, a buffer such as calcium phosphate is given in conjunction with treatment with a prebiotic composition (e.g., a composition comprising or consisting essentially of dried fruit or vegetable powder, FOS, GOS, and/or other appropriate polysaccharide), for part or all of the treatment with lactose. Thus, in an embodiment, some or all doses of a prebiotic composition are accompanied by a dose of a buffer such as calcium phosphate. In an embodiment, a buffer such as calcium phosphate is given initially with a prebiotic composition (such as a composition comprising or consisting essentially of dried fruit or vegetable powder, FOS, GOS, and/or other appropriate polysaccharide), but then its use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In an embodiment, a buffer such as calcium phosphate can be given for the first two days of treatment, and then the administration of buffer is discontinued. In an embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e. calcium. In an embodiment, a buffer can be used in a dose from 2 mg to 2000 mg, or 4 mg to 400 mg, or 4 mg to 200 mg, or 4 mg to 100 mg, or 8 mg to 50 mg, or 10 mg to 40 mg, or 20 mg to 30 mg, or 20, 21, 22, 23, 24, 25, 26, 27, 28, 29 or 30 mg. In an embodiment, a prebiotic composition further comprises an amount of a buffer from 1-50 mg, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg. In an embodiment, a buffer is used in a dose of 25 mg. In an embodiment, calcium phosphate is used in a dose of 25 mg. The dose can be given in combination with a prebiotic composition (e.g., a composition comprising or consisting essentially of dried fruit or vegetable powder, FOS, GOS, and/or other appropriate polysaccharide). In an embodiment, as a prebiotic composition dose increases, the dose of buffer increases as well. For example, an initial dose of a prebiotic composition can be 0.6 g to 1.0 g, e.g., 0.8 g, given in combination with 20-30 mg, e.g., 25 mg, of buffer, e.g., calcium phosphate. The dose of a prebiotic composition can be increased incrementally by 0.6 g to 1.0 g, e.g., 0.8 g, and the accompanying dose of buffer, e.g., calcium phosphate, can be increased by 20-30 mg, e.g., 25 mg, of buffer, e.g., calcium phosphate.

C. Compositions Comprising GOS and at Least One Probiotic Microbial Strain

In an embodiment, a prebiotic composition comprises FOS, GOS, or other appropriate polysaccharide, and at least one probiotic microbial strain (e.g. probiotic bacteria and/or fungi). The FOS, GOS, or other appropriate polysaccharide can comprise more than 1% of the weight of the composition while the at least one probiotic microbial strain will typically comprise less than 10%, 5%, 4%, 3%, or 2% by weight of the compositions. For example, the FOS, GOS, or other appropriate polysaccharide can be present at 1-99.75% by weight and the at least one probiotic bacteria strain at 0.25-2% by weight, or the FOS, GOS, or other appropriate polysaccharide can be present at 89-96% by weight and the bacteria at 1.2-3.7% by weight. In an embodiment, FOS, GOS, or other appropriate polysaccharide are present at 92% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In an embodiment, FOS, GOS, or other appropriate polysaccharide are present at 2% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 93% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 94% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 95% by weight and at least one probiotic microbial strain, (e.g., *Lactobacillus brevis, Lactobacillus plantarum, Leuconostoc mesenteroides, Pichia kudriavzevii*, and/or or other microbes from Table 1 or Table 2), is present at 1.5% by weight. In another embodiment, FOS, GOS, or other appropriate polysaccharide are present at 96% by weight and at least one probiotic microbial strain, (e.g. *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 97% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 98% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. In another embodiment, FOS, GOS, or other appropriate polysaccharide are present at 98.5% by weight and at least one probiotic microbial strain, (e.g., *Lactobacillus brevis, Lactobacillus plantarum, Leuconostoc mesenteroides, Pichia kudriavzevii*, and/or other microbes from Table 1 or Table 2), is present at 1.5% by weight. If the at least one probiotic microbial strain and FOS, GOS, or other appropriate polysaccharide do not make up 100% by weight of the prebiotic composition, the remaining ingredients can be any suitable ingredients intended for consumption by the subject in need thereof, e.g., human, including, but not limited to, other prebiotics (e.g., FOS and/or dried fruit or vegetable powder), one or more buffers, digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

D. Compositions Comprising FOS, GOS, or Other Appropriate Polysaccharide and a Buffer In another embodiment, a prebiotic composition comprises FOS, GOS, or other appropriate polysaccharide and a buffer (e.g., calcium phosphate tribasic). For example, FOS, GOS, or other appropriate polysaccharide can be present at 1-100% by weight and the buffer at 0.50-4% by weight, or FOS, GOS, or other appropriate polysaccharide can be present at 1-96% by weight and the buffer at 1 to 3.75% by weight. In an embodiment, FOS, GOS, or other appropriate polysaccharide are present at 1% by weight and buffer is present at 3% by weight. In an embodiment, FOS, GOS, or other appropriate polysaccharide are present at 5% by weight and buffer is present at 3% by weight. In an embodiment, FOS, GOS, or other appropriate polysaccharide are present at 10% by weight and buffer is present at 3% by weight. In an embodiment, FOS, GOS, or other appropriate polysaccharide are present at 15% by weight and buffer is present at 15% by weight. In an embodiment, FOS, GOS, or other appropriate polysaccharide are present at 20% by weight and buffer is present at 3% by weight. In an embodiment, FOS, GOS, or other appropriate polysaccharide are present at 25% by weight and buffer is present at 3% by weight. In an embodiment, FOS, GOS, or other appropriate polysaccharide are present at 30% by weight and buffer is present at 3% by weight. In an embodiment, FOS, GOS, or other appropriate polysaccharide are present at 35% by weight and buffer is present at 3% by weight. In an embodiment, FOS, GOS, or other appropriate polysaccharide are present at 40% by weight and buffer is present at 3% by weight. In an embodiment, FOS, GOS, or other appropriate polysaccharide are present at 50% by weight and buffer is present at 3% by weight. In an embodiment, FOS, GOS, or other appropriate polysaccharide are present at 60% by weight and buffer is present at 3% by weight. In an embodiment, FOS, GOS, or other appropriate polysaccharide are present at 70% by weight and buffer is present at 3% by weight. In another embodiment, FOS, GOS, or other appropriate polysaccharide are present at 90% by weight and buffer is present at 3% by weight. In another embodiment, FOS, GOS, or other appropriate polysaccharide are present at 92% by weight and buffer is present at 3% by weight. In another embodiment, FOS, GOS, or other appropriate polysaccharide are present at 93% by weight and buffer is present at 3% by weight. In another embodiment, FOS, GOS, or other appropriate polysaccharide are present at 94% by weight and buffer is present at 3% by weight. In another embodiment, FOS, GOS, or other appropriate polysaccharide are present at 95% by weight and buffer is present at 3% by weight. In another embodiment, FOS, GOS, or other appropriate polysaccharide are present at 96% by weight and buffer is present at 3% by weight. In another embodiment, FOS, GOS, or other appropriate polysaccharide are present at 97% by weight and buffer is present at 2% by weight. In another embodiment, FOS, GOS, or other appropriate polysaccharide are present at 98% by weight and buffer is present at 1% by weight. In another embodiment, FOS, GOS, or other appropriate polysaccharide are present at 99% by weight and buffer is present at 1% by weight. In another embodiment, FOS, GOS, or other appropriate polysaccharide are present at 100% by weight and buffer is present at less than 1% by weight. If the buffer and FOS, GOS, or other appropriate polysaccharide do not make up 100% by weight of the composition, the remaining ingredients can be any suitable ingredients intended for consumption by the subject (e.g., a human) including, but not limited to, probiotics (e.g., beneficial microbes, bacteria and/or fungi) or other prebiotics (e.g., FOS and/or dried fruit or vegetable powder), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

E. Compositions Comprising a Digestible Saccharide, a Probiotic Bacteria, and FOS, GOS, or Other Appropriate Polysaccharide In an embodiment, a prebiotic composition comprises a digestible saccharide (e.g. lactose, glucose, or galactose), at least one probiotic microbe (e.g. bacteria and/or yeast, e.g., *Lactobacillus brevis, Lactobacillus plantarum, Leuconostoc mesenteroides, Pichia kudriavzevii*, and/or other microbes from Table 1 and/or Table 2), and FOS, GOS, or other appropriate polysaccharide. In an embodiment, lactose can be present at 1-20% by weight, microbes at 0.25-20.10% by weight, and FOS, GOS, or other appropriate polysaccharide at 1-98.75% by weight. In another embodiment lactose can be present at 5-20% by weight, microbes at 0.91-1.95% by weight, and FOS, GOS, or other appropriate polysaccharide at 1 to 96% by weight. In another embodiment, lactose is present at 20% by weight, microbes at 1.5% by weight, and FOS, GOS, or other appropriate polysaccharide are present at 1% by weight. In another embodiment, lactose is present at 20% by weight, microbes at 1.5% by weight, and FOS, GOS, or other appropriate polysaccharide are present at 50% by weight. In another embodiment, lactose is present at 20% by weight, microbes at 1.5% by weight, and FOS, GOS, or other appropriate polysaccharide are present at 60% by weight. In another embodiment, lactose is present at 20% by weight, microbes at 1.5% by weight, and FOS, GOS, or other appropriate polysaccharide are present at 70% by weight. In another embodiment, lactose is present at 5% by weight, microbes at 1.5% by weight, and FOS, GOS, or other appropriate polysaccharide are present at 90% by weight. In another embodiment, lactose is present at 5% by weight, microbes at 1.5% by weight, and FOS, GOS, or other appropriate polysaccharide are present at 92% by weight. In another embodiment, lactose is present at 5% by weight, microbes at 1.5% by weight, and FOS, GOS, or other appropriate polysaccharide are present at 93% by weight. In another embodiment, lactose is present at 5% by weight, microbes at 1% by weight, and FOS, GOS, or other appropriate polysaccharide are present at 94% by weight. In another embodiment, lactose is present at 4.5% by weight, microbes at 1.5% by weight, and FOS, GOS, or other appropriate polysaccharide are present at 94% by weight. In another embodiment, lactose is present at 4.5% by weight, microbes at 0.5% by weight, and FOS, GOS, or other appropriate polysaccharide are present at 95% by weight. In another embodiment, lactose is present at 3.5% by weight, microbes at 0.5% by weight, and FOS, GOS, or other appropriate polysaccharide are present at 96% by weight. In another embodiment, lactose is present at 2.5% by weight, microbes at 0.5% by weight, and FOS, GOS, or other appropriate polysaccharides are present at 97% by weight. In another embodiment, lactose is present at 1.5% by weight, microbes at 0.5% by weight, and FOS, GOS, or other appropriate polysaccharide are present at 98% by weight. In another embodiment, lactose is present at 0.5% by weight, microbes at 0.5% by weight, and FOS, GOS, or other appropriate polysaccharide are present at 99% by weight. If the microbes, FOS, GOS, or other appropriate polysaccharide and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

F. Compositions Comprising FOS, GOS, or Other Appropriate Polysaccharide, a Probiotic Bacteria, and Buffer In an embodiment, a prebiotic composition comprises FOS, GOS, or other appropriate polysaccharide, at least one probiotic microbial strain (e.g. a bacterial and/or fungal strain, e.g., *Lactobacillus brevis, Lactobacillus plantarum, Leuconostoc mesenteroides, Pichia kudriavzevii*, and/or another microbe of Table 1 or Table 2), and buffer. In an embodiment, FOS, GOS, or other appropriate polysaccharide can be present at 1-100% by weight, a probiotic microbial strain at 0.25-2% by weight, and the buffer at 0.50-4% by weight. In another embodiment, FOS, GOS, or other appropriate polysaccharide can be present at 1-95% by weight, a probiotic b microbial strain at 0.91-1.95% by weight, and the buffer at 1.2-30.75% by weight. In another embodiment, FOS, GOS, or other appropriate polysaccharide are present at 1% by weight, a probiotic microbial strain at 1.5% by weight, and buffer is present at 3% by weight. In another embodiment, FOS, GOS, or other appropriate polysaccharide are present at 5% by weight, a probiotic microbial strain at 1.5% by weight, and buffer is present at 3% by weight. In another embodiment, FOS, GOS, or other appropriate polysaccharide are present at 10% by weight, a probiotic microbial strain at 1.5% by weight, and buffer is present at 3% by weight. In another embodiment, FOS, GOS, or other appropriate polysaccharide are present at 15% by weight, a probiotic microbial strain at 1.5% by weight, and buffer is present at 3% by weight. In another embodiment, FOS, GOS, or other appropriate polysaccharide are present at 20% by weight, a probiotic microbial strain at 1.5% by weight, and buffer is present at 3% by weight. In another embodiment, FOS, GOS, or other appropriate polysaccharide are present at 25% by weight, a probiotic microbial strain at 1.5% by weight, and buffer is present at 3% by weight. In another embodiment, FOS, GOS, or other appropriate polysaccharide are present at 30% by weight, a probiotic microbial strain at 1.5% by weight, and buffer is present at 3% by weight. In another embodiment, FOS, GOS, or other appropriate polysaccharide are present at 35% by weight, a probiotic microbial strain at 1.5% by weight, and buffer is present at 3% by weight. In another embodiment, FOS, GOS, or other appropriate polysaccharide are present at 40% by weight, a probiotic microbial strain at 1.5% by weight, and buffer is present at 3% by weight. In another embodiment, FOS, GOS, or other appropriate polysaccharide are present at 50% by weight, a probiotic microbial strain at 1.5% by weight, and buffer is present at 3% by weight. In another embodiment, FOS, GOS, or other appropriate polysaccharide are present at 60% by weight, a probiotic microbial strain at 1.5% by weight, and buffer is present at 3% by weight. In another embodiment, FOS, GOS, or other appropriate polysaccharide are present at 70% by weight, a probiotic microbial strain at 1.5% by weight, and buffer is present at 3% by weight. In another embodiment, FOS, GOS, or other appropriate polysaccharide are present at 90% by weight, a probiotic microbial strain at 1.5% by weight, and buffer is present at 3% by weight. In another embodiment, FOS, GOS, or other appropriate polysaccharide are present at 92% by weight, a probiotic microbial strain at 1.5% by weight, and buffer is present at 3% by weight. In another embodiment, FOS, GOS, or other appropriate polysaccharide are present at 93% by weight, a probiotic microbial strain at 1.5% by weight, and buffer is present at 3% by weight. In another embodiment, FOS, GOS, or other appropriate polysaccharide are present at 94% by weight, a probiotic microbial strain at 1.5% by weight, and buffer is present at 3% by weight. In another embodiment, FOS, GOS, or other appropriate polysaccharide are present at 95% by weight, a probiotic microbial strain at 1.5% by weight, and buffer is present at 3% by weight. In another embodiment, FOS, GOS, or other appropriate polysaccharide are present at 96% by weight, a probiotic microbial strain at 1.5% by weight, and buffer is present at 2% by weight. In another embodiment, FOS, GOS, or other appropriate polysaccharide are present at 97% by weight, a probiotic microbial strain at 1.5% by weight, and buffer is present at 1.5% by weight. In another embodiment, FOS, GOS, or other appropriate polysaccharide are present at 99% by weight, a probiotic microbial strain at 0.5% by weight, and buffer is present at 0.5% by weight. In another embodiment, FOS, GOS, or other appropriate polysaccharide are present at 100% by weight, a probiotic microbial strain at less than 0.5% by weight, and buffer is present at less than 0.5% by weight. If the probiotic microbial strain, buffer, and FOS, GOS, or other appropriate polysaccharide do not make up 100% of the composition, the remaining ingredients can be any suitable ingredients intended for the consumption of a subject (e.g., human) including, but not limited to, other prebiotics (e.g., FOS or dried fruit or vegetable powder), digestible saccharides (e.g., lactose, glucose or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

G. Compositions Comprising a Digestible Saccharide, FOS, GOS, or Other Appropriate Polysaccharide, and a Buffer In an embodiment, a prebiotic composition comprises a digestible saccharide (e.g. lactose, glucose, or galactose), FOS, GOS, or other appropriate polysaccharide, and a buffer. For example, lactose can be present at 1-20% by weight, FOS, GOS, or other appropriate polysaccharide at 1-100% by weight, and the buffer at 0.50-4% by weight, or the lactose can be present at 5-20% by weight, FOS, GOS, or other appropriate polysaccharide at 1-96% by weight, and the buffer at 1.2-30.75% by weight. In an embodiment, lactose is present at 20% by weight, FOS, GOS, or other appropriate polysaccharide at 1% by weight, and buffer is present at 3% by weight. In an embodiment, lactose is present at 5% by weight, FOS, GOS, or other appropriate polysaccharide at 1% by weight, and buffer is present at 3% by weight. In an embodiment, lactose is present at 20% by weight, FOS, GOS, or other appropriate polysaccharide at 10% by weight, and buffer is present at 3% by weight. In an embodiment, lactose is present at 20% by weight, FOS, GOS, or other appropriate polysaccharide at 15% by weight, and buffer is present at 3% by weight. In an embodiment, lactose is present at 20% by weight, FOS, GOS, or other appropriate polysaccharide at 20% by weight, and buffer is present at 3% by weight. In an embodiment, lactose is present at 20% by weight, FOS, GOS, or other appropriate polysaccharide at 25% by weight, and buffer is present at 3% by weight. In an embodiment, lactose is present at 20% by weight, FOS, GOS, or other appropriate polysaccharide at 30% by weight, and buffer is present at 3% by weight. In an embodiment, lactose is present at 20% by weight, FOS, GOS, or other appropriate polysaccharide at 35% by weight, and buffer is present at 3% by weight. In an embodiment, lactose is present at 20% by weight, FOS, GOS, or other appropriate polysaccharide at 40% by weight, and buffer is present at 3% by weight. In an embodiment, lactose is present at 20% by weight, FOS, GOS, or other appropriate polysaccharide at 50% by weight, and buffer is present at 3% by weight. In an embodiment, lactose is present at 20% by weight, FOS, GOS, or other appropriate polysaccharide at 60% by weight, and buffer is present at 3% by weight. In an embodiment, lactose is present at 20% by weight, FOS, GOS, or other appropriate polysaccharide at 70% by weight, and buffer is present at 3% by weight. In another embodiment, lactose is present at 5% by weight, FOS, GOS, or other appropriate polysaccharide at 90% by weight, and buffer is present at 3% by weight. In another embodiment, lactose is present at 5% by weight, FOS, GOS, or other appropriate polysaccharide at 92% by weight, and buffer is present at 3% by weight. In another embodiment, lactose is present at 4% by weight, FOS, GOS, or other appropriate polysaccharide at 93% by weight, and buffer is present at 3% by weight. In another embodiment, lactose is present at 3% by weight, FOS, GOS, or other appropriate polysaccharide at 94% by weight, and buffer is present at 3% by weight. In another embodiment, lactose is present at 2% by weight, FOS, GOS, or other appropriate polysaccharide at 95% by weight, and buffer is present at 3% by weight. In another embodiment, lactose is present at 1% by weight, FOS, GOS, or other appropriate polysaccharide at 96% by weight, and buffer is present at 3% by weight. If a suitable prebiotic, buffer and lactose do not make up 100% of the composition by weight, the remaining ingredients can be any suitable ingredients intended for consumption by a subject (e.g., human) including, but not limited to, microbes (e.g. bacteria), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

H. Compositions Comprising a Digestible Saccharide, Microbes (e.g. Bacteria), GOS, and a Buffer In an embodiment, a composition comprises a digestible saccharide (e.g. lactose, glucose, or galactose), microbes (e.g. bacteria and/or fungi, e.g., *Lactobacillus brevis, Lactobacillus plantarum, Leuconostoc mesenteroides, Pichia kudriavzevii*, and/or another microbe of Table 1 or Table 2), FOS, GOS, or other appropriate polysaccharide, and buffer. For example, lactose can be present at 1-20% by weight, microbes at 0.25-2.10% by weight, FOS, GOS, or other appropriate polysaccharide at 1-100% by weight, and the buffer at 0.50-4% by weight, or the lactose can be present at 5-20% by weight, microbes at 0.91-1.95% by weight, FOS, GOS, or other appropriate polysaccharide at 70-95% by weight, and the buffer at 1.2-30.75% by weight. In an embodiment, lactose is present at 20% by weight, microbes at 1.47% by weight, FOS, GOS, or other appropriate polysaccharide at 1% by weight, and buffer is present at 3% by weight. In an embodiment, lactose is present at 20% by weight, microbes at 1.47% by weight, FOS, GOS, or other appropriate polysaccharide at 10% by weight, and buffer is present at 3% by weight. In an embodiment, lactose is present at 20% by weight, microbes at 1.47% by weight, FOS, GOS, or other appropriate polysaccharide at 15% by weight, and buffer is present at 3% by weight. In an embodiment, lactose is present at 20% by weight, microbes at 1.47% by weight, FOS, GOS, or other appropriate polysaccharide at 20% by weight, and buffer is present at 3% by weight. In an embodiment, lactose is present at 20% by weight, microbes at 1.47% by weight, FOS, GOS, or other appropriate polysaccharide at 25% by weight, and buffer is present at 3% by weight. In an embodiment, lactose is present at 20% by weight, microbes at 1.47% by weight, FOS, GOS, or other appropriate polysaccharide at 30% by weight, and buffer is present at 3% by weight. In an embodiment, lactose is present at 20% by weight, bacteria at 1.47% by weight, FOS, GOS, or other appropriate polysaccharide at 35% by weight, and buffer is present at 3% by weight. In an embodiment, lactose is present at 20% by weight, microbes at 1.47% by weight, FOS, GOS, or other appropriate polysaccharide at 40% by weight, and buffer is present at 3% by weight. In an embodiment, lactose is present at 20% by weight, microbes at 1.47% by weight, FOS, GOS, or other appropriate polysaccharide at 50% by weight, and buffer is present at 3% by weight. In an embodiment, lactose is present at 20% by weight, microbes at 1.47% by weight, FOS, GOS, or other appropriate polysaccharide at 60% by weight, and buffer is present at 3% by weight. In an embodiment, lactose is present at 20% by weight, microbes at 1.47% by weight, FOS, GOS, or other appropriate polysaccharide at 70% by weight, and buffer is present at 3% by weight. In an embodiment, lactose is present at 5% by weight, microbes at 1.47% by weight, FOS, GOS, or other appropriate polysaccharide at 90% by weight, and buffer is present at 3% by weight. In an embodiment, lactose is present at 3% by weight, microbes at 1.47% by weight, FOS, GOS, or other appropriate polysaccharide at 92% by weight, and buffer is present at 3% by weight. In an embodiment, lactose is present at 2% by weight, microbes at 1.47% by weight, FOS, GOS, or other appropriate polysaccharide at 93% by weight, and buffer is present at 3% by weight. In an embodiment, lactose is present at 1% by weight, microbes at 1.47% by weight, FOS, GOS, or other appropriate polysaccharide at 94% by weight, and buffer is present at 3% by weight. In an embodiment, lactose is present at 0.5% by weight, microbes at 1.47% by weight, FOS, GOS, or other appropriate polysaccharide at 95% by weight, and buffer is present at 3% by weight. If the microbes, FOS, GOS, or other, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

I. Additional Ingredients

Additional ingredients include ingredients to improve handling, preservatives, antioxidants, flavorings and the like. For example, in an embodiment, a prebiotic composition in powdered form can include flavorings such that when mixed in a liquid (e.g., water), the powder can flavor the liquid with various flavors such as grape, strawberry, lime, lemon, chocolate, and the like. In an embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

Timing and Dosage of Probiotic and Treatments Known to Combat Musculoskeletal Disorders In an embodiment, probiotic microbes, such as *Lactobacillus brevis, Lactobacillus plantarum, Leuconostoc mesenteroides*, and/or *Pichia kudriavzevii*, are given prior to beginning treatment with a drug typically prescribed for treatment of a musculoskeletal disorder.

Thus, in an embodiment, some or all doses of a treatment or drug are accompanied by a dose of microbes, e.g., live cultured bacteria and/or yeast, e.g., *Lactobacillus brevis, Lactobacillus plantarum, Leuconostoc mesenteroides*, and/or *Pichia kudriavzevii*. In an embodiment, microbes, e.g., *Lactobacillus brevis, Lactobacillus plantarum, Leuconostoc mesenteroides*, and/or *Pichia kudriavzevii*, are given initially with another treatment or drug, but then use of the microbes is discontinued. For example, the initial one, two, three, four, five, six, seven, eight, nine, ten, or more than ten days of treatment with a treatment or drug further comprises doses of microbes, with the use of microbes discontinued after that time. In an embodiment, microbes, (e.g., bacteria in yogurt), or microbes by themselves, can be given for the first two days of treatment; then the administration of microbes is discontinued. In another embodiment, probiotic microbes, either alone or in combination with other substances or treatments are used after the treatment with a drug or treatment for musculoskeletal disorders is terminated. The microbes can be taken for any suitable period after the termination of treatment with the drug and can be taken daily or at regular or irregular intervals. Doses can be as described below. Any suitable amount of probiotic per serving can be used that allows an effective microbiota in the GI as demonstrated by, for example, decreased symptoms of a given musculoskeletal disorder.

Examples of anti-osteoporosis combination partners are but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide). In an embodiment, probiotic microbes, such as *Lactobacillus brevis, Lactobacillus plantarum, Leuconostoc mesenteroides*, and/or *Pichia kudriavzevii*, are given in conjunction with treatment, such as, but not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide).

Examples of treatments for osteomyelitis that may be used in combination with compositions disclosed herein, include, but are not limited to surgery and antibiotics. In some embodiments, antibiotics are given intravenously. In some embodiments, antibiotics are given orally. Typically, compositions disclosed herein are given after cessation of antibiotic therapy; however, in some cases, a suitable antibiotic or a suitable delivery route of antibiotic allows for concurrent use of compositions described herein and antibiotic therapy.

Examples of treatments for delayed or non-union fractures include bone stimulation and surgery, such as bone grafts or fixations.

Dosage Forms

A. General

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

In an embodiment, compositions described herein comprise one or more excipients. In an embodiment, the one or more excipients comprise one or more antiadherents, one or more binders, one or more coatings, one or more disintegrants, one or more fillers, one or more flavors, one or more colors, one or more lubricants, one or more glidants, one or more sorbents, one or more preservatives, one or more sweeteners, or a combination thereof. In an embodiment, the antiadherent is magnesium stearate. In an embodiment, the one or more binders are cellulose, microcrystalline cellulose, hydroxypropyl cellulose, xylitol, sorbitol, maltitol, gelatin, polyvinylpyrrolidone, polyethylene glycol, methyl cellulose, hydroxypropyl methylcellulose, or a combination thereof. In an embodiment, the one or more coatings are a hydroxypropyl methylcellulose film, shellac, corn protein zein, gelatin, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, stearic acid, or a combination thereof. In an embodiment, the one or more disintegrants are crosslinked polyvinylpyrrolidone (crospovidone), crosslinked sodium carboxymethyl cellulose (croscarmellose sodium), sodium starch glycolate, or a combination thereof. In an embodiment, the one or more fillers are calcium carbonate, magnesium stearate, dibasic calcium phosphate, cellulose, vegetable oil, vegetable fat, or a combination thereof. In an embodiment, the one or more flavors are mint, cherry, anise, peach, apricot, licorice, raspberry, vanilla, or a combination thereof. In an embodiment, the one or more lubricants are talc, silica, vegetable stearin, magnesium stearate, stearic acid, or a combination thereof. In an embodiment, the one or more glidants are fumed silica, talc, magnesium carbonate, or a combination thereof. In an embodiment, the one or more sorbents are fatty acids, waxes, shellac, plastics, plant fibers, or a combination thereof. In an embodiment, the one or more preservatives are vitamin A, vitamin E, vitamin C, retinyl palmitate, selenium, cysteine, methionine, citric acid, sodium citrate, methyl paraben, propyl paraben, or a combination thereof. In an embodiment, the one or more sweeteners are stevia, aspartame, sucralose, neotame, acesulfame potassium, saccharin or a combination thereof.

B. Oral Dosage Forms and Components

In one aspect provided herein are methods and compositions formulated for oral delivery to a subject in need thereof. In an embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof.

1. Forms

In an embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients including freeze-dried plant material serving both as prebiotic and as a filler. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents.

In an embodiment, a provided composition includes a softgel formulation. A softgel can contain a gelatin-based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In an embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel, Aquacoat® ECD, and Metolose®); polyvinylacetate phthalate (trade name Sureteric®); and methacrylic acid (trade name Eudragit®).

In an embodiment, an enteric coated prebiotic composition is administered to a subject. In another embodiment, an enteric coated probiotic composition is administered to a subject. In another embodiment, an enteric coated probiotic and prebiotic composition is administered to a subject. In an embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In an embodiment a prebiotic composition is provided as a tablet, capsule, or caplet with an enteric coating. In an embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In an embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In an embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In an embodiment, the dosage form is a gelatin capsule having a size indicated in Table 3.

TABLE 3

Gel Cap Sizes Allowable For Human Consumption: Empty Gelatin Capsule Physical Specifications

| | Outer Diameter Size (mm) | Height or Locked Length (mm) | Actual Volume (ml) |
|---|---|---|---|
| 000 | 9.97 | 26.14 | 1.37 |
| 00 | 8.53 | 23.30 | 0.95 |
| 0 | 7.65 | 21.7 | 0.68 |
| 1 | 6.91 | 19.4 | 0.50 |
| 2 | 6.35 | 18.0 | 0.37 |
| 3 | 5.82 | 15.9 | 0.3 |
| 4 | 5.31 | 14.3 | 0.21 |
| 5 | 4.91 | 11.1 | 0.13 |

Note:
sizes and volumes are approximate.

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semipermeable membrane and as swellable substances.

In another embodiment the prebiotic mixture is a plant or plant extract, either in solid or liquid form.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In an embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In an embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In an embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In an embodiment, compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which is herein incorporated by reference in its entirety).

In an embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In an embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, 1 g to 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

2. Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In an embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam-jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In an embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In an embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In an embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

In one aspect, controlled-release refers to delayed release of an agent, from a composition or dosage form in which the agent is released according to a desired profile in which the release occurs after a period of time.

When present in a controlled-release oral dosage form, the compositions described herein can be administered at a substantially lower daily dosage level than immediate-release forms.

In an embodiment, the controlled-release layer is capable of releasing 30 to 40% of the one or more active agents (e.g., prebiotic and/or probiotic) contained therein in the stomach of a subject in need thereof in 5 to 10 minutes following oral administration. In another embodiment, the controlled-release layer is capable of releasing 90% of the one or more active agents (e.g., prebiotic and/or probiotic) is released in 40 minutes after oral administration.

In some embodiments, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In an embodiment, a controlled release formulation weighs between 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In an embodiment citric acid and sodium bicarbonate are used.

In another aspect the dosage form can be in a candy form (e.g., matrix), such as a lollipop or lozenge. In an embodiment an effective amount of a prebiotic is dispersed within a candy matrix. In an embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartame, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In an embodiment a candy mass is prepared that comprises one or more layers which can comprise different amounts or rates of dissolution of the prebiotic. In an embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In an embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In an embodiment the pharmaceutical particles have a final size of 3-1000 μM, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μM. In another embodiment the pharmaceutical particles have a final size of 10-500 μM. In another embodiment the pharmaceutical particles have a final size of 50-600 μM. In another embodiment the pharmaceutical particles have a final size of 100-800 μM.

In an embodiment an oral dosage form (such as a powder, tablet, or capsule) is provided comprising a prebiotic composition comprising 0.7 g of FOS, GOS, or other FOS, GOS, or other appropriate polysaccharide, 0.2 g of lactose, 0.01 g of glucose, 0.01 g of galactose, 0.1-0.2 g of a binder, 0.1-0.2 g of a dispersant, 0.1-0.2 g of a solubilizer, wherein the FOS, GOS, or other FOS, GOS, or other appropriate polysaccharide are composed of 1-25% disaccharides, 1-25% trisaccharides, 1-25% tetrasaccharides, and 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising 1-99.9% by weight of FOS, GOS, or other FOS, GOS, or other appropriate polysaccharide 0.5-20% by weight of lactose, 0.1-2% by weight of glucose, 0.1-2% by weight of galactose, 0.05-2% by weight of a binder, 0.05-2% by weight of a dispersant, 0.05-2% by weight of a solubilizer, wherein the FOS, GOS, or other FOS, GOS, or other appropriate polysaccharide are composed of 1-25% by weight disaccharides, 1-25% by weight trisaccharides, 1-25% by weight tetrasaccharides and 1-25% by weight pentasaccharides.

In another embodiment an oral dosage form (such as a powder, tablet, or capsule) is provided comprising a prebiotic composition comprising 1, 10, 20, 30, 40, 50, 60, 70, 80, 90, 95, 99.5 100% by weight of FOS, GOS, or other FOS, GOS, or other appropriate polysaccharide 0, 5, 10, 15 or 20% by weight of lactose, 0.1, 0.5, 1 or 2% by weight of glucose, 0.1, 0.5, 1 or 2% by weight of galactose, 0.05, 0.1, 0.5, 1 or 2% by weight of a binder, 0.05, 0.1, 0.5, 1 or 2% by weight of a dispersant, 0.05, 0.1, 0.5, 1 or 2% by weight of a solubilizer, wherein the FOS, GOS, or other FOS, GOS, or other appropriate polysaccharide are composed of 1, 5, 10, 15, 20 or 25% by weight disaccharides, 1, 5, 10, 15, 20, or 25% by weight trisaccharides, 1, 5, 10, 15, 20 or 25% by weight tetrasaccharides, and 1, 5, 10, 15, 20 or 25% by weight pentasaccharides.

In another embodiment, an oral dosage form is provided comprising a prebiotic composition, wherein the oral dosage form is a syrup. The syrup can comprise 1%, 5%, 10%, 15%, 20%, 25%, 30%, 35%, 40%, 45%, 50%, 55%, 60%, 65%, 70%, 75%, 80%, or 85% solid. The syrup can comprise 15%, 20%, 25%, 30%, 35%, 40%, 45% or 50% liquid, for example, water. The solid can comprise a prebiotic composition. The solid can be, for example, 1-96%, 10-96%, 20-96%, 30-96%, 40-96%, 50-96%, 60-96%, 70-96%, 80-96% or 90-96% prebiotic composition. The solid can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or 96% prebiotic composition. In an embodiment a prebiotic composition comprises FOS, GOS, or other FOS, GOS, or other appropriate polysaccharide. In another embodiment a prebiotic composition comprises FOS, GOS, or other FOS, GOS, or other appropriate polysaccharide and another prebiotic. In another embodiment a prebiotic composition comprises FOS, GOS or other and inulin or GOS and FOS.

In an embodiment, the softgel capsule is 0.25 mL, 0.5 mL, 1.0 mL, 1.25 mL, 1.5 mL, 1.75 mL, or 2.0 mL. In another embodiment, a softgel capsule comprises 0.1 g to 2.0 g of prebiotic composition. In another embodiment, a softgel capsule comprises 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In an embodiment the prebiotic composition comprises FOS, GOS, or other FOS, GOS, or other appropriate polysaccharide. In another embodiment the prebiotic composition consists essentially of FOS, GOS, or other FOS, GOS, or other appropriate polysaccharide. In another embodiment, a softgel capsule comprises FOS, GOS, or other FOS, GOS, or other appropriate polysaccharide and inulin or FOS.

In another embodiment, the prebiotic composition is delivered in a gelatin capsule containing an amount of FOS, GOS, or other FOS, GOS, or other appropriate polysaccharide within the ranges listed in Table 4. In another embodiment, the number of pills taken per day is within the ranges listed in Table 4.

TABLE 4

Exemplary GOS Dosing Units: Exemplary GOS Composition Dosages in Gel Caps

| Size | GOS/Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In an embodiment a prebiotic composition comprising FOS, GOS, or other FOS, GOS, or other appropriate polysaccharide does not contain a preservative or an antioxidant.

In another embodiment, a prebiotic composition is formulated as a viscous fluid. In another embodiment, a prebiotic composition is formulated such that its water content is low enough that it does not support microbial growth. In an embodiment, this composition is an intermediate-moisture food, with a water activity between 0.6 and 0.85; in another embodiment this composition is a low-moisture food, with a water activity less than 0.6. Low-moisture foods limit microbial growth significantly and can be produced by one of ordinary skill in the art. For example, these products could be produced similarly to a liquid-centered cough drop. In another embodiment, a prebiotic composition is formulated as a viscous fluid without a preservative in a gel capsule. In another embodiment, a prebiotic composition comprising FOS, GOS, or other FOS, GOS, or other appropriate polysaccharide is a viscous fluid. In another embodiment, a prebiotic composition comprises a high percentage of FOS, GOS, or other FOS, GOS, or other appropriate polysaccharide that does not support microbial growth. In another embodiment, the prebiotic composition comprises FOS, GOS, or other FOS, GOS, or other appropriate polysaccharide and inulin or FOS.

In another embodiment, an oral dosage form is provided comprising a prebiotic composition, wherein the oral dosage form is a softgel. In an embodiment the softgel comprises a syrup. In an embodiment the syrup comprises a prebiotic composition. In an embodiment the prebiotic composition comprises FOS, GOS, or other FOS, GOS, or other appropriate polysaccharide. In another embodiment the prebiotic composition comprises more than 80% FOS, GOS, or other FOS, GOS, or other appropriate polysaccharide. In another embodiment the prebiotic composition comprises between 80-99.9% FOS, GOS, or other. In another embodiment the prebiotic composition comprises more than 80% FOS, GOS, or other FOS, GOS, or other appropriate polysaccharide. In another embodiment the prebiotic composition comprises 80, 81, 82, 83, 84, 85, 86, 87, 88, 89, 90, 91, 92, 93, 94, 95, 96, 97, 98, 99, or 99.9% FOS, GOS, or other FOS, GOS, or other appropriate polysaccharide.

In an embodiment a FOS, GOS, or other FOS, GOS, or other appropriate polysaccharide composition is formulated for delivery in a soft gel capsule. In an embodiment a FOS, GOS, or other FOS, GOS, or other appropriate polysaccharide composition formulated for delivery in a soft gel capsule is a high percentage FOS, GOS, or other FOS, GOS, or other appropriate polysaccharide composition, such as a 90-100% FOS, GOS, or other FOS, GOS, or other appropriate polysaccharide composition (e.g., 90, 91, 92, 93, 94, 95, 96, 97, 98, 99 or 100% FOS, GOS, or other FOS, GOS, or other appropriate polysaccharide composition by weight). In another embodiment a FOS, GOS, or other FOS, GOS, or other appropriate polysaccharide composition formulated for delivery in a soft gel capsule comprises 95% FOS, GOS, or other FOS, GOS, or other appropriate polysaccharide. In another embodiment a FOS, GOS, or other FOS, GOS, or other appropriate polysaccharide composition formulated for delivery in a soft gel capsule comprises 96% FOS, GOS, or other FOS, GOS, or other appropriate polysaccharide. In another embodiment, the FOS, GOS, or other FOS, GOS, or other appropriate polysaccharide composition is formulated such that its water content is low enough that it does not support microbial growth. In another embodiment, the FOS, GOS, or other FOS, GOS, or other appropriate polysaccharide composition is formulated as a viscous fluid without a preservative in a gel capsule. In another embodiment, the FOS, GOS, or other FOS, GOS, or other appropriate polysaccharide composition is formulated as a viscous fluid without an antioxidant in a gel capsule. In another embodiment the soft gel capsule comprises 0.1-2 g of a FOS, GOS, or other FOS, GOS, or other appropriate polysaccharide composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber (e.g., cellulose or lignin), or a neutralizing component. In an embodiment a prebiotic composition can be in the form of a chewable tablet.

In an embodiment a foaming component can be at least one member selected from the group consisting of sodium hydrogencarbonate, sodium carbonate, and calcium carbonate. In an embodiment a neutralizing component can be at least one member selected from the group consisting of citric acid, L-tartaric acid, fumaric acid, L-ascorbic acid, DL-malic acid, acetic acid, lactic acid, and anhydrous citric acid. In an embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatin, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and stevia, saccharin, and like sweeteners. The amounts of these additives can be properly selected based on their relation to other components and properties of the preparation, production method, etc.

In an embodiment, a FOS, GOS, or other FOS, GOS, or other appropriate polysaccharide composition is a chewable oral dosage formulation. In an embodiment the chewable formulation can comprises between 1-99.9% FOS, GOS, or other FOS, GOS, or other appropriate polysaccharide. In an embodiment, a FOS, GOS, or other FOS, GOS, or other appropriate polysaccharide composition comprises 80% FOS, GOS, or other FOS, GOS, or other appropriate polysaccharide 5% L-ascorbic acid, 2% anhydrous citric acid, 3% sodium hydrogencarbonate, 3% calcium carbonate, 2% sucrose fatty acid, 3% fruit juice powder, and 2% potassium carbonate.

In another embodiment, a FOS, GOS, or other FOS, GOS, or other appropriate polysaccharide composition comprises 85% FOS, GOS, or other FOS, GOS, or other appropriate polysaccharide, 5% L-ascorbic acid, 3% sodium hydrogencarbonate, 2% sodium carbonate, 2% sucrose fatty acid ester, 2% fruit juice powder, and 1% potassium carbonate.

In another embodiment, a FOS, GOS, or other FOS, GOS, or other appropriate polysaccharide composition comprises 90% FOS, GOS, or other FOS, GOS, or other appropriate polysaccharide, 2% L-ascorbic acid, 1% anhydrous citric acid, 2% sodium hydrogencarbonate, 2% sodium carbonate, 2% sucrose fatty acid ester, and 1% potassium carbonate.

In another embodiment, a FOS, GOS, or other FOS, GOS, or other appropriate polysaccharide composition comprises 95% FOS, GOS, or other FOS, GOS, or other appropriate polysaccharide, 2% L-ascorbic acid, 1% sodium hydrogencarbonate, and 2% fruit juice powder. In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, or potassium carbonate.

In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, and potassium carbonate.

Combination Therapy

In some embodiments, the compositions of the present invention can be used in conjunction with traditional treatments for a musculoskeletal disorder, such as an anti-osteoporosis or osteopenia therapy. In some embodiments, the present invention is administered together with at least one other therapy or agent. In some embodiments, the present invention is administered before the at least one other therapy or agent. In some embodiments, the present invention is administered after the at least one other therapy or agent. In other embodiments, the present invention is administered after cessation of another therapy or agent. The therapy includes, but is not limited to, approved therapies for osteoporosis, osteopenia, Paget's disease, stunting, osteoarthritis, osteomyelitis, delayed or on-union fractures, or any combination of the foregoing.

Some therapies for osteoporosis or osteopenia that are known in the art include: estrogen, estrogen agonists/antagonists (e.g. tamoxifen, raloxifene, toremifene, and bazedoxifine), bisphosphonates (e.g., alendronate, ibandronate, risedronate, and zoledronic acid), Denosumab, anabolic therapies (e.g. teriparatide, abaloparatide, romosozumab), and vitamin D. One of skill in the art would understand that the present invention may be used to supplement, increase efficacy of, or otherwise improve upon any of a number of known therapies for osteoporosis or osteopenia.

In certain embodiments, the methods disclosed herein comprise supplementation of Vitamin D by adjunct administration, e.g., concurrently or sequentially. In certain embodiments, the Vitamin D is administered daily, twice daily, thrice daily, every other day, or weekly. In certain embodiments, the Vitamin D is administered at a dose of 100-1,000 international units. In certain embodiments, the Vitamin D is administered at 400 international units. In certain embodiments, the Vitamin D is administered daily at 400 international units.

Medical Foods

An alternate embodiment of the present invention is a formulation as a medical food. As used herein, a medical food is understood to be a form of dietary supplement.

The consuming public has come to understand that foods possess more than basic nutrition (protein, carbohydrate, fat, etc). For example, 95% of consumers agree that "certain foods have health benefits that go beyond basic nutrition and may reduce the risk of disease or other health concerns." More than 50% of consumers believe that foods can replace the use of drugs. Replacing the use of drugs may have the benefit of reducing the incidence of adverse side effects suffered by patients following a pharmaceutical drug treatment regimen. In fact, medical foods are assumed to be generally safe, as people have historically consumed these foods safely in non-medical contexts.

The compositions of the disclosure may be administered under the supervision of a medical specialist, or may be self-administered. Medical foods could take the form of nutritional shakes or other liquids or meal replacements. Medical foods of the present invention could also take the form of a powder capable of being consumed upon addition to suitable food or liquid.

A medical food formulation of the present disclosure could confer benefits of a synthetic composition of microbes isolated from nutritionally beneficial plants, as well as the benefits of prebiotics, or other nutritionally beneficial inclusions, but not consumed to obtain nutrition from them but rather to provide a metabolic function different than a foodstuff. For example, medical foods of the disclosure may also include at least one vitamin, or vitamin precursor. Preferred vitamins possess antioxidant properties and include vitamins A, C and E, and/or their biochemical precursors. In an embodiment, the medical food of the disclosure includes at least one trace element, preferably selected from the group consisting of zinc, manganese and selenium. Medical foods of the disclosure also may include at least one additional antioxidant selected from the group consisting of carotenoids, N-acetylcysteine and L-glutamine. It is known to those of skill in the art how to construct medical foods containing these elements.

In certain aspects, medical foods disclosed herein include effective doses of microbes deemed useful for the indication(s) and effective doses of any vitamin, prebiotic, or other beneficial additive not consumed to obtain nutrition but to add a therapeutic benefit mediated by the production of SCFA or other immuno-stimulant molecules when passing through the GI tract.

Typically, the dietary supplements and medical foods of the present invention are consumed at least once daily, and preferably administered two times per day, optionally once in the morning and once in the afternoon or evening. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals.

Anyone perceived to be at risk from a musculoskeletal disorder, including osteoporosis or osteopenia, or already suffering from any of the foregoing, can potentially benefit from ingesting the compositions disclosed herein. According to the disclosure, it is believed to be possible to effectively ameliorate symptoms and conditions associated with musculoskeletal disorders with natural compounds, which do not show any severe side effects. Furthermore, the present methods are expected to be well-tolerated, for example without causing any discomfort or nausea, and simple to apply.

Methods of the Invention

The administration of the microbial compositions disclosed herein (e.g., DMA compositions as described herein, e.g., a DMA composition comprising a prebiotic) can be accomplished orally or rectally, although administration is not limited to these methods. In some embodiments, the microbial composition is administered orally. In some embodiments, the microbial composition is delivered rectally. In some embodiments, the administration of the microbial composition occurs at regular intervals. In some embodiments, the administration occurs daily. In some embodiments, the administration occurs once daily, twice daily, three times daily, etc. In some embodiments, the administration of the microbial composition occurs regularly for at least 1 week, at least 2 weeks, at least 3 weeks, at least 4 weeks, at least 6 weeks, at least 2 months, at least 3 months, at least 4 months, at least 5 months, at least 6 months, at least 8 months, at least 10 months, at least 12 months, at least 14 months, at least 16 months, at least 18 months, or at least 2 years. In some embodiments, the administration of the microbial composition occurs regularly for about 1 week, about 2 weeks, about 3 weeks, about 4 weeks, about 6 weeks, about 2 months, about 3 months, about 4 months, about 5 months, about 6 months, about 8 months, about 10 months, about 12 months, about 14 months, about 16 months, about 18 months, or about 2 years. In a particular embodiment, administration of the microbial composition occurs twice daily for at least about 6 months or at least about 12 months.

The microbial composition can be administered via typical pharmacological means, such as slurries, capsules, microcapsules, or solutions, although means of administration are not limited to these methods. In some embodiments, an enteric capsule or enteric microcapsule is used. In some embodiments, the pharmaceutical composition involving the microbial composition described herein will be fresh or frozen prior to application. In some embodiments, said pharmaceutical composition will be lyophilized or otherwise treated to increase stability or otherwise obtain a benefit from said treatment. In some embodiments, the composition can be administered as a medical food.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Manufacture of a Defined Microbial Assemblage

This example describes the manufacture of a DMA comprising four strains of microorganisms isolated from foods.

DMA Identity

Four microbial strains (strains of *Lactobacillus brevis, Lactobacillus plantarum, Leuconostoc mesenteroides*, and *Pichia kudriavzevii*) were isolated as described in U.S. patent application Ser. No. 16/694,876, which is herein incorporated by reference in its entirety. The genomes of these four strains were sequenced as described in Ser. No.

16/694,876 and aligned by nucleotide BLAST to 16S rRNA gene reference sequences and fungal ITS reference sequences from the NCBI database. The 16S rRNA gene sequences of the isolated bacterial strains *L. brevis, L. plantarum*, and *L. mesenteroides* correspond to the nucleotide sequences of SEQ ID NOs: 94, 100, and 93, respectively. The fungal ITS sequence of the isolated *P. kudriavzevii* strain corresponds to SEQ ID NO: 102. As shown in Table 5, all four strains were shown to have at least 98% nucleotide identity with an NCBI reference sequence.

TABLE 5

Nucleotide identity values of the 16S rRNA gene and ITS sequences of strains against NCBI reference sequences

| Species Name | 16S rRNA sequence (bacteria) or fungal ITS sequence (*P. kudriavzevii*) | Best-match by 16S rRNA gene or ITS region | % nucleotide identity between isolate sequence and reference sequence |
|---|---|---|---|
| *Lactobacillus plantarum* | SEQ ID NO: 100 | *L. plantarum* JCM 1149, ATCC 14917 | 98.91 |
| *Lactobacillus brevis* | SEQ ID NO: 94 | *L. brevis* ATCC 14869, DSM 20054 | 99.8 |
| *Leuconostoc mesenteroides* | SEQ ID NO: 93 | *Leuc. mesenteroides* DRC1506, JCM 31787 | 98.85 |
| *Pichia kudriavzevii* | SEQ ID NO: 102 | ATCC 6258 | 99.78 |

The four strains identified in Table 5 were used in the formulation of a medical food product, DMA-04. In this exemplary embodiment, DMA-04 was formulated as an orally delivered synbiotic capsule containing a mixture of the live microbial probiotic strains identified in Table 5, in combination with prebiotics (oligofructose and dried, ground blueberry powder) and inert formulation ingredients (magnesium stearate and silicon dioxide). An exemplary formulation of DMA-04 is summarized in Table 6.

TABLE 6

A Formulation of DMA-04

| Ingredient | Dose in Each Capsule (CFUs) | Daily Dose in Four Capsules (CFUs) | Ingredient in Each Capsule (mg) |
|---|---|---|---|
| *Lactobacillus brevis* | $7.5 \times 10^9$ | $3.0 \times 10^{10}$ | 10-30 |
| *Lactobacillus plantarum* | $7.5 \times 10^9$ | $3.0 \times 10^{10}$ | 10-30 |
| *Leuconostoc mesenteroides* | $7.5 \times 10^9$ | $3.0 \times 10^{10}$ | 10-30 |
| *Pichia kudriavzevii* | $1.25 \times 10^9$ | $5.0 \times 10^9$ | 60-120 |
| Oligofructose | Not applicable | Not applicable | 150-200 |
| Dried, ground blueberry powder | Not applicable | Not applicable | 150-200 |
| Magnesium stearate | Not applicable | Not applicable | 5-10 |
| Silicon dioxide | Not applicable | Not applicable | 5-10 |
| Total | $2.375 \times 10^{10}$ | $9.5 \times 10^{10}$ | 400-500 |

Manufacture of DMA-04

The manufacturing process for the four microbial strains included in DMA-04 involved bulk microbe production via fermentation. Bulk dry microbial biomass was produced according to the protocol summarized in FIG. 1. Briefly, microbial cultures were grown in liquid media via batch fermentation under controlled conditions of temperature, pH, gas flow, and agitation. The growth medium used for *L. brevis, L. plantarum*, and *L. mesenteroides* is summarized in Table 7, and the growth medium used for *P. kudriavzevii* is summarized in Table 8. The growth conditions used for each strain are summarized in Table 9. Feed parameters for *P. kudriavzevii* are summarized in Table 10. Cells were harvested by centrifugation, and supernatant was discarded. Concentrated cells were tested for cell titer and purity, and cells were subsequently resuspended in lyophilization buffer. The lyophilization buffer used for *L. brevis, L. plantarum*, and *L. mesenteroides* is summarized in Table 11, and the lyophilization buffer used for *P. kudriavzevii* is summarized in Table 12. Biomass was loaded into trays and frozen, and the frozen biomass was lyophilized under vacuum using primary and secondary drying steps. When necessary, lyophilized biomass was ground into a fine powder. The dry powdered biomass was loaded into bags, and the loaded bags were sealed and stored at 4° C. or −20° C.

TABLE 7

*L. brevis, L. plantarum*, and *L. mesenteroides* Growth Medium

| Medium Component | Concentration (g/L) |
|---|---|
| Peptone yeast | 13.0 |
| Yeast extract | 13.0 |
| D(+) Glucose | 20.0 |
| Di-Potassium hydrogen phosphate | 2.0 |
| Tween 80 | 1.0 |

TABLE 7-continued

| L. brevis, L. plantarum, and L. mesenteroides Growth Medium | |
|---|---|
| Medium Component | Concentration (g/L) |
| Sodium acetate | 0.8 |
| Magnesium sulfate | 0.1 |
| Manganese sulfate | 0.05 |
| Purified Water | Q.S. to 1 Liter |

TABLE 8

| P. kudriavzevii Growth Medium | |
|---|---|
| Medium Component | Concentration (g/L) |
| Yeast extract | 30.0 |
| Dextrose | 30.0 |
| $K_2$ $HPO_4$ | 2.0 |
| Sodium acetate | 5.0 |
| Ammonium Citrate | 2.0 |
| $MgSO_4$—$7H_2$ O | 0.2 |
| $MnSO_4$—$7H_2$ O | 0.03 |
| Antifoam 204 | 1 |

TABLE 9

Growth Conditions for DMA-04 Strains

| Parameter | *L. brevis* | *L. plantarum* | *L. mesenteroides* | *P. kudriavzevii* |
|---|---|---|---|---|
| Culture temperature | 30-37° C. | 30-37° C. | 30-37° C. | 37° C. |
| Aeration/Gas Addition | Anaerobic (mix of $CO_2$, hydrogen, and nitrogen) | Anaerobic (mix of $CO_2$, hydrogen, and nitrogen) | Anaerobic (mix of $CO_2$, hydrogen, and nitrogen) | Aerobic |
| Gas Flow Rate | 0.1 VVM | 0.1 VVM | 0.1 VVM | 0.5 VVM |
| pH | 5.5-5.9 | 5.5-5.9 | 5.5-5.9 | 5 |
| Agitation | | | | 200-1200 rpm |
| Dissolved Oxygen | | | | 25% |
| Inoculum | 0.1% | 0.1% | 0.1% | 2% |
| Harvest Time | 18 hours | 12-18 hours | 14-20 hours | 60-72 hours |

TABLE 10

Feed Parameters for *P. kudriavzevii*

| | |
|---|---|
| Fermenter Fill Level | 70% of fermenter operating volume |
| Feed Volume | 30% of fermenter operating volume |
| Feed Medium | 50% glucose |
| Feed Start Time | 10 hours after inoculation |
| Initial Feed Rate | 0.25% fermenter operating volume per hour |
| Feed Type | Linear |
| Feed Rate Increases | Double flow rate at 34 hours and at 52 hours |

TABLE 11

| L. brevis, L. plantarum, and L. mesenteroides Lyophilization Buffer | |
|---|---|
| Buffer Component | Concentration (%) |
| Oligofructose | 6.0 |
| Trehalose | 1.0 |
| Ascorbic Acid | 0.1 |
| Cell Concentrate | 92.9 |

TABLE 12

| P. kudriavzevii Lyophilization Buffer | |
|---|---|
| Buffer Component | Concentration (%) |
| Oligofructose | 5.0 |
| Sucrose | 5.0 |
| Ascorbic Acid | 0.1 |
| Cell Concentrate | 89.9 |

Powdered biomass of the individual microbial strains were manufactured and stored separately until being combined into the final product, DMA-04. Bulk biomass lots of individual strains were tested according to the methods and specifications summarized in Table 13. As shown in columns 4-7 of Table 13, all individual-strain biomass lots met the product quality specifications. The individual biomass lots were combined with prebiotics and flow aids to form DMA-04, e.g., according to the formulation specifications described in Table 6. The blended powder was packaged into size "0" capsules and filled into bottles (62 capsules per bottle). Bottles had a seal and screw cap closure. Labels were applied to bottles, and bottles were packaged into boxes for storage.

Combined DMA product lots were prepared at three dose levels: Low, Middle and High. These three product lots were tested for identity, potency and purity, as summarized in Table 14. As shown in columns 4-6 of Table 14, all product lots met the product quality specifications. Briefly, purity analyses included gross contamination tests, including visual observation of colony morphology on differential media and microscopic analyses of cell morphology. Samples were also tested for quantitation of certain heavy metals and microbial pathogens. Lastly, shotgun metagenomic DNA sequencing was used to detect genomic DNA from DMA-04 microbes and determine the presence of contaminating organisms present at levels of about 0.1-1%. As summarized in row 2 of Table 14, only the four DMA-04 microbial strains were present in the product lots, and the lots tested negative for contaminating microbes.

TABLE 13

| Analytical Specifications for Each Strain in DMA-04 | | | | | | |
|---|---|---|---|---|---|---|
| Attribute | Target Specification | Method | *L. brevis* | *L. plantarum* | *L. mesenteroides* | *P. kudravzevii* |
| Identity | Matches reference strain | 16S or ITS sequencing | Matches | Matches | Matches | Matches |
| Potency (Billion CFU) | Target titer +/− 50% | See Compendium of Methods for the Microbiological Examination of Foods, Chapter 20 | 340 | 600 | 500 | 19 |
| Water Activity (for dry biomass) | <0.30 | Water Activity meter | 0.19 | 0.08 | 0.10 | 0.14 |
| Total Aerobic Plate Count | <10,000/gram | United States Pharmacopeia (USP) Test <2021> | <100/gram | <100/gram | <100/gram | |
| Total Non-Lactic Acid Bacteria Count | <5,000/gram | International Organization for Standardization (ISO) 13559 | | | | 100 CFU/gram |
| *E. coli* | Negative/10 gram | United States Pharmacopeia (USP) Test <2022> | Negative | Negative | Negative | Negative |
| *Salmonella* sp. | Negative/10 gram | USP Test <2022> | Negative | Negative | Negative | Negative |
| *S. aureus* | Negative/10 gram | USP Test <2022> | Negative | Negative | Negative | Negative |
| Yeast/mold* | <100/gram | USP Test <2021> | <10/gram | <10/gram | <10/gram | N/A |

*Not applicable to *P. kudriavzevii*, as the strain is a yeast.

TABLE 14

| Batch Analysis of DMA-04 | | | | | |
|---|---|---|---|---|---|
| Parameter | Target Specification | Method | Result for Low Dose Lot | Result for Middle Dose Lot | Result for High Dose Lot |
| Identity | Matches reference strains | 16S rRNA gene sequencing or ITS-1 region sequencing | Matches for *L. brevis*, *L. plantarum*, *L. mesenteroides* and *P. kudriavzevii* | Matches for *L. brevis*, *L. plantarum*, *L. mesenteroides* and *P. kudriavzevii* | Matches for *L. brevis*, *L. plantarum*, *L. mesenteroides* and *P. kudriavzevii* |
| Total Lactic Acid Bacteria Potency (CFU/ml) | Low: $4.6 \times 10^9$ +/− $2.3 \times 10^9$ Mid: $2.3 \times 10^{10}$ +/− $1.1 \times 10^{10}$ High: $4.6 \times 10^{10}$ +/− $2.3 \times 10^{10}$ | Solarea SOP0013 for Microbial Enumeration | $4.82 \times 10^9$ | $2.33 \times 10^{10}$ | $4.93 \times 10^{10}$ |
| *P. kudriavzevii* Potency (CFU/ml) | Low: $2.58 \times 10^8$ +/− $1.29 \times 10^8$ Mid: $1.3 \times 10^9$ +/− $0.65 \times 10^9$ High: $2.58 \times 10^9$ +/− $1.29 \times 10^9$ | Solarea SOP0013 for Microbial Enumeration | $2.27 \times 10^8$ | $1.44 \times 10^9$ | $2.67 \times 10^9$ |
| *E. coli* | Negative/10 gram | USP Test <2022> | Negative | Negative | Negative |
| *Salmonella* sp. | Negative/10 gram | USP Test <2022> | Negative | Negative | Negative |
| *S. aureus* | Negative/10 gram | USP Test <2022> | Negative | Negative | Negative |
| Arsenic | <1 ppm | AOAC Official Methods 2011.19 & 993.14 | <140 ppb | <140 ppb | <140 ppb |
| Cadmium | <1 ppm | AOAC Official Methods 2011.19 & 993.14 | <70 ppb | <70 ppb | <70 ppb |
| Lead | <1 ppm | AOAC Official Methods 2011.19 & 993.14 | <70 ppb | <70 ppb | <70 ppb |
| Mercury | <1 ppm | AOAC Official Methods 2011.19 & 993.14 | <70 ppb | <70 ppb | <70 ppb |

Example 2: Synergistic Acetate Production by Defined Microbial Assemblages

This example describes an in vitro analysis evaluating the ability of defined microbial assemblages to produce acetate as compared to monocultures of the individual strains.

The four constituent strains of the DMA DMA-04 were evaluated for their ability to produce short chain fatty acids (SCFAs) as monocultures versus their ability to produce SCFAs when combined into a single culture. Cryostocks of the four constituent DMA-04 strains described in Table 5 (*L. brevis*: SBS4254; *P. kudriavzevii*: SBS4263; *L. mesenteroides*: SBS4255; and *L. plantarum*: SBS4260) were prepared by individually growing each strain in DeMan-Rogosa-Sharpe broth (MRS) or in Potato dextrose broth (PDB). Cells were collected, washed with phospho-buffered saline (PBS), resuspended in fresh media containing either 10% DMSO or 18% glycerol, and frozen. The concentration of viable CFUs in each frozen cryostock was determined by dilution plating.

Figure 2:
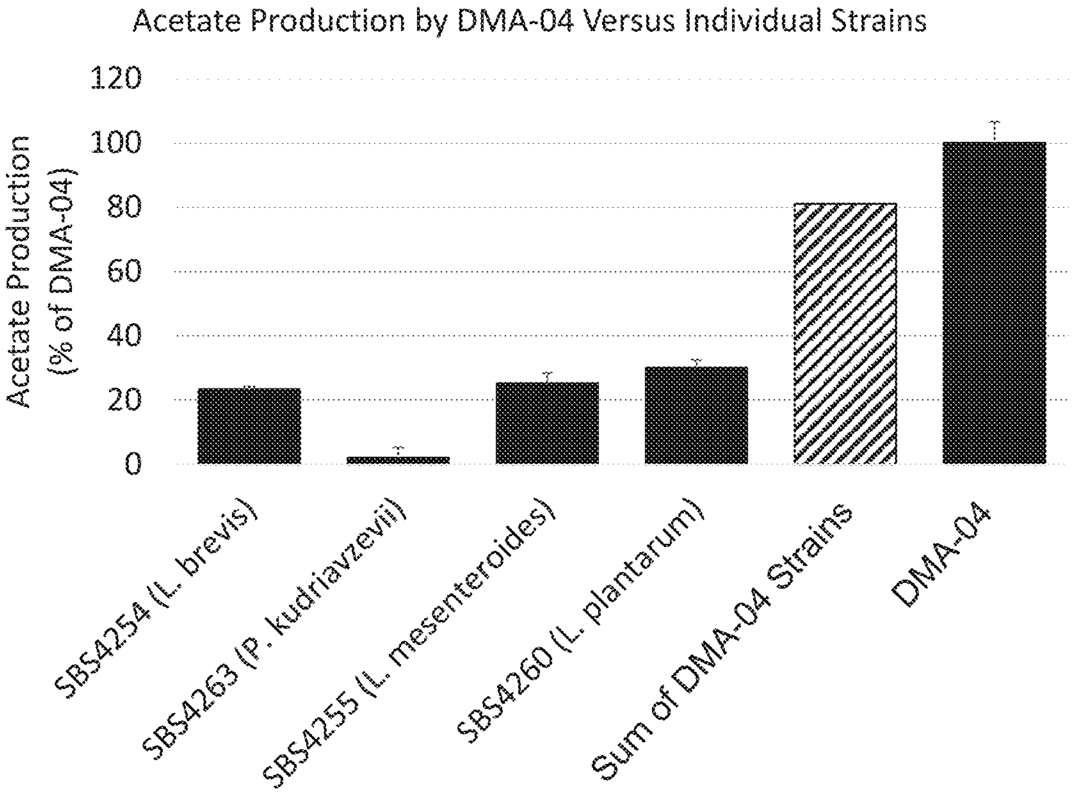
FIG. 2 are graphs summarizing acetate production by four microbial strains, either individually or in combination. DMA-04 constituent strains (SBS4254, SBS4263, SBS4255, and SBS4260) were used to inoculate medium containing blueberry powder and oligofructose, and supernatant acetate levels were quantified by gas chromatography after a 24-hour incubation period. Strains were tested either individually or in a combination ("DMA-04"). Acetate levels were quantified as a percentage of the combination treatment. The sum of the mean acetate levels produced by individual strains is illustrated as a striped bar ("Sum of DMA-04 Strains"). Data represent mean±SD; n=2.

Each cryostock was defrosted, and cells were collected and washed with PBS. Washed cells were used to inoculate culture medium containing blueberry powder and oligofructose. Washed cells from each cryostock were used to inoculate separate cultures at a concentration of $2.5 \times 10^6$ CFU/ml. For the "DMA-04" treatment, the culture medium was inoculated with $2.5 \times 10^6$ CFU/ml of each of the four strains, for a total combined concentration of $1 \times 10^7$ CFU/ml. The cultures were incubated anaerobically for 24 hours. Following the 24-hour incubation, cells from each culture were pelleted by centrifugation at 5000×g for 10 minutes, and culture supernatants were harvested for analysis. Final microbial titers were determined by dilution plating. Supernatant samples were acidified, and valeric acid was added as an internal control. Supernatant SCFAs were quantified by gas chromatography relative to a free fatty acid control (Restek). Acetate produced by the individual monocultures was quantified relative to acetate produced by the combined four-strain culture (FIG. 2). As shown in FIG. 2, the combination of the four individual DMA-04 strains into a single culture resulted in a synergistic improvement in acetate production.

Figure 3:
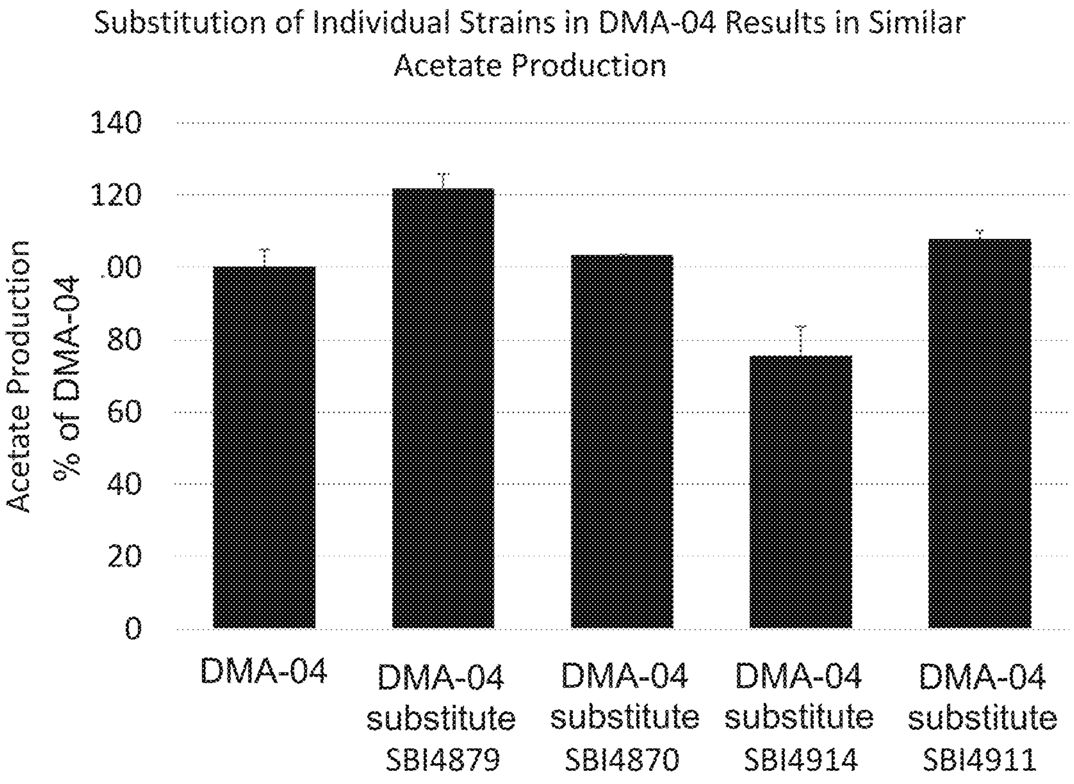
FIG. 3 are graphs summarizing acetate production by mixed cultures inoculated with four strains of microbes. Each culture was inoculated with three of the four constituent strains of DMA-04; the remaining DMA-04 strain was substituted with a different strain of the same species (either *L. brevis* SBI4879, *P. kudriavzevii* SBI4870, *L. mesenteroides* SBI4914, or *L. plantarum* SBI4911). A mixed culture containing all four constituent strains of DMA-04 was used as a control. Strains were used to inoculate medium containing blueberry powder and oligofructose, and supernatant acetate levels were quantified by gas chromatography after a 24-hour incubation period. Acetate levels of the "substitute" cultures were quantified as a percentage of the DMA-04 4-strain control culture. Data represent mean±SD; n=2.

In order to confirm that the effects of DMA-04 are independent of the specific strains of species comprising DMA-04, four variants of the DMA-04 DMA were generated, wherein one of the four DMA-04 strains was substituted for a different microbial isolate of the same species: *L. brevis* SBS4254 was substituted for *L. brevis* SBI4879, *P. kudriavzevii* SBS4263 was substituted for *P. kudravzevii* SBI4870, *L. mesenteroides* SBS4255 was substituted for *L. mesenteroides* SBI4914, and *L. plantarum* SBS4260 was substituted for *L. plantarum* SBI4911. Each of the variants of DMA-04 were generated and tested for their ability to produce acetate according to the protocol described hereinabove. Acetate produced by each of the DMA-04 variant DMAs was quantified relative to acetate produced by DMA-04 (FIG. 3). As shown in FIG. 3, substituting any one of the DMA-04 microbial strains for a different strain of the same species resulted in a DMA which exhibited a similar level of acetate production as DMA-04, confirming that the effects of DMA-04 are independent of the specific strain.

Example 3: Neurotransmitter Production by a Defined Microbial Assemblage

This example describes an in vitro analysis evaluating the ability of a defined microbial assemblage to produce neurotransmitters.

The ovarian hormones estrogen and progesterone influence neurotransmitters including gamma-aminobutyric acid (GABA), serotonin, and dopamine, impacting production and receptor expression. At perimenopause, the levels of these hormones decline as do their positive effects on neurotransmitters, resulting in degradations in cognition and mood. Microbes including bacteria and fungi are known to produce neurotransmitters such as GABA, melatonin, serotonin, and dopamine.

Microbially produced neurotransmitters including serotonin, melatonin, GABA, and dopamine are understood to affect host physiology and immunity through various mechanisms. Serotonin is synthesized from tryptophan (Trp) through a two-stage enzymatic reaction involving Trp hydroxylase and aromatic amino acid decarboxylase. In humans, approximately 90% of serotonin is produced by the enterochromaffin cells of the GI tract where it is understood to promote intestinal peristalsis In an anti-inflammatory role, serotonin has also previously been shown to induce T-cell differentiation into Tregs. Th17 cells are an inflammatory T-cell that secrete IL-17 and have been implicated in autoinflammatory diseases including but not limited rheumatoid arthritis. (Further, serotonin has previously been shown to reduce the production of IL-17 from Th17 cells and increase the production of IL-10 from Tregs, promoting an anti-inflammatory environment.) Melatonin is synthesized from serotonin in a two-step process. Melatonin's primary function is understood to be the regulation of circadian rhythm, but the compound has pleiotropic effects on the body. Potent anti-inflammatory effects of melatonin have previously been identified, including free radical scavenging and inhibition of inflammasome activation. Melatonin is also understood to play a role in the maintenance of bone, increasing bone regeneration and decreasing bone resorption. Several animal studies modeling osteoporosis have demonstrated the positive effects of melatonin supplementation on bone density. GABA is an inhibitory neurotransmitter in the central nervous system and exerts important functions in the immune system. GABA has previously been shown to decrease macrophage mediated inflammation and induce the production of Tregs. GABA has also previously been shown to decrease IL-1β mediated inflammation and increase production of tight junctions in epithelial cells, improving intestinal barrier function. Dopamine, a catecholamine, is abundantly present within the human intestinal tract in part due to microbial production. The bacterium *Enterococcus faecalis* has previously been shown to produce the neurotransmitter dopamine from the metabolite, L-3,4 dihydroxyphenylalanine (L-dopa). Furthermore, dopamine is recognized as a potent immunomodulatory compound. Dopamine is understood to reduce systemic inflammation through inhibition of the NLRP3 inflammasome, a proinflammatory signaling cascade, associated with robust secretion of proinflammatory mediators. Dopamine was also previously found to reduce neutrophil mediated reactive oxygen species production, and even inhibit neutrophil activation by the highly potent activator N-formyl-methionyl-leucyl-phenylalanine. Additionally, treatment with dopamine receptor agonists has previously been shown to reduce the levels of the pro-inflammatory cytokines IL-6 and IL-8 in serum.

Microbes and/or DMAs are evaluated for production of one or more neurotransmitters, including serotonin, melatonin, GABA, dopamine, or a combination thereof, using any appropriate method known in the art including, e.g., by quantifying amounts of one or more neurotransmitters in microbially-conditioned supernatant via ELISA. Alternatively, high performance liquid chromatography (HPLC) is used to quantify neurotransmitter production by potentially therapeutic microbes.

The four constituent strains of the DMA DMA-04 were evaluated for their ability to produce GABA and serotonin in vitro as monocultures versus their ability to produce SCFAs when combined into a single culture. Briefly, individual microbial strains were grown for 24-48 hours to achieve a high OD in brain heart infusion (BHI) or tryptic soy broth (TSB) for bacteria and potato dextrose broth (PDB) for yeast. Cultures were normalized by OD600 to achieve a uniform density and inoculated (10% final volume) into TSB containing 0.1% added tryptophan and grown for 48 hours. Culture supernatants were removed and analyzed by ELISA for GABA production (LS Bio) or serotonin production (ENZO) following the manufacturers' protocols. As summarized in Table 15, DMA-04 and its constituent strains were capable of producing GABA and serotonin.

TABLE 15

Production of Neurotransmitters by DMA-04 and Constituent Strains

| Strain or DMA | Genus and Species | GABA (pg/mL) | Serotonin (pg/mL) |
|---|---|---|---|
| SBS4254 | *Lactobacillus brevis* | 1.51 | 6.86 |
| SBS4260 | *Lactobacillus plantarum* | 1.84 | 5.70 |
| SBS4255 | *Leuconostoc mesenteroides* | 1.58 | 5.59 |
| SBS4263 | *Pichia kudriavzevii* | 1.56 | 3.60 |
| DMA-04 | Not applicable | 2.14 | 6.88 |

Example 4: A Defined Microbial Assemblage Protects Against Bone Loss in a Mouse Model of Osteoporosis This example describes a mouse study to evaluate the ability of a Defined Microbial Assemblage to protect against an ovariectomy-induced decrease in Bone Mineral Density in a mouse model of osteoporosis.

Figure 4:
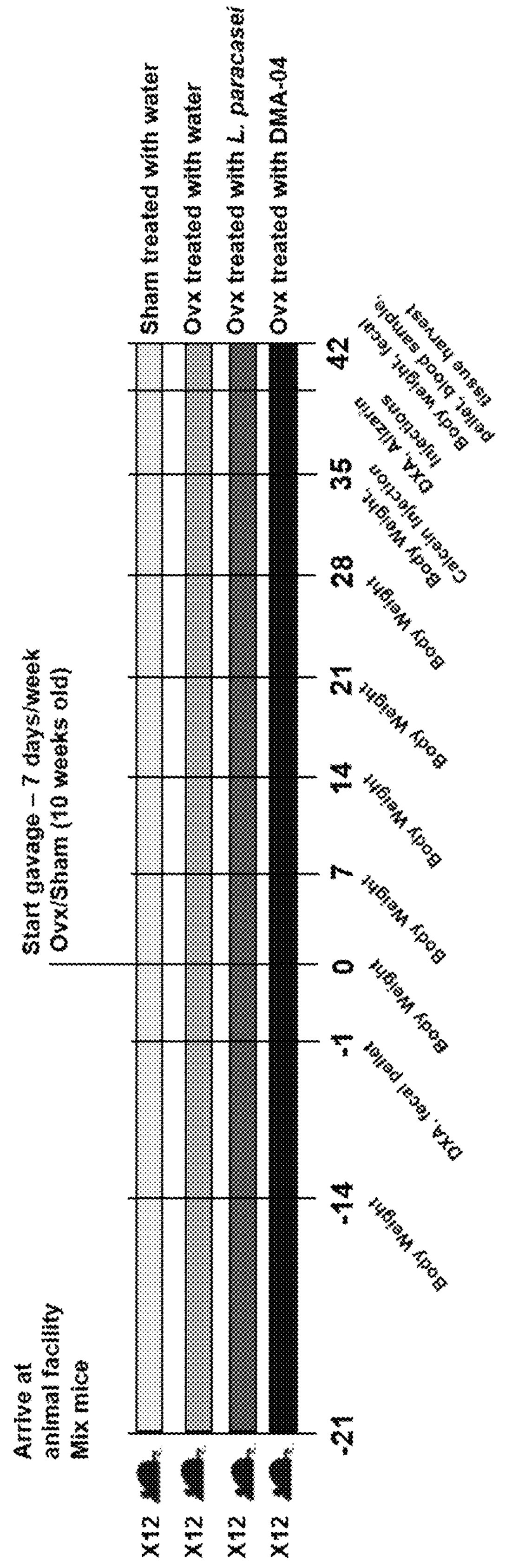
FIG. 4 is a diagram summarizing the experimental protocol described in Example 4, which was used to analyze the protective effect of a Defined Microbial Assemblage against ovariectomy-induced bone loss in mice.

The ability of the DMA DMA-04 to protect against an ovariectomy-induced decrease in BMD in a mouse model of in a murine estrogen withdrawal model of osteoporosis was evaluated using the protocol summarized in FIG. 4. Briefly, 48 7-week-old female C57BL/6J mice (12 mice per treatment group; Jackson Laboratories) were transferred to a quarantine facility and acclimated to a new diet (Irradiated Teklad Diet 2016; Envigo) for 3 weeks. For the final 2 weeks of the 3-week acclimation period, the subjects' bedding was mixed in order to normalize subject microbiomes. One day or two days prior to the end of the acclimation period ("Day −1" or "Day −2"), fecal samples were collected and a DXA scan was performed to obtain a baseline BMD measurement. At the end of the 3-week acclimation period ("Day 0"), ovariectomy surgery was performed on the mice in three of the four treatment groups. Mice in the remaining treatment group were sham-treated as a control. Beginning on Day 0 and every day for 42 days thereafter, the ovariectomized mice were treated with either (1) DMA-04, (2) a single strain of *Lactobacillus paracasei* (representing an established probiotic), or (3) water as a negative control. The non-ovariectomized, sham-treated mice were likewise treated with water. Mice were injected with calcine on Day 33 (9 days prior to termination of the study), and mice were injected with alizarin on Day 40 (2 days prior to termination of the study). Body weights were recorded weekly beginning on Day 0. A second DXA scan was completed and a second fecal sample was collected 6 weeks after Day 0.

Figure 5A:
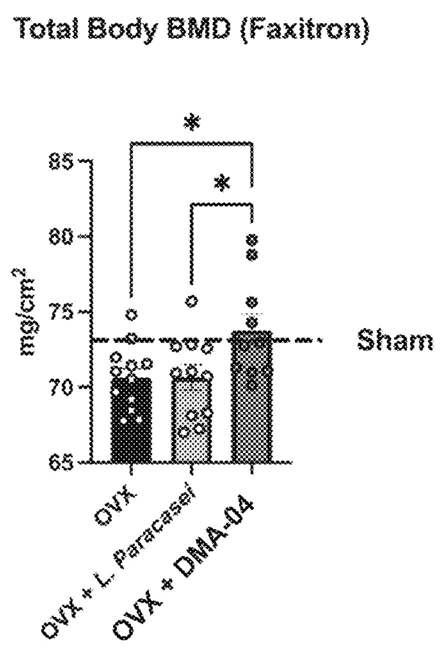
FIG. 5A-5D is a graph depicting the ability of DMA-04 or *Lactobacillus paracasei* to protect against an ovariectomy- (OVX-)induced decrease in bone mineral density (BMD) in a murine estrogen withdrawal model of osteoporosis. OVX mice were treated with *L. paracasei* or DMA-04 by oral gavage. Sham-treated (non-OVX) mice and OVX-mice treated with water and were used as controls. BMD was measured 42 days post-OVX and was quantified relative to the BMD of sham-treated mice. Data represent mean+/−SEM. n=12 per treatment. Significant differences between groups were identified by one-way ANOVA with Tukey multiple comparison tests (* $P<0.05$).
Figure 5B:
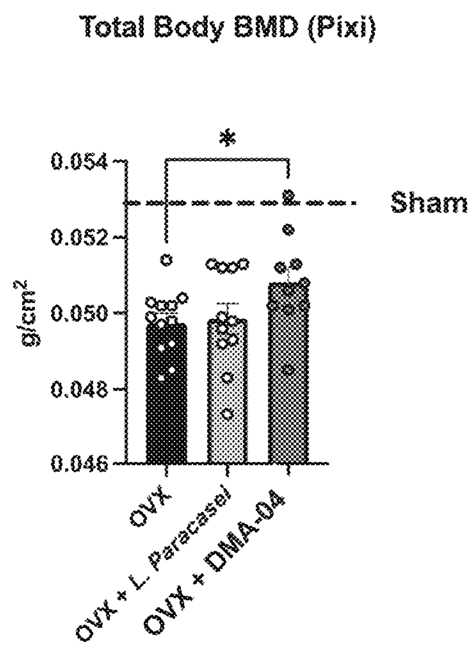
Figure 5C:
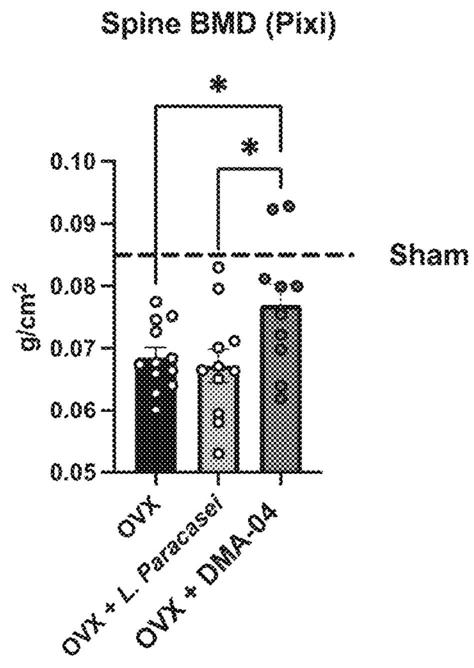
Figure 5D:
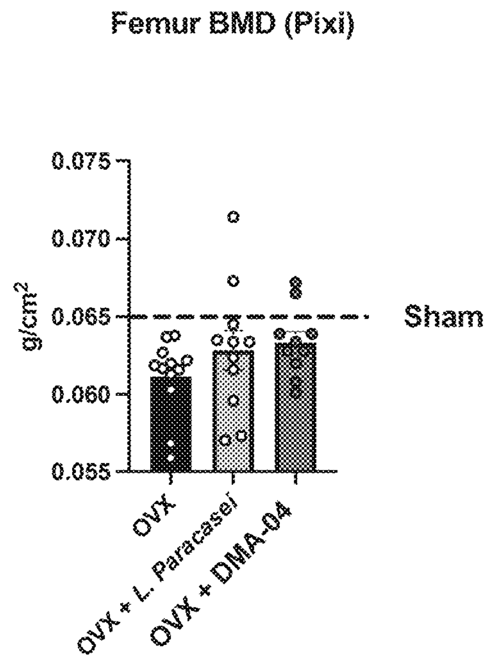

As shown in FIG. 5A-5B, treatment with the DMA DMA-04 was protective against an ovariectomy-induced loss in total body BMD, as measured by either a Faxitron DXA scan (FIG. 5A) or a Pixi DXA scan (FIG. 5B). By contrast, treatment with *L. paracasei*, a microbe which is commonly used as a probiotic, was not found to protect against a decrease in total body BMD. Treatment with DMA-04, but not *L. paracasei*, was likewise found to protect against an ovariectomy-induced decrease in spine BMD (FIG. SC). These results confirm that DMA-04 protects from bone loss in subjects with reduced estrogen levels and indicate that DMA-04 can be used to prevent bone loss in menopausal subjects.

Example 5: Food Trial to Evaluate Microbiome Changes Following Administration of a Defined Microbial Assemblage This example describes a randomized, double-blind, placebo-controlled, parallel-arm food trial which demonstrates the successful engraftment of microbial strains into a human subject following administration of a DMA.

A group of 32 participants (adult men and women aged 18-70 years, with a Body Mass Index (BMI) between 18.5 and 35 kg/m$^2$, with systolic blood pressure≤155 mm Hg, and with diastolic blood pressure≤95 mm Hg) was randomly divided into a placebo group and a treatment group. Sex was used as a stratification variable to ensure that sex was evenly distributed between groups. Trial participants, investigators, and all study staff involved in data collection were masked to participants' randomization assignments. Each participant in the treatment group was provided with 56 capsules containing the medical food synbiotic DMA DMA-04, which was manufactured, stored, and packaged as described in Example 1. The placebo group was provided with 56 capsules, each containing 500 mg of maltodextrin. All study products were identical in packaging and had the same appearance, taste, and texture. Participants consumed 2 capsules per day for 28 days, one with breakfast and one with dinner. Stool samples were collected for analysis immediately prior to beginning the study (Day 0), at the conclusion of the dosing period (Day 28), and an additional 28 days after the final dose (Day 56).

Gut microbiome composition was monitored by shotgun metagenomic analyses of stool samples collected on Day 0, Day 28, and Day 56. DNA was extracted from samples using the DNeasy 96 PowerSoil Pro QIAcube HT Kit (Qiagen 47021) according to manufacturer's instructions with a modification in the initial processing step on the QIAcube HT DNA extraction system (Qiagen 9001793). Mechanical lysis was performed with the PowerBead Pro beads (Qiagen 19311). Extracted DNA was quantitated using a high sensitivity dsDNA fluorometric assay (QuantIT, ThermoFisher, Q33120).

DNA libraries were generated using the Illumina DNA Prep (M) Tagmentation Kit (Illumina, 20018705) with IDT for Illumina DNA UD Index Sets A-D (Illumina 20027213-16) following manufacturer's instructions. Library quality was assessed by measuring DNA concentration using the high sensitivity dsDNA fluorometric assay (QuantIT, ThermoFisher, Q33120) and gel analysis. Individual libraries were pooled in equimolar amounts to create a sequencing pool. The pooled library was sequenced on the Illumina NovaSeq6000 using v1.5 300 bp PE sequencing reagents.

DNA libraries were sequenced to a target 5 Gbp per sample with a minimum of 2 Gbp. Sequencing quality was assessed by Illumina sequencing metrics.

Quality control of raw reads was performed using the SolexaQA++ package. Reads less than 50 bps and with a Phred quality score of less than 20 were discarded. Host sequencing reads were removed using Bowtie2 v 2.4.2. Nonpareil v3.0 was used to estimate the average coverage for each sequenced library. Taxonomic classification of metagenomic samples was performed using MetaPhlan3. Taxon relative abundances were calculated based on marker genes in a specific clade at different classification levels (species, genus, family). ITS coverage of *P. kudravzevii* in the metagenomes was calculated by mapping the metagenomics reads to the ITS sequence (coverage (X)=number of mapped reads*read length/ITS length). Functional profile was characterized using HUMAnN3 with default parameters and reference pathways databases including UniRef, KEGG, UniPathway, and MetaCyc.

Figure 6:
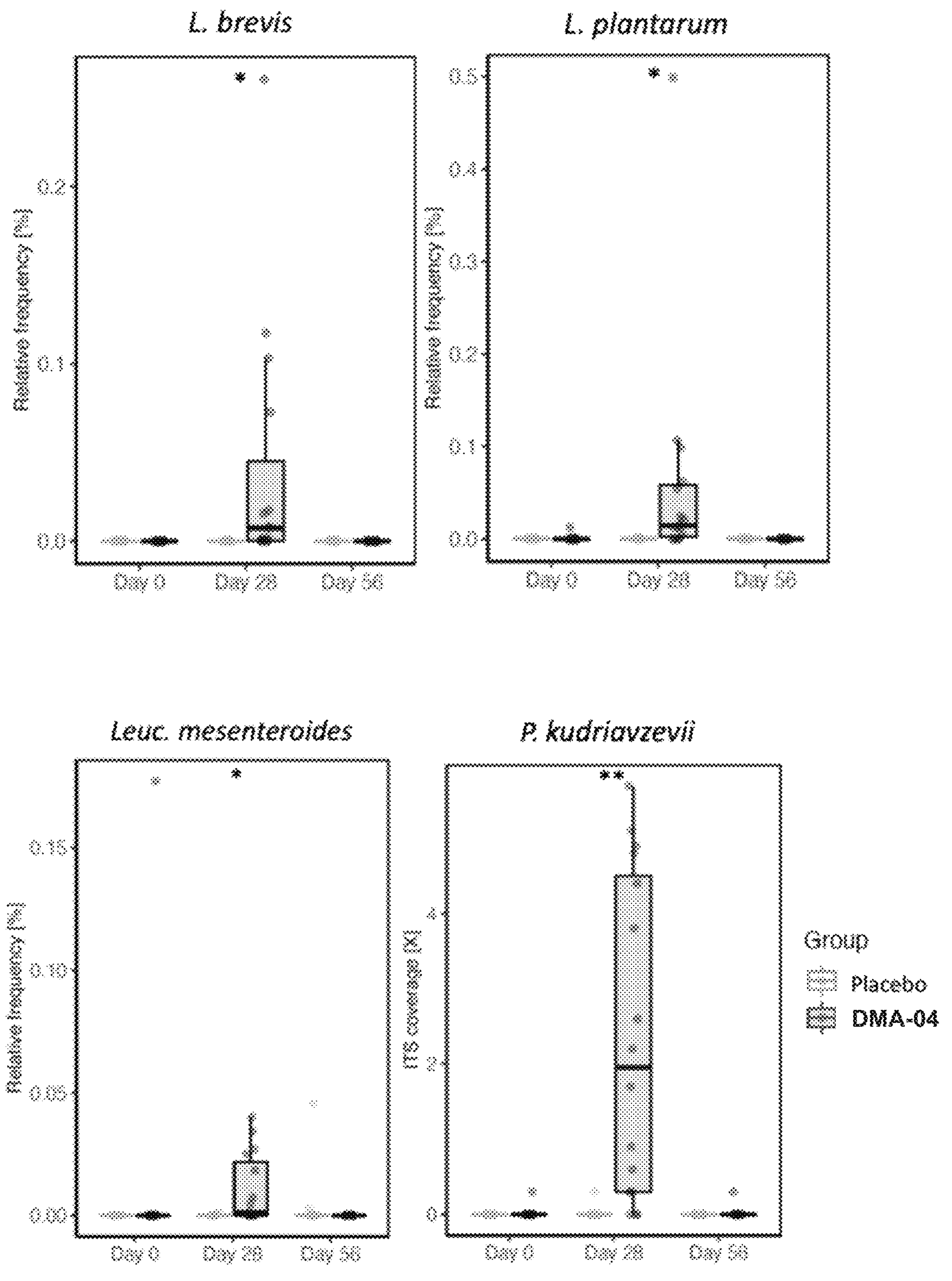
FIG. 6 summarizes detection of DMA-04 strains in the gut microbiome of participants prior to treatment with DMA-04 or a placebo ("Day 0"), after 28 days of twice-daily administration of DMA-04 or a placebo ("Day 28"), and after a 28-day washout period of non-administration of DMA-04 or the placebo ("Day 56"). Participant stool samples were obtained at the indicated timepoints, and the relative abundance of the indicated strain was determined by metagenomic sequencing. Statistical significance of differences in relative abundance of the bacterial strains between DMA-04 and placebo treatments was evaluated at each time point using an LDA Effect Size (LefSe) analysis, and an LDA score of ≥2.0 was considered significant (* $P<0.05$). Mann-Whitney test was used to compare the ITS coverage of *P. kudriavzevii* between DMA-04 and placebo treatments at each time point (** $P<0.01$). Boxes represent medians and upper and lower quartiles. Whiskers represent minimum and maximum values.

As shown in FIG. 6, DMA-04 strains were not detected in the treatment group participants or in the placebo group participants prior to administration of the test article ("Day 0"), with the exception of one participant with *L. plantarum*, one participant with *L. mesenteroides*, and one participant with *P. kudriavzevii*. All four DMA-04 strains increased variably in abundance after 28 days of administration of the DMA. Following a 28-day washout period (Day 56), all four strains decreased in abundance and were not detectable in any participants in the treatment group.

Figure 7A:
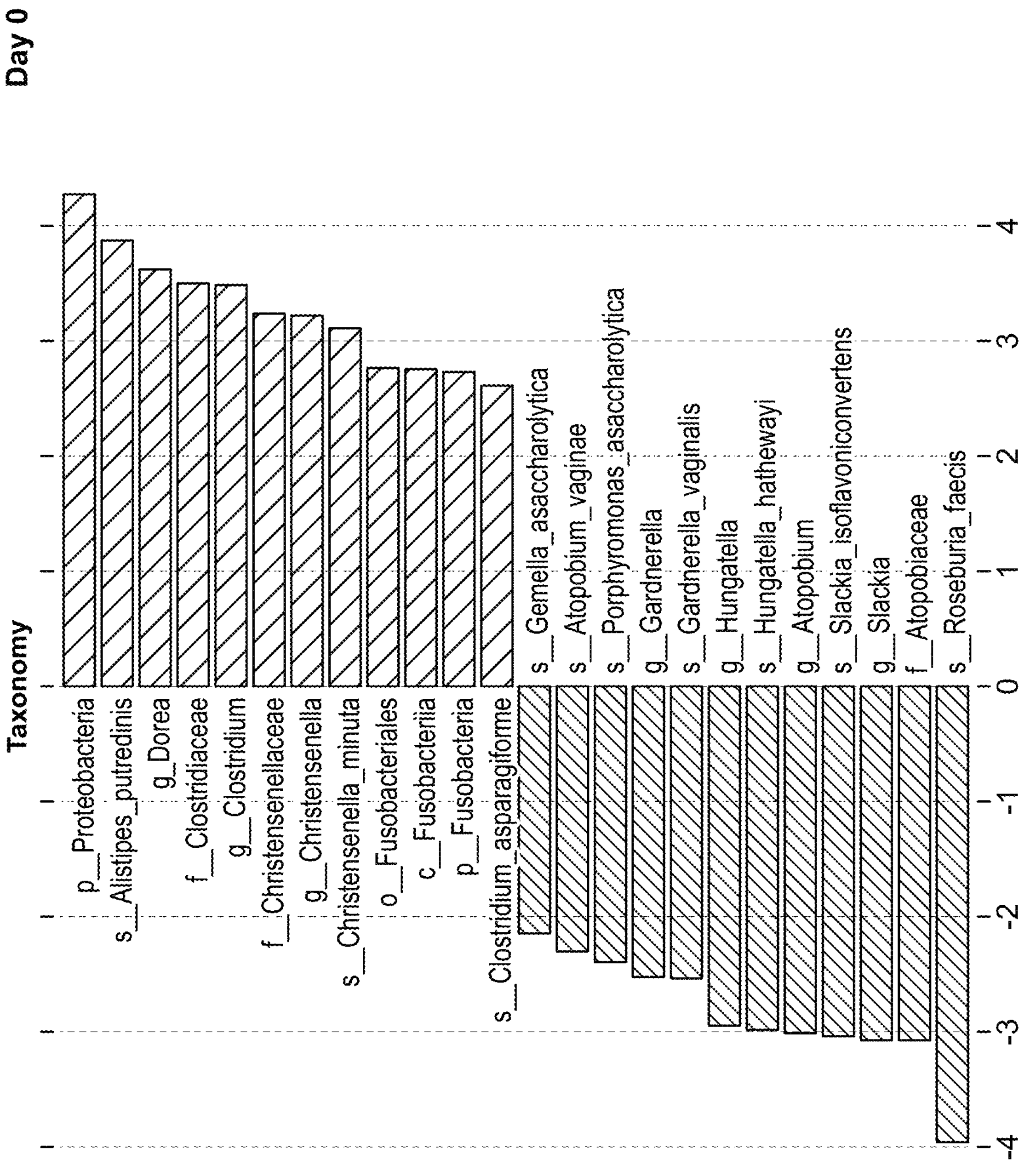
FIG. 7A-7B summarize differences in microbial taxa and metabolic pathways in subject gut microbiomes before (FIG. 7A) and after (FIG. 7B) 28 days of twice-daily administration of DMA-04 or a placebo. Participant stool samples were collected at the indicated timepoints and analyzed via metagenomic sequencing. Microbial taxa and metabolic pathways with differential abundance between placebo and DMA-04 treatment groups were determined by LDA Effect Size (LefSe) analysis ($p<0.05$ and LDA score≥2.0). The LDA score corresponds to the degree of difference in the magnitude of relative abundances of taxa and pathways that differ between the two groups.
Figure 7A:
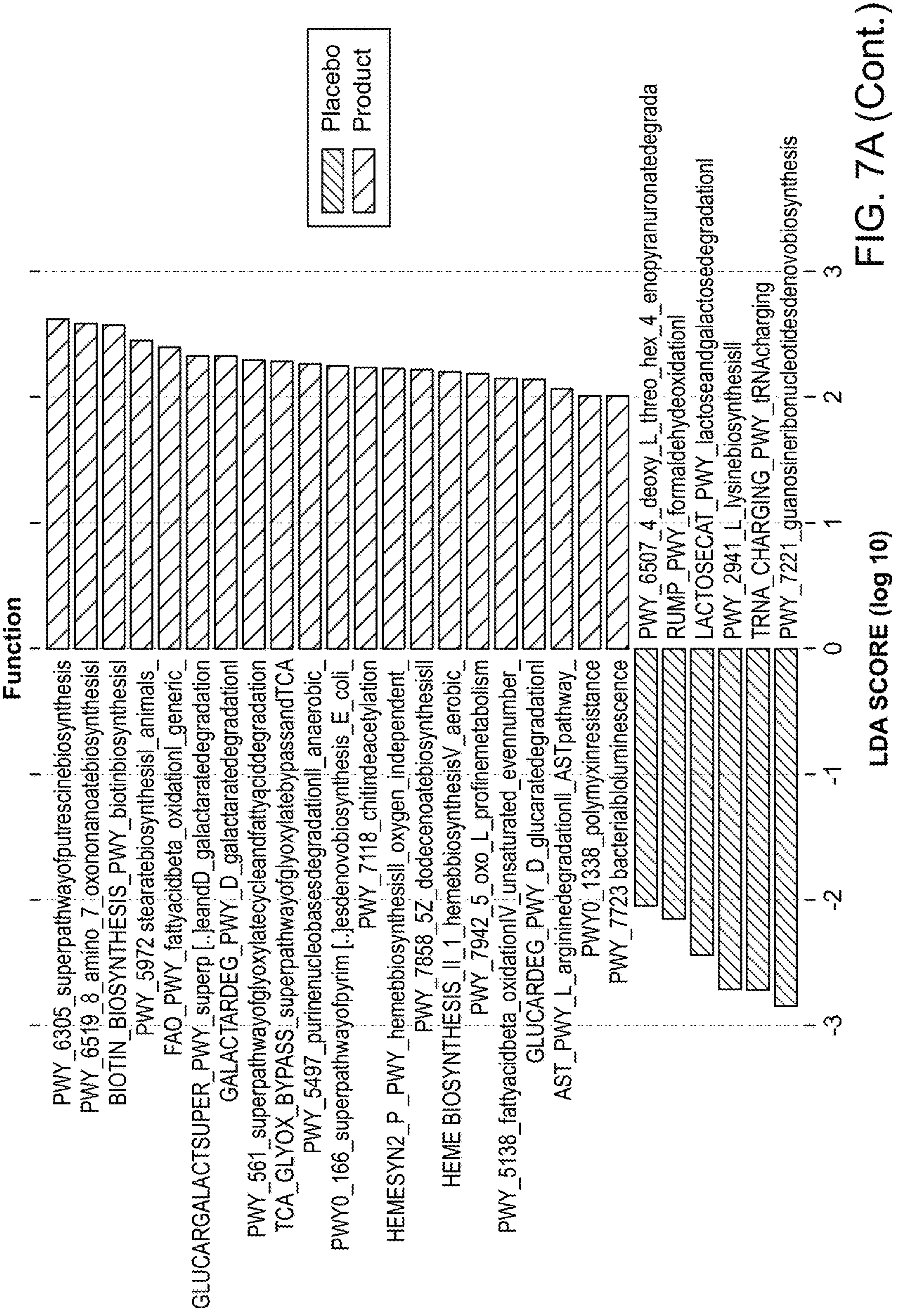
Figure 7B:
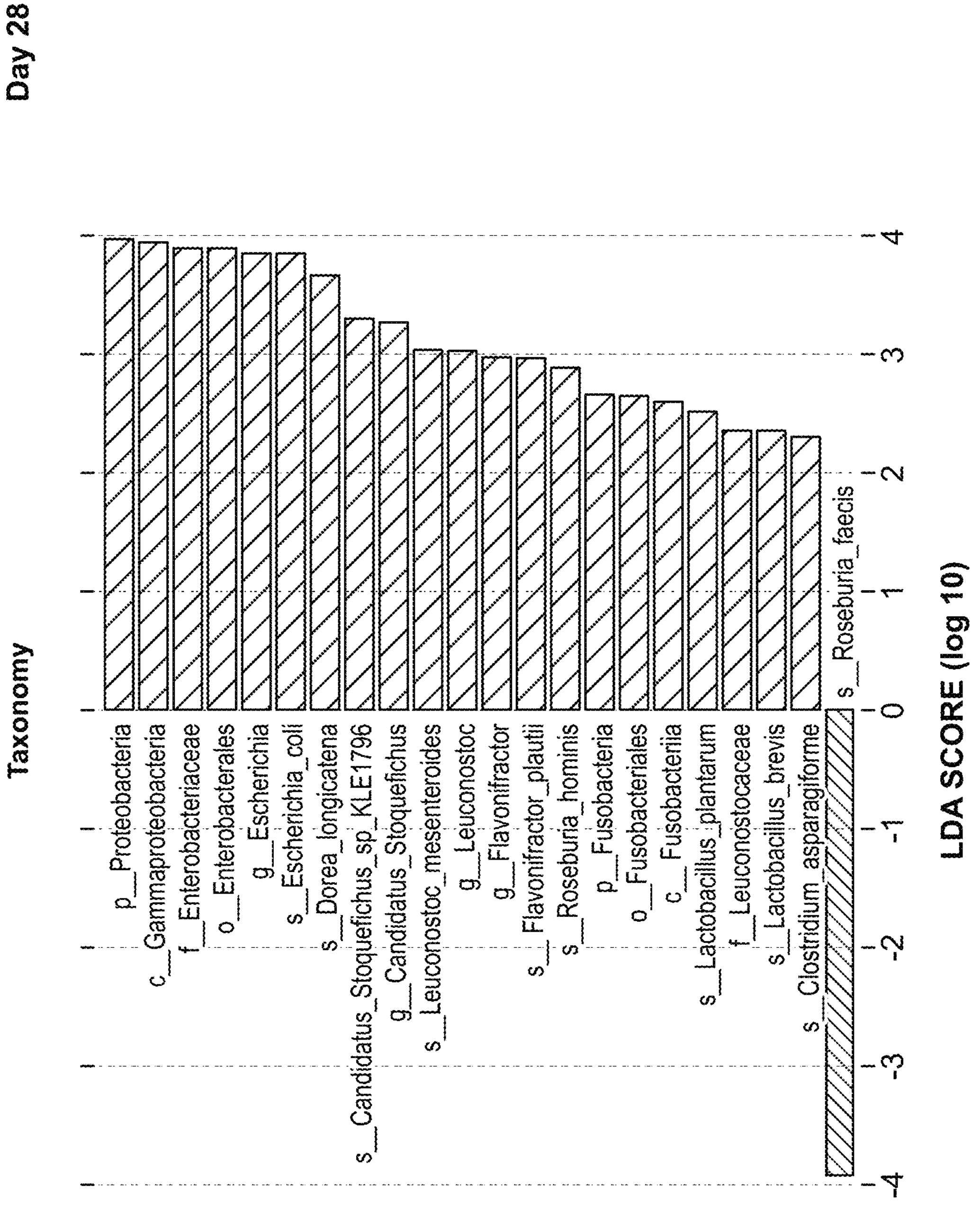
Figure 8:
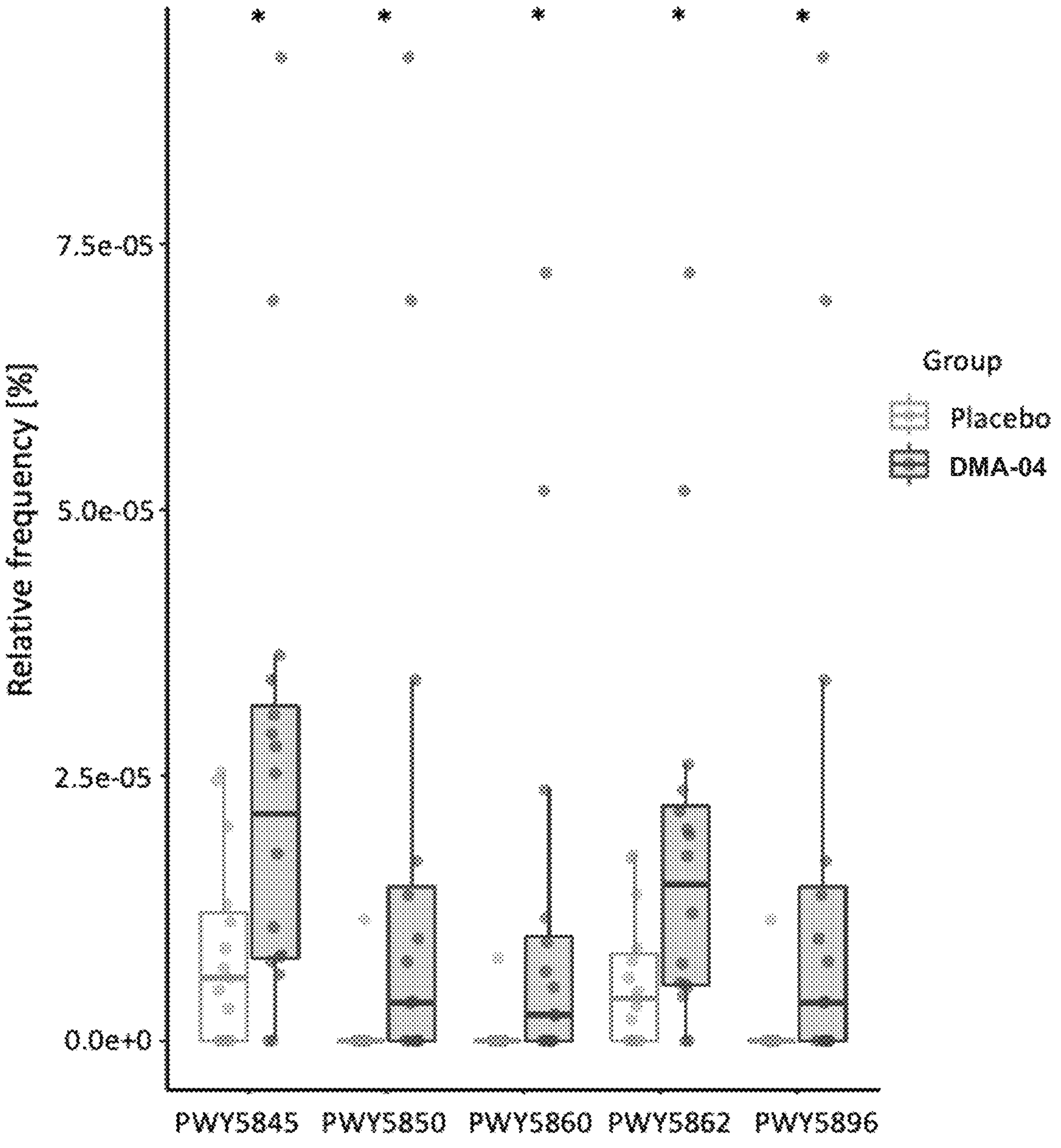
FIG. 8 summarizes differences in metabolic pathways associated with vitamin K biosynthesis in subject gut microbiomes after 28 days of twice-daily administration of DMA-04 or a placebo. Participant stool samples were collected on Day 28 and analyzed via metagenomic sequencing. Metabolic pathways with differential abundance between treatment groups at Day 28 were determined by LefSe analysis ($p<0.05$ and LDA score≥2.0). PWY-5845: superpathway of menaquinol-9 biosynthesis; PWY-5850: superpathway of menaquinol-6 biosynthesis; PWY-5860: superpathway of demethylmenaquinol-6 biosynthesis I; PWY-5862: superpathway of demethylmenaquinol-9 biosynthesis; PWY-5896: superpathway of menaquinol-10 biosynthesis. Boxes represent medians and upper and lower quartiles. Whiskers represent minimum and maximum values.

Linear Displacement Effect Size Analysis (LDA) was used to analyze changes in the abundance of microbial taxa and metabolic pathway genes between placebo and DMA-04 groups at different time points. On Day 0, 21 metabolic pathways were more abundant in the DMA-04 group than in the placebo group, and 6 metabolic pathways were more abundant in the placebo group than in the DMA-04 group (FIG. 7A). After 28 days of test product administration, 29 pathways were more abundant in the DMA-04 group, and 9 pathways were more abundant in the placebo group (FIG. 7B). In particular, pathways related to menaquinone (vitamin K2) production (super pathways of menaquinol-6, -9, and -10) were found to increase in abundance in the treatment group relative to the placebo group following administration of DMA-04 (FIG. 8). These data indicate that DMA-04 strains are able to pass through the intestinal tract and be identified in stool. These data also indicate that DMA-04 can provide relevant and potentially bone-protective functionalities, such as enhanced vitamin K2 production.

Example 6: Clinical Study of a Defined Microbial Assemblage for the Management of the Metabolic Processes of Osteopenia and Symptoms of Menopause This example describes a Phase 2/3 randomized, double blind, placebo-controlled food trial evaluating the efficacy of a Defined Microbial Assemblage (DMA) versus a placebo for the clinical dietary management of the metabolic processes of osteopenia and of symptoms of menopause.

Background

The human gut microbiome harbors a diverse set of microbial species that have coevolved with humans over millions of years. The composition of this ecosystem depends on both intrinsic and extrinsic factors, including host genetics and diet. The microorganisms inhabiting the gut benefit the host play a large role in shaping the immune system and play a large role in growth and development. However, alterations to the normal microbial flora have been implicated in various pathologies, including but not limited to allergic asthma, obesity, type 2 diabetes, osteoporosis, and Parkinson's disease. To manage these conditions, the use of health promoting probiotic microbes (live strains of bacteria and fungi that are orally administered and function along the gastrointestinal tract) and prebiotic dietary fibers (indigestible dietary fibers that specific commensal bacteria consume for fuel and metabolize into beneficial biproducts) have been described. Over the past decade, it has been increasingly appreciated that the gut microbiome has an important role in skeletal homeostasis.

The hormonal changes that occur during menopause, namely, reduction in estrogen, may affect bone density and vasomotor, and other physical, psychosocial, and sexual related symptoms. An approach that has shown promising results in the management of postmenopausal osteoporosis is the use of probiotics to maintain bone mass in postmenopausal women. Without wishing to be bound by theory, probiotics may increase the production of short chain fatty acid (SCFA) butyrate in the colon, leading to increased differentiation and proliferation of T-regulatory cells (Tregs). Tregs may affect the skeleton in several ways: (1) mitigating Th17-induced inflammation and osteoclastogenesis leading to decreased bone resorption and (2) Wnt10b-induced osteoblastogenesis leading to increased bone formation.

SCFAs present an intriguing therapeutic target, as they have been identified as anti-inflammatory mediators, decreasing inflammation via transcriptional regulation and immune cell activation. This is particularly relevant as postmenopausal osteoporosis has been identified as an inflammatory condition. In mice, ovariectomy (OVX) leads to decreased prevalence of beneficial commensal microbes in the gut microbiota, allowing other pathogenic bacteria to thrive. These alterations decrease intestinal barrier integrity, allowing intestinal microbes to penetrate the intestinal epithelium and lead to immune cell activation and endotoxemia, culminating in the systemic inflammation that leads to bone resorption. Estrogen deficiency promotes expansion and activation of effector T-cells including Th17 with an ensuing upregulation of osteoclastogenic factors such as TNF, IL-17, IFNγ, and RANKL, leading to a period of rapid bone resorption. In germ free mice, sex steroid deficiency does not stimulate T-cell expansion or TNF production in either the bone marrow or gut epithelium. Therefore, the microbiome is required for OVX-induced bone loss via expansion and activation of effector T-cell populations.

Investigational Product and Placebo

DMA-04 is an orally delivered capsule containing a mixture of live microbial probiotic strains (a DMA containing *Lactobacillus plantarum, Lactobacillus brevis, Leuconostoc mesenteroides*, and *Pichia kudriavzevii*) with natural prebiotics and inert formulation ingredients. DMA-04 is manufactured and prepared according to the methods described in Example 1. The formulation of the investigational product DMA-04 as used in this Example is described in Table 16.

TABLE 16

| An Exemplary Formulation of Investigational Product DMA-04 | | | |
|---|---|---|---|
| Ingredient | Dose in Each Capsule (CFUs) | Daily Dose in Two Capsules (CFUs) | Ingredient in Each Capsule (mg) |
| *Lactobacillus brevis* | $1.5 \times 10^{10}$ | $3.0 \times 10^{10}$ | 25-50 |
| *Lactobacillus plantarum* | $1.5 \times 10^{10}$ | $3.0 \times 10^{10}$ | 25-50 |
| *Leuconostoc mesenteroides* | $1.5 \times 10^{10}$ | $3.0 \times 10^{10}$ | 25-50 |
| *Pichia kudriavzevii* | $2.5 \times 10^{9}$ | $5.0 \times 10^{9}$ | 100-200 |
| Oligofructose | Not applicable | Not applicable | 150-200 |
| Dried, ground blueberry powder | Not applicable | Not applicable | 150-200 |
| Magnesium stearate | Not applicable | Not applicable | 5-10 |
| Silicon dioxide | Not applicable | Not applicable | 5-10 |
| Total | $4.75 \times 10^{10}$ | $9.5 \times 10^{10}$ | 500-600 |

Briefly, bulk microbe probiotics are manufactured at multiple sites, and individual lots are blended together with prebiotic fibers, encapsulated, and packaged in high-density polyethylene (HDPE) bottles and caps with a desiccant sleeve and oxygen absorber. Product bottles are stored under refrigerated conditions prior to administration.

A placebo for use in the study consists of maltodextrin and food coloring. The placebo formulation has the same appearance as the investigational product. The placebo is packaged and prepared in the same manner as the investigational product: the placebo formulation is encapsulated and packaged in HDPE bottles and caps with a desiccant sleeve and oxygen absorber.

Study Rationale

The hormonal changes that occur during menopause may affect bone density and vasomotor symptoms, as well as other physical, psychosocial, and sexual-related symptoms. In this study, the orally-dosed investigational product DMA-04 (prebiotic and probiotic) provided twice daily over a 12-month period helps support skeletal health and helps manage symptoms of menopause in otherwise healthy women in the early years of postmenopause (1-6 years post last menstruation).

Objectives

A primary objective of this study is to evaluate the Change in Bone Mineral Density (BMD) measured by dual energy X-ray absorptiometry (DXA) at lumbar spine (2-4 evaluable levels L1-L4) between baseline and completion of the study period (12 months).

A secondary objective of this study is to evaluate change in BMD measured by DXA at femoral neck and hip between baseline and completion of the study period (12 months).

An additional secondary objective of this study is to evaluate the change in volumetric BMD (vBMD) measured by quantitative computed tomography (qCT) at lumbar spine (L1-L4) between baseline and completion of the study period.

An additional secondary objective of this study is to evaluate changes in biochemical markers of bone turnover (CTX, P1NP) between baseline, 6 months, and completion of the study period.

An additional secondary objective of this study is to evaluate changes in levels of circulating inflammatory cytokines and markers of inflammation (CRP, IL-17, TNF, IL-1B, IL-4, RANKL, IFNγ) between baseline, 6 months, and completion of the study period.

An additional secondary objective of this study is to evaluate changes in the global Menopause Rating Scale (MRS) from baseline to months 2, 4, 6, 8, 10, and 12.

This study evaluates safety of the investigational product, as assessed by incidence of adverse events and serious adverse events. This study also evaluates tolerability of the investigational product, as assessed by Gastrointestinal Tolerability Questionnaire (GITQ) from baseline to month 12.

An additional secondary objective of this study is to evaluate changes in the global Menopause Rating Scale (MRS) from baseline to months 2, 4, 6, 8, 10, and 12.

Study Design

Overview of Study Design

Figure 9:
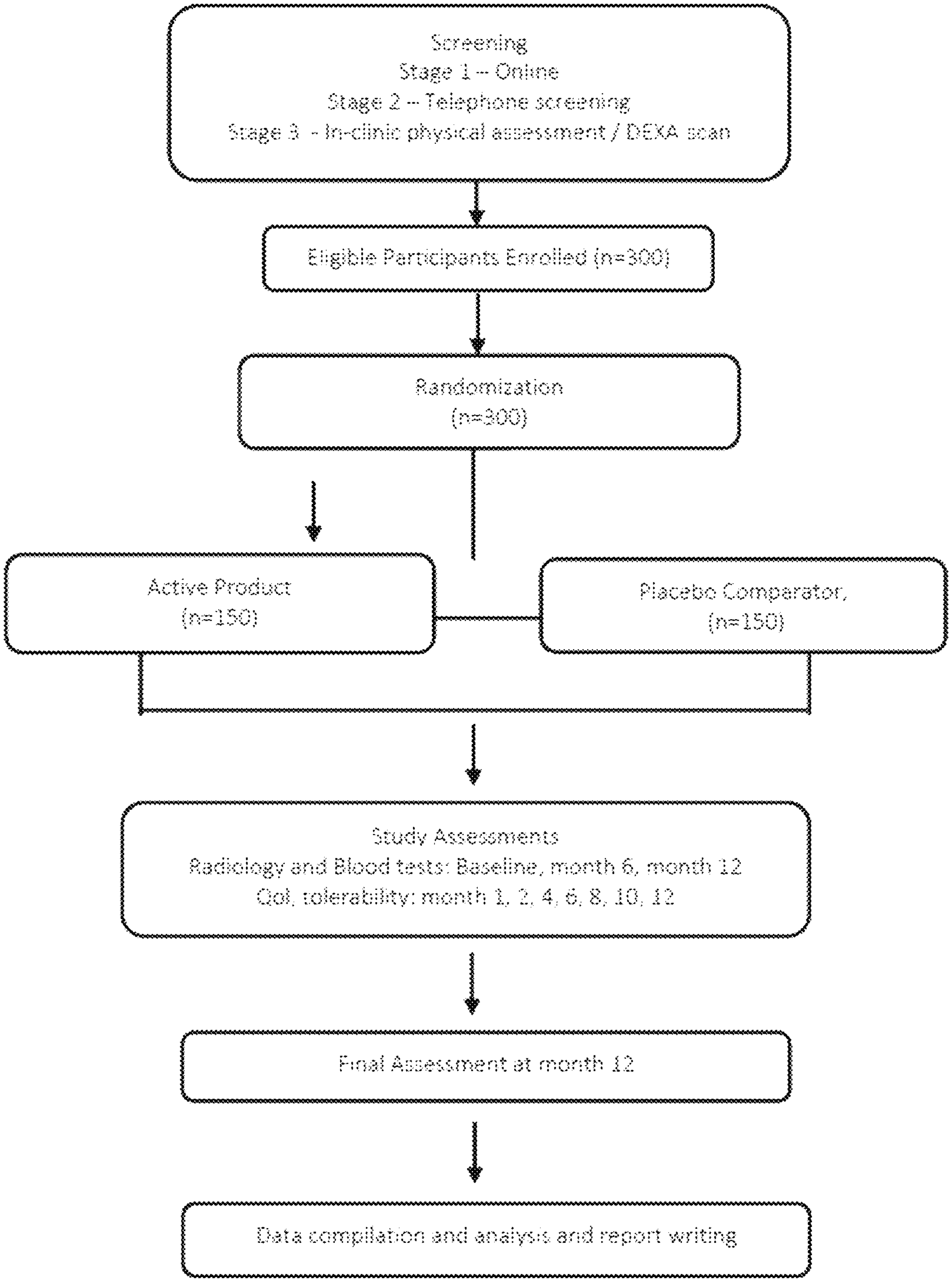
FIG. 9 is a diagram summarizing the clinical study protocol of DMA-04 described in Example 6.

An interventional, prospective, randomized, double-blind, placebo-controlled, parallel study is conducted. The duration of the study is 12 months. The study design is summarized in FIG. 9.

Written informed consent is obtained from eligible study participants prior to study initiation. Approximately 300 otherwise healthy women in the early stages of postmenopause (1-6 years post last menstruation) are enrolled as participants. Baseline demographics, medical history, and vital signs are recorded. Eligible participants are randomly allocated into one of two study groups. One group receives the investigational product, and the other group receives the comparator product, the placebo. Blinded study products with a randomization code on the label are supplied to study sites, and clinical staff administering the study products dispense the study products to participants and record the randomization code assigned to each participant. The participants are assessed at regular intervals (as described below) to complete the efficacy and safety assessments. In the event that a participant enrolled for study participation decides to withdraw from the study at any point prior to the final interview (occurring at 12 months), all study procedures applicable at final interview are performed at the time of withdrawal, provided that the participant is willing to undergo the assessments. If the participant does not attend these assessments, they are included in the modified intent-to-treat population and not the Per protocol population.

Historical and Clinical Assessments

Participant demographics, medical history, and concomitant medications are recorded. Vital signs such as weight, height, and blood pressure are also recorded. Adverse events (AE) and serious adverse event (SAE) are also recorded. Assessments include study assessments, such as radiology scans (DEXA and qCT scans), quality of life assessments, and diet/exercise assessments.

Assessments also include stool collections, which are carried out for gut microbiome analysis. Participants are provided with a stool collection kit, and follow instructions on the kit to collect and provide a stool sample for analysis.

Assessments also include pathology assessments. Blood tests are conducted and analyzed for both routine safety markers and for specified tests, including tests for inflammatory markers.

Administration of Test Article

Study test articles (either DMA-04 or the placebo) are administered to all participants by an investigator and clinical staff as described in the schedule below. The study test articles are allocated to the participants randomly through the randomization process. The investigators provide the information regarding the administration of the study product to the participant. Participants are instructed to administer the study product two times daily (one capsule in the morning with breakfast and one capsule in the evening with dinner) regularly for the administration period of 12 months. If required, rescue medication is used for pain relief and the medicine and the dose is recorded.

The test article is supplemented by adjunct administration of Vitamin D at a daily dose of 400 international units.

Validated Quality of Life Questionnaires

The gastrointestinal tolerability questionnaire (GITQ) and Menopause Rating Scale (MRS) are both used in this study.

The GITQ is a 12 item inventory of participant-reported gastrointestinal related discomfort. It is a patient self-report questionnaire assessment of the frequency and severity of gastrointestinal symptoms, e.g., gas and abdominal pain, calculated on a scale from Mild to Severe for all questions. This is used to determine whether use of the investigational product results in GI symptoms compared to the placebo.

The MRS score assesses menopausal symptoms. The scale was designed and standardized as a self-administered scale (a) to assess symptoms/complains of aging women under different conditions, (b) to evaluate the severity of symptoms over time, and (c) to measure changes pre- and post-menopause replacement therapy. The MRS has 11 items on a scale from no complaints (0) to very severe symptoms (4). Subscores are added to create a composite or total score. The hormonal changes that occur during menopause, namely reduction in estrogen, may affect vasomotor, and other physical, psychosocial and sexual related symptoms. The results of this study confirm that administration of the investigational drug DMA-04 as described herein reduces vasomotor symptoms associated with reduction in estrogen.

Schedule of Study Procedures

The schedule of study procedures is outlined in Table 17, and the summary of study visits are described below.

TABLE 17

Schedule of Study Procedures

| | Screen | Baseline | Week 1, 2, 4 | Month 2, 4 (e-consult) | Month 6 | Month 8, 10 (e-consult) | Month 12 |
|---|---|---|---|---|---|---|---|
| Confirm Eligibility/Enrollment | X | X | | | | | |
| Obtain Written Informed Consent | X | X | | | | | |
| Vital Signs (BP, height, weight) | X | X | | | X | | X |
| Blood Draw | X | X | | | X | | X |
| DXA Scan | X | | | | X | | X |
| qCT Scan | | X | | | | | X |
| Stool Sample | | X | | | X | | X |
| QOL Assessment (MRS) | | X | | X | X | X | X |
| Food freq and Exercise Log | | X | | | X | | X |
| Tolerability Assessment (GITQ) | | X | X | X | X | X | X |
| Safety Assessment | | | X | X | X | X | X |
| Start treatment | | X | | | | | X |
| Compliance | | | | X | X | X | X |

About 0 to 14 days prior to enrollment, potential participants are interviewed and screened for inclusion in the study. This includes: evaluation of inclusion/exclusion criteria, an explanation of study requirements, recordation of demographic and medical data (e.g. current illnesses and current medications/supplements), and sending the potential participants for pathology testing to analyze screening criteria.

Participants are interviewed prior to receiving the first dose (Week 0; "Baseline" in Table 17). This includes: confirming participant eligibility with respect to pathology and DEXA screening, confirming demographic and medical data (e.g., current illness and medications/supplements), obtaining informed consent, conducting a physical (including recording weight, height, and blood pressure), performing a radiology qCT scan, administering clinical questions, assessment by quality of life questionnaires, a blood draw for the remaining blood tests, randomization, study test product dispensing (including adjunct vitamin D), and provision of stool analysis kits (including a sample taken).

Participants are interviewed again at 1, 2, 4, and 8 weeks after the initial administration, and again every eight weeks thereafter. These interviews include: a compliance check, a safety and tolerability assessment by GITQ, and a menopause symptom assessment by MRS.

Participants are interviewed in a mid-study interview at about 24 to 26 weeks after the first administration. This interview includes: a compliance check, a safety and tolerability assessment by GITQ, a menopause symptom assessment check by MRS, a radiology DEXA scan, and a mid-study blood test.

Participants are interviewed again at study completion, about 48 to 52 weeks after the first administration. This interview includes: a compliance check; an assessment of changes to medication, illnesses, stresses, and life event changes; an assessment of weight and blood pressure; an adverse reactions check; assessment by GITO; assessment by MRS; a radiology DEXA scan; a qCT scan; a final-study blood test; and confirmation that pathology results are on file.

Inclusion/Exclusion/Withdrawal Criteria

The study population consists of otherwise healthy women in early postmenopause who are able to provide written consent. Study participants meet all of the inclusion criteria and none of the exclusion criteria.

Inclusion criteria include: (1) providing written informed consent; (2) stated eligibility throughout the entire study period (12 months) and willingness to fulfill all details of the protocol, including having a DEXA scan, a CT scan, providing stool samples for analysis of the gut microbiome, and having blood tests; (3) in early postmenopause, at least 1 year but a maximum of 6 years since the last menstruation or since having a total hysterectomy; (4) at least six months since the last intake of hormone replacement therapy; (5) dual energy X-ray absorptiometry (DXA)-derived Bone Mineral Density (BMD) T-score of less than −2.49 at the lumbar spine (L1-L4), femoral neck, and total hip but no site with BMD≤−2.5; (6) body mass index between 18.5 and 32.5 $kg/mg^2$; (7) normal levels of serum calcium (<11 mg/dL); and (8) normal cardiovascular parameters (systolic blood pressure≤155 mm Hg, diastolic blood pressure≤95 mm Hg) healthy and medication controlled.

Exclusion criteria include: (1) history of other bone disorders (e.g. Paget's disease or osteomalacia, osteogenesis imperfecta, osteoperosis, etc.); (2) history of cancer other than skin cancer, autoimmune disorders (rheumatoid arthritis, hashimoto's, graves' disease, etc.), type 2 diabetes, gastrointestinal disorders (ulcerative colitis, Crohn's disease, inflammatory bowel disease, irritable bowel syndrome), kidney disease or dysfunction or any other medical condition that could interfere with the conduct of the study; (3) history of chronic antibiotic use; (4) history of bariatric surgery; (5) history of partial colectomy; (6) women with spine abnormalities that would prohibit assessment of BMD; (7) Women who have undergone any joint replacement (hip, knee, etc.); (8) women who have undergone a partial hysterectomy; (9) women with untreated hyperparathyroidism; (10) Women previously treated with alcitonin, estrogens, estrogen derivatives, selective estrogen receptor modulators (SERMs), tibolone, progestins, anabolic steroids, or daily glucocorticoids in the past 6 months; (11) women treated with bisphosphonates or strontium in the past 5 years; (12) women previously treated with PTH, PTH analogs, gallium nitrate, romosozumab or denosumab; (13) per-oral use of corticosteroids; (14) smoking or use of nicotine products within the past 6-months; (15) any disease, that by the investigator's judgement, could interfere with the intestinal barrier function; (16) participation in other bone, diet, autoimmune, or gastrointestinal related clinical trials in the last 6 months; (17) desire and/or plans on changing current diet and/or exercise regime during the participation of this trial; (18) pregnancy or lactation; (19) consumption of dietary supplements (probiotics, prebiotics) in the month prior to the study or during the study, with the proviso that a participant willing to stop taking said supplements for 1 month may be enrolled following a 1-month washout period; and (20) consumption of antibiotics in the past two months, with the proviso that a participant placed on an antibiotic after enrollment in the study will be subject to a per protocol analysis.

A participant may be withdrawn from the study if any of the following conditions are met: (1) participant withdraws informed consent (with or without explanation, including those lost to follow-up); (2) adverse event or serious adverse event occurs (including a pathology abnormality) which, according to the investigator, makes study continuation impossible; (3) concomitant condition in which the prescribed additional therapy is prohibited by protocol as per the participant selection criteria; (4) protocol deviation, affecting the study results; (5) a participant becomes pregnant during the course of the study; (6) a participant may also be withdrawn based on the discretion of the investigator for any reason, if it is felt that her further continuation in the study will adversely affect him/her, or, in the interests of the study. The reason of discontinuation is reported. In the event than an enrolled participant decides to withdraw from the study at a point prior to the final interview, all study procedures applicable at final interview are completed, if possible.

INCORPORATION BY REFERENCE

All references, issued patents, and patent applications cited within the body of the instant specification are hereby incorporated by reference in their entirety, for all purposes.

Sequence Listing

| Seq ID No. | Description | Sequence |
|---|---|---|
| 1 | DP1 16S rRNA | AGTCAGACATGCAAGTCGAGCGGTAGAGAGAAGCTTGCTTCTCTTGA<br>GAGCGGCGGACGGGTGAGTAAAGCCTAGGAATCTGCCTGGTAGTGGG<br>GGATAACGTTCGGAAACGGACGCTAATACCGCATACGTCCTACGGGA<br>GAAAGCAGGGGACCTTCGGGCCTTGCGCTATCAGATGAGCCTAGGTC<br>GGATTAGCTAGTTGGTGAGGTAATGGCTCACCAAGGCGACGATCCGT<br>AACTGGTCTGAGAGGATGATCAGTCACACTGGAACTGAGACACGGTC<br>CAGACTCCTACGGGAGGCAGCAGTGGGGAATATTGGACAATGGGCGA<br>AAGCCTGATCCAGCCATGCCGCGTGTGTGAAGAAGGTCTTCGGATTG<br>TAAAGCACTTTAAGTTGGGAGGAAGGGCATTAACCTAATACGTTAGT |

-continued

Sequence Listing

| Seq ID No. | Description | Sequence |
|---|---|---|
| | | GTTTTGACGTTACCGACAGAATAAGCACCGGCTAACTCTGTGCCAGC<br>AGCCGCGGTAATACAGAGGGTGCAAGCGTTAATCGGAATTACTGGGC<br>GTAAAGCGCGCGTAGGTGGTTTGTTAAGTTGGATGTGAAATCCCCGG<br>GCTCAACCTGGGAACTGCATTCAAAACTGACTGACTAGAGTATGGTA<br>GAGGGTGGTGGAATTTCCTGTGTAGCGGTGAAATGCGTAGATATAGG<br>AAGGAACACCAGTGGCGAAGGCGACCACCTGGACTAATACTGACACT<br>GAGGTGCGAAAGCGTGGGGAGCAAACAGGATTAGATACCCTGGTAGT<br>CCACGCCGTAAACGATGTCAACTAGCCGTTGGGAGCCTTGAGCTCTTA<br>GTGGCGCAGCTAACGCATTAAGTTGACCGCCTGGGGAGTACGGCCGC<br>AAGGTTAAAACTCAAATGAATTGACGGGGGCCCGCACAAGCGGTGGA<br>GCATGTGGTTTAATTCGAAGCAACGCGAAGAACCTTACCAGGCCTTG<br>ACATCCAATGAACTTTCTAGAGATAGATTGGTGCCTTCGGGAACATTG<br>AGACAGGTGCTGCATGGCTGTCGTCAGCTCGTGTCGTGAGATGTTGG<br>GTTAAGTCCCGTAACGAGCGCAACCCTTGTCCTTAGTTACCAGCACGT<br>AATGGTGGGCACTCTAAGGAGACTGCCGGTGACAAACCGGAGGAAG<br>GTGGGGATGACGTCAAGTCATCATGGCCCTTACGGCCTGGGCTACAC<br>ACGTGCTACAATGGTCGGTACAGAGGGTTGCCAAGCCGCGAGGTGGA<br>GCTAATCCCATAAAACCGATCGTAGTCCGGATCGCAGTCTGCAACTC<br>GACTGCGTGAAGTCGGAATCGCTAGTAATCGCGAATCAGAATGTCGC<br>GGTGAATACGTTCCCGGGCCTTGTACACACCGCCCGTCACACCATGG<br>GAGTGGGTTGCACCAGAAGTAGCTAGTCTAACCTTCGGGAGGACGGT<br>TACCACGGTGTGATTCATGACTGGGGTGAAGTCGTAACAAGGTAGCC<br>GTAGGGGAACCTGCGGCTGGATCACCTCCTT |
| 2 | DP2 ITS sequence | TTGTTGCTCGAGTTCTTGTTTAGATCTTTTACAATAATGTGTATCTTTA<br>ATGAAGATGNGNGCTTAATTGCGCTGCTTTATTAGAGTGTCGCAGTAG<br>AAGTAGTCTTGCTTGAATCTCAGTCAACGTTTACACACATTGGAGTTT<br>TTTTACTTTAATTTAATTCTTTCTGCTTTGAATCGAAAGGTTCAAGGCA<br>AAAAACAAACACAAACAATTTTATTTTATTATAATTTTTTAAACTAAA<br>CCAAAATTCCTAACGGAAATTTTAAAATAATTTAAAACTTTCAACAAC<br>GGATCTCTTGGTTCTCGCATCGATGAAAAACGTACCGAATTGCGATAA<br>GTAATGTGAATTGCAAATACTCGTGAATCATTGAATTTTTGAACGCAC<br>ATTGCGCCCTTGAGCATTCTCAAGGGCATGCCTGTTTGAGCGTCATTT<br>CCTTCTCAAAAAATAATTTTTTATTTTTTGGTTGTGGGCGATACTCAGG<br>GTTAGCTTGAAATTGGAGACTGTTTCAGTCTTTTTTAATTCAACACTTA<br>NCTTCTTTGGAGACGCTGTTCTCGCTGTGATGTATTTATGGATTTATTC<br>GTTTTACTTTACAAGGGAAATGGTAATGTACCTTAGGCAAAGGGTTGC<br>TTTTAATATTCATCAAGTTTGACCTCAAATCAGGTAGGATTACCCGCT<br>GAACTTAAGCATATCAATAAGCGGAGGAAAAGAAACCAACTGGGATT<br>ACCTTAGTAACGGCGAGTGAAGCGGTAAAAGCTCAAATTTGAAATCT<br>GGTACTTTCAGTGCCCGAGTTGTAATTTGTAGAATTTGTCTTTGATTA<br>GGTCCTTGTCTATGTTCCTTGGAACAGGACGTCATAGAGGGTGAGANT<br>CCCGTTTGNNGAGGATACCTTTTCTCTGTANNACTTTTTCNAAGAGTC<br>GAGTTGNTTGGGAATGCAGCTCAAANNGGGTNGNAAATTCCATCTAA<br>AGCTAAATATTNGNCNAGAGACCGANAGCGACANTACAGNGATGGA<br>AAGANGAAA |
| 3 | DP3 16S rRNA | ATTGAGAGTTTGATCCTGGCTCAGGATGAACGCTGGCGGCGTGCCTA<br>ATACATGCAAGTCGAACGCACAGCGAAAGGTGCTTGCACCTTTCAAG<br>TGAGTGGCGAACGGGTGAGTAACACGTGGACAACCTGCCTCAAGGCT<br>GGGGATAACATTTGGAAACAGATGCTAATACCGAATAAAACTCAGTG<br>TCGCATGACACAAAGTTAAAAGGCGCTTTGGCGTCACCTAGAGATGG<br>ATCCGCGGTGCATTAGTTAGTTGGTGGGGTAAAGGCCTACCAAGACA<br>ATGATGCATAGCCGAGTTGAGAGACTGATCGGCCACATTGGGACTGA<br>GACACGGCCCAAACTCCTACGGGAGGCTGCAGTAGGGAATCTTCCAC<br>AATGGGCGAAAGCCTGATGGAGCAACGCCGCGTGTGTGATGAAGGCT<br>TTCGGGTCGTAAAGCACTGTTGTACGGGAAGAACAGCTAGAATAGGG<br>AATGATTTTAGTTTGACGGTACCATACCAGAAAGGGACGGCTAAATA<br>CGTGCCAGCAGCCGCGGTAATACGTATGTCCCGAGCGTTATCCGGATT<br>TATTGGGCGTAAAGCGAGCGCAGACGGTTGATTAAGTCTGATGTGAA<br>AGCCCGGAGCTCAACTCCGGAATGGCATTGGAAACTGGTTAACTTGA<br>GTGCAGTAGAGGTAAGTGGAACTCCATGTGTAGCGGTGGAATGCGTA<br>GATATATGGAAGAACACCAGTGGCGAAGGCGGCTTACTGGACTGTAA<br>CTGACGTTGAGGCTCGAAAGTGTGGGTAGCAAACAGGATTAGATACC<br>CTGGTAGTCCACACCGTAAACGATGAACACTAGGTGTTAGGAGGTTT<br>CCGCCTCTTAGTGCCGAAGCTAACGCATTAAGTGTTCCGCCTGGGGAG<br>TACGACCGCAAGGTTGAAACTCAAAGGAATTGACGGGGACCCGCACA<br>AGCGGTGGAGCATGTGGTTTAATTCGAAGCAACGCGAAGAACCTTAC<br>CAGGTCTTGACATCCTTTGAAGCTTTTAGAGATAGAAGTGTTCTCTTC<br>GGAGACAAAGTGACAGGTGGTGCATGGTCGTCGTCAGCTCGTGTCGT<br>GAGATGTTGGGTTAAGTCCCGCAACGAGCGCAACCCTTATTGTTAGTT<br>GCCAGCATTCAGATGGGCACTCTAGCGAGACTGCCGGTGACAAACCG<br>GAGGAAGGCGGGGACGACGTCAGATCATCATGCCCCTTATGACCTGG |

-continued

Sequence Listing

| Seq ID No. | Description | Sequence |
| --- | --- | --- |
| | | GCTACACACGTGCTACAATGGCGTATACAACGAGTTGCCAACCCGCG<br>AGGGTGAGCTAATCTCTTAAAGTACGTCTCAGTTCGGATTGTAGTCTG<br>CAACTCGACTACATGAAGTCGGAATCGCTAGTAATCGCGGATCAGCA<br>CGCCGCGGTGAATACGTTCCCGGGTCTTGTACACACCGCCCGTCACAC<br>CATGGGAGTTTGTAATGCCCAAAGCCGGTGGCCTAACCTTTTAGGAA<br>GGAGCCGTCTAAGGCAGGACAGATGACTGGGGTGAAGTCGTAACAA<br>GGTAGCCGTAGGAGAACCTGCGGCTGGATCACCTCCTTT |
| 4 | DP4 ITS sequence | CTTTGTTGTTAAAACTACCTTGTTGCTTTGGCGGGA<br>CCGCTCGGTCTCGAGCCGCTGGGGATTCGTCCCAGGCGAGCGCCCGC<br>CAGAGTTAAACCAAACTCTTGTTATTTAACCGG<br>TCGTCTGAGTTAAAATTTTGAATAAATCAAAACTTTCAACAACGGATC<br>TCTTGGTTCTCGCATCGATGAAGAACGCAGCG<br>AAATGCGATAAGTAATGTGAATTGCAGAATTCAGTGAATCATCGAAT<br>CTTTGAACGCACATTGCGCCCCTTGGTATTCCG<br>AGGGGCATGCCTGTTCGAGCGTCATTACACCACTCAAGCTATGCTTGG<br>TATTGGGCGTCGTCCTTAGTTGGGCGCGCCTT<br>AAAGACCTCGGCGAGGCCACTCCGGCTTTAGGCGTAGTAGAATTTAT<br>TCGAACGTCTGTCAAAGGAGAGGAACTCTGCCG<br>ACTGAAACCTTTATTTTTCTAGGTTGACCTCGGATCAGGTAGGGATAC<br>CCGCTGAACTTAAGCATATCAATAAGCGGAGG<br>AAAAGAAACCAACAGGGATTGCCCTAGTAACGGCGAGTGAAGCGGC<br>AACAGCTCAAATTTGAAAGCTAGCCTTCGGGTTC<br>GCATTGTAATTTGTAGAGGATGATTTGGGGAAGCCGCCTGTCTAAGTT<br>CCTTGGAACAGGACGTCATAGAGGGTGAGAAT<br>CCCGTATGTGACAGGAAATGGCACCCTATGTAAATCTCCTTCGACGA<br>GTCGAGTTGTTTGGGAATGCAGCTCTAAATGGG<br>AGGTAAATTTCTTCTAAAGCTAAATATTGGCGAGAGACCGATAGCGC<br>ACAAGTAGAGTGATCGAAAGATGAAAAGCACTT<br>TGGAAAGAGAGTTAAAAAGCACGTGAAATTGTTGAAAGGGAAGCGC<br>TTGCAATCAGACTTGTTTAAACTGTTCGGCCGGT |
| 5 | DP5 ITS sequence | GCGCTTATTGCGCGGCGAAAAAACCTTACACACAGTGTTTTTTGTTAT<br>TACANNAACTTTTGCTTTGGTCTGGACTAGAAATAGTTTGGGCCAGAG<br>GTTACTAAACTAAACTTCAATATTTATATTGAATTGTTATTTATTTAAT<br>TGTCAATTTGTTGATTAAATTCAAAAAATCTTCAAAACTTTCAACAAC<br>GGATCTCTTGGTTCTCGCATCGATGAAGAACGCAGCGAAATGCGATA<br>AGTAATATGAATTGCAGATTTTCGTGAATCATCGAATCTTTGAACGCA<br>CATTGCGCCCTCTGGTATTCCAGAGGGCATGCCTGTTTGAGCGTCATT<br>TCTCTCTCAAACCTTCGGGTTTGGTATTGAGTGATACTCTTAGTCGAA<br>CTAGGCGTTTGCTTGAAATGTATTGGCATGAGTGGTACTGGATAGTGC<br>TATATGACTTTCAATGTATTAGGTTTATCCAACTCGTTGAATAGTTTA<br>ATGGTATATTTCTCGGTATTCTAGGCTCGGCCTTACAATATAACAAAC<br>AAGTTTGACCTCAAATCAGGTAGGATTACCCGCTGAACTTAAGCATAT<br>CAATAAGCGGAGGAAAAGAAACCAACAGGGATTGCCTTAGTAACGG<br>CGAGTGAAGCGGCAAAAGCTCAAATTTGAAATCTGGCACCTTCGGTG<br>TCCGAGTTGTAATTTGAAGAAGGTAACTTTGGAGTTGGCTCTTGTCTA<br>TGTTCCTTGGAACAGGACGTCACAGAGGGTGAGAATCCCGTGCGATG<br>AGATGCCCAATTCTATGTAAAGTGCTTTCGAAGAGTCGAGTTGTTTGG<br>GAATGCAGCTCTAAGTGGGTGGTAAATTCCATCTAAAGCTAAATATT<br>GGCGAGAGACCGATAGCGAACAAGTACAGTGATGGAAAGATGAAAA<br>GAACTTTGAAAAGAGAGTGAAAAAGTACGTGAAATTGTTGAAAGGG<br>AAAGGGCTTGAGATCAGACTTGGTATTTTGCGATCCTTTCCTTCTTGG<br>TTGGGTTCCTCGCAGCTTACTGGGNCAGCATCGGTTTGGATGG |
| 6 | DP6 16S rRNA | GAAAGGCGGCTTCGGCTGTCACTTATGGATGGACCCGCGTCGCATTA<br>GCTAGTTGGTGAGGTAACGGCTCACCAAGGCAACGATGCGTAGCCGA<br>CCTGAGAGGGTGATCGGCCACACTGGGACTGAGACACGGCCCAGACT<br>CCTACGGGAGGCAGCAGTAGGGAATCTTCCGCAATGGACGAAAGTCT<br>GACGGAGCAACGCCGCGTGAGTGATGAAGGCTTTCGGGTCGTAAAAC<br>TCTGTTGTTAGGGAAGAACAAGTGCTAGTTGAATAAGCTGCACCTTG<br>ACGGTACCTAACCAGAAAGCCACGGCTAACTACGTGCCAGCAGCCGC<br>GGTAATACGTAGGTGGCAAGCGTTATCCGGAATTATTGGGCGTAAAG<br>CGCGCGCAGGTGGTTTCTTAAGTCTGATGTGAAAGCCCACGGCTCAA<br>CCGTGGAGGGTCATTGGAAACTGGGAGACTTGAGTGCAGAAGAGGA<br>AAGTGGAATTCCATGTGTAGCGGTGAAATGCGTAGAGATATGGAGGA<br>ACACCAGTGGCGAAGGCGACTTTCTGGTCTGTAACTGACACTGAGGC<br>GCGAAAGCGTGGGGAGCAAACAGGATTAGATACCCTGGTAGTCCACG<br>CCGTAAACGATGAGTGCTAAGTGTTAGAGGGTTTCCGCCCTTTAGTGC<br>TGAAGTTAACGCATTAAGCACTCCGCCTGGGGAGTACGGCCGCAAGG<br>CTGAAACTCAAAGGAATTGACGGGGGCCCGCACAAGCGGTGGAGCAT<br>GTGGTTTAATTCGAAGCAACGCGAAGAACCTTACCAGGTCTTGACAT<br>CCTCTGAAAACCCTAGAGATAGGGCTTCTCCTTCGGGAGCAGAGTGA |

-continued

Sequence Listing

| Seq ID No. | Description | Sequence |
|---|---|---|
| | | CAGGTGGTGCATGGTTGTCGTCAGCTCGTGTCGTGAGATGTTGGGTTA<br>AGTCCCGCAACGAGCGCAACCCTTGATCTTAGTTGCCATCATTAAGTT<br>GGGCACTCTAAGGTGACTGCCGGTGACAAACCGGAGGAAGGTGGGG<br>ATGACGTCAAATCATCATGCCCCTTATGACCTGGGCTACACACGTGCT<br>ACAATGGACGGTACAAAGAGCTGCAAGACCGCGAGGTGGAGCTAAT<br>CTCATAAAACCGTTCTCAGTTCGGATTGTAGGCTGCAACTCGCCTACA<br>TGAAGCTGGAATCGCTAGTAATCGCGGATCAGCAT |
| 7 | DP7 ITS | CCACNCTGCGTGGGCGACACGAAACACCGAAACCGAACGCACGCCGT<br>CAAGCAAGAAATCCACAAAACTTTCAACAACGGATCTCTTGGTTCTC<br>GCATCGATGAAGAGCGCAGCGAAATGCGATACCTAGTGTGAATTGCA<br>GCCATCGTGAATCATCGAGTTCTTGAACGCACATTGCGCCCGCTGGTA<br>TTCCGGCGGGCATGCCTGTCTGAGCGTCGTTTCCTTCTTGGAGCGGAG<br>CTTCAGACCTGGCGGGCTGTCTTTCGGGACGGCGCGCCCAAAGCGAG<br>GGGCCTTCTGCGCGAACTAGACTGTGCGCGCGGGGCGGCCGGCGAAC<br>TTATACCAAGCTCGACCTCAGATCAGGCAGGAGTACCCGCTGAACTT<br>AAGCATATCAATAAGCGGAGGAAAAGAAACCAACAGGGATTGCCCC<br>AGTAGCGGCGAGTGAAGCGGCAAAAGCTCAGATTTGGAATCGCTTCG<br>GCGAGTTGTGAATTGCAGGTTGGCGCCTCTGCGGCGGCGGCGGTCCA<br>AGTCCCTTGGAACAGGGCGCCATTGAGGGTGAGAGCCCCGTGGGACC<br>GTTTGCCTATGCTCTGAGGCCCTTCTGACGAGTCGAGTTGTTTGGGAA<br>TGCAGCTCTAAGCGGGTGGTAAATTCCATCTAAGGCTAAATACTGGC<br>GAGAGACCGATAGCGAACAAGTACTGTGAAGGAAAGATGAAAAGCA<br>CTTTGAAAAGAGAGTGAAACAGCACGTGAAATTGTTGAAAGGGAAG<br>GGTATTGCGCCCGACATGGAGCGTGCGCACCGCTGCCCCTCGTGGGC<br>GGCGCTCTGGGCGTGCTCTGGGCCAGCATCGGTTTTTGCCGCGGGAG<br>AAGGGCGGCGGGCATGTAGCTCTTC |
| 8 | DP8 ITS | GTTGCTCGAGTTCTTGTTTAGATCTTTTACNATAATGTGTATCTTTAAT<br>GAAGATGTGCGCTTAATTGCGCTGCTTTATTAGAGTGTCGCAGTAGAA<br>GTAGTCTTGCTTGAATCTCAGTCAACGTTTACACACATTGGAGTTTTTT<br>TACTTTAATTTAATTCTTTCTGCTTTGAATCGAAAGGTTCAAGGCAAA<br>AAACAAACACAAACAATTTTATTTTATTATAATTTTTTAAACTAAACC<br>AAAATTCCTAACGGAAATTTTAAAATAATTTAAAACTTTCAACAACG<br>GATCTCTTGGTTCTCGCATCGATGAAAAACGTAGCGAATTGCGATAA<br>GTAATGTGAATTGCAAATACTCGTGAATCATTGAATTTTTGAACGCAC<br>ATTGCGCCCTTGAGCATTCTCAAGGGCATGCCTGTTTGAGCGTCATTT<br>CCTTCTCAAAAGATAATTTTTTATTTTTTGGTTGTGGGCGATACTCAGG<br>GTTAGCTTGAAATTGGAGACTGTTTCAGTCTTTTTTAATTCAACACTTA<br>NCTTCTTTGGAGACGCTGTTCTCGCTGTGATGTATTTATGGATTTATTC<br>GTTTTACTTTACAAGGGAAATGGTAATGTACCTTAGGCAAAGGGTTGC<br>TTTTAATATTCATCAAGTTTGACCTCAAATCAGGTAGGATTACCCGCT<br>GAACTTAAGCATATCAATAAGCGGAGGAAAAGAAACCAACTGGGATT<br>ACCTTAGTAACGGCGAGTGAAGCGGTAAAAGCTCAAATTTGAAATCT<br>GGTACTTTCANNGCCCGAGTTGTAATTTGTAGAATTTGTCTTTGATTA<br>GGTCCTTGTCTATGTTCCTTGGANCAGGACGTCATANAGGGTGANTCC<br>CNTTTGGCGANGANACCTTTTCTCTGTANACTTTTTCNANAGTCGAGT<br>TGTTTNGGATGCAGCTCNAAGTGGGGNGG |
| 9 | DP9 16S rRNA | ATGAGAGTTTGATCTTGGCTCAGGATGAACGCTGGCGGCGTGCCTAA<br>TACATGCAAGTCGAACGAACTTCCGTTAATTGATTATGACGTACTTGT<br>ACTGATTGAGATTTTAACACGAAGTGAGTGGCGAACGGGTGAGTAAC<br>ACGTGGGTAACCTGCCCAGAAGTAGGGGATAACACCTGGAAACAGAT<br>GCTAATACCGTATAACAGAGAAAACCGCATGGTTTTCTTTTAAAAGAT<br>GGCTCTGCTATCACTTCTGGATGGACCCGCGGCGTATTAGCTAGTTGG<br>TGAGGCAAAGGCTCACCAAGGCAGTGATACGTAGCCGACCTGAGAGG<br>GTAATCGGCCACATTGGGACTGAGACACGGCCCAGACTCCTACGGGA<br>GGCAGCAGTAGGGAATCTTCCACAATGGACGCAAGTCTGATGGAGCA<br>ACGCCGCGTGAGTGAAGAAGGGTTTCGGCTCGTAAAGCTCTGTTGTT<br>AAAGAAGAACGTGGGTAAGAGTAACTGTTTACCCAGTGACGGTATTT<br>AACCAGAAAGCCACGGCTAACTACGTGCCAGCAGCCGCGGTAATACG<br>TAGGTGGCAAGCGTTATCCGGATTTATTGGGCGTAAAGCGAGCGCAG<br>GCGGTCTTTTAAGTCTAATGTGAAAGCCTTCGGCTCAACCGAAGAAGT<br>GCATTGGAAACTGGGAGACTTGAGTGCAGAAGAGGACAGTGGAACTC<br>CATGTGTAGCGGTGAAATGCGTAGATATATGGAAGAACACCAGTGGC<br>GAAGGCGGCTGTCTGGTCTGCAACTGACGCTGAGGCTCGAAAGCATG<br>GGTAGCGAACAGGATTAGATACCCTGGTAGTCCATGCCGTAAACGAT<br>GATTACTAAGTGTTGGAGGGTTTCCGCCCTTCAGTGCTGCAGCTAACG<br>CATTAAGTAATCCGCCTGGGGAGTACGACCGCAAGGTTGAAACTCAA<br>AAGAATTGACGGGGGCCCGCACAAGCGGTGGAGCATGTGGTTTAATT<br>CGAAGCTACGCGAAGAACCTTACCAGGTCTTGACATCTTCTGACAGTC<br>TAAGAGATTAGAGGTTCCCTTCGGGGACAGAATGACAGGTGGTGCAT<br>GGTTGTCGTCAGCTCGTGTCGTGAGATGTTGGGTTAAGTCCCGCAACG |

-continued

Sequence Listing

| Seq ID No. | Description | Sequence |
|---|---|---|
| | | AGCGCAACCCTTATTACTAGTTGCCAGCATTAAGTTGGGCACTCTAGT<br>GAGACTGCCGGTGACAAACCGGAGGAAGGTGGGGACGACGTCAAAT<br>CATCATGCCCCTTATGACCTGGGCTACACACGTGCTACAATGGATGGT<br>ACAACGAGTCGCGAGACCGCGAGGTTAAGCTAATCTCTTAAAACCAT<br>TCTCAGTTCGGACTGTAGGCTGCAACTCGCCTACACGAAGTCGGAATC<br>GCTAGTAATCGCGGATCAGCATGCCGCGGTGAATACGTTCCCGGGCC<br>TTGTACACACCGCCCGTCACACCATGAGAGTTTGTAACACCCAAAGC<br>CGGTGGGGTAACCTTTTAGGAGCTAGCCGTCTAAGGTGGGACAGATG<br>ATTAGGGTGAAGTCGTAACAAGGTAGCCGTAGGAGAACCTGCGGCTG<br>GATCACCTCCTT |
| 10 | DP10 16S rRNA | CAGATAGTTGGTGAGGTAACGGCTCACCAAGGCAACGATGCGTAGCC<br>GACCTGAGAGGGTGATCGGCCACACTGGGACTGAGACACGGCCCAGA<br>CTCCTACGGGAGGCAGCAGTAGGGAATCTTCCGCAATGGACGAAAGT<br>CTGACGGAGCAACGCCGCGTGAGTGATGAAGGTTTTCGGATCGTAAA<br>GCTCTGTTGTTAGGGAAGAACAAGTGCCGTTCAAATAGGGCGGCACC<br>TTGACGGTACCTAACCAGAAAGCCACGGCTAACTACGTGCCAGCAGC<br>CGCGGTAATACGTAGGTGGCAAGCGTTGTCCGGAATTATTGGGCGTA<br>AAGGGCTCGCAGGCGGTTTCTTAAGTCTGATGTGAAAGCCCCCGGCT<br>CAACCGGGGAGGGTCATTGGAAACTGGGGAACTTGAGTGCAGAAGA<br>GGAGAGTGGAATTCCACGTGTAGCGGTGAAATGCGTAGAGATGTGGA<br>GGAACACCAGTGGCGAAGGCGACTCTCTGGTCTGTAACTGACGCTGA<br>GGAGCGAAAGCGTGGGGAGCGAACAGGATTAGATACCCTGGTAGTCC<br>ACGCCGTAAACGATGAGTGCTAAGTGTTAGGGGGTTTCCGCCCCTTA<br>GTGCTGCAGCTAACGCATTAAGCACTCCGCCTGGGGAGTACGGTCGC<br>AAGACTGAAACTCAAAGGAATTGACGGGGGCCCGCACAAGCGGTGG<br>AGCATGTGGTTTAATTCGAAGCAACGCGAAGAACCTTACCAGGTCTT<br>GACATCCTCTGACAATCCTAGAGATAGGACGTCCCCTTCGGGGGCAG<br>AGTGACAGGTGGTGCATGGTTGTCGTCAGCTCGTGTCGTGAGATGTTG<br>GGTTAAGTCCCGCAACGAGCGCAACCCTTGATCTTAGTTGCCAGCATT<br>CAGTTGGGCACTCTAAGGTGACTGCCGGTGACAAACCGGAGGAAGGT<br>GGGGATGACGTCAAATCATCATGCCCCTTATGACCTGGGCTACACAC<br>GTGCTACAATGGACAGAACAAAGGGCAGCGAAACCGCGAGGTTAAG<br>CCAATCCCACAAATCTGTTCTCAGTTCGGATCGCAGTCTGCAACTCGA<br>CTGCGTGAAGCTGGAATCGCTAGTAATCGCGGATCAGCATGCCGCGG<br>TGAATACGTTCCCGGGCCTTGTACACACCGCCCGTCACACCACGAGA<br>GTTTGTAACACCCGAAGTCGGTGAGGTAACCTTTTAGGAGCCAGCCG<br>CCGAAGGTGGGACAGATGATTGGGGTGAAGTCGTAACAAGGTAGCCG<br>TATCGGAAGGTGCGGCTGGATCACCTCCTTT |
| 11 | DP11 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATGCCTAGGAATCTGCCTGGTAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCGACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGTTGTAGATTAATACTCTGCAATTTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTCGTTAAGTTGGATGTGAAAGCCCCGGGCTCAA<br>CCTGGGAACTGCATTCAAAACTGACGAGCTAGAGTATGGTAGAGGGT<br>GGTGGAATTTCCTGTGTAGCGGTGAAATGCGTAGATATAGGAAGGAA<br>CACCAGTGGCGAAGGCGACCACCTGGACTGATACTGACACTGAGGTG<br>CGAAAGCGTGGGGAGCAAACAGGATTAGATACCCTGGTAGTCCACGC<br>CGTAAACGATGTCAACTAGCCGTTGGAATCCTTGAGATTTTAGTGGCG<br>CAGCTAACGCATTAAGTTGACCGCCTGGGGAGTACGGCCGCAAGGTT<br>AAAACTCAAATGAATTGACGGGGGCCCGCACAAGCGGTGGAGCATGT<br>GGTTTAATTCGAAGCAACGCGAAGAACCTTACCAGGCCTTGACATCC<br>AATGAACTTTCCAGAGATGGATGGGTGCCTTCGGGAACATTGAGACA<br>GGTGCTGCATGGCTGTCGTCAGCTCGTGTCGTGAGATGTTGGGTTAAG<br>TCCCGTAACGAGCGCAACCCTTGTCCTTAGTTACCAGCACGTTATGGT<br>GGGCACTCTAAGGAGACTGCCGGTGACAAACCGGAGGAAGGTGGGG<br>ATGACGTCAAGTCATCATGGCCCTTACGGCCTGGGCTACACACGTGCT<br>ACAATGGTCGGTACAAAGGGTTGCCAAGCCGCGAGGTGGAGCTAATC<br>CCATAAAACCGATCGTAGTCCGGATCGCAGTCTGCAACTCGACTGCG<br>TGAAGTCGGAATCGCTAGTAATCGCGAATCAGAATGTCGCGGTGAAT<br>ACGTTCCCGGGCCTTGTACACACCGCCCGTCACATCCCACACGAATTG<br>CTTG |

-continued

Sequence Listing

| Seq ID No. | Description | Sequence |
|---|---|---|
| 12 | DP12 16S rRNA | TACGGAGAGTTTGATCCTGGCTCAGGATGAACGCTGGCGGCGTGCTT<br>AACACATGCAAGTCGAACGGTGAAGCCAAGCTTGCTTGGTGGATCAG<br>TGGCGAACGGGTGAGTAACACGTGAGCAACCTGCCCTGGACTCTGGG<br>ATAAGCGCTGGAAACGGCGTCTAATACTGGATATGAGCCTTCATCGC<br>ATGGTGGGGGTTGGAAAGATTTTTTGGTCTGGGATGGGCTCGCGGCCT<br>ATCAGCTTGTTGGTGAGGTAATGGCTCACCAAGGCGTCGACGGGTAG<br>CCGGCCTGAGAGGGTGACCGGCCACACTGGGACTGAGACACGGCCCA<br>GACTCCTACGGGAGGCAGCAGTGGGGAATATTGCACAATGGGCGAAA<br>GCCTGATGCAGCAACGCCGCGTGAGGGATGACGGCCTTCGGGTTGTA<br>AACCTCTTTTAGCAGGGAAGAAGCGAAAGTGACGGTACCTGCAGAAA<br>AAGCGCCGGCTAACTACGTGCCAGCAGCCGCGGTAATACGTAGGGCG<br>CAAGCGTTATCCGGAATTATTGGGCGTAAAGAGCTCGTAGGCGGTTT<br>GTCGCGTCTGCTGTGAAATCCCGAGGCTCAACCTCGGGCCTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGTAACTGACGCTGAGGAGCGAAAGGGTGGGGAG<br>CAAACAGGCTTAGATACCCTGGTAGTCCACCCCGTAAACGTTGGGAA<br>CTAGTTGTGGGGACCATTCCACGGTTTCCGTGACGCAGCTAACGCATT<br>AAGTTCCCCGCCTGGGGAGTACGGCCGCAAGGCTAAAACTCAAAGGA<br>ATTGACGGGGACCCGCACAAGCGGCGGAGCATGCGGATTAATTCGAT<br>GCAACGCGAAGAACCTTACCAAGGCTTGACATACACCAGAACGGGCC<br>AGAAATGGTCAACTCTTTGGACACTGGTGAACAGGTGGTGCATGGTT<br>GTCGTCAGCTCGTGTCGTGAGATGTTGGGTTAAGTCCCGCAACGAGC<br>GCAACCCTCGTTCTATGTTGCCAGCACGTAATGGTGGAACTCATGGG<br>ATACTGCCGGGGTCAACTCGGAGGAAGGTGGGGATGACGTCAAATCA<br>TCATGCCCCTTATGTCTTGGGCTTCACGCATGCTACAATGGCCGGTAC<br>AAAGGGCTGCAATACCGTGAGGTGGAGCGAATCCCAAAAAGCCGGTC<br>CCAGTTCGGATTGAGGTCTGCAACTCGACCTCATGAAGTCGGAGTCG<br>CTAGTAATCGCAGATCAGCAACGCTGCGGTGAATACGTTCCCGGGTC<br>TTGTACACACCGCCCGTCAAGTCATGAAAGTCGGTAACACCTGAAGC<br>CGGTGGCCCAACCCTTGTGGAGGGAGCCGTCGAAGGTGGGATCGGTA<br>ATTAGGACTAAGTCGTAACAAGGTAGCCGTACCGGAAGGTGCGGCTG<br>GATCACCTCCTTT |
| 13 | DP13 16S rRNA | AGTTAGCGGCGGACGGGTGAGTAACACGTGGGTAACCTGCCTATAAG<br>ACTGGGATAACTCCGGGAAACCGGGGCTAATACCGGATAACATTTTG<br>CACCGCATGGTGCGAAATTGAAAGGCGGCTTCGGCTGTCACTTATAG<br>ATGGACCTGCGGCGCATTAGCTAGTTGGTGAGGTAACGGCTCACCAA<br>GGCGACGATGCGTAGCCGACCTGAGAGGGTGATCGGCCACACTGGGA<br>CTGAGACACGGCCCAGACTCCTACGGGAGGCAGCAGTAGGGAATCTT<br>CCGCAATGGACGAAAGTCTGACGGAGCAACGCCGCGTGAACGATGA<br>AGGCTTTCGGGTCGTAAAGTTCTGTTGTTAGGGAAGAACAAGTGCTA<br>GTTGAATAAGCTGGCACCTTGACGGTACCTAACCAGAAAGCCACGGC<br>TAACTACGTGCCAGCAGCCGCGGTAATACGTAGGTGGCAAGCGTTAT<br>CCGGAATTATTGGGCGTAAAGCGCGCGCAGGTGGTTTCTTAAGTCTG<br>ATGTGAAAGCCCACGGCTCAACCGTGGAGGGTCATTGGAAACTGGGA<br>GACTTGAGTGCAGAAGAGGAAAGTGGAATTCCATGTGTAGCGGTGAA<br>ATGCGTAGAGATATGGAGGAACACCAGTGGCGAAGGCGACTTTCTGG<br>TCTGCAACTGACACTGAGGCGCGAAAGCGTGGGGAGCAAACAGGATT<br>AGATACCCTGGTAGTCCACGCCGTAAACGATGAGTGCTAAGTGTTAG<br>AGGGTTTCCGCCCTTTAGTGCTGAAGTTAACGCATTAAGCACTCCGCC<br>TGGGGAGTACGGCCGCAAGGCTGAAACTCAAAGGAATTGACGGGGG<br>CCCGCACAAGCGGTGGAGCATGTGGTTTAATTCGAAGCAACGCGAAG<br>AACCTTACCAGGTCTTGACATCCTCTGAAAACCCTAGAGATAGGGCTT<br>CCCCTTCGGGGGCAGAGTGACAGGTGGTGCATGGTTGTCGTCAGCTC<br>GTGTCGTGAGATGTTGGGTTAAGTCCCGCAACGAGCGCAACCCTTGA<br>TCTTAGTTGCCATCATTAAGTTGGGCACTCTAAGGTGACTGCCGGTGA<br>CAAACCGGAGGAAGGTGGGGATGACGTCAAATCATCATGCCCCTTAT<br>GACCTGGGCTACACACGTGCTACAATGGACGGTACAAAGAGTCGCAA<br>GACCGCGAGGTGGAGCTAATCTCATAAAACCGTTCTCAGTTCGGATT<br>GTAGGCTGCAACTCGCCTACATGAAGCTGGAATCGCTAGTAATCGCG<br>GATCAGCATGCCGCGGTGAATACGTTCCCGGGCCTTGTACACACCGC<br>CCGTCACACCACGAGAGTTTGTAACACCCGAAGTCGGTGGGGTAACC<br>TTTTGGAGCCAGCCGCCTAAGGTGGGACAGATGATTGGGGTGAAGTC<br>GTAACAAGGTAGCCGTATCGGAAGGTGCGGCTGGATCACCTCCTTT |
| 14 | DP14 16S rRNA | TACGGAGAGTTTGATCCTGGCTCAGGATGAACGCTGGCGGCGTGCTT<br>AACACATGCAAGTCGAACGATGACTTCTGTGCTTGCACAGAATGATT<br>AGTGGCGAACGGGTGAGTAACACGTGAGTAACCTGCCCTTAACTTCG<br>GGATAAGCCTGGGAAACCGGGTCTAATACCGGATACGACCTCCTGGC<br>GCATGCCATGGTGGTGGAAAGCTTTAGCGGTTTTGGATGGACTCGCG<br>GCCTATCAGCTTGTTGGTTGGGGTAATGGCCCACCAAGGCGACGACG<br>GGTAGCCGGCCTGAGAGGGTGACCGGCCACACTGGGACTGAGACACG |

-continued

Sequence Listing

| Seq ID No. | Description | Sequence |
|---|---|---|
| | | GCCCAGACTCCTACGGGAGGCAGCAGTGGGGAATATTGCACAATGGG CGAAAGCCTGATGCAGCGACGCCGCGTGAGGGATGACGGCCTTCGGG TTGTAAACCTCTTTCAGCAGGGAAGAAGCGAAAGTGACGGTACCTGC AGAAGAAGCGCCGGCTAACTACGTGCCAGCAGCCGCGGTAATACGTA GGGCGCAAGCGTTATCCGGAATTATTGGGCGTAAAGAGCTCGTAGGC GGTTTGTCGCGTCTGCTGTGAAAGCCCGGGGCTCAACCCCGGGTCTGC AGTGGGTACGGGCAGACTAGAGTGCAGTAGGGGAGACTGGAATTCCT GGTGTAGCGGTGAAATGCGCAGATATCAGGAGGAACACCGATGGCG AAGGCAGGTCTCTGGGCTGTAACTGACGCTGAGGAGCGAAAGCATGG GGAGCGAACAGGATTAGATACCCTGGTAGTCCATGCCGTAAACGTTG GGCACTAGGTGTGGGGGACATTCCACGTTTTCCGCGCCGTAGCTAAC GCATTAAGTGCCCCGCCTGGGGAGTACGGCCGCAAGGCTAAAACTCA AAGGAATTGACGGGGGCCCGCACAAGCGGCGGAGCATGCGGATTAA TTCGATGCAACGCGAAGAACCTTACCAAGGCTTGACATGAACCGGTA AGACCTGGAAACAGGTCCCCCACTTGTGGCCGGTTTACAGGTGGTGC ATGGTTGTCGTCAGCTCGTGTCGTGAGATGTTGGGTTAAGTCCCGCAA CGAGCGCAACCCTCGTTCTATGTTGCCAGCGGGTTATGCCGGGGACTC ATAGGAGACTGCCGGGGTCAACTCGGAGGAAGGTGGGGACGACGTC AAATCATCATGCCCCTTATGTCTTGGGCTTCACGCATGCTACAATGGC CGGTACAAAGGGTTGCGATACTGTGAGGTGGAGCTAATCCCAAAAAG CCGGTCTCAGTTCGGATTGAGGTCTGCAACTCGACCTCATGAAGTTGG AGTCGCTAGTAATCGCAGATCAGCAACGCTGCGGTGAATACGTTCCC GGGCCTTGTACACACCGCCCGTCAAGTCACGAAAGTTGGTAACACCC GAAGCCGGTGGCCTAACCCCTTGTGGGAGGGAGCCGTCGAAGGTGGG ACCGGCGATTGGGACTAAGTCGTAACAAGGTAGCCGTACCGGAAGGT GCGGCTGGATCACCTCCTTT |
| 15 | DP15 16S rRNA | TACGGAGAGTTTGATCCTGGCTCAGGACGAACGCTGGCGGCGTGCTT AACACATGCAAGTCGAACGATGATCAGGAGCTTGCTCCTGTGATTAG TGGCGAACGGGTGAGTAACACGTGAGTAACCTGCCCCTGACTCTGGG ATAAGCGTTGGAAACGACGTCTAATACTGGATATGATCACTGGCCGC ATGGTCTGGTGGTGGAAAGATTTTTTGGTTGGGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGATGACGGCCTTCGGGTTGT AAACCTCTTTTAGTAGGGAAGAAGCGAAAGTGACGGTACCTGCAGAA AAAGCACCGGCTAACTACGTGCCAGCAGCCGCGGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGCTTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGCGTGGGGAG CGAACAGGATTAGATACCCTGGTAGTCCACGCCGTAAACGTTGGGCG CTAGATGTAGGGACCTTTCCACGGTTTCTGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATACACCGGAAACGGC CAGAGATGGTCGCCCCCTTGTGGTCGGTGTACAGGTGGTGCATGGTTG TCGTCAGCTCGTGTCGTGAGATGTTGGGTTAAGTCCCGCAACGAGCGC AACCCTCGTTCTATGTTGCCAGCGCGTTATGGCGGGGACTCATAGGAG ACTGCCGGGGTCAACTCGGAGGAAGGTGGGGATGACGTCAAATCATC ATGCCCCTTATGTCTTGGGCTTCACGCATGCTACAATGGCCGGTACAA AGGGCTGCGATACCGTAAGGTGGAGCGAATCCCAAAAAGCCGGTCTC AGTTCGGATTGAGGTCTGCAACTCGACCTCATGAAGTCGGAGTCGCT AGTAATCGCAGATCAGCAACGCTGCGGTGAATACGTTCCCGGGCCTT GTACACACCGCCCGTCAAGTCATGAAAGTCGGTAACACCCGAAGCCG GTGGCCTAACCCTTGTGGAAGGAGCCGTCGAAGGTGGGATCGGTGAT TAGGACTAAGTCGTAACAAGGTAGCCGTACCGGAAGGTGCGGCTGGA TCACCTCCTTT |
| 17 | DP17 16S TRNA | GTGATTGACGTTACTCGCAGAAGAAGCACCGGCTAACTCCGTGCCAG CAGCCGCGGTAATACGGAGGGTGCAAGCGTTAATCGGAATTACTGGG CGTAAAGCGCACGCAGGCGGTTTGTTAAGTCAGATGTGAAATCCCCG CGCTTAACGTGGGAACTGCATTTGAAACTGGCAAGCTAGAGTCTTGT AGAGGGGGGTAGAATTCCAGGTGTAGCGGTGAAATGCGTAGAGATCT GGAGGAATACCGGTGGCGAAGGCGGCCCCCTGGACAAAGACTGACG CTCAGGTGCGAAAGCGTGGGGAGCAAACAGGATTAGATACCCTGGTA GTCCACGCTGTAAACGATGTCGACTTGGAGGTTGTGCCCTTGAGGCGT GGCTTCCGGAGCTAACGCGTTAAGTCGACCGCCTGGGGAGTACGGCC GCAAGGTTAAAACTCAAATGAATTGACGGGGGCCCGCACAAGCGGTG GAGCATGTGGTTTAATTCGATGCAACGCGAAGAACCTTACCTACTCTT GACATCCACGGAATTCGCCAGAGATGGCTTAGTGCCTTCGGGAACCG |

-continued

Sequence Listing

| Seq ID No. | Description | Sequence |
|---|---|---|
| | | TGAGACAGGTGCTGCATGGCTGTCGTCAGCTCGTGTTGTGAAATGTTG GGTTAAGTCCCGCAACGAGCGCAACCCTTATCCTTTGTTGCCAGCACG TAATGGTGGGAACTCAAAGGAGACTGCCGGTGATAAACCGGAGGAA GGTGGGGATGACGTCAAGTCATCATGGCCCTTACGAGTAGGGCTACA CACGTGCTACAATGGCATATACAAAGAGAAGCGAACTCGCGAGAGCA AGCGGACCTCATAAAGTATGTCGTAGTCCGGATTGGAGTCTGCAACT CGACTCCATGAAGTCGGAATCGCTAGTAATCGTAGATCAGAATGCTA CGG |
| 18 | DP18 16S rRNA | TGAAGAGTTTGATCATGGCTCAGATTGAACGCTGGCGGCAGGCCTAA CACATGCAAGTCGAGCGGATGAAAGGAGCTTGCTCCTGGATTCAGCG GCGGACGGGTGAGTAATGCCTAGGAATCTGCCTGGTAGTGGGGGACA ACGTTTCGAAAGGAACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCAGTAAATTAATACTTTGCTGTTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTG GTGGAATTTCCTGTGTAGCGGTGAAATGCGTAGATATAGGAAGGAAC ACCAGTGGCGAAGGCGACCACCTGGACTGATACTGACACTGAGGTGC GAAAGCGTGGGGAGCAAACAGGATTAGATACCCTGGTAGTCCACGCC GTAAACGATGTCAACTAGCCGTTGGGAGCCTTGAGCTCTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCCAGAGATGGATTGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTTATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAAAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAAGTAGCTAGTCTAACCTTCGGGAGGACGGTTACCACG GTGTGATTCATGACTGGGGTGAAGTCGTAACAAGGTAGCCGTAGGGG AACCTGCGGCTGGATCACCTCCTT |
| 19 | DP19 16S rRNA | TACGGAGAGTTTGATCCTGGCTCAGGACGAACGCTGGCGGCGTGCTT AACACATGCAAGTCGAACGATGATGCCCAGCTTGCTGGGTGGATTAG TGGCGAACGGGTGAGTAACACGTGAGTAACCTGCCCCTGACTCTGGG ATAAGCGTTGGAAACGACGTCTAATACTGGATATGACTGCCGGCCGC ATGGTCTGGTGGTGGAAAGATTTTTTGGTTGGGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGATGACGGCCTTCGGGTTGT AAACCTCTTTTAGTAGGGAAGAAGGGAGCTTGCTCTTGACGGTACCT GCAGAAAAAGCACCGGCTAACTACGTGCCAGCAGCCGCGGTAATACG TAGGGTGCAAGCGTTGTCCGGAATTATTGGGCGTAAAGAGCTCGTAG GCGGTTTGTCGCGTCTGCTGTGAAATCCCGAGGCTCAACCTCGGGCTT GCAGTGGGTACGGGCAGACTAGAGTGCGGTAGGGGAGATTGGAATTC CTGGTGTAGCGGTGGAATGCGCAGATATCAGGAGGAACACCGATGGC GAAGGCAGATCTCTGGGCCGTAACTGACGCTGAGGAGCGAAAGCATG GGGAGCGAACAGGATTAGATACCCTGGTAGTCCATGCCGTAAACGTT GGGCGCTAGATGTAGGGACCTTTCCACGGTTTCTGTGTCGTAGCTAAC GCATTAAGCGCCCCGCCTGGGGAGTACGGCCGCAAGGCTAAAACTCA AAGGAATTGACGGGGGCCCGCACAAGCGGCGGAGCATGCGGATTAA TTCGATGCAACGCGAAGAACCTTACCAAGGCTTGACATACACCGGAA ACGGCCAGAGATGGTCGCCCCCTTGTGGTCGGTGTACAGGTGGTGCA TGGTTGTCGTCAGCTCGTGTCGTGAGATGTTGGGTTAAGTCCCGCAAC GAGCGCAACCCTCGTTCTATGTTGCCAGCGCGTTATGGCGGGGACTCA TAGGAGACTGCCGGGGTCAACTCGGAGGAAGGTGGGGATGACGTCA AATCATCATGCCCCTTATGTCTTGGGCTTCACGCATGCTACAATGGCC GGTACAAAGGGCTGCGATACCGTAAGGTGGAGCGAATCCCAAAAAG CCGGTCTCAGTTCGGATTGAGGTCTGCAACTCGACCTCATGAAGTCGG AGTCGCTAGTAATCGCAGATCAGCAACGCTGCGGTGAATACGTTCCC GGGCCTTGTACACACCGCCCGTCAAGTCATGAAAGTCGGTAACACCC |

-continued

Sequence Listing

| Seq ID No. | Description | Sequence |
|---|---|---|
| | | GAAGCCGGTGGCCTAACCCTTGTGGAAGGAGCCGTCGAAGGTGGGAT CGGTGATTAGGACTAAGTCGTAACAAGGTAGCCGTACCGGAAGGTGC GGCTGGATCACCTCCTTT |
| 20 | DP20 16S rRNA | TGAAGAGTTTGATCCTGGCTCAGAGTGAACGCTGGCGGTAGGCCTAA CACATGCAAGTCGAACGGCAGCACAGTAAGAGCTTGCTCTTATGGGT GGCGAGTGGCGGACGGGTGAGGAATACATCGGAATCTACCTTTTCGT GGGGGATAACGTAGGGAAACTTACGCTAATACCGCATACGACCTTCG GGTGAAAGCAGGGGACCTTCGGGCCTTGCGCGGATAGATGAGCCGAT GTCGGATTAGCTAGTTGGCGGGGTAAAGGCCCACCAAGGCGACGATC CGTAGCTGGTCTGAGAGGATGATCAGCCACACTGGAACTGAGACACG GTCCAGACTCCTACGGGAGGCAGCAGTGGGGAATATTGGACAATGGG CGCAAGCCTGATCCAGCCATACCGCGTGGGTGAAGAAGGCCTTCGGG TTGTAAAGCCCTTTTGTTGGGAAAGAAAAGCAGTCGGCTAATACCCG GTTGTTCTGACGGTACCCAAAGAATAAGCACCGGCTAACTTCGTGCC AGCAGCCGCGGTAATACGAAGGGTGCAAGCGTTACTCGGAATTACTG GGCGTAAAGCGTGCGTAGGTGGTTGTTTAAGTCTGTTGTGAAAGCCCT GGGCTCAACCTGGGAATTGCAGTGGATACTGGGCGACTAGAGTGTGG TAGAGGGTAGTGGAATTCCCGGTGTAGCAGTGAAATGCGTAGAGATC GGGAGGAACATCCATGGCGAAGGCAGCTACCTGGACCAACACTGACA CTGAGGCACGAAAGCGTGGGGAGCAAACAGGATTAGATACCCTGGTA GTCCACGCCCTAAACGATGCGAACTGGATGTTGGGTGCAATTTGGCA CGCAGTATCGAAGCTAACGCGTTAAGTTCGCCGCCTGGGGAGTACGG TCGCAAGACTGAAACTCAAAGGAATTGACGGGGGCCCGCACAAGCG GTGGAGTATGTGGTTTAATTCGATGCAACGCGAAGAACCTTACCTGGT CTTGACATGTCGAGAACTTTCCAGAGATGGATTGGTGCCTTCGGGAAC TCGAACACAGGTGCTGCATGGCTGTCGTCAGCTCGTGTCGTGAGATGT TGGGTTAAGTCCCGCAACGAGCGCAACCCTTGTCCTTAGTTGCCAGCA CGTAATGGTGGGAACTCTAAGGAGACCGCCGGTGACAAACCGGAGG AAGGTGGGGATGACGTCAAGTCATCATGGCCCTTACGACCAGGGCTA CACACGTACTACAATGGTAGGGACAGAGGGCTGCAAACCCGCGAGG GCAAGCCAATCCCAGAAACCCTATCTCAGTCCGGATTGGAGTCTGCA ACTCGACTCCATGAAGTCGGAATCGCTAGTAATCGCAGATCAGCATT GCTGCGGTGAATACGTTCCCGGGCCTTGTACACACCGCCCGTCACACC ATGGGAGTTTGTTGCACCAGAAGCAGGTAGCTTAACCTTCGGGAGGG CGCTTGCCACGGTGTGGCCGATGACTGGGGTGAAGTCGTAACAAGGT AGCCGTATCGGAAGGTGCGGCTGGATCACCTCCTTT |
| 22 | DP22 16S rRNA | TTGAAGAGTTTGATCATGGCTCAGATTGAACGCTGGCGGCAGGCCTA ACACATGCAAGTCGAGCGGTAGCACAGGAGAGCTTGCTCTCCGGGTG ACGAGCGGCGGACGGGTGAGTAATGTCTGGGAAACTGCCTGATGGAG GGGGATAACTACTGGAAACGGTAGCTAATACCGCATGACGTCGCAAG ACCAAAGTGGGGGACCTTCGGGCCTCACGCCATCGGATGTGCCCAGA TGGGATTAGCTAGTAGGTGAGGTAATGGCTCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTGTGAAGAAGGCCTTAGGGT TGTAAAGCACTTTCAGCGAGGAGGAAGGCGTTGCAGTTAATAGCTGC AGCGATTGACGTTACTCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTTTGTTAAGTCAGATGTGAAATCCCC GAGCTTAACTTGGGAACTGCATTTGAAACTGGCAAGCTAGAGTCTTGT AGAGGGGGGTAGAATTCCAGGTGTAGCGGTGAAATGCGTAGAGATCT GGAGGAATACCGGTGGCGAAGGCGGCCCCCTGGACAAAGACTGACG CTCAGGTGCGAAAGCGTGGGGAGCAAACAGGATTAGATACCCTGGTA GTCCACGCTGTAAACGATGTCGACTTGGAGGTTGTGCCCTTGAGGCGT GGCTTCCGGAGCTAACGCGTTAAGTCGACCGCCTGGGGAGTACGGCC GCAAGGTTAAAACTCAAATGAATTGACGGGGGCCCGCACAAGCGGTG GAGCATGTGGTTTAATTCGATGCAACGCGAAGAACCTTACCTACTCTT GACATCCAGAGAATTCGCTAGAGATAGCTTAGTGCCTTCGGGAACTC TGAGACAGGTGCTGCATGGCTGTCGTCAGCTCGTGTTGTGAAATGTTG GGTTAAGTCCCGCAACGAGCGCAACCCTTATCCTTTGTTGCCAGCACG TAATGGTGGGAACTCAAAGGAGACTGCCGGTGATAAACCGGAGGAA GGTGGGGATGACGTCAAGTCATCATGGCCCTTACGAGTAGGGCTACA CACGTGCTACAATGGCATATACAAAGAGAAGCGAACTCGCGAGAGCA AGCGGACCTCATAAAGTATGTCGTAGTCCGGATTGGAGTCTGCAACT CGACTCCATGAAGTCGGAATCGCTAGTAATCGTAGATCAGAATGCTA CGGTGAATACGTTCCCGGGCCTTGTACACACCGCCCGTCACACCATGG GAGTGGGTTGCAAAAGAAGTAGGTAGCTTAACCTTCGGGAGGGCGCT TACCACTTTGTGATTCATGACTGGGGTGAAGTCGTAACAAGGTAACC GTAGGGGAACCTGCGGTTGGATCACCTCCTT |

-continued

Sequence Listing

| Seq ID No. | Description | Sequence |
|---|---|---|
| 23 | DP23 16S rRNA | TTGAAGAGTTTGATCATGGCTCAGATTGAACGCTGGCGGCAGGCCTA ACACATGCAAGTCGAACGGTAGCACAGAGAGCTTGCTCTTGGGTGAC GAGTGGCGGACGGGTGAGTAATGTCTGGGAAACTGCCCGATGGAGGG GGATAACTACTGGAAACGGTAGCTAATACCGCATAACGTCTTCGGAC CAAAGTGGGGGACCTTCGGGCCTCACACCATCGGATGTGCCCAGATG GGATTAGCTAGTAGGTGGGGTAATGGCTCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATACGGTTAATAACCGTGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTCAAGTCAGATGTGAAATCCCCGG GCTTAACCTGGGAACTGCATTTGAAACTGGCAGGCTTGAGTCTCGTAG AGGGGGGTAGAATTCCAGGTGTAGCGGTGAAATGCGTAGAGATCTGG AGGAATACCGGTGGCGAAGGCGGCCCCCTGGACGAAGACTGACGCTC AGGTGCGAAAGCGTGGGGAGCAAACAGGATTAGATACCCTGGTAGTC CACGCTGTAAACGATGTCGACTTGGAGGTTGTGCCCTTGAGGCGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTGGCCTTGA CATCCACAGAATTCGGCAGAGATGCCTTAGTGCCTTCGGGAACTGTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGGCCAGGGCTACACAC GTGCTACAATGGCGCATACAAAGAGAAGCGACCTCGCGAGAGCAAG CGGACCTCATAAAGTGCGTCGTAGTCCGGATCGGAGTCTGCAACTCG ACTCCGTGAAGTCGGAATCGCTAGTAATCGTAGATCAGAATGCTACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATGACTGGGGTGAAGTCGTAACAAGGTAACCG TAGGGGAACCTGCGGTTGGATCACCTCCTT |
| 24 | DP24 18S rRNA | CGGGGAATTAGGGTTCGATTCCGGAGAGGGAGCCTGAGAAACGGCTA CCACATCCAAGGAAGGCAGCAGGCGCGCAAATTACCCAATCCCGACA CGGGGAGGTAGTGACAATAAATAACAATACAGGGCCCTTTGGGTCTT GTAATTGGAATGAGTACAATTTAAATCCCTTAACGAGGAACAATTGG AGGGCAAGTCTGGTGCCAGCAGCCGCGGTAATTCCAGCTCCAATAGC GTATATTAAAGTTGTTGCAGTTAAAAAGCTCGTAGTTGAACTTCAGGC TTGGCGGGGTGGTCTGCCTCACGGTATGTACTATCCGGCTGAGCCTTA CCTCCTGGTGAGCCTGCATGTCGTTTATTCGGTGTGTAGGGGAACCAG GAATTTTACTTTGAAAAAATTAGAGTGTTCAAAGCAGGCATATGCCC GAATACATTAGCATGGAATAATAGAATAGGACGTGCGGTTCTATTTT GTTGGTTTCTAGGATCGCCGTAATGATTAATAGGGACGGTTGGGGGC ATTAGTATTCAGTTGCTAGAGGTGAAATTCTTAGATTTACTGAAGACT AACTACTGCGAAAGCATTTGCCAAGGACGTTTTCATTAATCAAGAAC GAAGGTTAGGGGATCAAAAACGATTAGATACCGTTGTAGTCTTAACA GTAAACTATGCCGACTAGGGATCGGGCCACGTTCATCTTTTGACTGGC TCGGCACCTTACGAGAAATCAAAGTCTTTGGGTTCTGGGGGGAGTAT GGTCGCAAGGCTGAAACTTAAAGGAATTGACGGAAGGGCACCACCA GGCGTGGAGCCTGCGGCTTAATTTGACTCAACACGGGGAAACTCACC AGGTCCAGACATAGTAAGGATTGACAGATTGATAGCTCTTTCTTGATT CTATGGGTGGTGGTGCATGGCCGTTCTTAGTTGGTGGAGTGATTTGTC TGGTTAATTCCGATAACGAACGAGACCTTAACCTGCTAAATAGTCCG GCCGGCTTCGGCTGGTCGCTGACTTCTTAGAGGGACTAACAGCGTTTA GCTGTTGGAAGTTTGAGGCAATAACAGGTCTGTGATGCCCTTAGATGT TCTGGGCCGCACGCGCGCTACACTGACTGAGCCAGCGAGTTTATAAC CTTGGCCGAAAGGTCTGGGTAATCTTGTGAAACTCAGTCGTGCTGGG GATAGAGCATTGCAATTATTGCTCTTCAACGAGGAATGCCTAGTAAG CGTGAGTCATCAGCTCACGTTGATTACGTCCCTGCCCTTTGTACACAC CGCCCGTCGCTACTACCGATTGAATGGCTTAGTGAGATCTCCGGATTG GCTTTGGGAAGCTGGCAACGGCTACCTATTGCTGAAAAGCTGATCAA ACTTGGTCATTTAGAGGAAGTAAAAGTCGTAACAAGGTTTCCGTAGG TGAACCTGCGGAAGGATCATT |
| 26 | DP26 16S rRNA | CTTGAGAGTTTGATCCTGGCTCAGAGCGAACGCTGGCGGCAGGCTTA ACACATGCAAGTCGAGCGGGCATCTTCGGATGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG |

-continued

Sequence Listing

| Seq ID No. | Description | Sequence |
|---|---|---|
| | | AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTATGGTAGAGGTTG GTGGAACTGCGAGTGTAGAGGTGAAATTCGTAGATATTCGCAAGAAC ACCGGTGGCGAAGGCGGCCAACTGGACCATTACTGACGCTGAGGCGC GAAAGCGTGGGGAGCAAACAGGATTAGATACCCTGGTAGTCCACGCC GTAAACGATGAATGCCAGCTGTTGGGGTGCTTGCACCTCAGTAGCGC AGCTAACGCTTTAAGCATTCCGCCTGGGGAGTACGGTCGCAAGATTA AAACTCAAAGGAATTGACGGGGGCCCGCACAAGCGGTGGAGCATGT GGTTTAATTCGAAGCAACGCGCAGAACCTTACCATCCCTTGACATGGC ATGTTACCCGGAGAGATTCGGGGTCCACTTCGGTGGCGTGCACACAG GTGCTGCATGGCTGTCGTCAGCTCGTGTCGTGAGATGTTGGGTTAAGT CCCGCAACGAGCGCAACCCACGTCCTTAGTTGCCATCATTCAGTTGGG CACTCTAGGGAGACTGCCGGTGATAAGCCGCGAGGAAGGTGTGGATG ACGTCAAGTCCTCATGGCCCTTACGGGATGGGCTACACACGTGCTAC AATGGCGGTGACAGTGGGACGCGAAGGAGCGATCTGGAGCAAATCC CCAAAAACCGTCTCAGTTCAGATTGCACTCTGCAACTCGAGTGCATGA AGGCGGAATCGCTAGTAATCGTGGATCAGCATGCCACGGTGAATACG TTCCCGGGCCTTGTACACACCGCCCGTCACACCATGGGAGTTGGTCTT ACCCGACGGCGCTGCGCCAACCGCAAGGAGGCAGGCGACCACGGTA GGGTCAGCGACTGGGGTGAAGTCGTAACAAGGTAGCCGTAGGGGAA CCTGCGGCTGGATCACCTCCTTT |
| 27 | DP27 16S rRNA | CTTGAGAGTTTGATCCTGGCTCAGAACGAACGCTGGCGGCATGCCTA ACACATGCAAGTCGAACGATGCTTTCGGGCATAGTGGCGCACGGGTG CGTAACGCGTGGGAATCTGCCCTCAGGTTCGGAATAACAGCTGGAAA CGGCTGCTAATACCGGATGATATCGCAAGATCAAAGATTTATCGCCT GAGGATGAGCCCGCGTTGGATTAGGTAGTTGGTGGGGTAAAGGCCTA CCAAGCCGACGATCCATAGCTGGTCTGAGAGGATGATCAGCCACACT GGGACTGAGACACGGCCCAGACTCCTACGGGAGGCAGCAGTGGGGA ATATTGGACAATGGGCGCAAGCCTGATCCAGCAATGCCGCGTGAGTG ATGAAGGCCCTAGGGTTGTAAAGCTCTTTTACCCGGGAAGATAATGA CTGTACCGGGAGAATAAGCCCCGGCTAACTCCGTGCCAGCAGCCGCG GTAATACGGAGGGGGCTAGCGTTGTTCGGAATTACTGGGCGTAAAGC GCACGTAGGCGGCTTTGTAAGTCAGAGGTGAAAGCCTGGAGCTCAAC TCCAGAACTGCCTTTGAGACTGCATCGCTTGAATCCAGGAGAGGTCA GTGGAATTCCGAGTGTAGAGGTGAAATTCGTAGATATTCGGAAGAAC ACCAGTGGCGAAGGCGGCTGACTGGACTGGTATTGACGCTGAGGTGC GAAAGCGTGGGGAGCAAACAGGATTAGATACCCTGGTAGTCCACGCC GTAAACGATGATAACTAGCTGTCCGGGCACTTGGTGCTTGGGTGGCG CAGCTAACGCATTAAGTTATCCGCCTGGGGAGTACGGCCGCAAGGTT AAAACTCAAAGGAATTGACGGGGGCCTGCACAAGCGGTGGAGCATGT GGTTTAATTCGAAGCAACGCGCAGAACCTTACCAGCGTTTGAC |
| 28 | DP28 18S rRNA | ATAGTCGGGGGCATCAGTATTCAATTGTCAGAGGTGAAATTCTTGGAT TTATTGAAGACTAACTACTGCGAAAGCATTTGCCAAGGATGTTTTCAT TAATCAGTGAACGAAAGTTAGGGGATCGAAGACGATCAGATACCGTC GTAGTCTTAACCATAAACTATGCCGACTAGGGATCGGGCGATGTTATC ATTTTGACTCGCTCGGCACCTTACGAGAAATCAAAGTCTTTGGGTTCT GGGGGGAGTATGGTCGCAAGGCTGAAACTTAAAGAAATTGACGGAA GGGCACCACCAGGCGTGGAGCCTGCGGCTTAATTTGACTCAACACGG GGAAACTCACCAGGTCCAGACACAATAAGGATTGACAGATTGAGAGC TCTTTCTTGATTTTGTGGGTGGTGGTGCATGGCCGTTCTTAGTTGGTGG AGTGATTTGTCTGCTTAATTGCGATAACGAACGAGACCTTAACCTGCT AAATAGCCCGGCCCGCTTTGGCGGGTCGCCGGCTTCTTAGAGGGACT ATCGGCTCAAGCCGATGGAAGTTTGAGGCAATAACAGGTCTGTGATG CCCTTAGATGTTCTGGGCCGCACGCGCGCTACACTGACAGAGCCAAC GAGTTCATTTCCTTGCCCGGAAGGGTTGGGTAATCTTGTTAAACTCTG TCGTGCTGGGGATAGAGCATTGCAATTATTGCTCTTCAACGAGGAATG CCTAGTAAGCGTACGTCATCAGCGTGCGTTGATTACGTCCCTGCCCTT TGTACACACCGCCCGTCGCTACTACCGATTGAATGGCTGAGTGAGGC CTTCGGACTGGCCCAGGGAGGTCGGCAACGACCACCCAGGGCCGGAA AGTTGGTCAAACTCCGTCATTTAGAGGAAGTAAAAGTCGTAACAAGG TTTCCGTAGGTGAACCTGCGGAAGGATCA |
| 29 | DP29 16S rRNA | TACGGAGAGTTTGATCCTGGCTCAGGACGAACGCTGGCGGCGTGCTT AACACATGCAAGTCGAACGATGAAGCCCAGCTTGCTGGGTTGATTAG TGGCGAACGGGTGAGTAACACGTGAGCAACGTGCCCATAACTCTGGG ATAACCTCCGGAAACGGTGGCTAATACTGGATATCTAACACGATCGC ATGGTCTGTGTTTGGAAAGATTTTTTGGTTATGGATCGGCTCACGGCC |

-continued

Sequence Listing

| Seq ID No. | Description | Sequence |
|---|---|---|
| | | TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGATGACGGCATTCGGGTTGT AAACCTCTTTTAGTAGGGAAGAAGCGAAAGTGACGGTACCTGCAGAA AAAGCACCGGCTAACTACGTGCCAGCAGCCGCTGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGTCTGCAGTG GGTACGGGCAGACTAGAGTGTGGTAGGGGAGATTGGAATTCCTGGTG TAGCGGTGGAATGCGCAGATATCAGGAGGAACACCGATGGCGAAGG CAGATCTCTGGGCCATTACTGACGCTGAGGAGCGAAAGCATGGGGAG CGAACAGGATTAGATACCCTGGTAGTCCATGCCGTAAACGTTGGGCG CTAGATGTGGGGACCATTCCACGGTTTCCGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATATACCGGAAACGTT CAGAAATGTTCGCC |
| 30 | DP30 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGACGTGATCGC ATGGTCGTGTTTGGAAAGATTTTTCGGTCTGGGATGGGCTCGCGGCCT ATCAGCTTGTTGGTGAGGTAATGGCTCACCAAGGCGTCGACGGGTAG CCGGCCTGAGAGGGTGACCGGCCACACTGGGACTGAGACACGGCCCA GACTCCTACGGGAGGCAGCAGTGGGGAATATTGCACAATGGGCGAAA GCCTGATGCAGCAACGCCGCGTGAGGGATGACGGCCTTCGGGTTGTA AACCTCTTTTAGCAGGGAAGAAGCGAAAGTGACGGTACCTGCAGAAA AAGCGCCGGCTAACTACGTGCCAGCAGCCGCGGTAATACGTAGGGCG CAAGCGTTATCCGGAATTATTGGGCGTAAAGAGCTCGTAGGCGGTTT GTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATATACGAGAACGGGCC AGAAATGGTCAACTCTTTGGACACTCGTAAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTGAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGTCGGTAACACCTGAAGC CGGTGGCCCAACCCTTGTGGAGGGAGCCGTCGAAGGTGGGATCGGTA ATTAGGACTAAGTCGTAACAAGGTAGCCGTACCGGAAGGTGCGGCTG GATCACCTCCTTT |
| 31 | DP31 16S rRNA | CAGCCGGGGGCATTAGTATTTGCACGCTAGAGGTGAAATTCTTGGATT GTGCAAAGACTTCCTACTGCGAAAGCATTTGCCAAGAATGTTTTCATT AATCAAGAACGAAGGTTAGGGTATCGAAAACGATTAGATACCGTTGT AGTCTTAACAGTAAACTATGCCGACTCCGAATCGGTCGATGCTCATTT CACTGGCTCGATCGGCGCGGTACGAGAAATCAAAGTTTTTGGGTTCTG GGGGGAGTATGGTCGCAAGGCTGAAACTTAAAGAAATTGACGGAAG GGCACCACCAGGAGTGGAGCCTGCGGCTTAATTTGACTCAACACGGG AAAACTCACCGGGTCCGGACATAGTAAGGATTGACAGATTGATGGCG CTTTCATGATTCTATGGGTGGTGGTGCATGGCCGTTCTTAGTTGGTGG AGTGATTTGTCTGGTTAATTCCGATAACGAACGAGACCTTGACCTGCT AAATAGACGGGTTGACATTTTGTTGGCCCCTTATGTCTTCTTAGAGGG ACAATCGACCGTCTAGGTGATGGAGGCAAAAGGCAATAACAGGTCTG TGATGCCCTTAGATGTTCCGGGCTGCACGCGCGCTACACTGACAGAG ACAACGAGTGGGGCCCCTTGTCCGAAATGACTGGGTAAACTTGTGAA ACTTTGTCGTGCTGGGGATGGAGCTTTGTAATTTTTGCTCTTCAACGA GGAATTCCTAGTAAGCGCAAGTCATCAGCTTGCGTTGACTACGTCCCT GCCCTTTGTACACACCGCCCGTCGCTACTACCGATTGAATGGCTTAGT GAGGACTTGGGAGAGTACATCGGGGAGCCAGCAATGGCACCCTGACG GCTCAAACTCTTACAAACTTGGTCATTTAGAGGAAGTAAAAGTCGTA ACAAGGTATCTGTAGGTGAACCTGCAGATGGATCATTTC |

-continued

Sequence Listing

| Seq ID No. | Description | Sequence |
|---|---|---|
| 32 | DP32 16S rRNA | ACTGAGCATTGACGTTACTCGCAGAAGAAGCACCGGCTAACTCCGTG CCAGCAGCCGCGGTAATACGGAGGGTGCAAGCGTTAATCGGAATTAC TGGGCGTAAAGCGCACGCAGGCGGTTTGTTAAGTCAGATGTGAAATC CCCGAGCTTAACTTGGGAACTGCATTTGAAACTGGCAAGCTAGAGTC TTGTAGAGGGGGGTAGAATTCCAGGTGTAGCGGTGAAATGCGTAGAG ATCTGGAGGAATACCGGTGGCGAAGGCGGCCCCCTGGACAAAGACTG ACGCTCAGGTGCGAAAGCGTGGGGAGCAAACAGGATTAGATACCCTG GTAGTCCACGCTGTAAACGATGTCGACTTGGAGGTTGTGCCCTTGAGG CGTGGCTTCCGGAGCTAACGCGTTAAGTCGACCGCCTGGGGAGTACG GCCGCAAGGTTAAAACTCAAATGAATTGACGGGGGCCCGCACAAGCG GTGGAGCATGTGGTTTAATTCGATGCAACGCGAAGAACCTTACCTACT CTTGACATCCAGAGAATTCGCTAGAGATAGCTTAGTGCCTTCGGGAA CTCTGAGACAGGTGCTGCATGGCTGTCGTCAGCTCGTGTTGTGAAATG TTGGGTTAAGTCCCGCAACGAGCGCAACCCTTATCCTTTGTTGCCAGC GAGTAATGTCGGGAACTCAAAGGAGACTGCCGGTGATAAACCGGAG GAAGGTGGGGATGACGTCAAGTCATCATGGCCCTTACGAGTAGGGCT ACACACGTGCTACAATGGCATATACAAAGAGAAGCGAACTCGCGAGA GCAAGCGGACCTCATAAAGTATGTCGTAGTCCGGATTGGAGTCTGCA ACTCGACTCCATGAAGTCGGAATCGCTAGTAATCGTAGATCAGAATG CTACGGTGAATACGTTCCCGGGCCTTGTACACACCGCCCGTCACACCA TGGGAGTGGGTTGCAAAAGAAGTAGGTAGCTTAACCTTCGGGAGGGC GCTTACCACTTTGTGATTCATGACTGGGGTGAAGTCGTAACAAGGTAA CCGTAGGGGAACCTGCGGTTGGATCACCTCCTT |
| 33 | DP33 16S rRNA | GGAGGAAGGCGTAGAGATCTGGAGGAATACCGGTGGCGAAGGCGGC CCCCTGGACAAAGACTGACGCTCAGGTGCGAAAGCGTGGGGAGCAA ACAGGATTAGATACCCTGGTAGTCCACGCCGTAAACGATGTCGACTT GGAGGTTGTGCCCTTGAGGCGTGGCTTCCGGAGCTAACGCGTTAAGT CGACCGCCTGGGGAGTACGGCCGCAAGGTTAAAACTCAAATGAATTG ACGGGGGCCCGCACAAGCGGTGGAGCATGTGGTTTAATTCGATGCAA CGCGAAGAACCTTACCTGGCCTTGACATCCACGGAATTCGGCAGAGA TGCCTTAGTGCCTTCGGGAACCGTGAGACAGGTGCTGCATGGCTGTCG TCAGCTCGTGTTGTGAAATGTTGGGTTAAGTCCCGCAACGAGCGCAA CCCTTATCCTTTGTTGCCAGCACGTAATGGTGGGAACTCAAAGGAGAC TGCCGGTGATAAACCGGAGGAAGGTGGGGATGACGTCAAGTCATCAT GGCCCTTACGGCCAGGGCTACACACGTGCTACAATGGCGCATACAAA GAGAAGCGACCTCGCGAGAGCAAGCGGACCTCATAAAGTGCGTCGTA GTCCGGATCGGAGTCTGCAACTCGACTCCGTGAAGTCGGAATCGCTA GTAATCGTAGATCAGAATGCTACGGTGAATACGTTCCCGGGCCTTGTA CACACCGCCCGTCACACCATGGGAGTGGGTTGCAAAAGAAGTAGGTA GCTTAACCTTCGGGAGGGCGCTTACCACTTTGTGATTCATGACTGGGG TGAAGTCGTAACAAGGTAACCGTAGGGGAACCTGCGGTTGGATCACC TCCTT |
| 34 | DP34 16S rRNA | TACGGAGAGTTTGATCCTGGCTCAGGACGAACGCTGGCGGCGTGCTT AACACATGCAAGTCGAACGATGAAGCCCAGCTTGCTGGGTGGATTAG TGGCGAACGGGTGAGTAACACGTGAGTAACCTGCCCTTGACTCTGGG ATAAGCGTTGGAAACGACGTCTAATACCGGATACGAGCTTCCACCGC ATGGTGAGTTGCTGGAAAGAATTTTGGTCAAGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGACGACGGCCTTCGGGTTGT AAACCTCTTTTAGCAGGGAAGAAGCGAAAGTGACGGTACCTGCAGAA AAAGCACCGGCTAACTACGTGCCAGCAGCCGCGGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGTCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGCTACTGACGCTGAGGAGCGAAAGGGTGGGGAG CAAACAGGCTTAGATACCCTGGTAGTCCACCCCGTAAACGTTGGGCG CTAGATGTGGGGACCATTCCACGGTTTCCGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATATACGAGAACGGGC CAGAAATGGTCAACTCTTTGGACACTCGTAAACAGGTGGTGCATGGT TGTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGACGACGTCAAATCA TCATGCCCCTTATGTCTTGGGCTTCACGCATGCTACAATGGCCAGTAC AAAGGGCTGCAATACCGTAAGGTGGAGCGAATCCCAAAAAGCTGGTC CCAGTTCGGATTGAGGTCTGCAACTCGACCTCATGAAGTCGGAGTCG CTAGTAATCGCAGATCAGCAACGCTGCGGTGAATACGTTCCCGGGCC |

-continued

Sequence Listing

| Seq ID No. | Description | Sequence |
|---|---|---|
| | | TTGTACACACCGCCCGTCAAGTCATGAAAGTCGGTAACACCCGAAGC CAGTGGCCTAACCGCAAGGATGGAGCTGTCTAAGGTGGGATCGGTAA TTAGGACTAAGTCGTAACAAGGTAGCCGTACCGGAAGGTGCGGCTGG ATCACCTCCTTT |
| 35 | DP35 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGAGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATCCAGCGAACTTAGCAGAGATGCTTTGGTGCCTTCGGGAACGCTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGAGTAGGGCTACACAC GTGCTACAATGGCGCATACAAAGAGAAGCGACCTCGCGAGAGCAAG CGGACCTCACAAAGTGCGTCGTAGTCCGGATCGGAGTCTGCAACTCG ACTCCGTGAAGTCGGAATCGCTAGTAATCGTGGATCAGAATGCCACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATTACTGGGGTGAAGTCGTAACAAGGTAACCGT AGGGGAACCTGCGGTTGGATCACCTCCTT |
| 36 | DP36 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGCGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATC |
| 37 | DP37 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGAACGCTAATACCGCATACGTCCTACGGGAGAAAG CAGGGGACCTTCGGGCCTTGCGCTATCAGATGAGCCTAGGTCGGATT AGCTAGTTGGTGGGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCATTACCTAATACGTGATGGTTTTG ACGTTACCGACAGAATAAGCACCGGCTAACTCTGTGCCAGCAGCCGC |

-continued

Sequence Listing

| Seq ID No. | Description | Sequence |
|---|---|---|
| | | GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC ACCAGTGGCGAAGGCGACCACCTGGACTGATACTGACACTGAGGTGC GAAAGCGTGGGGAGCAAACAGGATTAGATACCCTGGTAGTCCACGCC GTAAACGATGTCAACTAGCCGTTGGGAGCCTTGAGCTCTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCTAGAGATAGATTGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTAATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAGAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAAGTAGCTAGTCTAACCTTCGGGGGGACGGTTACCACG GTGTGATTCATGACTGGGGTGAAGTCGTAACAAGGTAGCCGTAGGGG AACCTGCGGCTGGATCACCTCCTT |
| 38 | DP38 16S TRNA | TACGGAGAGTTTGATCCTGGCTCAGGACGAACGCTGGCGGCGTGCTT AACACATGCAAGTCGAGCGGTAAGGCCTTTCGGGGTACACGAGCGGC GAACGGGTGAGTAACACGTGGGTGATCTGCCCTGCACTCTGGGATAA GCTTGGGAAACTGGGTCTAATACCGGATATGACCACAGCATGCATGT GTTGTGGTGGAAAGATTTATCGGTGCAGGATGGGCCCGCGGCCTATC AGCTTGTTGGTGGGGTAATGGCCTACCAAGGCGACGACGGGTAGCCG ACCTGAGAGGGTGACCGGCCACACTGGGACTGAGACACGGCCCAGAC TCCTACGGGAGGCAGCAGTGGGGAATATTGCACAATGGGCGGAAGCC TGATGCAGCGACGCCGCGTGAGGGATGAAGGCCTTCGGGTTGTAAAC CTCTTTCAGCAGGGACGAAGCGTGAGTGACGGTACCTGCAGAAGAAG CACCGGCTAACTACGTGCCAGCAGCCGCGGTAATACGTAGGGTGCGA GCGTTGTCCGGAATTACTGGGCGTAAAGAGTTCGTAGGCGGTTTGTCG CGTCGTTTGTGAAAACCCGGGGCTCAACTTCGGGCTTGCAGGCGATA CGGGCAGACTTGAGTGTTTCAGGGGAGACTGGAATTCCTGGTGTAGC GGTGAAATGCGCAGATATCAGGAGGAACACCGGTGGCGAAGGCGGG TCTCTGGGAAACAACTGACGCTGAGGAACGAAAGCGTGGGTAGCAAA CAGGATTAGATACCCTGGTAGTCCACGCCGTAAACGGTGGGCGCTAG GTGTGGGTTCCTTCCACGGGATCTGTGCCGTAGCTAACGCATTAAGCG CCCCGCCTGGGGAGTACGGCCGCAAGGCTAAAACTCAAAGGAATTGA CGGGGGCCCGCACAAGCGGCGGAGCATGTGGATTAATTCGATGCAAC GCGAAGAACCTTACCTGGGTTTGACATACACCGGAAAACCGTAGAGA TACGGTCCCCCTTGTGGTCGGTGTACAGGTGGTGCATGGCTGTCGTCA GCTCGTGTCGTGAGATGTTGGGTTAAGTCCCGCAACGAGCGCAACCC TTGTCTTATGTTGCCAGCACGTAATGGTGGGGACTCGTAAGAGACTGC CGGGGTCAACTCGGAGGAAGGTGGGGACGACGTCAAGTCATCATGCC CCTTATGTCCAGGGCTTCACACATGCTACAATGGCCAGTACAGAGGG CTGCGAGACCGTGAGGTGGAGCGAATCCCTTAAAGCTGGTCTCAGTT CGGATCGGGGTCTGCAACTCGACCCCGTGAAGTCGGAGTCGCTAGTA ATCGCAGATCAGCAACGCTGCGGTGAATACGTTCCCGGGCCTTGTAC ACACCGCCCGTCACGTCATGAAAGTCGGTAACACCCGAAGCCGGTGG CCTAACCCCTTACGGGGAGGGAGCCGTCGAAGGTGGGATCGGCGATT GGGACGAAGTCGTAACAAGGTAGCCGTACCGGAAGGTGCGGCTGGAT CACCTCCTTT |
| 39 | DP39 16S rRNA | CTTGAGAGTTTGATCCTGGCTCAGAACGAACGCTGGCGGCAGGCTTA ACACATGCAAGTCGAACGCCCCGCAAGGGGAGTGGCAGACGGGTGA GTAACGCGTGGGAATCTACCGTGCCCTGCGGAATAGCTCCGGGAAAC TGGAATTAATACCGCATACGCCCTACGGGGGAAAGATTTATCGGGGT ATGATGAGCCCGCGTTGGATTAGCTAGTTGGTGGGGTAAAGGCCTAC CAAGGCGACGATCCATAGCTGGTCTGAGAGGATGATCAGCCACATTG GGACTGAGACACGGCCCAAACTCCTACGGGAGGCAGCAGTGGGGAA TATTGGACAATGGGCGCAAGCCTGATCCAGCCATGCCGCGTGAGTGA TGAAGGCCTTAGGGTTGTAAAGCTCTTTCACCGGAGAAGATAATGAC GGTATCCGGAGAAGAAGCCCCGGCTAACTTCGTGCCAGCAGCCGCGG TAATACGAAGGGGGCTAGCGTTGTTCGGAATTACTGGGCGTAAAGCG CACGTAGGCGGATATTTAAGTCAGGGGTGAAATCCCAGAGCTCAACT CTGGAACTGCCTTTGATACTGGGTATCTTGAGTATGGAAGAGGTAAGT GGAATTCCGAGTGTAGAGGTGAAATTCGTAGATATTCGGAGGAACAC CAGTGGCGAAGGCGGCTTACTGGTCCATTACTGACGCTGAGGTGCGA AAGCGTGGGGAGCAAACAGGATTAGATACCCTGGTAGTCCACGCCGT |

-continued

Sequence Listing

| Seq ID No. | Description | Sequence |
|---|---|---|
| | | AAACGATGAATGTTAGCCGTCGGGCAGTATACTGTTCGGTGGCGCAG CTAACGCATTAAACATTCCGCCTGGGGAGTACGGTCGCAAGATTAAA ACTCAAAGGAATTGACGGGGGCCCGCACAAGCGGTGGAGCATGTGGT TTAATTCGAAGCAACGCGCAGAACCTTACCAGCTCTTGACATTCGGG GTTTGGGCAGTGGAGACATTGTCCTTCAGTTAGGCTGGCCCCAGAAC AGGTGCTGCATGGCTGTCGTCAGCTCGTGTCGTGAGATGTTGGGTTAA GTCCCGCAACGAGCGCAACCCTCGCCCTTAGTTGCCAGCATTTAGTTG GGCACTCTAAGGGGACTGCCGGTGATAAGCCGAGAGGAAGGTGGGG ATGACGTCAAGTCCTCATGGCCCTTACGGGCTGGGCTACACACGTGCT ACAATGGTGGTGACAGTGGGCAGCGAGACAGCGATGTCGAGCTAATC TCCAAAAGCCATCTCAGTTCGGATTGCACTCTGCAACTCGAGTGCATG AAGTTGGAATCGCTAGTAATCGCAGATCAGCATGCTGCGGTGAATAC GTTCCCGGGCCTTGTACACACCGCCCGTCACACCATGGGAGTTGGTTT TACCCGAAGGTAGTGCGCTAACCGCAAGGAGGCAGCTAACCACGGTA GGGTCAGCGACTGGGGTGAAGTCGTAACAAGGTAGCCGTAGGGGAA CCTGCGGCTGGATCACCTCCTTT |
| 40 | DP40 16S rRNA | TTGACGTTACCCGCAGAAGAAGCACCGGCTAACTCCGTGCCAGCAGC CGCGGTAATACGGAGGGTGCAAGCGTTAATCGGAATTACTGGGCGTA AAGCGCACGCAGGCGGTCTGTTAAGTCAGATGTGAAATCCCCGGGCT TAACCTGGGAACTGCATTTGAAACTGGCAGGCTTGAGTCTTGTAGAG GGGGGTAGAATTCCAGGTGTAGCGGTGAAATGCGTAGAGATCTGGAG GAATACCGGTGGCGAAGGCGGCCCCCTGGACAAAGACTGACGCTCAG GTGCGAAAGCGTGGGGAGCAAACAGGATTAGATACCCTGGTAGTCCA CGCCGTAAACGATGTCGACTTGGAGGTTGTTCCCTTGAGGAGTGGCTT CCGGAGCTAACGCGTTAAGTCGACCGCCTGGGGAGTACGGCCGCAAG GTTAAAACTCAAATGAATTGACGGGGGCCCGCACAAGCGGTGGAGCA TGTGGTTTAATTCGATGCAACGCGAAGAACCTTACCTACTCTTGACAT CCAGAGAACTTTCCAGAGATGGATTGGTGCCTTCGGGAACTCTGAGA CAGGTGCTGCATGGCTGTCGTCAGCTCGTGTTGTGAAATGTTGGGTTA AGTCCCGCAACGAGCGCAACCCTTATCCTTTGTTGCCAGCGCGTGATG GCGGGAACTCAAAGGAGACTGCCGGTGATAAACCGGAGGAAGGTGG GGATGACGTCAAGTCATCATGGCCCTTACGAGTAGGGCTACACACGT GCTACAATGGCGCATACAAAGAGAAGCGACCTCGCGAGAGCAAGCG GACCTCACAAAGTGCGTCGTAGTCCGGATCGGAGTCTGCAACTCGAC TCCGTGAAGTCGGAATCGCTAGTAATCGTGGATCAGAATGCCACGGT GAATACGT |
| 41 | DP41 16S rRNA | GTGGAGAGTTTGATCCTGGCTCAGGATGAACGCTGGCGGCGTGCTTA ACACATGCAAGTCGAACGGAAAGGCCCAAGCTTGCTTGGGTACTCGA GTGGCGAACGGGTGAGTAACACGTGGGTGATCTGCCCTGCACTTCGG GATAAGCCTGGGAAACTGGGTCTAATACCGGATAGGACGATGGTTTG GATGCCATTGTGGAAAGTTTTTTCGGTGTGGGATGAGCTCGCGGCCTA TCAGCTTGTTGGTGGGGTAATGGCCTACCAAGGCGTCGACGGGTAGC CGGCCTGAGAGGGTGTACGGCCACATTGGGACTGAGATACGGCCCAG ACTCCTACGGGAGGCAGCAGTGGGGAATATTGCACAATGGGCGCAAG CCTGATGCAGCGACGCCGCGTGGGGGATGACGGCCTTCGGGTTGTAA ACTCCTTTCGCTAGGGACGAAGCGTTTTGTGACGGTACCTGGAGAAG AAGCACCGGCTAACTACGTGCCAGCAGCCGCGGTAATACGTAGGGTG CGAGCGTTGTCCGGAATTACTGGGCGTAAAGAGCTCGTAGGTGGTTT GTCGCGTCGTTTGTGTAAGCCCGCAGCTTAACTGCGGGACTGCAGGC GATACGGGCATAACTTGAGTGCTGTAGGGGAGACTGGAATTCCTGGT GTAGCGGTGGAATGCGCAGATATCAGGAGGAACACCGATGGCGAAG GCAGGTCTCTGGGCAGTAACTGACGCTGAGGAGCGAAAGCATGGGTA GCGAACAGGATTAGATACCCTGGTAGTCCATGCCGTAAACGGTGGGC GCTAGGTGTGAGTCCCTTCCACGGGGTTCGTGCCGTAGCTAACGCATT AAGCGCCCCGCCTGGGGAGTACGGCCGCAAGGCTAAAACTCAAAGG AATTGACGGGGGCCCGCACAAGCGGCGGAGCATGTGGATTAATTCGA TGCAACGCGAAGAACCTTACCTGGGCTTGACATACACCAGATCGCCG TAGAGATACGGTTTCCCTTTGTGGTTGGTGTACAGGTGGTGCATGGTT GTCGTCAGCTCGTGTCGTGAGATGTTGGGTTAAGTCCCGCAACGAGC GCAACCCTTGTCTTATGTTGCCAGCACGTGATGGTGGGGACTCGTGAG AGACTGCCGGGGTTAACTCGGAGGAAGGTGGGGATGACGTCAAATCA TCATGCCCCTTATGTCCAGGGCTTCACACATGCTACAATGGTCGGTAC AACGCGCATGCGAGCCTGTGAGGGTGAGCGAATCGCTGTGAAAGCCG GTCGTAGTTCGGATTGGGGTCTGCAACTCGACCCCATGAAGTCGGAG TCGCTAGTAATCGCAGATCAGCAACGCTGCGGTGAATACGTTCCCGG GCCTTGTACACACCGCCCGTCACACCATGGGAGTGGGTTGCAAAAGA AGTAGGTAGCTTAACCTTCGGGAGGGCGCTTACCACTTTGTGAT |
| 42 | DP42 16S rRNA | TGAAGAGTTTGATCATGGCTCAGATTGAACGCTGGCGGCAGGCCTAA CACATGCAAGTCGAGCGGTAGAGAGGTGCTTGCACCTCTTGAGAGCG GCGGACGGGTGAGTAATACCTAGGAATCTGCCTGATAGTGGGGGATA |

-continued

Sequence Listing

| Seq ID No. | Description | Sequence |
|---|---|---|
| | | ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCTACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCATTAACCTAATACGTTAGTGTCTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTA GTGGAATTTCCTGTGTAGCGGTGAAATGCGTAGATATAGGAAGGAAC ACCAGTGGCGAAGGCGACTACCTGGACTGATACTGACACTGAGGTGC GAAAGCGTGGGGAGCAAACAGGATTAGATACCCTGGTAGTCCACGCC GTAAACGATGTCAACTAGCCGTTGGGAACCTTGAGTTCTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCCAGAGATGGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATGGGAGTGGGTT GCACCAGAAGTAGCTAGTCTAACCCTCGGGAGGACGGTTACCACGGT GTGATTCATGACTGGGGTGAAGTCGTAACAAGGTAGCCGTAGGGGAA CCTGCGGCTGGATCACCTCCTT |
| 43 | DP43 16S rRNA | CTGAGTTTGATCCTGGCTCAGATTGAACGCTGGCGGCATGCCTTACAC ATGCAAGTCGAACGGCAGCACGGAGCTTGCTCTGGTGGCGAGTGGCG AACGGGTGAGTAATATATCGGAACGTACCCTGGAGTGGGGGATAACG TAGCGAAAGTTACGCTAATACCGCATACGATCTAAGGATGAAAGTGG GGGATCGCAAGACCTCATGCTCGTGGAGCGGCCGATATCTGATTAGC TAGTTGGTAGGGTAAAAGCCTACCAAGGCATCGATCAGTAGCTGGTC TGAGAGGACGACCAGCCACACTGGAACTGAGACACGGTCCAGACTCC TACGGGAGGCAGCAGTGGGGAATTTTGGACAATGGGCGAAAGCCTGA TCCAGCAATGCCGCGTGAGTGAAGAAGGCCTTCGGGTTGTAAAGCTC TTTTGTCAGGGAAGAAACGGTGAGAGCTAATATCTCTTGCTAATGAC GGTACCTGAAGAATAAGCACCGGCTAACTACGTGCCAGCAGCCGCGG TAATACGTAGGGTGCAAGCGTTAATCGGAATTACTGGGCGTAAAGCG TGCGCAGGCGGTTTTGTAAGTCTGATGTGAAATCCCCGGGCTCAACCT GGGAATTGCATTGGAGACTGCAAGGCTAGAATCTGGCAGAGGGGGGT AGAATTCCACGTGTAGCAGTGAAATGCGTAGATATGTGGAGGAACAC CGATGGCGAAGGCAGCCCCCTGGGTCAAGATTGACGCTCATGCACGA AAGCGTGGGGAGCAAACAGGATTAGATACCCTGGTAGTCCACGCCCT AAACGATGTCTACTAGTTGTCGGGTCTTAATTGACTTGGTAACGCAGC TAACGCGTGAAGTAGACCGCCTGGGGAGTACGGTCGCAAGATTAAAA CTCAAAGGAATTGACGGGGACCCGCACAAGCGGTGGATGATGTGGAT TAATTCGATGCAACGCGAAAAACCTTACCTACCCTTGACATGGCTGG AATCCTTGAGAGATCAGGGAGTGCTCGAAAGAGAACCAGTACACAGG TGCTGCATGGCTGTCGTCAGCTCGTGTCGTGAGATGTTGGGTTAAGTC CCGCAACGAGCGCAACCCTTGTCATTAGTTGCTACGAAAGGGCACTC TAATGAGACTGCCGGTGACAAACCGGAGGAAGGTGGGGATGACGTC AAGTCCTCATGGCCCTTATGGGTAGGGCTTCACACGTCATACAATGGT ACATACAGAGCGCCGCCAACCCGCGAGGGGGAGCTAATCGCAGAAA GTGTATCGTAGTCCGGATTGTAGTCTGCAACTCGACTGCATGAAGTTG GAATCGCTAGTAATCGCGGATCAGCATGTCGCGGTGAATACGTTCCC GGGTCTTGTACACACCGCCCGTCACACCATGGGAGCGGGTTTTACCA GAAGTAGGTAGCTTAACCGTAAGGAGGGCGCTTACCACGGTAGGATT CGTGACTGGGGTGAAGTCGTAACAAGGTAGCCGTATCGGAAGGTGCG GCTGGATCACCTCCTTT |
| 44 | DP44 16S rRNA | TGGCGGCATGCCTTACACATGCAAGTCGAACGGCAGCATAGGAGCTT GCTCCTGATGGCGAGTGGCGAACGGGTGAGTAATATATCGGAACGTG CCCTAGAGTGGGGGATAACTAGTCGAAAGACTAGCTAATACCGCATA CGATCTACGGATGAAAGTGGGGGATCGCAAGACCTCATGCTCCTGGA GCGGCCGATATCTGATTAGCTAGTTGGTGGGGTAAAAGCTCACCAAG GCGACGATCAGTAGCTGGTCTGAGAGGACGACCAGCCACACTGGGAC TGAGACACGGCCCAGACTCCTACGGGAGGCAGCAGTGGGGAATTTTG GACAATGGGGGCAACCCTGATCCAGCAATGCCGCGTGAGTGAAGAAG |

-continued

Sequence Listing

| Seq ID No. | Description | Sequence |
|---|---|---|
| | | GCCTTCGGGTTGTAAAGCTCTTTTGTCAGGGAAGAAACGGTTCTGGAT AATACCTAGGACTAATGACGGTACCTGAAGAATAAGCACCGGCTAAC TACGTGCCAGCAGCCGCGGTAATACGTAGGGTGCAAGCGTTAATCGG AATTACTGGGCGTAAAGCGTGCGCAGGCGGTTGTGTAAGTCAGATGT GAAATCCCCGGGCTCAACCTGGGAATTGCATTTGAGACTGCACGGCT AGAGTGTGTCAGAGGGGGGTAGAATTCCACGTGTAGCAGTGAAATGC GTAGATATGTGGAGGAATACCGATGGCGAAGGCAGCCCCCTGGGATA ACACTGACGCTCATGCACGAAAGCGTGGGGAGCAAACAGGATTAGAT ACCCTGGTAGTCCACGCCCTAAACGATGTCTACTAGTTGTCGGGTCTT AATTGACTTGGTAACGCAGCTAACGCGTGAAGTAGACCGCCTGGGGA GTACGGTCGCAAGATTAAAACTCAAAGGAATTGACGGGGACCCGCAC AAGCGGTGGATGATGTGGATTAATTCGATGCAACGCGAAAAACCTTA CCTACCCTTGACATGGATGGAATCCCGAAGAGATTTGGGAGTGCTCG AAAGAGAACCATCACACAGGTGCTGCATGGCTGTCGTCAGCTCGTGT CGTGAGATGTTGGGTTAAGTCCCGCAACGAGCGCAACCCTTGTCATTA GTTGCTACGAAAGGGCACTCTAATGAGACTGCCGGTGACAAACCGGA GGAAGGTGGGGATGACGTCAAGTCCTCATGGCCCTTATGGGTAGGGC TTCACACGTCATACAATGGTACATACAGAGGGCCGCCAACCCGCGAG GGGGAGCTAATCCCAGAAAGTGTATCGTAGTCCGGATTGGAGTCTGC AACTCGACTCCATGAAGTTGGAATCGCTAGTAATCGCGGATCAGCAT GTCGCGGTGAATACGTTCCCGGGTCTTGTACACACCGCCCGTCACACC ATGGGAGCGGGTTTTACCAGAAGTGGGTAGCCTAACCGCAAGGAGGG CGCTCACCACGGTAGGATTCGTGACTGGGGTGAAGTCGTAACAAGGT AGCCGTATCGGAAGGTGCGGCTGGATCACCTCCTTT |
| 45 | DP45 16S rRNA | TACGGAGAGTTTGATCCTGGCTCAGGACGAACGCTGGCGGCGTGCTT AACACATGCAAGTCGAACGGTGACGCTAGAGCTTGCTCTGGTTGATC AGTGGCGAACGGGTGAGTAACACGTGAGTAACCTGCCCTTGACTCTG GGATAACTCCGGGAAACCGGGGCTAATACCGGATACGAGACGCGACC GCATGGTCGGCGTCTGGAAAGTTTTTCGGTCAAGGATGGACTCGCGG CCTATCAGCTTGTTGGTGAGGTAATGGCTCACCAAGGCGTCGACGGG TAGCCGGCCTGAGAGGGCGACCGGCCACACTGGGACTGAGACACGGC CCAGACTCCTACGGGAGGCAGCAGTGGGGAATATTGCACAATGGGCG AAAGCCTGATGCAGCGACGCCGCGTGAGGGATGAAGGCCTTCGGGTT GTAAACCTCTTTCAGTAGGGAAGAAGCGAAAGTGACGGTACCTGCAG AAGAAGCGCCGGCTAACTACGTGCCAGCAGCCGCGGTAATACGTAGG GCGCAAGCGTTGTCCGGAATTATTGGGCGTAAAGAGCTCGTAGGCGG TTTGTCGCGTCTGGTGTGAAAACTCAAGGCTCAACCTTGAGCTTGCAT CGGGTACGGGCAGACTAGAGTGTGGTAGGGGTGACTGGAATTCCTGG TGTAGCGGTGGAATGCGCAGATATCAGGAGGAACACCGATGGCGAA GGCAGGTCACTGGGCCACTACTGACGCTGAGGAGCGAAAGCATGGGG AGCGAACAGGATTAGATACCCTGGTAGTCCATGCCGTAAACGTTGGG CACTAGGTGTGGGGCTCATTCCACGAGTTCCGCGCCGCAGCTAACGC ATTAAGTGCCCCGCCTGGGGAGTACGGCCGCAAGGCTAAAACTCAAA GGAATTGACGGGGGCCCGCACAAGCGGCGGAGCATGCGGATTAATTC GATGCAACGCGAAGAACCTTACCAAGGCTTGACATACACCGGAATCA TGCAGAGATGTGTGCGTCTTCGGACTGGTGTACAGGTGGTGCATGGTT GTCGTCAGCTCGTGTCGTGAGATGTTGGGTTAAGTCCCGCAACGAGC GCAACCCTCGTCCTATGTTGCCAGCACGTTATGGTGGGGACTCATAGG AGACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCGATACCGCGAGGTGGAGCGAATCCCAAAAAGCCGGT CTCAGTTCGGATTGGGGTCTGCAACTCGACCCCATGAAGTCGGAGTC GCTAGTAATCGCAGATCAGCAACGCTGCGGTGAATACGTTCCCGGGC CTTGTACACACCGCCCGTCAAGTCACGAAAGTCGGTAACACCCGAAG CCGGTGGCCTAACCCCTTGTGGGATGGAGCCGTCGAAGGTGGGATTG GCGATTGGGACTAAGTCGTAACAAGGTAGCCGTACCGGAAGGTGCGG CTGGATCACCTCCTTT |
| 46 | DP46 16S rRNA | TTGAAGAGTTTGATCATGGCTCAGATTGAACGCTGGCGGCAGGCCTA ACACATGCAAGTCGGACGGTAGCACAGAGGAGCTTGCTCCTTGGGTG ACGAGTGGCGGACGGGTGAGTAATGTCTGGGGATCTGCCCGATAGAG GGGGATAACCACTGGAAACGGTGGCTAATACCGCATAACGTCGCAAG ACCAAAGAGGGGGACCTTCGGGCCTCTCACTATCGGATGAACCCAGA TGGGATTAGCTAGTAGGCGGGGTAATGGCCCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTATGAAGAAGGCCTTCGGGT TGTAAAGTACTTTCAGCGGGGAGGAAGGCGACAGGGTTAATAACCCT GTCGATTGACGTTACCCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTCTGTTAAGTCAGATGTGAAATCCCC GGGCTTAACCTGGGAACTGCATTTGAAACTGGCAGGCTTTAGTCTTGT |

-continued

| Seq ID No. | Description | Sequence |
|---|---|---|
| | | AGAGTGGGGTAGAATTCCAGGTGTAGCGGTGAAATGCGTAGAGATGT<br>GGAGGAACACCAGTGGCGAAGGCGGCTTTTTGGTCTGTAACTGACGC<br>TGAGGCGCGAAAGCGTGGGGAGCAAACAGGATTAGATACCCTGGTA<br>GTCCACGCCGTAAACGATGAGTGCTAAGTGTT |
| 47 | DP47 16S rRNA | AGGGTGCAAGCGTTAATCGGAATTACTGGGCGTAAAGCGCGCGTAGG<br>TGGTTTGTTAAGTTGAATGTGAAATCCCCGGGCTCAACCTGGGAACTG<br>CATTTGAAACTGGCAAGCTAGAGTCTCGTAGAGGGGGGTAGAATTCC<br>AGGTGTAGCGGTGAAATGCGTAGAGATCTGGAGGAATACCGGTGGCG<br>AAGGCGGCCCCCTGGACGAAGACTGACGCTCAGGTGCGAAAGCGTGG<br>GGAGCAAACAGGATTAGATACCCTGGTAGTCCACGCCGTAAACGATG<br>TCAACTAGCCGTTGGAAGCCTTGAGCTTTTAGTGGCGCAGCTAACGCA<br>TTAAGTTGACCGCCTGGGGAGTACGGCCGCAAGGTTAAAACTCAAAT<br>GAATTGACGGGGGCCCGCACAAGCGGTGGAGCATGTGGTTTAATTCG<br>AAGCAACGCGAAGAACCTTACCAGGCCTTGACATCCAATGAACTTTC<br>TAGAGATAGATTGGTGCCTTCGGGAACATTGAGACAGGTGCTGCATG<br>GCTGTCGTCAGCTCGTGTCGTGAGATGTTGGGTTAAGTCCCGCAACGA<br>GCGCAACCCTTGTCCTGTGTTGCCAGCGCGTAATGGCGGGGACTCGC<br>AGGAGACTGCCGGGGTCAACTCGGAGGAAGGTGGGGATGACGTCAA<br>ATCATCATGCCCCTTATGTCTTGGGCTTCACGCATGCTACAATGGCCG<br>GTACAAAGGGCTGCAATACCGTGAGGTGGAGCGAATCCCAAAAAGCC<br>GGTCCCAGTTCGGATTGAGGTCTGCAACTCGACCTCATGAAGTCGGA<br>GTCGCTAGTAATCGCAGATCAGCAACGCTGCGGTGAATACGTTCCCG<br>GGTCTTGTACACACCGCCCGTCAAGTCATGAAAGTCGGTAACACCTG<br>AAGCCGGTGGCCCAACCCTTGTGGAGGGAGCCGTCGAAGGTGGGATC<br>GGTAATTAGGACTAAGT |
| 48 | DP48 16S rRNA | CATGGAGAGTTTGATCCTGGCTCAGGACGAACGCTGGCGGCGTGCCT<br>AATACATGCAAGTCGAGCGGACAGATGGGAGCTTGCTCCCTGATGTT<br>AGCGGCGGACGGGTGAGTAACACGTGGGTAACCTGCCTGTAAGACTG<br>GGATAACTCCGGGAAACCGGGGCTAATACCGGATGCTTGATTGAACC<br>GCATGGTTCAATTATAAAAGGTGGCTTTTAGCTACCACTTACAGATGG<br>ACCCGCGGCGCATTAGCTAGTTGGTGAGGTAACGGCTCACCAAGGCA<br>ACGATGCGTAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGTT<br>TTCGGATCGTAAAACTCTGTTGTTAGGGAAGAACAAGTACCGTTCGA<br>ATAGGGCGGTACCTTGACGGTACCTAACCAGAAAGCCACGGCTAACT<br>ACGTGCCAGCAGCCGCGGTAATACGTAGGTGGCAAGCGTTGTCCGGA<br>ATTATTGGGCGTAAAGCGCGCGCAGGCGGTTTCTTAAGTCTGATGTGA<br>AAGCCCCCGGCTCAACCGGGGAGGGTCATTGGAAACTGGGGAACTTG<br>AGTGCAGAAGAGGAGAGTGGAATTCCACGTGTAGCGGTGAAATGCGT<br>AGAGATGTGGAGGAACACCAGTGGCGAAGGCGACTCTCTGGTCTGTA<br>ACTGACGCTGAGGCGCGAAAGCGTGGGGAGCGAACAGGATTAGATA<br>CCCTGGTAGTCCACGCCGTAAACGATGAGTGCTAAGTGTTAGAGGGT<br>TTCCGCCCTTTAGTGCTGCAGCAAACGCATTAAGCACTCCGCCTGGGG<br>AGTACGGTCGCAAGACTGAAACTCAAAGGAATTGACGGGGGCCCGCA<br>CAAGCGGTGGAGCATGTGGTTTAATTCGAAGCAACGCGAAGAACCTT<br>ACCAGGTCTTGACATCCTCTGACAACCCTAGAGATAGGGCTTCCCCTT<br>CGGGGGCAGAGTGACAGGTGGTGCATGGTTGTCGTCAGCTCGTGTCG<br>TGAGATGTTGGGTTAAGTCCCGCAACGAGCGCAACCCTTGATCTTAGT<br>TGCCAGCATTCAGTTGGGCACTCTAAGGTGACTGCCGGTGACAAACC<br>GGAGGAAGGTGGGGATGACGTCAAATCATCATGCCCCTTATGACCTG<br>GGCTACACACGTGCTACAATGGGCAGAACAAAGGGCAGCGAAGCCG<br>CGAGGCTAAGCCAATCCCACAAATCTGTTCTCAGTTCGGATCGCAGTC<br>TGCAACTCGACTGCGTGAAGCTGGAATCGCTAGTAATCGCGGATCAG<br>CATGCCGCGGTGAATACGTTCCCGGGCCTTGTACACACCGCCCGTCAC<br>ACCACGAGAGTTTGTAACACCCGAAGTCGGTGAGGTAACCTTTTGGA<br>GCCAGCCGCCGAAGGTGGGACAGATGATTGGGGTGAAGTCGTAACAA<br>GGTAGCCGTATCGGAAGGTGCGGCTGGATCACCTCCTTT |
| 49 | DP49 16S rRNA | TATGGAGAGTTTGATCCTGGCTCAGGACGAACGCTGGCGGCGTGCCT<br>AATACATGCAAGTCGAGCGGACGTTTTTGAAGCTTGCTTCAAAAACG<br>TTAGCGGCGGACGGGTGAGTAACACGTGGGCAACCTGCCTTATCGAC<br>TGGGATAACTCCGGGAAACCGGGGCTAATACCGGATAATATCTAGCA<br>CCTCCTGGTGCAAGATTAAAAGAGGGCCTTCGGGCTCTCACGGTGAG<br>ATGGGCCCGCGGCGCATTAGCTAGTTGGAGAGGTAATGGCTCCCCAA<br>GGCGACGATGCGTAGCCGACCTGAGAGGGTGATCGGCCACACTGGGA<br>CTGAGACACGGCCCAGACTCCTACGGGAGGCAGCAGTAGGGAATCTT<br>CCGCAATGGACGAAAGTCTGACGGAGCAACGCCGCGTGAGTGATGAA<br>GGGTTTCGGCTCGTAAAGCTCTGTTATGAGGGAAGAACACGTACCGT<br>TCGAATAGGGCGGTACCTTGACGGTACCTCATCAGAAAGCCACGGCT<br>AACTACGTGCCAGCAGCCGCGGTAATACGTAGGTGGCAAGCGTTGTC |

-continued

Sequence Listing

| Seq ID No. | Description | Sequence |
|---|---|---|
| | | CGGAATTATTGGGCGTAAAGCGCGCGCAGGCGGCCTTTTAAGTCTGA<br>TGTGAAATCTTGCGGCTCAACCGCAAGCGGTCATTGGAAACTGGGAG<br>GCTTGAGTACAGAAGAGGAGAGTGGAATTCCACGTGTAGCGGTGAAA<br>TGCGTAGATATGTGGAGGAACACCAGTGGCGAAGGCGACTCTCTGGT<br>CTGTAACTGACGCTGAGGCGCGAAAGCGTGGGGAGCAAACAGGATTA<br>GATACCCTGGTAGTCCACGCCGTAAACGATGAGTGCTAGGTGTTAGG<br>GGTTTCGATGCCCGTAGTGCCGAAGTTAACACATTAAGCACTCCGCCT<br>GGGGAGTACGGCCGCAAGGCTGAAACTCAAAGGAATTGACGGGGGC<br>CCGCACAAGCAGTGGAGCATGTGGTTTAATTCGAAGCAACGCGAAGA<br>ACCTTACCAGGTCTTGACATCCTTTGACCACTCTGGAGACAGAGCTTC<br>CCCTTCGGGGGCAAAGTGACAGGTGGTGCATGGTTGTCGTCAGCTCG<br>TGTCGTGAGATGTTGGGTTAAGTCCCGCAACGAGCGCAACCCTTGAC<br>CTTAGTTGCCAGCATTTAGTTGGGCACTCTAAGGTGACTGCCGGTGAC<br>AAACCGGAGGAAGGTGGGGATGACGTCAAATCATCATGCCCCTTATG<br>ACCTGGGCTACACACGTGCTACAATGGATGGTACAAAGGGTTGCGAA<br>GCCGCGAGGTGAAGCCAATCCCATAAAGCCATTCTCAGTTCGGATTG<br>TAGGCTGCAACTCGCCTGCATGAAGCTGGAATTGCTAGTAATCGCGG<br>ATCAGCATGCCGCGGTGAATACGTTCCCGGGCCTTGTACACACCGCCC<br>GTCACACCACGAGAGTTTGTAACACCCGAAGTCGGTGAGGTAACCTT<br>TTGGAGCCAGCCGCCGAAGGTGGGACAGATGATTGGGGTGAAGTCGT<br>AACAAGGTAGCCGTATCGGAAGGTGCGGCTGGATCACCTCCTTT |
| 50 | DP50 16S rRNA | TTGAAGAGTTTGATCATGGCTCAGATTGAACGCTGGCGGCAGGCCTA<br>ACACATGCAAGTCGAACGGTAGCACAGAGAGCTTGCTCTTGGGTGAC<br>GAGTGGCGGACGGGTGAGTAATGTCTGGGAAACTGCCCGATGGAGGG<br>GGATAACTACTGGAAACGGTAGCTAATACCGCATAACGTCGCAAGAC<br>CAAAGTGGGGGACCTTCGGGCCTCACACCATCGGATGTGCCCAGATG<br>GGATTAGCTAGTAGGTGGGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGAGGAGGAAGGCATTGTGGTTAATAACCGCAG<br>TGATTGACGTTACTCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTCAAGTCGGATGTGAAATCCCCGG<br>GCTCAACCTGGGAACTGCATTCGAAACTGGCAGGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT<br>CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCACGGAATTTAGCAGAGATGCTTTAGTGCCTTCGGGAACCGT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGGTT<br>CGGCCGGGAACTCAAAGGAGACTGCCAGTGATAAACTGGAGGAAGG<br>TGGGGATGACGTCAAGTCATCATGGCCCTTACGAGTAGGGCTACACA<br>CGTGCTACAATGGCATATACAAAGAGAAGCGACCTCGCGAGAGCAAG<br>CGGACCTCATAAAGTATGTCGTAGTCCGGATCGGAGTCTGCAACTCG<br>ACTCCGTGAAGTCGGAATCGCTAGTAATCGTAGATCAGAATGCTACG<br>GTGAATACGTTCCCGGGCCTTGTACACACCGCCCGTCACACCATGGG<br>AGTGGGTTGCAAAAGAAGTAGGTAGCTTAACCTTCGGGAGGGCGCTT<br>ACCACTTTGTGATTCATGACTGGGGTGAAGTCGTAACAAGGTAACCG<br>TAGGGGAACCTGCGGTTGGATCACCTCCTT |
| 51 | DP51 16S rRNA | TTGAAGAGTTTGATCATGGCTCAGATTGAACGCTGGCGGCAGGCCTA<br>ACACATGCAAGTCGAGCGGTAGCACAGGGAGCTTGCTCCTGGGTGAC<br>GAGCGGCGGACGGGTGAGTAATGTCTGGGAAACTGCCTGATGGAGGG<br>GGATAACTACTGGAAACGGTAGCTAATACCGCATAACGTCGCAAGAC<br>CAAAGAGGGGGACCTTCGGGCCTCTTGCCATCAGATGTGCCCAGATG<br>GGATTAGCTAGTAGGTGAGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGAGGAGGAAGGCATTAAGGTTAATAACCTTGG<br>TGATTGACGTTACTCGCAGAAGAAGCACCGGCTAACTCCGTGCCAGC<br>AGCCGCGGTAATACGGGGGGTGCAAGCGTTAATCGGAATTACTGGGC<br>GTAAAGCGCACGCAGGCGGTTTGTCAAGTCGGATGTGAAATCCCCGG<br>GCTCAACCTGGGAACTGCATTCGAAACGGGCAAGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT |

-continued

Sequence Listing

| Seq ID No. | Description | Sequence |
|---|---|---|
| | | CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCAGAGAACTTTCCAGAGATGGATTGGTGCCTTCGGGAACTCT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGAGT<br>AATGTCGGGAACTCAAAGGAGACTGCCAGTGACAAACTGGAGGAAG<br>GTGGGGATGACGTCAAGTCATCATGGCCCTTACGAGTAGGGCTACAC<br>ACGTGCTACAATGGCATATACAAAGAGAAGCGACCTCGCGAGAGCAA<br>GCGGACCTCACAAAGTATGTCGTAGTCCGGATCGGAGTCTGCAACTC<br>GACTCCGTGAAGTCGGAATCGCTAGTAATCGTAGATCAGAATGCTAC<br>GGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 52 | DP52 16S rRNA | ACGGAGAGTTTGATCCTGGCTCAGGATGAACGCTGGCGGCGTGCTTA<br>ACACATGCAAGTCGAACGATGATCCCAGCTTGCTGGGGGATTAGTGG<br>CGAACGGGTGAGTAACACGTGAGTAACCTGCCCTTGACTCTGGGATA<br>AGCCTGGGAAACTGGGTCTAATACCGGATATGACTGTCTGACGCATG<br>TCAGGTGGTGGAAAGCTTTTGTGGTTTTGGATGGACTCGCGGCCTATC<br>AGCTTGTTGGTGGGGTAATGGCCTACCAAGGCGACGACGGGTAGCCG<br>GCCTGAGAGGGTGACCGGCCACACTGGGACTGAGACACGGCCCAGAC<br>TCCTACGGGAGGCAGCAGTGGGGAATATTGCACAATGGGCGCAAGCC<br>TGATGCAGCGACGCCGCGTGAGGGATGACGGCCTTCGGGTTGTAAAC<br>CTCTTTCAGTAGGGAAGAAGCGAAAGTGACGGTACCTGCAGAAGAAG<br>CGCCGGCTAACTACGTGCCAGCAGCCGCGGTAATACGTAGGGCGCAA<br>GCGTTATCCGGAATTATTGGGCGTAAAGAGCTCGTAGGCGGTTTGTCG<br>CGTCTGCTGTGAAAGACCGGGGCTCAACTCCGGTTCTGCAGTGGGTA<br>CGGGCAGACTAGAGTGCAGTAGGGGAGACTGGAATTCCTGGTGTAGC<br>GGTGAAATGCGCAGATATCAGGAGGAACACCGATGGCGAAGGCAGG<br>TCTCTGGGCTGTAACTGACGCTGAGGAGCGAAAGCATGGGGAGCGAA<br>CAGGATTAGATACCCTGGTAGTCCATGCCGTAAACGTTGGGCACTAG<br>GTGTGGGGGACATTCCACGTTTTCCGCGCCGTAGCTAACGCATTAAGT<br>GCCCCGCCTGGGGAGTACGGCCGCAAGGCTAAAACTCAAAGGAATTG<br>ACGGGGGCCCGCACAAGCGGCGGAGCATGCGGATTAATTCGATGCAA<br>CGCGAAGAACCTTACCAAGGCTTGACATGAACCGGTAATACCTGGAA<br>ACAGGTGCCCCGCTTGCGGTCGGTTTACAGGTGGTGCATGGTTGTCGT<br>CAGCTCGTGTCGTGAGATGTTGGGTTAAGTCCCGCAACGAGCGCAAC<br>CCTCGTTCTATGTTGCCAGCGCGTTATGGCGGGGACTCATAGGAGACT<br>GCCGGGGTCAACTCGGAGGAAGGTGGGGACGACGTCAAATCATCATG<br>CCCCTTATGTCTTGGGCTTCACGCATGCTACAATGGCCGGTACAAAGG<br>GTTGCGATACTGTGAGGTGGAGCTAATCCCAAAAAGCCGGTCTCAGT<br>TCGGATTGGGGTCTGCAACTCGACCCCATGAAGTCGGAGTCGCTAGT<br>AATCGCAGATCAGCAACGCTGCGGTGAATACGTTCCCGGGCCTTGTA<br>CACACCGCCCGTCAAGTCACGAAAGTTGGTAACACCCGAAGCCGGTG<br>GCCTAACCCTTGTGGGGGGAGCCGTCGAAGGTGGGACCGGCGATTGG<br>GACTAAGTCGTAACAAGGTAGCCGTACCGGAAGGTGCGGCTGGATCA<br>CCTCCTTT |
| 53 | DP53 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATACCTAGGAATCTGCCTGATAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCTACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGCAGTTACCTAATACGTGATTGTCTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTTGTTAAGTTGAATGTGAAATCCCCGGGCTCAAC<br>CTGGGAACTGCATCCAAAACTGGCAAGCTAGAGTATGGTAGAGGGTA<br>GTGGAATTTCCTGTGTAGCGGTGAAATGCGTAGATATAGGAAGGAAC<br>ACCAGTGGCGAAGGCGACTACCTGGACTGATACTGACACTGAGGTGC<br>GAAAGCGTGGGGAGCAAACAGGATTAGATACCCTGGTAGTCCACGCC<br>GTAAACGATGTCAACTAGCCGTTGGGAGTCTTGAACTCTTAGTGGCGC<br>AGCTAACGCATTAAGTTGACCGCCTGGGGAGTACGGCCGCAAGGTTA<br>AAACTCAAATGAATTGACGGGGGCCCGCACAAGCGGTGGAGCATGTG<br>GTTTAATTCGAAGCAACGCGAAGAACCTTACCAGGCCTTGACATCCA<br>ATGAACTTTCTAGAGATAGATTGGTGCCTTCGGGAACATTGAGACAG |

-continued

Sequence Listing

| Seq ID No. | Description | Sequence |
|---|---|---|
| | | GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATG |
| 54 | DP54 16S rRNA | CTTGAGAGTTTGATCCTGGCTCAGAGCGAACGCTGGCGGCAGGCTTA ACACATGCAAGTCGAGCGGGCACCTTCGGGTGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTTTGGTAGAGGTTG GTGGAACTGCGAGTGTAGAGGTGAAATTCGTAGATATTCGCAAGAAC ACCAGTGGCGAAGGCGGCCAACTGGACCAATACTGACGCTGAGGCGC GAAAGCGTGGGGAGCAAACAGGATTAGATACCCTGGTAGTCCACGCC GTAAACGATGAATGCTAGCTGTTGGGGTGCTTGCACCTCAGTAGCGC AGCTAACGCTTTAAGCATTCCGCCTGGGGAGTACGGTCGCAAGATTA AAACTCAAAGGAATTGACGGGGGCCCGCACAAGCGGTGGAGCATGT GGTTTAATTCGAAGCAACGCGCAGAACCTTACCATCCCTTGACATGTC GTGCCATCCGGAGAGATCCGGGGTTCCCTTCGGGGACGCGAACACAG GTGCTGCATGGCTGTCGTCAGCTCGTGTCGTGAGATGTTGGGTTAAGT CCCGCAACGAGCGCAACCCACGTCCTTAGTTGCCATCATTTAGTTGGG CACTCTAGGGAGACTGCCGGTGATAAGCCGCGAGGAAGGTGTGGATG ACGTC |
| 55 | DP55 16S rRNA | TCGGAGAGTTTGATCCTGGCTCAGGATGAACGCTGGCGGCGTGCCTA ATACATGCAAGTCGAGCGAACTGATTAGAAGCTTGCTTCTATGACGTT AGCGGCGGACGGGTGAGTAACACGTGGGCAACCTGCCTGTAAGACTG GGATAACTTCGGGAAACCGAAGCTAATACCGGATAGGATCTTCTCCT TCATGGGAGATGATTGAAAGATGGTTTCGGCTATCACTTACAGATGG GCCCGCGGTGCATTAGCTAGTTGGTGAGGTAACGGCTCACCAAGGCA ACGATGCATAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGCT TTCGGGTCGTAAAACTCTGTTGTTAGGGAAGAACAAGTACAAGAGTA ACTGCTTGTACCTTGACGGTACCTAACCAGAAAGCCACGGCTAACTA CGTGCCAGCAGCCGCGGTAATACGTAGGTGGCAAGCGTTATCCGGAA TTATTGGGCGTAAAGCGCGCGCAGGCGGTTTCTTAAGTCTGATGTGAA AGCCCACGGCTCAACCGTGGAGGGTCATTGGAAACTGGGGAACTTGA GTGCAGAAGAGAAAAGCGGAATTCCACGTGTAGCGGTGAAATGCGTA GAGATGTGGAGGAACACCAGTGGCGAAGGCGGCTTTTTGGTCTGTAA CTGACGCTGAGGCGCGAAAGCGTGGGGAGCAAACAGGATTAGATAC CCTGGTAGTCCACGCCGTAAACGATGAGTGCTAAGTGTTAGAGGGTT TCCGCCCTTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAACTCTAGAGATAGAGCGTTCCCCTT CGGGGGACAGAGTGACAGGTGGTGCATGGTTGTCGTCAGCTCGTGTC GTGAGATGTTGGGTTAAGTCCCGCAACGAGCGCAACCCTTGATCTTA GTTGCCAGCATTTAGTTGGGCACTCTAAGGTGACTGCCGGTGACAAA CCGGAGGAAGGTGGGGATGACGTCAAATCATCATGCCCCTTATGACC TGGGCTACACACGTGCTACAATGGATGGTACAAAGGGCTGCAAGACC GCGAGGTCAAGCCAATCCCATAAAACCATTCTCAGTTCGGATTGTAG GCTGCAACTCGCCTACATGAAGCTGGAATCGCTAGTAATCGCGGATC AGCATGCT |
| 56 | DP56 16S rRNA | ATTGGAGAGTTTGATCCTGGCTCAGGACGAACGCTGGCGGCGTGCCT AATACATGCAAGTCGAGCGGACCTGATGGAGTGCTTGCACTCCTGAT GGTTAGCGGCGGACGGGTGAGTAACACGTAGGCAACCTGCCCTCAAG ACTGGGATAACTACCGGAAACGGTAGCTAATACCGGATAATTTATTT CACAGCATTGTGGAATAATGAAAGACGGAGCAATCTGTCACTTGGGG ATGGGCCTGCGGCGCATTAGCTAGTTGGTGGGGTAACGGCTCACCAA GGCGACGATGCGTAGCCGACCTGAGAGGGTGAACGGCCACACTGGG |

-continued

Sequence Listing

| Seq ID No. | Description | Sequence |
|---|---|---|
| | | ACTGAGACACGGCCCAGACTCCTACGGGAGGCAGCAGTAGGGAATCT<br>TCCGCAATGGGCGAAAGCCTGACGGAGCAACGCCGCGTGAGTGATGA<br>AGGTTTTCGGATCGTAAAGCTCTGTTGCCAAGGAAGAACGTCTTCTAG<br>AGTAACTGCTAGGAGAGTGACGGTACTTGAGAAGAAAGCCCCGGCTA<br>ACTACGTGCCAGCAGCCGCGGTAATACGTAGGGGGCAAGCGTTGTCC<br>GGAATTATTGGGCGTAAAGCGCGCGCAGGCGGTTCTTTAAGTCTGGT<br>GTTTAAACCCGAGGCTCAACTTCGGGTCGCACTGGAAACTGGGGAAC<br>TTGAGTGCAGAAGAGGAGAGTGGAATTCCACGTGTAGCGGTGAAATG<br>CGTAGATATGTGGAGGAACACCAGTGGCGAAGGCGACTCTCTGGGCT<br>GTAACTGACGCTGAGGCGCGAAAGCGTGGGGAGCAAACAGGATTAG<br>ATACCCTGGTAGTCCACGCCGTAAACGATGAATGCTAGGTGTTAGGG<br>GTTTCGATACCCTTGGTGCCGAAGTTAACACATTAAGCATTCCGCCTG<br>GGGAGTACGGTCGCAAGACTGAAACTCAAAGGAATTGACGGGGACC<br>CGCACAAGCAGTGGAGTATGTGGTTTAATTCGAAGCAACGCGAAGAA<br>CCTTACCAAGTCTTGACATCCCTCTGAATCCTCTAGAGATAGAGGCGG<br>CCTTCGGGACAGAGGTGACAGGTGGTGCATGGTTGTCGTCAGCTCGT<br>GTCGTGAGATGTTGGGTTAAGTCCCGCAACGAGCGCAACCCTTGATTT<br>TAGTTGCCAGCACATCATGGTGGGCACTCTAGAATGACTGCCGGTGA<br>CAAACCGGAGGAAGGCGGGGATGACGTCAAATCATCATGCCCCTTAT<br>GACTTGGGCTACACACGTACTACAATGGCTGGTACAACGGGAAGCGA<br>AGCCGCGAGGTGGAGCCAATCCTATAAAAGCCAGTCTCAGTTCGGAT<br>TGCAGGCTGCAACTCGCCTGCATGAAGTCGGAATTGCTAGTAATCGC<br>GGATCAGCATGCCGCGGTGAATACGTTCCCGGGTCTTGTACACACCG<br>CCCGTCACACCACGAGAGTTTACAACACCCGAAGTCGGTGGGGTAAC<br>CCGCAAGGGAGCCAGCCGCCGAAGGTGGGGTAGATGATTGGGGTGA<br>AGTCGTAACAAGGTAGCCGTATCGGAAGGTGCGGCTGGATCACCTCC<br>TTT |
| 57 | DP57 16S rRNA | ATTGGAGAGTTTGATCCTGGCTCAGGATGAACGCTGGCGGCGTGCCT<br>AATACATGCAAGTCGAGCGAATGGATTAAGAGCTTGCTCTTATGAAG<br>TTAGCGGCGGACGGGTGAGTAACACGTGGGTAACCTGCCCATAAGAC<br>TGGGATAACTCCGGGAAACCGGGGCTAATACCGGATAACATTTTGCA<br>CCGCATGGTGCGAAATTCAAAGGCGGCTTCGGCTGTCACTTATGGAT<br>GGACCCGCGTCGCATTAGCTAGTTGGTGAGGTAACGGCTCACCAAGG<br>CAACGATGCGTAGCCGACCTGAGAGGGTGATCGGCCACACTGGGACT<br>GAGACACGGCCCAGACTCCTACGGGAGGCAGCAGTAGGGAATCTTCC<br>GCAATGGACGAAAGTCTGACGGAGCAACGCCGCGTGAGTGATGAAG<br>GCTTTCGGGTCGTAAAACTCTGTTGTTAGGGAAGAACAAGTGCTAGTT<br>GAATAAGCTGGCACCTTGACGGTACCTAACCAGAAAGCCACGGCTAA<br>CTACGTGCCAGCAGCCGCGGTAATACGTAGGTGGCAAGCGTTATCCG<br>GAATTATTGGGCGTAAAGCGCGCGCAGGTGGTTTCTTAAGTCTGATGT<br>GAAAGCCCACGGCTCAACCGTGGAGGGTCATTGGAAACTGGGAGACT<br>TGAGTGCAGAAGAGGAAAGTGGAATTCCATGTGTAGCGGTGAAATGC<br>GTAGAGATATGGAGGAACACCAGTGGCGAAGGCGACTTTCTGGTCTG<br>TAACTGACACTGAGGCGCGAAAGCGTGGGGAGCAAACAGGATTAGA<br>TACCCTGGTAGTCCACGCCGTAAACGATGAGTGCTAAGTGTTAGAGG<br>GTTTCCGCCCTTTAGTGCTGAAGTTAACGCATTAAGCACTCCGCCTGG<br>GGAGTACGGCCGCAAGGCTGAAACTCAAAGGAATTGACGGGGGCCC<br>GCACAAGCGGTGGAGCATGTGGTTTAATTCGAAGCAACGCGAAGAAC<br>CTTACCAGGTCTTGACATCCTCTGACAACCCTAGAGATAGGGCTTCCC<br>CTTCGGGGGCAGAGTGACAGGTGGTGCATGGTTGTCGTCAGCTCGTG<br>TCGTGAGATGTTGGGTTAAGTCCCGCAACGAGCGCAACCCTTGATCTT<br>AGTTGCCATCATTAAGTTGGGCACTCTAAGGTGACTGCCGGTGACAA<br>ACCGGAGGAAGGTGGGGATGACGTCAAATCATCATGCCCCTTATGAC<br>CTGGGCTACACACGTGCTACAATGGACGGTACAAAGAGCTGCAAGAC<br>CGCGAGGTGGAGCTAATCTCATAAAACCGTTCTCAGTTCGGATTGTAG<br>GCTGCAACTCGCCTACATGAAGCTGGAATCGCTAGTAATCGCGGATC<br>AGCATGCCGCGGTGAATACGTTCCCGGGCCTTGTACACACCGCCCGTC<br>ACACCACGAGAGTTTGTAACACCCGAAGTCGGTGGGGTAACCTTTTT<br>GGAGCCAGCCGCCTAAGGTGGGACAGATGATTGGGGTGAAGTCGTAA<br>CAAGGTAGCCGTATCGGAAGGTGCGGCTGGATCACCTCCTTT |
| 58 | DP58 16S rRNA | AATGACGGTACCTGAAGAATAAGCACCGGCTAACTACGTGCCAGCAG<br>CCGCGGTAATACGTAGGGTGCAAGCGTTAATCGGAATTACTGGGCGT<br>AAAGCGTGCGCAGGCGGTTTTGTAAGTCTGATGTGAAATCCCCGGGC<br>TCAACCTGGGAATTGCATTGGAGACTGCAAGGCTAGAATCTGGCAGA<br>GGGGGGTAGAATTCCACGTGTAGCAGTGAAATGCGTAGATATGTGGA<br>GGAACACCGATGGCGAAGGCAGCCCCCTGGGTCAAGATTGACGCTCA<br>TGCACGAAAGCGTGGGGAGCAAACAGGATTAGATACCCTGGTAGTCC<br>ACGCCCTAAACGATGTCTACTAGTTGTCGGGTCTTAATTGACTTGGTA<br>ACGCAGCTAACGCGTGAAGTAGACCGCCTGGGGAGTACGGTCGCAAG<br>ATTAAAACTCAAAGGAATTGACGGGGACCCGCACAAGCGGTGGATGA<br>TGTGGATTAATTCGATGCAACGCGAAAAACCTTACCTACCCTTGACAT |

-continued

Sequence Listing

| Seq ID No. | Description | Sequence |
|---|---|---|
| | | GGCTGGAATCCTCGAGAGATTGGGGAGTGCTCGAAAGAGAACCAGTA CACAGGTGCTGCATGGCTGTCGTCAGCTCGTGTCGTGAGATGTTGGGT TAAGTCCCGCAACGAGCGCAACCCTTGTCATTAGTTGCTACGAAAGG GCACTCTAATGAGACTGCCGGTGACAAACCGGAGGAAGGTGGGGATG ACGTCAAGTCCTCATGGCCCTTATGGGTAGGGCTTCACACGTCATACA ATGGTACATACAGAGCGCCGCCAACCCGCGAGGGGGAGCTAATCGCA GAAAGTGTATCGTAGTCCGGATTGTAGTCTGCAACTCGACTGCATGA AGTTGGAATCGCTAGTAATCGCGGATCAGCATGTCGCGGTGAATACG TTCCCGGGTCTTGTACACACCGCCCGTCACACCATGGGAGCGGGTTTT ACCAGAAGTAGGTAGCTTAACCGTAAGGAGGGCGCTTACCACGGTAG GATTCGTGACTGGGGTGAAGTCGTAACAAGGTAGCCGTATCGGAAGG TGCGGCTGGATCACCTCCTTT |
| 59 | DP59 16S rRNA | TTGAAGAGTTTGATCATGGCTCAGATTGAACGCTGGCGGCAGGCCTA ACACATGCAAGTCGAACGGTAACAGGAAGCAGCTTGCTGCTTTGCTG ACGAGTGGCGGACGGGTGAGTAATGTCTGGGAAACTGCCTGATGGAG GGGGATAACTACTGGAAACGGTAGCTAATACCGCATAACGTCGCAAG ACCAAAGAGGGGGACCTTCGGGCCTCTTGCCATCAGATGTGCCCAGA TGGGATTAGCTAGTAGGTGGGGTAACGGCTCACCTAGGCGACGATCC CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTATGAAGAAGGCCTTCGGGT TGTAAAGTACTTTCAGCGGGGAGGAAGGCGATGCGGTTAATAACCGC GTCGATTGACGTTACCCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTCTGTCAAGTCGGATGTGAAATCCCC GGGCTCAACCTGGGAACTGCATCCGAAACTGGCAGGCTTGAGTCTCG TAGAGGGGGGTAGAATTCCAGGTGTAGCGGTGAAATGCGTAGAGATC TGGAGGAATACCGGTGGCGAAGGCGGCCCCCTGGACGAAGACTGAC GCTCAGGTGCGAAAGCGTGGGGAGCAAACAGGATTAGATACCCTGGT AGTCCACGCCGTAAACGATGTCGACTTGGAGGTTGTGCCCTTGAGGC GTGGCTTCCGGAGCTAACGCGTTAAGTCGACCGCCTGGGGAGTACGG CCGCAAGGTTAAAACTCAAATGAATTGACGGGGGCCCGCACAAGCGG TGGAGCATGTGGTTTAATTCGATGCAACGCGAAGAACCTTACCTGGTC TTGACATCCACAGAACTTGGCAGAGATGCCTTGGTGCCTTCGGGAACT GTGAGACAGGTGCTGCATGGCTGTCGTCAGCTCGTGTTGTGAAATGTT GGGTTAAGTCCCGCAACGAGCGCAACCCTTATCCTTTGTTGCCAGCGG TTAGGCCGGGAACTCAAAGGAGACTGCCAGTGATAAACTGGAGGAA GGTGGGGATGACGTCAAGTCATCATGGCCCTTACGACCAGGGCTACA CACGTGCTACAATGGCGCATACAAAGAGAAGCGATCTCGCGAGAGCC AGCGGACCTCATAAAGTGCGTCGTAGTCCGGATTGGAGTCTGCAACT CGACTCCATGAAGTCGGAATCGCTAGTAATCGTGAATCAGAATGTCA CGGTGAATACGTTCCCGGGCCTTGTACACACCGCCCGTCACACCATGG GAGTGGGTTGCAAAAGAAGTAGGTAGCTTAACCTTCGGGAGGGCGCT TACCACTTTGTGATTCATGACTGGGGTGAAGTCGTAACAAGGTAACC GTAGGGGAACCTGCGGTTGGATCACCTCCTT |
| 60 | DP60 16S rRNA | TCGGAGAGTTTGATCCTGGCTCAGGACGAACGCTGGCGGCGTGCCTA ATACATGCAAGTCGAGCGAATCGATGGGAGCTTGCTCCCTGAGATTA GCGGCGGACGGGTGAGTAACACGTGGGCAACCTGCCTATAAGACTGG GATAACTTCGGGAAACCGGAGCTAATACCGGATACGTTCTTTTCTCGC ATGAGAGAAGATGGAAAGACGGTTTTGCTGTCACTTATAGATGGGCC CGCGGCGCATTAGCTAGTTGGTGAGGTAATGGCTCACCAAGGCGACG ATGCGTAGCCGACCTGAGAGGGTGATCGGCCACACTGGGACTGAGAC ACGGCCCAGACTCCTACGGGAGGCAGCAGTAGGGAATCTTCCGCAAT GGACGAAAGTCTGACGGAGCAACGCCGCGTGAACGAAGAAGGCCTT CGGGTCGTAAAGTTCTGTTGTTAGGGAAGAACAAGTACCAGAGTAAC TGCTGGTACCTTGACGGTACCTAACCAGAAAGCCACGGCTAACTACG TGCCAGCAGCCGCGGTAATACGTAGGTGGCAAGCGTTGTCCGGAATT ATTGGGCGTAAAGCGCGCGCAGGTGGTTCCTTAAGTCTGATGTGAAA GCCCACGGCTCAACCGTGGAGGGTCATTGGAAACTGGGGAACTTGAG TGCAGAAGAGGAAAGTGGAATTCCAAGTGTAGCGGTGAAATGCGTAG AGATTTGGAGGAACACCAGTGGCGAAGGCGACTTTCTGGTCTGTAAC TGACACTGAGGCGCGAAAGCGTGGGGAGCAAACAGGATTAGATACC CTGGTAGTCCACGCCGTAAACGATGAGTGCTAAGTGTTAGAGGGTTT CCGCCCTTTAGTGCTGCAGCTAACGCATTAAGCACTCCGCCTGGGGAG TACGGCCGCAAGGCTGAAACTCAAAGGAATTGACGGGGGCCCGCACA AGCGGTGGAGCATGTGGTTTAATTCGAAGCAACGCGAAGAACCTTAC CAGGTCTTGACATCCTCTGACAACCCTAGAGATAGGGCGTTCCCCTTC GGGGGACAGAGTGACAGGTGGTGCATGGTTGTCGTCAGCTCGTGTCG TGAGATGTTGGGTTAAGTCCCGCAACGAGCGCAACCCTTGATCTTAGT TGCCAGCATTCAGTTGGGCACTCTAAGGTGACTGCCGGTGACAAACC GGAGGAAGGTGGGGATGACGTCAAATCATCATGCCCCTTATGACCTG |

-continued

Sequence Listing

| Seq ID No. | Description | Sequence |
|---|---|---|
| | | GGCTACACACGTGCTACAATGGATGGTACAAAGGGCTGCAAACCTGC GAAGGTAAGCGAATCCCATAAAGCCATTCTCAGTTCGGATTGTAGGC TGCAACTCGCCTACATGAAGCCGGAATCGCTAGTAATCGCGGATCAG CATGCCGCGGTGAATACGTTCCCGGGCCTTGTACACACCGCCCGTCAC ACCACGAGAGTTTGTAACACCCGAAGTCGGTGAGGTAACCTTTATGG AGCCAGCCGCCTAAGGTGGGACAGATGATTGGGGTGAAGTCGTAACA AGGTAGCCGTATCGGAAGGTGCGGCTGGATCACCTCCTTT |
| 61 | DP61 16S rRNA | GGAAGGCGGTCTGTCAAGTCGGATGTGAAATCCCCGGGCTCAACCTG GGAACTGCATTCGAAACTGGCAGGCTAGAGTCTTGTAGAGGGGGGTA GAATTCCAGGTGTAGCGGTGAAATGCGTAGAGATCTGGAGGAATACC GGTGGCGAAGGCGGCCCCCTGGACAAAGACTGACGCTCAGGTGCGAA AGCGTGGGGAGCAAACAGGATTAGATACCCTGGTAGTCCACGCCGTA AACGATGTCGACTTGGAGGTTGTTCCCTTGAGGAGTGGCTTCCGGAGC TAACGCGTTAAGTCGACCGCCTGGGGAGTACGGCCGCAAGGTTAAAA CTCAAATGAATTGACGGGGGCCCGCACAAGCGGTGGAGCATGTGGTT TAATTCGATGCAACGCGAAGAACCTTACCTACTCTTGACATCCACGGA ATTTAGCAGAGATGCTTTAGTGCCTTCGGGAACCGTGAGACAGGTGC TGCATGGCTGTCGTCAGCTCGTGTTGTGAAATGTTGGGTTAAGTCCCG CAACGAGCGCAACCCTTATCCTTTGTTGCCAGCGGTCCGGCCGGGAA CTCAAAGGAGACTGCCAGTGATAAACTGGAGGAAGGTGGGGATGAC GTCAAGTCATCATGGCCCTTACGAGTAGGGCTACACACGTGCTACAA TGGCGCATACAAAGAGAAGCGACCTCGCGAGAGCAAGCGGACCTCAT AAAGTGCGTCGTAGTCCGGATCGGAGTCTGCAACTCGACTCCGTGAA GTCGGAATCGCTAGTAATCGTAGATCAGAATGCTACGGTGAATACGT TCCCGGGCCTTGTACACACCGCCCGTCACACCATGGGAGTGGGTTGC AAAAGAAGTAGGTAGCTTAACCTTCGGGAGGGCGCTTACCACTTTGT GATTCATGACTGGGGTGAAGTCGTAACAAGGTAACCGTAGGGGAACC TGCGGTTGGATCACCTCCTT |
| 62 | DP62 16S rRNA | TGGCTCAGATTGAACGCTGGCGGCAGGCCTAACACATGCAAGTCGAA CGGTAGCACAGAGGAGCTTGCTCCTTGGGTGACGAGTGGCGGACGGG TGAGTAATGTCTGGGAAACTGCCCGATGGAGGGGGATAACTACTGGA AACGGTAGCTAATACCGCATAACGTCTTCGGACCAAAGTGGGGGACC TTCGGGCCTCACACCATCGGATGTGCCCAGATGGGATTAGCTAGTAG GTGGGGTAATGGCTCACCTAGGCGACGATCCCTAGCTGGTCTGAGAG GATGACCAGCCACACTGGAACTGAGACACGGTCCAGACTCCTACGGG AGGCAGCAGTGGGGAATATTGCACAATGGGCGCAAGCCTGATGCAGC CATGCCGCGTGTATGAAGAAGGCCTTCGGGTTGTAAAGTACTTTCAGT GGGGAGGAAGGCGTTAAGGTTAATAACCTTGGCGATTGACGTTACCC GCAGAAGAAGCACCGGCTAACTCCGTGCCAGCAGCCGCGGTAATACG GAGGGTGCAAGCGTTAATCGGAATTACTGGGCGTAAAGCGCACGCAG GCGGTCTGTCAAGTCGGATGTGAAATCCCCGGGCTCAACCTGGGAAC TGCATTCGAAACTGGCAGGCTAGAGTCTTGTAGAGGGGGGTAGAATT CCAGGTGTAGCGGTGAAATGCGTAGAGATCTGGAGGAATACCGGTGG CGAAGGCGGCCCCCTGGACAAAGACTGACGCTCAGGTGCGAAAGCGT GGGGAGCAAACAGGATTAGATACCCTGGTAGTCCACGCCGTAAACGA TGTCGACTTGGAGGTTGTTCCCTTGAGGAGTGGCTTCCGGAGCTAACG CGTTAAGTCGACCGCCTGGGGAGTACGG |
| 63 | DP63 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC ACCAGTGGCGAAGGCGACCACCTGGACTAATACTGACACTGAGGTGC GAAAGCGTGGGGAGCAAACAGGATTAGATACCCTGGTAGTCCACGCC GTAAACGATGTCAACTAGCCGTTGGAAGCCTTGAGCTTTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT |

-continued

Sequence Listing

| Seq ID No. | Description | Sequence |
|---|---|---|
| | | CCCGTAACGAGCGCAACCCTTGTTCTTAGTTACCAGCACGTTATGGTG<br>GGCACTCTAAGGAGACTGCCGGTGACAAACCGGAGGAAGGTGGGGA<br>TGACGTCAAGTCATCATGGCCCTTACGGCCTGGGCTACACACGTGCTA<br>CAATGGTCGGTACAGAGGGTTGCCAAGCCGCGAGGTGGAGCTAATCC<br>CATAAAACCGATCGTAGTCCGGATCGCAGTCTGCAACTCGACTGCGT<br>GAAGTCGGAATCGCTAGTAATCGCGAATCAGAATGTCGCGGTGAATA<br>CGTTCCCGGGCCTTGTACACACCGCCCGTCACACCATGGGAGTGGGTT<br>GCACCAGAAGTAGCTAGTCTAACCTTCGGGAGGACGGTTACCACGGT<br>GTGATTCATGACTGGGGTGAAGTCGTAACAAGGTAGCCGTAGGGGAA<br>CCTGCGGCTGGATCACCTCCTT |
| 64 | DP64 ITS sequence | GCTCGAGTTCTTGTTTAGATCTTTTACAATAATGTGTATCTTTACTGAA<br>GATGTGCGCTTAATTGCGCTGCTTCTTTAGAGTGTCGCAGTGAAAGTA<br>GTCTTGCTTGAATCTCAGTCAACGCTACACACATTGGAGTTTTTTTACT<br>TTAATTTAATTCTTTCTGCTTTGAATCGAAAGGTTCAAGGCAAAAAAC<br>AAACACAAACAATTTTATTTTATTATAATTTTTTAAACTAAACCAAAA<br>TTCCTAACGGAAATTTTAAAATAATTTAAAACTTTCAACAACGGATCT<br>CTTGGTTCTCGCATCGATGAAGAACGTAGCGAATTGCGATAAGTAAT<br>GTGAATTGCAGATACTCGTGAATCATTGAATTTTTGAACGCACATTGC<br>GCCCTTGAGCATTCTCAGGGGCATGCCTGTTTGAGCGTCATTTCCTTC<br>TCAAAAGATAATTTATTATTTTTTGGTTGTGGGCGATACTCAGGGTTA<br>GCTTGAAATTGGAGACTGTTTCAGTCTTTTTTAATTCAACACTTAGCTT<br>CTTTGGAGACGCTGTTCTCGCTGTGATGTATTTATGGATTTATTCGTTT<br>TACTTTACAAGGGAAATGGTAACGTACCTTAGGCAAAGGGTTGCTTTT<br>AATATTCATCAAGTTTGACCTCAAATCAGGTAGGATTACCCGCTGAAC<br>TTAAGCATATCAATAAGCGGAGGAAAAGAAACCAACTGGGATTACCT<br>TAGTAACGGCGAGTGAAGCGGTAAAAGCTCAAATTTGAAATCTGGTA<br>CTTTCAGTGCCCGAGTTGTAATTTGTAGAATTTGTCTTTGATTAGGTCC<br>TTGTCTATGTTCCTTGGNANCAGGACGTCATAGAGGGTGAGAATCCC<br>GTTTGGCGAGGATACCTTTTCTCTGTAAGACTTTTTCGAANANTCGAG<br>TTGTTTGGGAATGCAGCTCAAAGTGGGTGGTAAANTTCCATCTAAAG<br>CTAAATNTTGGCGAGAGACCGATAGCGAACNAGTACAGTGATGGAAA<br>GATGAAAAAGAANTTTN |
| 65 | DP65 16S rRNA | ATTGGAGAGTTTGATCCTGGCTCAGGATGAACGCTGGCGGCGTGCCT<br>AATACATGCAAGTCGAGCGAATGGATTAAGAGCTTGCTCTTATGAAG<br>TTAGCGGCGGACGGGTGAGTAACACGTGGGTAACCTGCCCATAAGAC<br>TGGGATAACTCCGGGAAACCGGGGCTAATACCGGATAACATTTTGAA<br>CTGCATGGTTCGAAATTGAAAGGCGGCTTCGGCTGTCACTTATGGATG<br>GACCCGCGTCGCATTAGCTAGTTGGTGAGGTAACGGCTCACCAAGGC<br>AACGATGCGTAGCCGACCTGAGAGGGTGATCGGCCACACTGGGACTG<br>AGACACGGCCCAGACTCCTACGGGAGGCAGCAGTAGGGAATCTTCCG<br>CAATGGACGAAAGTCTGACGGAGCAACGCCGCGTGAGTGATGAAGG<br>CTTTCGGGTCGTAAAACTCTGTTGTTAGGGAAGAACAAGTGCTAGTTG<br>AATAAGCTGGCACCTTGACGGTACCTAACCAGAAAGCCACGGCTAAC<br>TACGTGCCAGCAGCCGCGGTAATACGTAGGTGGCAAGCGTTATCCGG<br>AATTATTGGGCGTAAAGCGCGCGCAGGTGGTTTCTTAAGTCTGATGTG<br>AAAGCCCACGGCTCAACCGTGGAGGGTCATTGGAAACTGGGAGACTT<br>GAGTGCAGAAGAGGAAAGTGGAATTCCATGTGTAGCGGTGAAATGCG<br>TAGAGATATGGAGGAACACCAGTGGCGAAGGCGACTTTCTGGTCTGT<br>AACTGACACTGAGGCGCGAAAGCGTGGGGAGCAAACAGGATTAGAT<br>ACCCTGGTAGTCCACGCCGTAAACGATGAGTGCTAAGTGTTAGAGGG<br>TTTCCGCCCTTTAGTGCTGAAGTTAACGCATTAAGCACTCCGCCTGGG<br>GAGTACGGCCGCAAGGCTGAAACTCAAAGGAATTGACGGGGGCCCG<br>CACAAGCGGTGGAGCATGTGGTTTAATTCGAAGCAACGCGAAGAACC<br>TTACCAGGTCTTGACATCCTCTGAAAACCCTAGAGATAGGGCTTCTCC<br>TTCGGGAGCAGAGTGACAGGTGGTGCATGGTTGTCGTCAGCTCGTGT<br>CGTGAGATGTTGGGTTAAGTCCCGCAACGAGCGCAACCCTTGATCTTA<br>GTTGCCATCATTAAGTTGGGCACTCTAAGGTGACTGCCGGTGACAAA<br>CCGGAGGAAGGTGGGGATGACGTCAAATCATCATGCCCCTTATGACC<br>TGGGCTACACACGTGCTACAATGGACGGTACAAAGAGCTGCAAGACC<br>GCGAGGTGGAGCTAATCTCATAAAACCGTTCTCAGTTCGGATTGTAG<br>GCTGCAACTCGCCTACATGAAGCTGGAATCGCTAGTAATCGCGGATC<br>AGCATGCCGCGGTGAATACGTTCCCGGGCCTTGTACACACCGCCCGTC<br>ACACCACGAGAGTTTGTAACACCCGAAGTCGGTGGGGTAACCTTTTT<br>GGAGCCAGCCGCCTAAGGTGGGACAGATGATTGGGGTGAAGTCGTAA<br>CAAGGTAGCCGTATCGGAAGGTGCGGCTGGATCACCTCCTTT |
| 66 | DP66 ITS sequence | GATTTTTTGGGGTTGCTTCGAACTTGCAGACAGAGTGTCGAGACTTGT<br>GAGCCTGCGCTTAATTGCGCGGCCTAGAGTCGAGTGCTTGTTATTGGC<br>TGCGAGGGACGAGTGCCTTTTGAAAAAATCCATTACACACTGTGAAG<br>ATTTTTTTTCATACATTTTACTTCTTTGGGGCTTTCGAGCTCCAAAGGC<br>TATAAACACAAACCAAACTTTTTTTTTTATTATTTGTTAATCAAGAAA |

-continued

Sequence Listing

| Seq ID No. | Description | Sequence |
|---|---|---|
| | | TTTTCTTATTGAAATTAAATATTTTAAAACTTTCAACAACGGATCTCTT GGTTCTCGCATCGATGAAGAACGTAGCGAATTGCGATAAGTAATGTG AATTGCAGATTCTCGTGAATCATTGAATTTTTGAACGCACATTGCGCC CTCTGGTATTCCAGGGGGCATGCCTGTTTGAGCGTCATTTCCTTCTCA AAATCTCGATTTTGGTTGTGAGTGATACTCTGTTACAGGGTTAACTTG AAAGTGCTATTGCCCTAGCTACTCTTTTTTTTACTTGCTAAGAAAAAG ATTTTTGGATAATTTCAATGTATTTAGGTATTTATACCGACTTTCATTG GATGCTGAGAGTCTTGTCTAAGCGCTTTTGTGAGATTGAGCAGAAGG GATTAACAGTATTCATAAAGTTTGACCTCAAATCAGGTAGGATTACCC GCTGAACTTAAGCATATCAATAAGCGGAGGAAAAGAAACCAACCGG GATTGCCTCAGTAACGGCGAGTGAAGCGGCAAAAGCTCAAATTTGAA ATCTGGCACTTTCAGTGTCCGAGTTGTAATTTGTAGAAGTAGTTTTGG GACTGGTCCTTATCTATGTTTCTTGGAACAGGACGTCATAGAGGGTGA GANCCCGTATGATGAGGCCCCCAGTCCTTTGTAAAACGCTNCGAAGA GTCGAGTTGTTTGGGAATGCAGCTCTAAGTGGGTNGNAATTNNTCTA AAGCTAAATNNNNNNNANACNNTNGCGANAGTACNGTGATGNNGAT GANNACTTTGAAANANANTGAAAGTACGTGAA |
| 72 | DP72 16S rRNA | TTCGGAGAGTTTGATCCTGGCTCAGGACGAACGCTGGCGGCGTGCCT AATACATGCAAGTCGAGCGGACAGAAGGGAGCTTGCTCCCGGATGTT AGCGGCGGACGGGTGAGTAACACGTGGGTAACCTGCCTGTAAGACTG GGATAACTCCGGGAAACCGGAGCTAATACCGGATAGTTCCTTGAACC GCATGGTTCAAGGATGAAAGACGGTTTCGGCTGTCACTTACAGATGG ACCCGCGGCGCATTAGCTAGTTGGTGGGGTAATGGCTCACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGTT TTCGGATCGTAAAGCTCTGTTGTTAGGGAAGAACAAGTGCGAGAGTA ACTGCTCGCACCTTGACGGTACCTAACCAGAAAGCCACGGCTAACTA CGTGCCAGCAGCCGCGGTAATACGTAGGTGGCAAGCGTTGTCCGGAA TTATTGGGCGTAAAGGGCTCGCAGGCGGTTTCTTAAGTCTGATGTGAA AGCCCCCGGCTCAACCGGGGAGGGTCATTGGAAACTGGGAAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAACCCTAGAGATAGGGCTTTCCCTTC GGGGACAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTTAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCTGCGAGACCGCA AGGTTTAGCCAATCCCATAAATCTGTTCTCAGTTCGGATCGCAGTCTG CAACTCGACTGCGTGAAGCTGGAATCGCTAGTAATCGCGGATCAGCA TGCCGCGGTGAATACGTTCCCGGGCCTTGTACACACCGCCCGTCACAC CACGAGAGTTTGCAACACCCGAAGTCGGTGAGGTAACCTTTATGGAG CCAGCCGCCGAAGGTGGGGCAGATGATTGGGGTGAAGTCGTAACAAG GTAGCCGTATCGGAAGGTGCGGCTGGATCACCTCCTTT |
| 73 | DP73 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTGCCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAG |

-continued

Sequence Listing

| Seq ID No. | Description | Sequence |
|---|---|---|
| 74 | DP74 16S rRNA | GCCTAATACATGCAAGTCGTGCGGACCTTTTAAAAGCTTGCTTTTAAA AGGTTAGCGGCGAACGGGTGAGTAACACGTGGGCAACCTGCCTGTAA GATCGGGATAATGCCGGGAAACCGGGGCTAATACCGGATAGTTTTTT CCTCCGCATGGAGGAAAAAGGAAAGACGGCTTCGGCTGTCACTTACA GATGGGCCCGCGGCGCATTAGCTTGTTGGTGGGGTAACGGCTCACCA AGGCAACGATGCGTAGCCGACCTGAGAGGGTGATCGGCCACATTGGG ACTGAGACACGGCCCAAACTCCTACGGGAGGCAGCAGTAGGGAATCT TCCGCAATGGACGAAAGTCTGACGGAGCAACGCCGCGTGAGTGAAGA AGGCCTTCGGGTCGTAAAACTCTGTTGCCGGGGAAGAACAAGTGCCG TTCGAACAGGGCGGCGCCTTGACGGTACCCGGCCAGAAAGCCACGGC TAACTACGTGCCAGCAGCCGCGGTAATACGTAGGTGGCAAGCGTTGT CCGGAATTATTGGGCGTAAAGCGCGCGCAGGCGGCTTCTTAAGTCTG ATGTGAAATCTTGCGGCTCAACCGCAAGCGGTCATTGGAAACTGGGA GGCTTGAGTGCAGAAGAGGAGAGTGGAATTCCACGTGTAGCGGTGAA ATGCGTAGAGATGTGGAGGAACACCAGTGGCGAAGGCGGCTCTCTGG TCTGTAACTGACGCTGAGGCGCGAAAGCGTGGGGAGCAAACAGGATT AGATACCCTGGTAGTCCACGCCGTAAACGATGAGTGCTAAGTGTTAG AGGGTTTCCGCCCTTTAGTGCTGCAGCTAACGCATTAAGCACTCCGCC TGGGGAGTACGGCCGCAAGGCTGAAACTCAAAGGAATTGACGGGGG CCCGCACAAGCGGTGGAGCATGTGGTTTAATTCGAAGCAACGCGAAG AACCTTACCAGGTCTTGACATCCTCTGACCTCCCTGGAGACAGGGCCT TCCCCTTCGGGGGACAGAGTGACAGGTGGTGCATGGTTGTCGTCAGC TCGTGTCGTGAGATGTTGGGTTAAGTCCCGCAACGAGCGCAACCCTTG ACCTTAGTTGCCAGCATTCAG |
| 75 | DP75 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTCGTTAAGTTGGATGTGAAAGCCCCGGGCTCAA CCTGGGAACTGCATTCAAAACTGACGAGCTAGAGTATGGTAGAGGGT GGTGGAATTTCCTGTGTAGCGGTGAAATGCGTAGATATAGGAAGGAA CACCAGTGGCGAAGGCGACCACCTGGACTGATACTGACACTGAGGTG CGAAAGCGTGGGGAGCAAACAGGATTAGATACCCTGGTAGTCCACGC CGTAAACGATGTCAACTAGCCGTTGGAATCCTTGAGATTTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCCAGAGATGGATGGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTTATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAAAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAACGGGAGGACGGTTACCACGGTGTGATTCATGACTGG GGTGAAGTCGTAACAAGGTAGCCGTAGGGGAACCTGCGGCTGGATCA CCTCCTT |
| 76 | DP76 16S rRNA | CTTGAGAGTTTGATCCTGGCTCAGAACGAACGCTGGCGGCAGGCTTA ACACATGCAAGTCGAGCGCCCCGCAAGGGGAGCGGCAGACGGGTGA GTAACGCGTGGGAATCTACCTTTTGCTACGGAACAACAGTTGGAAAC GACTGCTAATACCGTATGTGCCCTTCGGGGGAAAGATTTATCGGCAA AGGATGAGCCCGCGTTGGATTAGCTAGTTGGTGAGGTAAAGGCTCAC CAAGGCGACGATCCATAGCTGGTCTGAGAGGATGATCAGCCACACTG GGACTGAGACACGGCCCAGACTCCTACGGGAGGCAGCAGTGGGGAA TATTGGACAATGGGCGCAAGCCTGATCCAGCCATGCCGCGTGAGTGA TGAAGGCCCTAGGGTTGTAAAGCTCTTTCACCGGTGAAGATAATGAC GGTAACCGGAGAAGAAGCCCCGGCTAACTTCGTGCCAGCAGCCGCGG TAATACGAAGGGGGCTAGCGTTGTTCGGATTTACTGGGCGTAAAGCG CACGTAGGCGGATTTTTAAGTCAGGGGTGAAATCCCGGGGCTCAACC CCGGAACTGCCTTTGATACTGGAAGTCTTGAGTATGGTAGAGGTGAG TGGAATTCCGAGTGTAGAGGTGAAATTCGTAGATATTCGGAGGAACA |

-continued

Sequence Listing

| Seq ID No. | Description | Sequence |
|---|---|---|
| | | CCAGTGGCGAAGGCGGCTCACTGGACCATTACTGACGCTGAGGTGCG AAAGCGTGGGGAGCAAACAGGATTAGATACCCTGGTAGTCCACGCCG TAAACGATGAATGTTAGCCGTCGGGGGGTTTACCTTTCGGTGGCGCA GCTAACGCATTAAACATTCCGCCTGGGGAGTACGGTCGCAAGATTAA AACTCAAAGGAATTGACGGGGGCCCGCACAAGCGGTGGAGCATGTG GTTTAATTCGAAGCAACGCGCAGAACCTTACCAGCCCTTGACATACC GGTCGCGGACACAGAGATGTGTCTTTCAGTTCGGCTGGACCGGATAC AGGTGCTGCATGGCTGTCGTCAGCTCGTGTCGTGAGATGTTGGGTTAA GTCCCGCAACGAGCGCAACCCTCGCCTTTAGTTGCCAGCATTTAGTTG GGCACTCTAAAGGGACTGCCAGTGATAAGCTGGAGGAAGGTGGGGAT GACGTCAAGTCCTCATGGCCCTTACGGGCTGGGCTACACACGTGCTAC AATGGTGGTGACAGTGGGCAGCAAGCACGCGAGTGTGAGCTAATCTC CAAAAGCCATCTCAGTTCGGATTGCACTCTGCAACTCGAGTGCATGA AGTTGGAATCGCTAGTAATCGCGGATCAGCATGCCGCGGTGAATACG TTCCCGGGCCTTGTACACACCGCCCGTCACACCATGGGAGTTGGTTTT ACCCGAAGGCACTGTGCTAACCGCAAGGAGGCAGGTGACCACGGTAG GGTCAGCGACTGGGGTGAAGTCGTAACAAGGTAGCCGTAGGGGAACC TGCGGCTGGATCACCTCCTTT |
| 77 | DP77 16S rRNA | TCGGAGAGTTTGATCCTGGCTCAGGATGAACGCTGGCGGCGTGCCTA ATACATGCAAGTCGAGCGAACTGATTAGAAGCTTGCTTCTATGACGTT AGCGGCGGACGGGTGAGTAACACGTGGGCAACCTGCCTGTAAGACTG GGATAACTTCGGGAAACCGAAGCTAATACCGGATAGGATCTTCTCCT TCATGGGAGATGATTGAAAGATGGTTTCGGCTATCACTTACAGATGG GCCCGCGGTGCATTAGCTAGTTGGTGAGGTAACGGCTCACCAAGGCA ACGATGCATAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGCT TTCGGGTCGTAAAACTCTGTTGTTAGGGAAGAACAAGTACAAGAGTA ACTGCTTGTACCTTGACGGTACCTAACCAGAAAGCCACGGCTAACTA CGTGCCAGCAGCCGCGGTAATACGTAGGTGGCAAGCGTTATCCGGAA TTATTGGGCGTAAAGCGCGCGCAGGCGGTTTCTTAAGTCTGATGTGAA AGCCCACGGCTCAACCGTGGAGGGTCATTGGAAACTGGGGAACTTGA GTGCAGAAGAGAAAAGCGGAATTCCACGTGTAGCGGTGAAATGCGTA GAGATGTGGAGGAACACCAGTGGCGAAGGCGGCTTTTTGGTCTGTAA CTGACGCTGAGGCGCGAAAGCGTGGGGAGCAAACAGGATTAGATAC CCTGGTAGTCCACGCCGTAAACGATGAGTGCTAAGTGTTAGAGGGTT TCCGCCCTTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAACTCTAGAGATAGAGCGTTCCCCTT CGGGGGACAGAGTGACAGGTGGTGCATGGTTGTCGTCAGCTCGTGTC GTGAGATGTTGGGTTAAGTCCCGCAACGAGCGCAACCCTTGATCTTA GTTGCCAGCATTCAGTTGGGCACTCTAAGGTGACTGCCGGTGACAAA CCGGAGGAAGGTGGGGATGACGTCAAATCATCATGCCCCTTATGACC TGGGCTACACACGTGCTACAATGGATGGTACAAAGGGCTGCAAGACC GCGAGGTCAAGCCAATCCCATAAAACCATTCTCAGTTCGGATTGTAG GCTGCAACTCGCCTACATGAAGCTGGAATCGCTAGTAATCGCGGATC AGCATGCCGCGGTGAATACGTTCCCGGGCCTTGTACACACCGCCCGTC ACACCACGAGAGTTTGTAACACCCGAAGTCGGTGGAGTAACCGTAAG GAGCTAGCCGCCTAAGGTGGGACAGATGATTGGGGTGAAGTCGTAAC AAGGTAGCCGTATCGGAAGGTGCGGCTGGATCACCTCCTTT |
| 78 | DP78 16S rRNA | TTGAAGAGTTTGATCATGGCTCAGATTGAACGCTGGCGGCAGGCCTA ACACATGCAAGTCGAACGGTAGCACAGAGAGCTTGCTCTTGGGTGAC GAGTGGCGGACGGGTGAGTAATGTCTGGGAAACTGCCCGATGGAGGG GGATAACTACTGGAAACGGTAGCTAATACCGCATAACGTCTTCGGAC CAAAGTGGGGGACCTTCGGGCCTCACACCATCGGATGTGCCCAGATG GGATTAGCTAGTAGGTGGGGTAATGGCTCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGTGGGGAGGAAGGCGATGAAGTTAATAGCTTCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTCAAGTCGGATGTGAAATCCCCGG GCTCAACCTGGGAACTGCATTCGAAACTGGCAGGCTAGAGTCTTGTA GAGGGGGGTAGAATTCCAGGTGTAGCGGTGAAATGCGTAGAGATCTG GAGGAATACCGGTGGCGAAGGCGGCCCCCTGGACAAAGACTGACGCT CAGGTGCGAAAGCGTGGGGAGCAAACAGGATTAGATACCCTGGTAGT CCACGCCGTAAACGATGTCGACTTGGAGGTTGTGCCCTTGAGGCGTG GCTTCCGGAGCTAACGCGTTAAGTCGACCGCCTGGGGAGTACGGCCG CAAGGTTAAAACTCAAATGAATTGACGGGGGCCCGCACAAGCGGTGG |

-continued

Sequence Listing

| Seq ID No. | Description | Sequence |
|---|---|---|
| | | AGCATGTGGTTTAATTCGATGCAACGCGAAGAACCTTACCTGGCCTTG<br>ACATCCACGGAATTCGGCAGAGATGCCTTAGTGCCTTCGGGAACCGT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGAGT<br>AATGTCGGGAACTCAAAGGAGACTGCCGGTGATAAACCGGAGGAAG<br>GTGGGGATGACGTCAAGTCATCATGGCCCTTACGGCCAGGGCTACAC<br>ACGTGCTACAATGGCGCATACAAAGAGAAGCGACCTCGCGAGAGCA<br>AGCGGACCTCATAAAGTGCGTCGTAGTCCGGATCGGAGTCTGCAACT<br>CGACTCCGTGAAGTCGGAATCGCTAGTAATCGTAGATCAGAATGCTA<br>CGGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 79 | DP79 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATACCTAGGAATCTGCCTGATAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCTACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGCAGTTACCTAATACGTGACTGTCTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTTGTTAAGTTGAATGTGAAATCCCCGGGCTCAAC<br>CTGGGAACTGCATCCAAAACTGGCAAGCTAGAGTATGGTAGAGGGTA<br>GTGGAATTTCCTGTGTAGCGGTGAAATGCGTAGATATAGGAAGGAAC<br>ACCAGTGGCGAAGGCGACTACCTGGACTGATACTGACACTGAGGTGC<br>GAAAGCGTGGGGAGCAAACAGGATTAGATACCCTGGTAGTCCACGCC<br>GTAAACGATGTCAACTAGCCGTTGGGAGTCTTGAACTCTTAGTGGCGC<br>AGCTAACGCATTAAGTTGACCGCCTGGGGAGTACGGCCGCAAGGTTA<br>AAACTCAAATGAATTGACGGGGGCCCGCACAAGCGGTGGAGCATGTG<br>GTTTAATTCGAAGCAACGCGAAGAACCTTACCAGGCCTTGACATCCA<br>ATGAACTTTCTAGAGATAGATTGGTGCCTTCGGGAACATTGAGACAG<br>GTGCTGCATGGCTGTCGTCAGCTCGTGTCGTGAGATGTTGGGTTAAGT<br>CCCGTAACGAGCGCAACCCTTGTCCTTAGTTACCAGCACGTAATGGTG<br>GGCACTCTAAGGAGACTGCCGGTGACAAACCGGAGGAAGGTGGGGA<br>TGACGTCAAGTCATCATGGCCCTTACGGCCTGGGCTACACACGTGCTA<br>CAATGGTCGGTACAAAGGGTTGCCAAGCCGCGAGGTGGAGCTAATCC<br>CATAAAACCGATCGTAGTCCGGATCGCAGTCTGCAACTCGACTGCGT<br>GAAGTCGGAATCGCTAGTAATCGTGAATCAGAATGTCACGGTGAATA<br>CGTTCCCGGGCCTTGTACACACCGCCCGTCACACCATGGGAGTGGGTT<br>GCACCAGAAGTAGCTAGTCTAACCTTCGGGAGGACGGTTACCACGGT<br>GTGATTCATGACTGGGGTGAAGTCGTAACAAGGTAGCCGTAGGGGAA<br>CCTGCGGCTGGATCACCTCCTT |
| 80 | DP80 16S rRNA | CTTGAGAGTTTGATCCTGGCTCAGAGCGAACGCTGGCGGCAGGCTTA<br>ACACATGCAAGTCGAGCGGGCACCTTCGGGTGTCAGCGGCAGACGGG<br>TGAGTAACACGTGGGAACGTACCCTTCGGTTCGGAATAACGCTGGGA<br>AACTAGCGCTAATACCGGATACGCCCTTTTGGGGAAAGGTTTACTGCC<br>GAAGGATCGGCCCGCGTCTGATTAGCTAGTTGGTGGGGTAACGGCCT<br>ACCAAGGCGACGATCAGTAGCTGGTCTGAGAGGATGATCAGCCACAC<br>TGGGACTGAGACACGGCCCAGACTCCTACGGGAGGCAGCAGTGGGG<br>AATATTGGACAATGGGCGCAAGCCTGATCCAGCCATGCCGCGTGAGT<br>GATGAAGGCCTTAGGGTTGTAAAGCTCTTTTGTCCGGGACGATAATG<br>ACGGTACCGGAAGAATAAGCCCCGGCTAACTTCGTGCCAGCAGCCGC<br>GGTAATACGAAGGGGGCTAGCGTTGCTCGGAATCACTGGGCGTAAAG<br>GGCGCGTAGGCGGCCATTCAAGTCGGGGGTGAAAGCCTGTGGCTCAA<br>CCACAGAATTGCCTTCGATACTGTTTGGCTTGAGTTTGGTAGAGGTTG<br>GTGGAACTGCGAGTGTAGAGGTGAAATTCGTAGATATTCGCAAGAAC<br>ACCAGTGGCGAAGGCGGCCAACTGGACCAATACTGACGCTGAGGCGC<br>GAAAGCGTGGGGAGCAAACAGGATTAGATACCCTGGTAGTCCACGCC<br>GTAAACGATGAATGCTAGCTGTTGGGGTGCTTGCACCTCAGTAGCGC<br>AGCTAACGCTTTAAGCATTCCGCCTGGGGAGTACGGTCGCAAGATTA<br>AAACTCAAAGGAATTGACGGGGGCCCGCACAAGCGGTGGAGCATGT<br>GGTTTAATTCGAAGCAACGCGCAGAACCTTACCATCCCTTGACATGTC<br>GTGCCATCCGGAGAGATCCGGGGTTCCCTTCGGGGACGCGAACACAG<br>GTGCTGCATGGCTGTCGTCAGCTCGTGTCGTGAGATGTTGGGTTAAGT<br>CCCGCAACGAGCGCAACCCACGTCCTTAGTTGCCATCATTTAGTTGGG<br>CACTCTAGGGAGACTGCCGGTGATAAGCCGCGAGGAAGGTGTGGATG<br>ACGTC |

-continued

Sequence Listing

| Seq ID No. | Description | Sequence |
|---|---|---|
| 81 | DP81 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAGGGGATGG GCCCGCGGCGCATTAGCTAGTTGGTAAGGTAACGGCTTACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC TTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTGAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 82 | DP82 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTCAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 83 | DP83 16S rRNA | ACGGAGAGTTTGATCCTGGCTCAGGACGAACGCTGGCGGCGTGCCTA ATACATGCAAGTCGAGCGGAGTTTCAAGAAGCTTGCTTTTTGAAACTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG |

-continued

Sequence Listing

| Seq ID No. | Description | Sequence |
|---|---|---|
| | | GCCCGCGGCGCATTAGCTAGTTGGTAAGGTAACGGCTTACCAAGGCA<br>ACGATGCGTAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGAGGAAGGC<br>CTTCGGGTCGTAAAGCTCTGTTGTGAGGGAAGAAGCGGTACCGTTCG<br>AATAGGGCGGTACCTTGACGGTACCTCACCAGAAAGCCACGGCTAAC<br>TACGTGCCAGCAGCCGCGGTAATACGTAGGTGGCAAGCGTTGTCCGG<br>AATTATTGGGCGTAAAGCGCGCGCAGGCGGCTTCTTAAGTCTGATGT<br>GAAATCTCGGGGCTCAACCCCGAGCGGCCATTGGAAACTGGGGAGCT<br>TGAGTGCAGAAGAGGAGAGTGGAATTCCACGTGTAGCGGTGAAATGC<br>GTAGAGATGTGGAGGAACACCAGTGGCGAAGGCGACTCTCTGGTCTG<br>TAACTGACGCTGAGGCGCGAAAGCGTGGGGAGCAAACAGGATTAGA<br>TACCCTGGTAGTCCACGCCGTAAACGATGAGTGCTAGGTGTTAGGGG<br>TTTCGATGCCCGTAGTGCCGAAGTTAACACATTAAGCACTCCGCCTGG<br>GGAGTACGGCCGCAAGGCTGAAACTCAAAGGAATTGACGGGGACCC<br>GCACAAGCAGTGGAGCATGTGGTTTAATTCGAAGCAACGCGAAGAAC<br>CTTACCAGGTCTTGACATCCTTTGACCACCCAAGAGATTGGGCTTCCC<br>CTTCGGGGGCAAAGTGACAGGTGGTGCATGGTTGTCGTCAGCTCGTG<br>TCGTGAGATGTTGGGTTAAGTCCCGCAACGAGCGCAACCCTTGATCTT<br>AGTTGCCAGCATTCAGTTGGGCACTCTAAGGTGACTGCCGGTGACAA<br>ACCGGAGGAAGGTGGGGATGACGTCAAATCATCATGCCCCTTATGAC<br>CTGGGCTACACACGTGCTACAATGGATGGTACAAAGGGCAGCGAAGC<br>CGCGAGGTGAAGCCAATCCCATAAAGCCATTCTCAGTTCGGATTGCA<br>GGCTGCAACTCGCCTGCATGAAGCCGGAATTGCTAGTAATCGCGGAT<br>CAGCATGCCGCGGTGAATACGTTCCCGGGTCTTGTACACACCGCCCGT<br>CACACCACGAGAGTTTGTAACACCCGAAGTCGGTGAGGCAACCTTTT<br>GGAGCCAGCCGCCTAAGGTGGGACAAATGATTGGGGTGAAGTCGTAA<br>CAAGGTAGCCGTATCGGAAGGTGCGGCTGGATCACCTCCTTT |
| 84 | DP84 16S rRNA | TACGGAGAGTTTGATCCTGGCTCAGGATGAACGCTGGCGGCGTGCTT<br>AACACATGCAAGTCGAACGGTGAAGCCAAGCTTGCTTGGTGGATCAG<br>TGGCGAACGGGTGAGTAACACGTGAGCAACCTGCCCTGGACTCTGGG<br>ATAAGCGCTGGAAACGGCGTCTAATACTGGATATGAGCTCTCATCGC<br>ATGGTGGGGGTTGGAAAGATTTTTTGGTCTGGGATGGGCTCGCGGCCT<br>ATCAGCTTGTTGGTGAGGTAATGGCTCACCAAGGCGTCGACGGGTAG<br>CCGGCCTGAGAGGGTGACCGGCCACACTGGGACTGAGACACGGCCCA<br>GACTCCTACGGGAGGCAGCAGTGGGGAATATTGCACAATGGGCGAAA<br>GCCTGATGCAGCAACGCCGCGTGAGGGATGACGGCCTTCGGGTTGTA<br>AACCTCTTTTAGCAGGGAAGAAGCGAAAGTGACGGTACCTGCAGAAA<br>AAGCGCCGGCTAACTACGTGCCAGCAGCCGCGGTAATACGTAGGGCG<br>CAAGCGTTATCCGGAATTATTGGGCGTAAAGAGCTCGTAGGCGGTTT<br>GTCGCGTCTGCTGTGAAATCCCGAGGCTCAACCTCGGGCCTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGTAACTGACGCTGAGGAGCGAAAGGGTGGGGAG<br>CAAACAGGCTTAGATACCCTGGTAGTCCACCCCGTAAACGTTGGGAA<br>CTAGTTGTGGGGACCATTCCACGGTTTCCGTGACGCAGCTAACGCATT<br>AAGTTCCCCGCCTGGGGAGTACGGCCGCAAGGCTAAAACTCAAAGGA<br>ATTGACGGGGACCCGCACAAGCGGCGGAGCATGCGGATTAATTCGAT<br>GCAACGCGAAGAACCTTACCAAGGCTTGACATACACCAGAACGGGCC<br>AGAAATGGTCAACTCTTTGGACACTGGTGAACAGGTGGTGCATGGTT<br>GTCGTCAGCTCGTGTCGTGAGATGTTGGGTTAAGTCCCGCAACGAGC<br>GCAACCCTCGTTCTATGTTGCCAGCACGTAATGGTGGGAACTCATGGG<br>ATACTGCCGGGGTCAACTCGGAGGAAGGTGGGGATGACGTCAAATCA<br>TCATGCCCCTTATGTCTTGGGCTTCACGCATGCTACAATGGCCGGTAC<br>AAAGGGCTGCAATACCGTGAGGTGGAGCGAATCCCAAAAAGCCGGTC<br>CCAGTTCGGATTGAGGTCTGCAACTCGACCTCATGAAGTCGGAGTCG<br>CTAGTAATCGCAGATCAGCAACGCTGCGGTGAATACGTTCCCGGGTC<br>TTGTACACACCGCCCGTCAAGTCATGAAAGGAGCCGTCGAAGGTGGG<br>ATCGGTAATTAGGACTAAGTCGTAACAAGGTAGCCGTACCGGAAGGT<br>GCGGCTGGATCACCTCCTTT |
| 85 | DP85 16S rRNA | TGCAGTCGTACGCTTCTTTTTCCNCCGGAGCTTGCTCCACCGGAAAAA<br>GAGGAGTGGCGAACGGGTGAGTAACACGTGGGTAACCTGCCCATCAG<br>AAGGGGATAACACTTGGAAACAGGTGCTAATACCGTATAACAATCGA<br>AACCGCATGGTTTTGATTTGAAAGGCGCTTTCGGGTGTCGCTGATGGA<br>TGGACCCGCGGTGCATTAGCTAGTTGGTGAGGTAACGGCTCACCAAG<br>GCCACGATGCATAGCCGACCTGAGAGGGTGATCGGCCACATTGGGAC<br>TGAGACACGGCCCAAACTCCTACGGGAGGCAGCAGTAGGGAATCTTC<br>GGCAATGGACGAAAGTCTGACCGAGCAACGCCGCGTGAGTGAAGAA<br>GGTTTTCGGATCGTAAAACTCTGTTGTTAGAGAAGAACAAGGATGAG<br>AGTAACTGTTCATCCCTTGACGGTATCTAACCAGAAAGCCACGGCTA<br>ACTACGTGCCAGCAGCCGCGGTAATACGTAGGTGGCAAGCGTTGTCC |

-continued

Sequence Listing

| Seq ID No. | Description | Sequence |
|---|---|---|
| | | GGATTTATTGGGCGTAAAGCGAGCGCAGGCGGTTTCTTAAGTCTGAT<br>GTGAAAGCCCCCGGCTCAACCGGGGAGGGTCATTGGAAACTGGGAGA<br>CTTGAGTGCAGAAGAGGAGAGTGGAATTCCATGTGTAGCGGTGAAAT<br>GCGTAGATATATGGAGGAACACCAGTGGCGAAGGCGGCTCTCTGGTC<br>TGTAACTGACGCTGNNCTCGAAAGCGTGGGGAGCAAACAGGATTAGA<br>TACCCTGGTAGTCCACGCCGTAAACGATGAGTGCTAAGTGTTGGAGG<br>GTTTCCGCCCTTCAGTGCTGCAGCTAACGCATTAAGCACTCCGCCTGG<br>GGAGTACGACCGCAAGGTTGAAACTCAAGGAATTGACGGGGGCCCGC<br>ACAGCGGTGGAGCATGNNGNTTANNGANCACGCGANANNTACNNNC<br>TNACATCNTTGACNCTCTANAGATAGAGCTTCCCTTCGGGGCAAGTG<br>ACNG |
| 86 | DP86 16S rRNA | CGATGCGTAGCCGACCTGAGAGGGTGATCGGCCACACTGGGACTGAG<br>ACACGGCCCAGACTCCTACGGGAGGCAGCAGTAGGGAATCTTCCGCA<br>ATGGACGAAAGTCTGACGGAGCAACGCCGCGTGAGTGATGAAGGTTT<br>TCGGATCGTAAAGCTCTGTTGTTAGGGAAGAACAAGTGCCGTTCAAA<br>TAGGGCGGCACCTTGACGGTACCTAACCAGAAAGCCACGGCTAACTA<br>CGTGCCAGCAGCCGCGGTAATACGTAGGTGGCAAGCGTTGTCCGGAA<br>TTATTGGGCGTAAAGGGCTCGCAGGCGGTTTCTTAAGTCTGATGTGAA<br>AGCCCCCGGCTCAACCGGGGAGGGTCATTGGAAACTGGGGAACTTGA<br>GTGCAGAAGAGGAGAGTGGAATTCCACGTGTAGCGGTGAAATGCGTA<br>GAGATGTGGAGGAACACCAGTGGCGAAGGCGACTCTCTGGTCTGTAA<br>CTGACGCTGAGGAGCGAAAGCGTGGGGAGCGAACAGGATTAGATAC<br>CCTGGTAGTCCACGCCGTAAACGATGAGTGCTAAGTGTTAGGGGGTT<br>TCCGCCCCTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAATCCTAGAGATAGGACGTCCCCTTC<br>GGGGGCAGAGTGACAGGTGGTGCATGGTTGTCGTCAGCTCGTGTCGT<br>GAGATGTTGGGTTAAGTCCCGCAACGAGCGCAACCCTTGATCTTAGTT<br>GCCAGCATTCAGTTGGGTGTTCTTTGAAAACT |
| 87 | DP87 16S rRNA | TTTGAGAGTTTGATCCTGGCTCAGGACGAACGCTGGCGGCGTGCCTA<br>ATACATGCAAGTCGAACGAACTCTGGTATTGATTGGTGCTTGCATCAT<br>GATTTACATTTGAGTGAGTGGCGAACTGGTGAGTAACACGTGGGAAA<br>CCTGCCCAGAAGCGGGGGATAACACCTGGAAACAGATGCTAATACCG<br>CATAACAACTTGGACCGCATGGTCCGAGCTTGAAAGATGGCTTCGGC<br>TATCACTTTTGGATGGTCCCGCGGCGTATTAGCTAGATGGTGGGGTAA<br>CGGCTCACCATGGCAATGATACGTAGCCGACCTGAGAGGGTAATCGG<br>CCACATTGGGACTGAGACACGGCCCAAACTCCTACGGGAGGCAGCAG<br>TAGGGAATCTTCCACAATGGACGAAAGTCTGATGGAGCAACGCCGCG<br>TGAGTGAAGAAGGGTTTCGGCTCGTAAAACTCTGTTGTTAAAGAAGA<br>ACATATCTGAGAGTAACTGTTCAGGTATTGACGGTATTTAACCAGAA<br>AGCCACGGCTAACTACGTGCCAGCAGCCGCGGTAATACGTAGGTGGC<br>AAGCGTTGTCCGGATTTATTGGGCGTAAAGCGAGCGCAGGCGGTTTTT<br>TAAGTCTGATGTGAAAGCCTTCGGCTCAACCGAAGAAGTGCATCGGA<br>AACTGGGAAACTTGAGTGCAGAAGAGGACAGTGGAACTCCATGTGTA<br>GCGGTGAAATGCGTAGATATATGGAAGAACACCAGTGGCGAAGGCG<br>GCTGTCTGGTCTGTAACTGACGCTGAGGCTCGAAAGTATGGGTAGCA<br>AACAGGATTAGATACCCTGGTAGTCCATACCGTAAACGATGAATGCT<br>AAGTGTTGGAGGGTTTCCGCCCTTCAGTGCTGCAGCTAACGCATTAAG<br>CATTCCGCCTGGGGAGTACGGCCGCAAGGCTGAAACTCAAAGGAATT<br>GACGGGGGCCCGCACAAGCGGTGGAGCATGTGGTTTAATTCGAAGCT<br>ACGCGAAGAACCTTACCAGGTCTTGACATACTATGCAAATCTAAGAG<br>ATTAGACGTTCCCTTCGGGGACATGGATACAGGTGGTGCATGGTTGTC<br>GTCAGCTCGTGTCGTGAGATGTTGGGTTAAGTCCCGCAACGAGCGCA<br>ACCCTTATTATCAGTTGCCAGCATTAAGTTGGGCACTCTGGTGAGACT<br>GCCGGTGACAAACCGGAGGAAGGTGGGGATGACGTCAAATCATCATG<br>CCCCTTATGACCTGGGCTACACACGTGCTACAATGGATGGTACAACG<br>AGTTGCGAACTCGCGAGAGTAAGCTAATCTCTTAAAGCCATTCTCAGT<br>TCGGATTGTAGGCTGCAACTCGCCTACATGAAGTCGGAATCGCTAGT<br>AATCGCGGATCAGCATGCCGCGGTGAATACGTTCCCGGGCCTTGTAC<br>ACACCGCCCGTCACACCATGAGAGTTTGTAACACCCAAAGTCGGTGG<br>GGTAACCTTTTAGGAACCAGCCGCCTAAGGTGGGACAGATGATTAGG<br>GTGAAGTCGTAACAAGGTAGCCGTAGGAGAACCTGCGGCTGGATCAC<br>CTCCTT |
| 88 | DP88 16S rRNA | TAGTGGGTTTGATCCTGGCTCAGGACGAACGCTGGCGGCGTGCCTAA<br>TACATGCAAGTCGAGCGGACAGATGGGAGCTTGCTCCCTGATGTTAG<br>CGGCGGACGGGTGAGTAACACGTGGGTAACCTGCCTGTAAGACTGGG<br>ATAACTCCGGGAAACCGGGGCTAATACCGGATGGTTGTCTGAACCGC<br>ATGGTTCAGACATAAAAGGTGGCTTCGGCTACCACTTACAGATGGAC<br>CCGCGGCGCATTAGCTAGTTGGTGAGGTAACGGCTCACCAAGGCGAC |

-continued

Sequence Listing

| Seq ID No. | Description | Sequence |
|---|---|---|
| | | GATGCGTAGCCGACCTGAGAGGGTGATCGGCCACACTGGGACTGAGA |
| | | CACGGCCCAGACTCCTACGGGAGGCAGCAGTAGGGAATCTTCCGCAA |
| | | TGGACGAAAGTCTGACGGAGCAACGCCGCGTGAGTGATGAAGGTTTT |
| | | CGGATCGTAAAGCTCTGTTGTTAGGGAAGAACAAGTGCCGTTCAAAT |
| | | AGGGCGGCACCTTGACGGTACCTAACCAGAAAGCCACGGCTAACTAC |
| | | GTGCCAGCAGCCGCGGTAATACGTAGGTGGCAAGCGTTGTCCGGAAT |
| | | TATTGGGCGTAAAGGGCTCGCAGGCGGTTTCTTAAGTCTGATGTGAA |
| | | AGCCCCCGGCTCAACCGGGGAGGGTCATTGGAAACTGGGGAACTTGA |
| | | GTGCAGAAGAGGAGAGTGGAATTCCACGTGTAGCGGTGAAATGCGTA |
| | | GAGATGTGGAGGAACACCAGTGGCGAAGGCGACTCTCTGGTCTGTAA |
| | | CTGACGCTGAGGAGCGAAAGCGTGGGGAGCGAACAGGATTAGATAC |
| | | CCTGGTAGTCCACGCCGTAAACGATGAGTGCTAAGTGTTAGGGGGTT |
| | | TCCGCCCCTTAGTGCTGCAGCTAACGCATTAAGCACTCCGCCTGGGGA |
| | | GTACGGTCGCAAGACTGAAACTCAAAGGAATTGACGGGGGCCCGCAC |
| | | AAGCGGTGGAGCATGTGGTTTAATTCGAAGCAACGCGAAGAACCTTA |
| | | CCAGGTCTTGACATCCTCTGACAATCCTAGAGATAGGACGTCCCCTTC |
| | | GGGGGCAGAGTGACAGGTGGTGCATGGTTGTCGTCAGCTCGTGTCGT |
| | | GAGATGTTGGGTTAAGTCCCGCAACGAGCGCAACCCTTGATCTTAGTT |
| | | GCCAGCATTCAGTTGGGCACTCTAAGGTGACTGCCGGTGACAAACCG |
| | | GAGGAAGGTGGGGATGACGTCAAATCATCATGCCCCTTATGACCTGG |
| | | GCTACACACGTGCTACAATGGACAGAACAAAGGGCAGCGAAACCGC |
| | | GAGGTTAAGCCAATCCCACAAATCTGTTCTCAGTTCGGATCGCAGTCT |
| | | GCAACTCGACTGCGTGAAGCTGGAATCGCTAGTAATCGCGGATCAGC |
| | | ATGCCGCGGTGAATACGTTCCCGGGCCTTGTACACACCGCCCGTCACA |
| | | CCACGAGAGTTTGTAACACCCGAAGTCGGTGAGGTAACCTTTATGGA |
| | | GCCAGCCGCCGAAGGTGGGACAGATGATTGGGGTGAAGTCGTAACAA |
| | | GGTAGCCGTATCGGAAGGTGCGGCTGGATCACCTCCTTT |
| 89 | DP89 16S rRNA | GTAACGGCTCACCAAGGCAACGATGCGTAGCCGACCTGAGAGGGTGA |
| | | TCGGCCACACTGGGACTGAGACACGGCCCAGACTCCTACGGGAGGCA |
| | | GCAGTAGGGAATCTTCCGCAATGGACGAAAGTCTGACGGAGCAACGC |
| | | CGCGTGAGTGATGAAGGTTTTCGGATCGTAAAGCTCTGTTGTTAGGGA |
| | | AGAACAAGTACCGTTCGAATAGGGCGGTACCTTGACGGTACCTAACC |
| | | AGAAAGCCACGGCTAACTACGTGCCAGCAGCCGCGGTAATACGTAGG |
| | | TGGCAAGCGTTGTCCGGAATTATTGGGCGTAAAGGGCTCGCAGGCGG |
| | | TTTCTTAAGTCTGATGTGAAAGCCCCCGGCTCAACCGGGGAGGGTCAT |
| | | TGGAAACTGGGGAACTTGAGTGCAGAAGAGGAGAGTGGAATTCCAC |
| | | GTGTAGCGGTGAAATGCGTAGAGATGTGGAGGAACACCAGTGGCGA |
| | | AGGCGACTCTCTGGTCTGTAACTGACGCTGAGGAGCGAAAGCGTGGG |
| | | GAGCGAACAGGATTAGATACCCTGGTAGTCCACGCCGTAAACGATGA |
| | | GTGCTAAGTGTTAGGGGGTTTCCGCCCCTTAGTGCTGCAGCTAACGCA |
| | | TTAAGCACTCCGCCTGGGGAGTACGGTCGCAAGACTGAAACTCAAAG |
| | | GAATTGACGGGGGCCCGCACAAGCGGTGGAGCATGTGGTTTAATTCG |
| | | AAGCAACGCGAAGAACCTTACCAGGTCTTGACATCCTCTGACAATCC |
| | | TAGAGATAGGACGTCCCCTTCGGGGGCAGAGTGACAGGTGGTGCATG |
| | | GTTGTCGTCAGCTCGTGTCGTGAGATGTTGGGTTAAGTCCCGCAACGA |
| | | GCGCAACCCTTGATCTTAGTTGCCAGCATTCAGTTGGGCACTCTAAGG |
| | | TGACTGCCGGTGACAAACCGGAGGAAGGTGGGGATGACGTCAAATCA |
| | | TCATGCCCCTTATGACCTGGGCTACACACGTGCTACAATGGACAGAA |
| | | CAAAGGGCAGCGAAACCGCGAGGTTAAGCCAATCCCACAAATCTGTT |
| | | CTCAGTTCGGATCGCAGTCTGCAACTCGACTGCGTGAAGCTGGAATC |
| | | GCTAGTAATCGCGGATCAGCATGCCGCGGTGAATACGTTCCCGGGCC |
| | | TTGTACACACCGCCCGTCACACCACGAGAGTTTGTAACACCCGAAGT |
| | | CGGTGAGGTAACCTTTTAGGAGCCAGCCGCCGAAGGTGGGACAGATG |
| | | ATTGGGGTGAAGTCGTAACAAGGTAGCCGTATCGGAAGGTGCGGCTG |
| | | GATCACCTCCTTT |
| 90 | DP90 16S rRNA | TTTGAGAGTTTGATCCTGGCTCAGGACGAACGCTGGCGGCGTGCCTA |
| | | ATACATGCAAGTCGAACGAACTCTGGTATTGATTGGTGCTTGCATCAT |
| | | GATTTACATTTGAGTGAGTGGCGAACTGGTGAGTAACACGTGGGAAA |
| | | CCTGCCCAGAAGCGGGGGATAACACCTGGAAACAGATGCTAATACCG |
| | | CATAACAACTTGGACCGCATGGTCCGAGCTTGAAAGATGGCTTCGGC |
| | | TATCACTTTTGGATGGTCCCGCGGCGTATTAGCTAGATGGTGGGGTAA |
| | | CGGCTCACCATGGCAATGATACGTAGCCGACCTGAGAGGGTAATCGG |
| | | CCACATTGGGACTGAGACACGGCCCAAACTCCTACGGGAGGCAGCAG |
| | | TAGGGAATCTTCCACAATGGACGAAAGTCTGATGGAGCAACGCCGCG |
| | | TGAGTGAAGAAGGGTTTCGGCTCGTAAAACTCTGTTGTTAAAGAAGA |
| | | ACATATCTGAGAGTAACTGTTCAGGTATTGACGGTATTTAACCAGAA |
| | | AGCCACGGCTAACTACGTGCCAGCAGCCGCGGTAATACGTAGGTGGC |
| | | AAGCGTTGTCCGGATTTATTGGGCGTAAAGCGAGCGCAGGCGGTTTTT |
| | | TAAGTCTGATGTGAAAGCCTTCGGCTCAACCGAAGAAGTGCATCGGA |
| | | AACTGGGAAACTTGAGTGCAGAAGAGGACAGTGGAACTCCATGTGTA |
| | | GCGGTGAAATGCGTAGATATATGGAAGAACACCAGTGGCGAAGGCG |

-continued

| Seq ID No. | Description | Sequence |
|---|---|---|
| | | GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT GCCGGTGACAAACCGGAGGAAGGTGGGGATGACGTCAAATCATCATG CCCCTTATGACCTGGGCTACACACGTGCTACAATGGATGGTACAACG AGTTGCGAACTCGCGAGAGTAAGCTAATCTCTTAAAGCCATTCTCAGT TCGGATTGTAGGCTGCAACTCGCCTACATGAAGTCGGAATCGCTAGT AATCGCGGATCAGCATGCCGCGGTGAATACGTTCCCGGGCCTTGTAC ACACCGCCCGTCACACCATGAGAGTTTGTAACACCCAAAGTCGGTGG GGTAACCTTTTAGGAACCAGCCGCCTAAGGTGGGACAGATGATTAGG GTGAAGTCGTAACAAGGTAGCCGTAGGAGAACCTGCGGCTGGATCAC CTCCTT |
| 92 | DP92 16S rRNA | CGATGCGTAGCCGACCTGAGAGGGTGATCGGCCACACTGGGACTGAG ACACGGCCCAGACTCCTACGGGAGGCAGCAGTAGGGAATCTTCCGCA ATGGACGAAAGTCTGACGGAGCAACGCCGCGTGAGTGATGAAGGTTT TCGGATCGTAAAGCTCTGTTGTTAGGGAAGAACAAGTACCGTTCGAA TAGGGCGGTACCTTGACGGTACCTAACCAGAAAGCCACGGCTAACTA CGTGCCAGCAGCCGCGGTAATACGTAGGTGGCAAGCGTTGTCCGGAA TTATTGGGCGTAAAGGGCTCGCAGGCGGTTTCTTAAGTCTGATGTGAA AGCCCCCGGCTCAACCGGGGAGGGTCATTGGAAACTGGGGAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAATCCTAGAGATAGGACGTCCCCTTC GGGGGCAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTCAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCAGCGAAACCGC GAGGTTAAGCCAATCCCACAAATCTGTTCTCAGTTCGGATCGCAGTCT GCAACTCGACTGCGTGAAGCTGGAATCGCTAGTAATCGCGGATCAGC ATGCCGCGGTGAATACGTTCCCGGGCCTTGTACACACCGCCCGTCACA CCACGAGAGTTTGTAACACCCGAAGTCGGTGAGGTAACCTTTTAGGA GCCAGCCGCCGAAGGTGGGACAGATGATTGGGGTGAAGTCGTAACAA GGTAGCCGTATCGGAAGGTGCGGCTGGATCACCTCCTTT |
| 93 | DP93 16S rRNA | ATTGAGAGTTTGATCCTGGCTCAGGATGAACGCTGGCGGCGTGCCTA ATACATGCAAGTCGAACGCACAGCGAAAGGTGCTTGCACCTTTCAAG TGAGTGGCGAACGGGTGAGTAACACGTGGACAACCTGCCTCAAGGCT GGGGATAACATTTGGAAACAGATGCTAATACCGAATAAAACTTAGTG TCGCATGACAAAAAGTTAAAAGGCGCTTCGGCGTCACCTAGAGATGG ATCCGCGGTGCATTAGTTAGTTGGTGGGGTAAAGGCCTACCAAGACA ATGATGCATAGCCGAGTTGAGAGACTGATCGGCCACATTGGGACTGA GACACGGCCCAAACTCCTACGGGAGGCTGCAGTAGGGAATCTTCCAC AATGGGCGAAAGCCTGATGGAGCAACGCCGCGTGTGTGATGAAGGCT TTCGGGTCGTAAAGCACTGTTGTATGGGAAGAACAGCTAGAATAGGA AATGATTTTAGTTTGACGGTACCATACCAGAAAGGGACGGCTAAATA CGTGCCAGCAGCCGCGGTAATACGTATGTCCCGAGCGTTATCCGGATT TATTGGGCGTAAAGCGAGCGCAGACGGTTTATTAAGTCTGATGTGAA AGCCCGGAGCTCAACTCCGGAATGGCATTGGAAACTGGTTAACTTGA GTGCAGTAGAGGTAAGTGGAACTCCATGTGTAGCGGTGGAATGCGTA GATATATGGAAGAACACCAGTGGCGAAGGCGGCTTACTGGACTGCAA CTGACGTTGAGGCTCGAAAGTGTGGGTAGCAAACAGGATTAGATACC CTGGTAGTCCACACCGTAAACGATGAACACTAGGTGTTAGGAGGTTT CCGCCTCTTAGTGCCGAAGCTAACGCATTAAGTGTTCCGCCTGGGGAG TACGACCGCAAGGTTGAAACTCAAAGGAATTGACGGGGACCCGCACA AGCGGTGGAGCATGTGGTTTAATTCGAAGCAACGCGAAGAACCTTAC CAGGTCTTGACATCCTTTGAAGCTTTTAGAGATAGAAGTGTTCTCTTC GGAGACAAAGTGACAGGTGGTGCATGGTCGTCGTCAGCTCGTGTCGT GAGATGTTGGGTTAAGTCCCGCAACGAGCGCAACCCTTATTGTTAGTT GCCAGCATTCAGATGGGCACTCTAGCGAGACTGCCGGTGACAAACCG GAGGAAGGCGGGGACGACGTCAGATCATCATGCCCCTTATGACCTGG |

-continued

Sequence Listing

| Seq ID No. | Description | Sequence |
|---|---|---|
| | | GCTACACACGTGCTACAATGGCGTATACAACGAGTTGCCAACCCGCG AGGGTGAGCTAATCTCTTAAAGTACGTCTCAGTTCGGATTGTAGTCTG CAACTCGACTACATGAAGTCGGAATCGCTAGTAATCGCGGATCAGCA CGCCGCGGTGAATACGTTCCCGGGTCTTGTACACACCGCCCGTCACAC CATGGGAGTTTGTAATGCCCAAAGCCGGTGGCCTAACCTTTTAGGAA GGAGCCGTCTAAGGCAGGACAGATGACTGGGGTGAAGTCGTAACAA GGTAGCCGTAGGAGAACCTGCGGCTGGATCACCTCCTTT |
| 94 | DP94 16S rRNA | ATCTGCCCAGAAGCAGGGGATAACACTTGGAAACAGGTGCTAATACC GTATAACAACAAAATCCGCATGGATTTTGTTTGAAAGGTGGCTTCGGC TATCACTTCTGGATGATCCCGCGGCGTATTAGTTAGTTGGTGAGGTAA AGGCCCACCAAGACGATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAATGCCGCG TGAGTGAAGAAGGGTTTCGGCTCGTAAAACTCTGTTGTTAAAGAAGA ACACCTTTGAGAGTAACTGTTCAAGGGTTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTTAACCGGAGAAGTGCATCGGA AACTGGGAGACTTGAGTGCAGAAGAGGACAGTGGAACTCCATGTGTA GCGGTGGAATGCGTAGATATATGGAAGAACACCAGTGGCGAAGGCG GCTGTCTAGTCTGTAACTGACGCTGAGGCTCGAAAGCATGGGTAGCG AACAGGATTAGATACCCTGGTAGTCCATGCCGTAAACGATGAGTGCT AAGTGTTGGAGGGTTTCCGCCCTTCAGTGCTGCAGCTAACGCATTAAG CACTCCGCCTGGGGAGTACGACCGCAAGGTTGAAACTCAAAGGAATT GACGGGGGCCCGCACAAGCGGTGGAGCATGTGGTTTAATTCGAAGCT ACGCGAAGAACCTTACCAGGTCTTGACATCTTCTGCCAATCTTAGAGA TAAGACGTTCCCTTCGGGGACAGAATGACAGGTGGTGCATGGTTGTC GTCAGCTCGTGTCGTGAGATGTTGGGTTAAGTCCCGCAACGAGCGCA ACCCTTATTATCAGTTGCCAGCATTCAGTTGGGCACTCTGGTGAGACT GCCGGTGACAAACCGGAGGAAGGTGGGGATGACGTCAAATCATCATG CCCCTTATGACCTGGGCTACACACGTGCTACAATGGACGGTACAACG AGTTGCGAAGTCGTGAGGCTAAGCTAATCTCTTAAAGCCGTTCTCAGT TCGGATTGTAGGCTGCAACTCGCCTACATGAAGTTGGAATCGCTAGTA ATCGCGGATCAGCATGCCGCGGTGAATACGTTCCCGGGCCTTGTACA CACCGCCCGTCACACCATGAGAGTTTGTAACACCCAAAGCCGGTGAG ATAACCTTCGGGAGTCAGCCGTCTAAGGTGGGACAGATGATTAGGGT GAAGTCGTAACAAGGTAGCCGTAGGAGAACCTGCGGCTGGATCACCT CCTT |
| 95 | DP95 16S rRNA | TGCTAATACCGCATAGATCCAAGAACCGCATGGTTCTTGGCTGAAAG ATGGCGTAAGCTATCGCTTTTGGATGGACCCGCGGCGTATTAGCTAGT TGGTGAGGTAATGGCTCACCAAGGCGATGATACGTAGCCGAACTGAG AGGTTGATCGGCCACATTGGGACTGAGACACGGCCCAAACTCCTACG GGAGGCAGCAGTAGGGAATCTTCCACAATGGACGCAAGTCTGATGGA GCAACGCCGCGTGAGTGAAGAAGGCTTTCGGGTCGTAAAACTCTGTT GTTGGAGAAGAATGGTCGGCAGAGTAACTGTTGTCGGCGTGACGGTA TCCAACCAGAAAGCCACGGCTAACTACGTGCCAGCAGCCGCGGTAAT ACGTAGGTGGCAAGCGTTATCCGGATTTATTGGGCGTAAAGCGAGCG CAGGCGGTTTTTTAAGTCTGATGTGAAAGCCCTCGGCTTAACCGAGGA AGCGCATCGGAAACTGGGAAACTTGAGTGCAGAAGAGGACAGTGGA ACTCCATGTGTAGCGGTGAAATGCGTAGATATATGGAAGAACACCAG TGGCGAAGGCGGCTGTCTGGTCTGTAACTGACGCTGAGGCTCGAAAG CATGGGTAGCGAACAGGATTAGATACCCTGGTAGTCCATGCCGTAAA CGATGAATGCTAGGTGTTGGAGGGTTTCCGCCCTTCAGTGCCGCAGCT AACGCATTAAGCATTCCGCCTGGGGAGTACGACCGCAAGGTTGAAAC TCAAAGGAATTGACGGGGGCCCGCACAAGCGGTGGAGCATGTGGTTT AATTCGAAGCAACGCGAAGAACCTTACCAGGTCTTGACATCTTTTGAT CACCTGAGAGATCAGGTTTCCCCTTCGGGGGCAAAATGACAGGTGGT GCATGGTTGTCGTCAGCTCGTGTCGTGAGATGTTGGGTTAAGTCCCGC AACGAGCGCAACCCTTATGACTAGTTGCCAGCATTTAGTTGGGCACTC TAGTAAGACTGCCGGTGACAAACCGGAGGAAGGTGGGGATGACGTC AAATCATCATGCCCCTTATGACCTGGGCTACACACGTGCTACAATGGA TGGTACAACGAGTTGCGAGACCGCGAGGTCAAGCTAATCTCTTAAAG CCATTCTCAGTTCGGACTGTAGGCTGCAACTCGCCTACACGAAGTCGG AATCGCTAGTAATCGCGGATCAGCACGCCGCGGTGAATACGTTCCCG GGCCTTGTACACACCGCCCGTCACACCATGAGAGTTTGTAACACCCG AAGCCGGTGGCGTAACCCTTTTAGGGAGCGAGCCGTCTAAGGTGGGA CAAATGATTAGGGTGAAGTCGTAACAAGGTAGCCGTAGGAGAACCTG CGGCTGGATCACCTCCTTT |

-continued

Sequence Listing

| Seq ID No. | Description | Sequence |
|---|---|---|
| 96 | DP96 16S rRNA | ACACGGCCCAAACTCCTACGGGAGGCAGCAGTAGGGAATCTTCCACA<br>ATGGACGCAAGTCTGATGGAGCAACGCCGCGTGAGTGAAGAAGGCTT<br>TCGGGTCGTAAAACTCTGTTGTTGGAGAAGAATGGTCGGCAGAGTAA<br>CTGTTGTCGGCGTGACGGTATCCAACCAGAAAGCCACGGCTAACTAC<br>GTGCCAGCAGCCGCGGTAATACGTAGGTGGCAAGCGTTATCCGGATT<br>TATTGGGCGTAAAGCGAGCGCAGGCGGTTTTTTAAGTCTGATGTGAA<br>AGCCCTCGGCTTAACCGAGGAAGCGCATCGGAAACTGGGAAACTTGA<br>GTGCAGAAGAGGACAGTGGAACTCCATGTGTAGCGGTGAAATGCGTA<br>GATATATGGAAGAACACCAGTGGCGAAGGCGGCTGTCTGGTCTGTAA<br>CTGACGCTGAGGCTCGAAAGCATGGGTAGCGAACAGGATTAGATACC<br>CTGGTAGTCCATGCCGTAAACGATGAATGCTAGGTGTTGGAGGGTTTC<br>CGCCCTTCAGTGCCGCAGCTAACGCATTAAGCATTCCGCCTGGGGAGT<br>ACGACCGCAAGGTTGAAACTCAAAGGAATTGACGGGGGCCCGCACA<br>AGCGGTGGAGCATGTGGTTTAATTCGAAGCAACGCGAAGAACCTTAC<br>CAGGTCTTGACATCTTTTGATCACCTGAGAGATCAGGTTTCCCCTTCG<br>GGGGCAAAATGACAGGTGGTGCATGGTTGTCGTCAGCTCGTGTCGTG<br>AGATGTTGGGTTAAGTCCCGCAACGAGCGCAACCCTTATGACTAGTT<br>GCCAGCATTTAGTTGGGCACTCTAGTAAGACTGCCGGTGACAAACCG<br>GAGGAAGGTGGGGATGACGTCAAATCATCATGCCCCTTATGACCTGG<br>GCTACACACGTGCTACAATGGATGGTACAACGAGTTGCGAGACCGCG<br>AGGTCAAGCTAATCTCTTAAAGCCATTCTCAGTTCGGACTGTAGGCTG<br>CAACTCGCCTACACGAAGTCGGAATCGCTAGTAATCGCGGATCAGCA<br>CGCCGCGGTGAATACGTTCCCGGGCCTTGTACACACCGCCCGTCACAC<br>CATGAGAGTTTGTAACACCCGAAGCCGGTGGCGTAACCCTTTTAGGG<br>AGCGAGCCGTCTAAGGTGGGACAAATGATTAGGGTGAAGTCGTAACA<br>AGGTAGCCGTAGGAGAACCTGCGGCTGGATCACCTCCTTT |
| 97 | DP97 16S rRNA | AATGAGAGTTTGATCCTGGCTCAGGACGAACGCTGGCGGCGTGCCTA<br>ATACATGCAAGTCGAGCGATGATTAAAGATAGCTTGCTATTTTTATGA<br>AGAGCGGCGAACGGGTGAGTAACGCGTGGGAAATCTGCCGAGTAGC<br>GGGGGACAACGTTTGGAAACGAACGCTAATACCGCATAACAATGAGA<br>ATCGCATGATTCTTATTTAAAAGAAGCAATTGCTTCACTACTTGATGA<br>TCCCGCGTTGTATTAGCTAGTTGGTAGTGTAAAGGACTACCAAGGCG<br>ATGATACATAGCCGACCTGAGAGGGTGATCGGCCACACTGGGACTGA<br>GACACGGCCCAGACTCCTACGGGAGGCAGCAGTAGGGAATCTTCGGC<br>AATGGGGGCAACCCTGACCGAGCAACGCCGCGTGAGTGAAGAAGGTT<br>TTCGGATCGTAAAACTCTGTTGTTAGAGAAGAACGTTAAGTAGAGTG<br>GAAAATTACTTAAGTGACGGTATCTAACCAGAAAGGGACGGCTAACT<br>ACGTGCCAGCAGCCGCGGTAATACGTAGGTCCCAAGCGTTGTCCGGA<br>TTTATTGGGCGTAAAGCGAGCGCAGGTGGTTTCTTAAGTCTGATGTAA<br>AAGGCAGTGGCTCAACCATTGTGTGCATTGGAAACTGGGAGACTTGA<br>GTGCAGGAGAGGAGAGTGGAATTCCATGTGTAGCGGTGAAATGCGTA<br>GATATATGGAGGAACACCGGAGGCGAAAGCGGCTCTCTGGCCTGTAA<br>CTGACACTGAGGCTCGAAAGCGTGGGGAGCAAACAGGATTAGATACC<br>CTGGTAGTCCACGCCGTAAACGATGAGTGCTAGCTGTAGGGAGCTAT<br>AAGTTCTCTGTAGCGCAGCTAACGCATTAAGCACTCCGCCTGGGGAG<br>TACGACCGCAAGGTTGAAACTCAAAGGAATTGACGGGGGCCCGCACA<br>AGCGGTGGAGCATGTGGTTTAATTCGAAGCAACGCGAAGAACCTTAC<br>CAGGTCTTGACATACTCGTGATATCCTTAGAGATAAGGAGTTCCTTCG<br>GGACACGGGATACAGGTGGTGCATGGTTGTCGTCAGCTCGTGTCGTG<br>AGATGTTGGGTTAAGTCCCGCAACGAGCGCAACCCTTATTACTAGTTG<br>CCATCATTAAGTTGGGCACTCTAGTGAGACTGCCGGTGATAAACCGG<br>AGGAAGGTGGGGATGACGTCAAATCATCATGCCCCTTATGACCTGGG<br>CTACACACGTGCTACAATGGATGGTACAACGAGTCGCCAACCCGCGA<br>GGGTGCGCTAATCTCTTAAAACCATTCTCAGTTCGGATTGCAGGCTGC<br>AACTCGCCTGCATGAAGTCGGAATCGCTAGTAATCGCGGATCAGCAC<br>GCCGCGGTGAATACGTTCCCGGGCCTTGTACACACCGCCCGTCACACC<br>ACGGAAGTTGGGAGTACCCAAAGTAGGTTGCCTAACCGCAAGGAGGG<br>CGCTTCCTAAGGTAAGACCGATGACTGGGGTGAAGTCGTAACAAGGT<br>AGCCGTATCGGAAGGTGCGGCTGGATCACCTCCTTT |
| 98 | DP98 16S rRNA | AATGAGAGTTTGATCCTGGCTCAGGACGAACGCTGGCGGCGTGCCTA<br>ATACATGCAAGTCGAGCGATGATTAAAGATAGCTTGCTATTTTTATGA<br>AGAGCGGCGAACGGGTGAGTAACGCGTGGGAAATCTGCCGAGTAGC<br>GGGGGACAACGTTTGGAAACGAACGCTAATACCGCATAACAATGAGA<br>ATCGCATGATTCTTATTTAAAAGAAGCAATTGCTTCACTACTTGATGA<br>TCCCGCGTTGTATTAGCTAGTTGGTAGTGTAAAGGACTACCAAGGCG<br>ATGATACATAGCCGACCTGAGAGGGTGATCGGCCACACTGGGACTGA<br>GACACGGCCCAGACTCCTACGGGAGGCAGCAGTAGGGAATCTTCGGC<br>AATGGGGGCAACCCTGACCGAGCAACGCCGCGTGAGTGAAGAAGGTT<br>TTCGGATCGTAAAACTCTGTTGTTAGAGAAGAACGTTAAGTAGAGTG<br>GAAAATTACTTAAGTGACGGTATCTAACCAGAAAGGGACGGCTAACT<br>ACGTGCCAGCAGCCGCGGTAATACGTAGGTCCCAAGCGTTGTCCGGA |

-continued

Sequence Listing

| Seq ID No. | Description | Sequence |
|---|---|---|
| | | TTTATTGGGCGTAAAGCGAGCGCAGGTGGTTTCTTAAGTCTGATGTAA AAGGCAGTGGCTCAACCATTGTGTGCATTGGAAACTGGGAGACTTGA GTGCAGGAGAGGAGAGTGGAATTCCATGTGTAGCGGTGAAATGCGTA GATATATGGAGGAACACCGGAGGCGAAAGCGGCTCTCTGGCCTGTAA CTGACACTGAGGCTCGAAAGCGTGGGGAGCAAACAGGATTAGATACC CTGGTAGTCCACGCCGTAAACGATGAGTGCTAGCTGTAGGGAGCTAT AAGTTCTCTGTAGCGCAGCTAACGCATTAAGCACTCCGCCTGGGGAG TACGACCGCAAGGTTGAAACTCAAAGGAATTGACGGGGGCCCGCACA AGCGGTGGAGCATGTGGTTTAATTCGAAGCAACGCGAAGAACCTTAC CAGGTCTTGACATACTCGTGATATCCTTAGAGATAAGGAGTTCCTTCG GGACACGGGATACAGGTGGTGCATGGTTGTCGTCAGCTCGTGTCGTG AGATGTTGGGTTAAGTCCCGCAACGAGCGCAACCCTTATTACTAGTTG CCATCATTAAGTTGGGCACTCTAGTGAGACTGCCGGTGATAAACCGG AGGAAGGTGGGGATGACGTCAAATCATCATGCCCCTTATGACCTGGG CTACACACGTGCTACAATGGATGGTACAACGAGTCGCCAACCCGCGA GGGTGCGCTAATCTCTTAAAACCATTCTCAGTTCGGATTGCAGGCTGC AACTCGCCTGCATGAAGTCGGAATCGCTAGTAATCGCGGATCAGCAC GCCGCGGTGAATACGTTCCCGGGCCTTGTACACACCGCCCGTCACACC ACGGAAGTTGGGAGTACCCAAAGTAGGTTGCCTAACCGCAAGGAGGG CGCTTCCTAAGGTAAGACCGATGACTGGGGTGAAGTCGTAACAAGGT AGCCGTATCGGAAGGTGCGGCTGGATCACCTCCTTT |
| 100 | DP100 16S rRNA | TTTGAGAGTTTGATCCTGGCTCAGGACGAACGCTGGCGGCGTGCCTA ATACATGCAAGTCGAACGAACTCTGGTATTGATTGGTGCTTGCATCAT GATTTACATTTGAGTGAGTGGCGAACTGGTGAGTAACACGTGGGAAA CCTGCCCAGAAGCGGGGGATAACACCTGGAAACAGATGCTAATACCG CATAACAACTTGGACCGCATGGTCCGAGCTTGAAAGATGGCTTCGGC TATCACTTTTGGATGGTCCCGCGGCGTATTAGCTAGATGGTGGGGTAA CGGCTCACCATGGCAATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAACGCCGCG TGAGTGAAGAAGGGTTTCGGCTCGTAAAACTCTGTTGTTAAAGAAGA ACATATCTGAGAGTAACTGTTCAGGTATTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTCAACCGAAGAAGTGCATCGGA AACTGGGAAACTTGAGTGCAGAAGAGGACAGTGGAACTCCATGTGTA GCGGTGAAATGCGTAGATATATGGAAGAACACCAGTGGCGAAGGCG GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT GCCGGTGACAAACCGGAGGAAGGTGGGGATGACGTCAAATCATCATG CCCCTTATGACCTGGGCTACACACGTGCTACAATGG |
| 101 | DP101 16S rRNA | ATGAGAGTTTGATCTTGGCTCAGGATGAACGCTGGCGGCGTGCCTAA TACATGCAAGTCGAACGAACTTCCGTTAATTGATTATGACGTACTTGT ACTGATTGAGATTTTAACACGAAGTGAGTGGCGAACGGGTGAGTAAC ACGTGGGTAACCTGCCCAGAAGTAGGGGATAACACCTGGAAACAGAT GCTAATACCGTATAACAGAGAAAACCGCATGGTTTTCTTTTAAAAGAT GGCTCTGCTATCACTTCTGGATGGACCCGCGGCGTATTAGCTAGTTGG TGAGGCAAAGGCTCACCAAGGCAGTGATACGTAGCCGACCTGAGAGG GTAATCGGCCACATTGGGACTGAGACACGGCCCAGACTCCTACGGGA GGCAGCAGTAGGGAATCTTCCACAATGGACGCAAGTCTGATGGAGCA ACGCCGCGTGAGTGAAGAAGGGTTTCGGCTCGTAAAGCTCTGTTGTT AAAGAAGAACGTGGGTAAGAGTAACTGTTTACCCAGTGACGGTATTT AACCAGAAAGCCACGGCTAACTACGTGCCAGCAGCCGCGGTAATACG TAGGTGGCAAGCGTTATCCGGATTTATTGGGCGTAAAGCGAGCGCAG GCGGTCTTTTAAGTCTAATGTGAAAGCCTTCGGCTCAACCGAAGAAGT GCATTGGAAACTGGGAGACTTGAGTGCAGAAGAGGACAGTGGAACTC CATGTGTAGCGGTGAAATGCGTAGATATATGGAAGAACACCAGTGGC GAAGGCGGCTGTCTGGTCTGCAACTGACGCTGAGGCTCGAAAGCATG GGTAGCGAACAGGATTAGATACCCTGGTAGTCCATGCCGTAAACGAT GATTACTAAGTGTTGGAGGGTTTCCGCCCTTCAGTGCTGCAGCTAACG CATTAAGTAATCCGCCTGGGGAGTACGACCGCAAGGTTGAAACTCAA AGAATTGACGGGGGCCCGCACAAGCGGTGGAGCATGTGGTTTAATT CGAAGCTACGCGAAGAACCTTACCAGGTCTTGACATCTTCTGACAGTC TAAGAGATTAGAGGTTCCCTTCGGGGACAGAATGACAGGTGGTGCAT |

-continued

Sequence Listing

| Seq ID No. | Description | Sequence |
|---|---|---|
| | | GGTTGTCGTCAGCTCGTGTCGTGAGATGTTGGGTTAAGTCCCGCAACG<br>AGCGCAACCCTTATTACTAGTTGCCAGCATTAAGTTGGGCACTCTAGT<br>GAGACTGCCGGTGACAAACCGGAGGAAGGTGGGGACGACGTCAAAT<br>CATCATGCCCCTTATGACCTGGGCTACACACGTGCTACAATGGATGGT<br>ACAACGAGTCGCGAGACCGCGAGGTTAAGCTAATCTCTTAAAACCAT<br>TCTCAGTTCGGACTGTAGGCTGCAACTCGCCTACACGAAGTCGGAATC<br>GCTAGTAATCGCGGATCAGCATGCCGCGGTGAATACGTTCCCGGGCC<br>TTGTACACACCGCCCGTCACACCATGAGAGTTTGTAAC |
| 102 | DP102 ITS sequence | TCCGTAGGTGAACCTGCGGAAGGATCATTACTGTGATTTAGTACTACA<br>CTGCGTGAGCGGAACGAAAACAACAACACCTAAAATGTGGAATATAG<br>CATATAGTCGACAAGAGAAATCTACGAAAAACAAACAAAACTTTCAA<br>CAACGGATCTCTTGGTTCTCGCATCGATGAAGAGCGCAGCGAAATGC<br>GATACCTAGTGTGAATTGCAGCCATCGTGAATCATCGAGTTCTTGAAC<br>GCACATTGCGCCCCTCGGCATTCCGGGGGGCATGCCTGTTTGAGCGTC<br>GTTTCCATCTTGCGCGTGCGCAGAGTTGGGGGAGCGGAGCGGACGAC<br>GTGTAAAGAGCGTCGGAGCTGCGACTCGCCTGAAAGGGAGCGAAGCT<br>GGCCGAGCGAACTAGACTTTTTTTCAGGGACGCTTGGCGGCCGAGAG<br>CGAGTGTTGCGAGACAACAAAAAGCTCGACCTCAAATCAGGTAGGAA<br>TACCCGCTGAACTTAAGCATATCAATAAGCGGAGGAAAAGAAACCAA<br>CAGGGATTGCCTCAGTAGCGGCGAGTGAAGCGGCAAGAGCTCAGATT<br>TGAAATCGTGCTTTGCGGCACGAGTTGTAGATTGCAGGTTGGAGTCTG<br>TGTGGAAGGCGGTGTCCAAGTCCCTTGGAACAGGGCGCCCAGGAGGG<br>TGAGAGCCCCGTGGGATGCCGGCGGAAGCAGTGAGGCCCTTCTGACG<br>AGTCGAGTTGTTTGGGAATGCAGCTCCAAGCGGGTGGTAAATTCCAT<br>CTAAGGCTAAATACTGGCGAGAGACCGATAGCGAACAAGTACTGTGA<br>AGGAAAGATGAAAAGCACTTTGAAAAGAGAGTGAAACAGCACGTGA<br>AATTGTTGAAAGGGAAGGGTATTGCGCCCGACATGGGGATTGCGCAC<br>CGCTGCCTCTCGTGGGCGGCGCTCTGGGCTTTCCCTGGGCCAGCATCG<br>GTTCTTGCTGCAGGAGAAGGGGTTCTGGAACGTGGCTCTTCGGAGTGT<br>TATAGCCAGGGCCAGATGCTGCGTGCGGGGACCGAGGACTGCGGCCG<br>TGTAGGTCACGGATGCTGGCAGAACGGCGCAACACCGCCCGTCTTGA<br>AACATGGACCAAGGAGTCTAACGTCTATGCGAGTGTTTGGGTGTGAA<br>ACCCGTACGCGTAATGAAAGTGAACGTAGGTCGGACCCCCTGCCCTC<br>GGGGAGGGGAGCACGATCGACCGATCCCGATGTTTATCGGAAGGATT<br>TGAGTAGGAGCATAGCTGTTGGGACCCGAAAGATGGTGAACTATGCC<br>TGAATAGGGTGAAGCCAGAGGAAACTCTGGTGGAGGCTCGTAGCGGT<br>TCTGACGTGCAAATCGATCGTCGAATTTGGGTATAGGGGCGAAAGAC<br>TAATCGAACCATCTAGTAGCTGGTTCCTGCCGAAGTTTCCCTCAGGA |
| 67 | DP67 16S rRNA | TCGAGCGGACAGATGGGAGCTTGCTCCCTGATGTTAGCGGCGGACGG<br>GTGAGTAACACGTGGGTAACCTGCCTGTAAGACTGGGATAACTCCGG<br>GAAACCGGGGCTAATACCGGATGCTTGTTTGAACCGCATGGTTCAAA<br>CATAAAAGGTGGCTTCGGCTACCACTTACAGATGGACCCGCGGCGCA<br>TTAGCTAGTTGGTGAGGTAATGGCTCACCAAGGCAACGATGCGTAGC<br>CGACCTGAGAGGGTGATCGGCCACACTGGGACTGAGACACGGCCCAG<br>ACTCCTACGGGAGGCAGCAGTAGGGAATCTTCCGCAATGGACGAAAG<br>TCTGACGGAGCAACGCCGCGTGAGTGATGAAGGTTTTCGGATCGTAA<br>AGCTCTGTTGTTAGGGAAGAACAAGTGCCGTTCAAATAGGGCGGCAC<br>CTTGACGGTACCTAACCAGAAAGCCACGGCTAACTACGTGCCAGCAG<br>CCGCGGTAATACGTAGGTGGCAAGCGTTGTCCGGAATTATTGGGCGT<br>AAAGGGCTCGCAGGCGGTTTCTTAAGTCTGATGTGAAAGCCCCCGGC<br>TCAACCGGGGAGGGTCATTGGAAACTGGGGAACTTGAGTGCAGAAGA<br>GGAGAGTGGAATTCCACGTGTAGCGGTGAAATGCGTAGAGATGTGGA<br>GGAACACCAGTGGCGAAGGCGACTCTCTGGTCTGTAACTGACGCTGA<br>GGAGCGAAAGCGTGGGGAGCGAACAGGATTAGATACCCTGGTAGTCC<br>ACGCCGTAAACGATGAGTGCTAAGTGTTAGGGGGTTTCCGCCCCTTA<br>GTGCTGCAGCTAACGCATTAAGCACTCCGCCTGGGGAGTACGGTCGC<br>AAGACTGAAACTCAAAGGAATTGACGGGGGCCCGCACAAGCGGTGG<br>AGCATGTGGTTTAATTCGAAGCAACGCGAAGAACCTTACCAGGTCTT<br>GACATCCTCTGACACCCTAGAGATAGGGCTTCCCCTTCGGGG |
| 68 | DP68 16S rRNA | TGCAGTCGAGCGGACAGATGGGAGCTTGCTCCCTGATGTTAGCGGCG<br>GACGGGTGAGTAACACGTGGGTAACCTGCCTGTAAGACTGGGATAAC<br>TCCGGGAAACCGGGGCTAATACCGGATGCTTGTTTGAACCGCATGGT<br>TCAAACATAAAAGGTGGCTTCGGCTACCACTTACAGATGGACCCGCG<br>GCGCATTAGCTAGTTGGTGAGGTAATGGCTCACCAAGGCAACGATGC<br>GTAGCCGACCTGAGAGGGTGATCGGCCACACTGGGACTGAGACACGG<br>CCCAGACTCCTACGGGAGGCAGCAGTAGGGAATCTTCCGCAATGGAC<br>GAAAGTCTGACGGAGCAACGCCGCGTGAGTGATGAAGGTTTTCGGAT<br>CGTAAAGCTCTGTTGTTAGGGAAGAACAAGTGCCGTTCAAATAGGGC<br>GGCACCTTGACGGTACCTAACCAGAAAGCCACGGCTAACTACGTGCC<br>AGCAGCCGCGGTAATACGTAGGTGGCAAGCGTTGTCCGGAATTATTG |

-continued

Sequence Listing

| Seq ID No. | Description | Sequence |
|---|---|---|
| | | GGCGTAAAGGGCTCGCAGGCGGTTTCTTAAGTCTGATGTGAAAGCCC CCGGCTCAACCGGGGAGGGTCATTGGAAACTGGGGAACTTGAGTGCA GAAGAGGAGAGTGGAATTCCACGTGTAGCGGTGAAATGCGTAGAGAT GTGGAGGAACACCAGTGGCGAA |
| 69 | DP69 16S rRNA | TGCAGTCGAGCGGACAGATGGGAGCTTGCTCCCTGATGTTAGCGGCG GACGGGTGAGTAACACGTGGGTAACCTGCCTGTAAGACTGGGATAAC TCCGGGAAACCGGGGCTAATACCGGATGCTTGTTTGAACCGCATGGT TCAAACATAAAAGGTGGCTTCGGCTACCACTTACAGATGGACCCGCG GCGCATTAGCTAGTTGGTGAGGTAATGGCTCACCAAGGCAACGATGC GTAGCCGACCTGAGAGGGTGATCGGCCACACTGGGACTGAGACACGG CCCAGACTCCTACGGGAGGCAGCAGTAGGGAATCTTCCGCAATGGAC GAAAGTCTGACGGAGCAACGCCGCGTGAGTGATGAAGGTTTTCGGAT CGTAAAGCTCTGTTGTTAGGGAAGAACAAGTGCCGTTCAAATAGGGC GGCACCTTGACGGTACCTAACCAGAAAGCCACGGCTAACTACGTGCC AGCAGCCGCGGTAATACGTAGGTGGCAAGCGTTGTCCGGAATTATTG GGCGTAAAGGGCTCGCAGGCGGTTTCTTAAGTCTGATGTGAAAGCCC CCGGCTCAACCGGGGAGGGTCATTGGAAACTGGGGAACTTGAGTGCA GAAGAGGAGAGTGGAATTCCACGTGTAGCGGTG |
| 70 | DP70 16S rRNA | TGCAAGTCGAGCGGACAGATGGGAGCTTGCTCCCTGATGTTAGCGGC GGACGGGTGAGTAACACGTGGGTAACCTGCCTGTAAGACTGGGATAA CTCCGGGAAACCGGGGCTAATACCGGATGGTTGTTTGAACCGCATGG TTCAAACATAAAAGGTGGCTTCGGCTACCACTTACAGATGGACCCGC GGCGCATTAGCTAGTTGGTGAGGTAACGGCTCACCAAGGCAACGATG CGTAGCCGACCTGAGAGGGTGATCGGCCACACTGGGACTGAGACACG GCCCAGACTCCTACGGGAGGCAGCAGTAGGGAATCTTCCGCAATGGA CGAAAGTCTGACGGAGCAACGCCGCGTGAGTGATGAAGGTTTTCGGA TCGTAAAGCTCTGTTGTTAGGGAAGAACAAGTACCGTTCGAATAGGG CGGTACCTTGACGGTACCTAACCAGAAAGCCACGGCTAACTACGTGC CAGCAGCCGCGGTAATACGTAGGTGGCAAGCGTTGTCCGGAATTATT GGGCGTAAAGGGCTCGCAGGCGGTTTCTTAAGTCTGATGTGAAAGCC CCCGGCTCAACCGGGGAGGGTCATTGGAAACTGGGGAACTTGAGTGC AGAAGAGGAGAGTGGAATTCCACGTGTAGCGGTGAAATGCGTAGAG ATGTGGAGGAACACCAGTGGCGAAGGCGACTCTCTGGTCTGTAACTG ACGCTGANGAGCGAAAGCGTGGGGAGCGAACAGGATTAGATACCCT GGTAGTCCACGCCGTAAACGATGAGTGCTAAGTGTTA |
| 71 | DP71 16S rRNA | TTACTTGGAGTCCGAACTCTCACTTTTTAACCCTGTGCATCTGTTAATT GGAATAGTAGCTCTTCGGAGTGAACCACCATTCACTTATAAAACACA AAGTCTATGAATGTATACAAATTTATAACAAAACAAAACTTTCAACA ACGGATCTCTTGGCTCTCGCATCGATGAAGAACGCAGCGAAATGCGA TACGTAATGTGAATTGCAGAATTCAGTGAATCATCGAATCTTTGAACG CACCTTGCGCTCCTTGGTATTCCGAGGAGCATGCCTGTTTGAGTGTCA TGAAATCTTCAACCCACCTCTTTCTTAGTGAATCTGGTGGTGCTTGGTT TCTGAGCGCTGCTCTGCTTCGGCTTAGCTCGTTCGTAATGCATTAGCA TCCGCAACCGAACTTCGGATTGACTTGGCGTAATAGACTATTCGCTGA GGATTCTAGTTTACTAGAGCCGAGTTGGGTTAAAGGAAGCTCCTAATC CTAAAGTCTATTTTTTGATTAGATCTCAAATCAGGTAGGACTACCCGC TGAACTTAAGCATATCAATAAGCGGAGGAAAAGAAACTAACAAGGA TTCCCCTAGTAGCGGCGAGCGAAGCGGGAAGAGCTCAAATTTATAAT CTGGCACCTTCGGTGTCCGAGTTGTAATCTCTAGAAGTGTTTTCCGCG TTGGACCGCACACAAGTCTGTTGGAATACAGCGGCATAGTGGTGAAA CCCCCGTATATGGTGCGGACGCCCAGCGCTTTGTGATACACTTTCAAT GAGTCGAGTTGTTTGGGAATGCAGCTCAAATTGGGTGGTAAATTCCAT CTAAAGCTAAATATTGGCGAGAGACCGATAGCGAACAAGTACCGTGA GGGAAAGATGAAAAGCACTTTGGAAAGAGAGTTAACAGTACGTGAA ATTGTTGGAA |
| 21 | DP21 18S rRNA | GGGGGCATCAGTATTCAGTTGTCAGAGGTGAAATTCTTGGATTTACTG AAGACTAACTACTGCGAAAGCATTTGCCAAGGACGTTTTCATTAATCA AGAACGAAAGTTAGGGGATCGAAGATGATCAGATACCGTCGTAGTCT TAACCATAAACTATGCCGACTAGGGATCGGGTGTTGTTCTTTTTTTGA CGCACTCGGCACCTTACGAGAAATCAAAGTCTTTGGGTTCTGGGGGG AGTATGGTCGCAAGGCTGAAACTTAAAGGAATTGACGGAAGGGCACC ACCAGGAGTGGAGCCTGCGGCTTAATTTGACTCAACACGGGGAAACT CACCAGGTCCAGACACAATAAGGATTGACAGATTGAGAGCTCTTTCT TGATTTTGTGGGTGGTGGTGCATGGCCGTTCTTAGTTGGTGGAGTGAT TTGTCTGCTTAATTGCGATAACGAACGAGACCTTAACCTACTAAATAG TGCTGCTAGCTTTTGCTGGTATAGTCACTTCTTAGAGGGACTATCGAT TTCAAGTCGATGGAAGTTTGAGGCAATAACAGGTCTGTGATGCCCTTA GACGTTCTGGGCCGCACGCGCGCTACACTGACGGAGCCAGCGAGTTC TAACCTTGGCCGAGAGGTCTGGGTAATCTTGTGAAACTCCGTCGTGCT |

-continued

Sequence Listing

| Seq ID No. | Description | Sequence |
|---|---|---|
| | | GGGGATAGAGCATTGTAATTATTGCTCTTCAACGAGGAATTCCTAGTA AGCGCAAGTCATCAGCTTGCGTTGATTACGTCCCTGCCCTTTGTACAC ACCGCCCGTCGCTACTACCGATTGAATGGCTTAGTGAGGCTTCCGGAT TGGTTTAAAGAAGGGGGCAACTCCATCTTGGAACCGAAAAGCTAGTC AAACTTGGTCATTTAGAGGAAGTAAAAGTCGTAACAAGGTTTCCGTA GGTGAACCTGCGGAAGGATCATT |
| 99 | DP99 16S rRNA | GATTTGAAGAGCTTGCTCAGATATGACGATGGACATTGCAAAGAGTG GCGAACGGGTGAGTAACACGTGGGAAACCTACCTCTTAGCAGGGGAT AACATTTGGAAACAGATGCTAATACCGTATAACAATAGCAACCGCAT GGTTGCTACTTAAAAGATGGTTCTGCTATCACTAAGAGATGGTCCCGC GGTGCATTAGTTAGTTGGTGAGGTAATGGCTCACCAAGACGATGATG CATAGCCGAGTTGAGAGACTGATCGGCCACAATGGGACTGAGACACG GCCCATACTCCTACGGGAGGCAGCAGTAGGGAATCTTCCACAATGGG CGAAAGCCTGATGGAGCAACGCCGCGTGTGTGATGAAGGGTTTCGGC TCGTAAAACACTGTTGTAAGAGAAGAATGACATTGAGAGTAACTGTT CAATGTGTGACGGTATCTTACCAGAAAGGAACGGCTAAATACGTGCC AGCAGCCGCGGTAATACGTATGTTCCAAGCGTTATCCGGATTTATTGG GCGTAAAGCGAGCGCAGACGGTTATTTAAGTCTGAAGTGAAAGCCCT CAGCTCAACTGAGGAATTGCTTTGGAAACTGGATGACTTGAGTGCAG TAGAGG |

What is claimed is:

1. A dietary supplement comprising a combination of four heterologous microbes comprising *Lactobacillus brevis, Lactobacillus plantarum, Leuconostoc mesenteroides*, and *Pichia kudriavzevii*, wherein the heterologous microbes are co-formulated as a synthetic microbial consortium comprising about $1.0\times10^8$ to about $1.0\times10^{12}$ CFU of each of the heterologous microbes, wherein the *Pichia kudriavzevii* comprises a fungal ITS sequence having at least 97% identity to SEQ ID NO: 102 at the fungal ITS sequence, formulated in an amount effective for lessening a decrease in, maintaining, or improving bone health in a human subject, wherein the dietary supplement is formulated for oral delivery.

2. The dietary supplement of claim 1, further comprising a prebiotic selected from the group consisting of oligofructose, a dried fruit or vegetable powder, and combinations thereof.

3. The dietary supplement of claim 1 further comprising a vitamin, wherein the vitamin is selected from the group consisting of vitamins C, D, E, K1, K2, and combinations thereof.

4. The dietary supplement of claim 1, wherein lessening a decrease in, maintaining, or improving bone health in the subject comprises (i) lessening a decrease in, maintaining, or improving bone mineral density (BMD), measured as areal BMD (aBMD) or volumetric BMD (vBMD) in the subject, and/or (ii) lessening a decrease in, maintaining, or improving trabecular bone score (TBS) in the subject.

5. The dietary supplement of claim 1, wherein administration of the dietary supplement to the subject results in (i) altering the amount of at least one biochemical marker of bone turnover in the subject, and/or (ii) decreasing the amount of at least one circulatory inflammatory cytokine or marker of inflammation in the subject, wherein the amount of the at least one biochemical marker of bone turnover and/or at least one circulatory inflammatory cytokine or marker of inflammation is altered as compared to a suitable control; wherein the suitable control comprises: (a) a control group that has not been administered the dietary supplement, and/or (b) the amount of the at least one biochemical marker of bone turnover and/or the at least one circulatory inflammatory cytokine or marker of inflammation in the subject prior to the first administration of the dietary supplement.

6. The dietary supplement of claim 5, wherein the at least one biochemical marker of bone turnover comprises CTX and/or P1NP.

7. The dietary supplement of claim 6, wherein:

(i) the amount of CTX decreases;

(ii) the amount of P1NP increases; and/or (iii) the ratio of P1NP to CTX increases.

8. The dietary supplement of claim 5, wherein the at least one circulatory inflammatory cytokine or marker of inflammation is selected from the group consisting of CRP, IL-17, TNF, IL-1B, IL-4, RANKL, IFNγ, and combinations thereof.

9. The dietary supplement of claim 1, formulated as a medical food.

10. A dietary supplement comprising a combination of four heterologous microbes comprising *Lactobacillus brevis, Lactobacillus plantarum, Leuconostoc mesenteroides*, and *Pichia kudriavzevii*, wherein the heterologous microbes are co-formulated as a synthetic microbial consortium comprising about $1.0\times10^8$ to about $1.0\times10^{12}$ CFU of each of the heterologous microbes, wherein the *Pichia kudriavzevii* comprises a fungal ITS sequence having at least 97%, at least 98% identity to any one of SEQ ID NO: 102 at the fungal ITS sequence, formulated for improving one or more symptoms of menopause in a human subject, wherein the dietary supplement is formulated for oral delivery.

11. The dietary supplement of claim 10, wherein the dietary supplement further comprises a prebiotic, selected from the group consisting of oligofructose, a dried fruit or vegetable powder, and combinations thereof.

12. The dietary supplement of claim 10 further comprising a vitamin, wherein the vitamin is selected from the group consisting of vitamin C, D, E, K1, K2, and combinations thereof.

13. The dietary supplement of claim 10, wherein, following administration of the dietary supplement to the subject over a period of time, the one or more symptoms of menopause are improved as compared to a suitable control, and wherein the suitable control comprises: (i) a control group that has not been administered the dietary supplement and/or (ii) the presence or severity of the subject's one or more symptoms prior to the first administration of the dietary supplement.

14. The dietary supplement of claim 10, wherein the one or more symptoms of menopause are selected from the group consisting of: hot flushes, sweating, episodes of sweating, night sweats, heart discomfort, unusual awareness of heart beat, heart skipping, heart racing, heart tightness, depressive mood, feeling down, feeling sad, feeling on verge of tears, lack of drive, mood swings, irritability, feeling nervous, inner tension, feeling aggressive, anxiety, inner restlessness, feeling panicky, physical exhaustion, mental exhaustion, general decrease in performance, impaired memory, decrease in concentration, forgetfulness, sexual problems, change in sexual desire, change in sexual activity, change in sexual satisfaction, bladder problems, difficulty in urinating, increased need to urinate, bladder incontinence, dryness of the vagina, sensation of dryness or burning in the vagina, difficulty with sexual intercourse, joint and muscular discomfort, pain in the joints, and rheumatoid arthritis, optionally wherein the one or more symptoms of menopause comprise a vasomotor symptom, wherein the vasomotor symptom is selected from the group consisting of hot flushes, sweating, night sweats, and combinations thereof.

15. The dietary supplement of claim 10, wherein severity of the one or more symptoms of menopause is measured by the Menopause Rating Scale (MRS); optionally wherein the improvement of the symptom is measured in the same subject about 2 months, 4 months, 6 months, 8 months, 10 months, and/or 12 months after the first administration of the dietary supplement.

16. The dietary supplement of claim 15, wherein the concentration is about $2.5\times10^9$ to $3.0\times10^{10}$ CFU of each of the heterologous microbes.

17. A conventional food product comprising a combination of four heterologous microbes consisting of *Lactobacillus brevis, Lactobacillus plantarum, Leuconostoc mesenteroides*, and *Pichia kudriavzevii*, wherein at least one of the *Pichia kudriavzevii* comprises a fungal ITS sequence having at least 97% identity to SEQ ID NO: 102 at the fungal ITS sequence, formulated in an amount effective for (i) lessening a decrease in, maintaining, or improving bone health in a human subject or (ii) improving one or more symptoms of menopause, wherein the conventional food product further comprises a prebiotic, selected from oligofructose and/or a dried fruit or vegetable powder.

18. The food product of claim 17, wherein consumption of the food product by a human subject results in (i) altering the amount of at least one biochemical marker of bone turnover in the subject and/or (ii) decreasing the amount of at least one circulatory inflammatory cytokine or marker of inflammation in the subject, wherein the amount of the at least one biochemical marker of bone turnover and/or at least one circulatory inflammatory cytokine or marker of inflammation is altered as compared to a suitable control; wherein the suitable control comprises: (a) a control group that has not been administered the dietary supplement, and/or (b) the amount of the at least one biochemical marker of bone turnover and/or the at least one circulatory inflammatory cytokine or marker of inflammation in the subject prior to the first administration of the dietary supplement.

* * * * *